US007951381B2

(12) United States Patent
Funk et al.

(10) Patent No.: US 7,951,381 B2
(45) Date of Patent: May 31, 2011

(54) METHOD OF STIMULATING EPITHELIAL CELL PROLIFERATION BY ADMINISTRATION OF GASTROINTESTINAL PROLIFERATIVE FACTOR

(75) Inventors: Walter Funk, Hayward, CA (US); Makoto Kakitani, Takasaki (JP); Takeshi Oshima, Maebashi (JP); Eun Ju Park, Los Altos, CA (US); Mikio Yagi, Saitama (JP); Kazuma Tomizuka, Takasaki (JP)

(73) Assignees: Kyowa Hakko Kirin Co., Ltd., Tokyo (JP); Arca Biopharma Inc., Bloomfield, CO (US)

( * ) Notice: Subject to any disclaimer, the term of this patent is extended or adjusted under 35 U.S.C. 154(b) by 0 days.

(21) Appl. No.: 12/589,727

(22) Filed: Oct. 27, 2009

(65) Prior Publication Data

US 2010/0137210 A1 Jun. 3, 2010

Related U.S. Application Data

(60) Continuation of application No. 11/805,883, filed on May 24, 2007, now abandoned, which is a division of application No. 11/046,644, filed on Jan. 27, 2005, now abandoned.

(60) Provisional application No. 60/539,605, filed on Jan. 27, 2004, provisional application No. 60/619,241, filed on Oct. 15, 2004.

(51) Int. Cl.
*A61K 38/18* (2006.01)
*C07K 14/475* (2006.01)

(52) U.S. Cl. ........ 424/198.1; 514/1.1; 514/7.6; 530/399

(58) Field of Classification Search .................. None
See application file for complete search history.

(56) References Cited

U.S. PATENT DOCUMENTS

| 6,824,973 | B2 | 11/2004 | Tang et al. |
| 7,411,052 | B2 | 8/2008 | Tang |
| 2004/0005560 | A1 | 1/2004 | Isogai et al. |
| 2005/0054829 | A1 | 3/2005 | Wiley et al. |
| 2005/0130145 | A1 | 6/2005 | Yue et al. |
| 2005/0169995 | A1 | 8/2005 | Kuo |
| 2006/0149049 | A1 | 7/2006 | Tang |
| 2006/0263803 | A1 | 11/2006 | Tang |

FOREIGN PATENT DOCUMENTS

| JP | 2003-530124 | 10/2003 |
| WO | WO 01/77169 A2 | 10/2001 |
| WO | WO 03/029405 A2 | 4/2003 |
| WO | WO 03/029437 A2 | 4/2003 |
| WO | WO-03054152 A3 * | 7/2003 |
| WO | WO 2005/040418 A2 | 5/2005 |
| WO | WO 2005/110009 A2 | 11/2005 |

OTHER PUBLICATIONS

Allegra, "Cancer Chemotherapy: Principles and Practice," Lippincott and Company, Philidelphia, Chapter 5: Antifolates, pp. 110-153 (1990).
Arkell, et al., "Update on Oral Candidosis," Nurse Times 99(48):52-53 (2003) *Abstract Only*.
Berthrong, "Pathalogical Changes Secondary to Radiation," *World J Surg* 10:155-170 (1986).
Boric, et al., "Go Hunting in Sequence Databases But Watch Out for the Traps," *Trends in Genetics* 12(10):425-427 (1996).
Bork, "Powers And Pitfalls In Sequence Analysis: The 70% Hurdle," *Genome Res 10*:398-400 (2000).
Bouma, et al., "The Immunological And Genetic Basis Of Inflammatory Bowel Disease," *Nature Reviews* 3:521-533 (2003).
Brenner, "Errors in Genome Fucntion," *Trends in Genetics* 15(4):132-133 (1999).
Dibaise, et al., "Intestinal Rehabilitation And the Short Bowel Syndrome: Part 2," *Am J Gastroent 99*:1823-1832, 2004.
Doerks, et al., "Protein Annotation: Detective Work for Function Prediction," *Trends in Genetics* 14(6):248-250 (1998).
Guzman-Stein, et al., "Abdominal Radiation Causes Bacterial Translocation," *J Surg Res 46*:104-107 (1989).
Kamata, et al., "R-Spondin, A Novel Gene With Thrombospondin Type 1 Domain, Was Expressed In The Dorsal Neural Tube And Affected in Wnts Mutants," *Biochim Biophys Acta 1676*:51-62 (2004).
Kim, et al., Mitogenic Influence Of Human R-Spondinl On The Intestinal Epithelium, *Science 309*:1256-1259 (2005).
Merck Manual Online Medical Library, www.merck.com/mmpe, 14 total pages, printed on Apr. 29, 2009.
Ngo, et al., "Computational Complexity, Protein Structure Prediction, And The Levinthal Paradox," *The Protein Folding Problem And Tertiary Structural Prediction* pp. 492-495 (1994).
Ota, et al., Genebank Accession No. Q8N7L5 (2002).
Scully, et al., "Oral Mucosal Disease: Lichen Planus" *Brit J Oral Maxillofacial Surg 46*:15-21 (2008).
Skolnick, et al., "From Genes To Protein Structure And Function: Novel Applications Of Computational Approaches in the Genomic Era," *Trends in Biotech 18*(1):34-39 (2000).
Smith, et al., "The Challenges of Genome Sequence Annotation or 'The Devil in the Details'," *Nature Biotech 15*:1222-1223 (1997).
Wells, "Additivity of Mutational Effects in Proteins." *Biochemistry* 29(37):8509-8517 (1990).

* cited by examiner

*Primary Examiner* — Bridget E Bunner
(74) *Attorney, Agent, or Firm* — Stephen A. Bent; Foley & Lardner LLP

(57) ABSTRACT

The invention relates to pharmaceutical compositions comprising gastrointestinal proliferative factor (GIPF) polynucleotides and polypeptides. The invention further relates to the therapeutic use of GIPF to prevent or treat conditions or disorders associated with the degeneration of the epithelial mucosa.

7 Claims, 107 Drawing Sheets

```
CGGGTCGACGATTTCGTCGCGCCCTCGCCCCTCCCGGGCCTGCCCCCGTCGCGACTGGCAGCACGAAGCTGAGATTG
TGGTTTCCTGGTGATTCAGGTGGGAGTGGGCCAGAAGATCACCGCTGGCAAGGACTGGTGTTTGTCAACTGTAAGGA
CTCATGGAACAGATCTACCAGGGATTCTCAGACCTTAGTTTGAGAAATGCTGCAATTAAAGGCAAATCCTATCACTC
TGAGTGATCGCTTTGGTGTCGAGGCAATCAACCATAAAGATAAATGCAAATATGGAAATTGCATAACAGTACTCAGT
ATTAAGGTTGGTTTTTGGAGTAGTCCCTGCTGACGTGACAAAAAGATCTCTCATATGATATTCCGAGGTATCTTTGA
GGAAGTCTCTCTTTGAGGACCTCCCTTTGAGCTGATGGAGAACTGGGCTCCCCACACCCTCTCTGTCCCCAGCTGAG
ATTATGGTGGATTTGGGCTACGGCCCAGGCCTGGGCCTCCTGCTGCTGACCCAGCCCCAGAGGTGTTAGCAAGAGCC
GTGTGCTATCCACCCTCCCCGAGACCACCCCTCCGACCAGGGGCCTGGAGCTGGCGCGTGACTATGCGGCTTGGGCT
GTGTGTGGTGGCCCTGGTTCTGAGCTGGACGCACCTCACCATCAGCAGCCGGGGGATCAAGGGGAAAAGGCAGAGGC
GGATCAGTGCCGAGGGGAGCCAGGCCTGTGCCAAAGGCTGTGAGCTCTGCTCTGAAGTCAACGGCTGCCTCAAGTGC
TCACCCAAGCTGTTCATCCTGCTGGAGAGGAACGACATCCGCCAGGTGGGCGTCTGCTTGCCGTCCTGCCCACCTGG
ATACTTCGACGCCCGCAACCCCGACATGAACAAGTGCATCAAATGCAAGATCGAGCACTGTGAGGCCTGCTTCAGCC
ATAACTTCTGCACCAAGTGTAAGGAGGGCTTGTACCTGCACAAGGGCCGCTGCTATCCAGCTTGTCCCGAGGGCTCC
TCAGCTGCCAATGGCACCATGGAGTGCAGTAGTCCTGCGCAATGTGAAATGAGCGAGTGGTCTCCGTGGGGGCCCTG
CTCCAAGAAGCAGCAGCTCTGTGGTTTCCGGAGGGGCTCCGAGGAGCGGACACGCAGGGTGCTACATGCCCCTGTGG
GGGACCATGCTGCCTGCTCTGACACCAAGGAGACCCGGAGGTGCACAGTGAGGAGAGTGCCGTGTCCTGAGGGGCAG
AAGAGGAGGAAGGGAGGCCAGGGCCGGCGGGAGAATGCCAACAGGAACCTGGCCAGGAAGGAGAGCAAGGAGGCGGG
TGCTGGCTCTCGAAGACGCAAGGGGCAGCAACAGCAGCAGCAGCAAGGGACAGTGGGGCCACTCACATCTGCAGGGC
CTGCCTAGGGACACTGTCCAGCCTCCAGGCCCATGCAGAAAGAGTTCAGTGCTACTCTGCGTGATTCAAGCTTTCCT
GAACTGGAACGTCGGGGGCAAAGCATACACACACACTCCAATCCATCCATGCATACACAGACACAAGACACACACGC
TCAAACCCCTGTCCACATATACAACCATACATACTTGCACATGTGTGTTCATGTACACACGCAGACACAGACACCAC
ACACACACATACACACACACACACACGCACACCTGAGGCCACCAGAAGACACTTCCATCCCTCGGGCCCAGCAGT
ACACACTTGGTTTCCAGAGCTCCCAGTGGACATGTCAGAGACAACACTTCCCAGCATCTGAGACCAAACTGCAGAGG
GGAGCCTTCTGGAGAAGCTGCTGGGATCGGACCAGCCACTGTGGCAGATGGGAGCCAAGCTTGAGGACTGCTGGTGG
CCTGGGAAGAAACCTTCTTCCCATCCTGTTCAGCACTCCCAGCTGTGTGACTTTATCGTTGGAGAGTATTGTTACCT
TCCAGGATACATATCAGGGTTAACCTGACTTTGAAAACTGCTTAAAGGTTTATTTCAAATTAAAACAAAAAAATCAA
CGACAGCAGTAGACACAGGCACCACATTCCTTTGCAGGGTGTGAGGGTTTGGCGAGGTATGCGTAGGAGCAAGAAGG
GACAGGGAATTTCAAGAGACCCCAAATAGCCTGCTCAGTAGAGGGTCATGCAGACAAGGAAGAAAACTTAGGGGCTG
CTCTGACGGTGGTAAACAGGCTGTCTATATCCTTGTTACTCAGAGCATGGCCCGGCAGCAGTGTTGTCACAGGGCAG
CTTGTTAGGAATGATAATCTCAGGTCTCATTCCAGACCTGGAGAGCCATGAGTCTAAATTTTAAGATTCCTGATGAT
TGGCATGTTACCCAAATTTGAGAAGTGCT
```

Fig. 1A

MRLGLCVVALVLSWTHLTISSRGIKGKRQRRISAEGSQACAKGCELCSEVNGCLKCSPKLFILL
ERNDIRQVGVCLPSCPPGYFDARNPDMNKCIKCKIEHCEACFSHNFCTKCKEGLYLHKGRCYPA
CPEGSSAANGTMECSSPAQCEMSEWSPWGPCSKKQQLCGFRRGSEERTRRVLHAPVGDHAACSD
TKETRRCTVRRVPCPEGQKRRKGĠQGRRENANRNLARKESKEAGAGSRRRKGQQQQQQQGTVGP
LTSAGPA

Fig. 1B

```
>gi|18490982|ref|NP_116173.2| thrombospondin; thrombospondin-like
        gene [Homo sapiens]
 gb|AAK34947.1|AF251057_1 thrombospondin [Homo sapiens]
 gb|AAH22367.1| Thrombospondin [Homo sapiens]
        Length = 272

Score =( 252 bits (644), Expect = 4e-66
 Identities = 116/252 (46%), Positives = 159/252 (63%), Gaps = 15/252 (5%)

Query:  10  LVLSWTHLTISSRGIKGKRQRRISAEGSQACAKGCELCSEVNGCLKCSPKLFILLERNDI  69
            ++L++      S   +G+RQRR+    SQ C  GC  CS+ NGCL C P+LF  LER  +
Sbjct:  11  IILNFMEYIGSQNASRGRRQRRMHPNVSQGCQGGCATCSDYNGCLSCKPRLFFALERIGM  70

Query:  70  RQVGVCLPSCPPGYFDARNPDMNKCIKCKIEHCEACFSHNFCTKCKEGLYLHKGRCYPAC  129
            +Q+GVCL SCP GY+   R PD+NKC KC + C+ CF+ NFCTKCK G YLH G+C   C
Sbjct:  71  KQIGVCLSSCPSGYYGTRYPDINKCTKCKAD-CDTCFNKNFCTKCKSGFYLHLGKCLDNC  129

Query: 130  PEGSSAANGTMECSSPAQCEMSEWSPWGPCSKKQQLCGFRRGSEERTRRVLHAPVGDHAA  189
            PEG  A N TMEC S   CE+SEW+PW PC+KK + CGF+RG+E  R  ++     P
Sbjct: 130  PEGLEANNHTMECVSIVHCEVSEWNPWSPCTKKGKTCGFKRGTETRVREIIQHPSAKGNL  189

Query: 190  CSDTKETRRCTVRRVPCPEGQKRRKGGQGRRENANRNLARKESKEAGAGSR---------  240
            C  T ETR+CTV+R  C +G++ +KG + +R+ N+      ESKEA    S+
Sbjct: 190  CPPTNETRKCTVQRKKCQKGERGKKGRERKRKKPNKG----ESKEAIPDSKSLESSKEIP  245

Query: 241  -RRKGQQQQQQQ  251
             +R+ +QQQ+++
Sbjct: 246  EQRENKQQQKKR  257
```

Fig. 4A

```
>sp|P07996|TSP1_HUMAN Thrombospondin 1 precursor - Homo sapiens
          (Human)._From.original.residues_501-through-657
          Length = 157

Score = 73 (30.8 bits), Expect = 1.0e-05, P = 1.0e-05
 Identities = 38/165 (23%), Positives = 61/165 (36%)

Query:     14 WTHLTISSRGIKGKRQRRISAEGSQACAKGC-------ELCSE----VNGCLKCSPKLFI 62
              W   +++   G    KR R  +    Q  K C        ++C++      ++GCL  +P  F
Sbjct:    501 WDICSVTCGGGVQKRSRLCNNPTPQFGGKDCVGDVTENQICNKQDCPIDGCLS-NP-CFA 58

Query:     63 LLERNDIRQVGVCLPSCPPGYFDARNPDMNKCIKCKIEHCEACFSHNFCTKCKEGLYLHK 122
              ++                  +CPPGY              +CK E   +ACF+HN      +C+
Sbjct:     59 GVKCTSYPDGSWKCGACPPGY-SGNGIQCTDVDECK-EVPDACFNHNGEHRCEN---TDP 113

Query:    123 G-RCYPACPEGSSAANGTMECSSPAQCEMSEWSPWGPCSKKQQLC 166
              G  C P CP  + +        +       A         P  PC+       C
Sbjct:    114 GYNCLP-CPPRFTGSQPFGQGVEHATANKQVCKPRNPCTDGTHDC 657
```

Fig. 4B

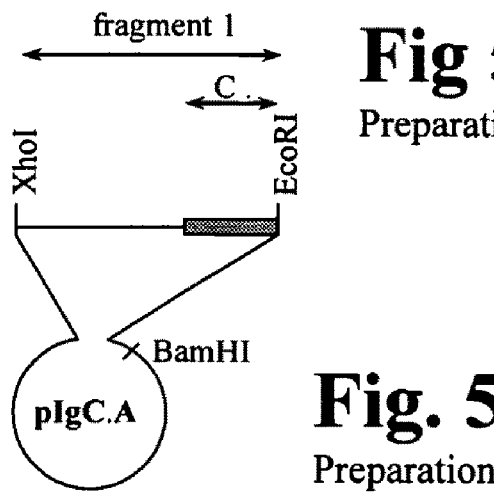
Fig 5B
Preparation of IgC fragment 1.
Fig. 5C
Preparation of IgC fragment 2.
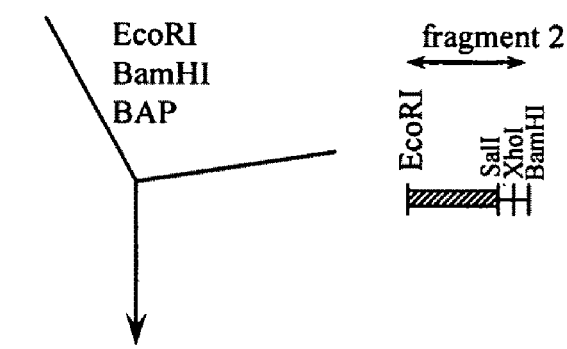
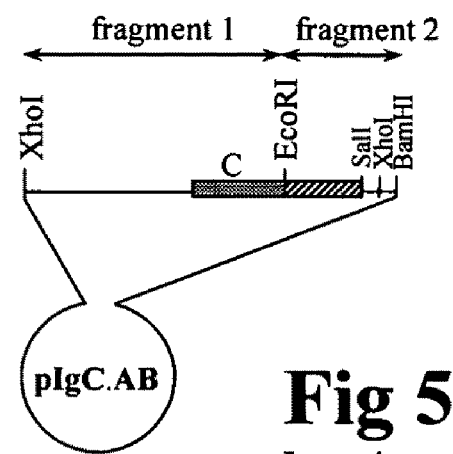
Fig 5D
Insertion of Puromycin gene into pIgC.AB
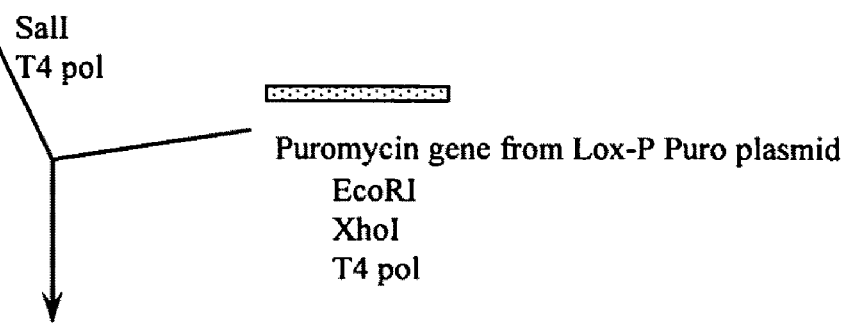

Insertion of IRES gene into pIgC.ABP

Fig. 5F
Construction of p.C.Sal
Fig. 5G
Construction of pKI.
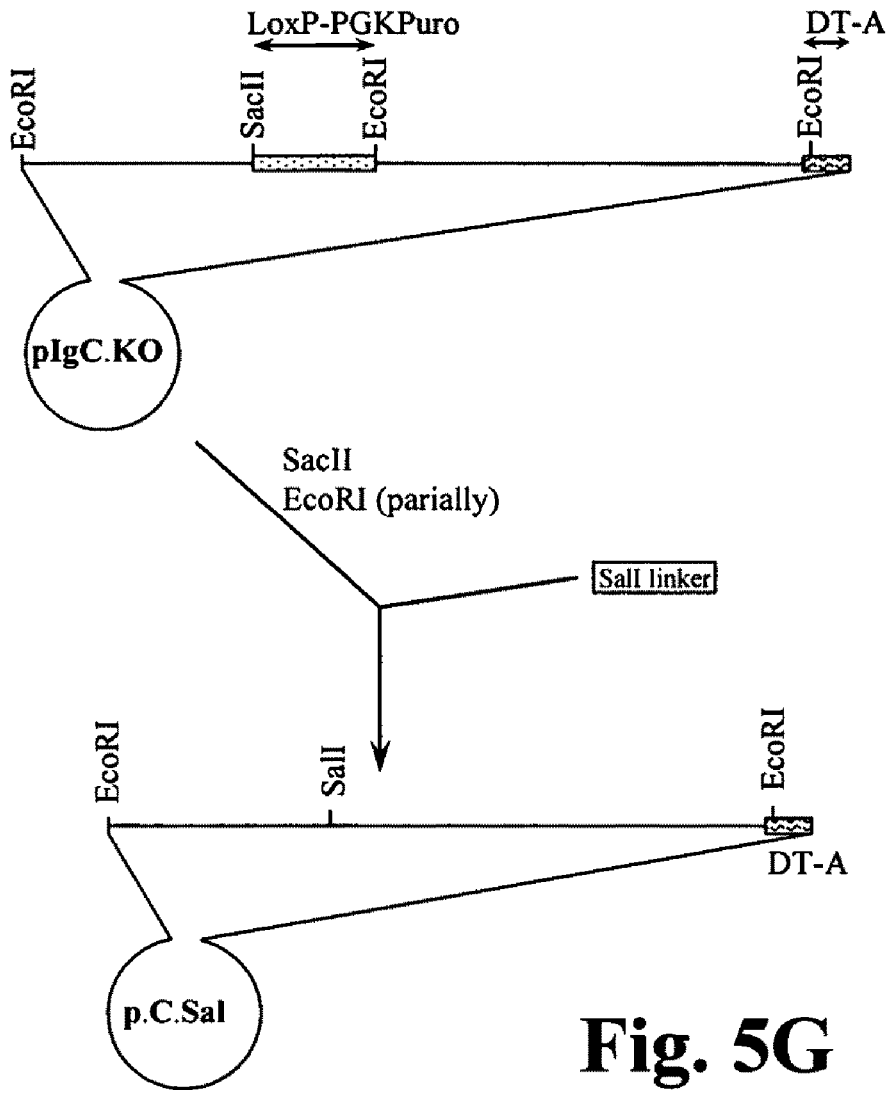
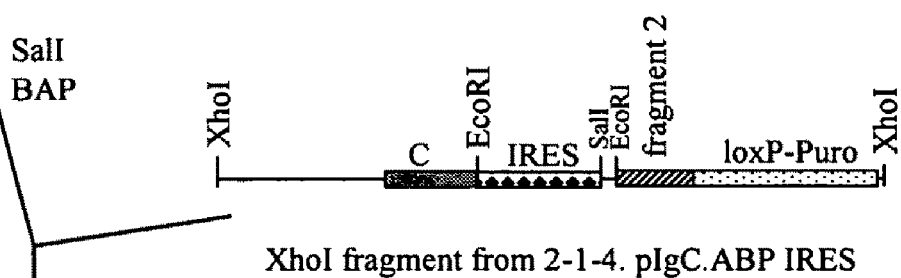
XhoI fragment from 2-1-4. pIgC.ABP IRES

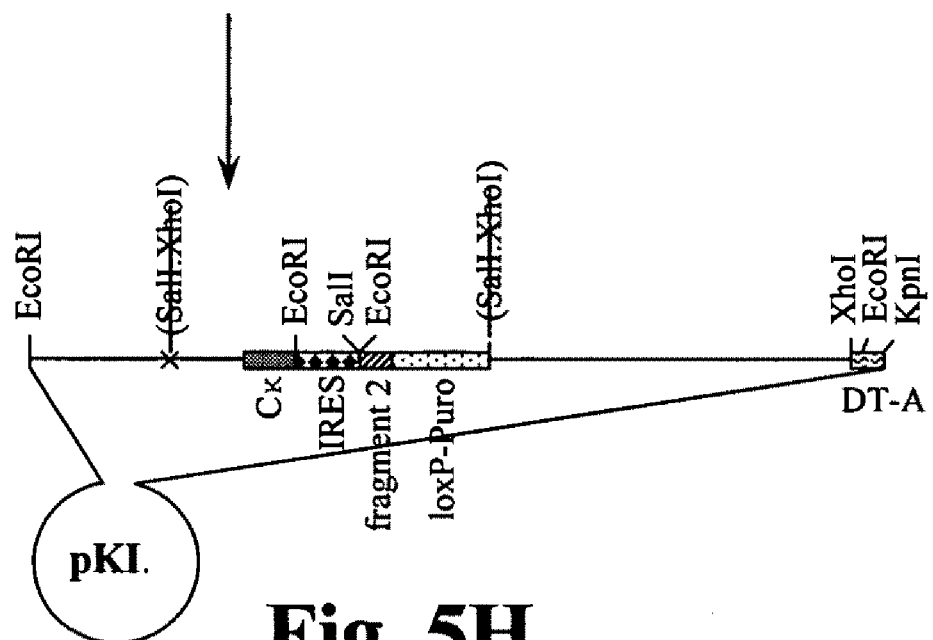
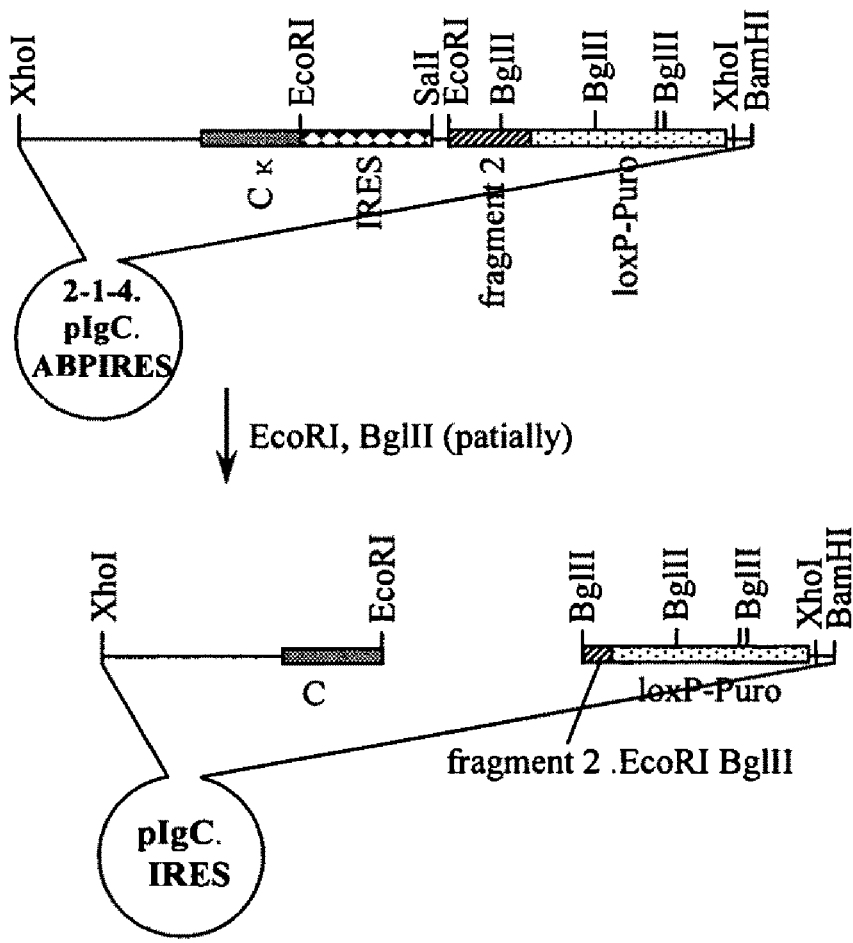
Fig. 5H
Preparation of pIgC. .IRES plasmid

Fig. 5I
P2 promoter
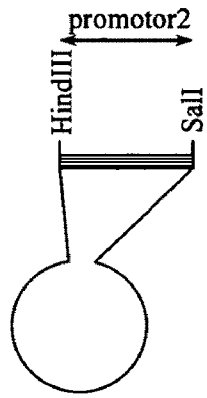
Fig. 5J
patial C.polyA
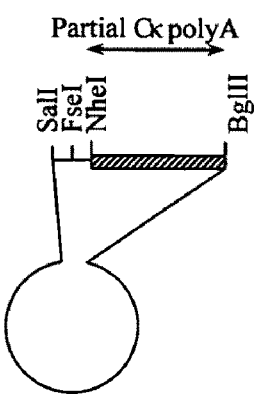
Fig. 5K
total C.polyA
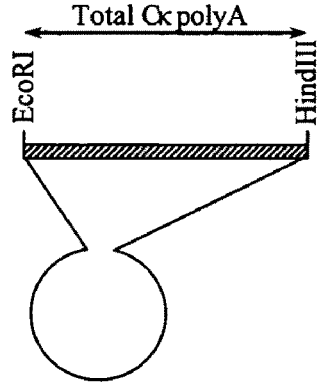
Fig. 5L  Construction of DNA fragment A.
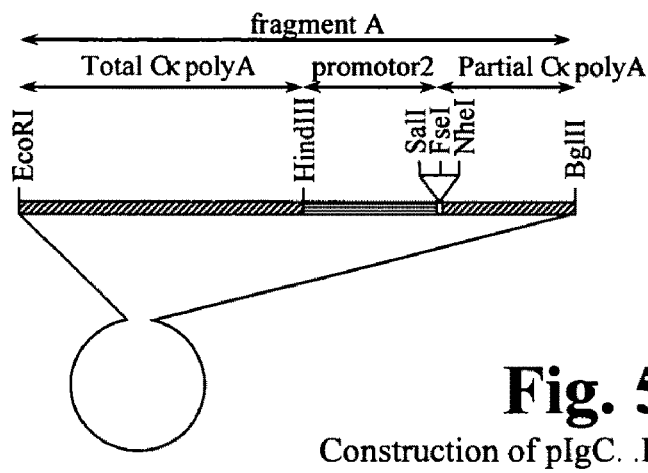
Fig. 5M
Construction of pIgC..IRES ProA plasmid
EcoRI, BglII
fragment A
2-1-7. pIgC..IRES CIAP

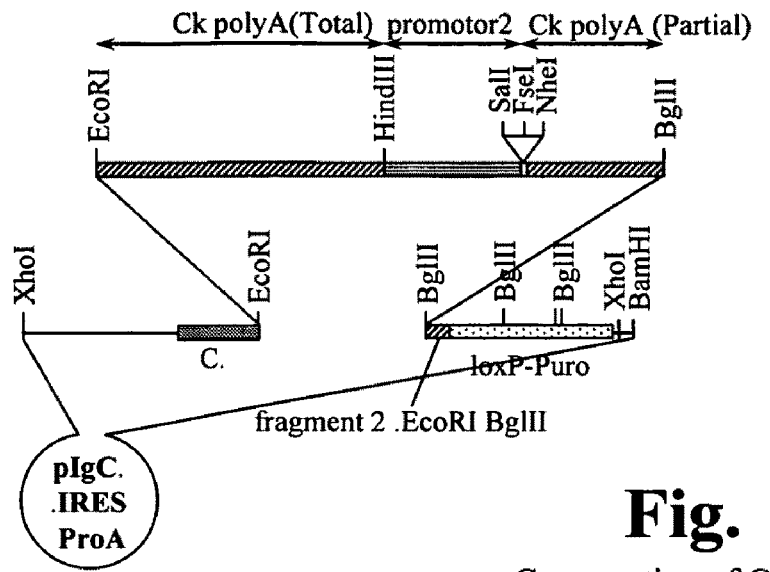
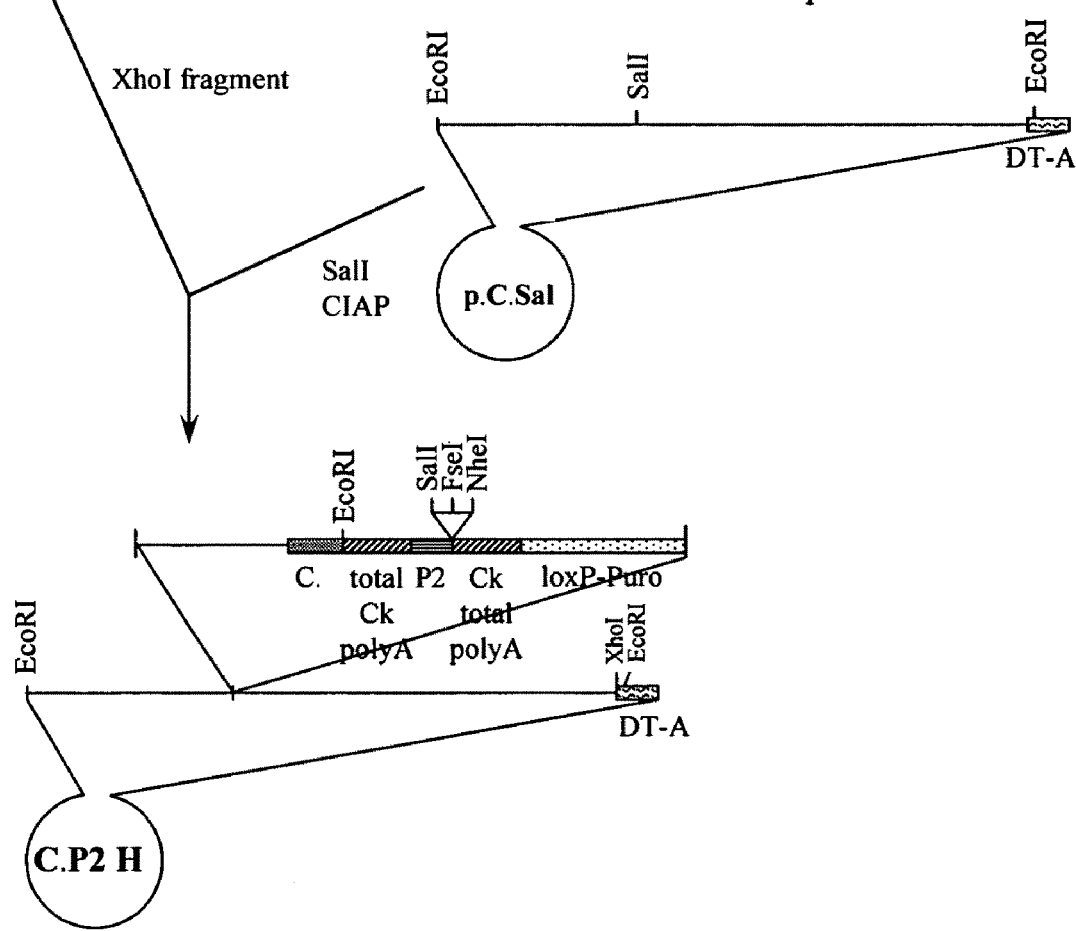
Fig. 5N
Construction of C.P2 H plasmid

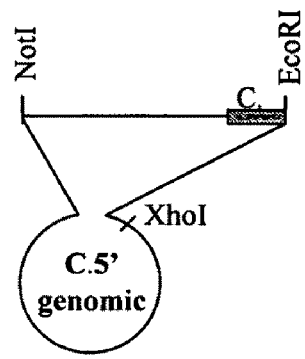
Fig. 5O
Construction of C.5' genomic plasmid
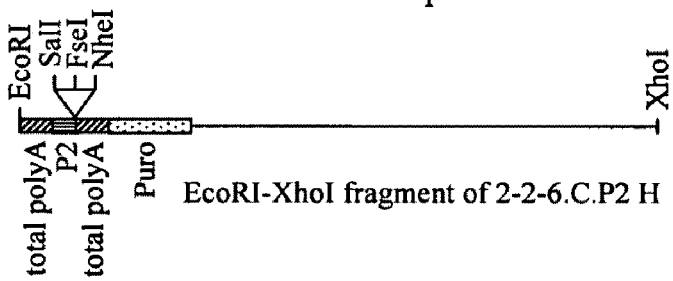
Fig. 5P
Construction of C.P2 KI .DT plasmid
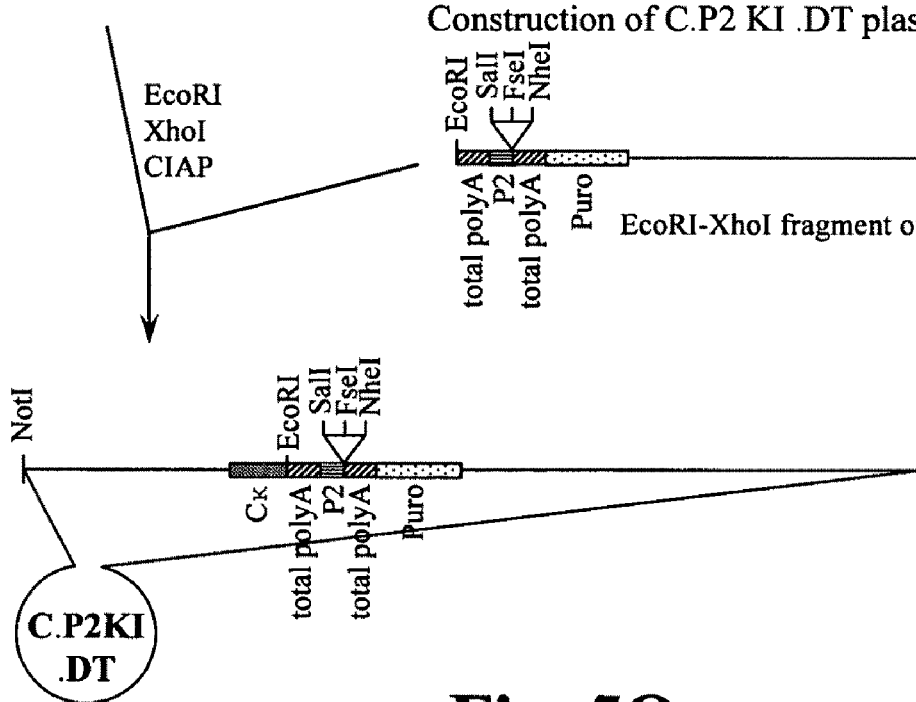
Fig. 5Q
Construction of C.P2 KI vector
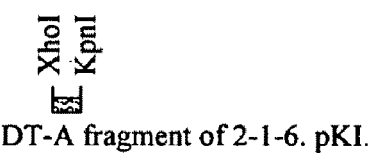

Construction of GIPF-KI vector

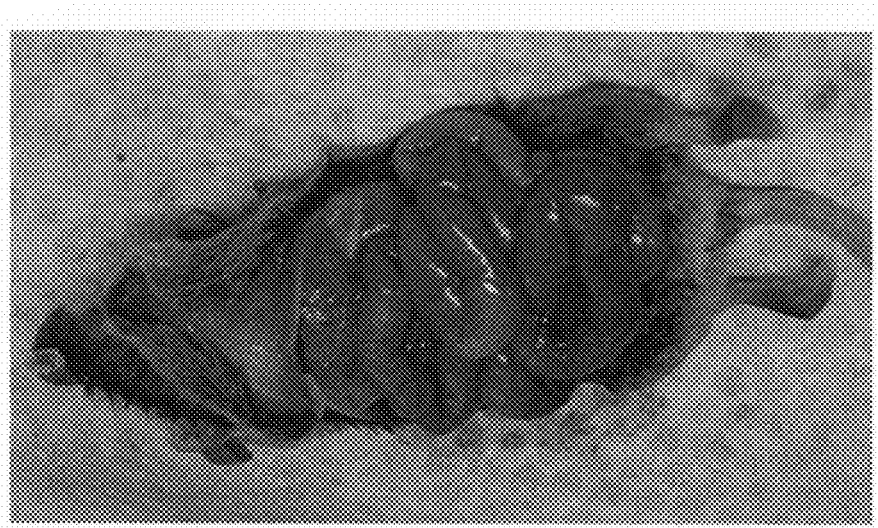
Fig. 7

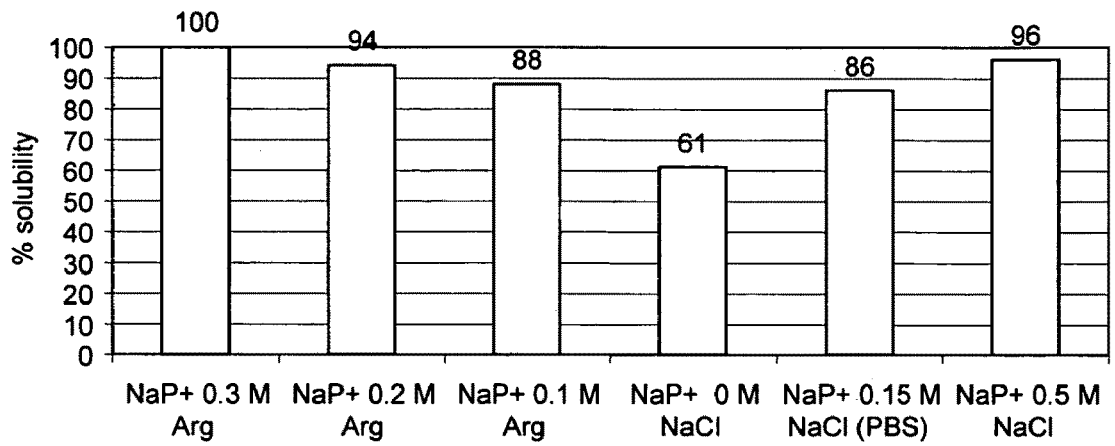
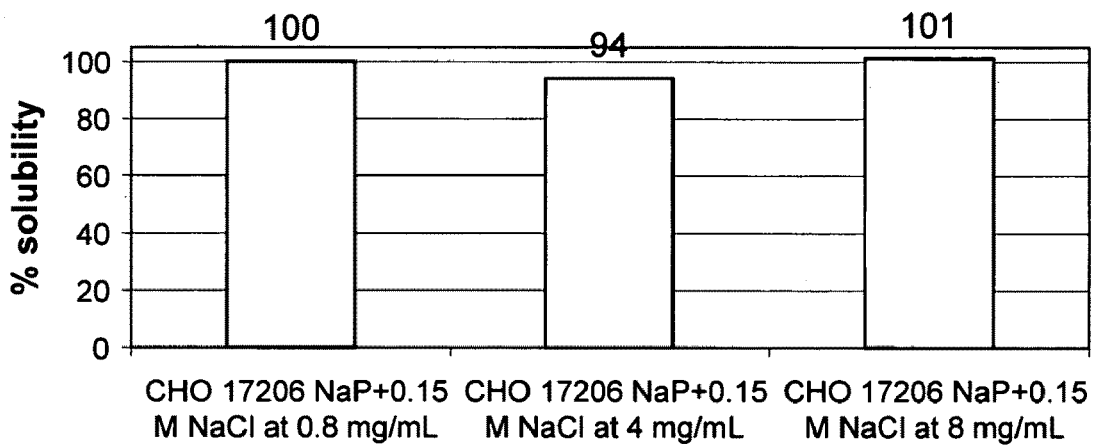
Fig. 17

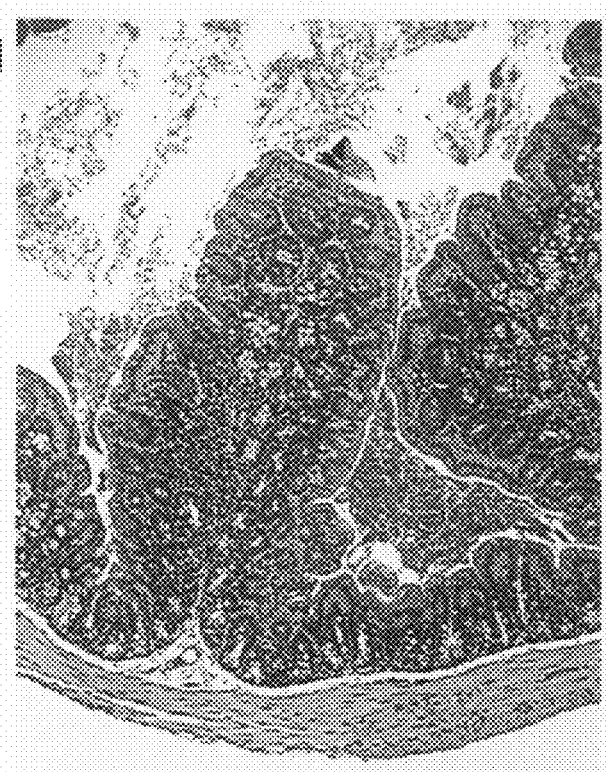
Fig. 21
Intestinal epithelial cell proliferation after GIPF protein injection: colon

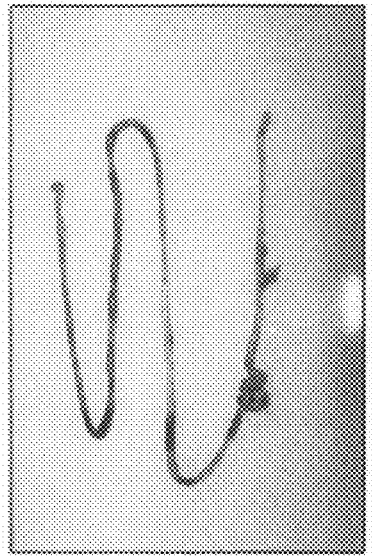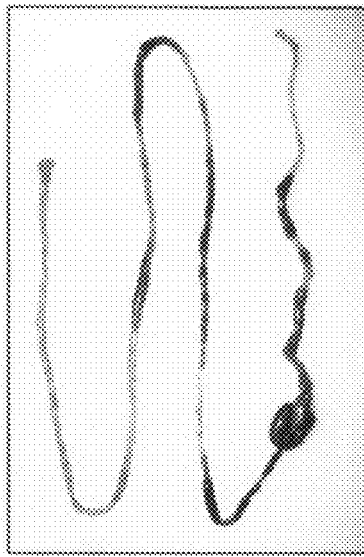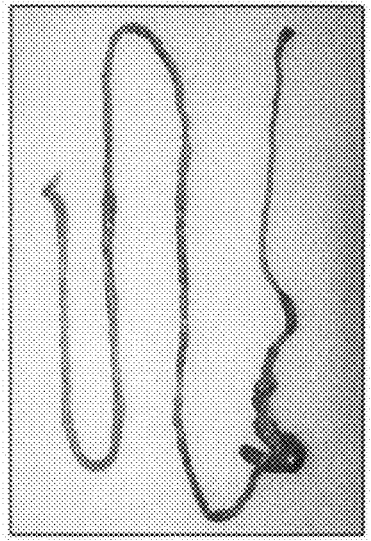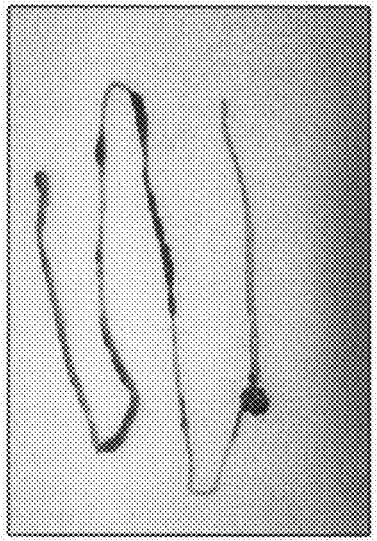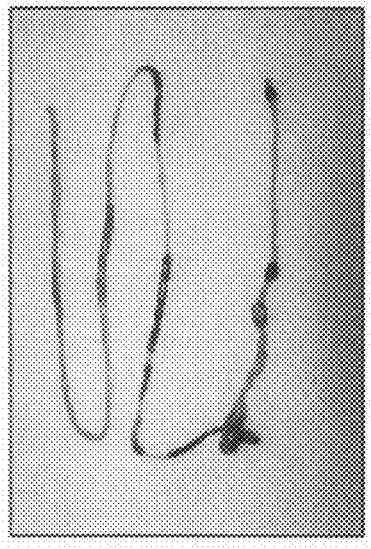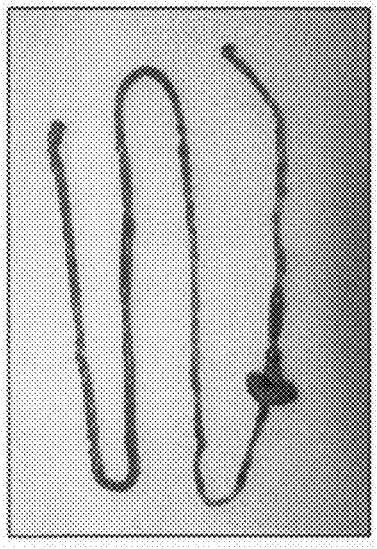
Fig. 25

Fig. 54A
Preparation of Villin promoter long (11.2kb) fragment
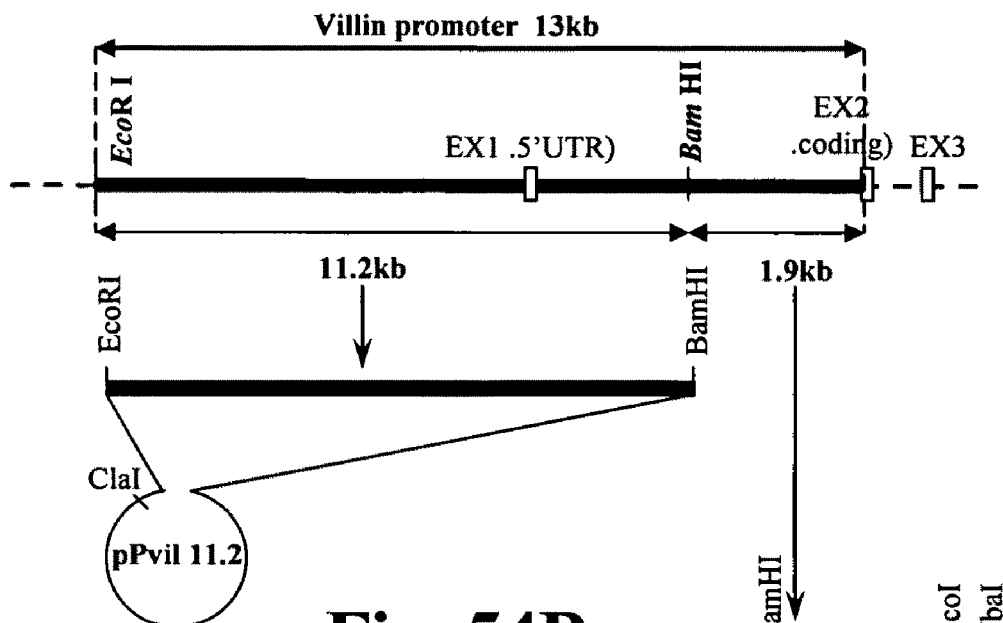
Fig. 54B
Preparation of Villin promoter short (1.9kb) fragment
Fig. 54C
Preparation of GIPF fragment
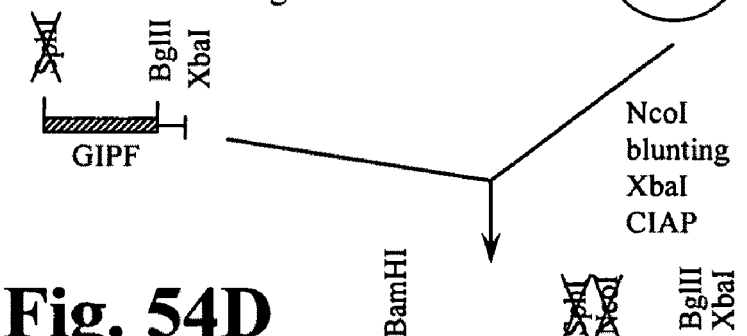
Fig. 54D
Construction of pPvil 2-01
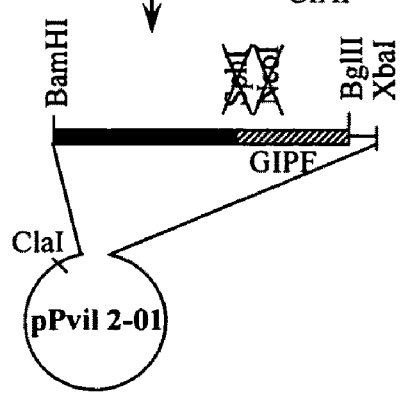

Fig. 54E
Construction of pIRES-GFP
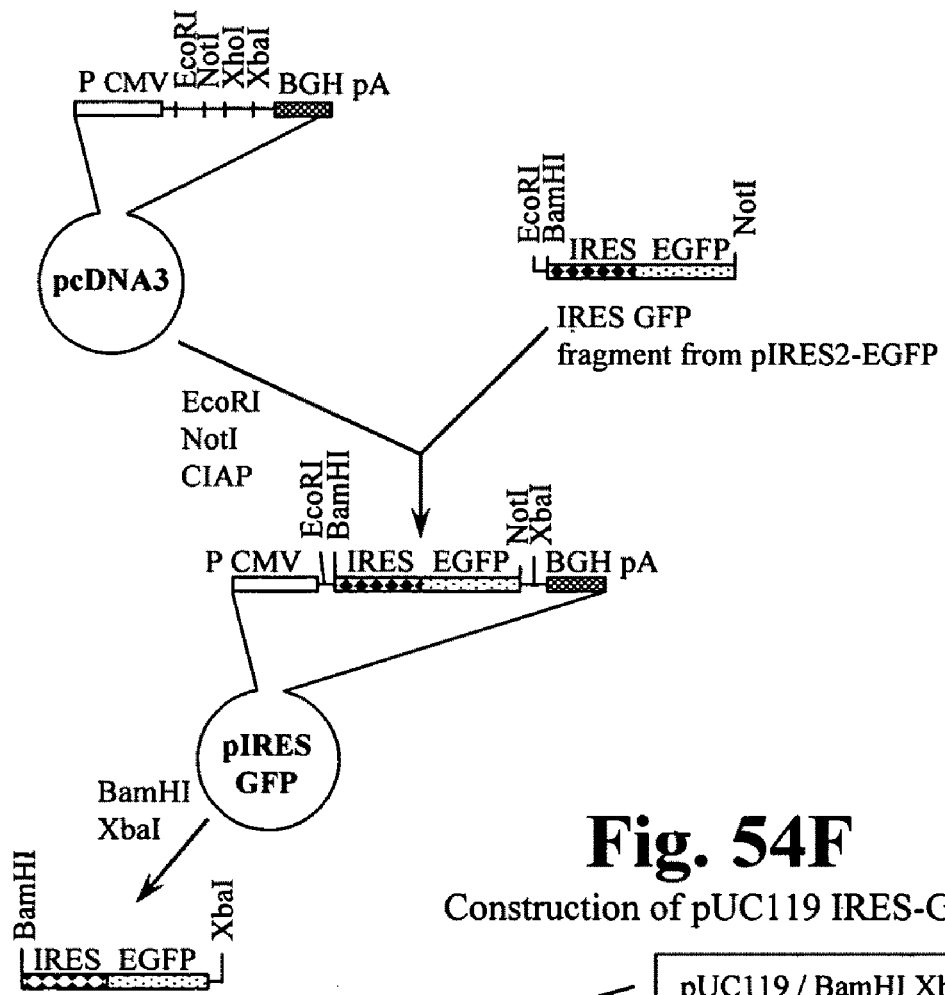
Fig. 54F
Construction of pUC119 IRES-GFP
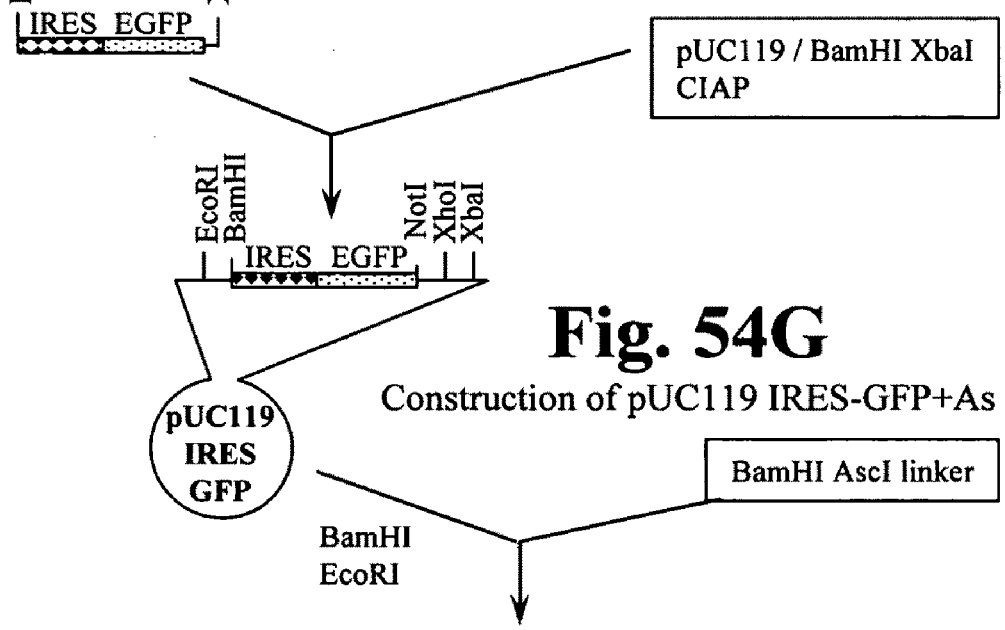
Fig. 54G
Construction of pUC119 IRES-GFP+As Construction of pUC119 IRES-GFP+ loxP Preparation of BGH polyA fragment Preparation of IRES-GFP-pA-loxP fragment.

Construction of pPvil 2-01GFP

Construction of pPv-total

Fig. 54M
Construction of pLoxP-STneoR
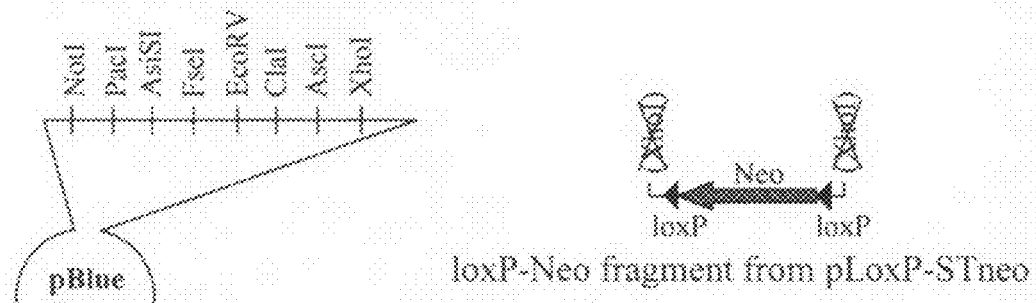
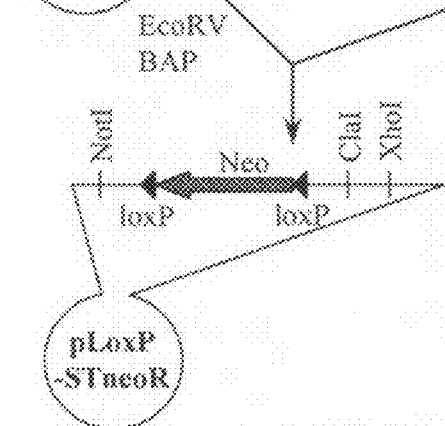
Fig. 54N
Construction of pPv01GFP
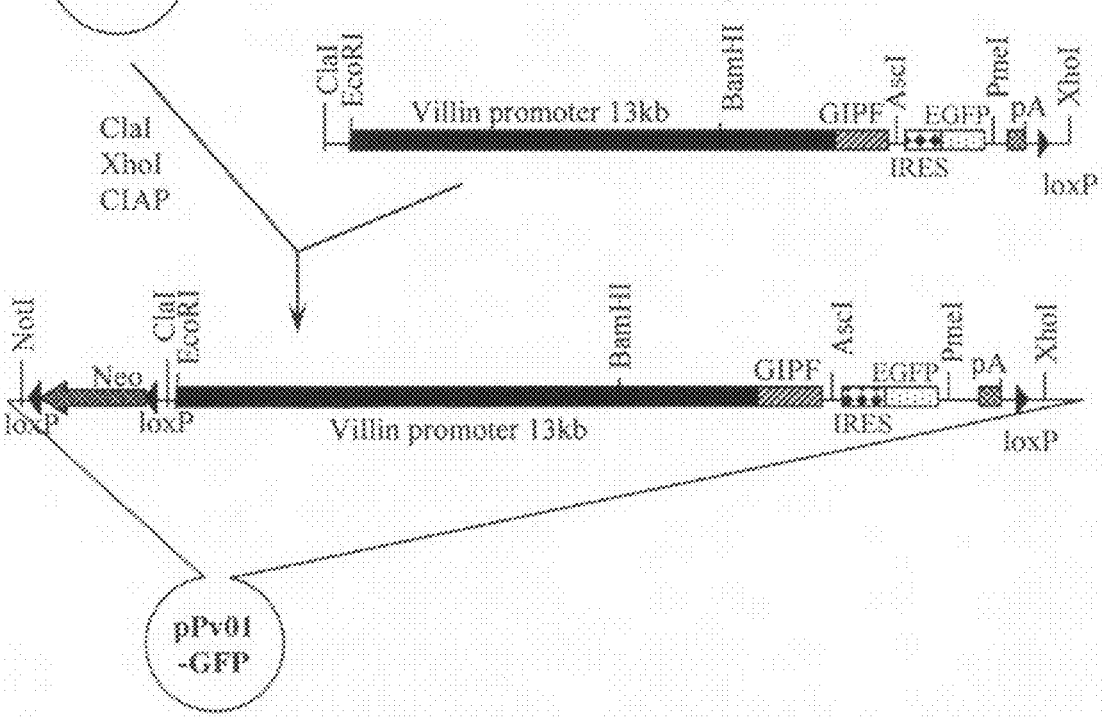

Preparation of Wnt3a fragment

Preparation of IRES-Wnt3a+pA fragment

Construction of pPv01Wnt3a

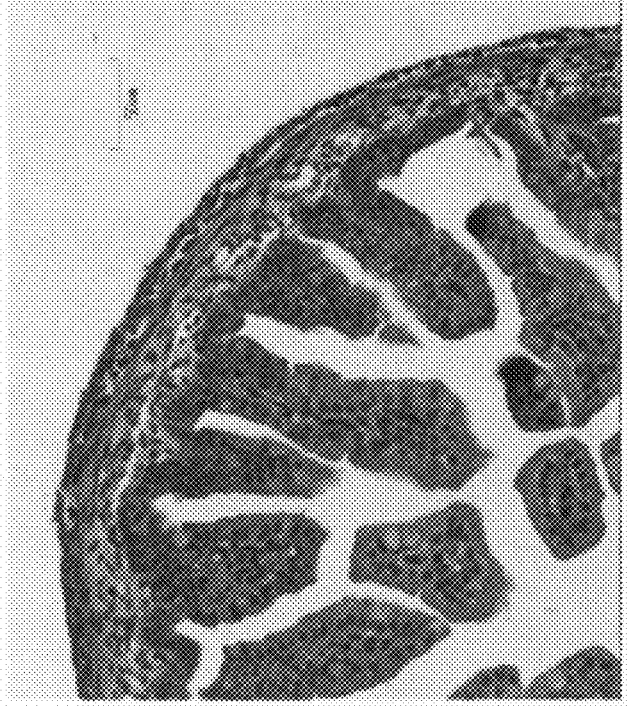
Fig. 61

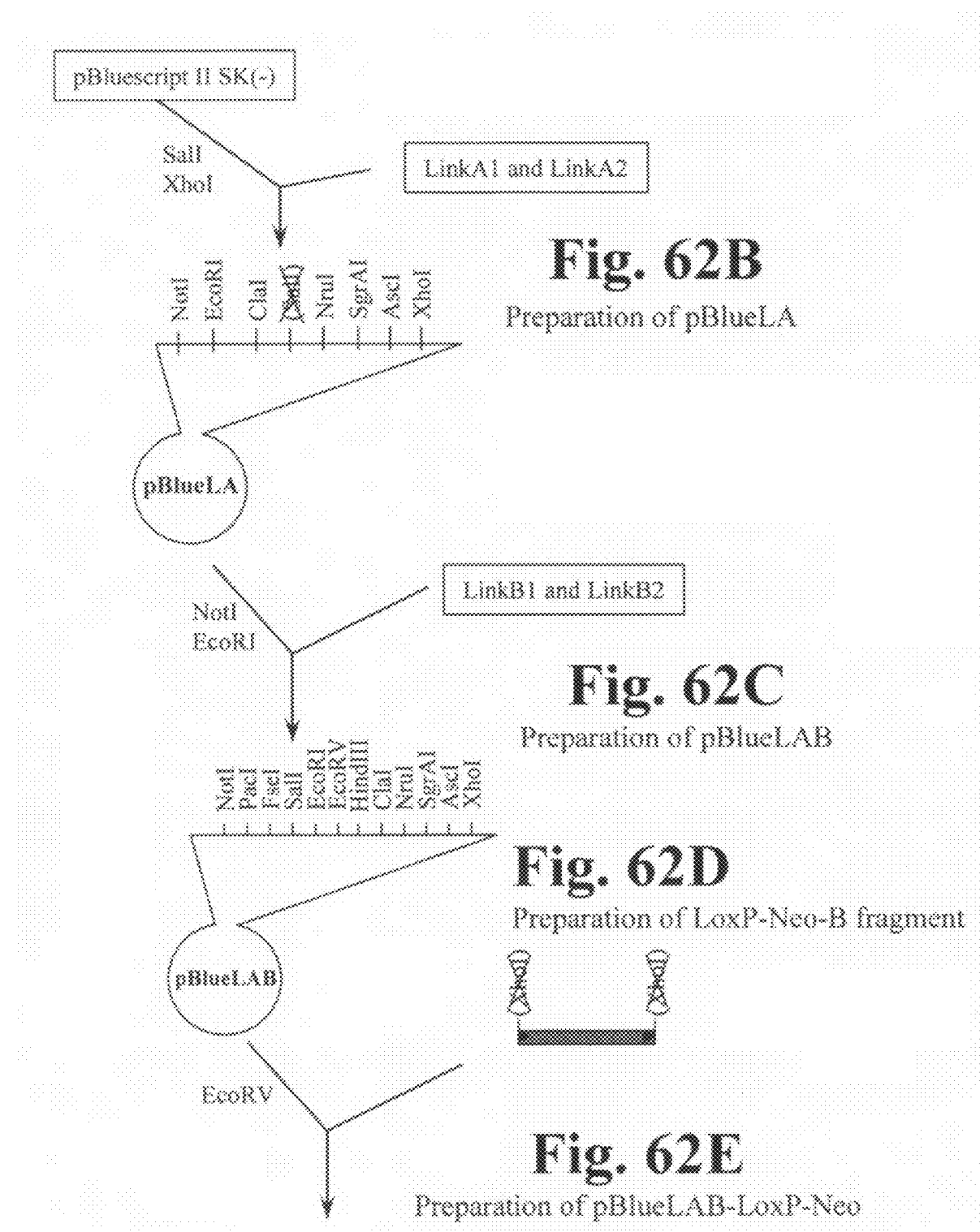

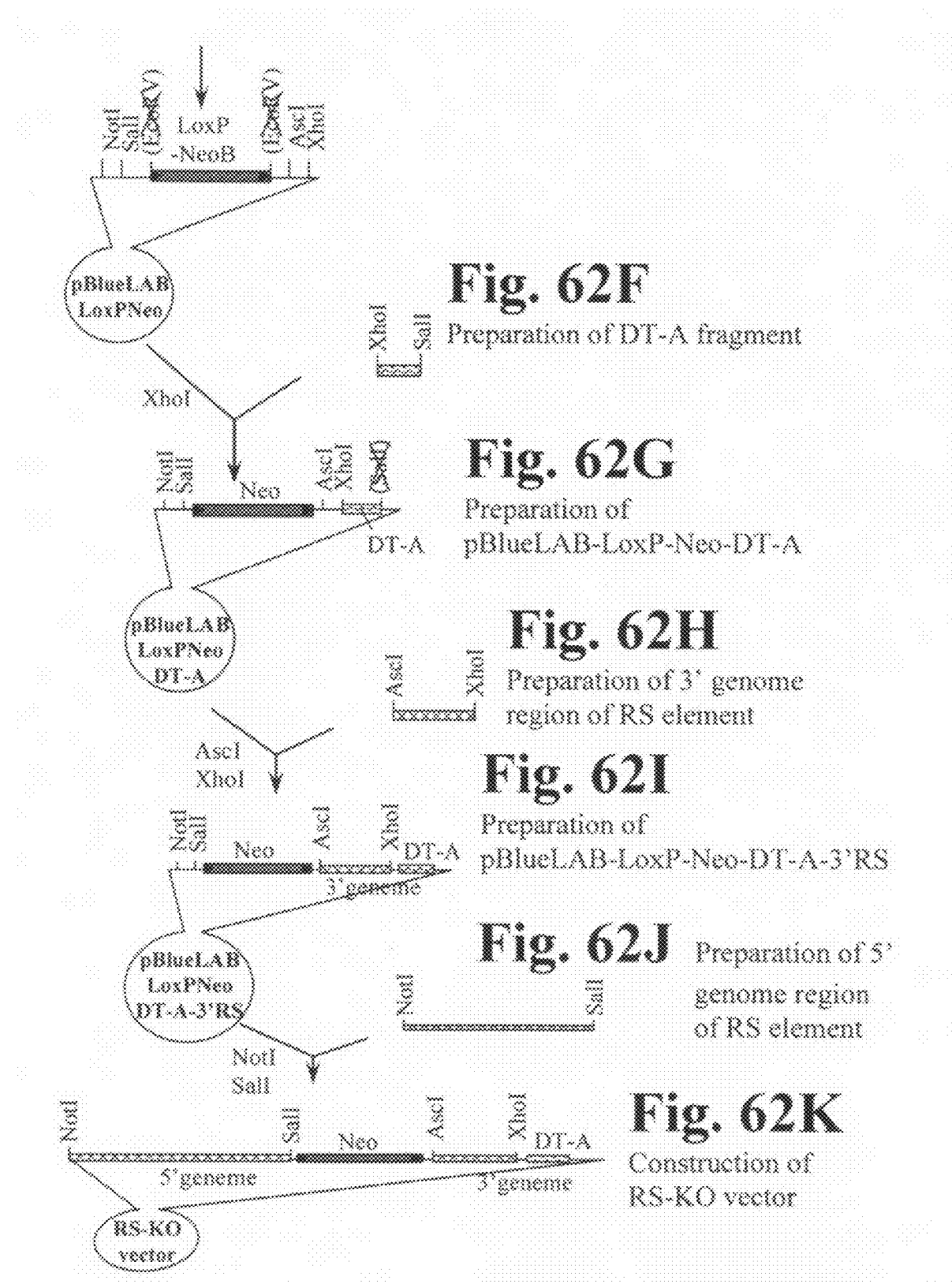

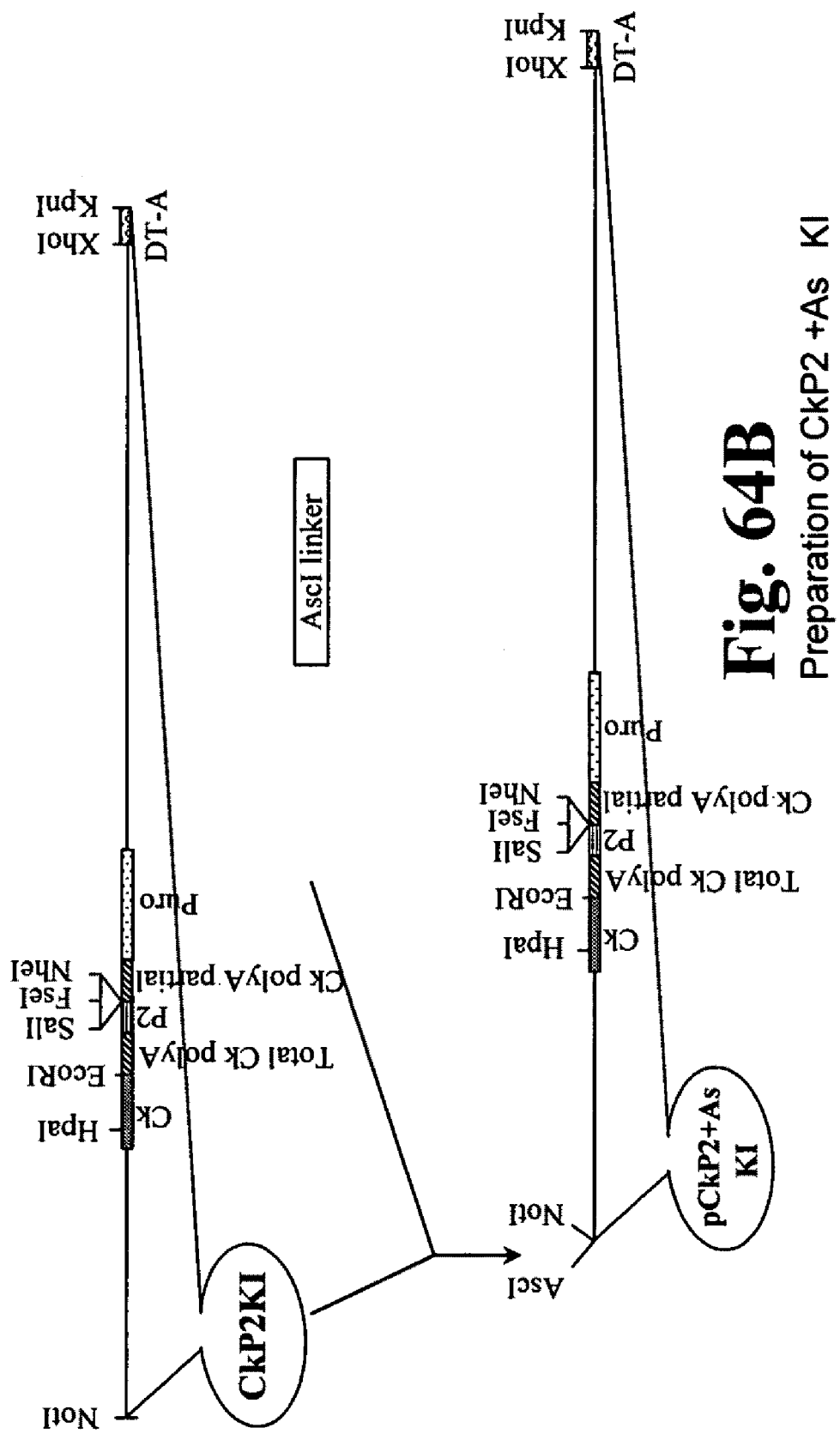
Fig. 64B Preparation of CkP2 +As KI

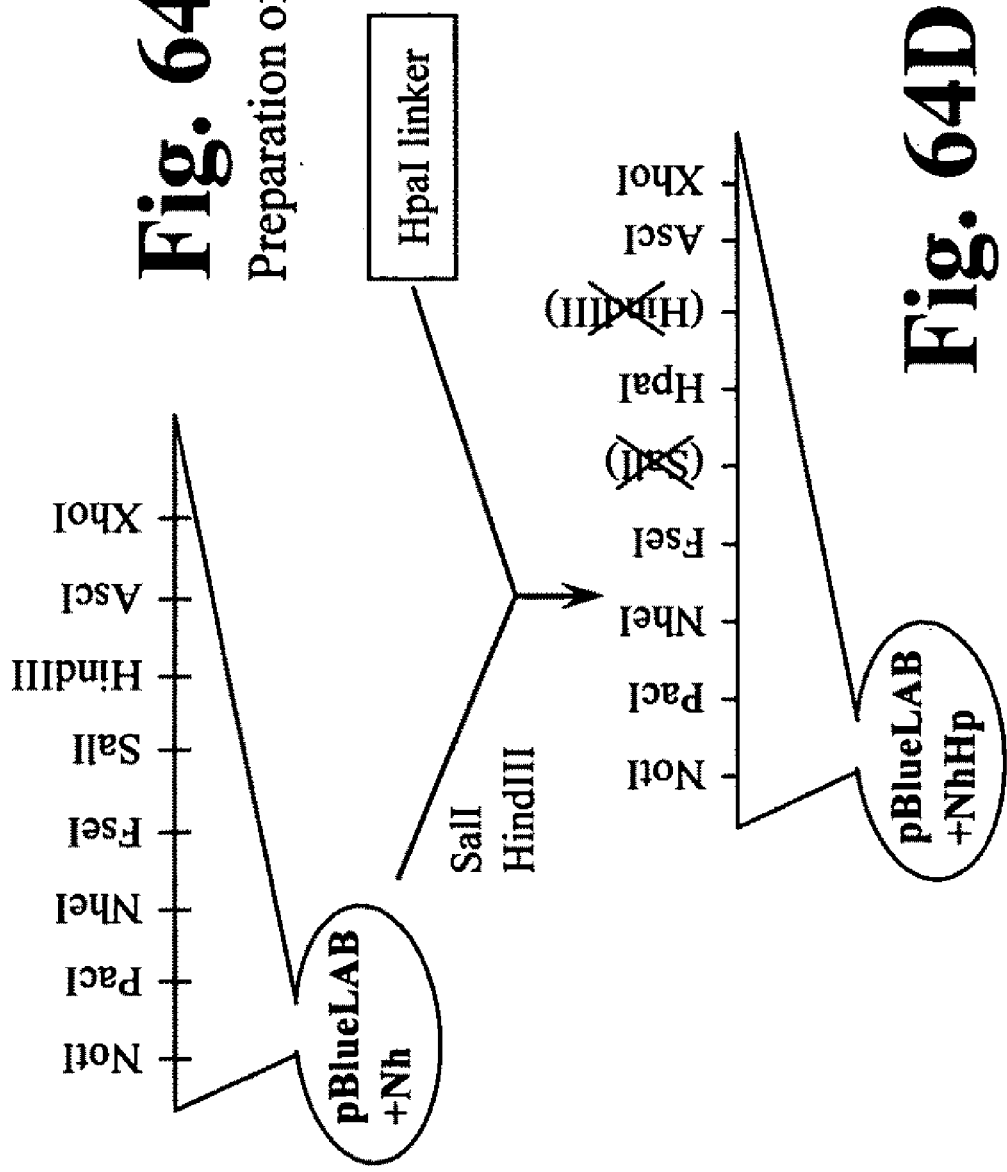

Preparation of pCkpAP2

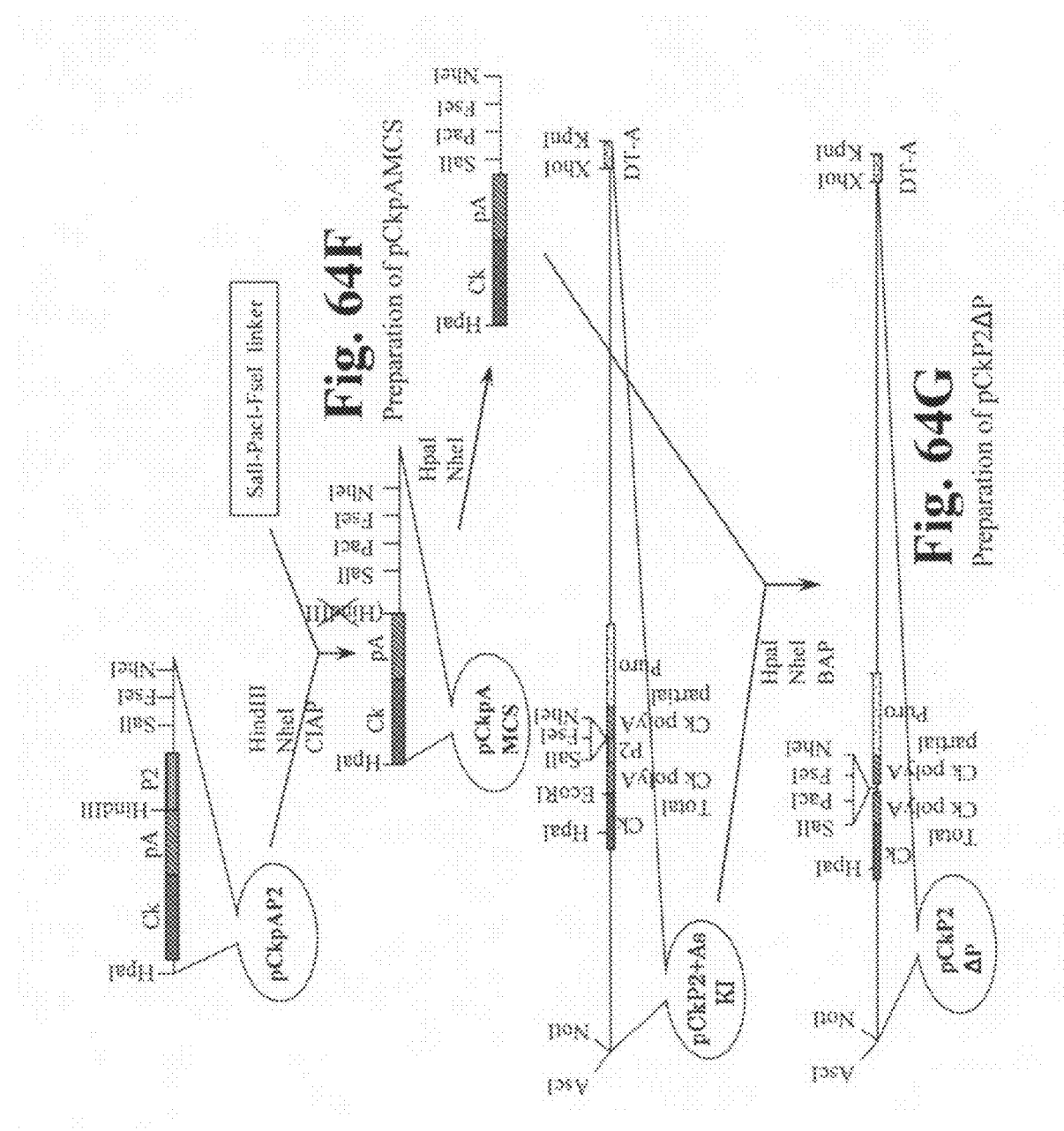

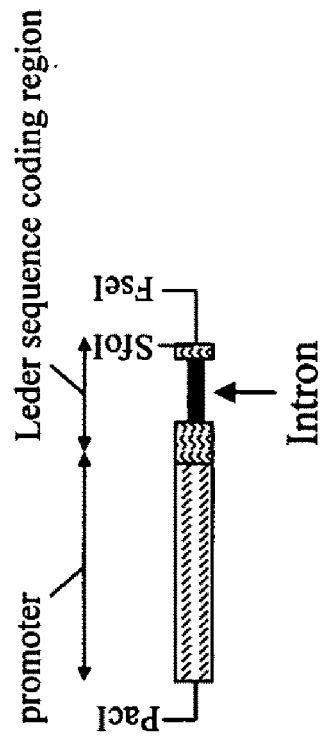
Fig. 64H
Preparation of pBS+PFN
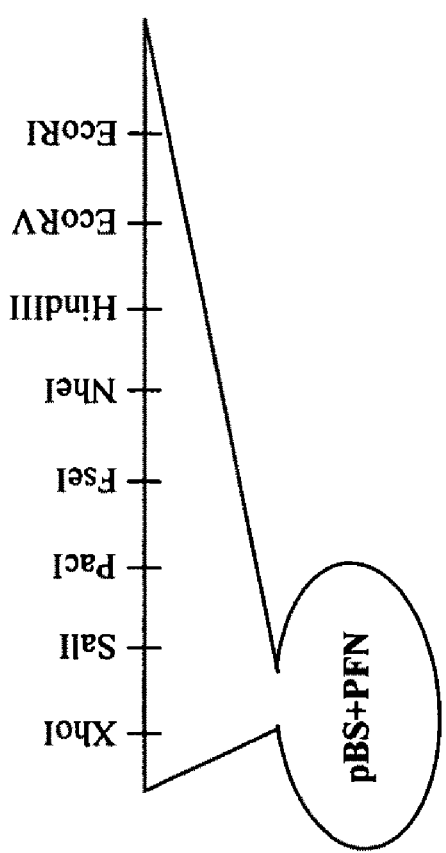
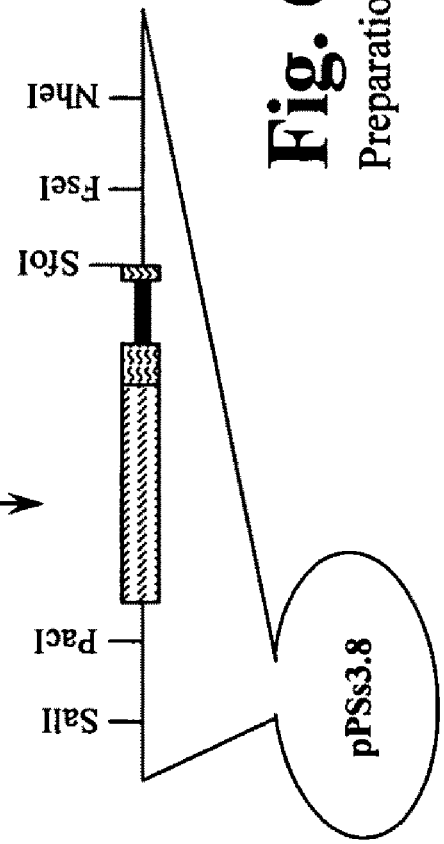
Fig. 64I
Preparation of pPSs3.8

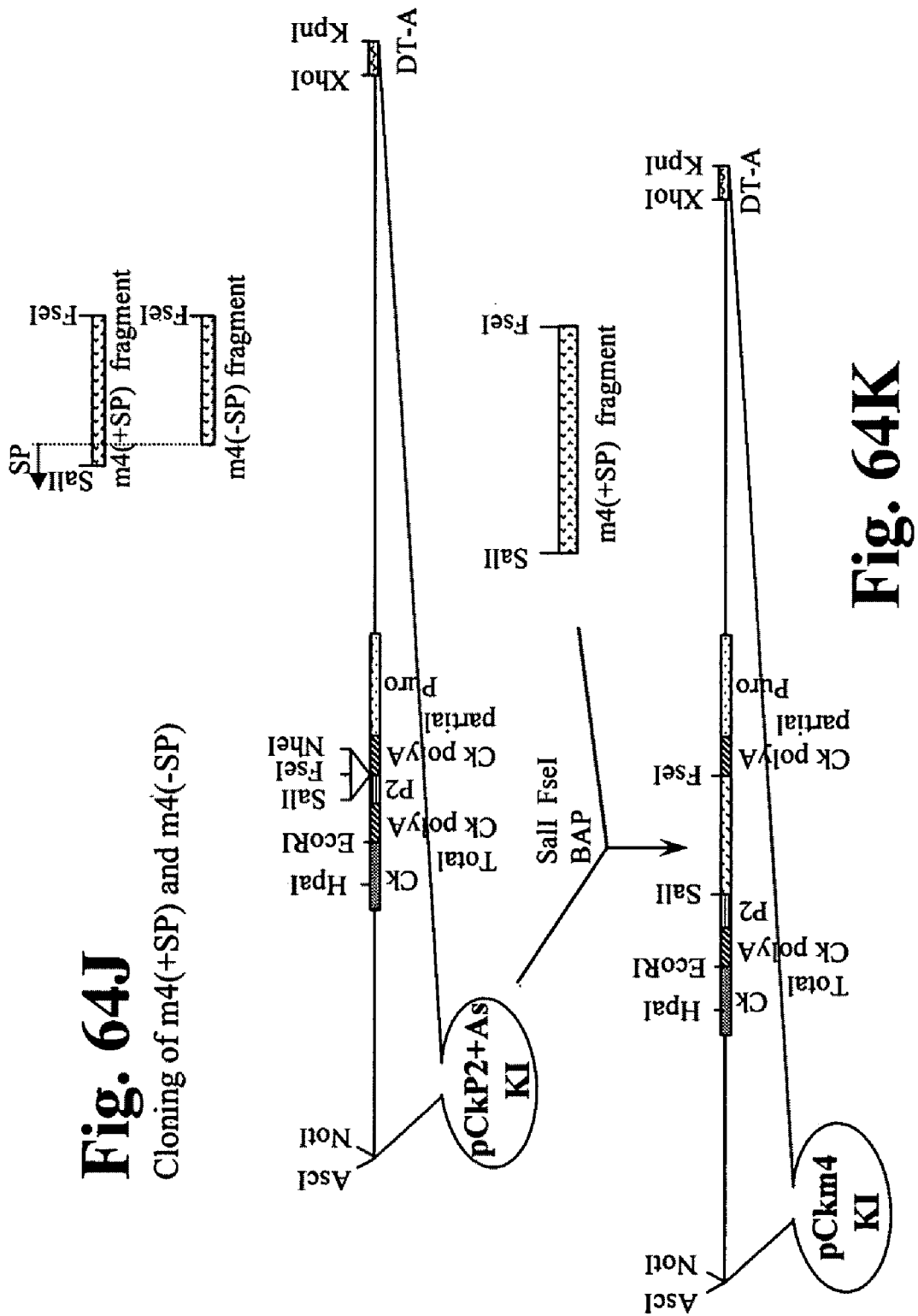

Preparation of pPSs3.8m4

Construction of pPSm4KI

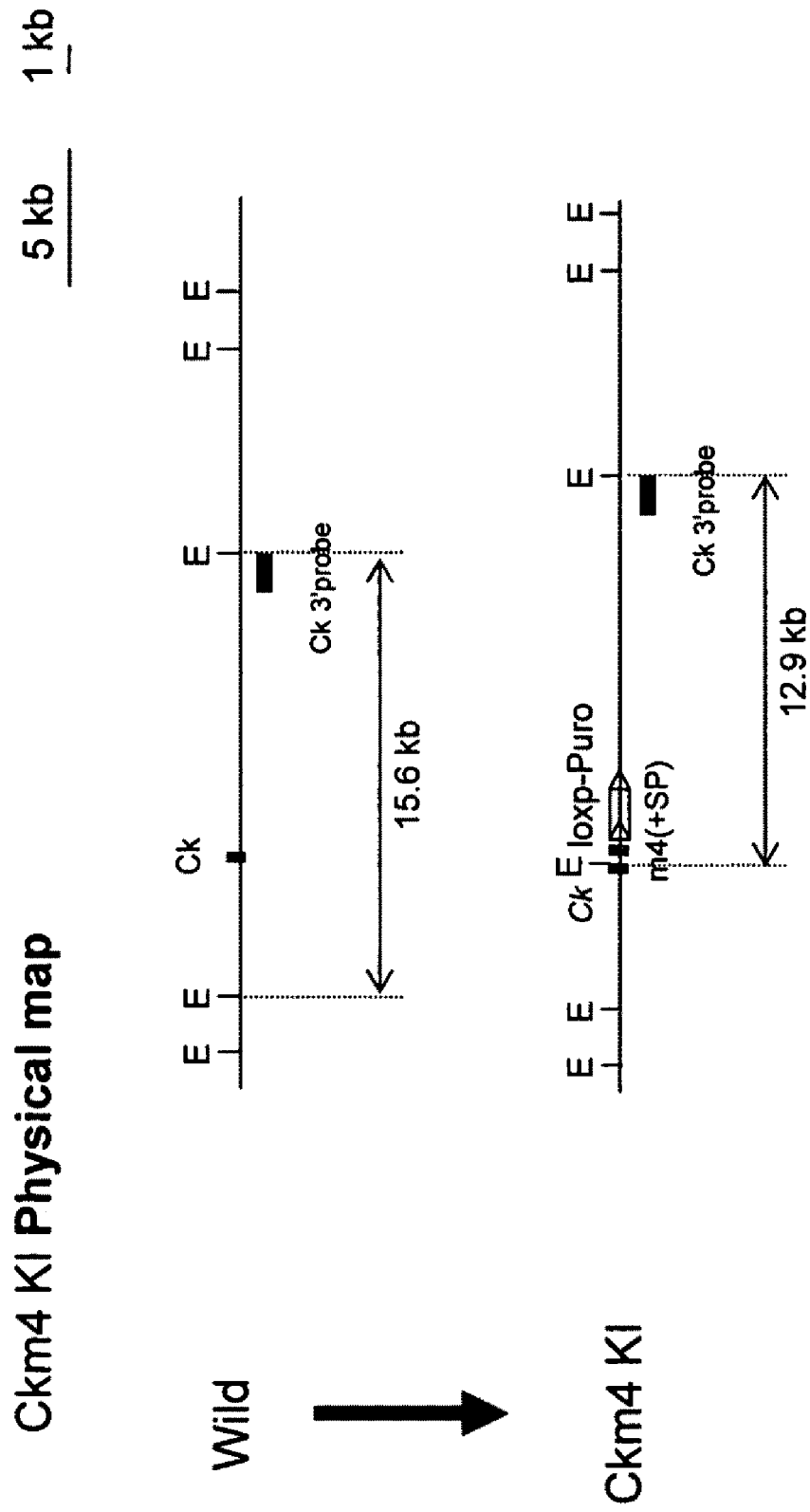

Cloning of VR+kz and VR

Construction of Ck VR KI

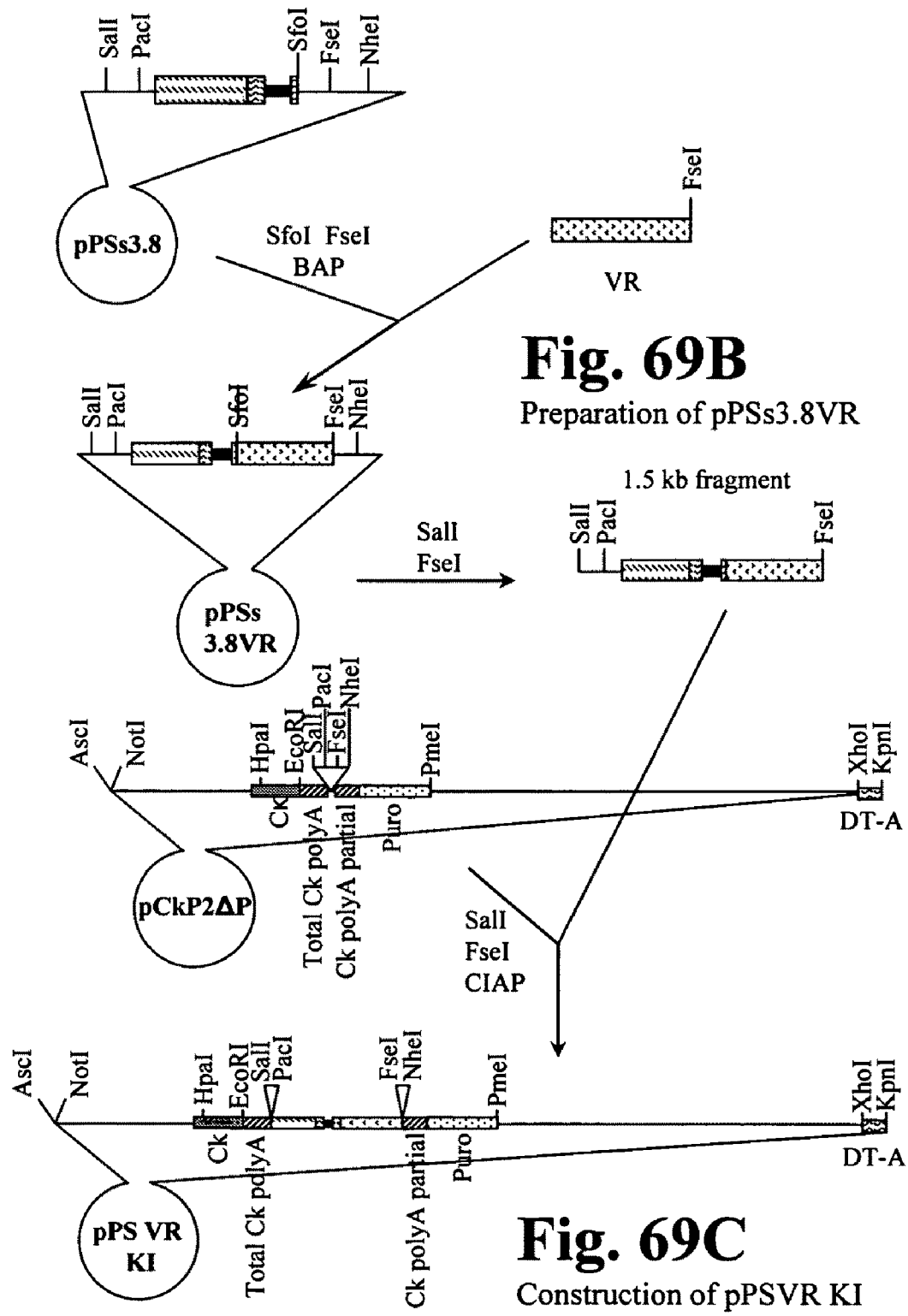

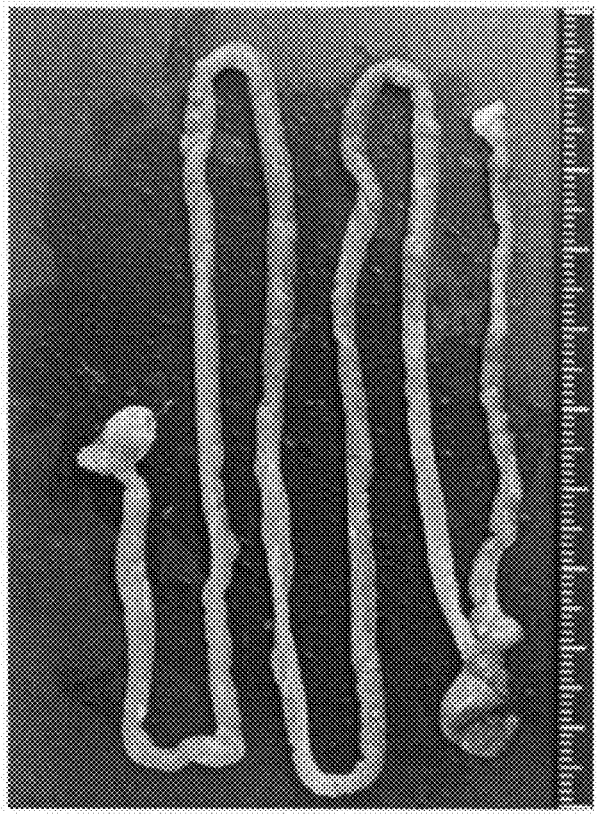
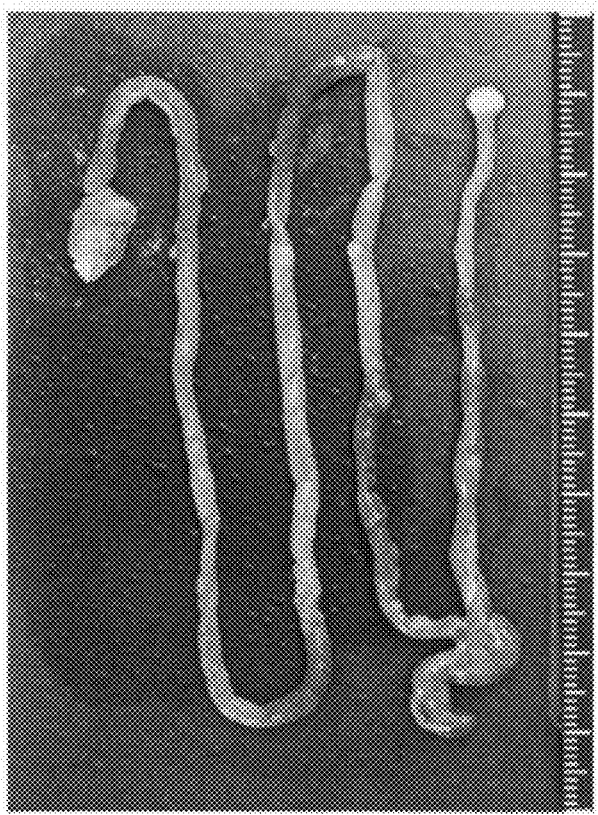
Fig. 76

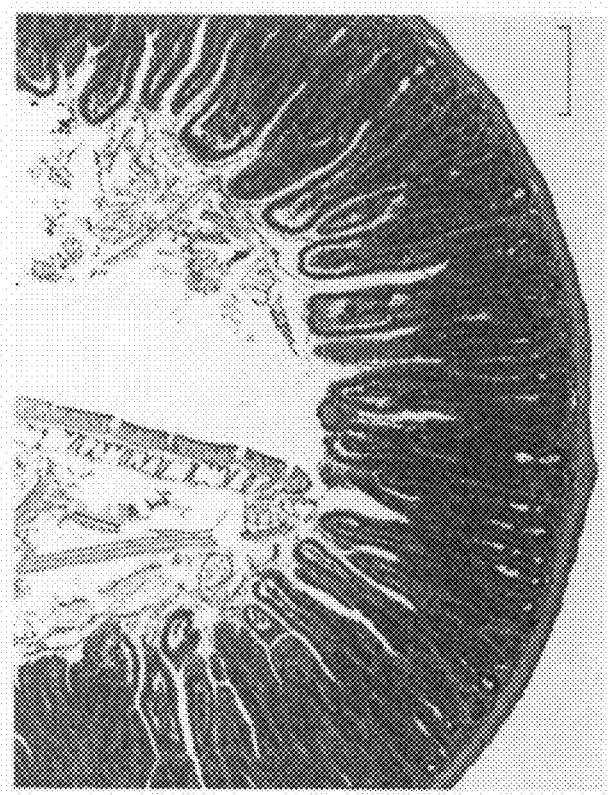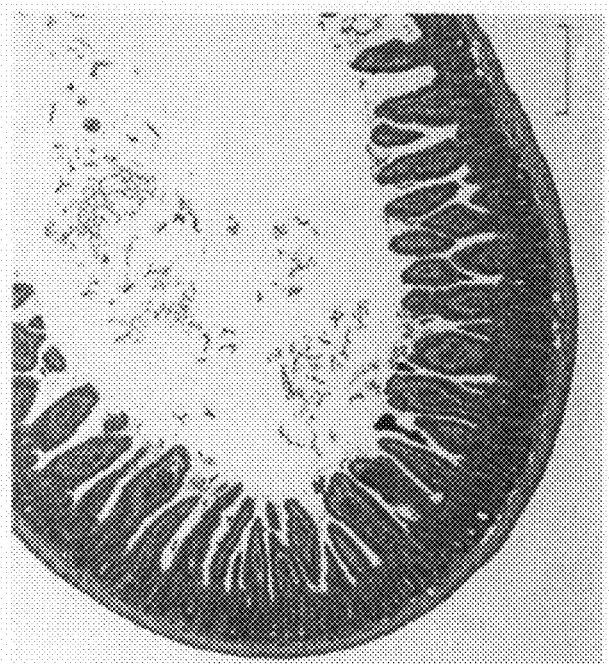
Fig. 77

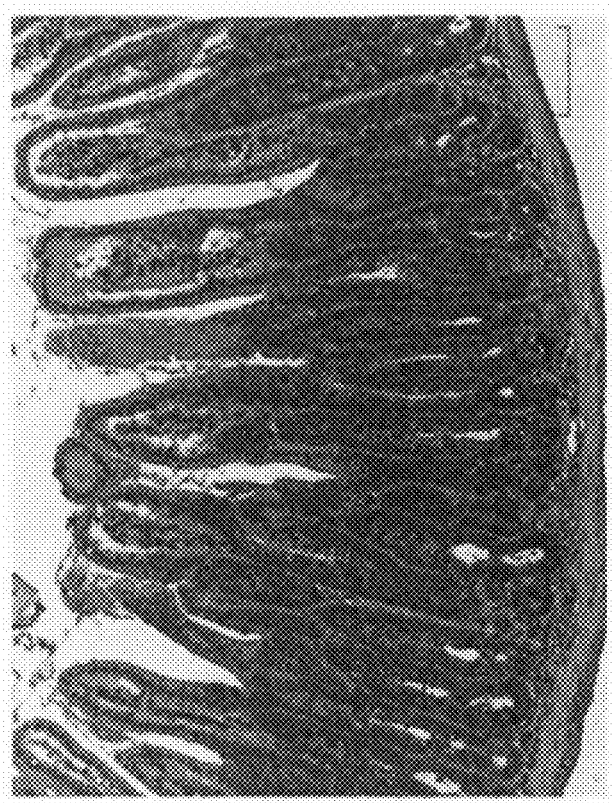
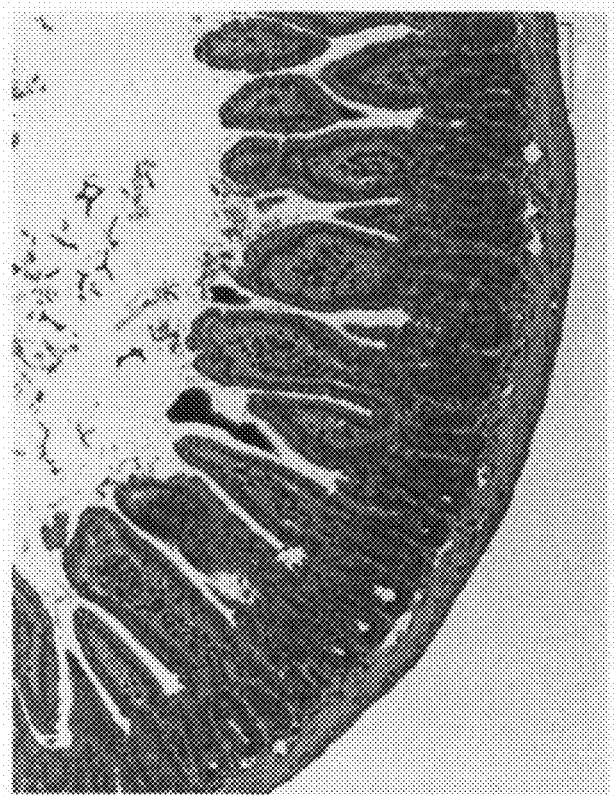
Fig. 78

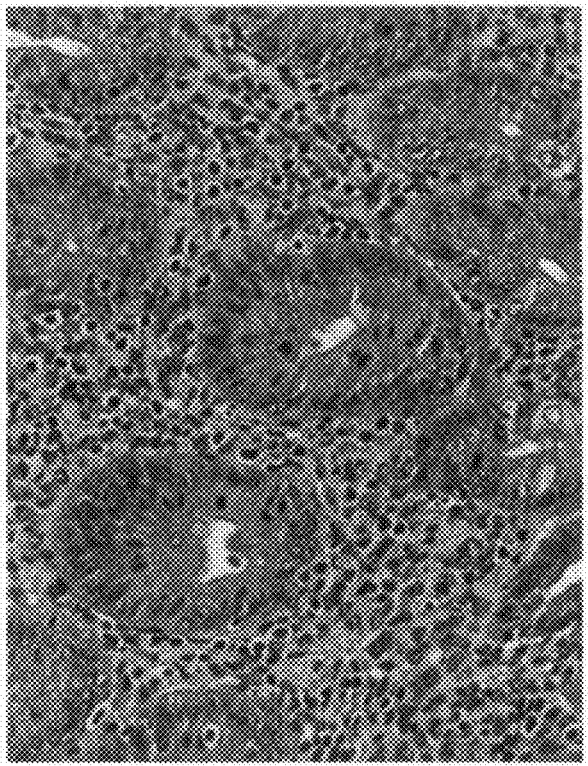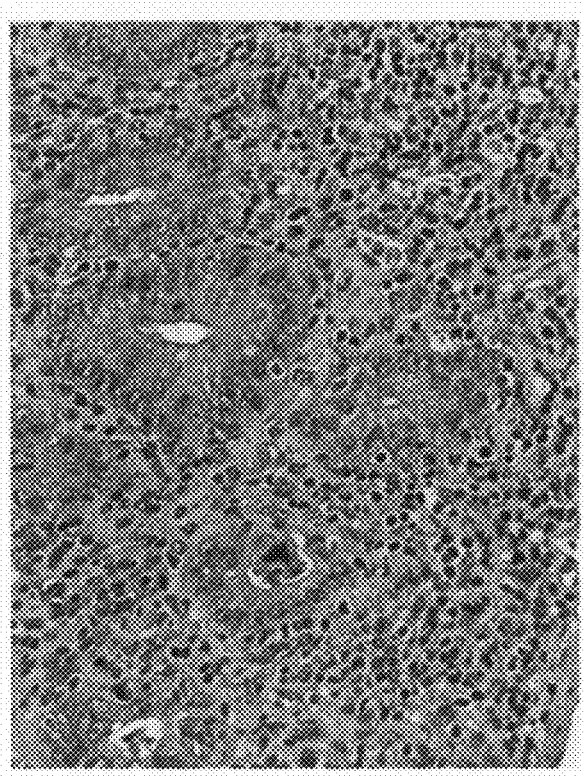
Fig. 80

METHOD OF STIMULATING EPITHELIAL CELL PROLIFERATION BY ADMINISTRATION OF GASTROINTESTINAL PROLIFERATIVE FACTOR

RELATED APPLICATIONS

This application is a continuation of U.S. patent application Ser. No. 11/805,883, filed May 24, 2007 now abandoned, which is a divisional application of U.S. patent application Ser. No. 11/046,644, filed Jan. 27, 2005, now abandoned, from which applications priority is claimed pursuant to 35 U.S.C. §120, and claims benefit under 35 U.S.C. §119(e)(1) of U.S. Provisional Application No. 60/539,605, filed Jan. 27, 2004 and U.S. Provisional Application No. 60/619,241, filed Oct. 15, 2004, which applications are hereby incorporated by reference in their entireties.

1. BACKGROUND

1.1 Field of the Invention

The present invention relates generally to compositions that comprise gastrointestinal proliferation factor polypeptides and polynucleotides, and methods for using the same.

1.2 Sequence Listing

A sequence listing is provided.

1.3 Background

Ionizing radiation therapy and cytotoxic chemotherapy produce injuries to the oral and gastrointestinal mucosa, which remain significant problems for patients undergoing antineoplastic treatments. Mucositis is the inflammation of the mucous membranes and is a particularly common problem in this patient population due to the use of chemotherapy and radiation therapy used with curative or palliative intent. The mucosal injuries to the gastrointestinal tract seen with radiation and chemotherapy (to these areas) include the destruction of crypt cells, a decrease in villous height and ulceration and necrosis of the gastrointestinal epithelium (Berthrong M, World J Surg 10:155-170 (1986)), which underlie disorders including gastrointestinal mucositis and enterocolitis. To the patients this can mean abdominal pain, bloody diarrhea, malabsorption and in some cases bacterial translocation (Guzman et al., J Surg Res 46:104-107 (1989)). In addition, chemotherapy and ionizing radiation can affect other mucous membranes including those of the oropharynx and lips, and those of the esophagus. It is well known that combined modality therapy of concurrent radiation and chemotherapy can produce highly symptomatic stomatitis in patients with head and neck cancer, and esophagitis in patients with small cell lung cancer.

Chemotherapy and radiation therapy cause injury to the oral and gastrointestinal mucosa through direct and indirect toxicity. The mechanism for direct mucositis is nonspecific cell killing of rapidly dividing basal epithelial cells that results in epithelial thinning, inflammation, decreased cell renewal, and ultimately ulceration. These painful lesions also produce an increased risk for local and systemic infection. Indirect mucotoxicity is a byproduct of chemotherapy-induced myelosuppression, which permits bacterial and viral infections at the site of direct mucosal injury. The severity of these effects may preclude dose escalation, delay treatment, and warrant dose reductions, thus limiting the effectiveness of cancer therapy.

Prophylaxis and therapy for chemotherapy and radiation therapy-induced (mucosal) gastrointestinal injuries (mucositis) commonly entails prescription of suboptimal doses of chemotherapy or radiotherapy, a downward dose modification in subsequent treatment courses following toxicity, or the use of specific antidotes such as leucovorin after moderate-dose or high-dose methotrexate (Allegra C J. Antifolates. In: Chabner and Collins, eds. Cancer Chemotherapy: Principles and Practice. Philadelphia, Pa. JP Lippincoft Co; 1990:110-153.)

Injury to the gastrointestinal mucosa is also associated with chronic inflammatory disorders of the gastrointestinal tract, which are collectively referred to as inflammatory bowel disease. Cytokine-based therapies are available for the treatment of inflammatory bowel disease (Bouma and Strober Nature Rev 3:521-533 (2003)). However, resection of the small intestine is often indicated in patients with inflammatory bowel disease such as Crohn's disease. Surgical resection of the small intestine may also be necessary following traumatic injury, vascular accidents, and cancer. Surgical resection that leaves less than 200 cm of viable small bowel places a patient at risk for developing short-bowel syndrome (SBS). SBS is a disorder that is clinically defined by malabsorption, diarrhea, fluid and electrolyte disturbances, and malnutrition. The management of patients with SBS frequently requires long-term, if not life long use of parenteral nutrition (DiBaise et al., Am J Gastroenterol 99:1823-1832 (2004)).

Thus, there is a need to find agents that may be used prophylactically or therapeutically to increase the tolerance to antineoplastic treatments, to advance current therapies for treating inflammatory bowel disease, and to restore the digestive and absorptive processes that are compromised following surgical resection of the intestine.

2. SUMMARY OF THE INVENTION

The present invention is based, in part, on the discovery that GastroIntestinal Proliferative Factor (GIPF) induces the proliferation of epithelial cells of the gastrointestinal tract. Thus, compositions comprising GIPF, fragments or analogs thereof, may be used for the treatment of conditions where epithelialization is desirable, such as for the treatment of gastrointestinal disorders including chemotherapy and radiation therapy-induced mucositis, mucositis of the oropharynx, lips and esophagus, inflammatory bowel disease, and other conditions including wounds, burns, ophthalmic disorders, and any disorder where stimulation of epithelial cell proliferation or regeneration is desired.

Accordingly, in one embodiment, the invention is directed to a composition comprising a therapeutically effective amount of a GIPF polypeptide and a pharmaceutically acceptable carrier.

The compositions of the present invention include isolated polynucleotides encoding GIPF polypeptides, including recombinant DNA molecules, and cloned genes or degenerate variants thereof, especially naturally occurring variants such as allelic variants. Specifically, the polynucleotides of the present invention are based on a GIPF polynucleotide isolated from a cDNA library prepared from human fetal skin mRNA (SEQ ID NO: 2).

The compositions of the present invention also include vectors such as expression vectors containing the polynucleotides of the invention, cells genetically engineered to contain such polynucleotides and cells genetically engineered to express such polynucleotides.

The compositions of the invention comprise isolated polynucleotides that include, but are not limited to, a GIPF polynucleotide, a fragment, or variant thereof; a polynucleotide comprising the full length protein coding sequence of SEQ ID NO: 2 or 3 (for example, SEQ ID NO: 4; GIPFwt); a polynucleotide comprising the V5-His-tagged protein coding sequence of SEQ ID NO: 5 (for example SEQ ID NO: 6; GIPFt); a polynucleotide comprising the nucleotide sequence of the dominant mature protein coding sequence of SEQ ID NO: 9 (for example SEQ ID NO: 10); a polynucleotide comprising the nucleotide sequence of the mature protein coding sequence of SEQ ID NO: 11 (for example SEQ ID NO: 12); a polynucleotide comprising the nucleotide sequence of the thrombospondin domain of SEQ ID NO: 13 (for example SEQ ID NO: 14); a polynucleotide of SEQ ID NO: 15 comprising the nucleotide sequence that encodes a dominant mature protein sequence that lacks the furin cleavage site (for example SEQ ID NO: 16); the polynucleotide of SEQ ID NO: 17 comprising the nucleotide sequence that encodes a GIPF polypeptide that comprises a mutated furin cleavage site (SEQ ID NO: 18); and polynucleotides that encode GIPF polypeptides that comprise varying lengths of the full-length GIPF (SEQ ID NOs: 84, 86, 88, 90, 92, 94, 96, 98, 100, 102, 104 and 177). The polynucleotide compositions of the present invention also include, but are not limited to, a polynucleotide that hybridizes under stringent hybridization conditions to (a) the complement of any of the nucleotide sequences set forth in SEQ ID NO: 2, 3, 5, 9, 11, 13, 15, 17, 84, 86, 88, 90, 92, 94, 96, 98, 100, 102, 104 or 177; (b) a nucleotide sequence encoding any of SEQ ID NO: 4, 6, 8, 10, 12, 14, 16, 18, 85, 87, 89, 91, 93, 95, 97, 99, 101, 103, 105 or 178; a polynucleotide which is an variant (e.g., an allelic variant) of any polynucleotides recited above having at least 70% (e.g., 75%, 80%, 85%, 90%, 92%, 94%, 96%, 98%, or 99%) polynucleotide sequence identity to the polynucleotides; a polynucleotide which encodes a species homolog (e.g., an ortholog) of any of the polypeptides recited above; or a polynucleotide that encodes a polypeptide comprising a specific domain or truncation of the polypeptide of SEQ ID NO: 4 or 6.

This invention further provides cloning or expression vectors comprising at least a fragment of the polynucleotides set forth above and host cells or organisms transformed with these expression vectors. Useful vectors include plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The pharmaceutical compositions of the present invention include polypeptides comprising, but not limited to, an isolated polypeptide selected from the group comprising the amino acid sequence of SEQ ID NO: 4, 6, 10, 12, 14, 16, 18, 85, 87, 89, 91, 93, 95, 97, 99, 101, 103, 105 or 178. Polypeptides of the invention also include polypeptides with biological activity that are encoded by (a) any of the polynucleotides having a nucleotide sequence set forth in the SEQ ID NO: 2, 3, 5, 9, 11, 13, 15, 17, 84, 86, 88, 90, 92, 94, 96, 98, 100, 102, 104, 177 above; or (b) polynucleotides that hybridize to the complement of the polynucleotides of (a) under stringent hybridization conditions. Biologically or immunologically active analogs of any of the protein sequences listed as SEQ ID NO: 4, 6, 10, 12, 14, 16, 18, 85, 87, 89, 91, 93, 95, 97, 99, 101, 103, 105 or 178, and substantial equivalents thereof that retain biological are also contemplated. The polypeptides of the invention may be wholly or partially chemically synthesized but are preferably produced by recombinant means using the genetically engineered cells (e.g. host cells) of the invention. The invention includes polypeptides that are at least 85%, 90%, 92%, 94%, 96%, 98%, or 99% identical to any of SEQ ID NO: 4, 6, 10, 12, 14, 16, 18, 85, 87, 89, 91, 93, 95, 97, 99, 101, 103, 105 and 178. The invention also includes polypeptides that differ in sequence from any of SEQ ID NO: 4, 6, 10, 12, 14, 16, 18, 85, 87, 89, 91, 93, 95, 97, 99, 101, 103, 105 and 178 and at 20, 15, 10, 9, 8, 7, 6, 5, 4, 3, 2 or 1 amino acid residues. The amino acid changes can be conservative or non-conservative.

The invention also relates to methods for producing a GIPF polypeptide comprising culturing host cells comprising an expression vector containing at least a fragment of a GIPF polynucleotide encoding the GIPF polypeptide of the invention in a suitable culture medium under conditions permitting expression of the desired polypeptide, and purifying the protein or peptide from the culture or from the host cells. Preferred embodiments include those in which the protein produced by such a process is a mature or dominant mature form of the protein.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantifying the polypeptide in tissue.

In further embodiments, the subject invention is directed to a method of stimulating epithelial cell proliferation. The method comprises contacting epithelial cells with a composition that includes a therapeutically effective amount of a GIPF polypeptide, fragment or analog thereof, and a pharmaceutically acceptable carrier. Specifically, a subject in need of stimulation (including cytoprotection, proliferation and/or differentiation) of epithelial cells will be administered therapeutically-effective or prophylactically-effective amounts of GIPF protein, fragments or analogs thereof.

In all the methods described, epithelial cells may be contacted with the GIPF polypeptides in vitro or in vivo.

Methods are also provided for preventing, treating, or ameliorating a medical condition which comprises the step of administering to a mammalian subject a therapeutically effective amount of a composition comprising a peptide of the present invention and a pharmaceutically acceptable carrier.

In particular, the GIPF polypeptides of the invention may be used to induce the proliferation and/or differentiation of gastrointestinal crypt cells to regenerate the epithelial layer of the alimentary tract. Thus, the GIPF polypeptides and polynucleotides of the invention may be used in the treatment of chemotherapy or radiation therapy-induced mucositis and enterocolitis, and inflammatory bowel disease. They may also be used in the treatment of diseases, and other conditions including wounds, burns, ophthalmic disorders, and any disorder where stimulation of epithelial cell proliferation or regeneration is desired.

Polynucleotides and polypeptides of the invention may also be used as markers of differentiation and development of gastrointestinal epithelium.

The methods of the invention also provide methods for the treatment of disorders as recited herein which comprise the administration of a therapeutically effective amount of a composition comprising a polynucleotide or polypeptide of the invention and a pharmaceutically acceptable carrier to a mammalian subject exhibiting symptoms or tendencies related to disorders as recited herein. In addition, the invention encompasses methods for treating diseases or disorders as recited herein comprising the step of administering a composition comprising compounds and other substances that modulate the overall activity of the target gene products and a pharmaceutically acceptable carrier. Compounds and other substances can effect such modulation either on the level of target gene/protein expression or target protein activity. Specifically, methods are provided for preventing, treating or ameliorating a medical condition, including mucositis and inflammatory bowel disease, wounds, which comprises administering to a mammalian subject, including but not limited to humans, a therapeutically effective amount of a composition comprising a polypeptide of the invention or a therapeutically effective amount of a composition comprising a binding partner of GIPF polypeptides of the invention. The mechanics of the particular condition or pathology will dictate whether the polypeptides of the invention or binding partners of these would be beneficial to the individual in need of treatment.

The invention further provides methods for manufacturing medicaments useful in the above-described methods.

The present invention further relates to methods for detecting the presence of the polynucleotides or polypeptides of the invention in a sample (e.g., tissue or sample). Such methods can, for example, be utilized as part of prognostic and diagnostic evaluation of disorders as recited herein and for the identification of subjects exhibiting a predisposition to such conditions.

The invention provides a method for detecting a polypeptide of the invention in a sample comprising contacting the sample with a compound that binds to and forms a complex with the polypeptide under conditions and for a period sufficient to form the complex and detecting formation of the complex, so that if a complex is formed, the polypeptide is detected.

The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can enhance the therapeutic activity of the GIPF polypeptides, and ameliorate symptoms of disorders as recited herein. Such methods can include, but are not limited to, assays for identifying compounds and other substances that interact with (e.g., bind to) the polypeptides of the invention.

The invention provides a method for identifying a compound that binds to the polypeptide of the present invention comprising contacting the compound with the polypeptide under conditions and for a time sufficient to form a polypeptide/compound complex and detecting the complex, so that if the polypeptide/compound complex is detected, a compound that binds to the polypeptide is identified.

Also provided is a method for identifying a compound that binds to the polypeptide comprising contacting the compound with the polypeptide in a cell for a time sufficient to form a polypeptide/compound complex wherein the complex drives expression of a reporter gene sequence in the cell and detecting the complex by detecting reporter gene sequence expression so that if the polypeptide/compound complex is detected a compound that binds to the polypeptide is identified.

Another embodiment of the invention provides gene therapy by delivery of GIPF polypeptides for the treatment of conditions or disorders recited herein.

In a related embodiment, the invention is directed to use of a vector comprising a gene encoding a GIPF polypeptide operably associated with an expression control sequence that provides for expression of the GIPF polypeptide in the manufacture of a medicament for treating disorders as recited herein. More particularly, the invention provides for use of an adenoviral vector of the invention, e.g., as set out below, in the manufacture of a medicament for treating mucositis or inflammatory bowel disease.

In addition to the foregoing methods and uses, the invention provides a novel virus vector comprising a gene encoding a GIPF polypeptide operably associated with an expression control sequence. In a preferred embodiment, the virus vector is an adenovirus vector. The virus vectors of the invention can provide a gene encoding any GIPF polypeptide, as set forth above.

The invention further provides a pharmaceutical composition comprising any of the virus vectors of the invention and a pharmaceutically acceptable carrier.

In yet another aspect, the invention concerns a transgene construct comprising a nucleic acid encoding a native human GIPF protein, analog or a fragment thereof, under the control of transcriptional regulatory sequences directing its expression to B-cells. The transgene construct preferably comprises a B-cell specific promoter, such as an immunoglobulin kappa chain promoter.

In another aspect, the invention concerns a transgenic non-human mammal that produces in its B-cells detectable levels of a native human GIPF protein, analog or a fragment thereof, wherein said transgenic mammal has stably integrated into its genome a nucleic acid sequence encoding a native human GIPF protein, analog or a fragment thereof having the biological activity of native human GIPF, operably linked to transcriptional regulatory sequences directing its expression to B-cells. The transcriptional regulatory sequences preferably comprise a B-cell specific promoter, such as the immunoglobulin kappa chain promoter. Without limitation, the non-human transgenic mammal may, for example, be mouse, rat, rabbit, pig, sheep, goat or cattle.

In another aspect the invention concerns a method of screening drug candidates for the treatment of a disease or disorder recited herein comprising (a) administering a drug candidate to a transgenic mouse that expresses in its B-cells a GIPF polypeptide, and develops intestinal distension associated with hyperproliferation of epithelial cells, and (b) evaluating the effect of the candidate drug on the hyperproliferation of the epithelial cells. The drug candidates may modulate (i.e. increase or decrease) the expression or activity of the polynucleotides and/or polypeptides of the invention.

The invention also includes a method of treating or ameliorating a medical condition, including mucositis and inflammatory bowel disease, and wounds, which comprises administering to a mammalian subject, including but not limited to humans, a therapeutically effective amount of a GIPF polypeptide together with a cytokine.

In another aspect the invention includes pharmaceutical compositions comprising a polypeptide of the invention, a second therapeutic agent, e.g., a cytokine, and a pharmaceutically acceptable carrier.

The invention features, a composition comprising a therapeutically effective amount of a GIPF polypeptide, fragment, or analog thereof, and a pharmaceutically acceptable carrier.

The invention also features a pharmaceutical composition comprising a polypeptide comprising a biologically active fragment of GIPF and a pharmaceutically acceptable carrier. In various embodiments, the GIPF is human GIPF; and the polypeptide comprises a biologically active fragment of the polypeptide of SEQ ID NO:4.

In another embodiment the invention features a pharmaceutical composition comprising a polypeptide comprising a polypeptide fragment of SEQ ID NO:4 wherein the polypeptide fragment comprises an amino acid sequence selected from the group consisting of SEQ ID NO: 10, 12, 14, 16, 18, 85, 87, 89, 91, 93, 95, 97, 99, 101, 103, 105, and 178.

In various embodiments of the compositions and methods, the polypeptide is glycosylated; the polypeptide is not glycosylated; the polypeptide stimulates epithelial cell proliferation; and the polypeptide comprises an amino acid sequence that is at least 80% identical to the amino acid sequence of SEQ ID NO:4.

The invention also features: a method of stimulating epithelial cell proliferation in a subject comprising administering to said subject a composition comprising a GIPF polypeptide, fragment or analog thereof and a carrier; a method of treatment comprising administering to a mammalian subject in need thereof a therapeutically effective amount of a composition comprising a GIPF polypeptide and a pharmaceutically acceptable carrier; a method of treating mucositis, inflammatory bowel disease, or short bowel syndrome comprising administering to a mammalian subject in need thereof a therapeutically effective amount of a composition comprising a GIPF polypeptide and a pharmaceutically acceptable carrier; a method for stimulating epithelial cell proliferation in the gastrointestinal tract of a patient, the method comprising administering a therapeutically effective amount of a composition comprising a GIPF polypeptide and a pharmaceutically acceptable carrier. In various embodiments: epithelial cell proliferation in the esophagus is stimulated, epithelial cell proliferation in the small intestine is stimulated; epithelial cell proliferation in the large intestine is stimulated; epithelial cell proliferation in the oral cavity is stimulated and epithelial cell proliferation in the stomach is stimulated.

The invention also features a method for treating a patient at risk for damage to epithelial cells lining at least a portion of the gastrointestinal tract, the method comprising administering a therapeutically effective amount of a composition comprising a GIPF polypeptide and a pharmaceutically acceptable carrier. In certain embodiments: the patient has undergone or will undergo radiation therapy and the patient has undergone or will undergo chemotherapy.

The invention includes a method for treating a patient that has undergone radiation therapy or chemotherapy comprising administering a therapeutically effective amount of a composition comprising a GIPF polypeptide and a pharmaceutically acceptable carrier.

In other embodiments, the invention features an adenoviral vector comprising a gene encoding GIPF operably associated with an expression control sequence as well as a pharmaceutical composition comprising such a vector.

In other embodiments, the invention features a method of stimulating epithelial cell proliferation in a subject comprising administering to said subject the pharmaceutical composition comprising features an adenoviral vector comprising a gene encoding GIPF operably associated with an expression control sequence.

The invention also features a transgene construct comprising a nucleic acid encoding a GIPF protein, wherein said nucleic acid is operably linked to transcriptional regulatory sequences directing its expression in B-cells. In certain embodiments, the transgene construct comprises a B-cell specific promoter.

The invention also features a transgenic mouse that produces in its B-cells cells detectable levels of a native human GIPF protein, wherein said transgenic mouse has stably integrated into its genome a nucleic acid sequence encoding a GIPF protein, operably linked to transcriptional regulatory sequences directing its expression to B-cells. In some embodiments, the transcriptional regulatory sequences comprise a B-cell promoter.

The invention features a method of identifying a drug candidate for the treatment of mucositis, inflammatory bowel disease or short bowel syndrome, comprising:

(a) administering a test compound to a transgenic mouse that expresses in its B-cells a recombinant GIPF polypeptide and exhibits increased intestinal epithelial cell proliferation compared to an otherwise identical mouse not expressing a recombinant GIPF polypeptide intestinal epithelial cell proliferation; and (b) evaluating the effect of said test compound on intestinal epithelial cell proliferation, wherein an increase in intestinal cell proliferation identifies the test compound as a drug candidate for the treatment of mucositis, inflammatory bowel disease or short bowel syndrome. In certain embodiments, the intestinal epithelial cell is a crypt cell.

The invention also features: an isolated polynucleotide selected from the group consisting of SEQ ID NO: 9, 11, 13, 15, 17, 84, 86, 88, 90, 92, 94, 96, 98, 100, 102, and 104; an isolated polynucleotide encoding a polypeptide with biological activity, said polynucleotide having greater than about 95% sequence identity to polynucleotide selected from the group consisting of SEQ ID NO: 9, 11, 13, 15, 17, 84, 86, 88, 90, 92, 94, 96, 98, 100, 102, and 104.

The invention also features: an isolated polypeptide selected from the group consisting of SEQ ID NO: 12, 14, 16, 18, 85, 87, 89, 91, 93, 95, 97, 99, 101, 103, and 105; and an isolated polypeptide comprising an amino acid sequence which is at least 95% identical to the amino acid sequence selected from the group consisting of SEQ ID NO: 12, 14, 16, 18, 85, 87, 89, 91, 93, 95, 97, 99, 101, 103, and 105.

The invention further features an expression vector comprising expression regulatory elements operatively linked to a polynucleotide of SEQ ID NO: 5, 9, 11, 13, 15, 17, 84, 86, 88, 90, 92, 94, 96, 98, 100, 102, and 104.

The invention also features a host cell transformed or transfected with a polynucleotide of SEQ ID NO: 5, 9, 11, 13, 15, 17, 84, 86, 88, 90, 92, 94, 96, 98, 100, 102, 104 or 177. In some embodiments the cell is prokaryotic, in others it is eukaryotic.

The invention also features a method for producing a polypeptide comprising the amino acid sequence of SEQ ID NO: 12, 14, 16, 18, 85, 87, 89, 91, 93, 95, 97, 99, 101, 103, or 105, the method comprising:

(a) culturing an isolated cell comprising a nucleic acid molecule encoding a polypeptide of SEQ ID NO: 12, 14, 16, 18, 85, 87, 89, 91, 93, 95, 97, 99, 101, 103, or 105 in culture medium under conditions suitable for expressing the polypeptide; and (b) purifying the polypeptide from the cell or the culture medium.

The invention features a method for producing a pharmaceutical composition comprising a polypeptide comprising the amino acid sequence of SEQ ID NO: 12, 14, 16, 18, 85, 87, 89, 91, 93, 95, 97, 99, 101, 103, 105 or 178, the method comprising (a) culturing an isolated cell comprising a nucleic acid molecule encoding a polypeptide of SEQ ID NO: 12, 14, 16, 18, 85, 87, 89, 91, 93, 95, 97, 99, 101, 103, 105, or 178 in culture medium under conditions suitable for expressing the polypeptide;

(b) purifying the polypeptide from the cell or the culture medium; and (c) combining the purified polypeptide with a pharmaceutically acceptable carrier.

The invention features a method for producing a pharmaceutical composition comprising a polypeptide comprising the amino acid sequence of SEQ ID NO: 12, 14, 16, 18, 85, 87, 89, 91, 93, 95, 97, 99, 101, 103, 105 or 178, the method comprising (a) synthesizing comprising a polypeptide comprising the amino acid sequence of SEQ ID NO: 12, 14, 16, 18, 85, 87, 89, 91, 93, 95, 97, 99, 101, 103, 105 or 178;

(b) purifying the polypeptide; and (c) combining the purified polypeptide with a pharmaceutically acceptable carrier.

The invention also features an expression vector construct comprising a nucleic acid encoding a GIPF protein, wherein the nucleic acid is operably linked to transcriptional regulatory sequences directing expression of the GIPF protein in intestinal epithelial cells.

In another aspect the invention includes a transgenic mouse that produces in its intestinal epithelial cells detectable levels of a GIPF protein, wherein said transgenic mouse has stably integrated into its genome a nucleic acid sequence encoding a GIPF protein, wherein the nucleic acid sequence encoding the GIPF protein is operably linked to transcriptional regulatory sequences directing expression of the GIPF protein in intestinal epithelial cells.

In another aspect the invention features an expression vector construct comprising a nucleic acid encoding a GIPF protein and a Wnt3a protein, wherein the nucleic acid is operably linked to transcriptional regulatory sequences directing its expression in intestinal epithelial cells.

The invention also features a transgenic mouse that produces in its intestinal epithelial cells detectable levels of a native GIPF and Wnt3a protein, wherein said transgenic mouse has stably integrated into its genome a nucleic acid sequence encoding a GIPF protein, operably linked to transcriptional regulatory sequences directing expression of the GIPF protein in intestinal epithelial cells.

In some embodiments the transgenic mouse exhibits intestinal distension.

Additional aspects and advantages of the invention will be apparent to those skilled in the art upon consideration of the following description, which details the practice of the invention.

3. BRIEF DESCRIPTION OF THE DRAWINGS

FIG. 1 depicts the DNA sequence (SEQ ID NO: 2) (A) and corresponding amino acid sequence for the full-length GIPF (SEQ ID NO: 4) (B). SEQ ID NO: 2 includes the 5 prime and 3 prime untranslated regions in conjunction with the open reading frame.

Figure 2A:
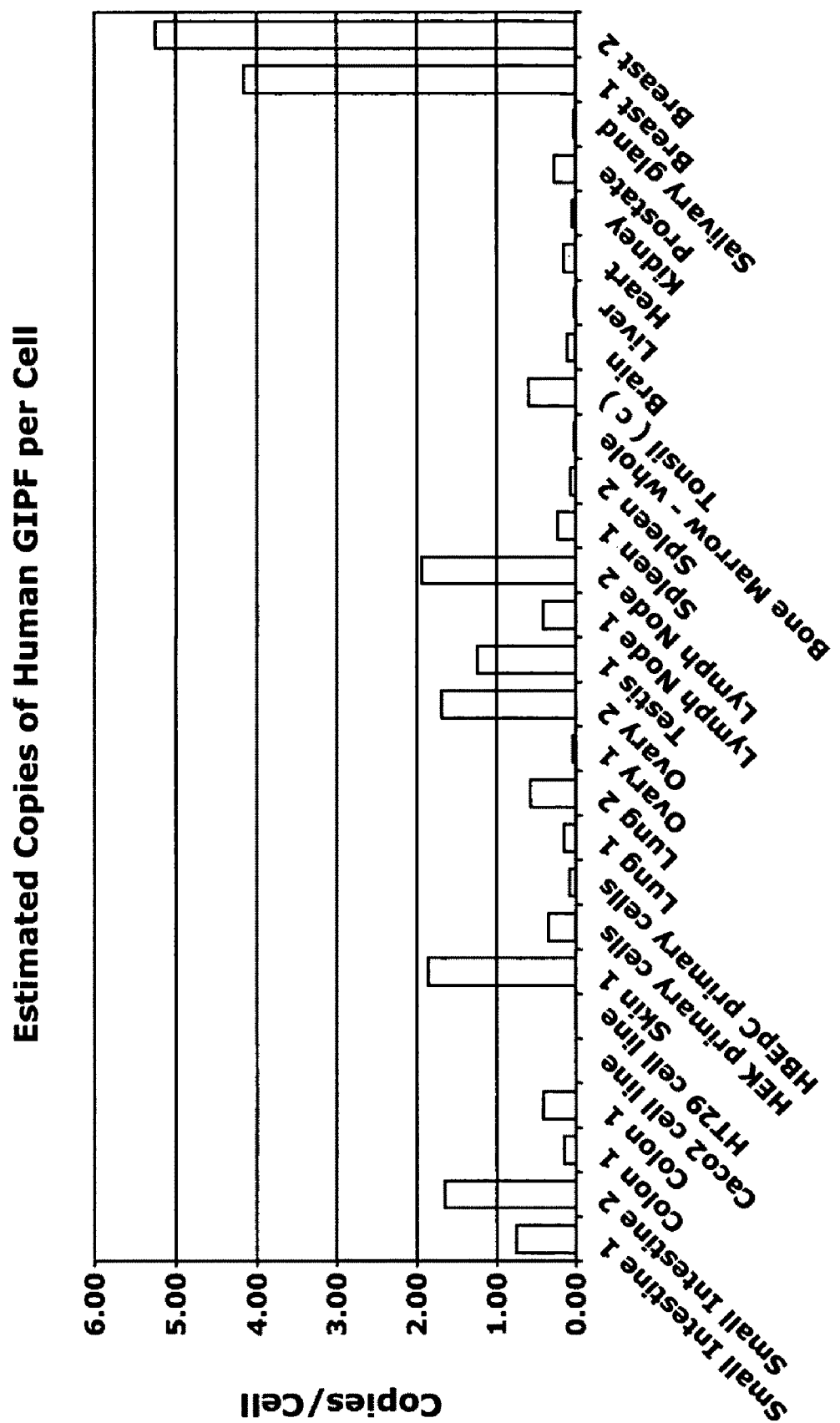
FIG. 2 depicts the expression of GIPF mRNA in tissues from human (A) and mouse (B).

FIG. 4A shows the BLASTP amino acid sequence alignment between the GIPF protein encoded by SEQ ID NO: 2 or 3 (i.e. SEQ ID NO: 4) and human stem cell growth factor A1 SEQ ID NO: 23 (SEQ ID NO: 10 from PCT WO 01/77169 A2), indicates that the two sequences share 63% similarity over amino acid residues 10 through 251 of SEQ ID NO: 4 and amino acid residues 11 through 257 of SEQ ID NO: 23, and 46% identity over the amino acid residues 10 through 251 of SEQ ID NO: 4 and amino acid residues 11 through 257 of SEQ ID NO: 23.

FIG. 4B shows the BLASTP amino acid sequence alignment between the GIPF protein encoded by SEQ ID NO: 2 or 3 (i.e. SEQ ID NO: 4) GIPF polypeptide and a specific region of human thrombospondin 1 (amino acid residues 501 through 657 of SwissProt accession number P07996; SEQ ID NO: 28). The figure indicates that the two sequences share 36% similarity and 26% identity over amino acid residues 14 through 166 of SEQ ID NO: 4 and amino acid residues 501 through 657 of SEQ ID NO: 28, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

Figure 5A:
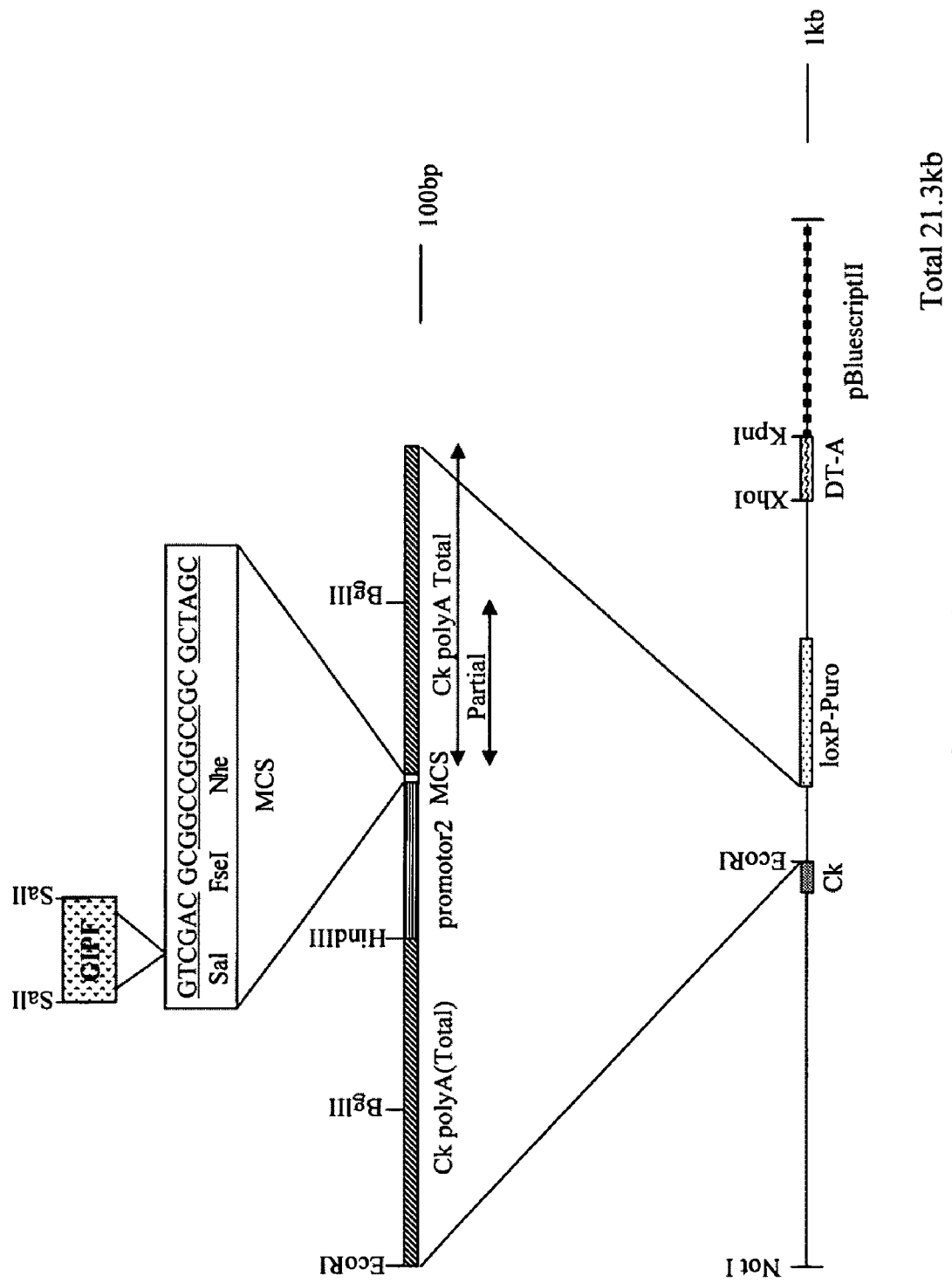
Figure 5E:
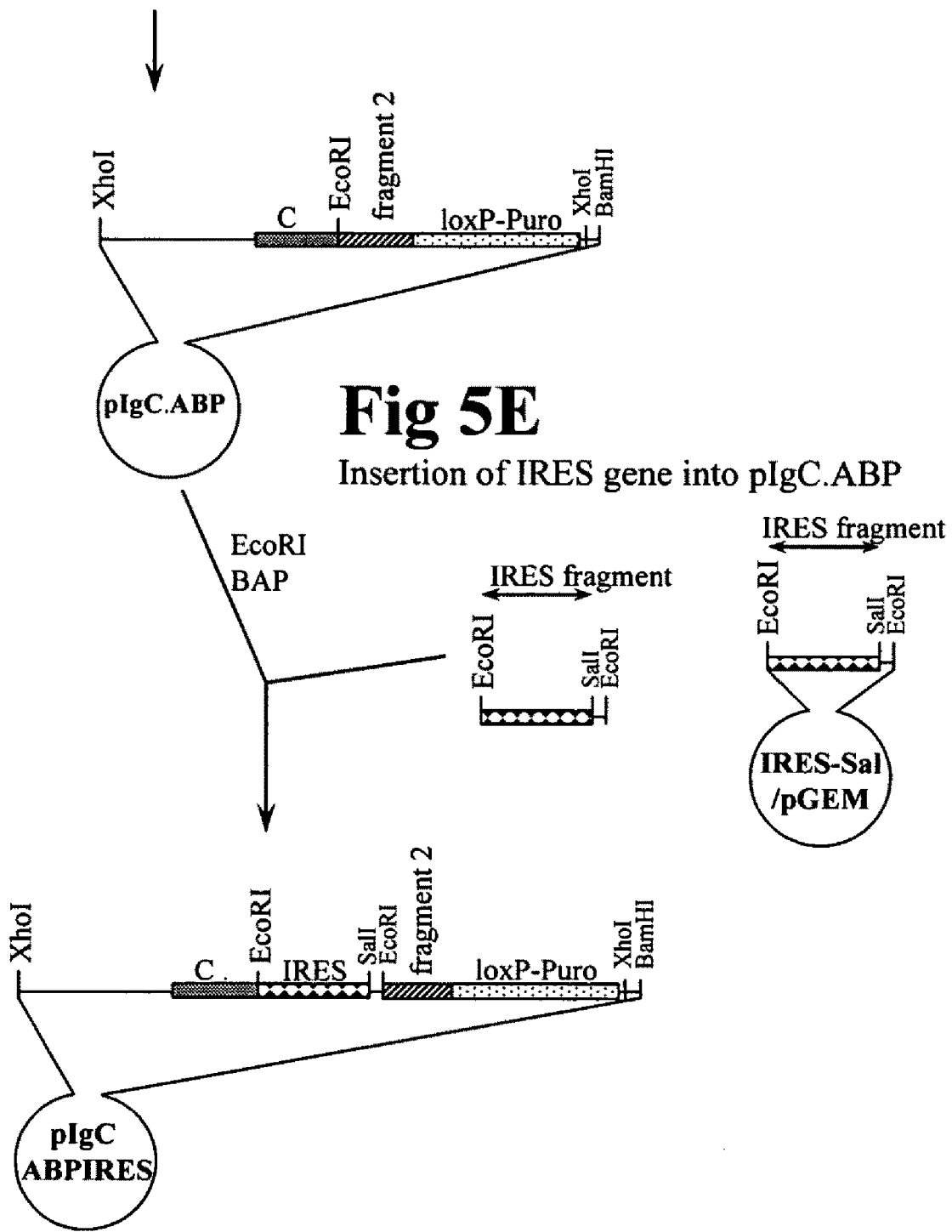
Figure 5R:
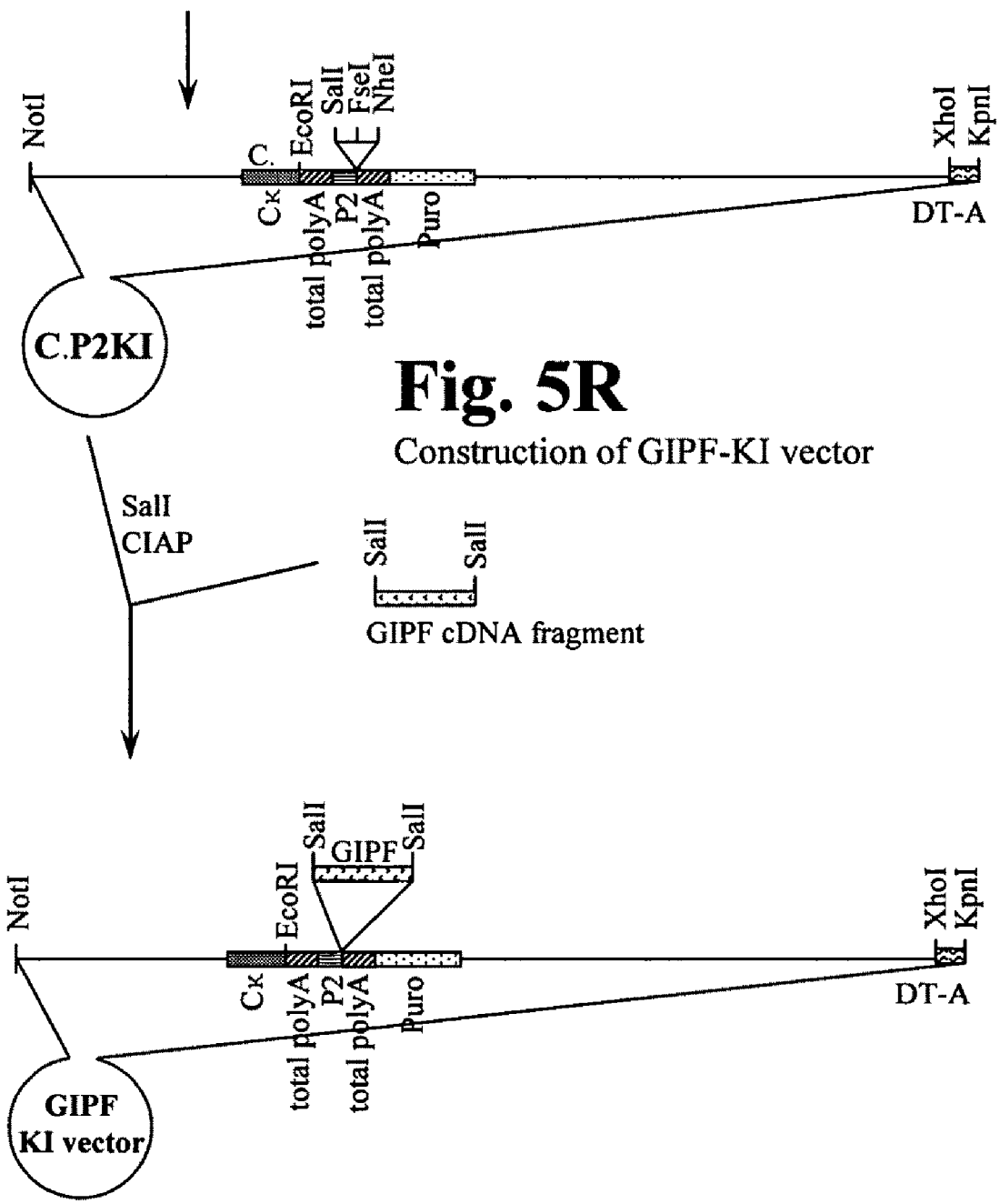

FIGS. 5A-5R depicts the steps of the method used to generate the GIPF-knock-in (GIPF-KI) vector of the invention. A preferred method for generating transgenic mice that express GIPF in their B cells is also described.

Figure 6:
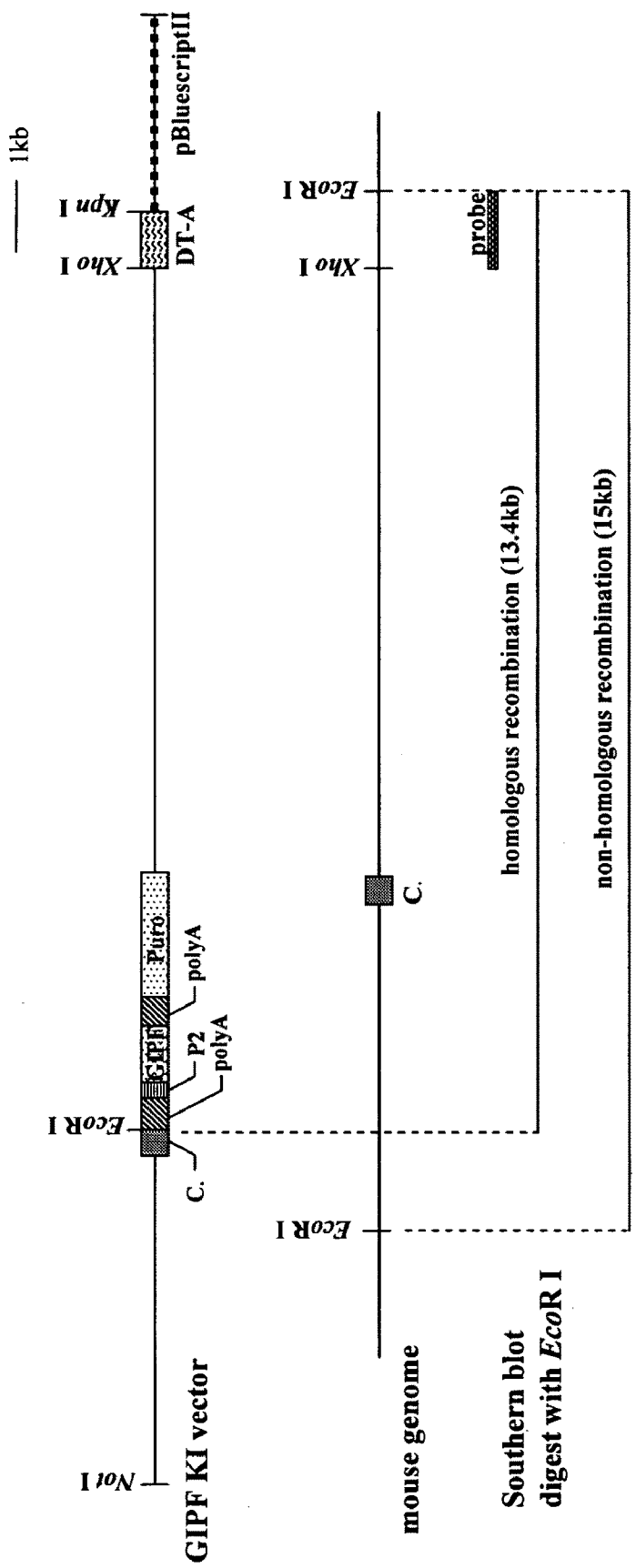

FIG. 6 depicts the location of the probe utilized in Southern blot analysis to select ES clones resulting from homologous recombination, as well as the EcoRI digest fragment sizes of mouse genomic DNA that has undergone homologous or non-homologous recombination.

FIG. 7 shows the gross pathology of the intestinal tract of the GIPF-KI mice: control (A) GIPF-KI (B).

Figure 8:
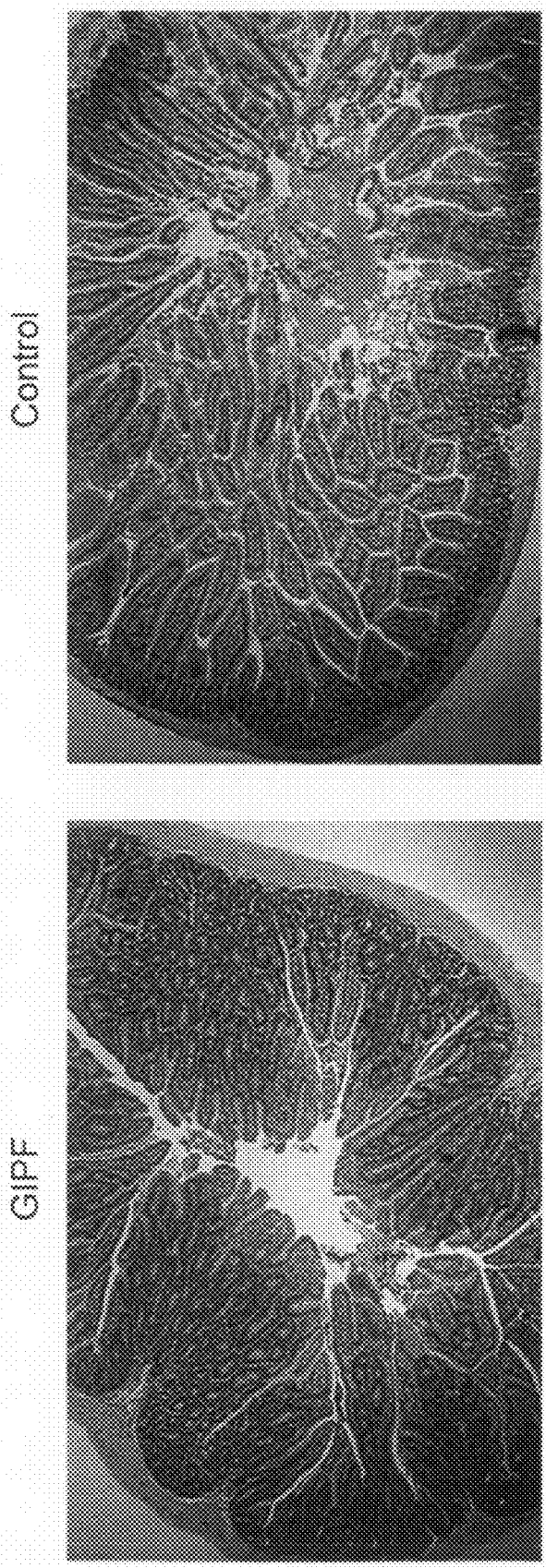

FIG. 8 H&E staining of transverse sections of small intestine of GIPF-KI (A) and control chimeric (B) mice, respectively.

Figure 9:
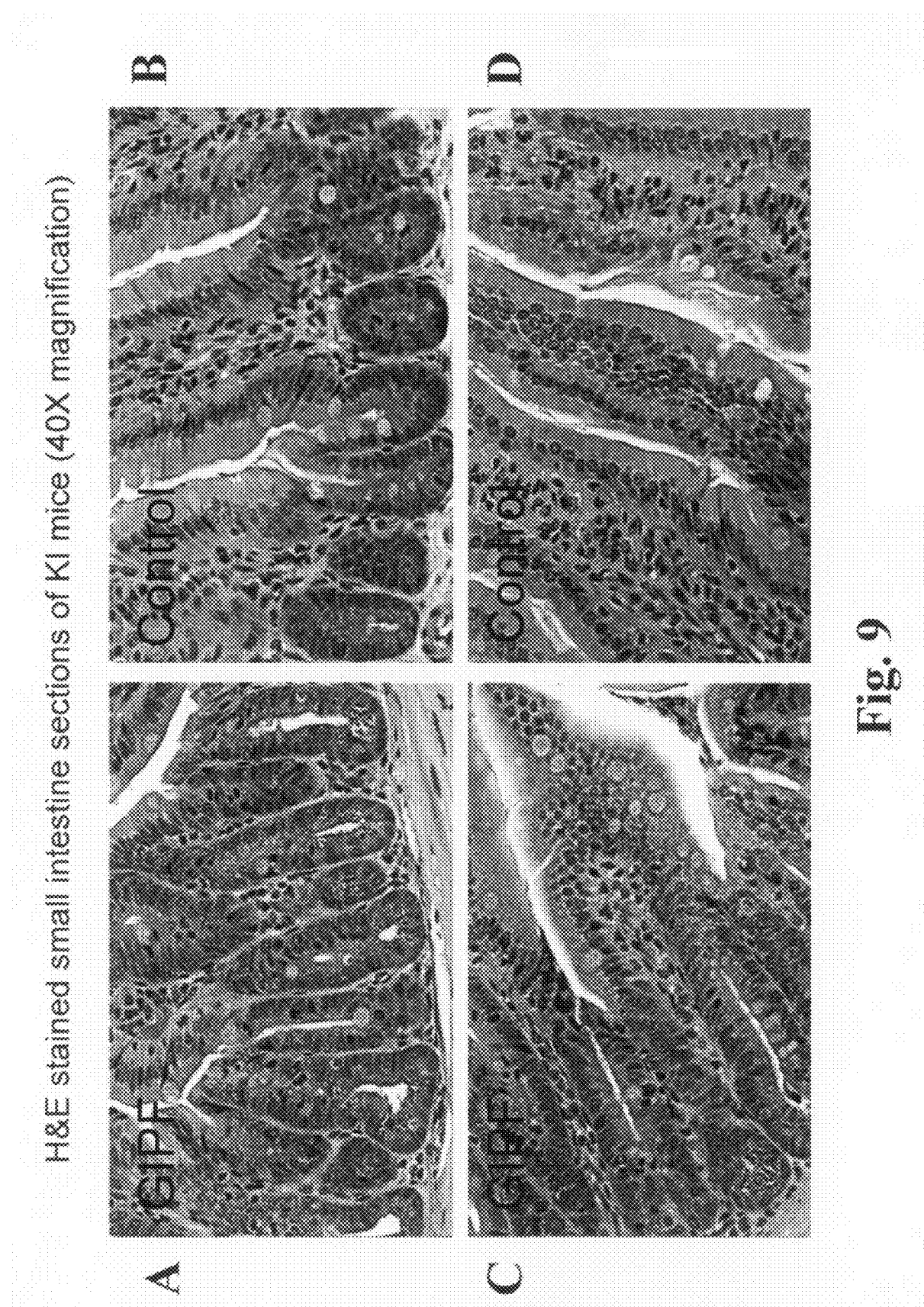

FIG. 9 shows H&E staining of the intestinal sections of FIG. 8 seen under higher magnification. Panels A and C correspond to the GIPF-KI section seen in panel A of FIG. 8, and panels B and D correspond to the intestinal section derived from a control chimeric mouse seen in panel B of FIG. 8.

Figure 10:
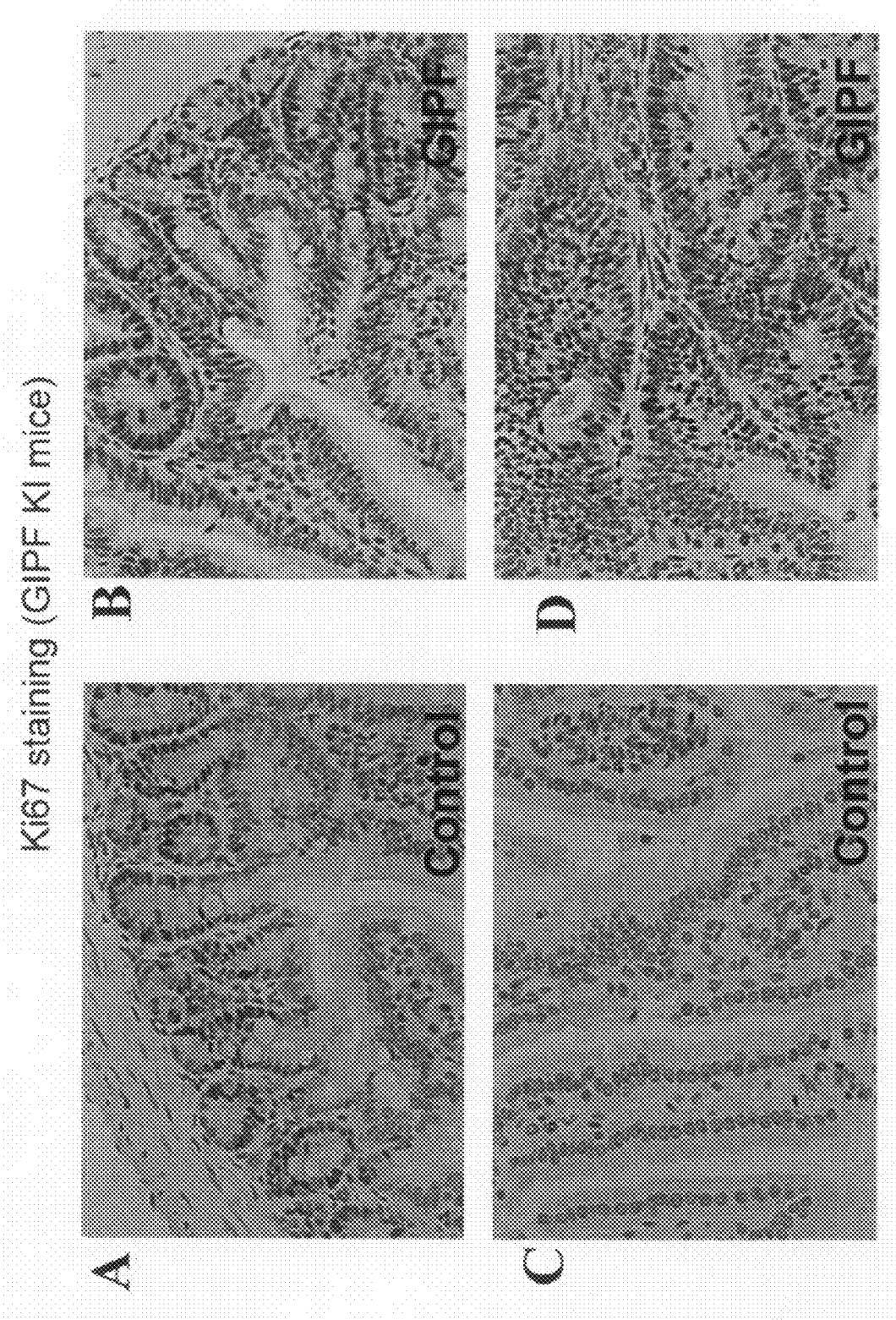

FIG. 10 shows Ki67 staining of cross-sections of the small intestine from a control chimeric mouse (A and C), and from a GIPF-KI mouse (B and D).

Figure 11:
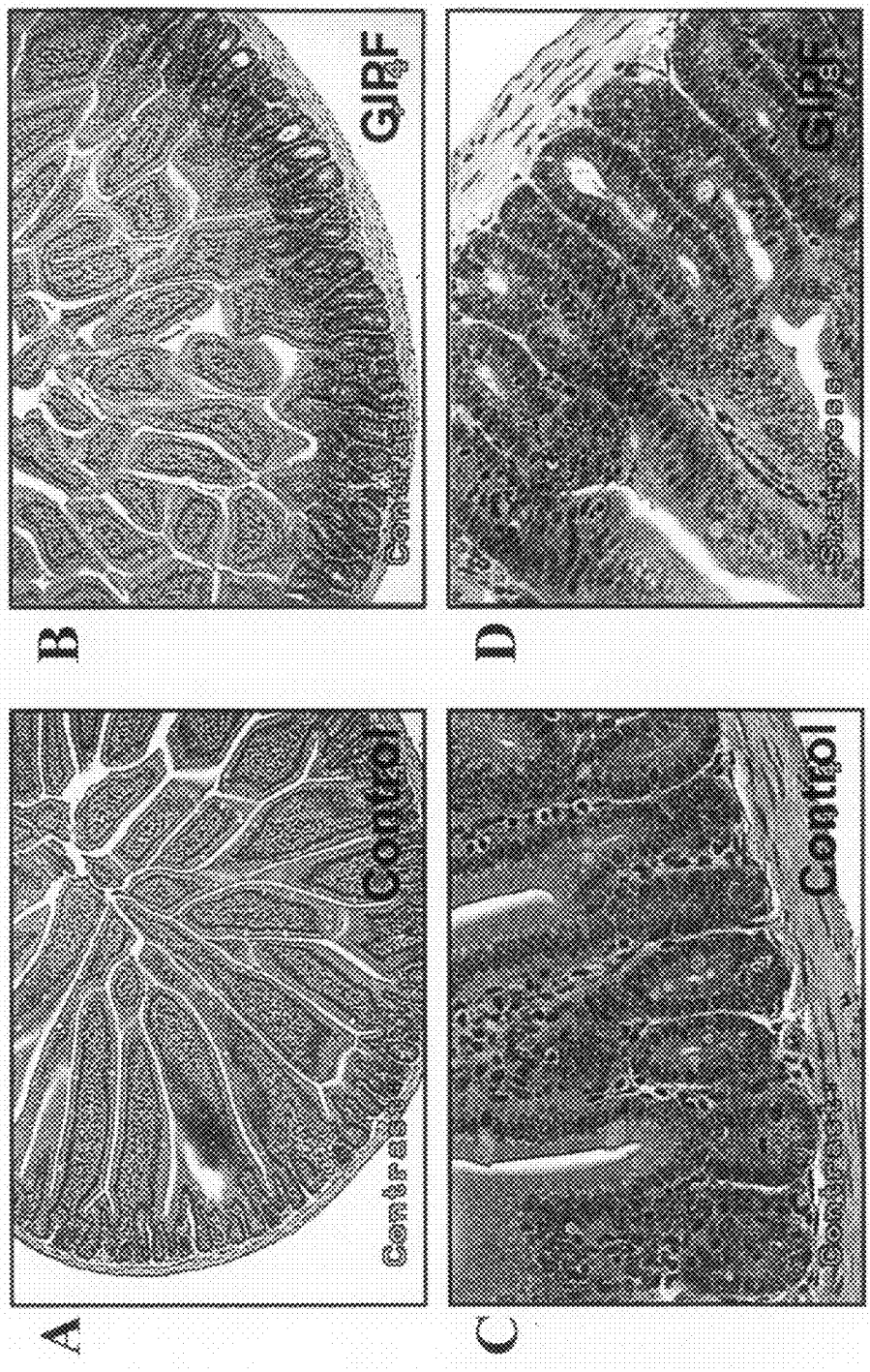

FIG. 11 Cross-sections of small intestine derived from a control mouse (A and C), and from a mouse treated with $1\times10^{10}$ viral particles (B and D). The sections were obtained three days following injection of the empty or GIPF adenovirus, respectively.

Figure 12:
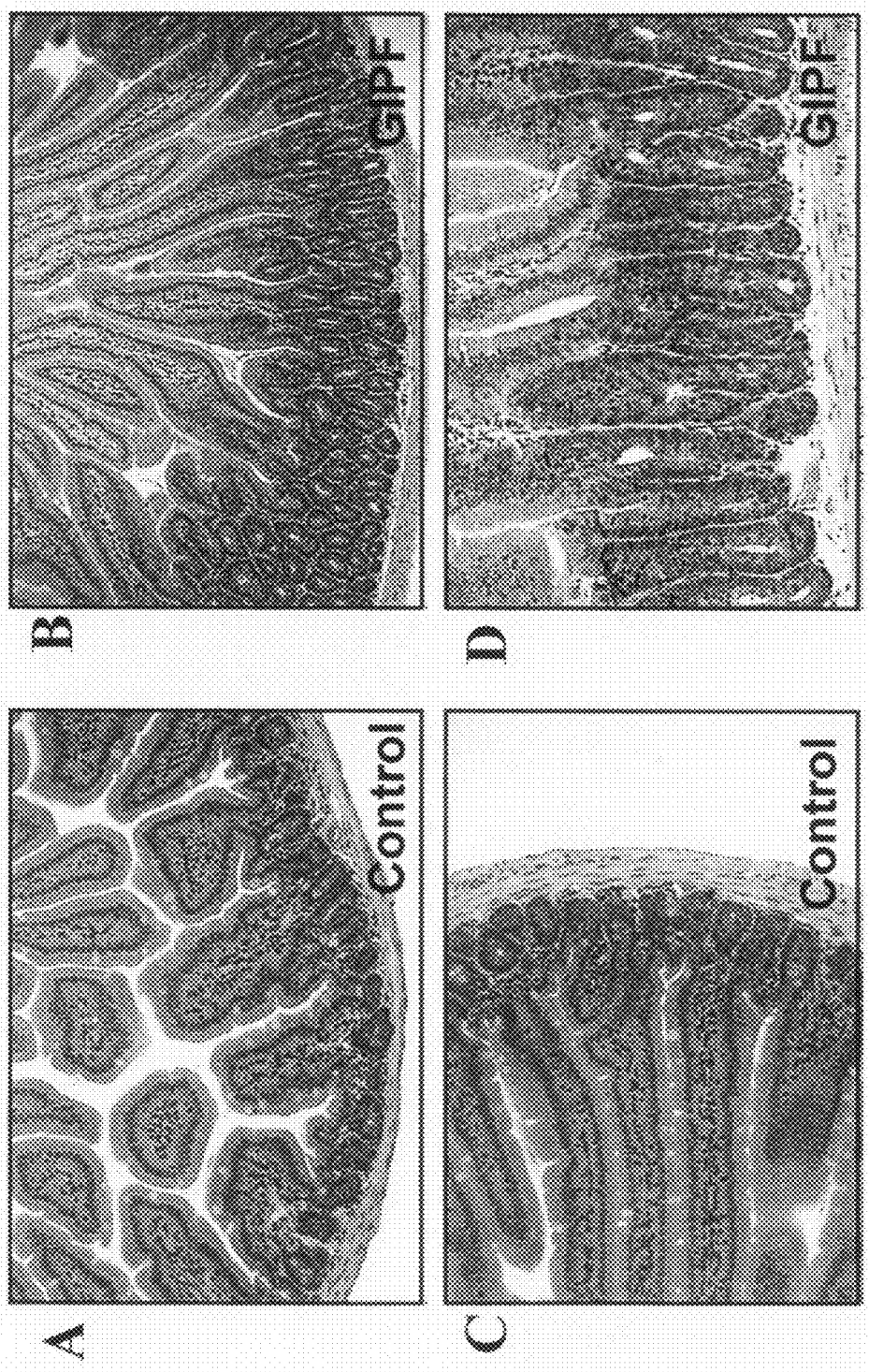

FIG. 12 Cross-sections of small intestine derived from control (A and C), and from a mouse treated with $1\times10^{10}$ viral particles (VP) (FIGS. 12 B and D). The sections were obtained five days following injection of the empty or GIPF adenovirus, respectively.

Figure 13:
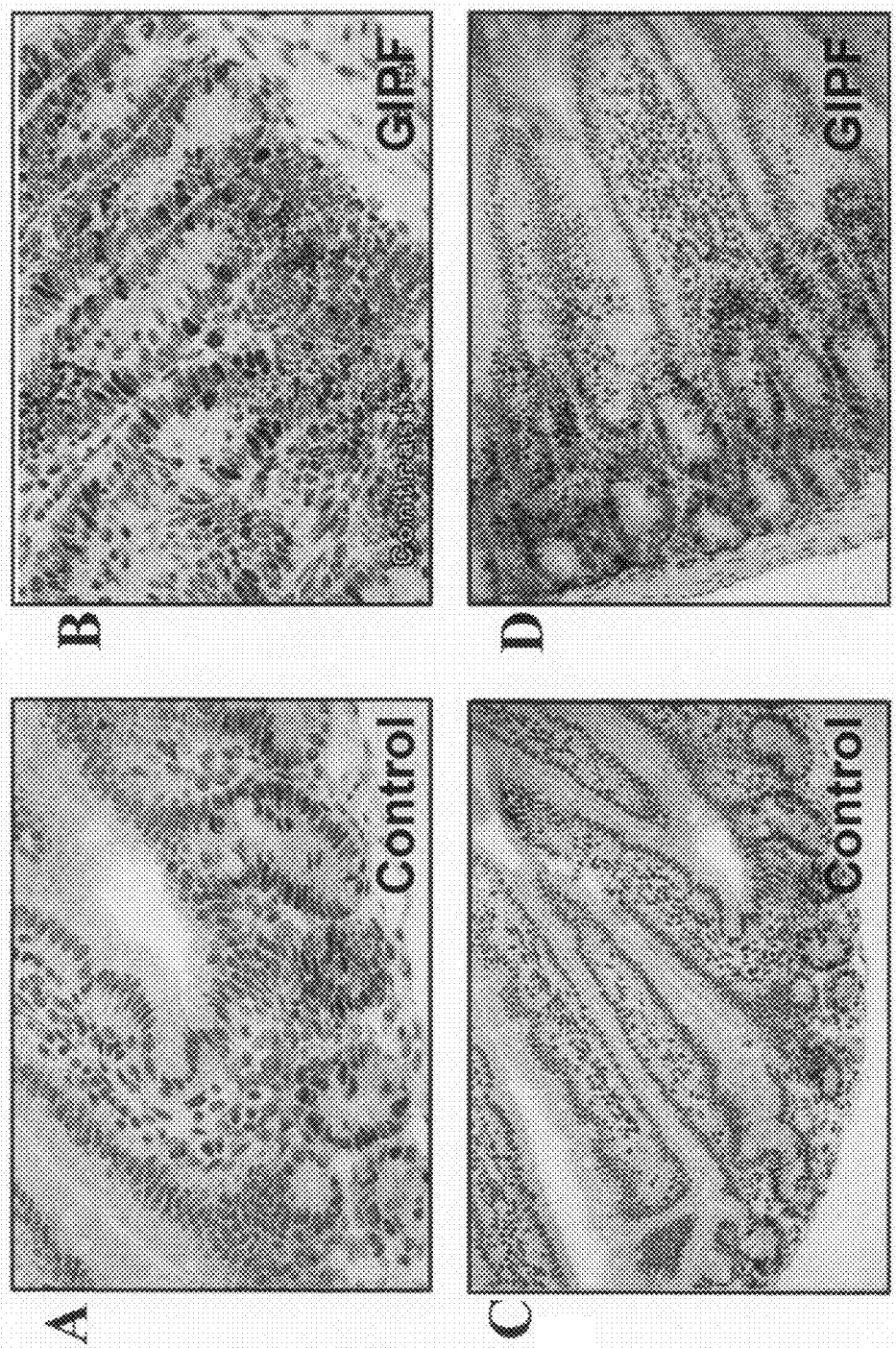

FIG. 13 Incorporation of BrdU into proliferating crypt cells of the small intestine of control mice (A and C) and mice treated with $1\times10^{10}$ viral particles (VP) (B and D).

Figure 14:
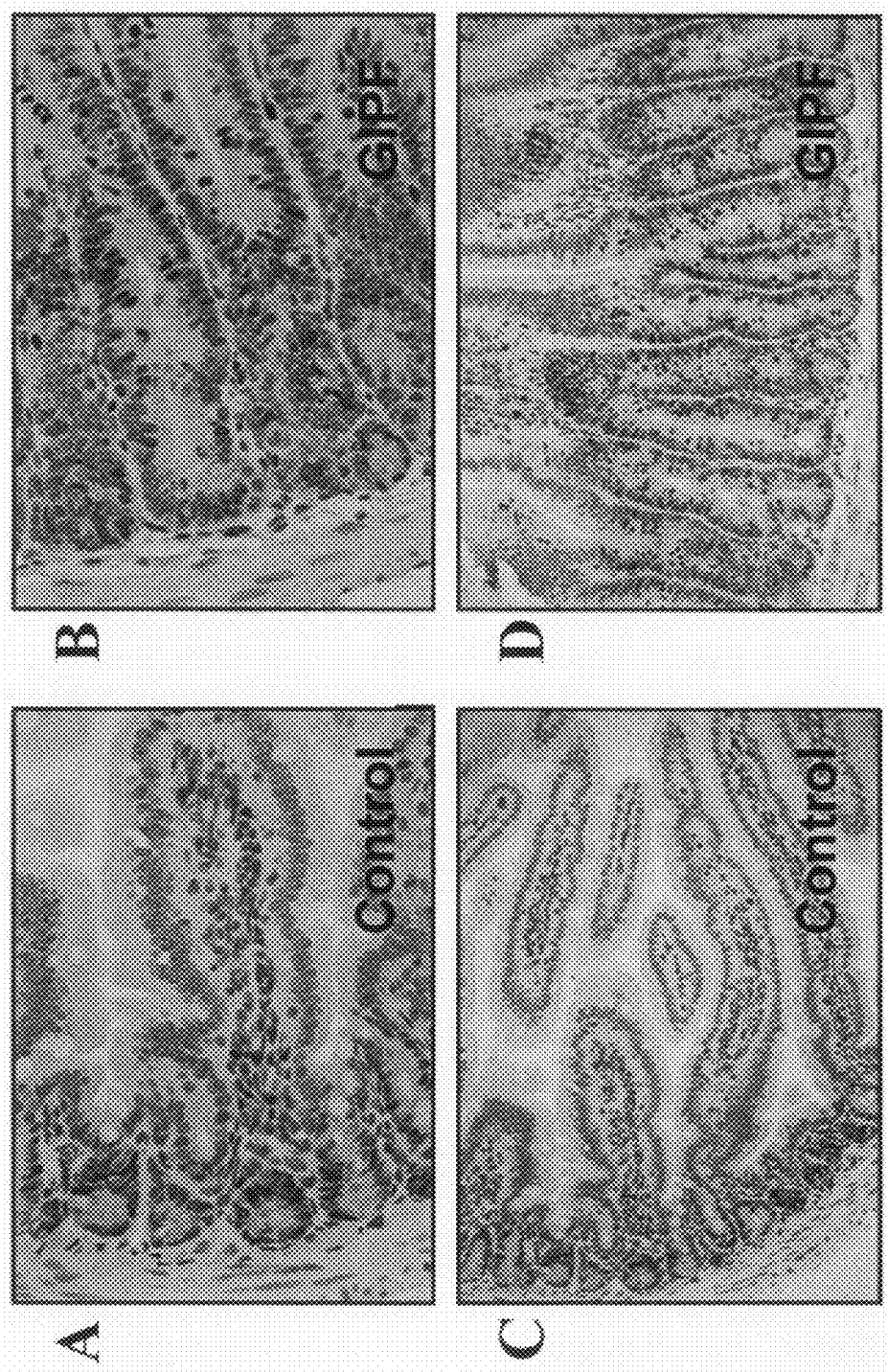

FIG. 14 Ki67 staining of proliferating crypt cells of the small intestine of control (A and C) and GIPF-adenovirus-treated mice (B and D).

Figure 15:
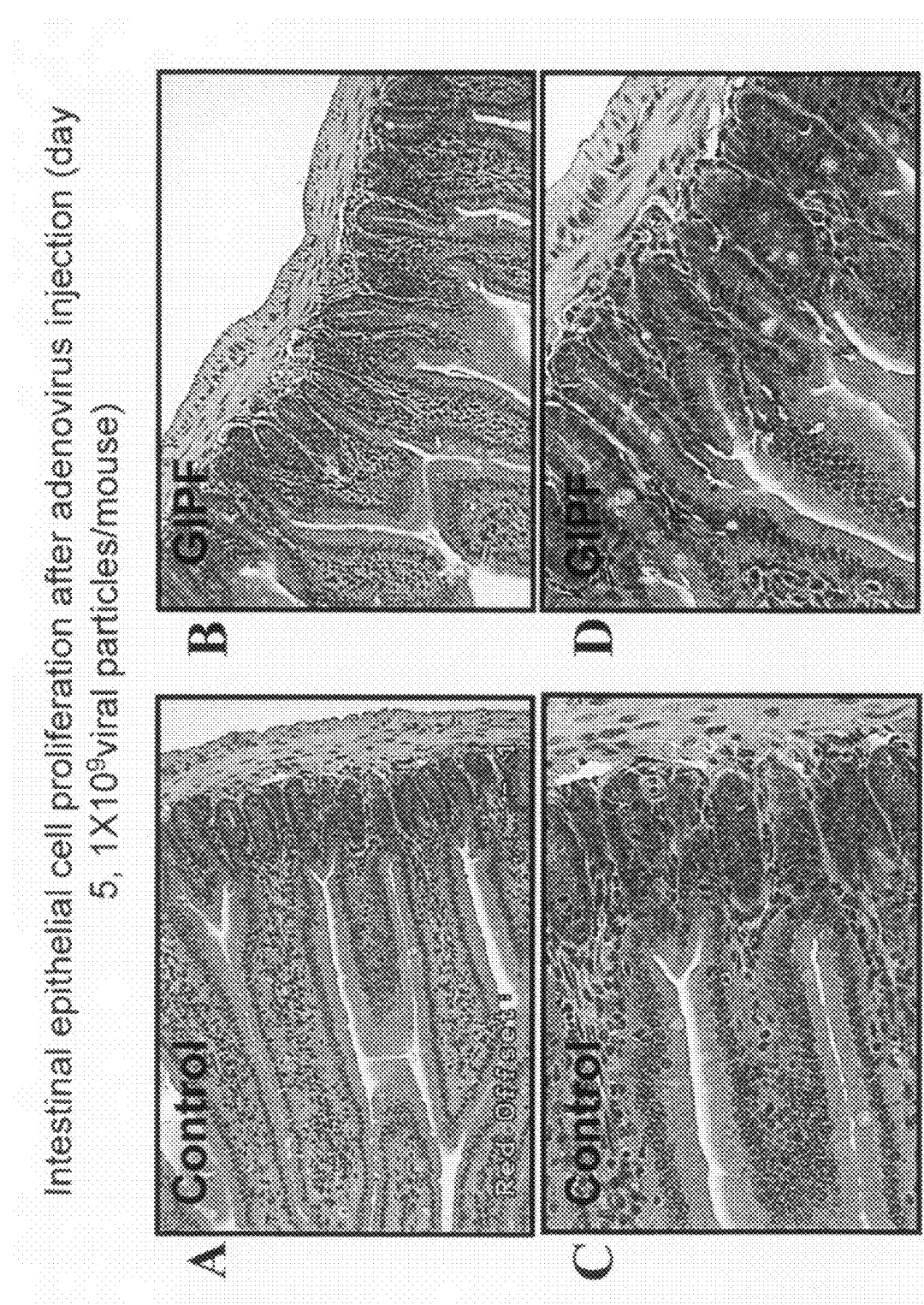

FIG. 15 H&E staining of cross sections derived from the small intestine of control mice (A and C) and mice that had been treated with GIPF-adenovirus at $1\times10^9$ viral particles (B and D).

Figure 16:
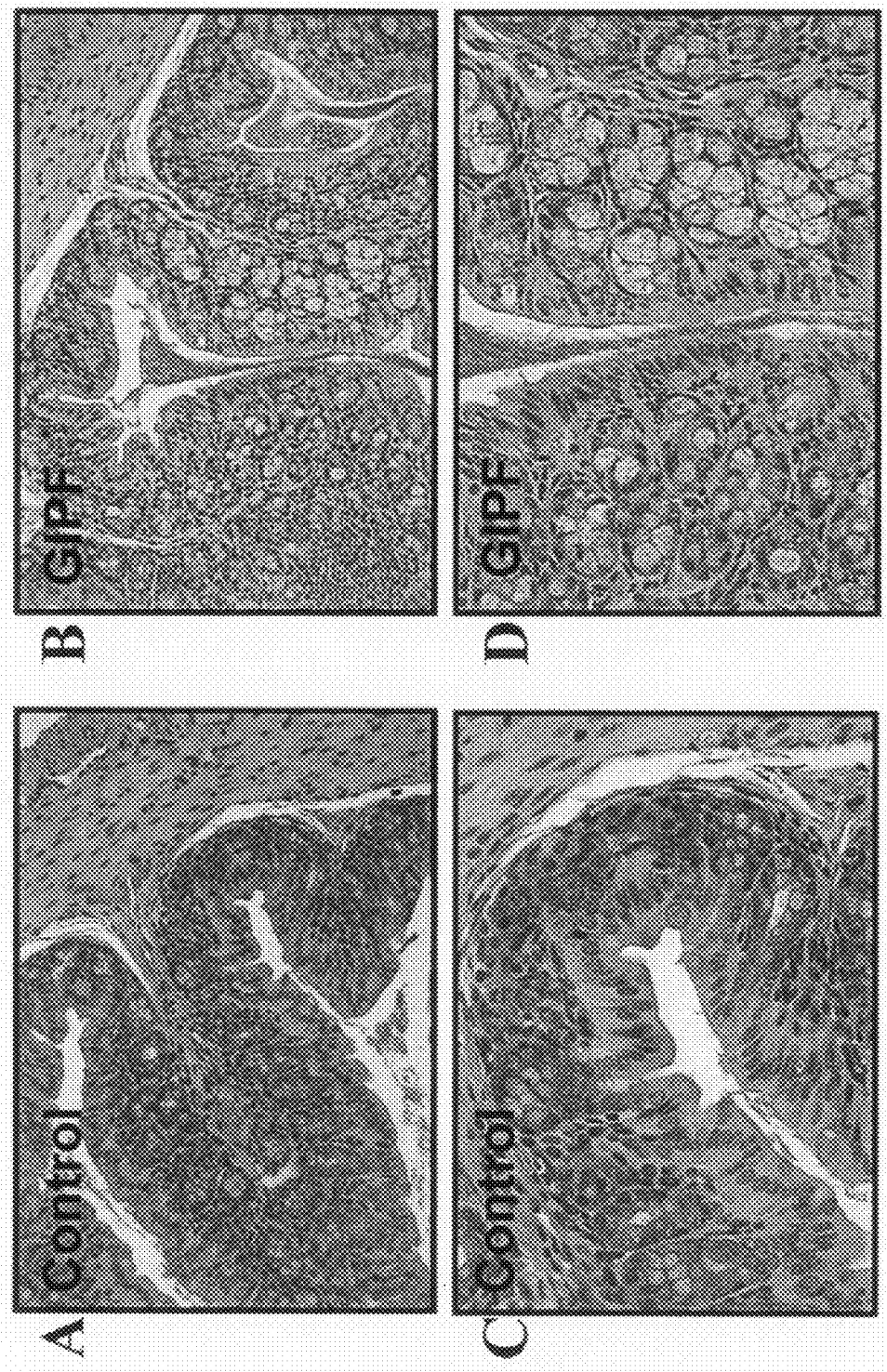

FIG. 16 H&E staining of cross-sections derived from the colon of control (A and C) and GIPF-adenovirus-treated mice (B and D).

FIG. 17 Solubility requirements of native V5-His-tagged GIPF protein purified from CHO cells. (A) The effect of NaCl and arginine (Arg) is shown on the solubility of the GIPF protein at pH 7. (B) The solubility of purified protein is shown in PBS (20 mM sodium phosphate, 0.15 M NaCl, pH 7).

Figure 18:
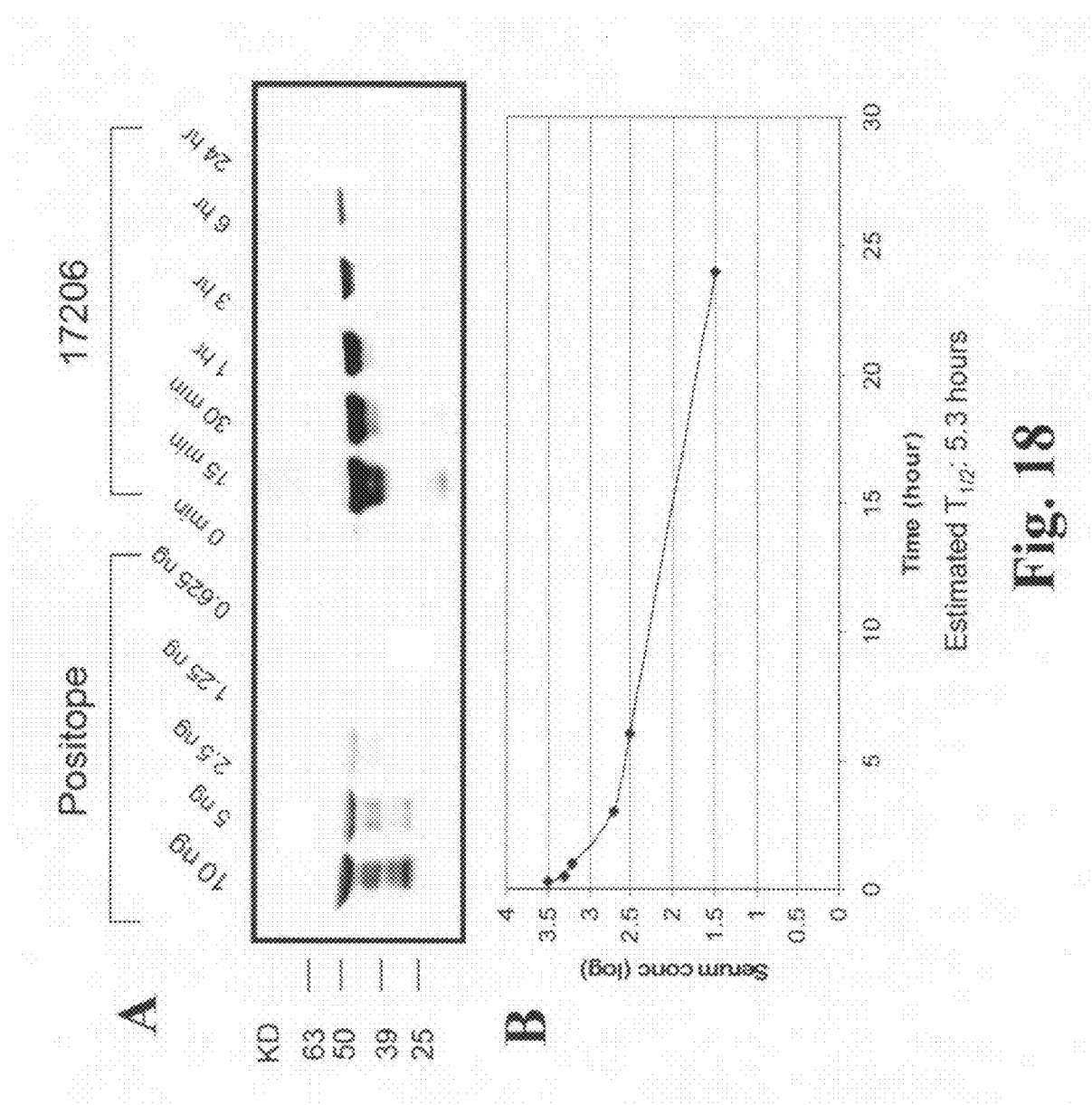

FIG. 18 Pharmacokinetics of V5-His-tagged GIPF protein in mouse serum or GIPF adenovirus, respectively. (A) No significant degradation of serum GIPF protein was detected. (B) The half-life of GIPF protein in serum was estimated to be 5.3 hours.

Figure 20:
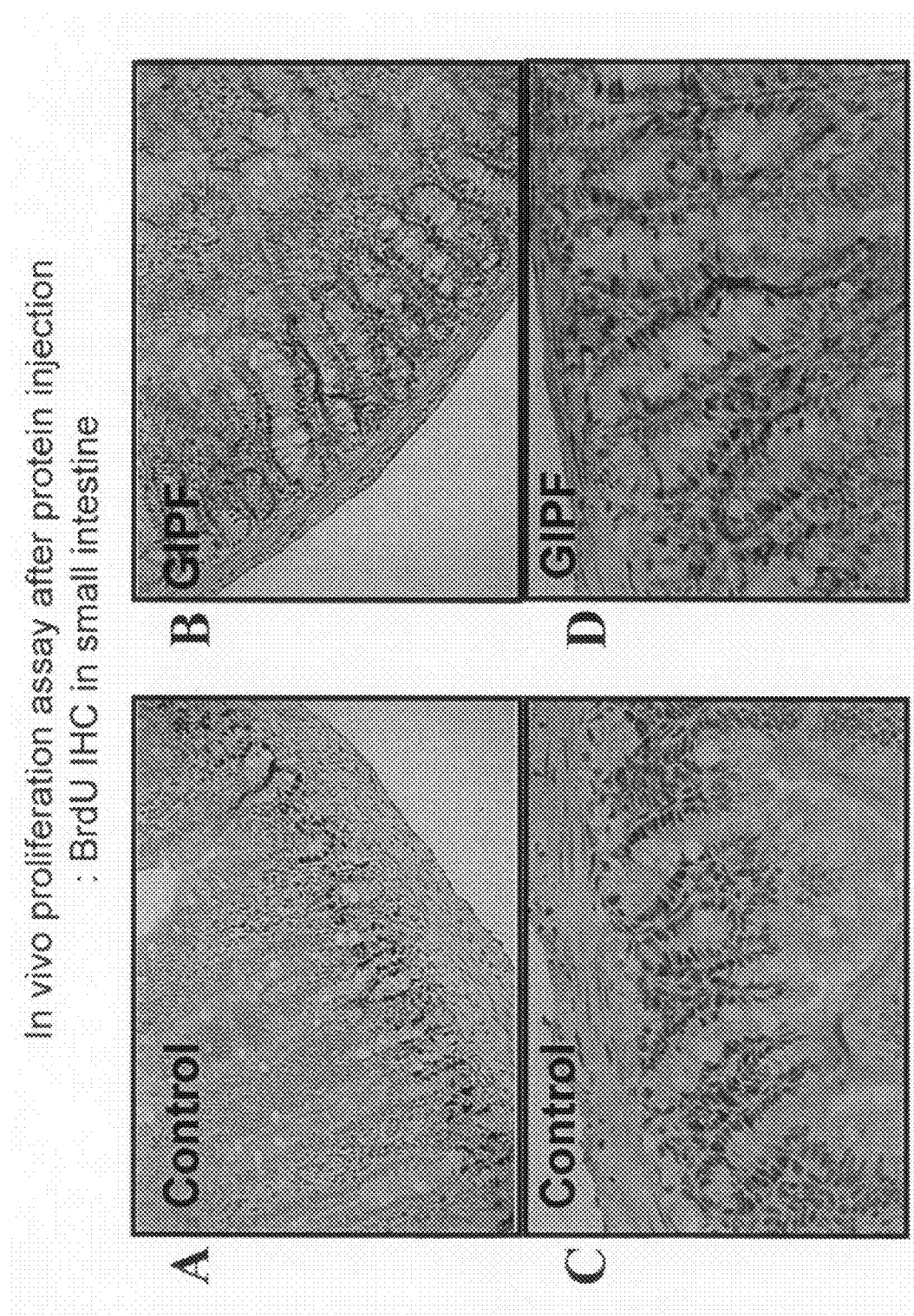

FIG. 20 Incorporation of BrdU into proliferating crypt cells of the small intestine of control mice (A and C) and mice that had been treated with purified GIPF protein (B and D).

FIG. 21 H&E staining of cross sections derived from the colon of control mice (A) and mice that had been treated with purified GIPF protein (B).

Figure 22:
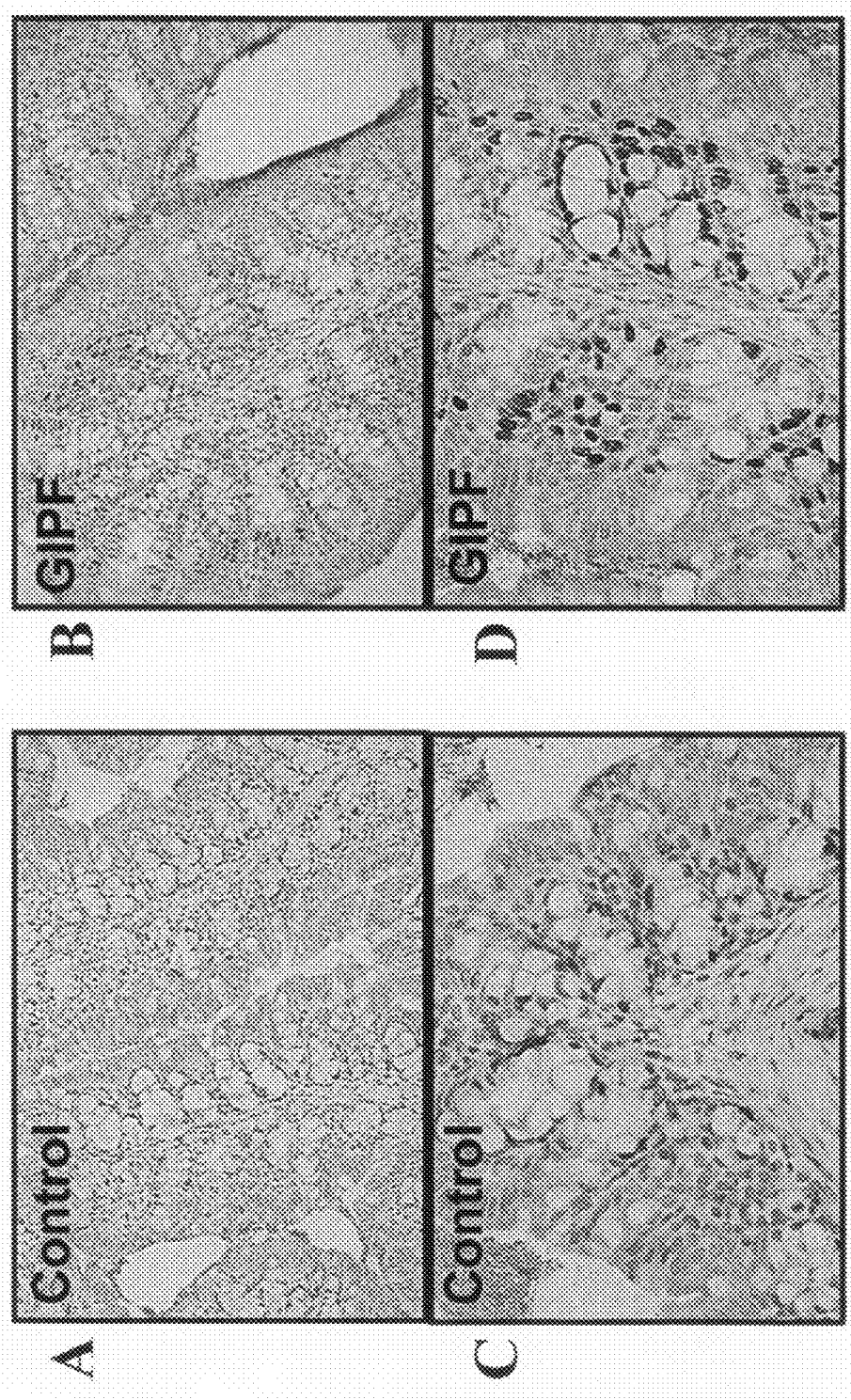

FIG. 22 Incorporation of BrdU into proliferating crypt cells of the colon of control mice (A and C) and mice that had been treated with purified GIPF protein (B and D).

Figure 23:
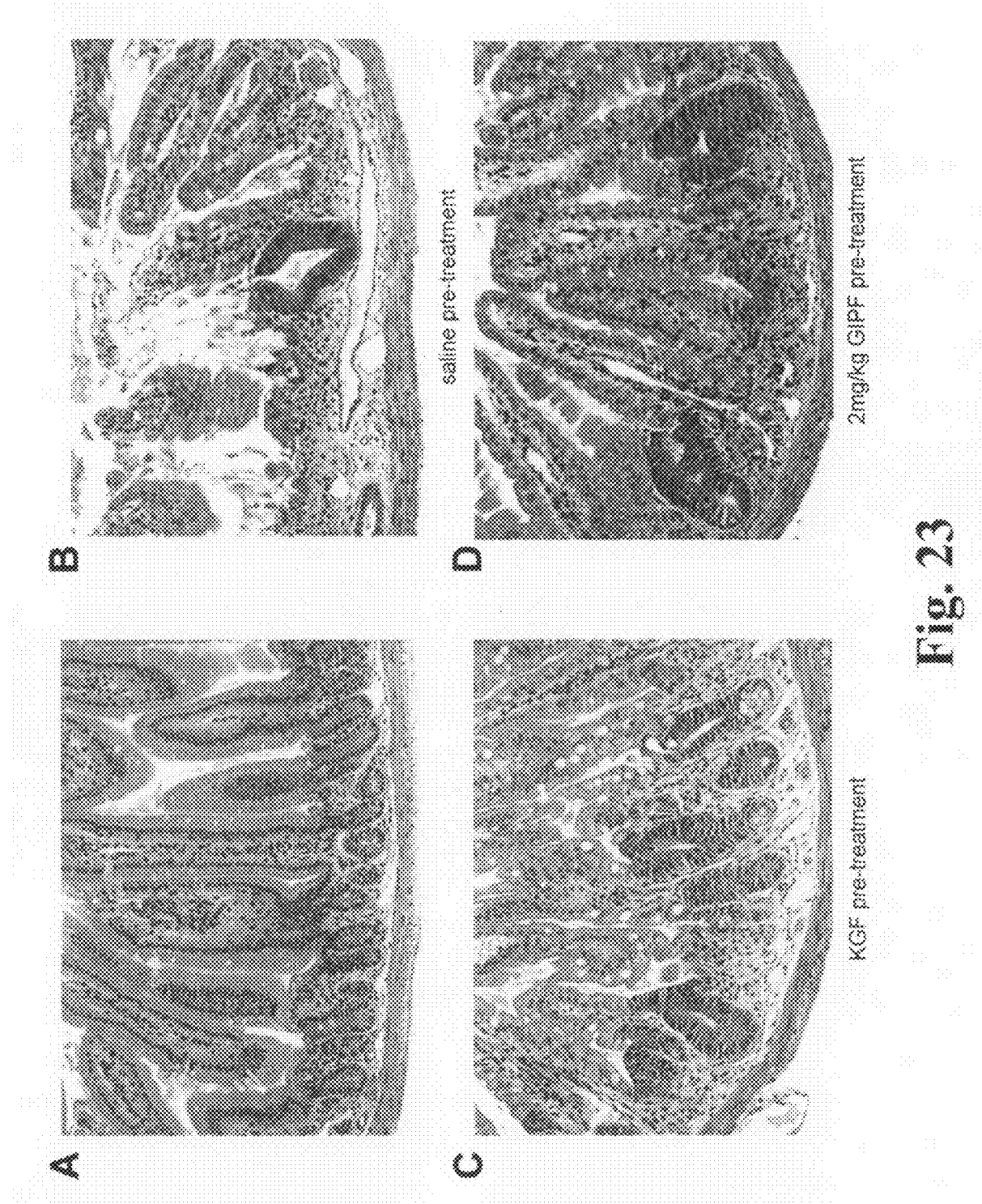

FIG. 23 H&E staining of cross sections derived from the small intestine of non-irradiated mice (A), irradiated mice treated with saline (B), KGF (C) or GIPFwt (D).

Figure 24:
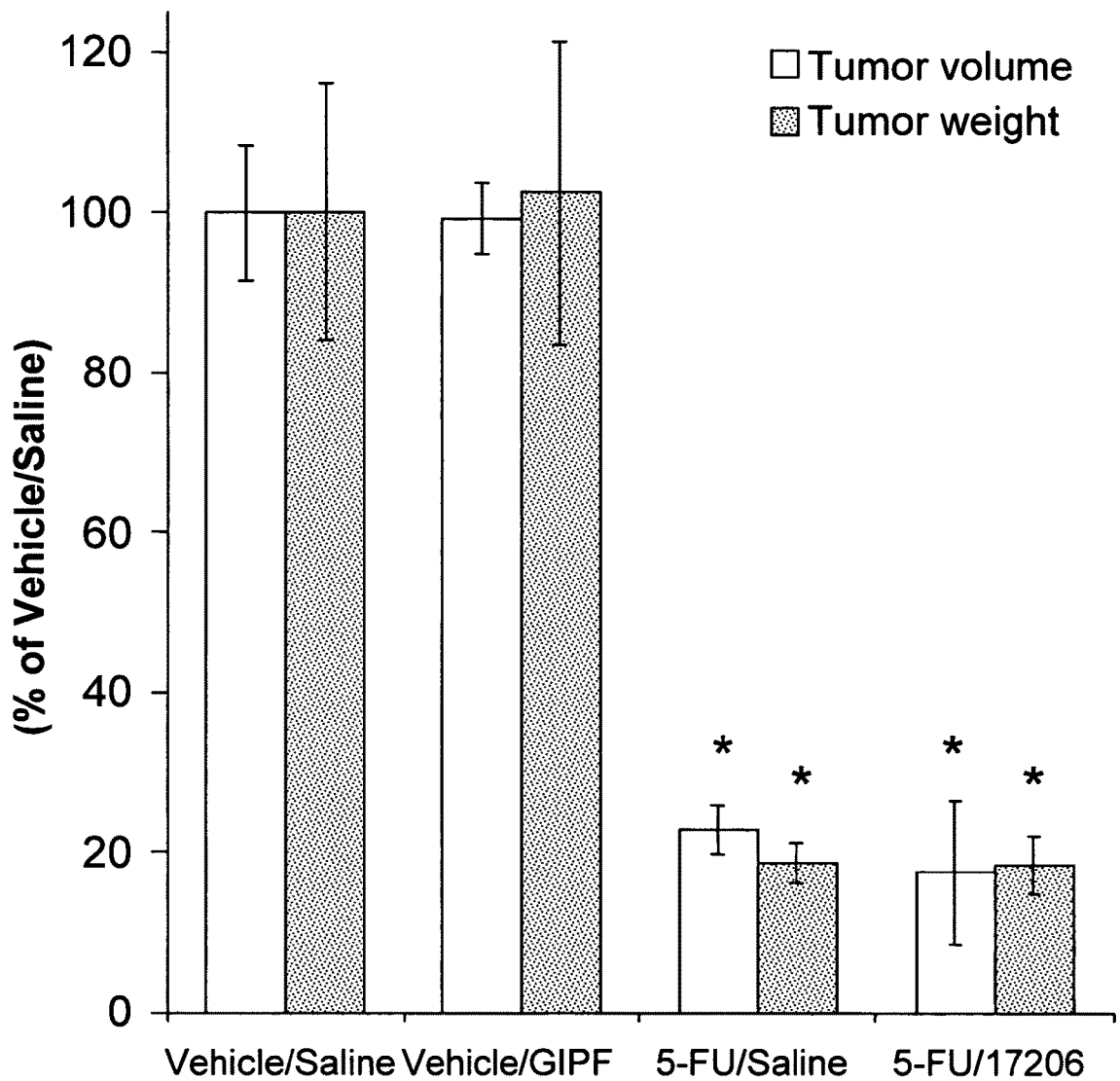

FIG. 24 Effect of 5-FU on the size of tumors in control mice and mice receiving GIPFwt.

FIG. 25 Effect of GIPF on the gross pathology of the small intestine and colon of normal (E and F) and tumor-bearing mice (A-D).

Figure 26:
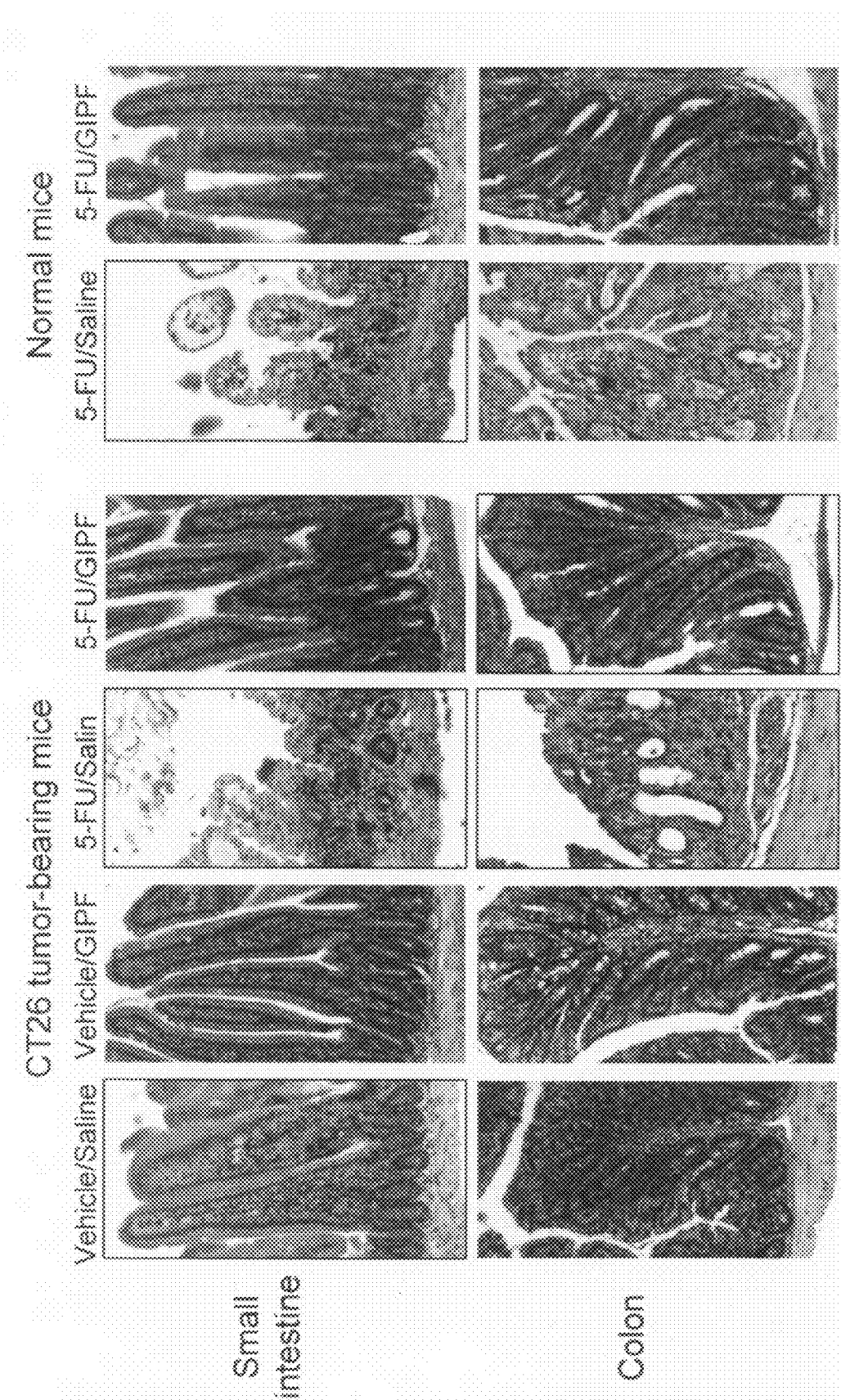

FIG. 26 H&E staining of cross sections derived from the small intestine and colon of normal and tumor-bearing mice that had received 5-FU and/or GIPF.

Figure 27:
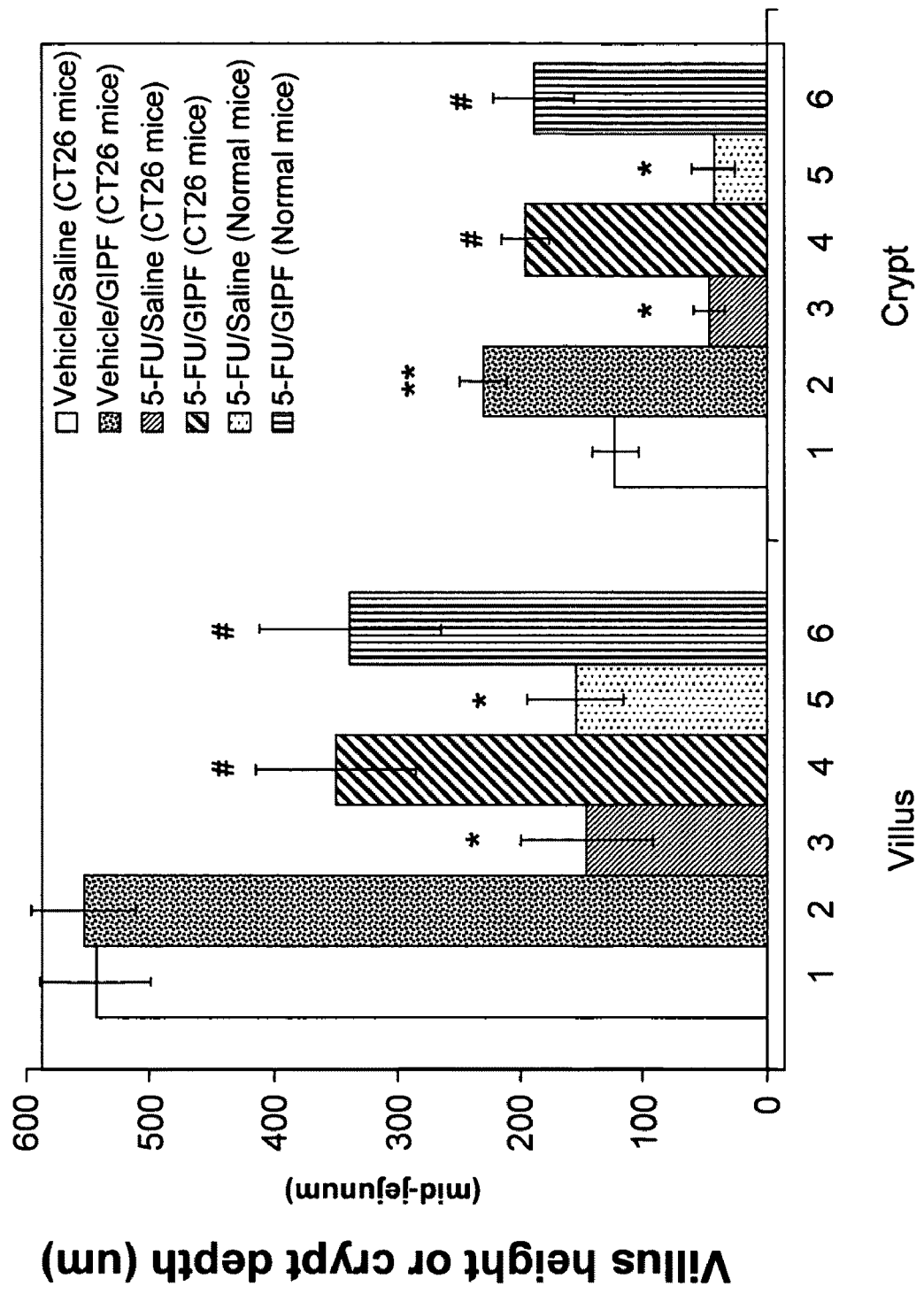

FIG. 27 Micromorphometry measurements of the villus height and crypt depth show the effect of GIPF on the intestinal epithelium of mice that received 5-FU.

Figure 28:
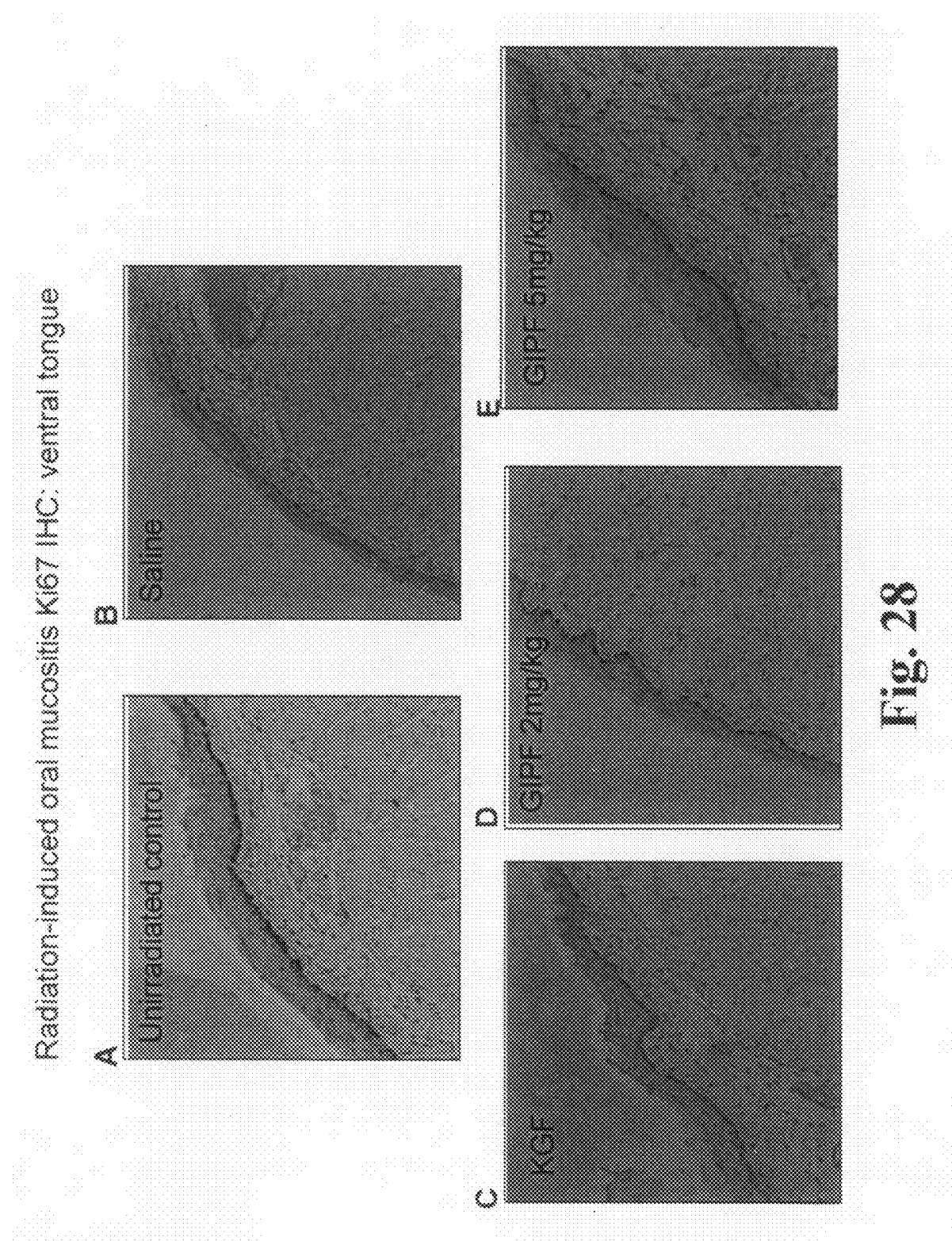

FIG. 28 Ki67 staining of proliferating epithelial cells of the ventral tongue of control mice (A and B), and mice treated with KGF or GIPF (C-E) and submitted to total body irradiation.

Figure 29:
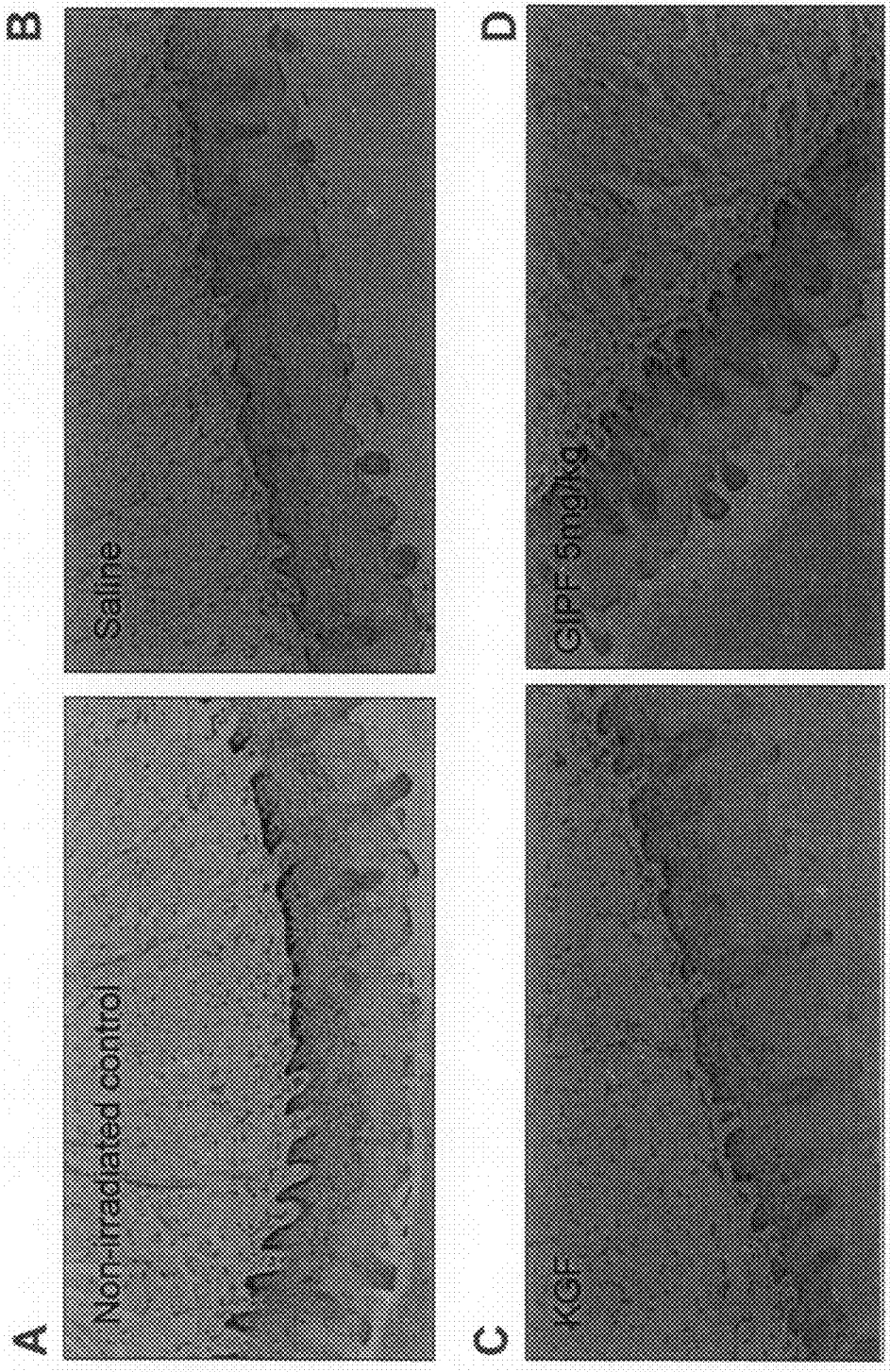

FIG. 29 Ki67 staining of proliferating epithelial cells of the dorsal tongue of control mice (A and B), and mice treated with KGF or GIPF (C and D) and submitted to total body irradiation.

Figure 30:
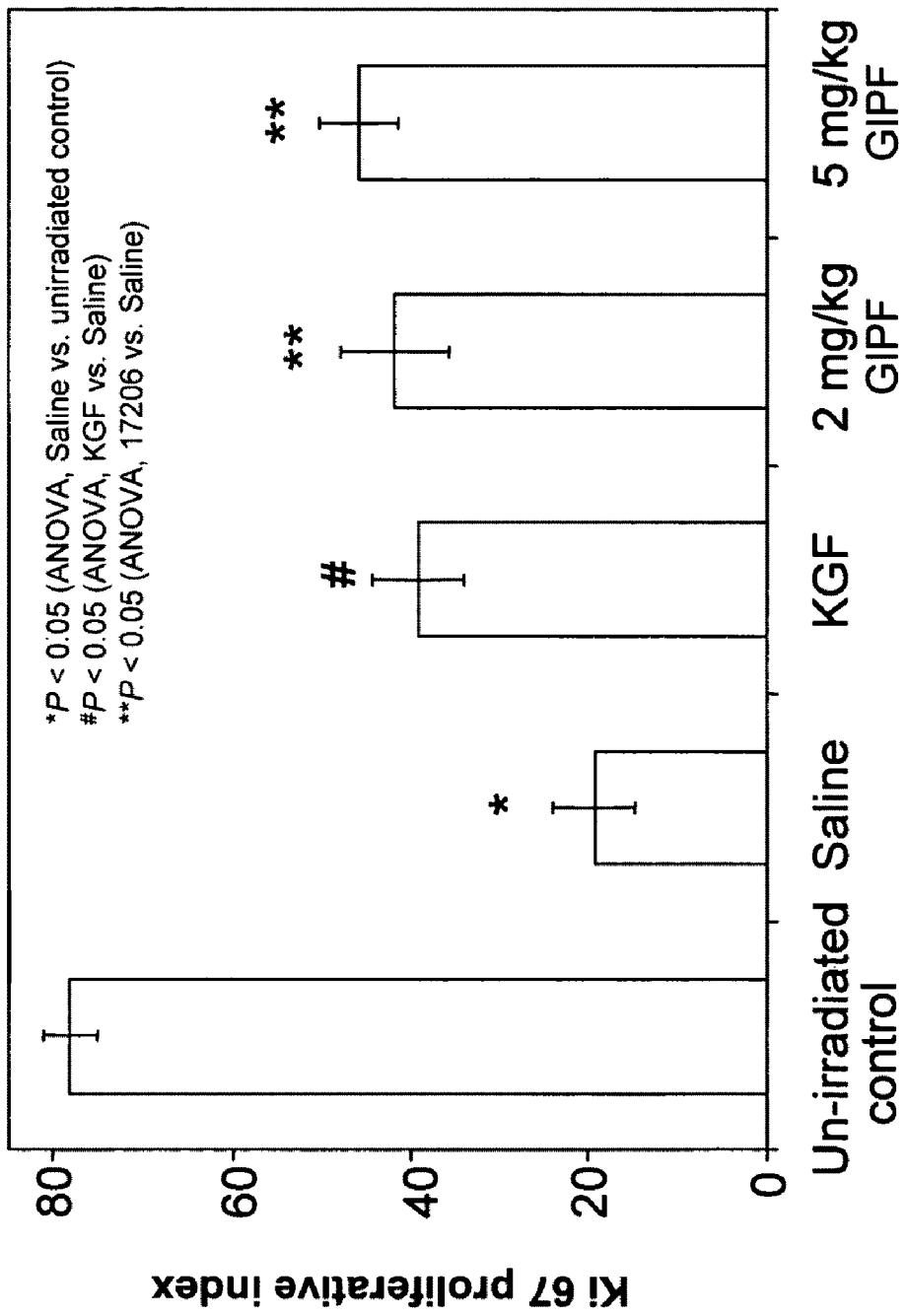

FIG. 30 Proliferative index of ventral tongue epithelium from mice treated with KGF or GIPF and submitted to total body irradiation.

Figure 31:
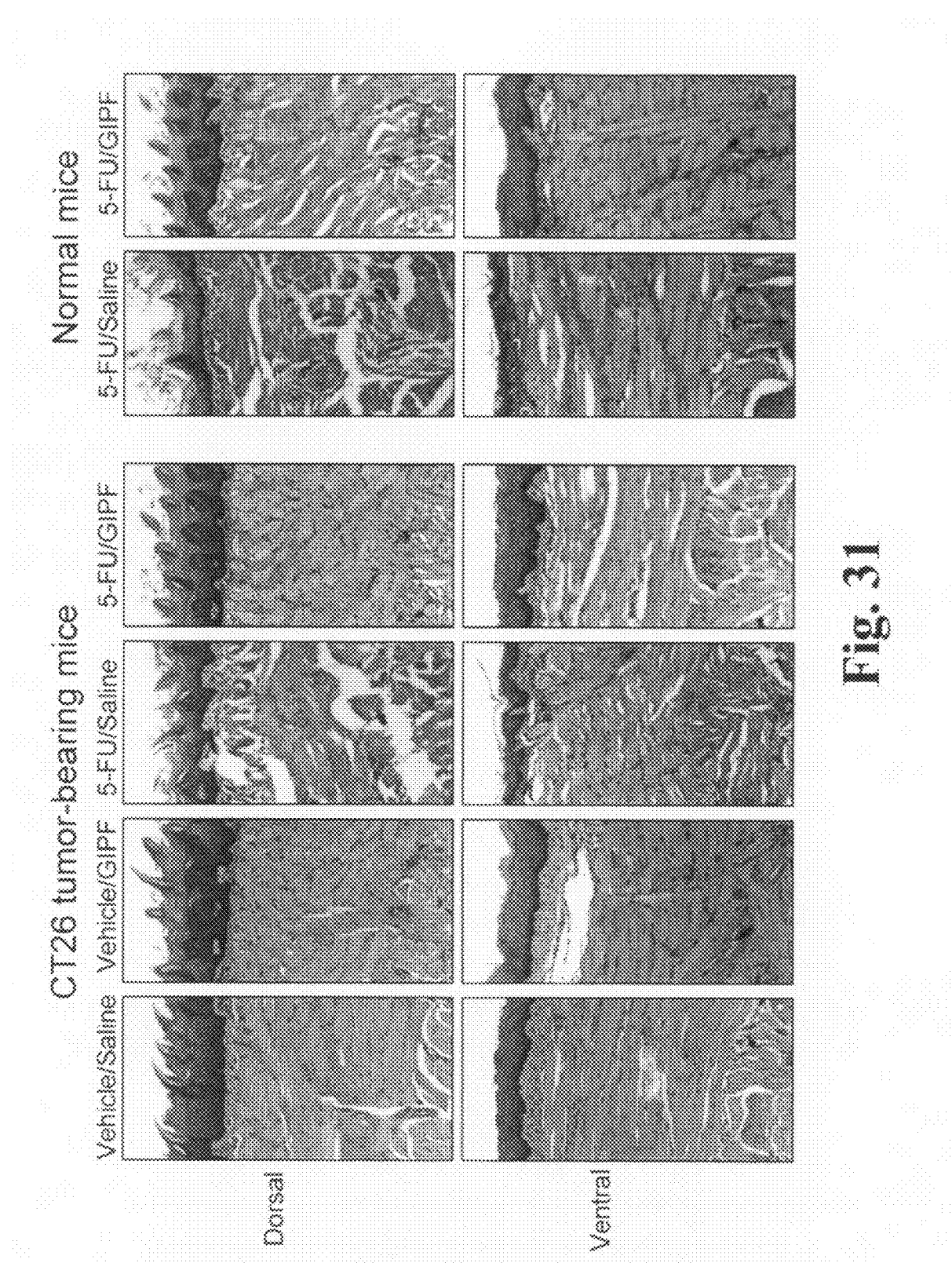

FIG. 31 H&E staining of sections derived from the tongue of mice treated with GIPF and submitted to total body irradiation.

Figure 32:
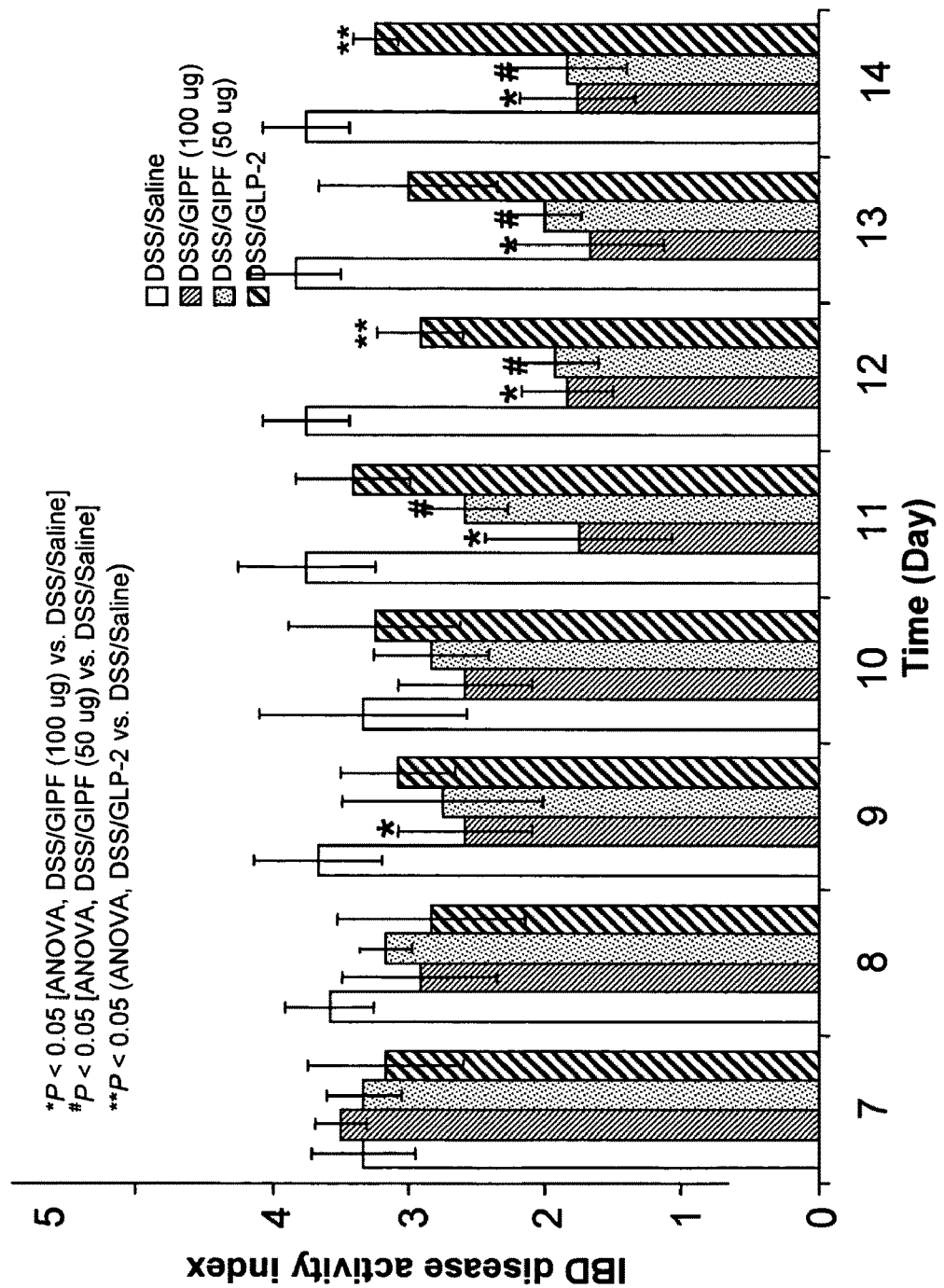

FIG. 32 Effect of GIPF on the inflammatory bowel disease activity index (IBDAI) of mice with DSS-iduced colitis.

Figure 33:
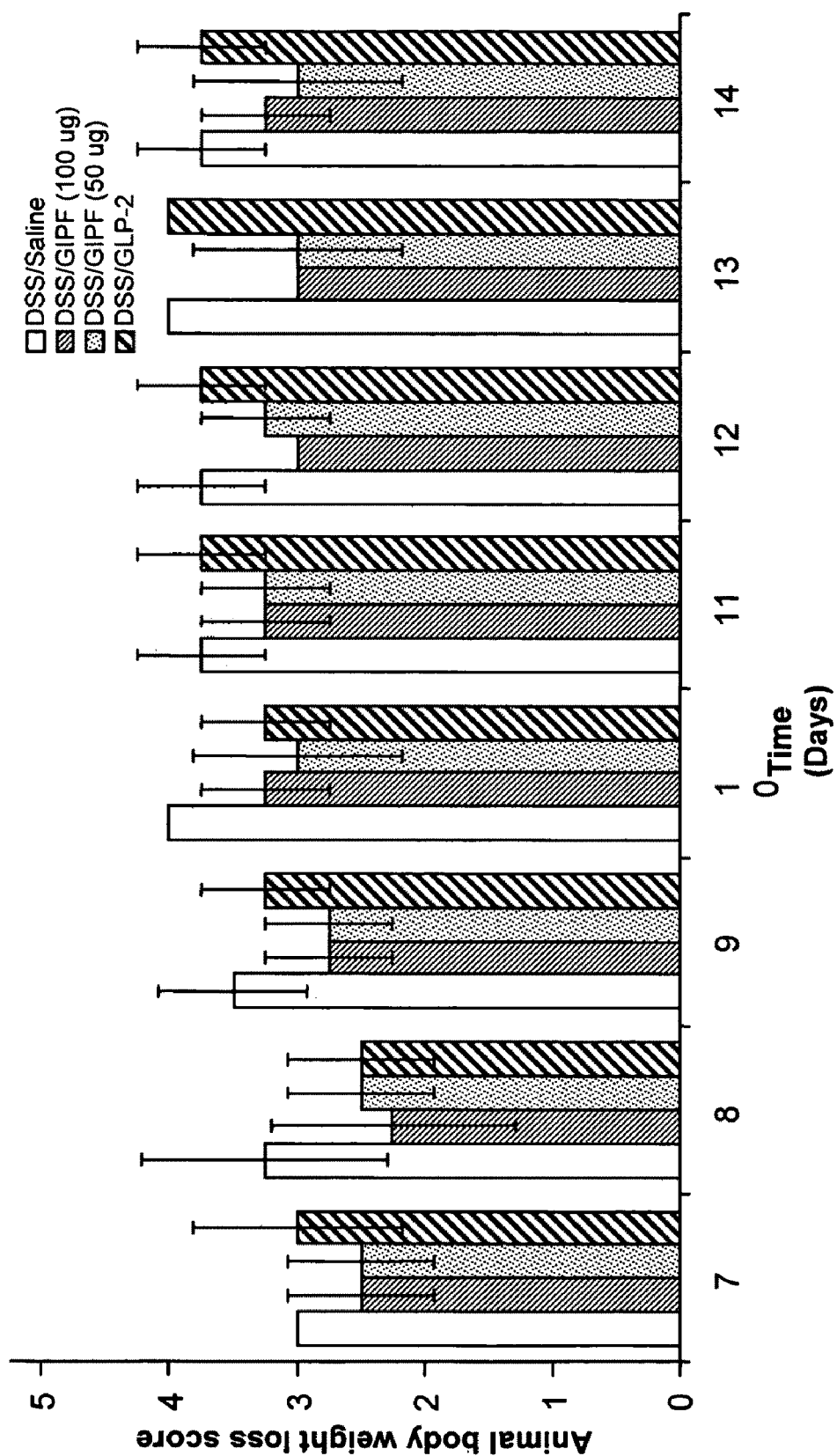

FIG. 33 Effect of GIPF on the score for animal body weight in mice with DSS-induced colitis.

Figure 34:
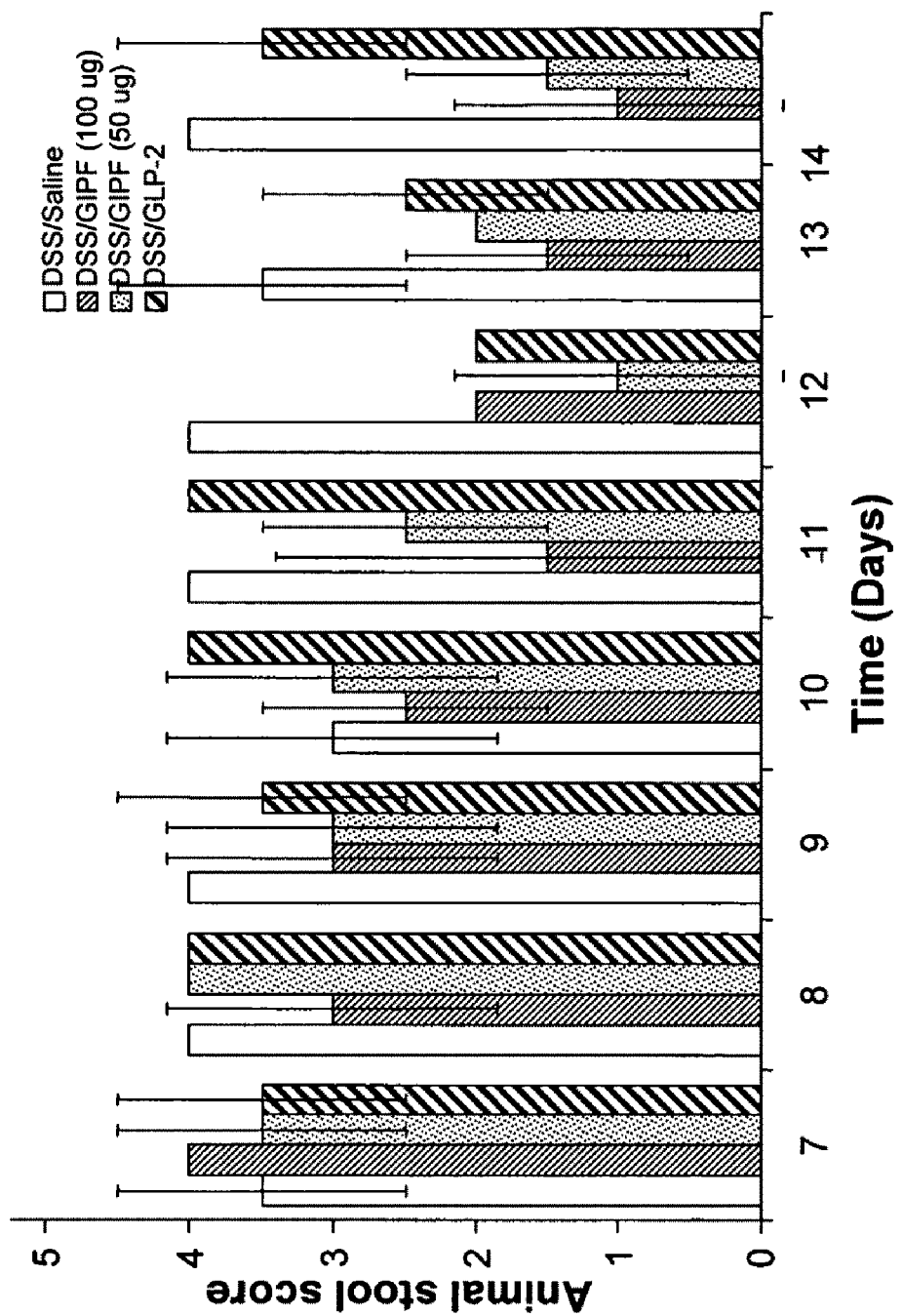

FIG. 34 Effect of GIPF on the score for stool consistency in mice with DSS-induced colitis.

Figure 35:
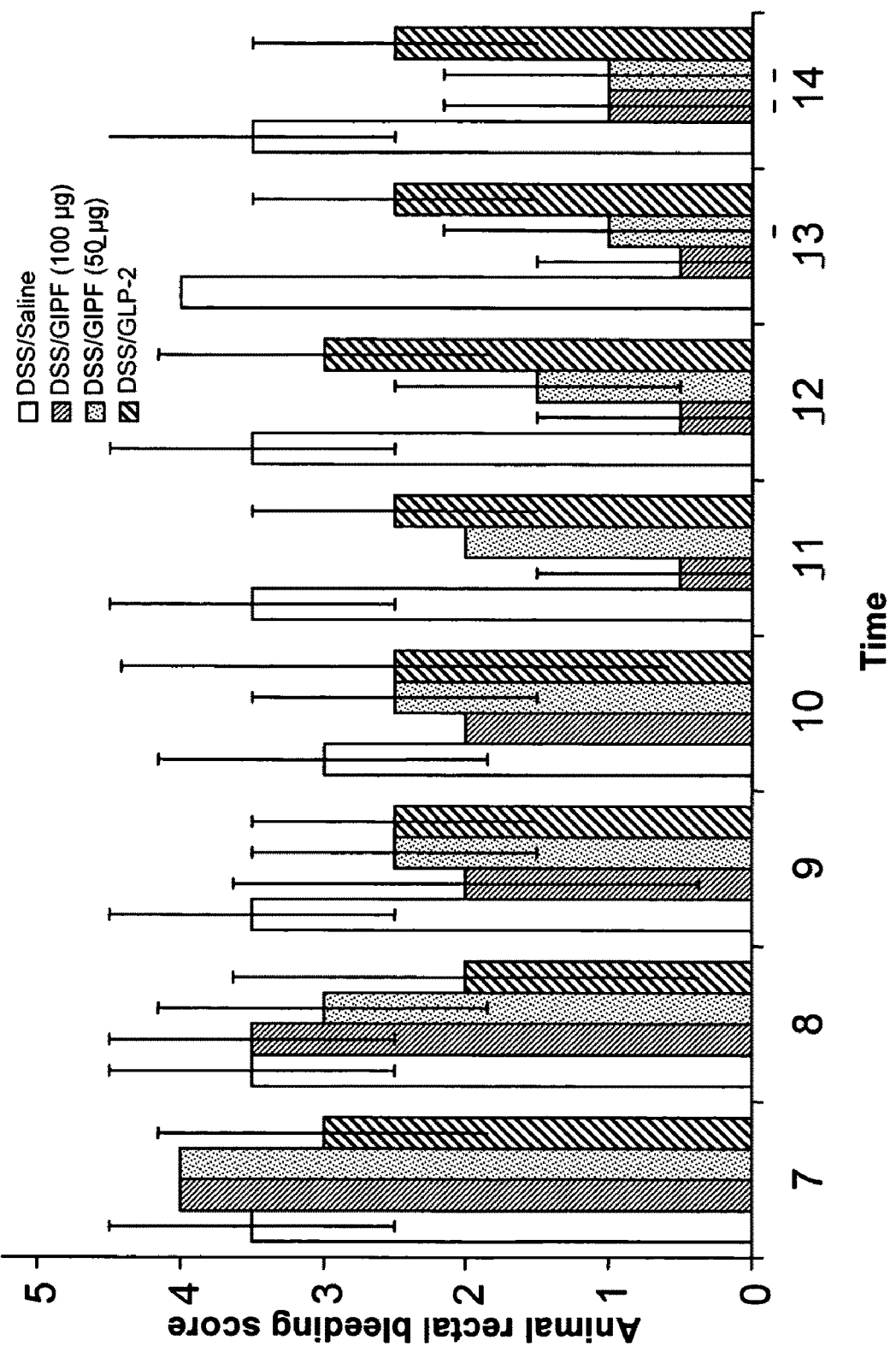

FIG. 35 Effect of GIPF on the score for rectal bleeding in mice with DSS-induced colitis.

Figure 36:
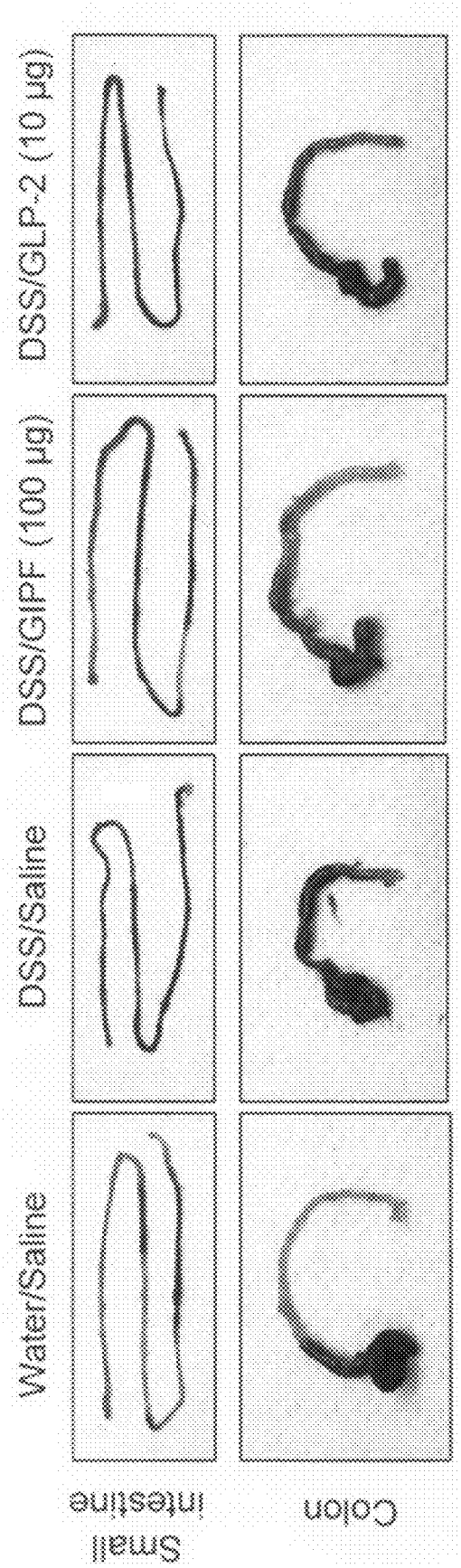

FIG. 36 Effect of GIPF on the gross pathology of the small intestine and colon of control and DSS-treated mice.

Figure 37:
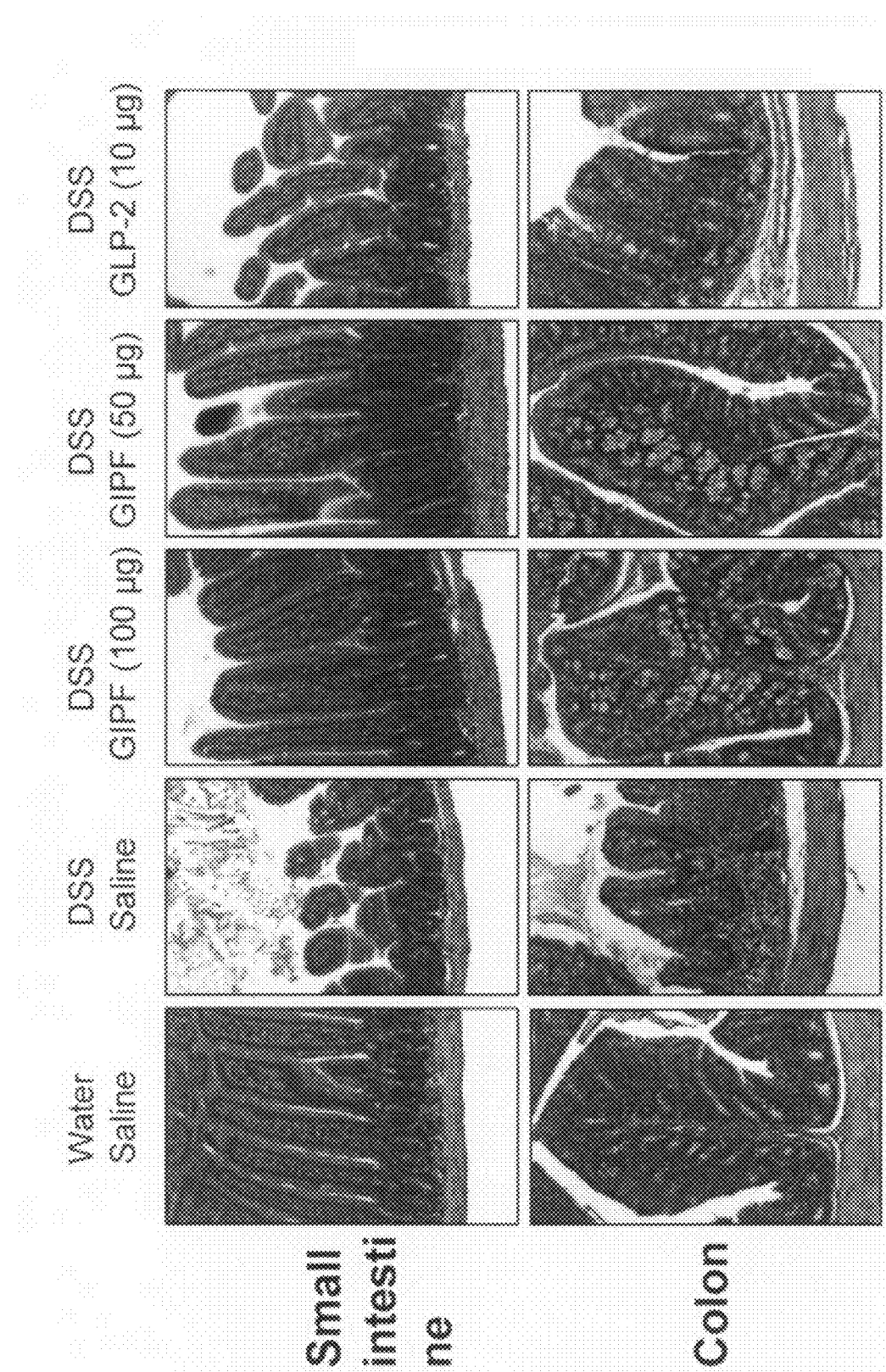

FIG. 37 H&E staining of cross sections derived from the small intestine and colon of mice that had received DSS and/or GIPF.

Figure 38:
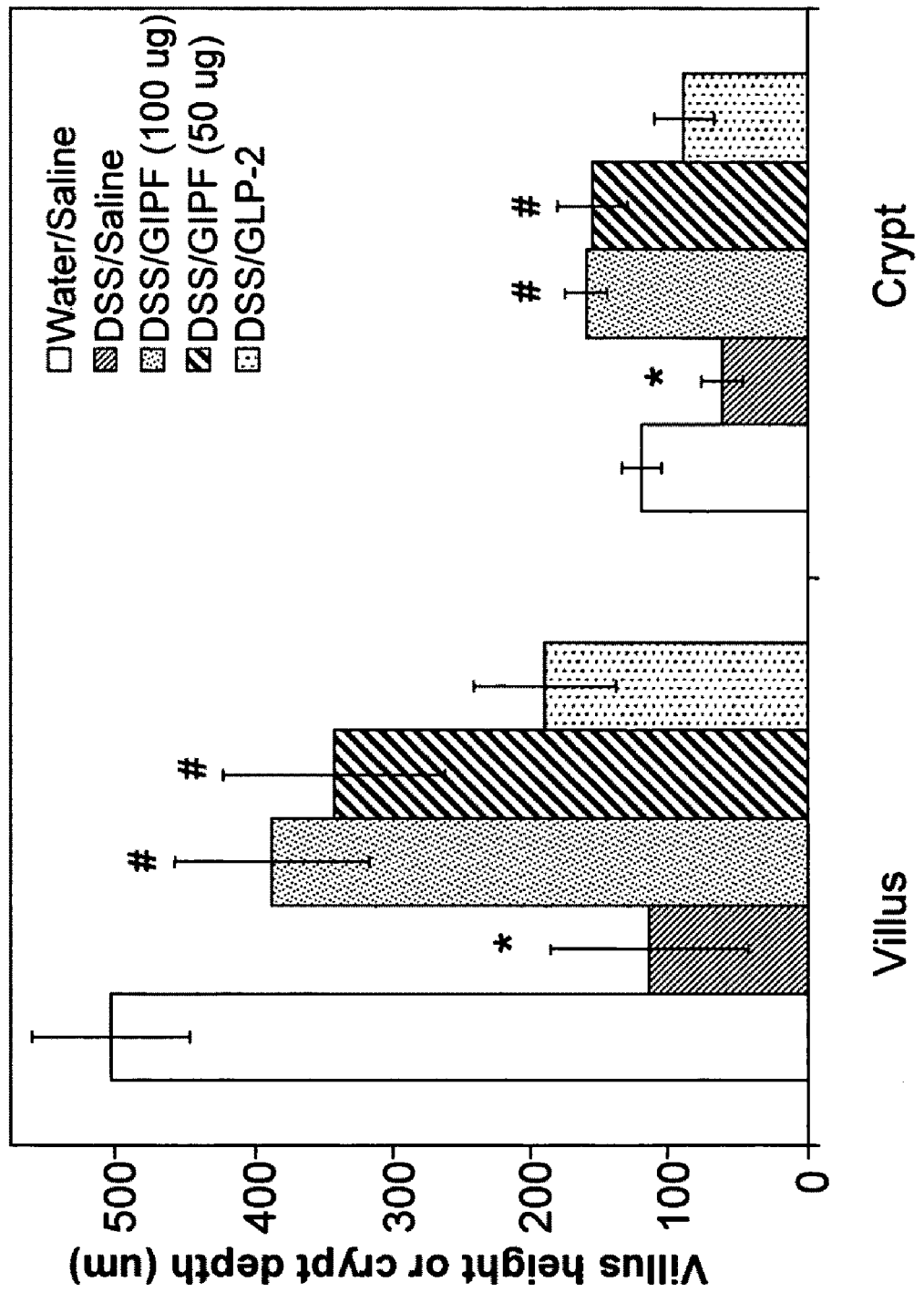

FIG. 38 Micromorphometry measurements of the villus height and crypt depth show the effect of GIPF on the intestinal epithelium of mice with DSS-induced colitis.

Figure 39:
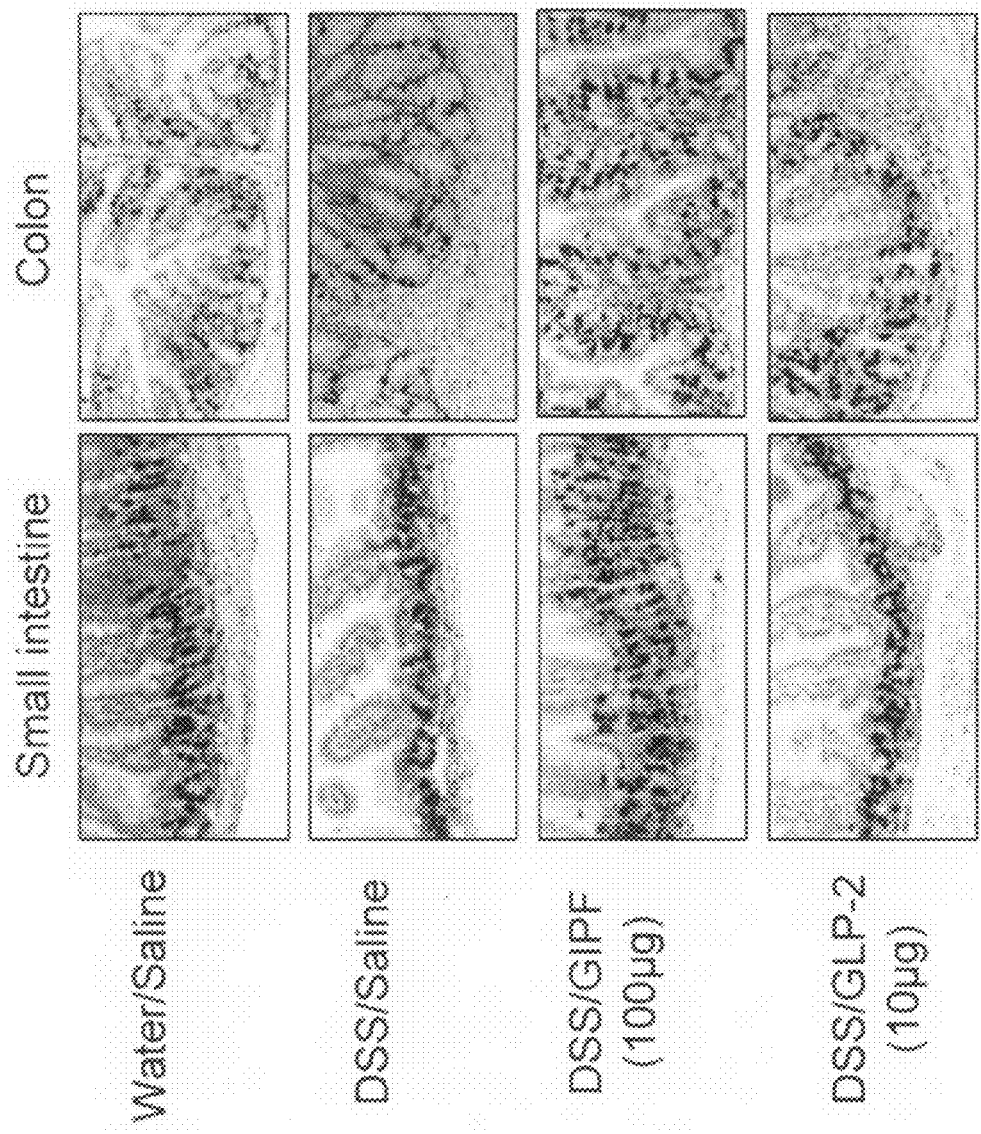

FIG. 39 Incorporation of BrdU into proliferating crypt cells of the small intestine and colon of mice that had received DSS and/or GIPF.

Figure 40:
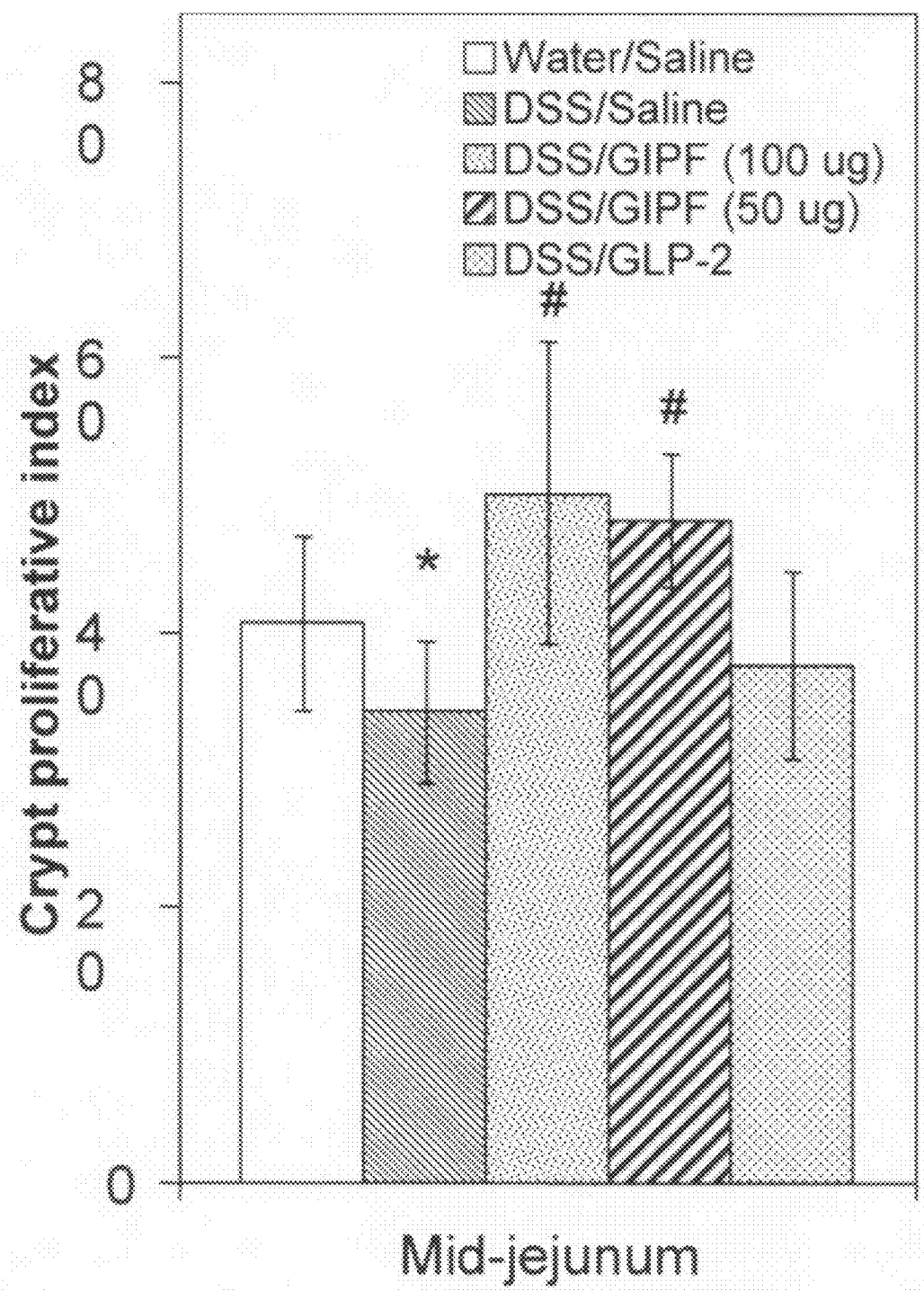

FIG. 40 Effect of GIPF on the proliferation of the small intestinal epithelium of mice with DSS-induced colitis.

Figure 41:
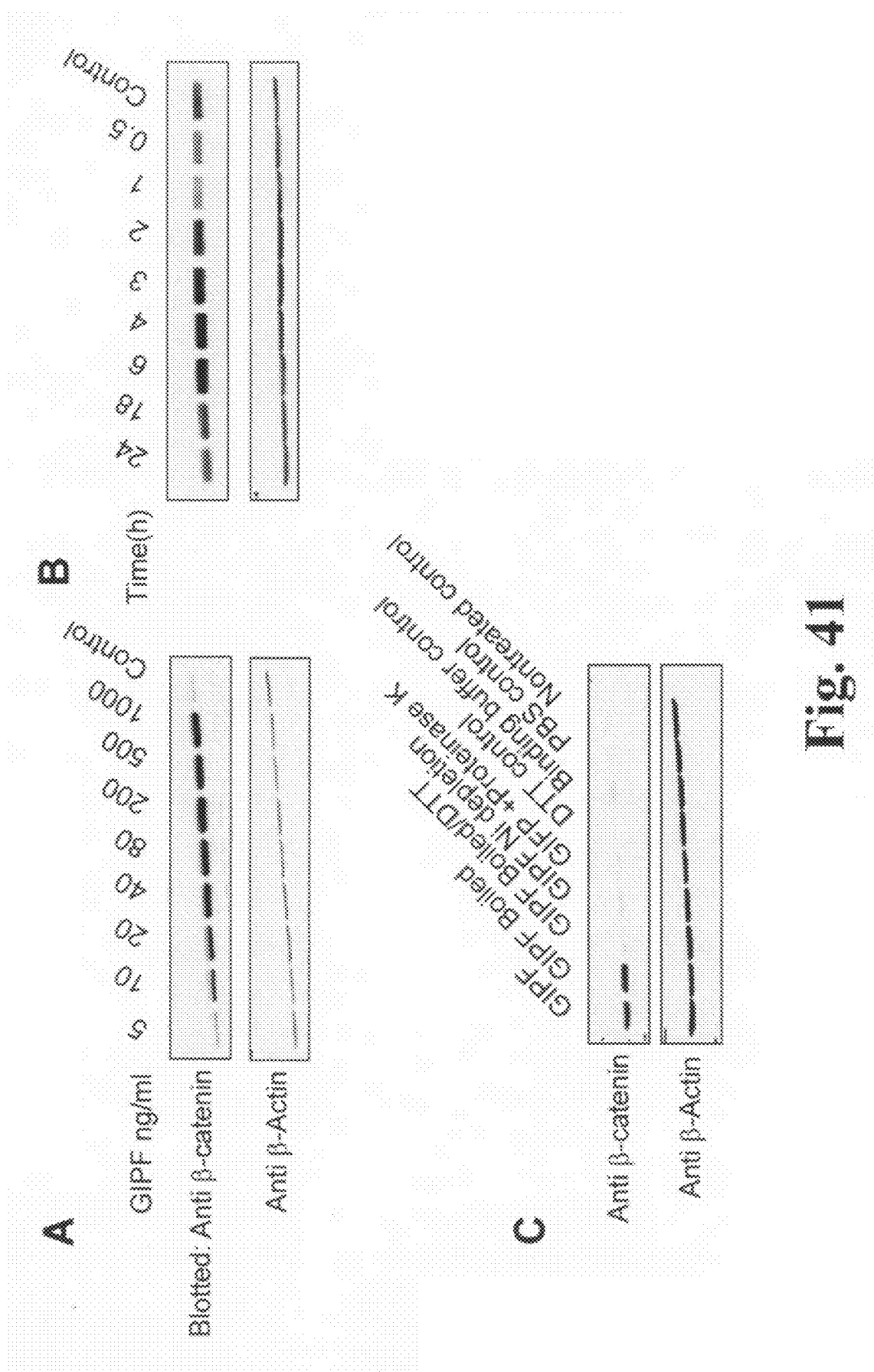

FIG. 41 Effect of GIPF on the stabilization of β-catenin in human endocrinic and kidney epithelial cells. GIPF induced the dose-dependent (A) and time-dependent (B) stabilization of β-catenin in HEK293 cells. The stabilizing effect of GIPF is not disrupted by boiling (C).

Figure 42:
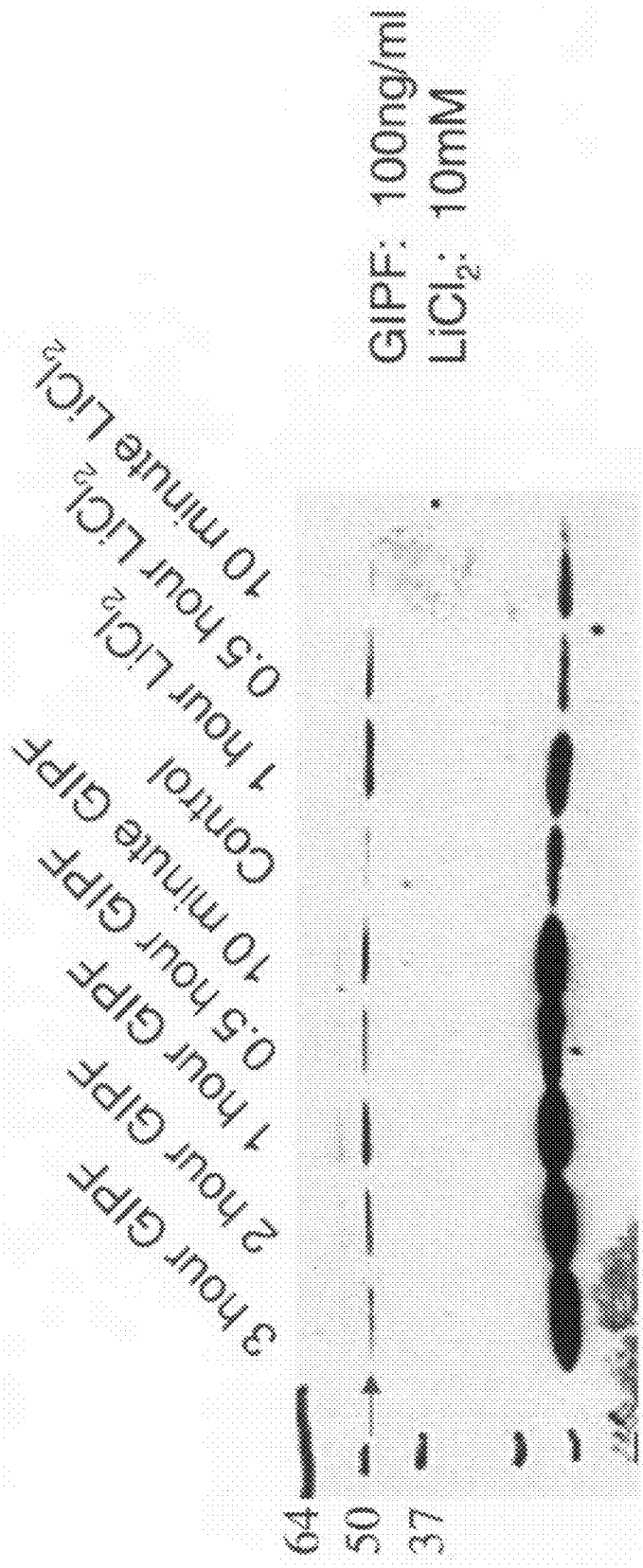

FIG. 42 Effect of GIPF on the phosphorylation of GSK3β.

Figure 43:
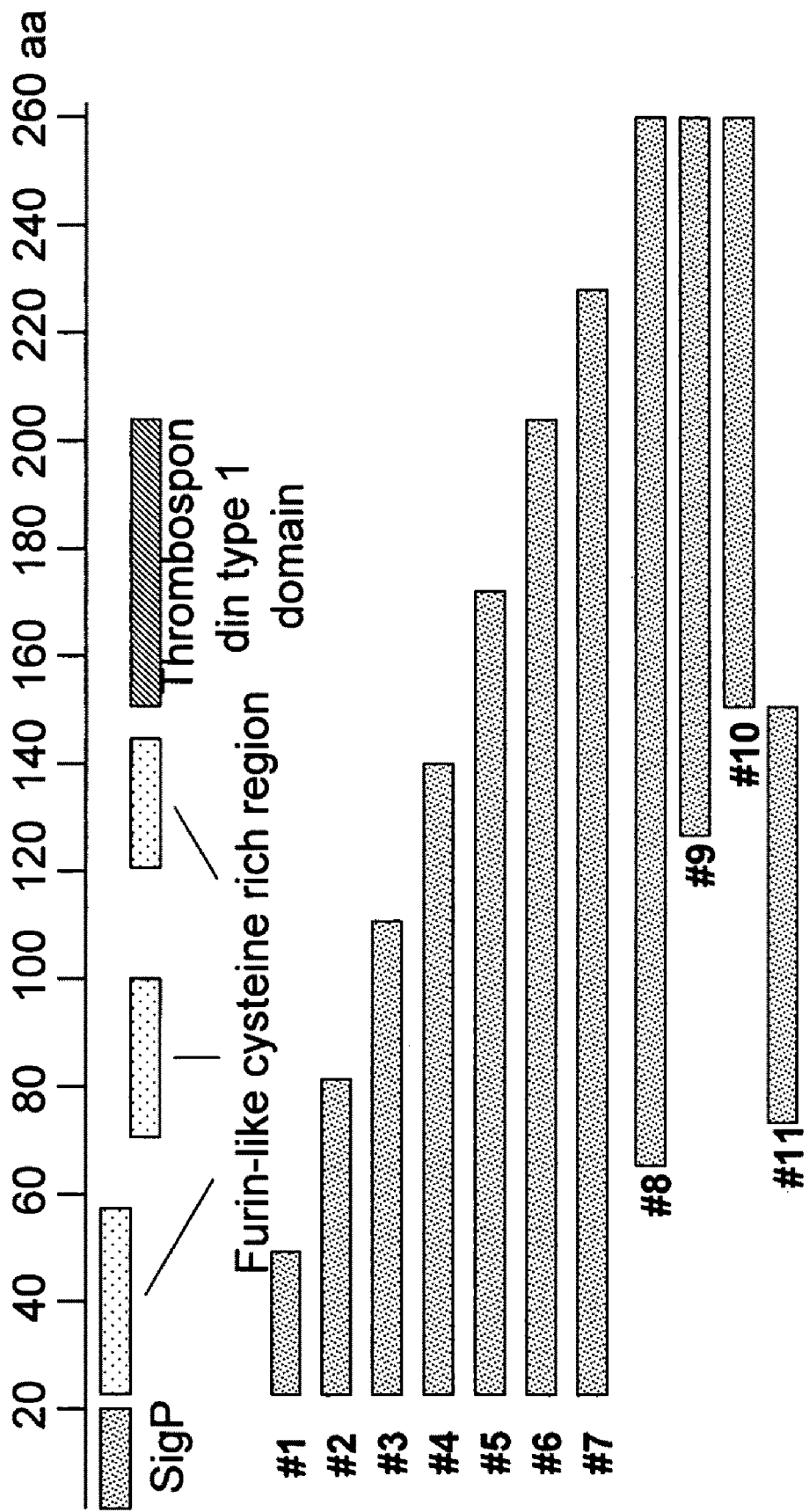

FIG. 43 Schematic representation GIPF polypeptide analogs designed to determine the ability of various regions of GIPF in stabilizing β-catenin. The fragment numbers 1-11 respectively correspond to polypeptide SEQ ID NOs; 85, 87, 89, 91, 93, 95, 97, 99, 101, 103, and 105.

Figure 44:
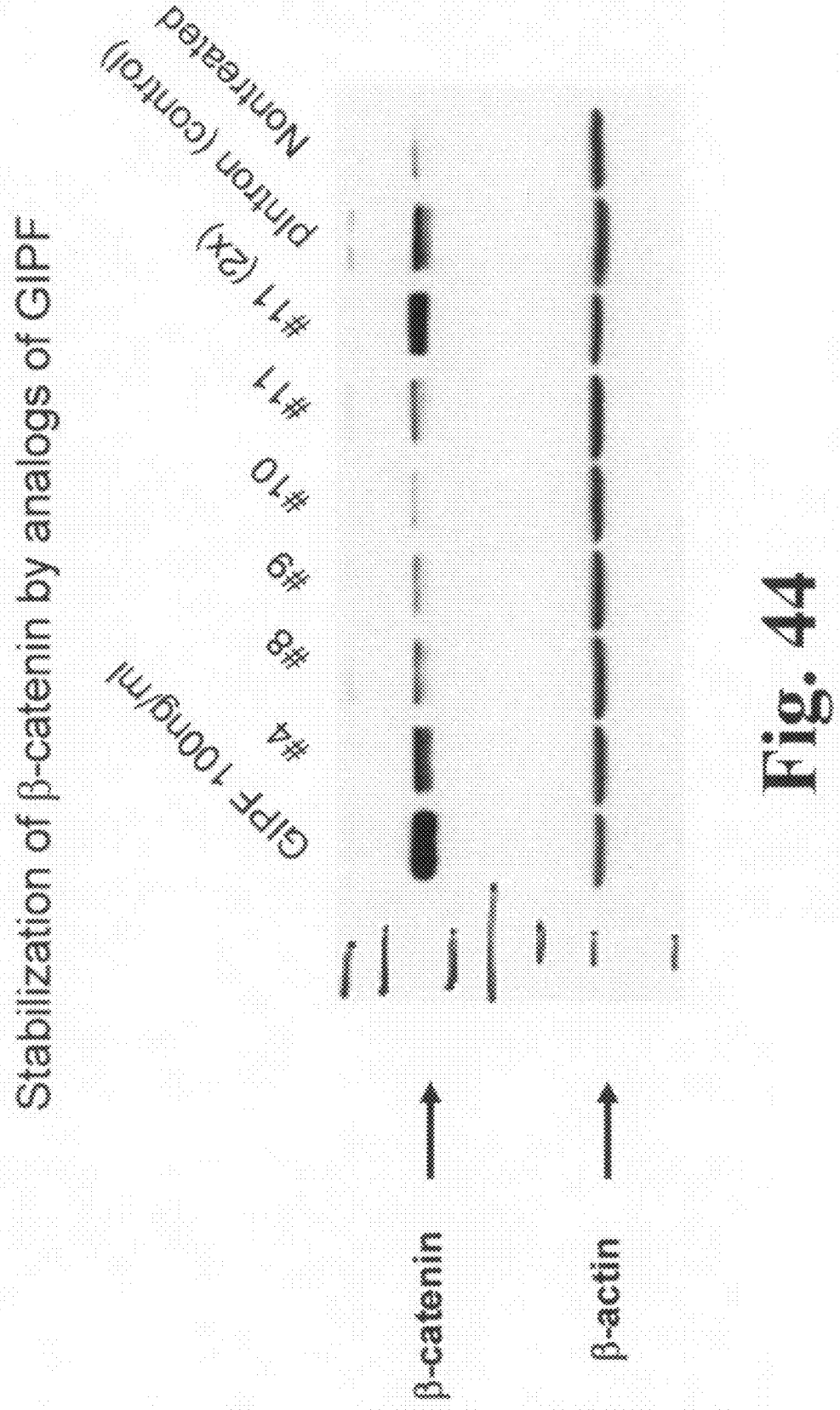

FIG. 44 Stabilization of β-catenin by the GIPF analogs depicted in FIG. 43.

Figure 45:
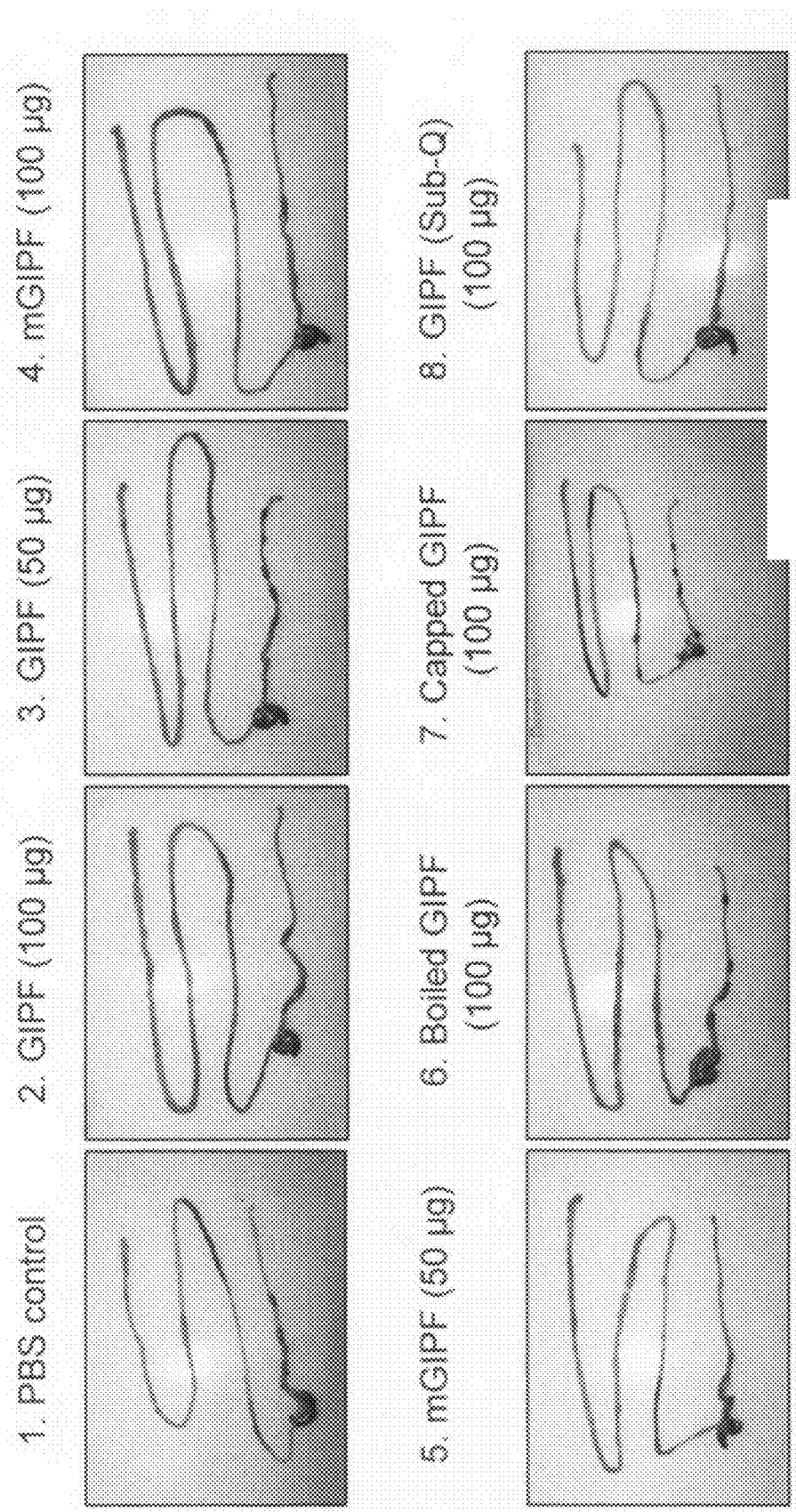

FIG. 45 Comparison of the activity of human and mouse GIPF on the gross pathology of mouse intestines.

Figure 46:
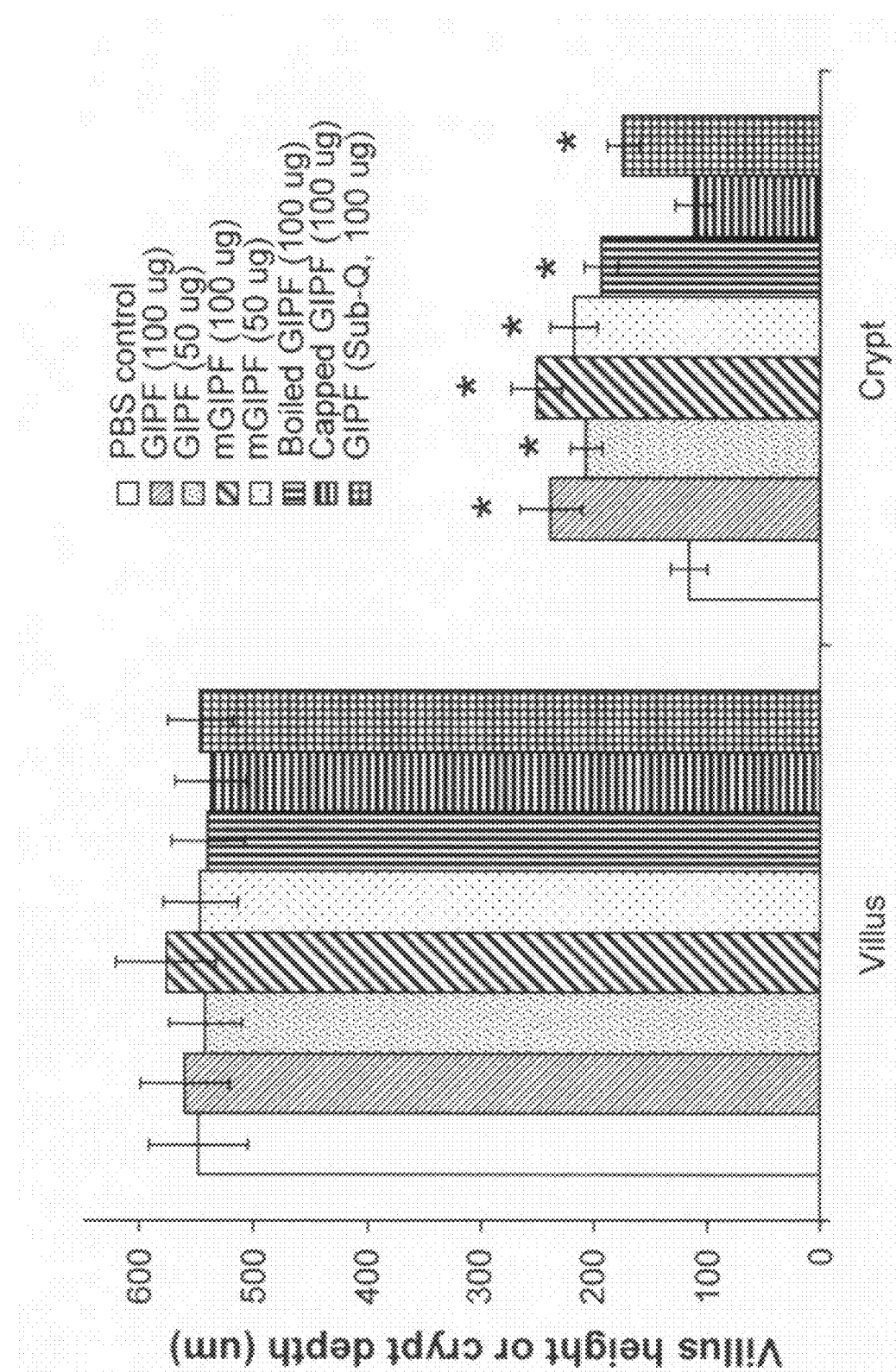

FIG. 46 Effect of GIPF on intestinal crypt depth.

Figure 47:
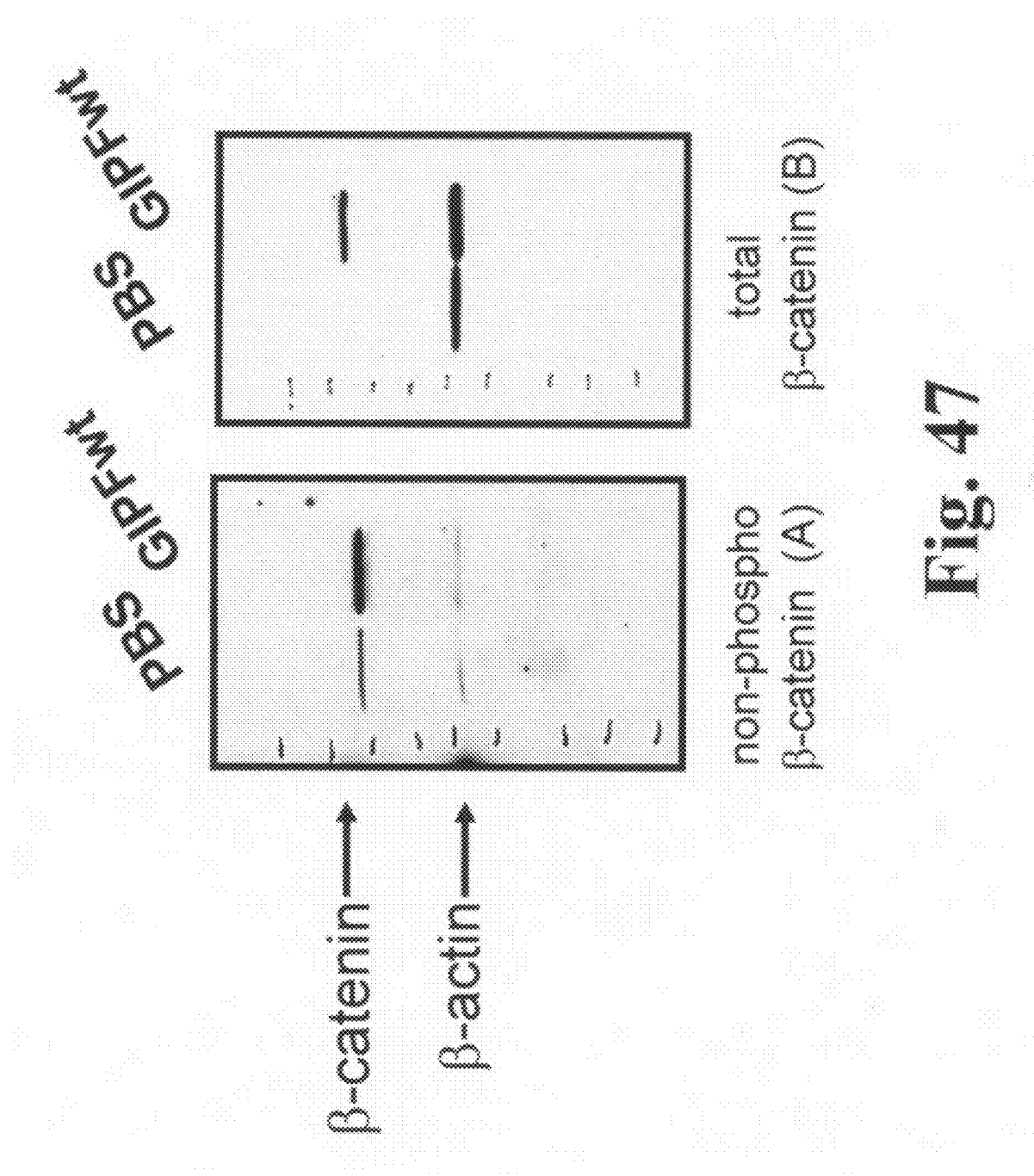

FIG. 47 Effect of GIPF on the stabilization of β-catenin in isolated crypt cells.

Figure 48:
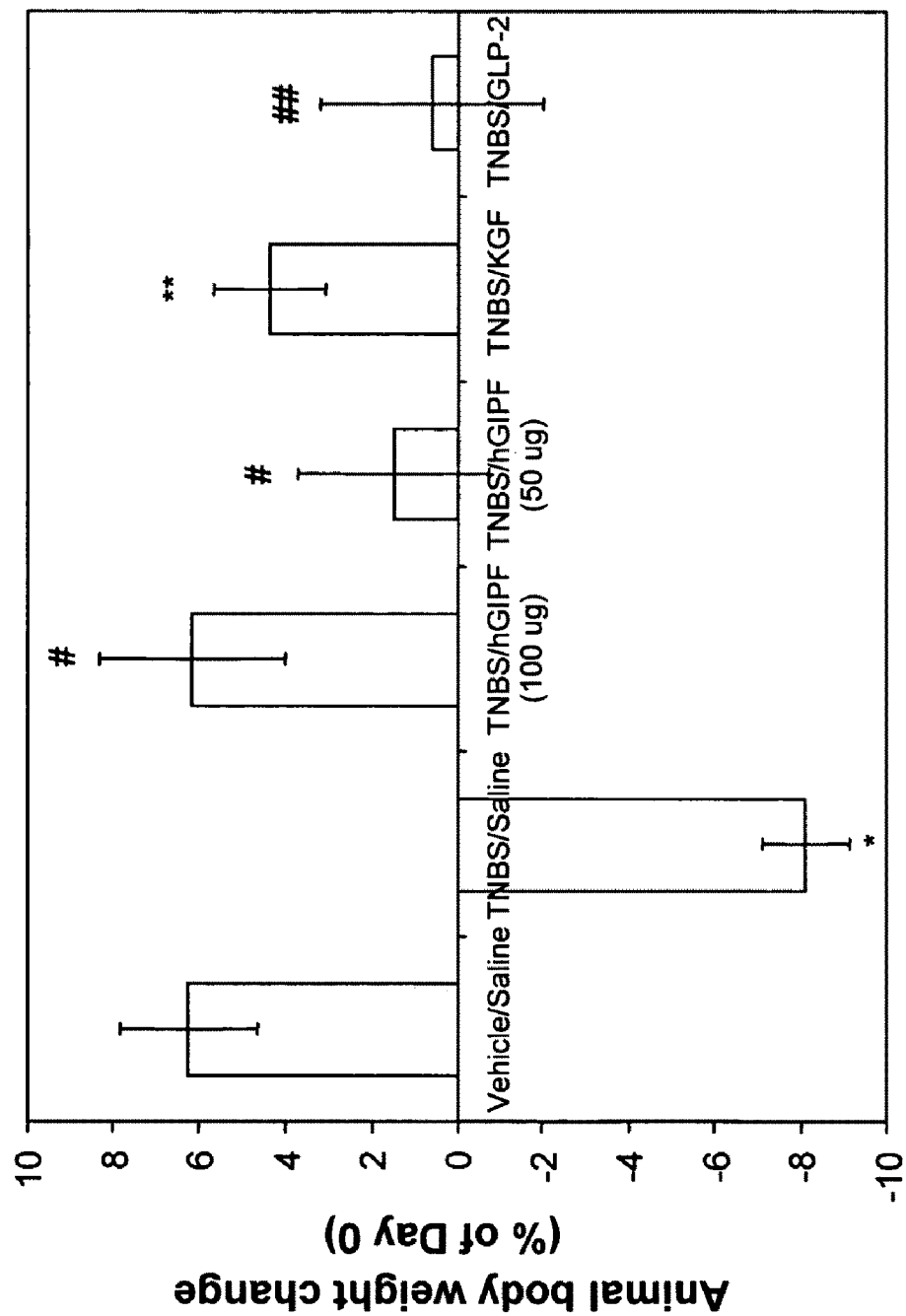

FIG. 48 Effect of GIPF on body weight of animals with TNBS-induced colitis.

Figure 49:
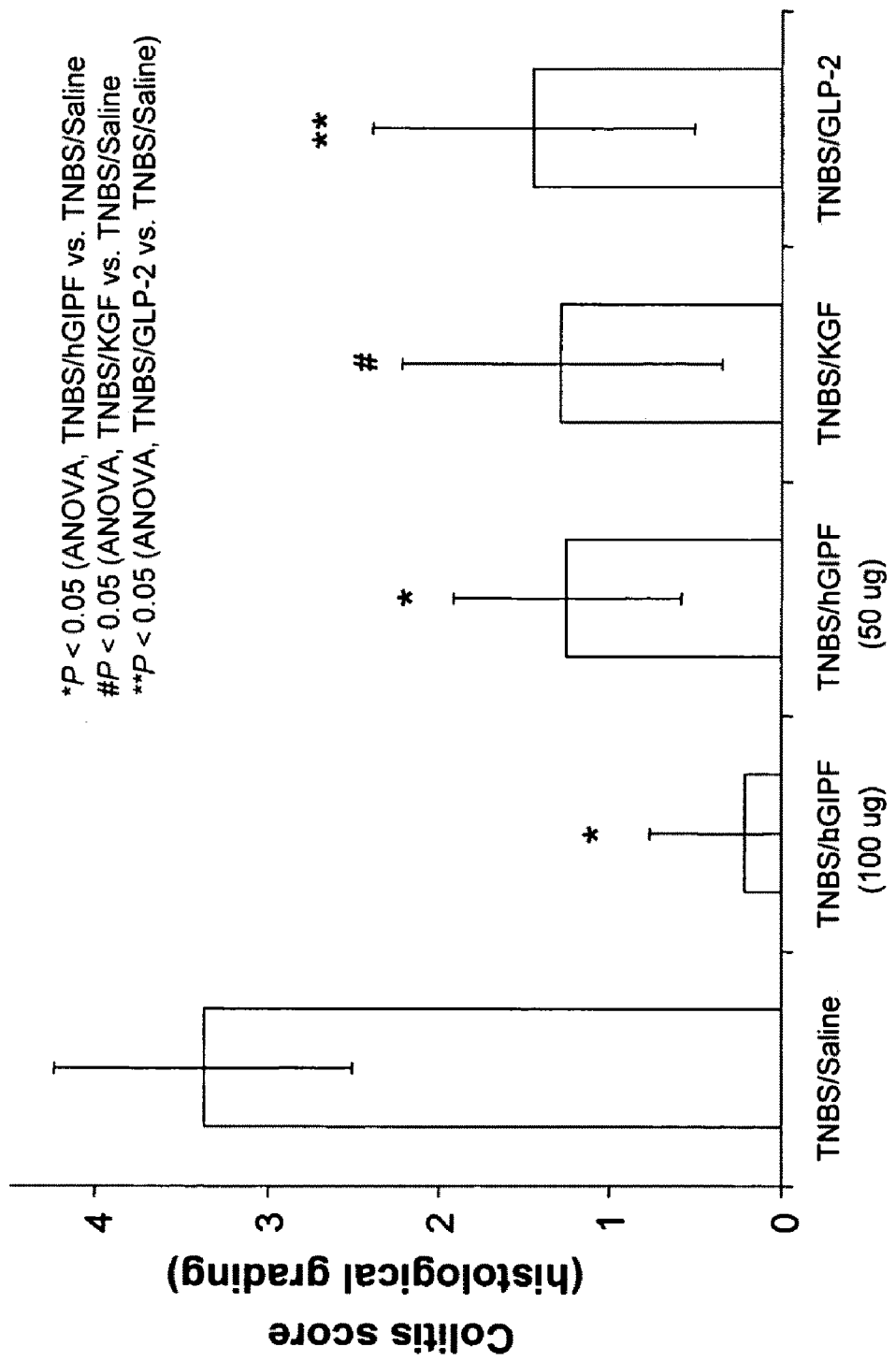

FIG. 49 Effect of GIPF on the colitis score in animals with TNBS-induced colitis.

Figure 50:
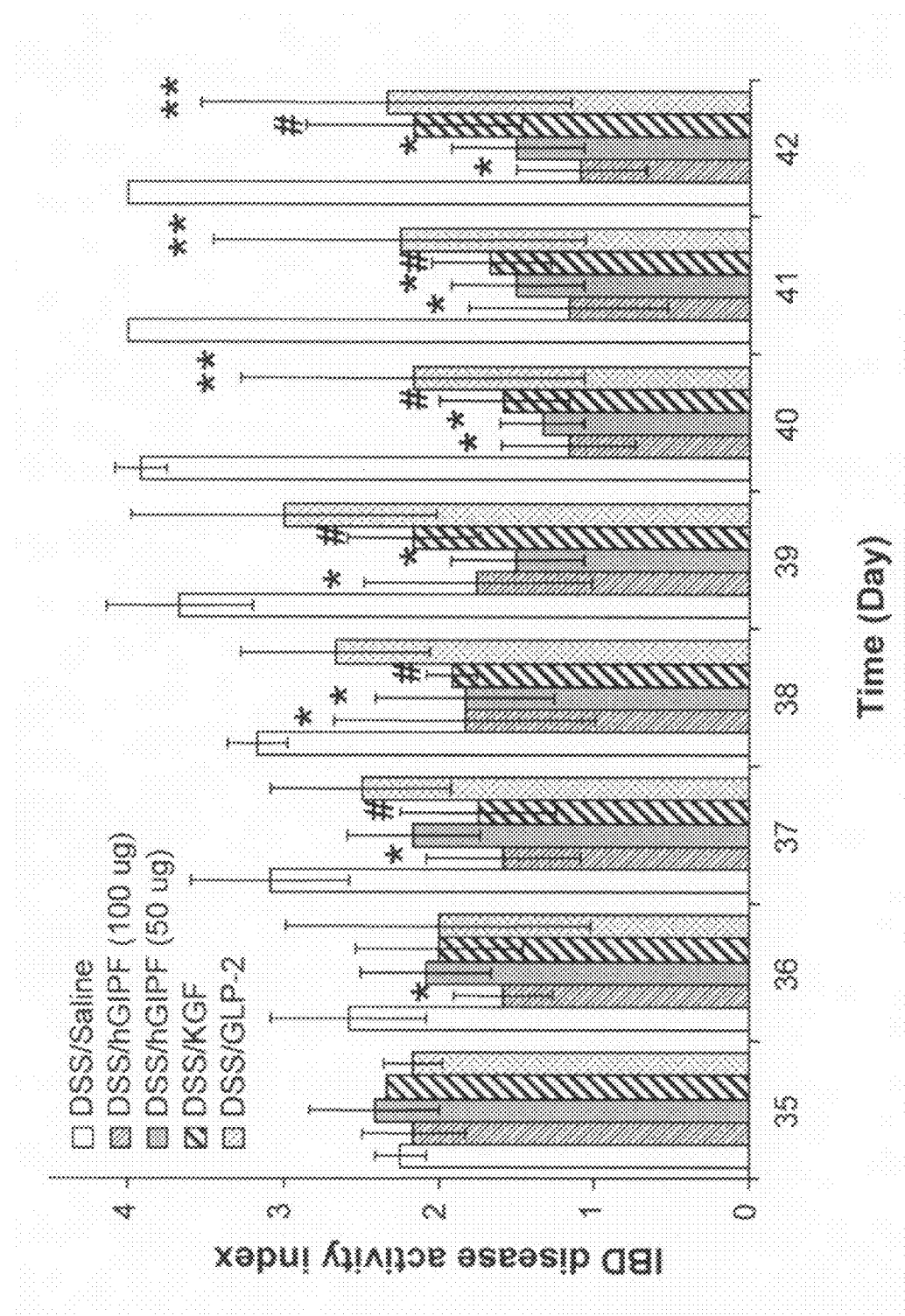

FIG. 50 Effect of GIPF on chronic colitis induced by DSS.

Figure 51:
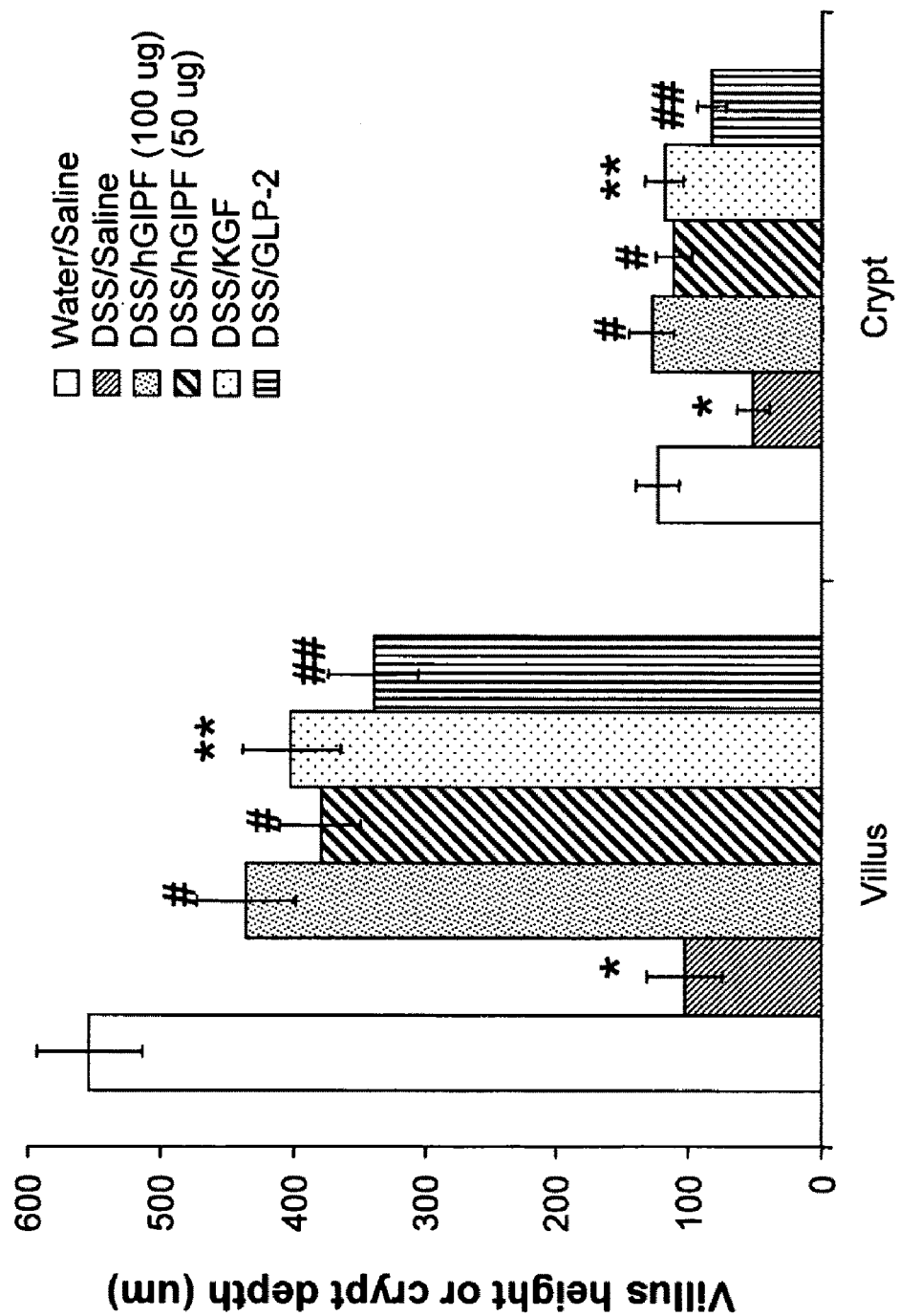

FIG. 51 Effect of GIPF on villus height and crypt depth in animals with DSS-induced chronic colitis.

Figure 52:
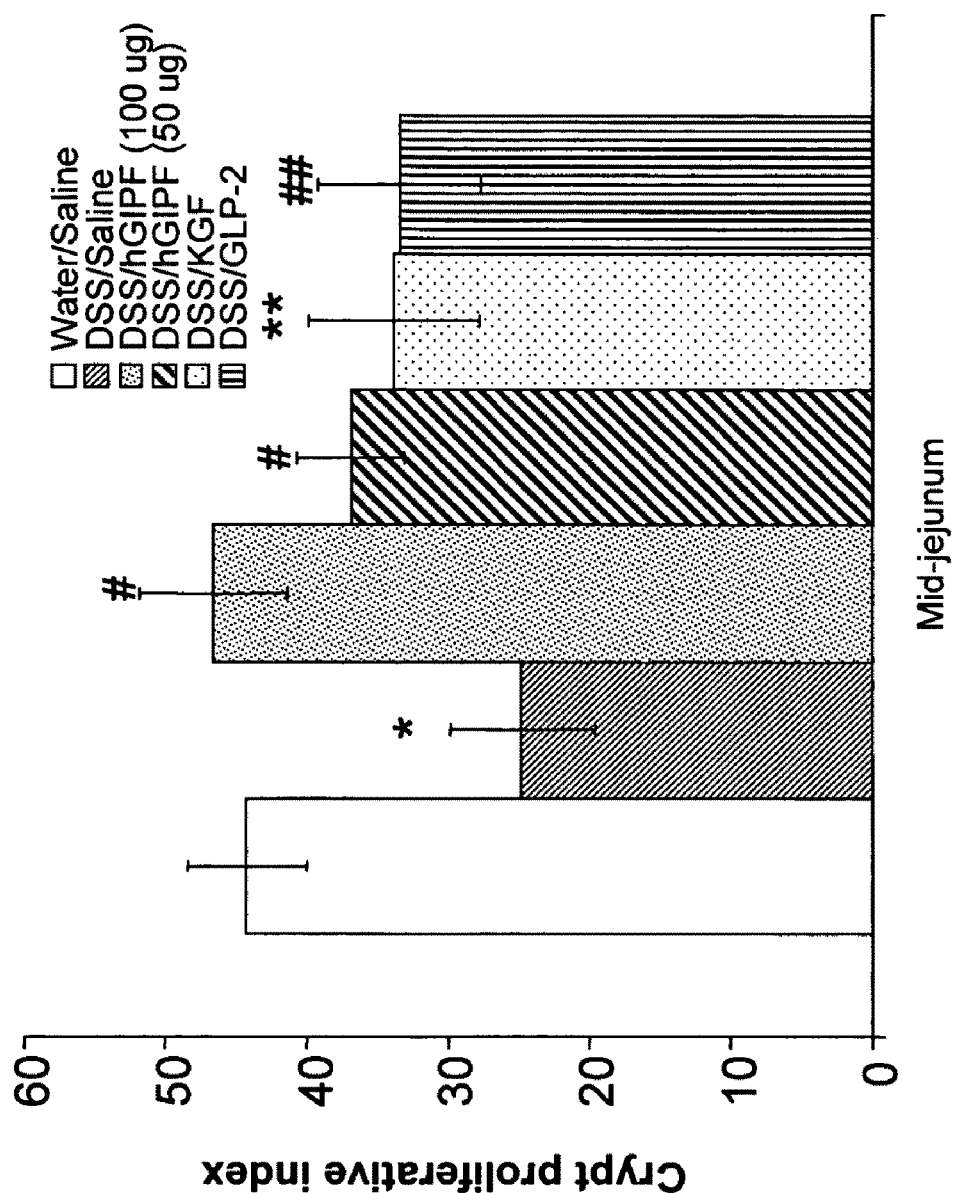

FIG. 52 Effect of GIPF on the crypt proliferative index of animals with DSS-induced chronic colitis.

Figure 53:
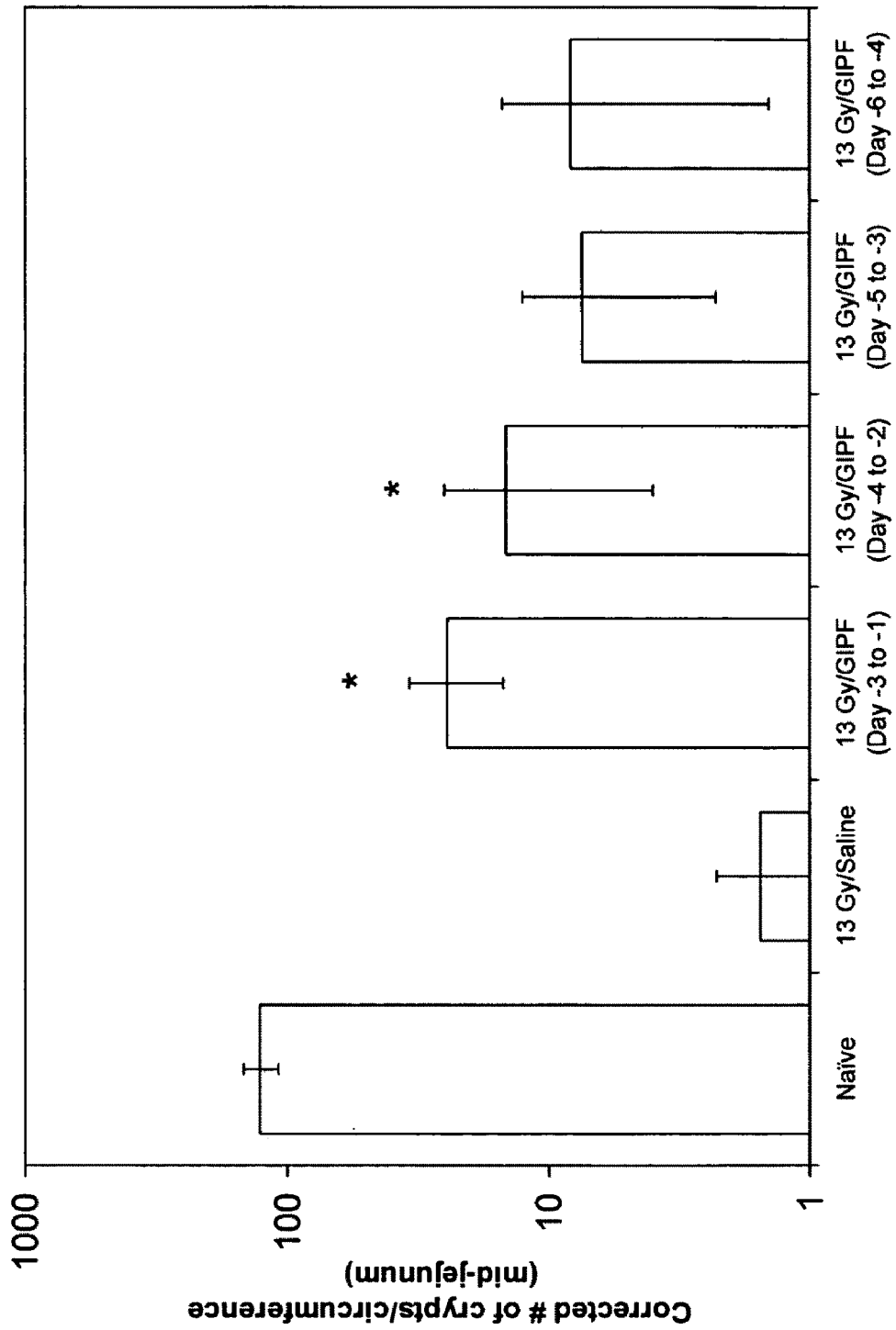

FIG. 53 Effect of GIPF on the survival of crypts following irradiation.

FIG. 54 A-N Diagrammatic representation of the construction of a transgene for the villin-driven expression of GIPF in the epithelium of transgenic mice.

Figure 55:
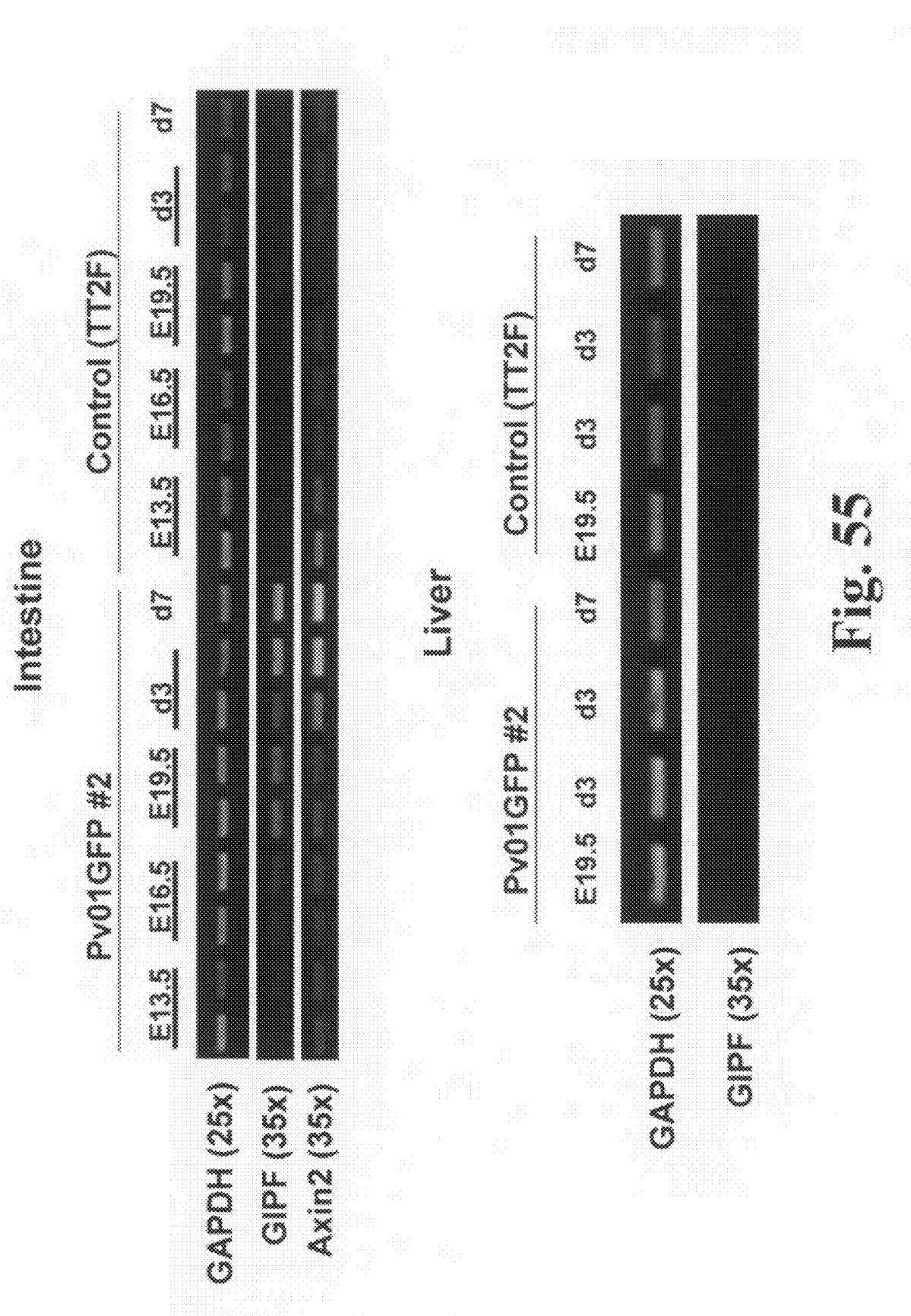

FIG. 55 Embryonic expression of GIPF in the intestinal epithelium and liver of transgenic mice.

Figure 56:
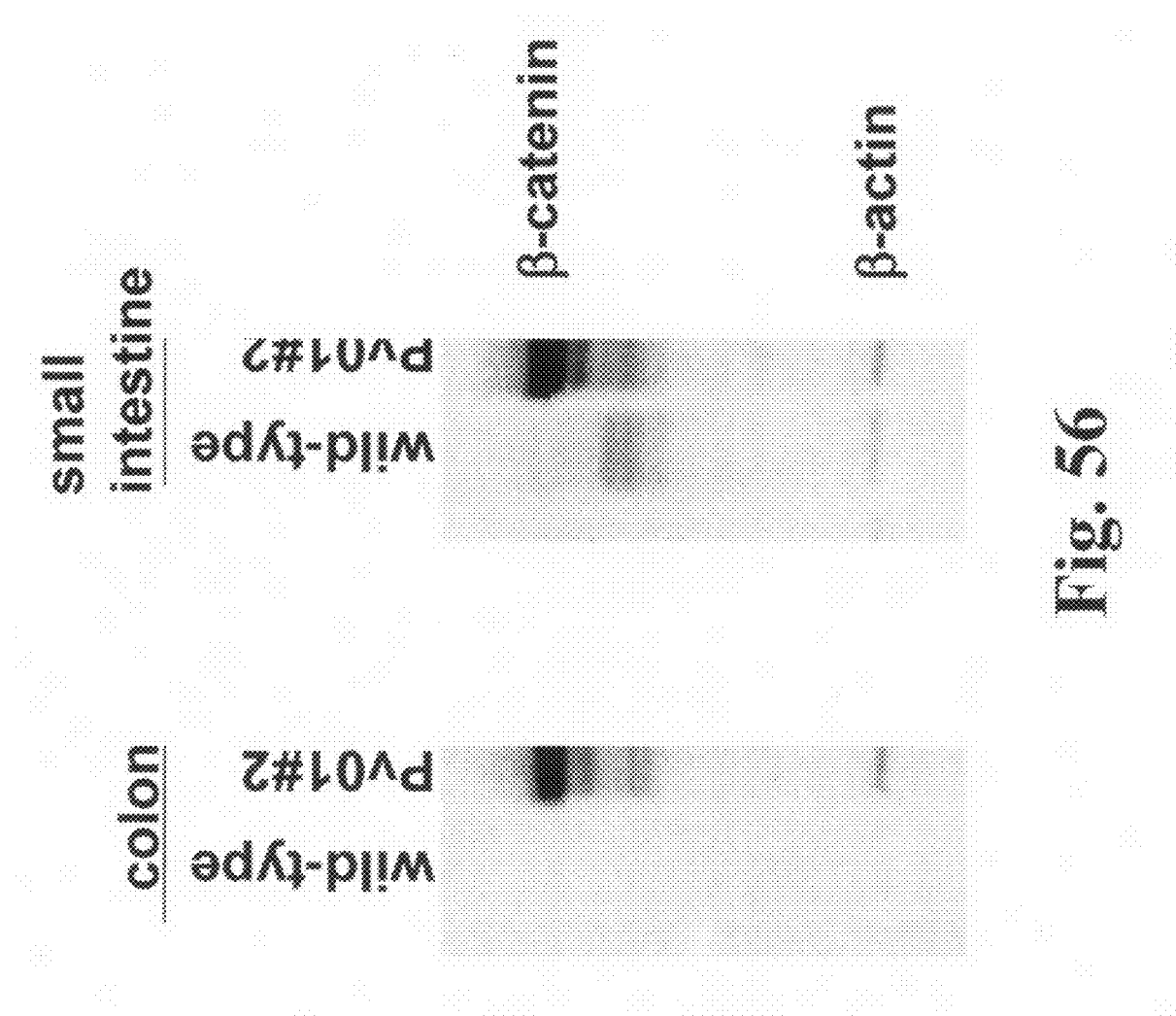

FIG. 56 Stabilization of β-catenin in transgenic mice that express GIPF.

Figure 57:
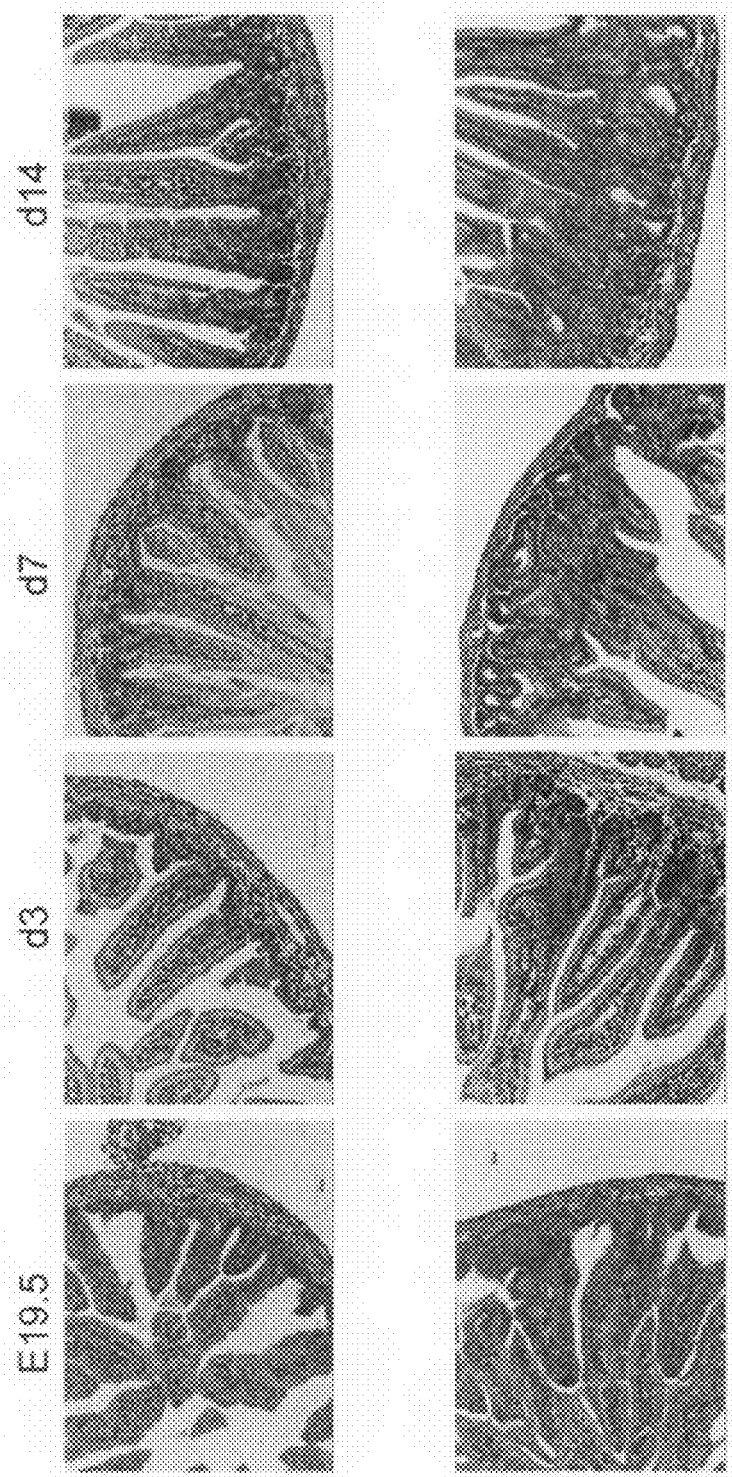

FIG. 57 H&E staining of sections of the small intestine of transgenic mice that express GIPF.

FIG. 58 A-C Diagrammatic representation of the construction of a transgene for the villin-driven expression of GIPF and Wnt3a in transgenic mice.

Figure 59:
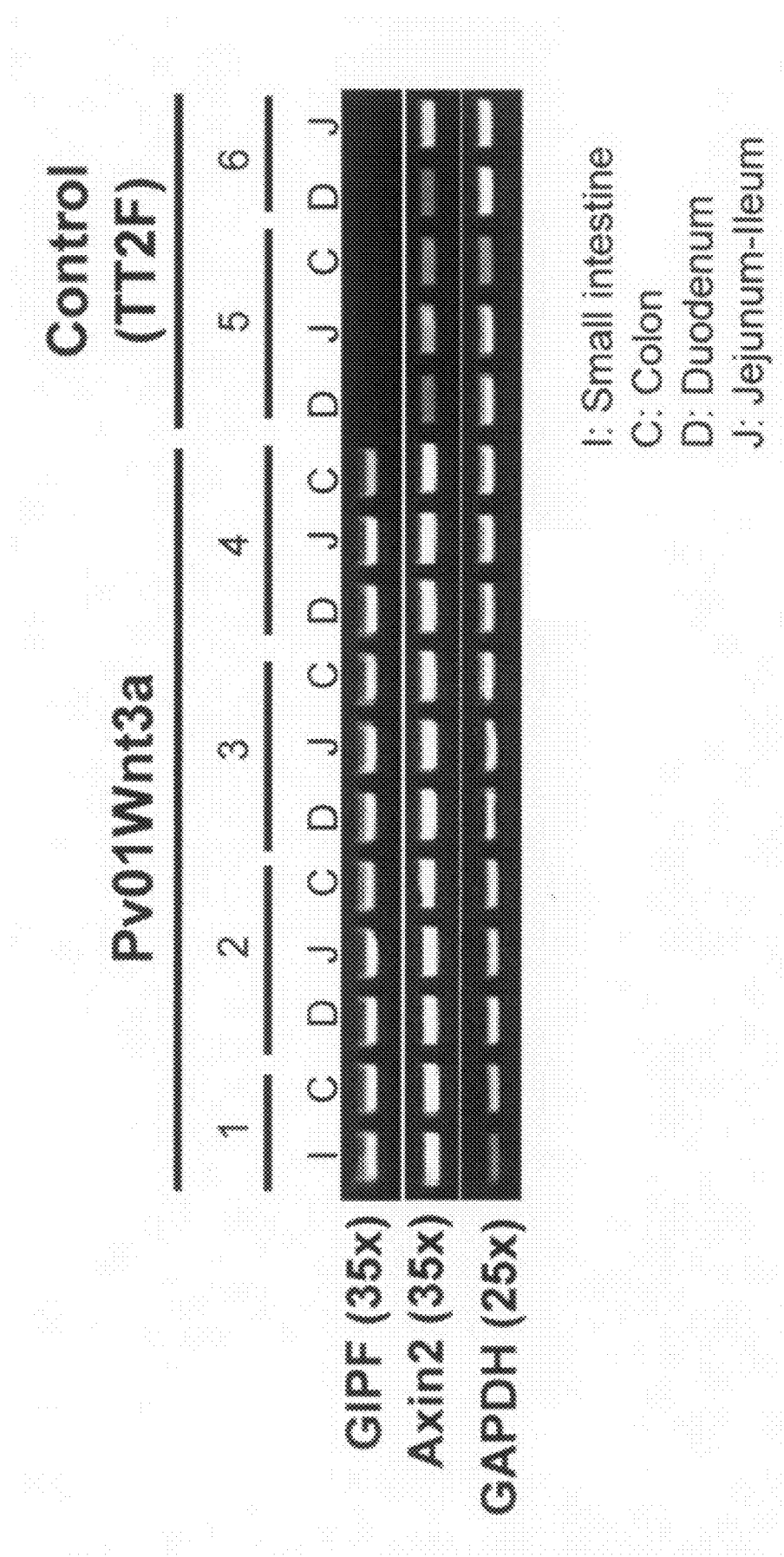

FIG. 59 Embryonic expression of GIPF and Wnt3a in the small and large intestine of transgenic mice.

Figure 60:
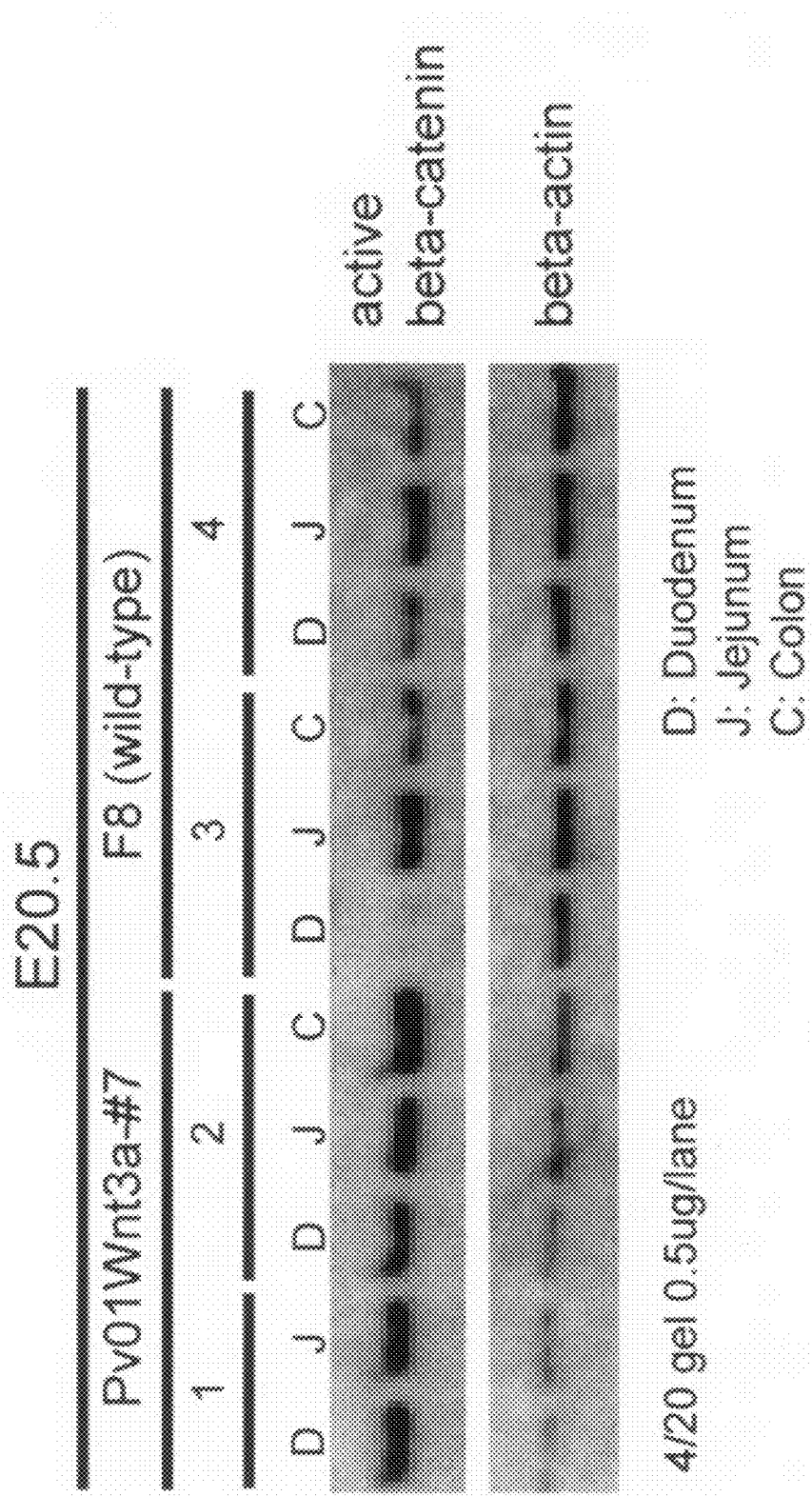

FIG. 60 Stabilization of β-catenin in transgenic mice that express GIPF and Wnt3a.

FIG. 61 H&E staining of sections of the small intestine of a transgenic mouse embryo that expresses GIPF and Wnt3a.

FIG. 62 A-K Diagrammatic representation of the construction of the RS-KO vector.

Figure 63:
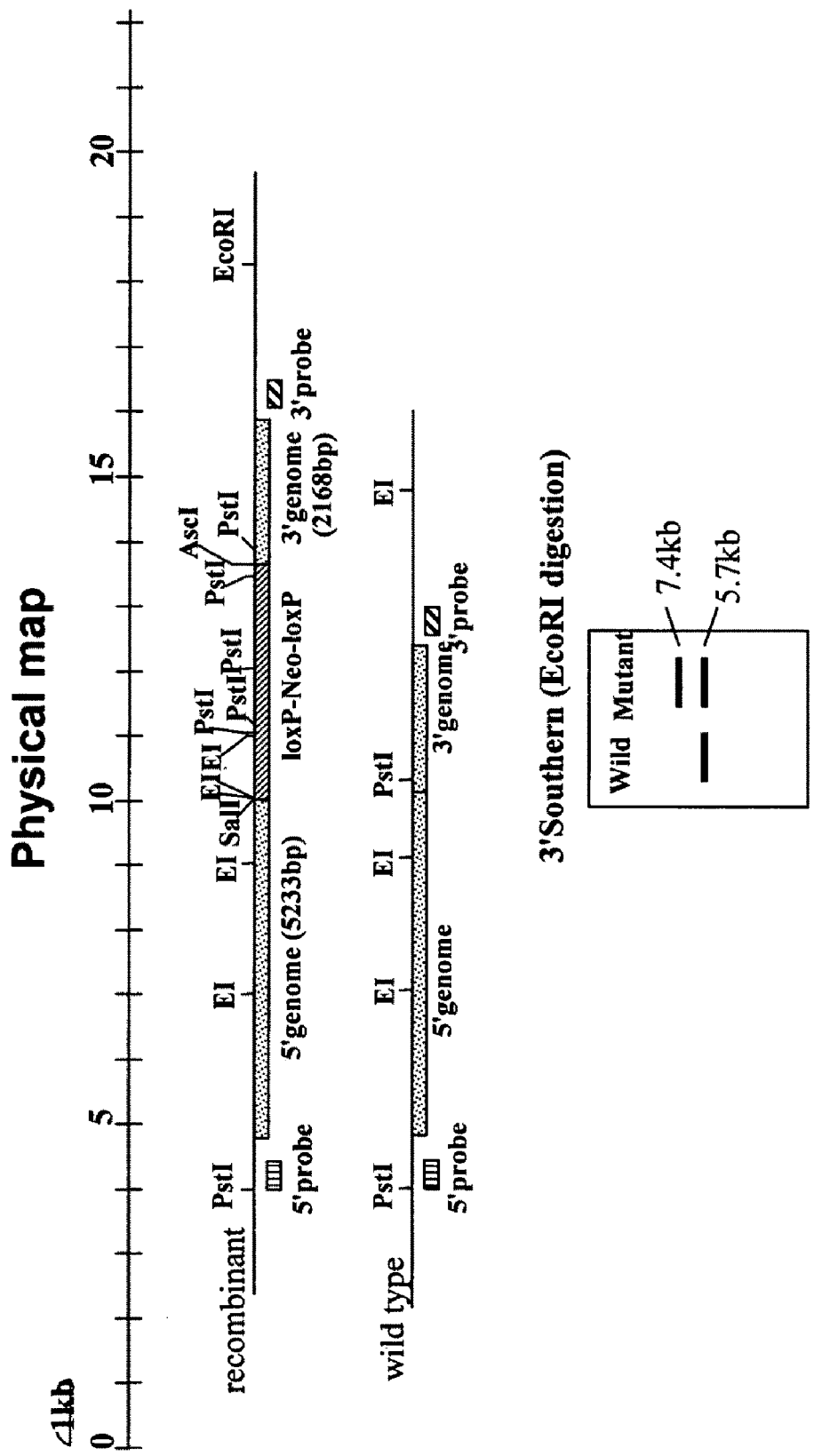

FIG. 63 Genomic map of wild type and recombinant RS-KO clones.

Figure 64A:
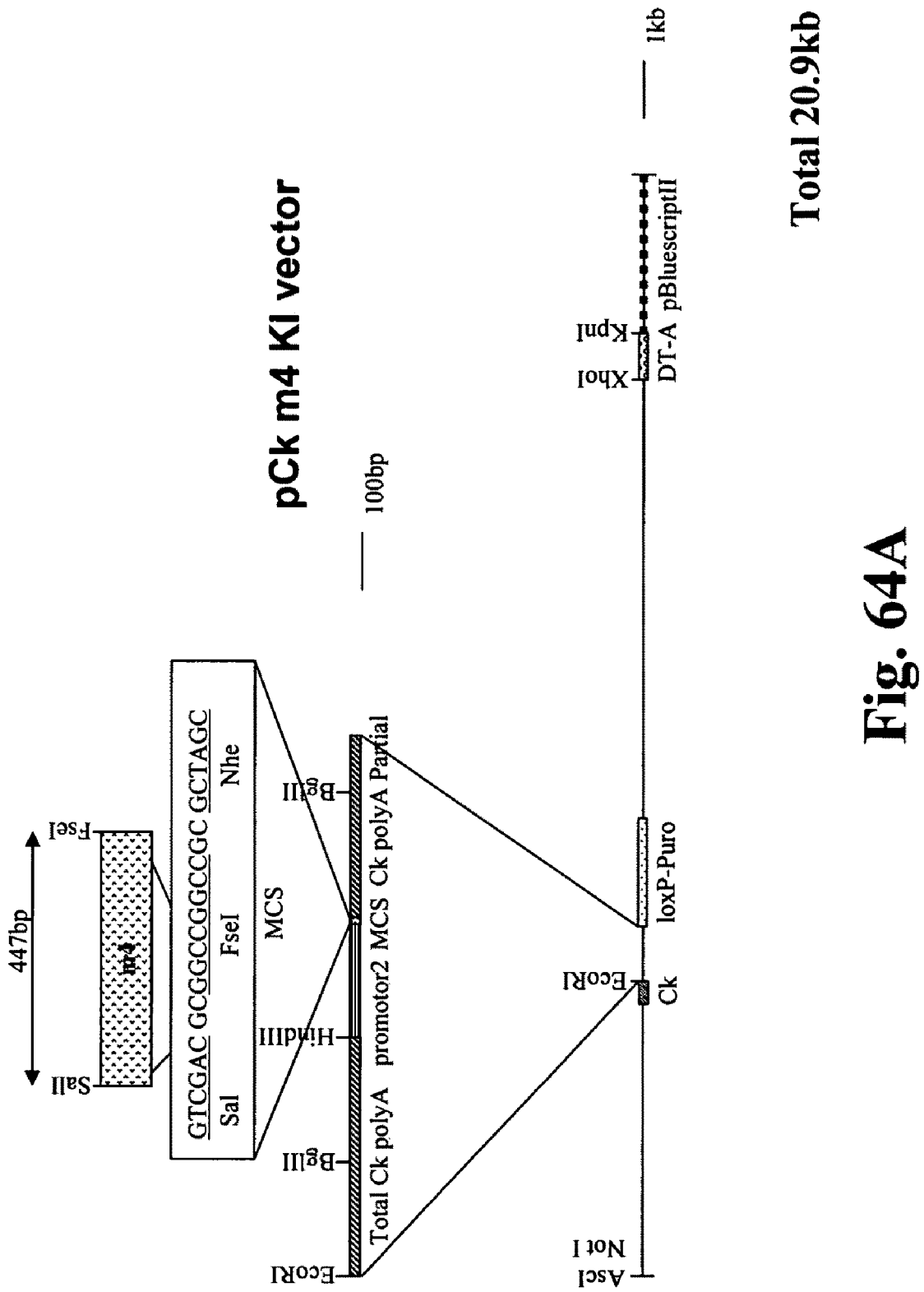

FIG. 64 A-K Diagrammatic representation of the construction of a knock-in vector pCk m4 KI for the expression of GIPF deletion mutant (SEQ ID NO: 91) in transgenic mice.

Figure 65A:
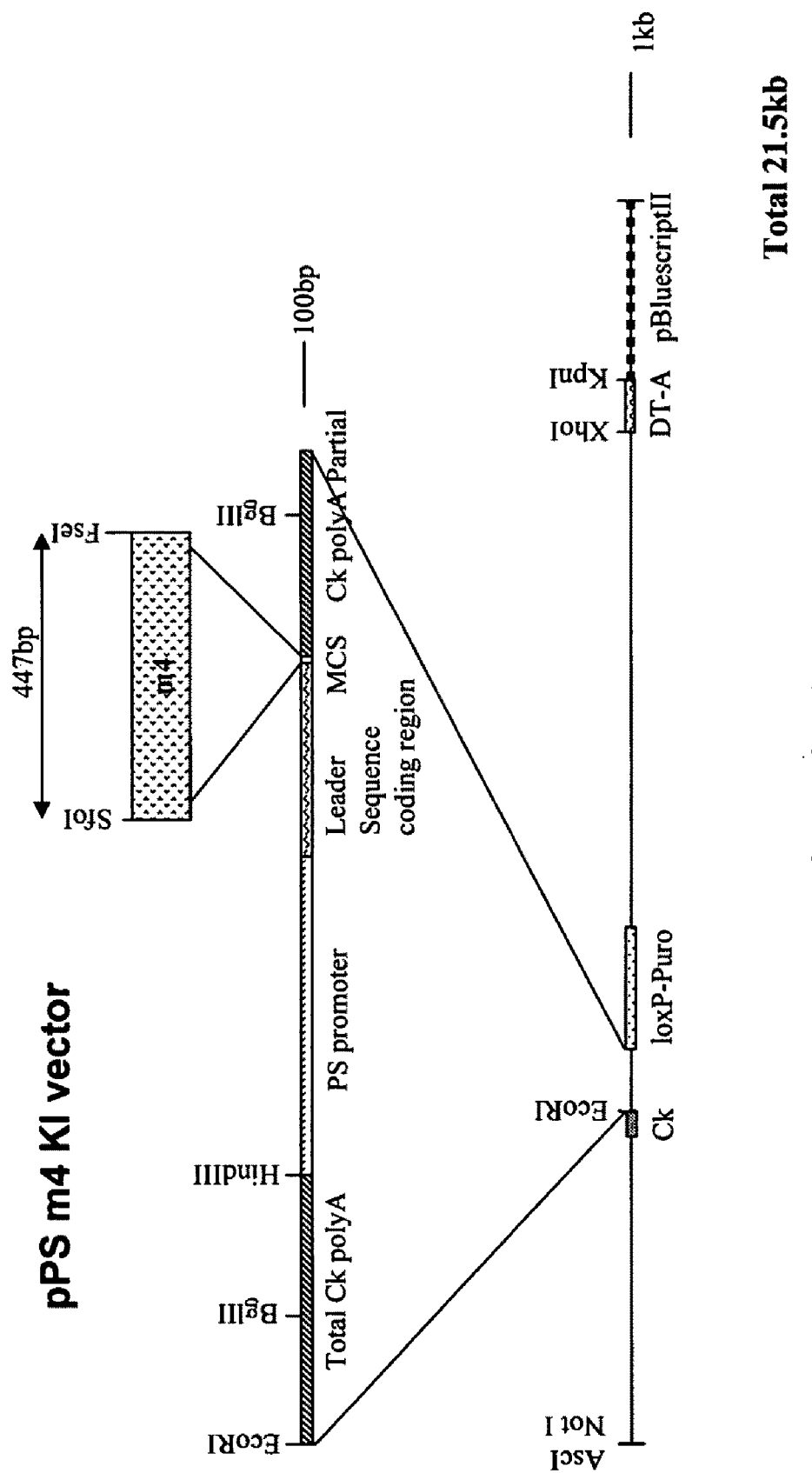

FIG. 65 A-C Diagrammatic representation of the construction of a knock-in vector pPS m4 KI for the expression of GIPF deletion mutant (SEQ ID NO: 91) in transgenic mice.

FIG. 66 Genomic map of wild type and recombinant Ck m4 KI clones.

Figure 67:
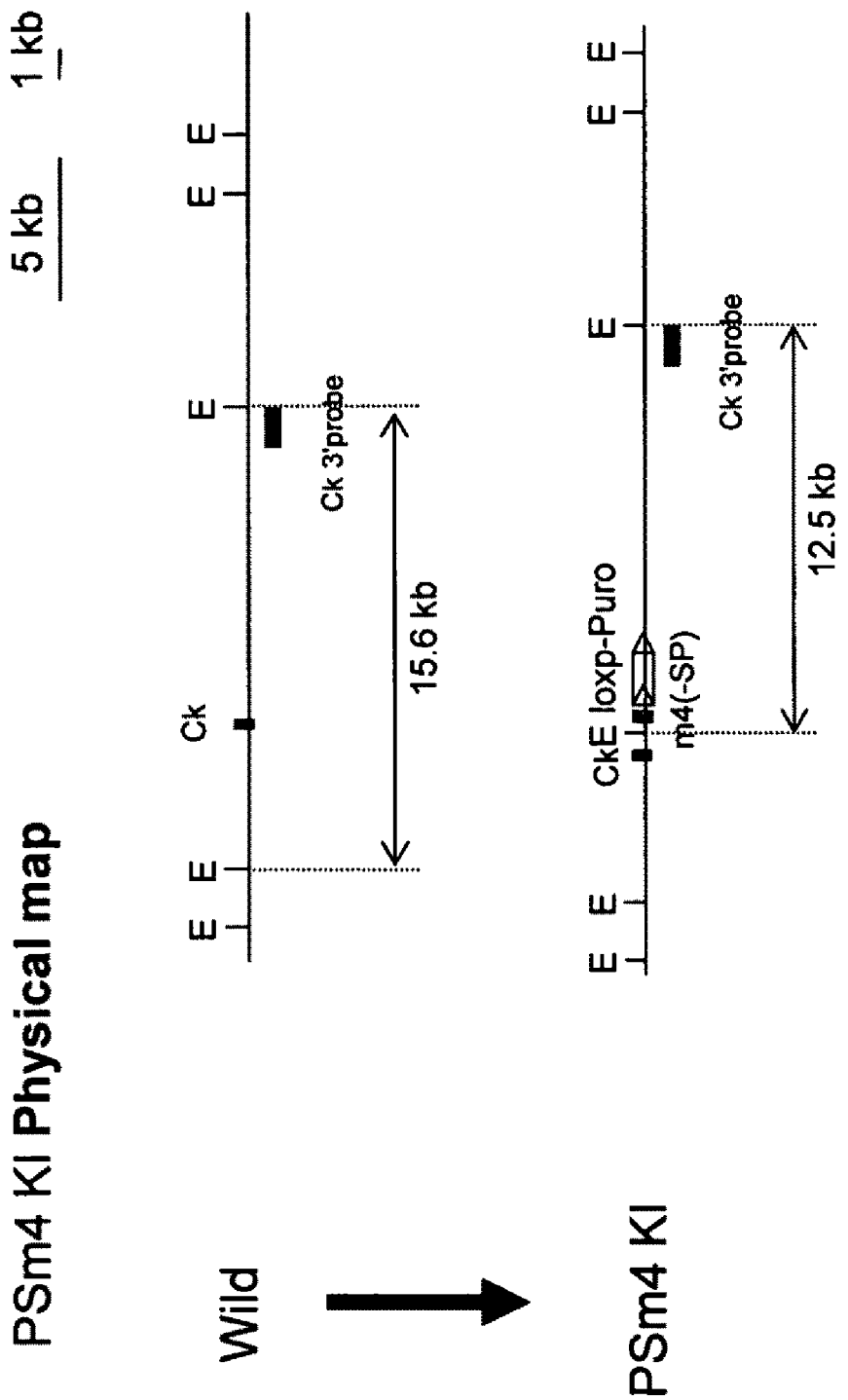

FIG. 67 Genomic map of wild type and recombinant PS m4 KI clones.

Figure 68A:
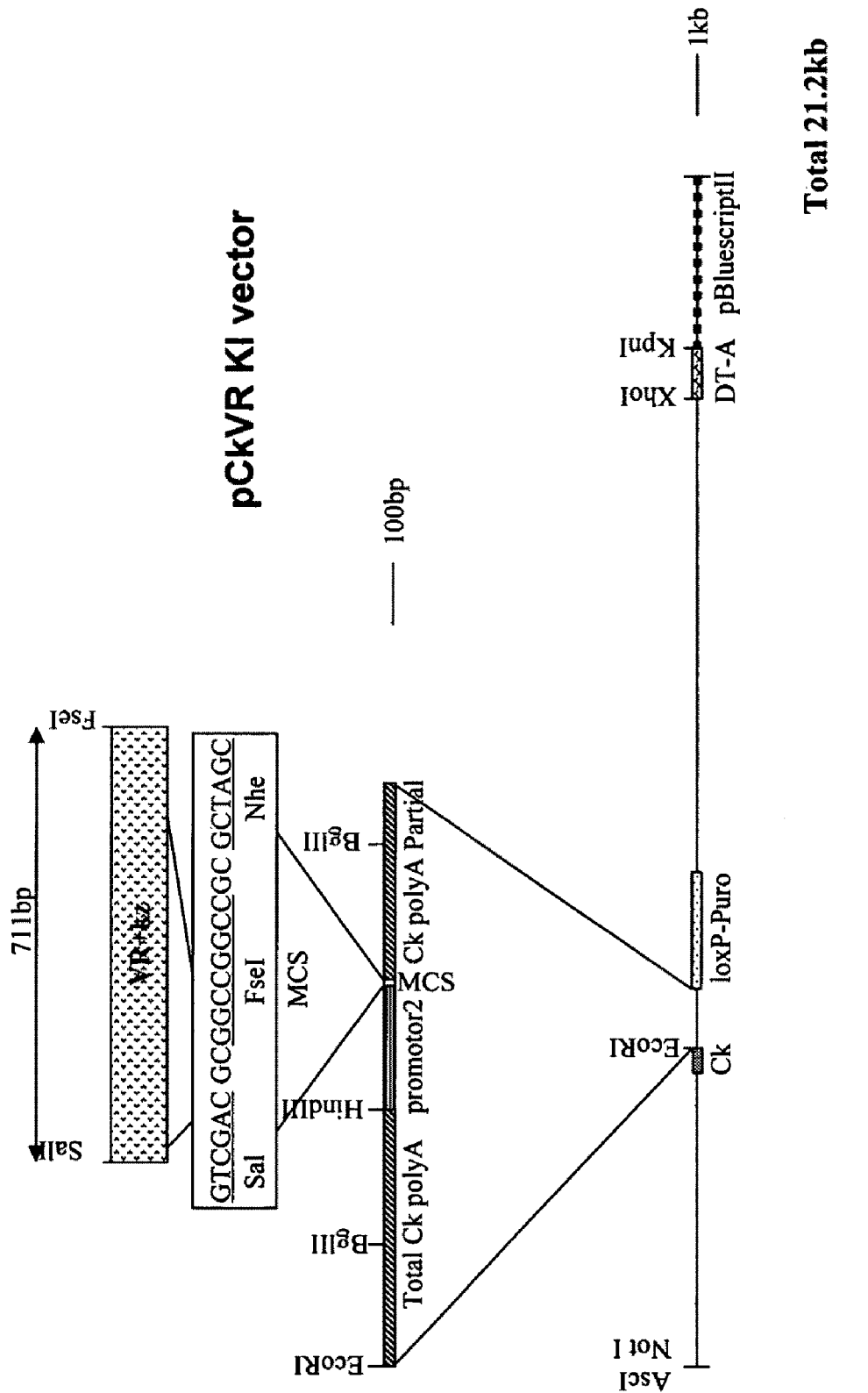

FIG. 68 A-C Diagrammatic representation of the construction of a knock-in vector pCk VR KI for the expression of GIPF variant (SEQ ID NO: 177; GenBank Accession Number AK098225) in transgenic mice.

FIG. 69 A-C Diagrammatic representation of the construction of a knock-in vector pPS VR KI for the expression of GIPF variant (SEQ ID NO: 177; GenBank Accession Number AK098225) in transgenic mice.

Figure 70:
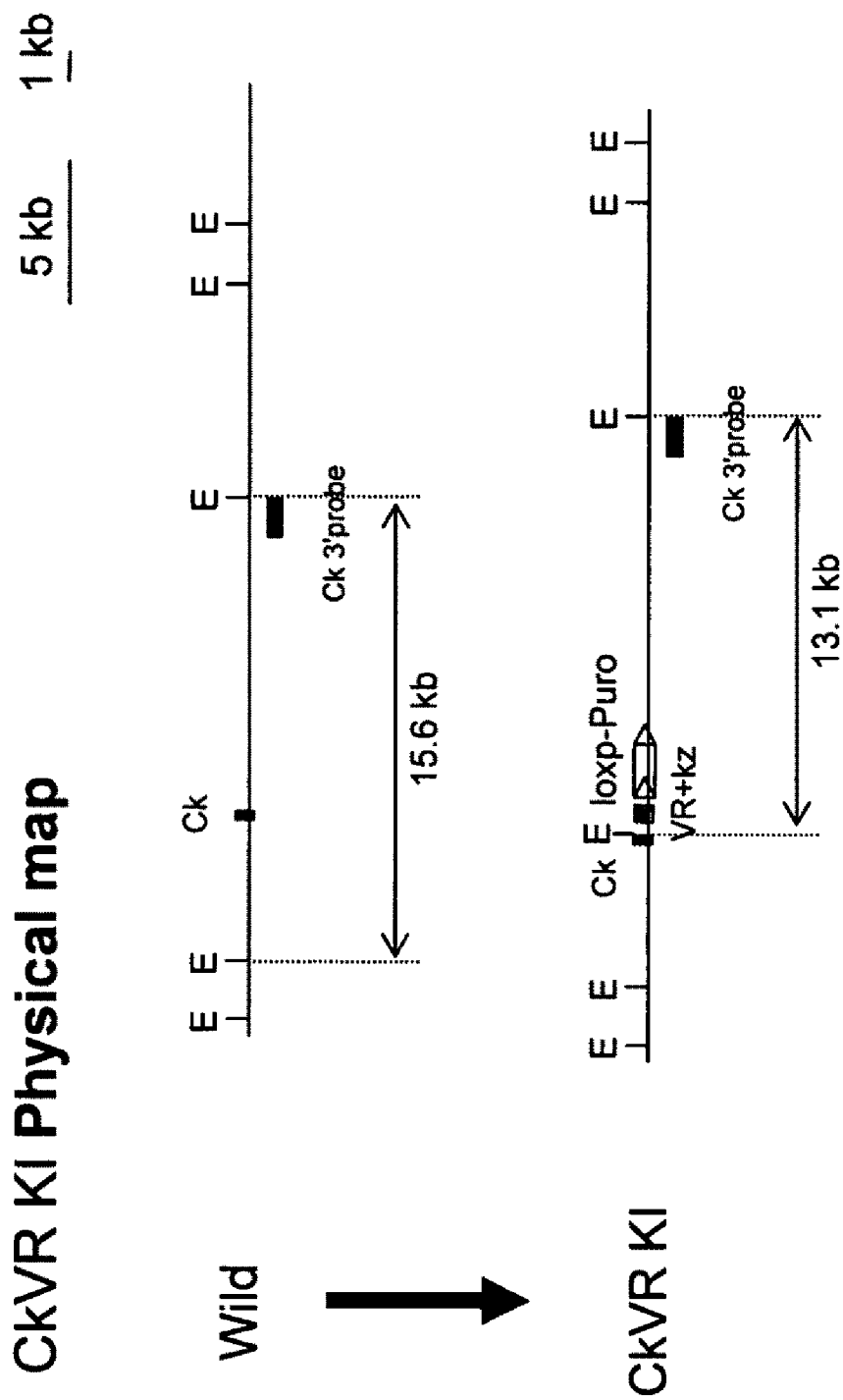

FIG. 70 Genomic map of wild type and recombinant Ck VR KI clones.

Figure 71:
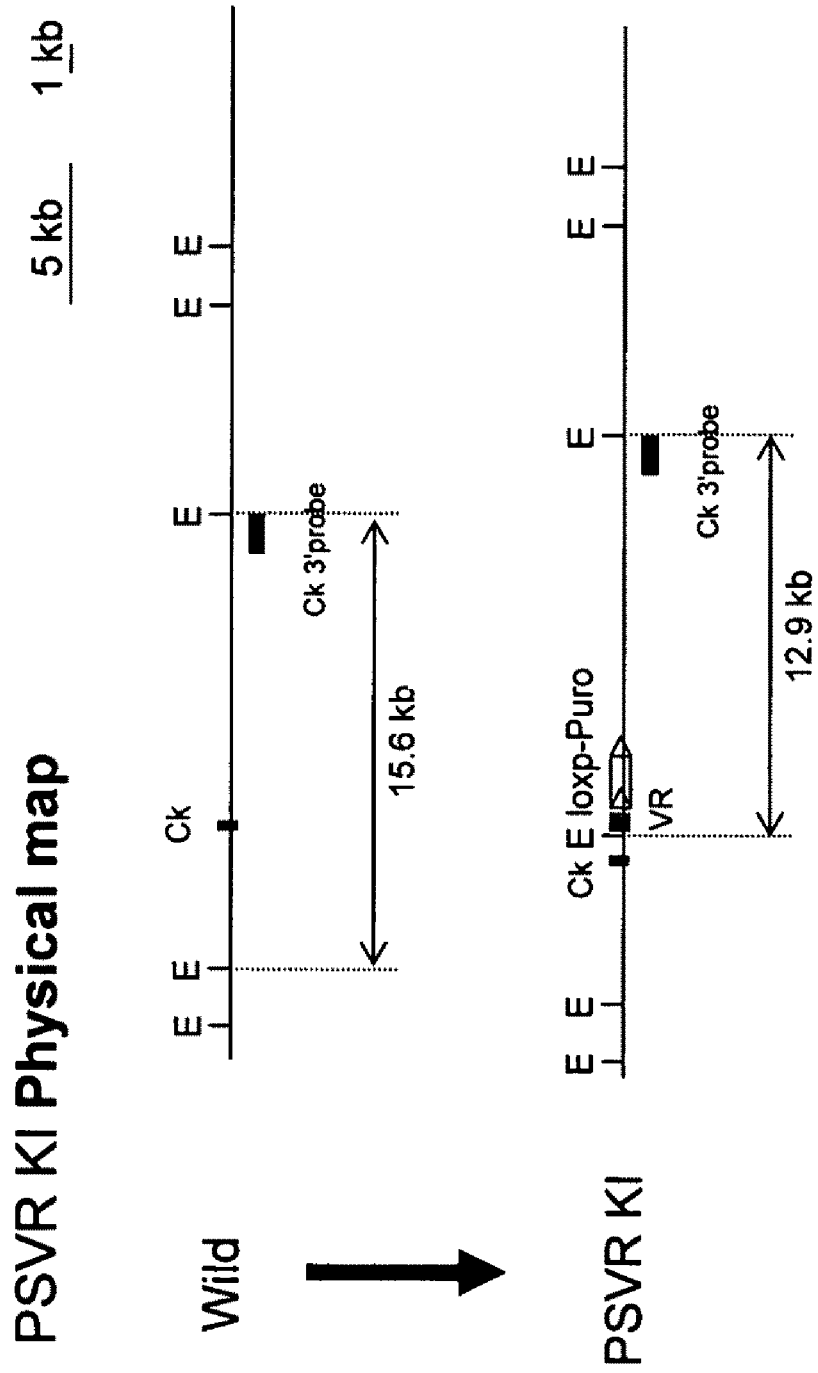

FIG. 71 Genomic map of wild type and recombinant PS VR KI clones.

Figure 72:
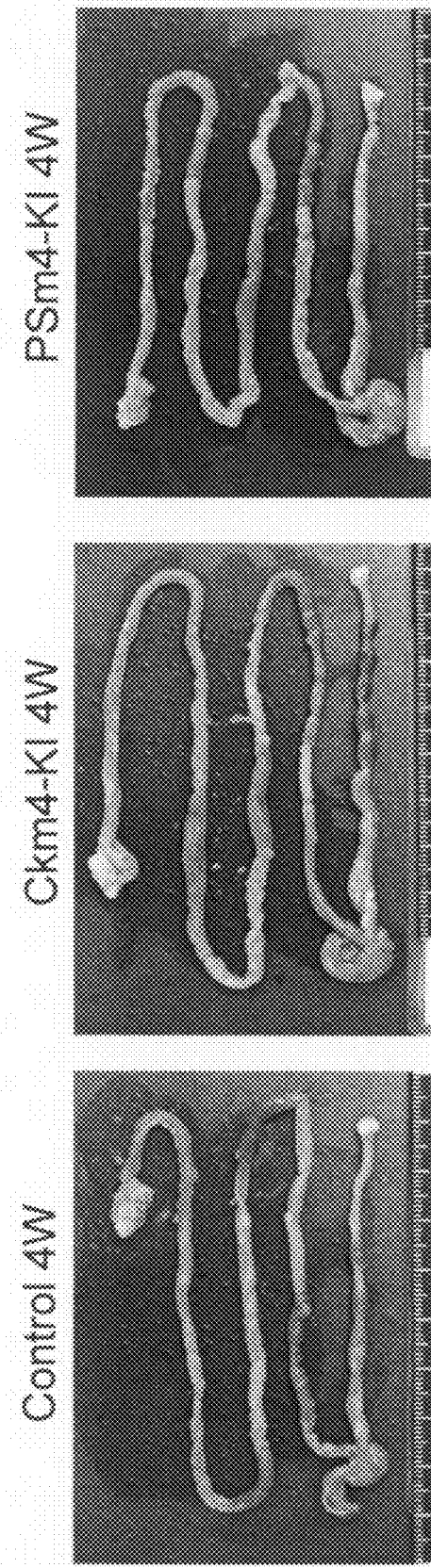

FIG. 72 Comparison of small and large intestines of control and transgenic mice expressing the GIPF deletion mutant SEQ ID NO: 91.

Figure 73:
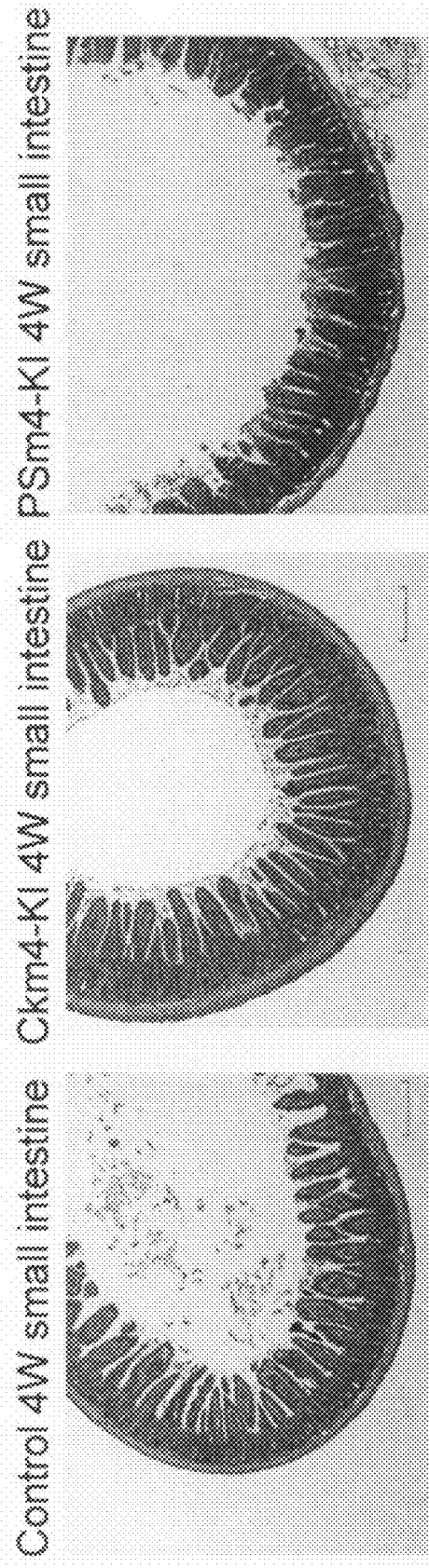

FIG. 73 H&E staining of cross-sections of small intestine from transgenic mice expressing GIPF deletion mutant SEQ ID NO: 91 (low magnification).

Figure 74:
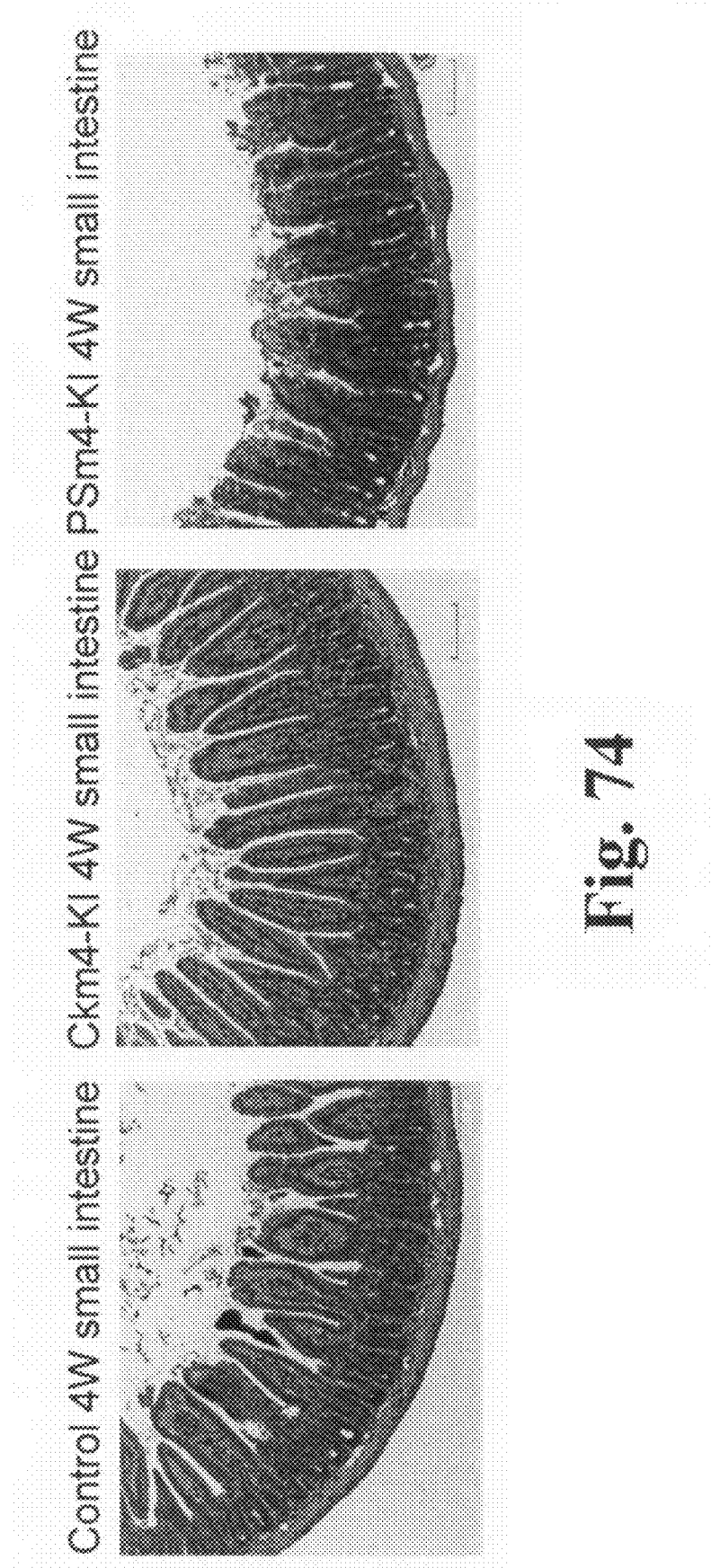

FIG. 74 H&E staining of cross-sections of small intestine from transgenic mice expressing GIPF deletion mutant SEQ ID NO: 91 (high magnification).

Figure 75:
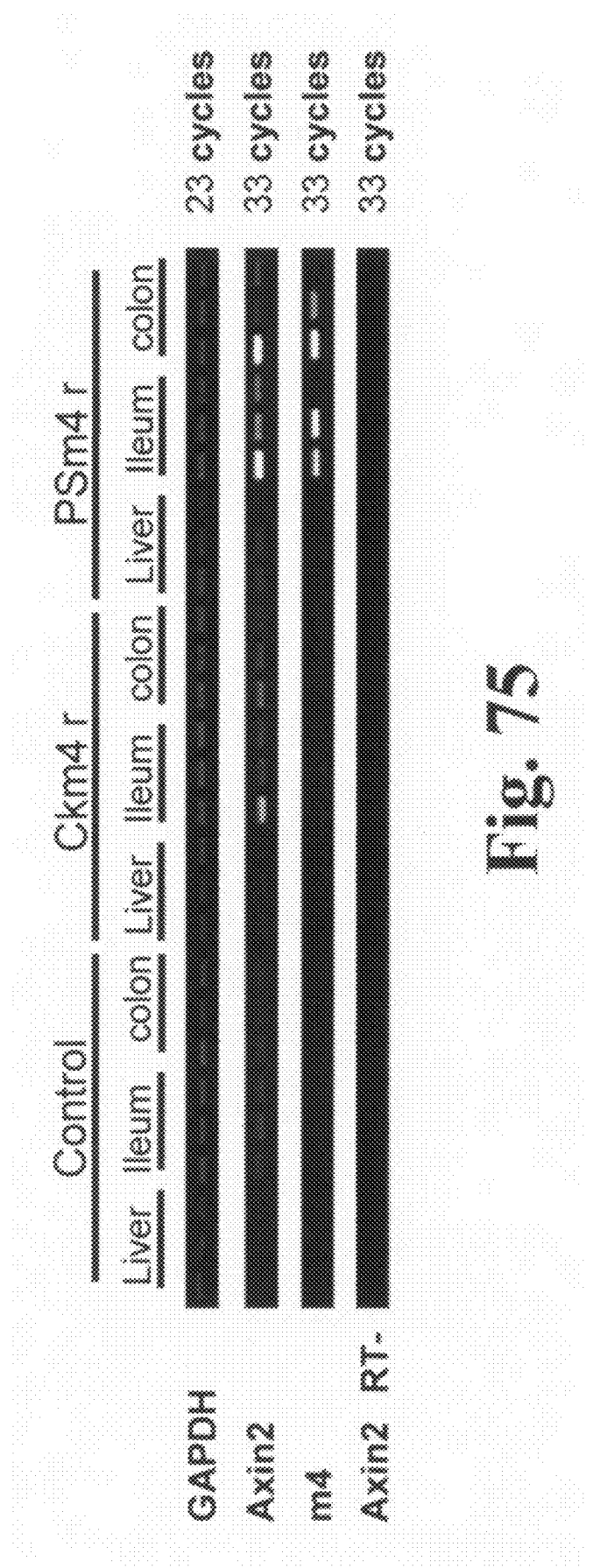

FIG. 75 Stabilization of Axin-2 in transgenic mice that express GIPF deletion mutant SEQ ID NO: 91.

FIG. 76 Comparison of small and large intestines of control and transgenic mice (PSVR KI) expressing GIPF variant (SEQ ID NO: 177; GenBank Accession Number AK098225) to that of a control animal.

FIG. 77 H&E staining of cross-sections of small intestine from control and transgenic mice (PSVR KI) expressing GIPF variant (SEQ ID NO: 177; GenBank Accession Number AK098225) (low magnification).

FIG. 78 H&E staining of cross-sections of small intestine from control and transgenic mice (PSVR KI) expressing GIPF variant (SEQ ID NO: 177; GenBank Accession Number AK098225) (high magnification).

Figure 79:
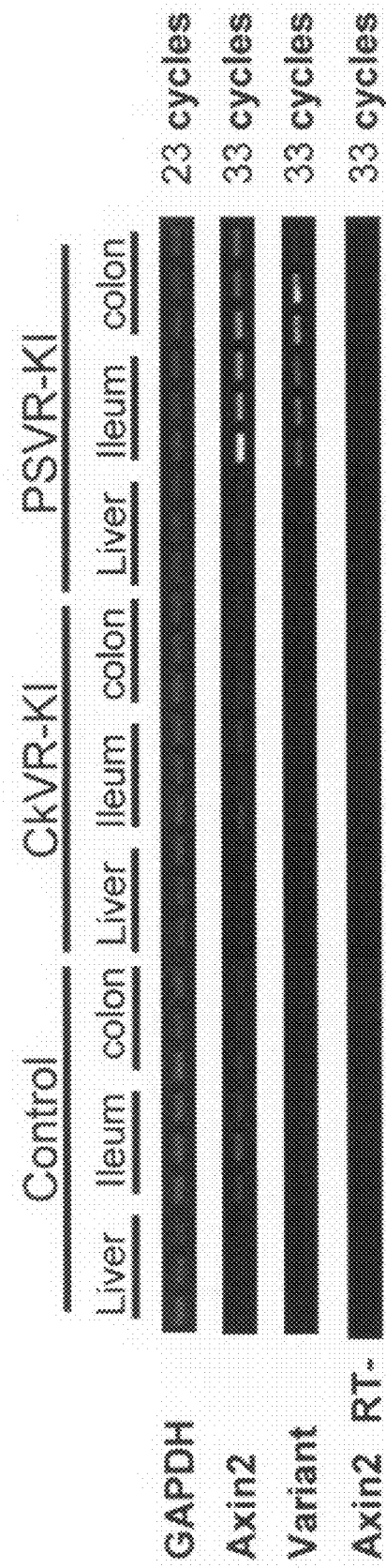

FIG. 79 Stabilization of Axin-2 in control and transgenic mice that express GIPF variant (SEQ ID NO: 177; GenBank Accession Number AK098225).

FIG. 80 H&E staining of sections from the large intestine of control animal and an animal in which chronic IBD was induced by T-cell transfer (example 37).

4. DETAILED DESCRIPTION OF THE INVENTION

Figure 3:
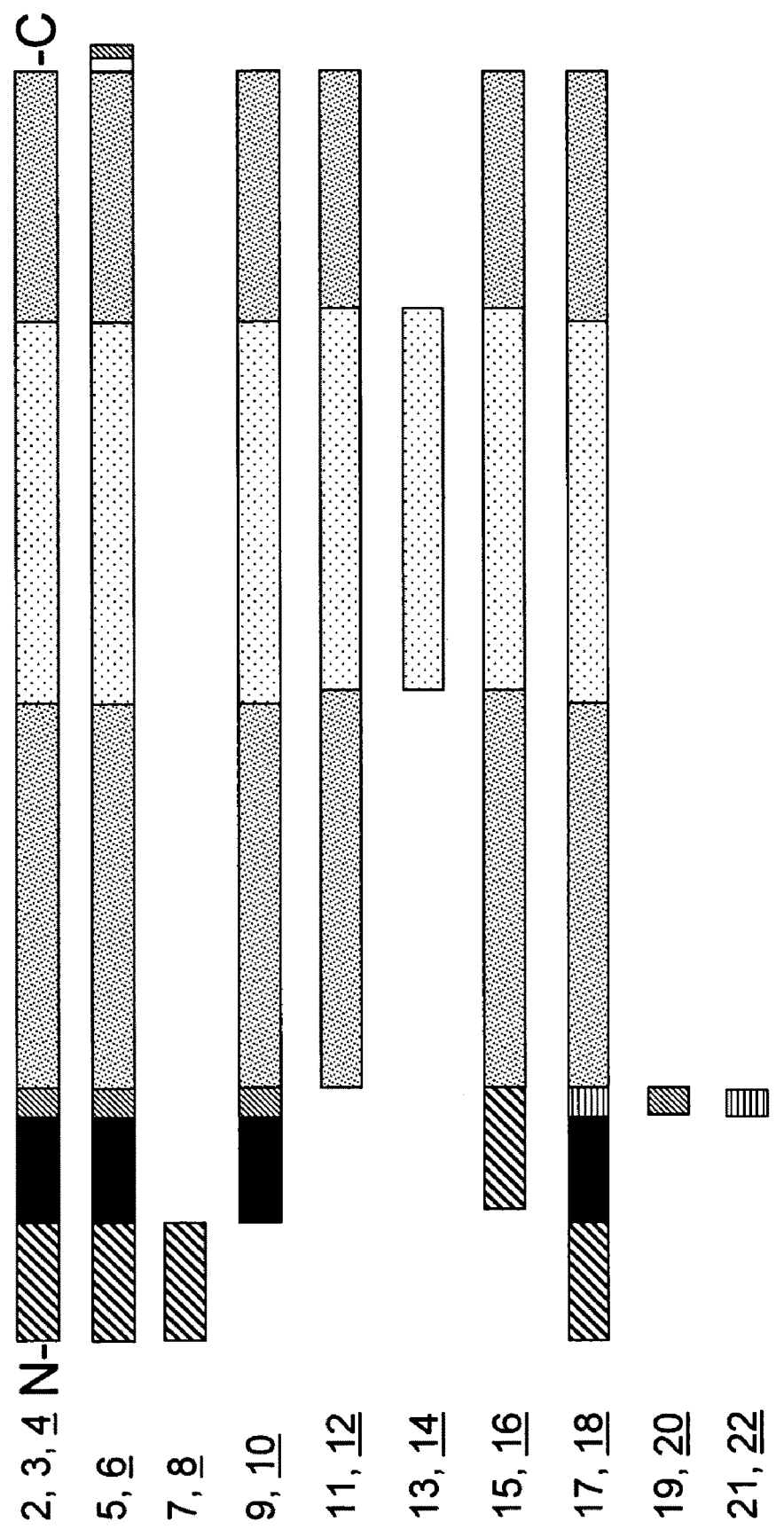
FIG. 3 is a schematic representation of the GIPF polypeptides of the compositions of the invention. The numbers that are underlined correspond to the SEQ ID NOs of the polypeptides, and the remaining numbers are the SEQ ID NOs of the encoding polynucleotide sequences.

The polypeptides of the invention are depicted in FIG. 3, and are described in detail below.

The GIPF polypeptide of SEQ ID NO: 4 is a 263-amino acid protein with a predicted molecular mass of approximately 29 kDa unglycosylated. SEQ ID NO:2 is a cDNA encoding GIPF polypeptide. The initial methionine starts at position 603 of SEQ ID NO: 2 and the putative stop codon begins at position 1392 of SEQ ID NO: 2. Protein database searches with the BLAST algorithm (Altschul S. F. et al., J. Mol. Evol. 36:290-300 (1993) and Altschul S. F. et al., J. Mol. Biol. 21:403-10 (1990), herein incorporated by reference) indicate that SEQ ID NO: 4 is homologous to SEQ ID NO: 23 Stem Cell Growth Factor A-1 (SEQ ID NO: 10 from PCT WO 01/77169 A2) (FIG. 4A), and human thrombospondin 1 (SEQ ID NO: 28) (FIG. 4B).

A predicted approximately twenty-residue signal peptide (SEQ ID NO: 8) extends from residue 1 to residue 20 of SEQ ID NO: 4. The extracellular portion is useful on its own. The signal peptide region was predicted using the Neural Network Signal P VI.I program (Nielsen et al., Int. J. Neural Syst. 8:581-599 (1997)), incorporated herein by reference) and/or using Neural Network SignalP VI.I program (Nielsen et al, (1997) Int. J. Neural Syst. 8, 581-599). One of skill in the art will recognize that the actual cleavage site may be different than that predicted by the computer program. SEQ ID NO: 10 is the GIPF polypeptide of SEQ ID NO: 4 that lacks the putative signal peptide (SEQ ID NO: 8).

Two species of polypeptides derived from SEQ ID NO: 4 have been cloned and purified in mammalian cell culture. SEQ ID NO: 10 is the polypeptide form purified from cellular medium of Chinese Hamster Ovary (CHO) cells that are transfected with a vector construct comprising nucleotide sequence of SEQ ID NO: 3. The polypeptide of SEQ ID NO: 10 is herein known as the dominant mature form of GIPF. SEQ ID NO: 9 is a nucleotide sequence that encodes the polypeptide of SEQ ID NO: 10. The N-terminal sequence for this polypeptide form was determined through Edman degradation sequencing (Speicher, D. W. Methods 6: 248-261 (1994); Tempst et al., Methods 6: 248-261 (1994)). SEQ ID NO: 12 is the mature polypeptide form isolated from the cellular medium of human embryonic kidney 293 cells that are transfected with a vector construct comprising SEQ ID NO: 3. SEQ ID NO: 11 is a corresponding nucleotide sequence that encodes the polypeptide of SEQ ID NO: 12. Through Edman degradation sequencing, it has been determined that the polypeptide of SEQ ID NO: 12 lacks the first 31 amino acid residues of SEQ ID NO: 4. The 31 amino acid peptide comprises a consensus site (SEQ ID NO: 20) for furin protease cleavage (Zhou et al., J Biol Chem 274:20745-20748 (1999), herein incorporated by reference in its entirety).

Using the Pfam software program (Sonnhammer et al., Nucleic Acids Res., Vol. 26(1) pp. 320-322 (1998) herein incorporated by reference) the GIPF polypeptide (SEQ ID NO: 4) was examined for domains with homology to known peptide domains. GIPF polypeptide of SEQ ID NO: 4 is expected to have a thrombospondin type 1 domain (SEQ ID NO: 14 encoded by the nucleotide sequence of SEQ ID NO 13). The Pfam score for the thrombospondin type 1 domain contained within SEQ ID NO: 4 is 0.0034, and is predicted to be from amino acid residue 151 through 206 of SEQ ID NO: 4. The thrombospondin domain may be useful on its own.

Other forms of GIPF include a polypeptide having the amino acid sequence of SEQ ID NO:4 except that the valine at position 50 of SEQ ID NO:4 is replaced by an isoleucine (GIPF-I. Another form of GIPF-I has the amino acid sequence of SEQ ID NO:10 except that the valine at position 30 of SEQ ID NO:10 is replaced by an isoleucine. A third form of GIPF-I has the amino acid sequence of SEQ ID NO:12 except that the valine at position 19 of SEQ ID NO:12 is replaced by an isoleucine. Yet another form of GIPF includes the amino acid sequence common to SEQ ID NO:4 and SEQ ID NO:178. Thus, this polypeptide has the amino acid sequence of amino acids 32-263 of SEQ ID NO:4 (SEQ ID NO:12).

Using eMATRIX software package (Stanford University, Stanford, Calif.) (Wu et al., J. Comp. Biol., vol. 6, pp. 219-235 (1999), herein incorporated by reference), GIPF polypeptide of SEQ ID NO: 4 is expected to have domains outlined in the table below, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

| SEQ ID NO: | p value | Identification No. | eMATRIX domain name | Amino acid Sequence (position) |
|---|---|---|---|---|
| 24 | 8.63e-10 | IPB001862A | Membrane attack complex components/ perforin/ complement C9 | PAQCEMSEWSPWGP CS (145-160) |
| 25 | 9.03e-10 | IPB002174A | Furin-like cysteine rich region | GKRQRRISAEGSQACA KGCELCSEVNGCLKCS (26-57) |
| 26 | 9.80e-08 | IPB000433 | ZZ Zinc finger signature | IEHCEACFSHNFCTKC KP (99-115) |

In order to control the production of either the dominant mature or the mature polypeptide form that was predominantly produced by CHO and/or 293 cells (SEQ ID NO: 10 and SEQ ID NO: 12, respectively), synthetic constructs have been made. SEQ ID NO: 16 is a nucleotide sequence included in a vector system that results in the expression of a polypeptide (SEQ ID NO: 16) in which the predicted signal peptide (SEQ ID NO: 8) adjoins the predominant mature form produced in 293 cells (SEQ ID NO: 10). SEQ ID NO: 17 is a nucleotide construct produced by site-directed mutagenesis (Weiner et al., Gene 126:35-41 (1993)) to contain a mutation in the furin-protease cleavage consensus site (SEQ ID NO: 22). This mutation changes the first arginine (R) residue of SEQ ID NO: 20 to a glutamine (Q). The arginine to glutamine mutation enables the production of the dominant mature form of GIPF by 293 cells (SEQ ID NO: 10).

Thrombospondins are a family of extracellular matrix proteins that are involved in cell-cell and cell-matrix communication (Lawler et al., Curr. Opin. Cell Bio. 12:634-640 (2000)). More than five different thrombospondins are known with distinct patterns of tissue distribution. Some tissues like heart, cartilage, and brain express most of the thrombospondin gene products. Thrombospondin-1 is a major constituent of blood platelets. Thrombospondin-1 appears to function at the cell surface to bring together membrane proteins and cytokines and other soluble factors. Membrane proteins that bind thrombospondin-1 include integrins, integrin-associated protein (CD47), CD36, proteoglycans. Transforming growth factor β (TGFβ) and platelet-derived growth factor also bind thrombospondin-1.

Thrombospondin-1 is a large protein with many distinct domains. It contains a globular domain at both amino and carboxy terminus, a region of homology with procollagen, and three types of repeated sequence motifs termed thrombospondin (TSP) type 1, type 2, and type 3 repeats. TSP1 repeats have been found in various different proteins including, complement components (C6, C7, C8A etc.) extracellular matrix proteins like ADAMTS, mindin, axonal guidance molecule like F-spondin semaphorins, and also SCO-spondin, and TRAP proteins of *Plasmodium*.

Thrombospondin type 1 (TSP1) repeat can activate TGFβ epithelial tissues which are involved in regulation of cell growth, differentiation, adhesion, migration, and death. TSP1 is further involved in protein binding, heparin binding, cell attachment, neurite outgrowth, inhibition of proliferation, inhibition of angiogenesis, and activation of apoptosis. TSP1 domains of Plasmodium circumsporozoite (CS) protein and TRAP proteins are implicated in salivary gland invasion by the sporozoite.

TSP1 sequences are characterized by conserved cysteines, closely spaced tryptophans, and a cluster of basic residues. Spatial configuration of TSP1 sequences shows two β-sheet domains which are shown to bind heparin (Kilpelainen et al (200) J. Biol Chem. 275, 13564-13570, incorporated herein by reference). A similar spatial fold has been described for heparin-binding growth associated molecule (HB-GAM). HB-GAM is identical to mitogenic and neurite outgrowth-promoting protein pleitrophin; osteoblast specific factor-1; heparin-binding neurotrophic factor; and heparin affin regulatory peptide. Expression of HB-GAM was shown to be associated with extracellular matrix of axonal tracts and synapses, and also with basement membranes outside of brain and in the cartilage matrix. Recently, N-syndecan has been shown to be a receptor for HB-GAM in brain and has been suggested to play roles in regulation of hippocampal long-term potentiation, a form of brain plasticity implicated in memory and learning. Therefore, TSP1 containing proteins may act as growth promoters and may exhibit GIPF activities.

In addition, thrombospondin, synthesized in bone marrow and deposited within the extracellular matrix, functions as a cytoadhesion molecule for primary pluripotent progenitor cells, as well as for hematopoietic progenitor cells committed to erythroid, granulocytic, and megakaryocytic lineages. Thus thrombospondins may be important in blood cell development (Long and Dixit (1990) Blood 75, 2311-2318, incorporated herein by reference).

GIPF polypeptides and polynucleotides of the invention may be used to induce proliferation or differentiation of gastrointestinal crypt cells. They may also be used in the treatment of conditions where epithelialization is required, such as for the treatment of gastrointestinal disorders including chemotherapy and radiation therapy-induced mucositis, mucositis of the oropharynx, lips and esophagus, inflammatory bowel disease, and other conditions including wounds, burns, ophthalmic disorders, and any disorder where stimulation of epithelial cell proliferation or regeneration is desired. The polynucleotides and polypeptides of the invention may further be utilized to generate new tissues and organs that may aid patients in need of transplanted tissues.

4.1 DEFINITIONS

In describing the present invention the following terms will be employed and are intended to be defined as indicated below.

It must be noted that as used herein and in the appended claims, the singular forms "a", "an" and "the" include plural references unless the context clearly dictates otherwise.

The term "GIPF" refers to the "gastrointestinal proliferative factor" that is particularly active on epithelial cells.

In accordance with the present invention, the term "GIPF protein(s)" or "GIPF polypeptide(s) refers to the full-length protein defined by amino acids $Met^1$ to $Ala^{263}$ (SEQ ID NO: 4), fragments and analogs thereof.

The term "full-length GIPF," "long form of GIPF", "wild type GIPF", or "native GIPF" as used herein all refer to the polypeptide that contains 263 amino acid residues (SEQ ID NO: 4), as shown in FIG. 1B.

The term "GIPFwt" or "hGIPF" refer to the human wild type, full-length GIPF polypeptide (SEQ ID NO: 4); the term "GIPFt" refers to the V5His6-tagged polypeptide of human GIPF (SEQ ID NO: 6); and "mGIPFt" refers to the V5His6-tagged GIPF from mouse (SEQ ID NO: 69).

The term "fragment" refers to a polypeptide derived from the native GIPF that does not include the entire sequence of GIPF. Such a fragment may be a truncated version of the full-length molecule, for example SEQ ID NO: 9, and 12, as well as an internally deleted polypeptide, for example SEQ ID NO: 16. A GIPF fragment may have GIPF bioactivity as determined by the effect of GIPF on the proliferation of epithelial cells in vitro and/or in vivo, as described herein.

The term "analog" refers to derivatives of the reference molecule. The analog may retain biological activity, as described above. In general, the term "analog" refers to compounds having a native polypeptide sequence and structure with one or more amino acid additions, substitutions (generally conservative in nature) and/or deletions, relative to the native molecule, so long as the modifications do not destroy activity. SEQ ID NO: 18 is an example of a GIPF analog. Preferably, the analog has at least the same biological activity as the parent molecule, and may even display enhanced activity over the parent molecule. Methods for making polypeptide analogs are known in the art. Particularly preferred analogs include substitutions that are conservative in nature, i.e., those substitutions that take place within a family of amino acids that are related in their side chains. Specifically, amino acids are generally divided into four families: (1) acidic: aspartate and glutamate; (2) basic: lysine, arginine, histidine; (3) non-polar: alanine, valine, leucine, isoleucine, proline, phenylalanine, methionine, tryptophan; and (4) uncharged polar: glycine, asparagine, glutamine, cysteine, serine, threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid will preserve the biological activity of GIPF.

Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant analogs encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The terms "polypeptide" and "protein" refer to a polymer of amino acid residues and are not limited to a minimum length of the product. The terms also include, unless otherwise indicated, modifications of the polypeptide that do not change the sequence of amino acids, for example, glycosylated, acetylated and phosphorylated forms. A polypeptide or protein, for purposes of the present invention, may be synthetically or recombinantly produced, as well as isolated from natural sources.

By "purified" and "isolated" is meant, when referring to a polypeptide or polynucleotide, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present in the sample. In one embodiment, the polynucleotide or polypeptide is purified such that it constitutes at least 95% by weight of the indicated biological macromolecules present but water, buffers, and other small molecules, especially molecules having a molecular weight of less than 1000 daltons, can be present.

An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "translated protein coding portion" means a sequence which encodes for the full length protein which may include any leader sequence or a processing sequence.

The term "dominant mature protein coding sequence" refers to a sequence which encodes a peptide or protein without any leader/signal sequence. The "dominant mature protein portion" refers to that portion of the protein without the leader/signal sequence. The "mature" form refers to a GIPF polypeptide that lacks the leader/signal sequence and the furin cleavage site. The peptide may have the leader sequence and/or the furin cleavage site removed during processing in the cell or the protein may have been produced synthetically or using a polynucleotide only encoding for the mature protein coding sequence. It is contemplated that the mature or dominant mature protein portion may or may not include an initial methionine residue. The initial methionine is often removed during processing of the peptide.

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

By a "recombinant polypeptide" is intended a polypeptide which has been prepared by recombinant DNA techniques as described herein. In general, the gene coding for the desired polypeptide is cloned and then expressed in transformed organisms, as described farther below. The host organism expresses the foreign gene to produce the polypeptide under expression conditions. Alternatively, the promoter controlling expression of an endogenous polypeptide can be altered to render a recombinant polypeptide.

The term "active" refers to those forms of the polypeptide that retain the biologic and/or immunologic activities of any naturally occurring polypeptide. According to the invention, the terms "biologically active" or "biological activity" refer to a protein or peptide having structural, regulatory or biochemical functions of a naturally occurring molecule. Likewise "biologically active" or "biological activity" refers to the capability of the natural, recombinant or synthetic GIPF peptide, or any peptide thereof, to induce a specific biological response in appropriate animals or cells and to bind with specific antibodies.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134-143) and factors released from damaged cells (e.g. Interleukin-1 Receptor Antagonist, see Arend, W. P. et. al. (1998) Annu. Rev. Immunol. 16:27-55)

The term "polynucleotide" or "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" or "probe" or "primer" are used interchangeably and refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the probe is from about 6 nucleotides to about 200 nucleotides, preferably from about 15 to about 50 nucleotides, more preferably from about 17 to 30 nucleotides and most preferably from about 20 to 25 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to a portion of SEQ ID NO: 1, 2, 5, 7, 9, 11, 13, 15, 17, 84, 86, 88, 90, 92, 94, 96, 98, 100, 102, 104 or 177.

Probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241-250). They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The nucleic acid sequences of the present invention also include the sequence information from any of the nucleic acid sequences of SEQ ID NO: 1, 2, 5, 7, 9, 11, 13, 15, 17, 84, 86, 88, 90, 92, 94, 96, 98, 100, 102, 104 or 177. The sequence information can be a segment of SEQ ID NO: 1, 2, 5, 7, 9, 11, 13, 15, 17, 84, 86, 88, 90, 92, 94, 96, 98, 100, 102, 104 or 177 that uniquely identifies or represents the sequence information of SEQ ID NO: 1, 2, 5, 7, 9, 11, 13, 15, 17, 84, 86, 88, 90, 92, 94, 96, 98, 100, 102, 104 or 177. One such segment can be a twenty-mer nucleic acid sequence because the probability that a twenty-mer is fully matched in the human genome is 1 in 300. In the human genome, there are three billion base pairs in one set of chromosomes. Because $4^{20}$ possible twenty-mers exist, there are 300 times more twenty-mers than there are base pairs in a set of human chromosomes. Using the same analysis, the probability for a seventeen-mer to be fully matched in the human genome is approximately 1 in 5. When these segments are used in arrays for expression studies, fifteen-mer segments can be used. The probability that the fifteen-mer is fully matched in the expressed sequences is also approximately one in five because expressed sequences comprise less than approximately 5% of the entire genome sequence.

Similarly, when using sequence information for detecting a single mismatch, a segment can be a twenty-five mer. The probability that the twenty-five mer would appear in a human genome with a single mismatch is calculated by multiplying the probability for a full match $(1 \div 4^{25})$ times the increased probability for mismatch at each nucleotide position ($3 \times 25$). The probability that an eighteen mer with a single mismatch can be detected in an array for expression studies is approximately one in five. The probability that a twenty-mer with a single mismatch can be detected in a human genome is approximately one in five.

The term "open reading frame," ORF, means a series of nucleotide triplets coding for amino acids without any termination codons and is a sequence translatable into protein.

The terms "operably linked" or "operably associated" refer to functionally related nucleic acid sequences. For example, a promoter is operably associated or operably linked with a coding sequence if the promoter controls the transcription of the coding sequence. While operably linked nucleic acid sequences can be contiguous and in the same reading frame, certain genetic elements e.g. repressor genes are not contiguously linked to the coding sequence but still control transcription/translation of the coding sequence.

The terms "recombinant DNA molecule," or "recombinant polynucleotide" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The term "stringent" is used to refer to conditions that are commonly understood in the art as stringent. Stringent conditions can include highly stringent conditions (i.e., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 90% sequence identity. Substantially equivalent nucleotide sequence of the invention can have lower percent sequence identities, taking into account, for example, the redundancy or degeneracy of the genetic code. Preferably, nucleotide sequence has at least about 65% identity, more preferably at least about 75% identity, and most preferably at least about 95% identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626-645). Identity between sequences can also be determined by other methods known in the art, e.g. by varying hybridization conditions.

The term "vector" refers to a nucleic acid molecule capable of transporting another nucleic acid to which it has been linked. The term "expression vector" includes plasmids, cosmids or phages capable of synthesizing the GIPF protein encoded by the respective recombinant gene carried by the vector. Preferred vectors are those capable of autonomous replication and expression of nucleic acids to which they are linked.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed. The term "infection" refers to the introduction of nucleic acids into a suitable host cell by use of a virus or viral vector.

The term "transcriptional regulatory elements" and transcriptional regulatory sequences" are used interchangeably to refer to DNA sequences necessary for the expression of an operably linked coding sequence in a particular organism. The control sequences that are suitable for prokaryotes, for example, include a promoter, optionally an operator sequence, and a ribosome binding site. Eukaryotic cells are known to utilize promoters, enhancers, splicing signals and polyadenylation signals. These terms are intended to encompass all elements that promote or regulate transcription, including promoters, core elements required for basic interaction of RNA polymerase and transcription factors, upstream elements, enhancers, and response elements (Lewin, "Genes V" (Oxford University Press, Oxford) pages 847-873).

A coding sequence is "under the control" of transcriptional and translational control sequences in a cell when RNA polymerase transcribes the coding sequence into mRNA, which is then optionally trans-RNA spliced and translated into the protein encoded by the coding sequence.

The term "tissue-specific promoter" means a nucleotide sequence that serves as a promoter, i.e. regulates expression of a selected DNA sequence operably linked to the promoter, and which effects the expression of the selected DNA sequence in specific cells, such as B-cells. In an illustrative embodiment, gene constructs utilizing B-cell specific promoters can be used to preferentially direct expression of a GIPF protein or protein fragment in B-cells.

The term "expression modulating fragment," EMF, means a series of nucleotides that modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs is nucleic acid fragments which induce the expression of an operably linked ORF in response to a specific regulatory factor or physiological event.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "transgene" refers to a nucleic acid sequence which is partly or entirely heterologous i.e. foreign, to the transgenic animal or cell into which it is introduced, or, is homologous to an endogenous gene of the transgenic animal or cell into which it is introduced, but which is designed to be inserted, or is inserted into the animal's genome in such a way as to alter the genome of the cell into which it is inserted. e.g. it is inserted at a location which differs from that of the natural gene). A transgene can be operably linked to one or more transcriptional regulatory sequences and any other nucleic acids, such as introns, that may be necessary for optimal expression of a selected nucleic acid.

Accordingly, a "transgene construct" refers to a nucleic acid which includes a transgene, and optionally such other nucleic acid sequences as transcriptionally regulatory sequences, polyadenylation sites, replication origins, marker genes etc. which may be useful in the general manipulation of the transgene for insertion in the genome of a host organism.

The term "transgenic" is used herein as an adjective to describe the property, for example, of an animal or construct, of harboring a transgene. For instance, as used herein, a "transgenic organism" is any animal, preferably a non-human mammal, in which one or more of the cells of the animal contain heterologous nucleic acids introduced by way of human intervention, such as by transgenic techniques known in the art. The nucleic acid is introduced into the cell, directly, or indirectly by introduction into a precursor of the cell, by way of a deliberate genetic manipulation, such as by microinjection or by infection with a recombinant virus. The nucleic acid may be integrated within a chromosome, or it may be extrachromosomally replicating DNA. In the transgenic animals described herein, the transgene causes cells to express or overexpress GIPF proteins.

The term "pluripotent" refers to the capability of a cell to differentiate into a number of differentiated cell types that are present in an adult organism. A pluripotent cell is restricted in its differentiation capability in comparison to a totipotent cell.

The term "embryonic stem cells (ES)" refers to a cell that can give rise to many differentiated cell types in an embryo or an adult, including the germ cells. The term "germ line stem cells (GSCs)" refers to stem cells derived from primordial stem cells that provide a steady and continuous source of germ cells for the production of gametes. The term "primordial germ cells (PGCs)" refers to a small population of cells set aside from other cell lineages particularly from the yolk sac, mesenteries, or gonadal ridges during embryogenesis that have the potential to differentiate into germ cells and other cells. PGCs are the source from which GSCs and ES cells are derived. The PGCs, the GSCs and the ES cells are capable of self-renewal. Thus these cells not only populate the germ line and give rise to a plurality of terminally differentiated cells that comprise the adult specialized organs, but are able to regenerate themselves. The term "totipotent" refers to the capability of a cell to differentiate into all of the cell types of an adult organism. The term "pluripotent" refers to the capability of a cell to differentiate into a number of differentiated cell types that are present in an adult organism. A pluripotent cell is restricted in its differentiation capability in comparison to a totipotent cell.

The terms "founder line" and "founder animal" refer to those animals that are the mature product of the embryos to which the transgene was added i.e. those animals that grew from the embryos into which DNA was inserted and that were implanted into one or more surrogate hosts.

The terms "progeny" and "progeny of the transgenic animal" refer to any and all offspring of every generation subsequent to the originally transformed mammals.

The term "non-human mammal" refers to all members of the class Mammalia except humans. "Mammal" refers tot any animal classified as a mammal, including humans, domestic and farm animals, and zoo, sports, or pet animals, such as a mouse, rat, rabbit, pig, sheep, goat, cattle and higher primates.

The terms "treat" or "treatment" refer to both therapeutic and prophylactic or preventative measures, wherein the object is to prevent or lessen an undesired physiological change or condition, such as chemotherapy or radiation therapy-induced mucositis. For the purposes of this invention, beneficial or desired clinical results include, but are not limited to alleviation of symptoms, diminishment of extent of the disease, stabilized state of the disease, whether detectable or undetectable.

A "disorder" is any condition that would benefit from treatment with a molecule identified using the transgenic animal model of the invention. This includes chronic and acute disorders or diseases including those pathological conditions which predispose the mammal to the disorder in question. Non-limiting examples of disorders to be treated herein include mucositis, inflammatory bowel disease and skin lesions. A preferred disorder to be treated in accordance with the present invention is mucositis.

"Inflammatory bowel disease (IBD)" herein refers to idiopathic or chronic inflammatory disease of either or both the small intestine and large bowel, and includes Crohn's disease, ulcerative colitis, IBD caused by infectious agents, and antibiotic associated IBD.

"Mucositis" herein refers to inflammation of the mucous membranes of the alimentary tract including the oropharynx and lips, esophagus, and large and small intestine.

"Short Bowel Syndrome" or "SBS" herein refers to a condition of nutritional malabsorption resulting from anatomical or functional loss of a significant length of the small intestine.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an effective amount of a GIPF fragment for use with the present methods is an amount sufficient to stimulate epithelial cell stimulation or proliferation, and preferably an amount sufficient to cause increased regeneration of the gastrointestinal epithelium in a subject suffering from chemotherapy or radiation therapy-induced mucositis, inflammatory bowel disease, or other disorders where epithelial cell proliferation is desired. Such amounts are described below. An appropriate "effective" amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiological range" is meant a pH in the range of approximately 7.0 to 8.0 inclusive. Preferred physiological pH is in the range of approximately 7.2 to 7.6 inclusive.

As used herein, the term "subject" encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

4.2 COMPOSITIONS OF THE INVENTION 4.2.1 Nucleic Acid Compositions

The invention is based on the discovery that compositions comprising the epithelial cell growth factor polypeptide, GIPF, and the polynucleotides encoding the GIPF polypeptide stimulate the growth and proliferation of intestinal epithelial cells including crypt cells. Therefore, the use of these compositions for the diagnosis and treatment of conditions wherein stimulation of epithelial cell proliferation or regeneration is desired, is contemplated.

The isolated polynucleotides of the invention include, but are not limited to a polynucleotide comprising any of the nucleotide sequences of SEQ ID NO: 2, 3, 5, 7, 9, 11, 13, 15, 17, 84, 86, 88, 90, 92, 94, 96, 98, 100, 102, 104 or 177; a polynucleotide comprising the full length protein coding sequence of SEQ ID NO: 3, 5, 7, 9, 11, 13, 15, 17, 84, 86, 88, 90, 92, 94, 96, 98, 100, 102, 104 or 177; (for example coding for SEQ ID NO: 4, 6, 8, 10, 12, 14, 16, 18, 85, 87, 89, 91, 93, 95, 97, 99, 101, 103, 105 or 178); and a polynucleotide comprising the nucleotide sequence encoding the mature and dominant mature protein coding sequence of the polypeptide of SEQ ID NO: 4. The polynucleotides of the present invention also include, but are not limited to, a polynucleotide that hybridizes under stringent conditions to (a) the complement of any of the nucleotides sequences of SEQ ID NO: 2, 3, 5, 7, 9, 11, 13, 15, 17, 84, 86, 88, 90, 92, 94, 96, 98, 100, 102, 104 or 177; (b) a polynucleotide encoding any one of the polypeptides of SEQ ID NO: 4, 6, 8, 10, 12, 14, 16, 18, 85, 87, 89, 91, 93, 95, 97, 99, 101, 103, 105 or 178; (c) a polynucleotide which is an allelic variant of any polynucleotides recited above; (d) a polynucleotide which encodes a species homolog of any of the proteins recited above; or (e) a polynucleotide that encodes a polypeptide comprising a specific domain or truncation of the polypeptides of SEQ ID NO: 4, 6, 8, 10, 12, 14, 16, 18, 85, 87, 89, 91, 93, 95, 97, 99, 101, 103, 105 or 178. Domains of interest include extracellular, transmembrane, or cytoplasmic domains, or combinations thereof; and catalytic and substrate binding domains.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides compositions comprising genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotide of SEQ ID NO: 2 can be obtained by screening appropriate cDNA or genomic DNA libraries under suitable hybridization conditions using any of the polynucleotides of SEQ ID NO: 2, 3, 5, 7, 9, 11, 13, 15, 17, 84, 86, 88, 90, 92, 94, 96, 98, 100, 102, 104 or 177 or a portion thereof as a probe. Alternatively, the polynucleotides of SEQ ID NO: 2, 3, 5, 7, 9, 11, 13, 15, 17, 84, 86, 88, 90, 92, 94, 96, 98, 100, 102, 104 or 177 may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99% sequence identity to a polynucleotide recited above.

Included within the scope of the nucleic acid sequences of the invention are nucleic acid sequence fragments that hybridize under stringent conditions to any of the nucleotide sequences of SEQ ID NO: 1, 6, 8, 10, 12, 14, 17, 84, 86, 88, 90, 92, 94, 96, 98, 100, 102, 104 or 177, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in SEQ ID NO: 2, 3, 5, 7, 9, 11, 13, 15, 17, 84, 86, 88, 90, 92, 94, 96, 98, 100, 102, 104 or 177, a representative fragment thereof, or a nucleotide sequence at least 90% identical, preferably 95% identical, to SEQ ID NO: 2, 3, 5, 7, 9, 11, 13, 15, 17, 84, 86, 88, 90, 92, 94, 96, 98, 100, 102, 104 or 177 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The nearest neighbor result for the nucleic acids of the present invention can be obtained by searching a database using an algorithm or a program. Preferably, a BLAST which stands for Basic Local Alignment Search Tool is used to search for local sequence alignments (Altshul, S. F. J Mol. Evol. 36 290-300 (1993) and Altschul S. F. et al. J. Mol. Biol. 21:403-410 (1990))

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encodes proteins which are identical, homologous or related to that encoded by the polynucleotides.

The nucleic acid sequences of the invention are further directed to sequences which encode analogs of the described nucleic acids. These amino acid sequence analogs may be prepared by methods known in the art by introducing appropriate nucleotide changes into a native or variant polynucleotide. There are two variables in the construction of amino acid sequence variants: the location of the mutation and the nature of the mutation. Nucleic acids encoding the amino acid sequence analogs are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as sufficient adjacent nucleotides on both sides of the changed amino acid to form a stable duplex on either side of the site being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487-6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

In accordance with the invention, polynucleotide sequences comprising the dominant mature or mature protein coding sequences, coding for any one of SEQ ID NO: 6 or 8, or functional equivalents thereof, may be used to generate recombinant DNA molecules that direct the expression of that nucleic acid, or a functional equivalent thereof, in appropriate host cells. Also included are the cDNA inserts of any of the clones identified herein.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The present invention further provides recombinant constructs comprising a nucleic acid having any of the nucleotide sequences of SEQ ID NO: 2, 3, 5, 7, 9, 11, 13, 15, 17, 84, 86, 88, 90, 92, 94, 96, 98, 100, 102, 104 or 177 or a fragment thereof or any other GIPF polynucleotides. In one embodiment, the recombinant constructs of the present invention comprise a vector, such as a plasmid or viral vector, into which a nucleic acid having any of the nucleotide sequences of SEQ ID NO: 2, 3, 5, 7, 9, 11, 13, 15, 17, 84, 86, 88, 90, 92, 94, 96, 98, 100, 102, 104 or 177 or a fragment thereof is inserted. In the case of a vector comprising one of the ORFs of the present invention, the vector may further comprise regulatory sequences, including for example, a promoter, operably linked to the ORF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, and pSVL (Pharmacia). In one embodiment, the nucleic acid of SEQ ID NO: 3 is inserted in the CκP2KI vector of the invention as described in the examples.

The isolated polynucleotide of the invention may be operably linked to an expression control sequence such as the pMT2 or pED expression vectors disclosed in Kaufman et al., *Nucleic Acids Res*. 19, 4485-4490 (1991), in order to produce the protein recombinantly. Many suitable expression control sequences are known in the art. General methods of expressing recombinant proteins are also known and are exemplified in R. Kaufman, *Methods in Enzymology* 185, 537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus*, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

In addition to the use of expression vectors in the practice of the present invention, the present invention further includes novel expression vectors comprising promoter elements operatively linked to polynucleotide sequences encoding a protein of interest. One example of such a vector is the pcDNA/vector, which is described in Example 8.

4.2.2 Hosts

The present invention further provides host cells genetically engineered with the vectors of this invention, which may be, for example, a cloning vector or an expression vector that contain the polynucleotides of the invention. For example, such host cells may contain nucleic acids of the invention introduced into the host cell using known transformation, transfection or infection methods. The vector may be, for example, in the form of a plasmid, a viral particle, a phage etc. The engineered host cells can be cultured in conventional nutrient media modified as appropriate for activating promoters, selecting transformants or amplifying GIPF genes. The culture conditions, such as temperature, pH, and the like, are those previously used with the host cell selected for expression, and will be apparent to the ordinarily skilled artisan. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the GIPF polypeptides. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Preferably, GIPF proteins are expressed in Chinese Hamster Ovary (CHO) cells, and human embryonic kidney 293 cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida, Pichia pastoris* or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

4.2.3 Chimeric and Fusion Proteins

The invention also provides GIPF chimeric or fusion proteins. As used herein, a GIPF "chimeric protein" or "fusion protein" comprises a GIPF polypeptide operatively-linked to a non-GIPF polypeptide. A "GIPF polypeptide" refers to a polypeptide having an amino acid sequence corresponding to a GIPF protein, whereas a "non-GIPF polypeptide" refers to a polypeptide having an amino acid sequence corresponding to a protein that is not substantially homologous to the GIPF protein, e.g., a protein that is different from the GIPF protein and that is derived from the same or a different organism. Within a GIPF fusion protein the GIPF polypeptide can correspond to all or a portion of a GIPF protein. In one embodiment, a GIPF fusion protein comprises at least one biologically active portion of a GIPF protein. In another embodiment, a GIPF fusion protein comprises at least two biologically active portions of a GIPF protein. In yet another embodiment, a GIPF fusion protein comprises at least three biologically active portions of a GIPF protein. Within the fusion protein, the term "operatively-linked" is intended to indicate that the GIPF polypeptide and the non-GIPF polypeptide are fused in-frame with one another. The non-GIPF polypeptide can be fused to the N-terminus or C-terminus of the GIPF polypeptide.

In one embodiment, the fusion protein is a GST-GIPF fusion protein in which the GIPF sequences are fused to the C-terminus of the GST (glutathione S-transferase) sequences. Such fusion proteins can facilitate the purification of recombinant GIPF polypeptides. In another embodiment, the fusion protein is a GIPF protein containing a heterologous signal sequence at its N-terminus. In certain host cells (e.g., mammalian host cells), expression and/or secretion of GIPF can be increased through use of a heterologous signal sequence. Preferably, the GIPF polypeptide is fused with a V5-His tag for easy detection with an anti-V5 antibody and for rapid purification as described in the examples.

A GIPF chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A GIPF-encoding nucleic acid can be cloned into such an expression vector such that the fusion moiety is linked in-frame to the GIPF protein.

4.2.4 Polypeptide Compositions

The pharmaceutical compositions of the invention comprise isolated GIPF polypeptides that include, but are not limited to, a polypeptide comprising: the amino acid sequence set forth as any one of SEQ ID NO: 4, 6, 8, 10, 12, 14, 16, 18, 85, 87, 89, 91, 93, 95, 97, 99, 101, 103, 105 or 178, or an amino acid sequence encoded by any one of the nucleotide sequences SEQ ID NO: 2, 3, 5, 7, 9, 11, 13, 15, 17, 84, 86, 88, 90, 92, 94, 96, 98, 100, 102, 104 or 177. Polypeptides of the invention also include polypeptides preferably with biological or immunological activity that are encoded by: (a) a polynucleotide having any one of the nucleotide sequences set forth in SEQ ID NO: 2, 3, 5, 7, 9, 11, 13, 15, 17, 84, 86, 88, 90, 92, 94, 96, 98, 100, 102, or 104 or (b) polynucleotides encoding any one of the amino acid sequences set forth as SEQ ID NO:4, 6, 8, 10, 12, 14, 16, 18, 85, 87, 89, 91, 93, 95, 97, 99, 101, 103, 105 or 178 or (c) polynucleotides that hybridize to the complement of the polynucleotides of either (a) or (b) under stringent hybridization conditions. The invention also provides biologically active or immunologically active variants of any of the amino acid sequences set forth as SEQ ID NO: 4, 6, 8, 10, 12, 14, 16, 18, 85, 87, 89, 91, 93, 95, 97, 99, 101, 103, 105 or 178; and "substantial equivalents" thereof (e.g., with at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99%, most typically at least about 99% amino acid identity) that retain biological activity. Polypeptides encoded by allelic variants may have a similar, increased, or decreased activity compared to polypeptides comprising SEQ ID NO: 4, 6, 8, 10, 12, 14, 16, 18, 85, 87, 89, 91, 93, 95, 97, 99, 101, 103, 105 or 178.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments may be fused to carrier molecules such as immunoglobulins for many purposes, including increasing the valency of protein binding sites.

The present invention also provides both full-length and dominant mature forms (for example, without a signal sequence or precursor sequence) or mature forms (for example, lacking the signal sequence and the furin cleavage site) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form.

Protein compositions of the present invention may further comprise an acceptable carrier, such as a hydrophilic, e.g., pharmaceutically acceptable, carrier.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. The synthetically-constructed protein sequences, by virtue of sharing primary, secondary or tertiary structural and/or conformational characteristics with proteins may possess biological properties in common therewith, including protein activity. This technique is particularly useful in producing small peptides and fragments of larger polypeptides. Fragments are useful, for example, in generating antibodies against the native polypeptide. Thus, they may be employed as biologically active or immunological substitutes for natural, purified proteins in screening of therapeutic compounds and in immunological processes for the development of antibodies.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

In an alternative method, the polypeptide or protein is purified from bacterial cells which are transformed with GIPF-encoding DNA to produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immunoaffinity chromatography. See, e.g., Scopes, *Protein Purification: Principles and Practice*, Springer-Verlag (1994); Sambrook, et al., in *Molecular Cloning: A Laboratory Manual*; Ausubel et al., *Current Protocols in Molecular Biology*. Polypeptide fragments that retain biological/immunological activity include fragments comprising greater than about 100 amino acids, or greater than about 200 amino acids, and fragments that encode specific protein domains.

The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The proteins provided herein also include proteins characterized by amino acid sequences similar to those of purified proteins but into which modification are naturally provided or deliberately engineered. For example, modifications, in the peptide or DNA sequence, can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity. Regions of the protein that are important for protein function may be determined by the eMATRIX program.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include GIPF analogs. This embraces fragments of GIPF polypeptide, as well as GIPF polypeptides which comprise one or more amino acids deleted, inserted, or substituted. Also, analogs of the GIPF polypeptide of the invention embrace fusions of the GIPF polypeptides or modifications of the GIPF polypeptides, wherein the GIPF polypeptide or analog is fused to another moiety or moieties, e.g., targeting moiety or another therapeutic agent. Such analogs may exhibit improved properties such as activity and/or stability. Examples of moieties which may be fused to the GIPF polypeptide or an analog include, for example, targeting moieties which provide for the delivery of polypeptide to the small intestine, e.g., antibodies to the small intestine, or antibodies to receptor and ligands expressed on gastrointestinal cells. Other moieties which may be fused to GIPF polypeptide include therapeutic agents which are used for treatment, for example cytokines or other medications, of gastrointestinal disorders, and other conditions as recited herein.

4.2.5 Gene Therapy

The invention provides gene therapy to treat the diseases cited herein. Delivery of a functional gene encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25-20 (1998). For additional reviews of gene therapy technology see Friedmann, Science, 244: 1275-1281 (1989); Verma, Scientific American: 68-84 (1990); and Miller, Nature, 357: 455-460 (1992).

As discussed above, a "vector" is any means for the transfer of a nucleic acid according to the invention into a host cell. Preferred vectors are viral vectors, such as retroviruses, herpes viruses, adenoviruses and adeno-associated viruses. Thus, a gene or nucleic acid sequence encoding a GIPF protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and therapy procedures are DNA-based vectors and retroviral vectors. Methods for constructing and using viral vectors are known in the art [see, e.g., Miller and Rosman, BioTechniques 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein-Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci. 2:320-330 (1991)], defective herpes virus vector lacking a glycoprotein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [J. Clin. Invest. 90:626-630 (1992); see also La Salle et al., Science 259:988-990 (1993)]; and a defective adeno-associated virus vector [Samulski et al., J. Virol. 61:3096-3101 (1987); Samulski et al., J. Virol. 63:3822-3828 (1989); Lebkowski et al., Mol. Cell. Biol. 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, Nature Medicine (1995)]. In addition, it is advantageous to employ a viral vector that is engineered to express a minimal number of antigens.

In a preferred embodiment, the vector is an adenovirus vector. As shown in the Examples, the adenovirus vector has shown itself to be particularly effective for delivery of the GIPF polypeptide, as shown by the unexpectedly efficient effects of stimulating intestinal epithelial cell proliferation resulting in marked, diffuse thickening of the mucosa by crypt epithelial hyperplasia and a marked increase in crypt length and complex branching. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: May 1, Beard et al., Virology 75 (1990) 81), ovine, porcine, avian, and simian (example: SAV) origin.

Preferably, the replication defective adenoviral vectors of the invention comprise the ITRs, an encapsidation sequence and the nucleic acid of interest. Still more preferably, at least the E1 region of the adenoviral vector is non-functional. Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 and E3 region. Examples of E1-deleted adenoviruses are disclosed in EP 185,573, the contents of which are incorporated herein by reference.

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, CMV and RSV genes and the like.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence.

Some promoters useful for practice of this invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Thus, the promoters which may be used to control gene expression include, but are not limited to, the cytomegalovirus (CMV) promoter, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the b-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. In addition to the use of viral vectors in the practice of the present invention, the present invention further includes a novel vector comprising operator and promoter elements operatively linked to polynucleotide sequences encoding a protein of interest. The novel adenoviral vector is the pAdenoVator-CMV5-Intron vector, which is described in detail in Examples.

4.2.6 Transgenic Animals

The polynucleotides of the present invention also make possible the development of chimeric animals that specifically express GIPF polypeptides in B cells. Such animals are useful as models for studying the in vivo activities of polypeptide as well as for studying modulators of the polypeptides of the invention. A preferred embodiment of the invention relates to a transgenic knock-in (KI) mouse model that was designed to determine the biological function of GIPF in a rapid manner. The transgenic KI animal model is described in International Application PCT/JP02/11236, and published as WO2003/041495. The transgenic model relates to a GIPF transgene that encodes the B-cell specific expression of GIPF under the control of the immunoglobulin kappa light chain promoter. The transgene is introduced into TT2F ES cells, which contain intact immunoglobulin heavy and light chain loci, and the ES cells that contain the GIPF transgene are implanted into mice that lack both alleles for the antibody heavy chain (IgH-KO$\Delta$H$^{-/-}$) (Kitamura et al., Nature 350: 423-426 (1991), herein incorporated by reference in its entirety). Thus, the expression of the immunoglobulin kappa light chains can only occur in functional B cells that are derived from the ES cells that express the IG chains (WO 00/10383; EP 1106061A1). Similarly, the expression of GIPF by B-cells occurs only in the GIPF-KI chimeric mice. The transgenic animal model of the invention thus allows for a speedy phenotypic analysis of chimeric animals, rather than heterozygous or homozygous animals containing transgenes transmitted through the germline. In addition, the expression of the transgene is restricted to B cells, which secrete the GIPF protein into the animal's circulation, thus exposing every tissue to GIPF, and allowing for a rapid assessment of the biological effect of GIPF, or any other encoded polypeptide. It is intended that the transgenic system of the present invention can be used for expressing and assessing the biological function of any polypeptide. Another advantage of the transgenic model of the invention relates to the temporal expression of the transgene. The activity of the kappa light chain promoter begins at approximately 14 days post-gestation and the remarkable elevation of circulating immunoglobulin concentration is observed after weaning, thus avoiding any potentially deleterious effects that GIPF might have on the early development of the mouse. An exemplary embodiment of the transgenic animal of the invention is described in the Examples.

4.2.6.1 General Method of Making Transgenic Non-Human Mammals

The transgenic animals of the present invention all include within a plurality of their cells a transgene of the present invention, which transgene alters the phenotype of the "host cell" with respect to the specific expression of GIPF by B cells, which secrete GIPF polypeptides into the circulation of the transgenic animal. Various aspects of transgenic animal technology are well known in the art, and are described in detail in literature, such as Hogan et al., Manipulating the Mouse Embryo (Cold Spring Harbor Laboratory, Cold Spring Harbor, N.Y., [1986]). Although the making of transgenic animals is illustrated herein with reference to transgenic mice, this is only for illustrative purpose, and is not to be construed as limiting the scope of the invention. This specific disclosure can be readily adapted by those skilled in the art to incorporate GIPF transgene sequences into any non-human mammal utilizing the methods and materials described below. Animals suitable for transgenic experiments can be obtained from standard commercial sources such as Taconic (Germantown, N.Y.).

A. Transgene Construct

Construction of transgenes can be accomplished using any suitable genetic engineering techniques well known in the art, including, without limitation, the standard techniques of restriction endonuclease digestion, ligation, transformation, plasmid purification, DNA sequencing etc as described in Sambrook et al., Molecular Cloning: A Laboratory Manual (Cold Spring Harbor Laboratory, N.Y., (1989)).

The transgenes of the present invention are typically operably linked to transcriptional regulatory sequences, such as promoters and/or enhancers, to regulate expression of the transgene in a particular manner. In certain embodiments, the useful transcriptional regulatory sequences are those that are highly regulated with respect to activity, both temporally and spatially. Thus, the promoters of choice can be those that are active only in particular tissues or cell types. Promoters/enhancers which may be used to control the expression of the transgene in vivo include, but are not limited to, the human cytomegalovirus (CMV) promoter/enhancer (Karasuyama et al., J. Exp. Med. 169: 13 [1989]), the human β-actin promoter (Gunning et al., Proc. Natl. Acad. Sci. USA 84: 4831-4835 [1987]), the glucocorticoid-inducible promoter present in the mouse mammary tumor virus long terminal repeat (MMTV LTR) (Kiessig et al., Mol. Cell. Biol. 4: 1354-1362 [1984]), the long terminal repeat sequences of Moloney murine leukemia virus (MuLV LTR) (Weiss et al. [1985] RNA Tumor Viruses, Cold Spring Harbor Laboratory, Cold Spring Harbor, N.Y.), the SV40 early or late region promoter (Benoist et al. Nature 290: 304-310 [1981]; Templeton et al. Mol. Cell. Biol., 4: 817 [1984]; and Sprague et al., J. Virol., 45: 773 [1983]), the promoter contained in the 3' long terminal repeat of Rous sarcoma virus (RSV) (Yamamoto et al., Cell 22: 787-797 [1980]), the herpes simplex virus (HSV) thymidine kinase promoter/enhancer (Wagner et al. Proc. Natl. Acad. Sci. USA 82: 3567-71 [1981]), metallothionein (MT) promoter (Palmiter et al., Nature 300: 611-615 [1982]), and the herpes simplex virus LAT promoter (Wolfe et al. Nature Genetics 1: 379-384 [1992]). Preferably the promoter is the P2 promoter of the immunoglobulin kappa light chain (REF).

In addition to the transgene and the transcriptional regulatory sequence, the vectors useful for preparing the transgenes of this invention typically contain one or more other elements useful for optimizing expression of the transgene in the host animal. Thus, the transgene construct may include transcription termination elements, such as to direct polyadenylation of an mRNA transcript, as well as intronic sequences. For example, the transgene can be flanked at its 3' end by SV40 sequences (SV40 intron/pA) which add the transcription termination and polyadenylation signals to the transgene transcript. In yet other embodiments, the transgene can include intron sequences. In many instances, the expression of a transgene is increased by the presence of one or more introns in the coding sequence.

In still other embodiments, the transgene construct may include additional elements which facilitate its manipulation in cells (e.g., in bacterial cells) prior to insertion in the intended recipient cell. For instance, the vector may include origin of replication elements for amplification in prokaryotic cells. Moreover, the transgene construct may contain selectable markers for isolating cells, either from the recipient animal, or cells generated as intermediate in making the transgenic animal (i.e., bacterial cells used for amplifying the construct or ES cells used for introducing the transgene). Selectable marker genes may encode proteins necessary for the survival and/or growth of transfected cells under selective culture conditions. Typical selection marker genes encode proteins that, for example: (i) confer resistance to antibiotics or other toxins, e.g., ampicillin, tetracycline or kanamycin for prokaryotic host cells, and neomycin, hygromycin or methotrexate for mammalian cells; or (ii) complement auxotrophic deficiencies of the cell.

B. Cells Used for Introduction of Transgene

In an exemplary embodiment, the "transgenic non-human mammals" of the invention are produced by introducing GIPF transgene into the germline of the non-human mammal. Embryonal target cells at various developmental stages can be used to introduce GIPF transgene. Different methods are used depending on the stage of development of the embryonal target cell. The specific line(s) of any animal used to practice this invention are selected for general good health, good embryo yields, good pronuclear visibility in the embryo, and good reproductive fitness.

In one embodiment, the transgene construct is introduced into a single stage embryo. Generally, the female animals are superovulated by hormone treatment, mated and fertilized eggs are recovered. For example, in case of mice, females six weeks of age are induced to superovulate with a 5 IU injection (0.1 ml, i.p.) of pregnant mare serum gonadotropin (PMSG; Sigma) followed 48 hours later by a 5 IU injection (0.1 ml, i.p.) of human chorionic gonadotropin (hCG; Sigma). FVB strain of mice are used in this case. Females are then mated immediately with a stud male overnight. Such females are next examined for copulation plugs. Those that have mated are euthanized by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Normally, fertilized embryos are incubated in suitable media until the pronuclei appear. At about this time, the transgene is introduced into the female or male pronucleus as described below. In some species such as mice, the male pronucleus is preferred. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

In addition to similar biological considerations, physical ones also govern the amount (e.g., volume) of exogenous genetic material, which can be added to the nucleus of the zygote, or to the genetic material which forms a part of the zygote nucleus. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional.

C. Methods of Introducing Transgene

Each transgene construct to be inserted into the cell must first be in the linear form since the frequency of recombination is higher with linear molecules of DNA as compared to the circular molecules. Therefore, if the construct has been inserted into a vector, linearization is accomplished by digesting the DNA with a suitable restriction endonuclease selected to cut only within the vector sequence and not within the transgene sequence.

Introduction of the transgene into the embryo may be accomplished by any means known in the art so long as it is not destructive to the cell, nuclear membrane or other existing cellular or genetic structures. Some of the widely used methods include microinjection, electroporation, or lipofection. Following introduction of the transgene, the embryo may be incubated in vitro for varying amounts of time, or reimplanted into the surrogate host, or both. One common method is to incubate the embryos in vitro for about 1-7 days, depending on the species, and then reimplant them into the surrogate host.

The zygote is the best target for introducing the transgene construct by microinjection method. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. Proc. Natl. Acad. Sci. USA 82: 4438-4442 (1985)). As a consequence, all cells of the transgenic animal will carry the incorporated transgene. This will in general also be reflected in the efficient transmission of the transgene to offspring of the founder since 50% of the germ cells will harbor the transgene.

Retroviral infection can also be used to introduce transgene into a non-human mammal. The developing non-human embryo can be cultured in vitro to the blastocyst stage. During this time, the blastomeres can be targets for retroviral infection (Jaenich, R. Proc. Natl. Acad. Sci. USA 73: 1260-1264 (1976)). Efficient infection of the blastomeres is obtained by enzymatic treatment to remove the zona pellucida (Manipulating the Mouse Embryo, Hogan eds., Cold Spring Harbor Laboratory Press, Cold Spring Harbor, (1986)). The viral vector system used to introduce the transgene is typically a replication-defective retrovirus carrying the transgene (Jahner et al. Proc. Natl. Acad. Sci. USA 82: 6927-6931 (1985)). Van der Putten et al. Proc. Natl. Acad. Sci. USA 82: 6148-6152 (1985)). Transfection is easily and efficiently obtained by culturing the blastomeres on a monolayer of virus-producing cells (Van der Putten, supra; Stewart et al. EMBO J. 6: 383-388 (1987)). Alternatively, infection can be performed at a later stage. Virus or virus-producing cells can also be injected into the blastocoele (Jahner et al. Nature 298: 623-628 (1982)). Most of the founders will be mosaic for the transgene since incorporation occurs only in a subset of the cells which formed the transgenic animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

Insertion of the transgene construct into the ES cells can be accomplished using a variety of methods well known in the art including for example, electroporation, microinjection, and calcium phosphate treatment. A preferred method of insertion is electroporation, in which the ES cells and the transgene construct DNA are exposed to an electric pulse using an electroporation machine and following the manufacturer's guidelines for use. After electroporation, the ES cells are typically allowed to recover under suitable incubation conditions. The cells are then screened for the presence of the transgene.

D. Implantation of Embryos

Pseudopregnant, foster or surrogate mothers are prepared for the purpose of implanting embryos, which have been modified by introducing the transgene. Such foster mothers are typically prepared by mating with vasectomized males of the same species. The stage of the pseudopregnant foster mother is important for successful implantation, and it is species dependent. For mice, this stage is about 2-3 days pseudopregnant. Recipient females are mated at the same time as donor females. Although the following description relates to mice, it can be adapted for any other non-human mammal by those skilled in the art. At the time of embryo transfer, the recipient females are anesthetized with an intra-peritoneal injection of 0.015 ml of 2.5% avertin per gram of body weight. The oviducts are exposed by a single midline dorsal incision. An incision is then made through the body wall directly over the oviduct. The ovarian bursa is then torn with watchmaker's forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures. The number of embryos implanted into a particular host will vary by species, but will usually be comparable to the number of offspring the species naturally produces.

Where the ES cell have been used to introduce the transgene, the transformed ES cells are incorporated into the embryo as described earlier, and the embryos may be implanted into the uterus of a pseudopregnant foster mother for gestation.

E. Screening for the Presence or Expression of Transgene

Transgenic offspring of the surrogate host may be screened for the presence and/or expression of the transgene by any suitable method. Offspring that are born to the foster mother may be screened initially for mosaic coat color where the coat color selection strategy (as described above) has been employed. Alternatively, or additionally, screening is often accomplished by Southern blot or PCR of DNA prepared from tail tissue, using a probe that is complementary to at least a portion of the transgene. Western blot analysis or immunohistochemistry using an antibody against the protein encoded by the transgene may be employed as an alternative or additional method for screening for the presence of the transgene product. Alternatively, the tissues or cells believed to express the transgene at the highest levels are tested for the RNA expression of the transgene using Northern analysis or RT-PCR.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

F. Breeding of the Transgenic Animals

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods. Typically, crossing and backcrossing is accomplished by mating siblings or a parental strain with an offspring, depending on the goal of each particular step in the breeding process.

A preferred embodiment of the invention relates to mice that lack both alleles for antibody heavy chain (IgH-KO$\Delta$H$^{-/-}$), and have very low levels of circulating antibodies (Kitamura et al., Nature 350:423-426 (1991)). In one aspect, the invention concerns a transgenic non-human mammal that produces in its B-cells GIPF protein or a fragment thereof. The transgenic mammal has stably integrated into its genome a nucleic acid sequence encoding GIPF or a fragment thereof having the biological activity of the native protein, operably linked to transcriptional regulatory sequences directing its expression in B-cells. The transcriptional regulatory sequences preferably comprise a B-cell specific promoter, such as the immunoglobulin kappa chain promoter. Without limitation, the non-human transgenic mammal may, for example, be mouse, rat, rabbit, pig, goat, goat or cattle.

4.2.7 Crypt Cell and Tissue Growth Activity

The GIPF polypeptide of the invention exhibits growth factor activity and is involved in the proliferation and differentiation of intestinal crypt cells. GIPF may also exhibit growth factor activity on other epithelial cells of the gastrointestinal tract. Administration of the polypeptide of the invention to crypt cells in vivo or ex vivo may maintain and expand cell populations in a totipotential state which would be useful for re-engineering damaged or diseased tissues, transplantation, manufacture of bio-pharmaceuticals and the development of bio-sensors. The ability to produce large quantities of human cells has important working applications for the production of human proteins which currently must be obtained from non-human sources or donors, implantation of cells to treat tissues for grafting such gastrointestinal cells.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL-6 receptorfused to IL-6, macrophage inflammatory protein 1-alpha (MIP-1-alpha), G-CSF, GM-CSF, thrombopoietin (TPO), platelet factor 4 (PF-4), platelet-derived growth factor (PDGF), neural growth factors, basic fibroblast growth factor (bFGF), keratinocyte growth factor-2 (KGF2), and glucagons-like peptide 2 (GLP-2).

Intestinal epithelial cells including crypt cells can be transfected with a polynucleotide of the invention to induce autocrine expression of the polypeptide of the invention. This will allow for generation of undifferentiated cell lines that are useful as is or that can then be differentiated into the desired mature cell types. These stable cell lines can also serve as a source of undifferentiated mRNA to create cDNA libraries and templates for polymerase chain reaction experiments. These studies would allow for the isolation and identification of differentially expressed genes in crypt cell populations that regulate crypt proliferation and/or maintenance.

Expansion and maintenance of epithelial stem cell populations will be useful in the treatment of many pathological conditions. For example, polypeptides of the present invention may be used to manipulate crypt cells in culture to give rise to gastrointestinal epithelial cells that can be used to augment or replace cells damaged by illness, autoimmune disease, accidental damage or genetic disorders, inflammation caused by ionizing radiation, chemotherapy, infection and inflammation.

Expression of the polypeptide of the invention and its effect on crypt cells can also be manipulated to achieve controlled differentiation of the crypt cells into more differentiated cell types. A broadly applicable method of obtaining pure populations of a specific differentiated cell type from undifferentiated stem cell populations involves the use of a cell-type specific promoter driving a selectable marker In vitro cultures of intestinal epithelial cells including crypt cells can be used to determine if the polypeptide of the invention exhibits growth factor activity. Crypt cells are isolated from disaggregated colonic crypts from human and murine colonic mucosa, and the clonogenic activity of GIPF can be assessed using the method described by Whitehead et al., Gastroenterology 117:858-865 (1999), which is herein incorporated by reference in its entirety. Growth factor activity may be assed in the presence of the polypeptide of the invention alone or in combination with other growth factors or cytokines.

The compositions of the present invention may also be useful for proliferation of intestinal epithelial cells including crypt cells and for regeneration of oral and gastrointestinal tissue, i.e. for the treatment of injuries sustained by the epithelial layer which involve degeneration, death or trauma to epithelial crypt cells. More specifically, a composition may be used in the treatment of diseases of the gastrointestinal tract as recited herein.

Compositions of the invention may also be useful to promote better or faster closure of non-healing wounds, including without limitation pressure ulcers, ulcers associated with vascular insufficiency, surgical and traumatic wounds, and the like. Assays for wound healing activity include, without limitation, those described in: Winter, Epidermal Wound Healing, pp. 71-112 (Maibach, H. I. and Rovee, D. T., eds.), Year Book Medical Publishers, Inc., Chicago, as modified by Eaglstein and Mertz, J. Invest. Dermatol 71:382-84 (1978).

4.2.8 Immunomodulatory Activity

A polypeptide of the present invention may exhibit activity relating to regulation of immune system components including, but not limited to cytokine production and/or activity, and/or cells of the immune system. A polynucleotide of the invention can encode a polypeptide exhibiting such attributes. Regulation of cytokines and/or cells of the immune system may include increasing and/or decreasing levels of cytokines or numbers of particular cells of the immune system.

With such immunomodulatory activity, polypeptides of the invention may be used to treat various immune disorders. These disorders include, but are not limited to inflammatory bowel disease (IBD), which includes ulcerative colitis and/or Crohn's disease, and mucositis as a consequence of anti-cancer therapies including radiation treatment and/or chemotherapy. The cause of these immune disorders may be, for example, idiopathic (i.e. of unknown cause), genetic, by infectious agents (eg. viruses, bacteria, fungi), and/or by damage induced by anti-cancer therapies (eg. radiation therapy and/or chemotherapy).

Modulation of immune responses and/or components of the immune system may be accomplished in a number of ways. Down-regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process that requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of tolerizing agent.

Inflammatory bowel disease is almost always mediated by one of two pathways: excessive T helper 1 (Th1)-cell response associated with high levels of IL-12, IFN-gamma, and/or TNF or excessive T helper 2 (Th2)-cell response associated with high levels of IL-4, IL-5, and/or IL-13 (Bouma et al., herein incorporated by reference in its entirety). Therefore a mechanism through which polypeptides of the invention could mediate immunomodulatory activity in disease treatment would be to down-regulate the numbers of Th1 and/or Th2 cell populations. Alternatively, another activity could be to decrease the levels of cytokines (eg. IL-12, IFN-gamma, TNF, IL-4, IL-5, and/or IL-13) that are associated with and/or mediate the inflammatory response.

The activity of the polypeptide of the present invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Bertagnolli et al., J. Immunol. 145:1706-1712, 1990; Bertagnolli et al., Cellular Immunology 133: 327-341, 1991; Bertagnolli, et al., I. Immunol. 149:3778-3783, 1992; Bowman et al., I. Immunol. 152:1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1-3.12.14, John Wiley and Sons, Toronto. 1994; and Measurement of mouse and human interferon-γ, Schreiber, R. D. In Current Protocols in Immunology. J. E. e.a. Coligan eds. Vol 1 pp. 6.8.1-6.8.8, John Wiley and Sons, Toronto. 1994.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.)

4.2.9 Chemotactic/Chemokinetic Activity

A polypeptide of the present invention may be involved in chemotactic or chemokinetic activity for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against a tumor or an infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1-6.12.28; Taub et al. J. Clin. Invest. 95:1370-1376, 1995; Lind et al. APMIS 103:140-146, 1995; Muller et al Eur. J. Immunol. 25:1744-1748; Gruber et al. J. of Immunol. 152:5860-5867, 1994; Johnston et al. J. of Immunol. 153:1762-1768, 1994.

4.2.10 Drug Screening

The transgenic non-human mammals and their progeny of the present invention provide several important uses that will be readily apparent to one of ordinary skill in the art. The transgenic animals are particularly useful in screening compounds that modulate (i.e. increase or decrease) the activity of the GIPF polypeptides. Screening for a useful compound involves administering the candidate compound over a range of doses to the transgenic animal, and assaying at various time points for the effect(s) of the compound on the activity of the GIPF protein. The compound may be administered prior to or at the onset of abdominal distension. Administration may be oral, or by suitable injection, depending on the chemical nature of the compound being evaluated. The cellular response to the compound is evaluated over time using appropriate biochemical and/or histological assays.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see *Science* 282:63-68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). For reviews and examples of peptidomimetic libraries, see Al-Obeidi et al., *Mol. Biotechnol*, 9(3):205-23 (1998); Hruby et al., *Curr Opin Chem Biol*, 1(1):114-19 (1997); Dorner et al., *Bioorg Med Chem*, 4(5):709-15 (1996) (alkylated dipeptides).

4.3 Diseases Amenable to GIPF Therapy

In one aspect, the present invention provides pharmaceutical reagents and methods useful for treating diseases and conditions wherein epithelialization is desired. GIPF polypeptides are useful to increase cytoprotection, proliferation and/or differentiation of epithelial cells of the oral and gastrointestinal tract. Specifically, GIPF polypeptides are useful to treat or prevent diseases or conditions that include without limitation gastrointestinal diseases, mucositis of the gastrointestinal tract, mucositis of the oropharynx, lips and esophagus (oral mucositis), inflammatory bowel disease, short bowel syndrome, gastric and duodenal ulcers, erosions of the gastrointestinal tract including erosive gastritis, esophagitis, esophageal reflux and other conditions including wounds, burns, ophthalmic disorders, and any disorder where stimulation of epithelial cell proliferation or regeneration is desired. Treatment of diseases that result in insufficient production of mucus throughout the oral and gastrointestinal tract is also contemplated.

Mucositis, which includes oral and gastrointestinal mucositis, is a complication of some cancer therapies in which the lining of the digestive system becomes inflamed. GIPF is useful for preventing and/or ameliorating the degeneration of the mucosa of the alimentary tract that is caused by chemotherapy and/or radiation therapy given to a patient for the treatment of cancer, or is given as an adjuvant therapy following the removal of a tumor. Exemplary chemotherapeutic agents include, without limitation, BCNU, busulfan, carboplatin, cyclophosphamide, tannorubicin, doxorubicin, etoposide, 5-fluorouracil, gemcitabine, ifophamide, irinotecan, melphalan, methotrexate, navelbine, topotecan, and taxol, and exemplary treatment regimens include without limitation, BEAM (busulfan, etoposide, cytosine, arabinoside, methotrexate); cyclophosphamide and total body irradiation; cyclophosphamine, total body irradiation and etoposide; cyclophosphamide and busulfan; and 5-fluorouracil with leucovorin or levamisole. Treatment, pretreatment or post-treatment with GIPF is useful to generate a cytoprotective effect or regeneration or both, for example, of the mucosa of the small intestine and colon, allowing increased dosages of therapies while reducing their potential side effects.

Inflammatory bowel disease that can be treated with GIPF includes general inflammatory bowel disease that is characterized by chronic, relapsing, inflammatory disorders of unknown origin, Crohn's disease, dysplasia associated with inflammatory bowel disease, intermediate colitis, ulcerative colitis; non-infectious colitis including active colitis, antibiotic-associated colitis, collagenous colitis, diversion colitis, eosinophilic colitis, graft versus host disease, granulomatous colitis, ischaemic colitis, hemorrhagic colitis, malacoplakia, necrotizing enterocolitis, radiation enterocolitis, typhlitis; infectious colitis including adenovirus and amebic colitis, balantidiasis, HSV/AIDS associated colitis, and colitis caused by trypanosomes, *E. coli, Mycobacterium avium* intracellulare, Sotavirus, *Salmonella, Shigella, Campylobacter jejuni, Clostridium, Botulinum*, and colitis associated with schistosomiasis, spirochetosis, syphilis, trichuriasis, tuberculosis typhoid fever, *Vibrio cholera*, and *Yersinia*.

Short bowel syndrome is a group of problems affecting people who have had half or more of their small intestine removed. The most common reason for removing part of the small intestine is to treat Crohn's disease. In addition, surgical resection of part of the intestine may be required to remove cancerous growths. Diarrhea is the main symptom of short bowel syndrome. Other symptoms include cramping, bloating, and heartburn. Many people with short bowel syndrome are malnourished because their remaining small intestine is unable to absorb enough water, vitamins, and other nutrients from food. They may also become dehydrated, which can be life threatening. Problems associated with dehydration and malnutrition include weakness, fatigue, depression, weight loss, bacterial infections, and food sensitivities. Short bowel syndrome is treated through changes in diet, intravenous feeding, vitamin and mineral supplements, and medicine to relieve symptoms. GIPF polypeptides may be useful to increase the proliferation of the unresected intestinal tissue, thereby increasing the absorptive surface area of the intestine, and ameliorate the symptoms associated with short bowel syndrome.

The cytoprotective and/or regenerative activity of GIPF polypeptides can be tested in in vivo models of radiation induced mucositis (Withers and Elkind, Int J Radiat 17:261-267 (1970), herein incorporated by reference) in in vivo chemotherapy-induced mucositis (Soris et al., Oral Surg Oral Med Oral Pathol 69:437-443 (1990); Moore, Cancer Chemother Pharmacol 15:11-15 (1985); Farell et al., Cell Prolif 35:78-85 (2002), all of which are incorporated by reference in their entirety); in a dextran sulfate sodium (DSS) model of colitis and small intestinal ulceration or inflammation (Jeffers et al., Gastroenterology 123:1151-1162 (2002), Han et al., Am J Physiol Gastrointest Liver Physiol 279: G1011-G1022 (2000); and in a surgical model of short bowel syndrome (SBS) (Scott et al. Am J Physiol G911-G921 (1998); Helmrath et al., J Am Coll Surg 183:441-449 (1996)), herein incorporated by reference in their entirety).

Comparisons of GIPF mRNA and protein expression levels between diseased cells, tissue and corresponding normal samples are made to determine if the subject is responsive to GIPF therapy. Methods for detecting and quantifying the expression of GIPF polypeptide mRNA or protein use standard nucleic acid and protein detection and quantitation techniques that are well known in the art and are described in Sambrook, et al., *Molecular Cloning: A Laboratory Manual*, Cold Spring Harbor Laboratory, NY (1989) or Ausubel, et al., *Current Protocols in Molecular Biology*, John Wiley & Sons, New York, N.Y. (1989), both of which are incorporated herein by reference in their entirety. Standard methods for the detection and quantification of GIPF mRNA include in situ hybridization using labeled GIPF riboprobes (Gemou-Engesaeth, et al., *Pediatrics* 109: E24-E32 (2002), herein incorporated by reference in its entirety), Northern blot and related techniques using GIPF polynucleotide probes (Kunzli, et al., *Cancer* 94: 228 (2002), herein incorporated by reference in its entirety, herein incorporated by reference in its entirety), RT-PCR analysis using GIPF-specific primers (Angchaiskisiri, et al., *Blood* 99:130 (2002)), and other amplification detection methods, such as branched chain DNA solution hybridization assay (Jardi, et al., *J. Viral Hepat.* 8:465-471 (2001), herein incorporated by reference in its entirety), transcription-mediated amplification (Kimura, et al., *J. Clin. Microbiol.* 40:439-445 (2002)), microarray products, such as oligos, cDNAs, and monoclonal antibodies, and real-time PCR (Simpson, et al., *Molec. Vision,* 6:178-183 (2000), herein incorporated by reference in its entirety). Standard methods for the detection and quantification of GIPF protein include western blot analysis (Sambrook, et al., *Molecular Cloning: A Laboratory Manual*, Cold Spring Harbor Laboratory, NY (1989), Ausubel, et al., *Current Protocols in Molecular Biology*, John Wiley & Sons, New York, N.Y. (1989)), immunocytochemistry (Racila, et al., *Proc. Natl. Acad. Sci. USA* 95:4589-4594 (1998) supra), and a variety of immunoassays, including enzyme-linked immunosorbant assay (ELISA), radioimmuno assay (RIA), and specific enzyme immunoassay (EIA) (Sambrook, et al., *Molecular Cloning: A Laboratory Manual*, Cold Spring Harbor Laboratory, NY (1989), Ausubel, et al., *Current Protocols in Molecular Biology*, John Wiley & Sons, New York, N.Y. (1989)).

The diseases and conditions treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

4.3.1 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

One embodiment of the invention is the administration of an effective amount of GIPF polypeptides or other composition of the invention to individuals affected by a disease or disorder that can be treated the peptides of the invention. While the mode of administration is not particularly important, parenteral administration is preferred. Exemplary modes of administration are to deliver a subcutaneous or intravenous bolus. The dosage of GIPF polypeptides or other composition of the invention will normally be determined by the prescribing physician. It is to be expected that the dosage will vary according to the age, weight, condition and response of the individual patient. Typically, the amount of polypeptide administered per dose will be in the range of about 0.01 µg/kg to 100 mg/kg of body weight, with the preferred dose being about 0.1 µg/kg to 10 mg/kg of patient body weight. For parenteral administration, GIPF polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the polypeptide or other active ingredient. The preparation of such solutions is within the skill of the art.

4.3.2 Pharmaceutical Formulations

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors and various growth factors such as any of the FGFs, epidermal growth factor (EGF), platelet-derived growth factor (PDGF), transforming growth factors (TGF-α and TGF-β), insulin-like growth factor (IGF), keratinocyte growth factor (KGF), and the like, as well as cytokines described herein.

The pharmaceutical composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. Conversely, protein or other active ingredients of the present invention may be included in formulations of the particular cytokine, lymphokine, other hematopoietic factor, thrombolytic or anti-thrombotic factor, or anti-inflammatory agent to minimize side effects of the clotting factor, cytokine, lymphokine, other hematopoietic factor, thrombolytic or anti-thrombotic factor, or anti-inflammatory agent (such as IL-1 Ra, IL-1 Hy1, IL-1 Hy2, anti-TNF, corticosteroids, immunosuppressive agents). A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

4.3.3 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal (IP), parenteral or intravenous injection. Intravenous administration to the patient is preferred.

Alternatively, one may administer the compound in a local rather than systemic manner, for example, via injection of the compound directly into the tissue, often in a depot or sustained release formulation.

In another embodiment, the implantation of cells producing GIPF (cell therapy) into a subject in need of proliferation and/or stimulation of epithelial cells is contemplated. Cells that do not normally express GIPF or that express low levels of GIPF may be modified to produce therapeutic levels of GIPF by transformation with a polynucleotide that encodes GIPF. The cells may be of the same species as the subject, or may be derived from a different species. Preferably, the cells are derived from the subject in need of GIPF therapy. Human or nonhuman cells may be implanted in a subject using a biocompatible, semi-permeable polymeric enclosure to allow release of GIPF protein, or may be implanted directly without encapsulation.

In another embodiment, in vivo gene therapy is contemplated. A nucleotide sequence encoding GIPF is introduced directly into a subject for secretion of the protein to prevent or treat the diseases as recited herein. The nucleotide encoding GIPF may be injected directly into the tissue to be treated, or it may be delivered into the cells of the affected tissue by a viral vector e.g. adenovirus vector or retrovirus vector. Physical transfer of appropriate vectors containing a GIPF-encoding nucleic acid may also be achieved by methods including liposome-mediated transfer, direct injection of naked DNA, receptor-mediated transfer, or microparticle bombardment.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

4.3.4 Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active ingredient of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethyl cellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredient of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins or other active ingredient of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

4.3.5 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

An exemplary dosage regimen for polypeptides or other compositions of the invention will be in the range of about 0.01 µg/kg to 100 mg/kg of body weight daily, with the preferred dose being about 0.1 µg/kg to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

4.3.6 Diagnostic Assays And Kits

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

4.3.7 Screening Assays

Using the isolated proteins and polynucleotides of the invention, the present invention further provides methods of obtaining and identifying modulatory agents which bind to a polypeptide encoded by an ORF corresponding to the nucleotide sequence set forth in SEQ ID NO: 2, 3, 5, 9, 11, 13, 15, 17, 84, 86, 88, 90, 92, 94, 96, 98, 100, 102, 104 or 177, or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

The modulatory agents may increase or decrease the proliferative activity of GIPF on epithelial cells.

In general, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a target gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like, capable of binding to a specific peptide sequence, in order to generate rationally designed antipeptide peptides, for example see Hurby et al., Application of Synthetic Peptides: Antisense Peptides," In Synthetic Peptides, A User's Guide, W.H. Freeman, NY (1992), pp. 289-307, and Kaspczak et al., Biochemistry 28:9230-8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent. Agents which bind to a protein encoded by one of the ORFs of the present invention can be formulated using known techniques to generate a pharmaceutical composition.

5. EXAMPLES

Example 1

Isolation of SEQ ID NO: 1 from a Human cDNA Library

The novel nucleic acid of SEQ ID NO: 1 was obtained from a human cDNA library prepared from fetal skin (Invitrogen), using standard PCR, sequencing by hybridization sequence signature analysis, and Sanger sequencing techniques. The inserts of the library were amplified with PCR using primers specific for vector sequences flanking the inserts. These samples were spotted onto nylon membranes and interrogated with oligonucleotide probes to give sequence signatures. The clones were clustered into groups of similar or identical sequences, and a single representative clone was selected from each group for gel sequencing. The 5' sequence of the amplified insert was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. The insert of SEQ ID NO: 1 was described as a novel sequence in international publication WO 03/(029405).

Example 2

Assemblage of SEQ ID NO: 2

The nucleic acid (SEQ ID NO: 2) of the invention was assembled from sequences that were obtained from a cDNA library by methods described in Example 1 above, and in some cases obtained from one or more public databases. The final sequence was assembled using the EST sequences as seed. Then a recursive algorithm was used to extend the seed into an extended assemblage, by pulling additional sequences from different databases (i.e. Nuvelo's database containing EST sequences, dbEST version 124, gbpri 124, and UniGene version 124) that belong to this assemblage. The algorithm terminated when there were no additional sequences from the above databases that would extend the assemblage. Inclusion of component sequences into the assemblage was based on a BLASTN hit to the extending assemblage with BLAST score greater than 300 and percent identity greater than 95%.

Using PHRAP (Univ. of Washington) or CAP4 (Paracel), a full-length gene cDNA sequence and its corresponding protein sequence were generated from the assemblage. Any frame shifts and incorrect stop codons were corrected by hand editing. During editing, the sequence was checked using FASTY and BLAST against Genbank (i.e. dbEST version 124, gbpri 124, UniGene version 124, Genpept release 124). Other computer programs which may have been used in the editing process were phredphrap and Consed (University of Washington) and ed-ready, ed-ext and cg-zip-2 (Hyseq, Inc.). The full-length nucleotide and amino acid sequences are shown in the Sequence Listing as SEQ ID NOS: 2 and 4, respectively.

In order to express GIPF (SEQ ID NO: 4), the full-length GIPF DNA was PCR amplified from Marathon-ready cDNA libraries (Clontech). The primary PCR product was further amplified using nested PCR primers that generated GIPF polypeptide when expressed in suitable cell lines, as described below.

Example 3

Expression of GIPF in Murine and Human Tissues

Figure 2B:
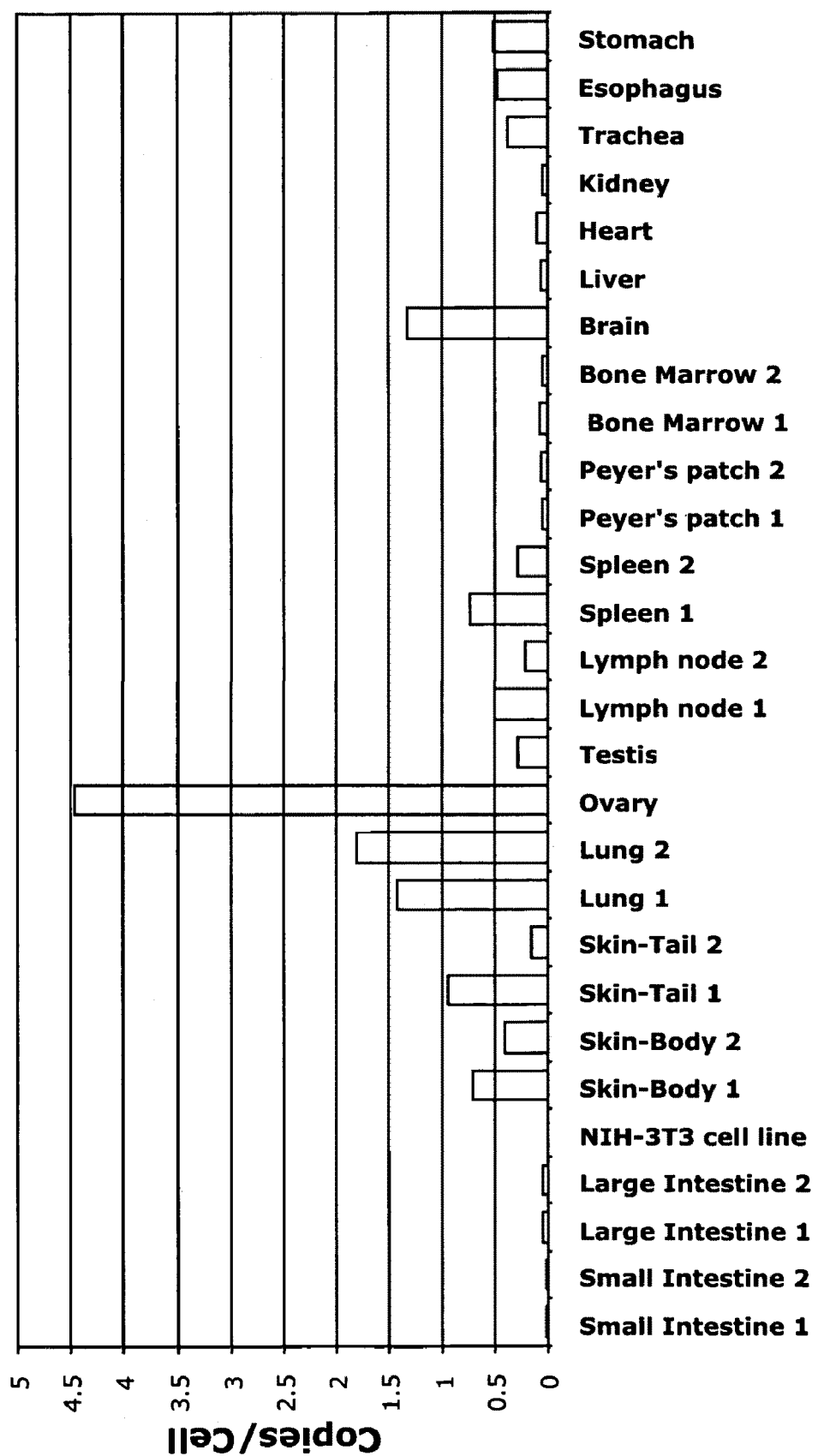

A. Tissue Distribution of GIPF mRNA:

FIG. 2 shows the relative expression of GIPF mRNA that was derived from human (A) and murine (B) tissues.

Total mRNA was derived from the tissues indicated in FIG. 2 according to the protocol provided by the manufacturer (Qiagen, Valencia, Calif.). The RNA was subjected to quantitative real-time PCR (TaqMan) (Simpson et al., Molec Vision 6:178-183 (2000)) to determine the relative expression of GIPF in the tissues shown. The forward and reverse primers that were used in the PCR reactions of human RNA were: 5' GACCATGCTGCCTGCTCTGACAC 3' (forward; SEQ ID NO: 29), and 5' CACCCGCCTCCTTGCTCTCC 3' (reverse; SEQ ID NO: 30), respectively; and the forward and reverse primers that were used in the PCR reactions of murine RNA were: 5' GGGGGAGACCACACCACCTGCT 3' (SEQ ID NO: 31), and 5' TTGGACCTCGGCTCCTTGCTGTTC 3' (SEQ ID NO: 32), respectively. DNA sequences encoding Elongation Factor 1, β-actin, and ATP synthase 6 were used as a positive control and normalization factors in all samples. All assays were performed in triplicate with the resulting values averaged.

The Y axis shows the number of copies of GIPF mRNA per cell assuming that each cell has 400,000 mRNA transcripts of a median length of 1.2 Kb, and that 2% of the total RNA in a cell is mRNA. FIG. 2 shows that GIPF mRNA is expressed at low levels in all the tissues tested. The highest levels of GIPF mRNA were seen in mouse skin, lung, ovary and brain, and in human small intestine, skin, skin, ovary, testis, and breast.

B. Tissue Distribution of GIPF Protein:

Expression of GIPF in human tissue samples was detected using rabbit polyclonal anti-GIPF antibodies (Table 1). The rabbit polyclonal antibodies were generated by immunizing rabbits with a peptide that was predicted to be immunogenic, and having amino acid sequence Glu Ser Lys Glu Ala Gly Ala Gly Ser Arg Arg Arg Lys Gly Gln (SEQ ID NO: 67). Anti-GIPF antibody was affinity purified from rabbit serum using GIPF peptide coupled to Affi-Gel 10 (Bio-Rad), and stored in phosphate-buffered saline with 0.1% sodium azide. Tissue samples of adrenal gland, bladder, breast, colon, kidney, liver, lung, ovary, pancreas, placenta, prostate, skin, small intestine, spleen, stomach, testis, thyroid, tonsil and uterus were prepared for immunohistochemical analysis (IHC) (LifeSpan Biosciences, Inc., Seattle, Wash.) by fixing tissues in 10% formalin, embedding in paraffin, and sectioning using standard techniques. Sections were probed using the GIPF-specific antibody and visualized with a biotin-conjugated anti-rabbit secondary using AEC as substrate.

The cellular localization of GIPF in human tissues is shown in Table 1. The most intense staining was seen in the cytoplasm of a subset of pancreatic islet cells and in the cytoplasm of intraepithelial neuroendocrine cells of the intestine and stomach. Prominent staining was also present in the adrenal cortex, gastric foveolar epithelium, and renal tubular epithelium. Lymphocytes were frequently positive and showed predominantly nuclear staining. In the skin, focal positivity was present in the stratum granulosum and in pilosebaceous units. A few cell types showed less intense cytoplasmic and nuclear staining, including respiratory epithelium, type II pneumocytes, prostatic epithelium, and breast epithelium. Focal faint nuclear staining was present in hepatocytes, colonic epithelium, placental trophoblasts, breast epithelium, ovary, and thyroid follicular epithelium.

Ganglion cells showed blush staining, while other cell types including glandular epithelium, smooth muscle, endothelium, intravascular neutrophils, and fibroblasts tested negative for GIPF.

TABLE 1

| Organ/Tissue | Subcellular Location | Staining |
| --- | --- | --- |
| Adrenal gland, epithelium | Nuclear and cytosolic | Focal, moderate |
| Bladder, epithelium | Nuclear and cytosolic | Light |
| Breast, epithelium | Nuclear and cytosolic | Moderate |
| Colon, epithelium | Nuclear and cytosolic | Moderate |
| Colon, neuroendocrine cells | Nuclear and cytosolic | Faint |
| Kidney cortex, glomeruli | Nuclear | Light |
| Kidney cortext, epithelium | Cytosolic | Moderate |
| Kidney medulla, glomeruli | Nuclear | Strong |
| Kidney medulla, epithelium | Cytosolic | Moderate |
| Liver, hepatocytes | Nuclear | Moderate |
| Lung, respiratory epithelium | Nuclear and cytosolic | Moderate |
| Lung, type II pneumocytes | Predominantly nuclear | Moderate |
| Lung, alveolar macrophages | Predominantly nuclear | Moderate |
| Ovary, epithelium | Nuclear | Moderate |
| Pancreas, islets of Langerhans | Cytosolic | Strong |
| Placenta, trophoblasts | Nuclear | Light |
| Prostate, epithelium | Nuclear | Moderate |
| Skin, epidermal layer | Cytosolic | Focal |
| Small intestine, neuroendocrine cells | Cytosolic, punctate nuclear | Strong |
| Small intestine, inflammatory cells | Predominantly nuclear | Moderate |
| Spleen, lymphocytes | Predominantly nuclear | Strong |
| Stomach, neuroendocrine cells | Nuclear and cytosolic | Focal, moderate to strong |
| Stomach, epithelium | Nuclear and cytosolic | Moderate to strong |
| Testis, Leydig cells | Cytosolic | Light, sporadic |
| Thymus, lymphocytes | Nuclear and cytosolic | Moderate |
| Thyroid, follicular epithelium | Nuclear | Light |
| Tonsil, lymphocytes | Nuclear and cytosolic | Moderate |
| Uterus, endometrial stroma | Nuclear | Moderate, sporadic |

Example 4

Transgenic GIPF Animals

A. Construction of the GIPF-KI Vector.

The construction of the transgene GIPF-knock-in (GIPF-KI) vector (FIG. 5A) was performed according to the method described below, and depicted in FIGS. 5B-5R.

The DNA encoding the mouse Immunoglobulin kappa Constant region (IgCκ) and the proximal region was obtained by amplification of two fragments as follows:

FIG. 5B Preparation of IgCκ Fragment 1.

The forward (igkc1; SEQ ID NO: 34) and reverse (igkc2; SEQ ID NO: 35) primers for PCR were synthesized based on the sequence of the mouse Immunoglobulin kappa Constant region (IgCκ) and the proximal region that was obtained from GenBank (gi: V00777; SEQ ID NO: 33), and used to amplify the DNA that encodes fragment 1 of the IgCκ fragment 1. igkc1: ATCTCGAGGAACCACTTTCCTGAGGACA-CAGTGATAGG (SEQ ID NO: 34) was prepared by adding a Xho I recognition sequence at 5' end site, and igkc2: ATGAATTCCTAACACTCATTCCTGT-TGAAGCTCTTGAC (SEQ ID NO: 35) was prepared by adding an EcoR I recognition sequence at 5' end site. PCR was carried out using 25 ng of a clone of pBluescript SK II (+), which contains the mouse Constant and Joining regions (WO 00/10383), and served as template. The PCR product was digested with restriction enzymes EcoR I and Xho I and ligated into pBluescript II KS(−) vector (Stratagene) that was pre-digested with the restriction enzymes EcoR I and Xho I. The resulting plasmid pIgCκA contained the designated cDNA sequence of the mouse IgCκ fragment 1 with no substitution in nucleotide sequence within the region between Xho I and EcoR I.

FIG. 5C Preparation of IgCκ Fragment 2.

The forward (igkc3; SEQ ID NO: 36) and reverse (igkc4; SEQ ID NO: 37) primers for PCR were synthesized based on the sequence of the mouse downstream region of Immunoglobulin kappa Constant region (IgCκ) that was obtained from GenBank (gi: V00777; SEQ ID NO: 33), and used to amplify the DNA that encodes IgCκ fragment 2. Igkc3: ATGAATTCAGACAAAGGTCCTGAGACGCCACC (SEQ ID NO:36) was prepared by adding an EcoR I recognition sequence at 5'end site, and igkc4: ATGGATCCTCGAGTC-GACTGGATTTCAGGGCAACTAAACATT (SEQ ID NO:37) was prepared by adding BamH I, Xho I, and Sal I recognition sequence at 5' end site. PCR was carried out using 25 ng of the clone of pBluescript SK II (+) that contains the mouse Constant and Joining regions, and served as template (WO 00/10383). The PCR product was digested with restriction enzymes EcoR I and BamH I and ligated into the pIgCκA vector (see above), pre-digested with the restriction enzymes EcoR I and BamH I. The resulting plasmid pIgCκAB contained the designated cDNA fragments 1 and 2 derived from the mouse Immunoglobulin Constant region with no substitution in nucleotide sequence within the region between EcoR I and BamH I.

FIG. 5D Insertion of Puromycin Gene into pIgCκAB

The Lox-P Puro plasmid (WO 00/10383) was digested with restriction enzymes EcoR/and Xho I and treated with T4DNA polymerase. The resulting fragment was ligated into pIgCκAB vector (see above) pre-digested with the restriction enzyme Sal I and treated with T4DNA polymerase. After verifying the connecting regions between pIgCκAB and the Lox-P Puro fragment, the plasmid pIgCκ ABP was obtained.

FIG. 5E Insertion of IRES cDNA into pIgCκ ABP

The following forward (iresfw; SEQ ID NO:38) and reverse (iresrv; SEQ ID NO: 39) primers for PCR were synthesized based on the sequence of the IRES region of the pIREShyg plasmid (Clontech). iresfw: ATGAATTCGC-CCCTCTCCCTCCCCCCCCCCTA (SEQ ID NO: 38) was prepared by adding an EcoR I recognition sequence at 5' end site, and iresrv: ATGAATTCGTCGACTTGTGGCAAGCT-TATCATCGTGTT (SEQ ID NO: 39) was prepared by adding EcoR/and Sal I recognition sequences at the 5'end site. PCR was carried out using 150 ng of pIREShyg plasmid (Clontech) as a template. The PCR product was digested with the restriction enzyme EcoR I and ligated into the pGEM-T vector (Promega) which had been digested in advance with the restriction enzyme EcoR I. The plasmid IRES-Sal/pGEM was obtained that contained the designated cDNA sequence with no substitutions in nucleotide sequence. The IRES-Sal/pGEM plasmid was digested with restriction enzyme EcoR/ and ligated into the pIgCκABP plasmid (see above) which had been digested in advance with the restriction enzyme EcoR I. After verifying the sequence of connecting regions between pIgCκ ABP and IRES-Sal, the plasmid pIgCκ ABP IRES was obtained.

FIG. 5F Construction of PΔCκ Sal Plasmid

The IgCk KO vector (WO 00/10383) was digested with restriction enzyme Sac II and then partially digested with restriction enzyme EcoRI. A 14.6 Kb band that lacked the LoxP-PGK Puro region was isolated and ligated with a SacII/EcoRI compatible linker generated by annealing the following two oligonucleotides (Sal1 plus and Sal1 minus), in order to replace the LoxP-PGKPuro region with a Sal I restriction site. After sequence verification the pΔCκSal plasmid was obtained. Sal1 plus: 5' AGTCGACA 3' (SEQ ID NO: 40) and Sal1 minus: 5'AATTTGTCGACTGC 3' (SEQ ID NO: 41).

FIG. 5G Construction of PKIκ Plasmid

The pIgCκABP IRES plasmid was digested with the restriction enzyme Xho I and the resulting fragment consisting of C region, IRES and loxP-Puromycin was ligated with pΔCκSal vector (see above) which had been digested in advance with the restriction enzyme Sal I. After sequence verification the PKIκ plasmid was obtained.

FIG. 5H Preparation of pIgCκΔ IRES Fragment

The pIgCκ ABPIRES plasmid was partially digested with restriction enzymes EcoR I and Bgl II and the resulting pIgCκΔ IRES fragment that lacked a portion of the IRES gene was isolated.

FIG. 5I Preparation of Mouse P2 Promoter Fragment by PCR

The following primers for PCR were synthesized based on the sequence of the mouse Immunoglobulin kappa promoter obtained from GenBank (gi: aj231225; SEQ ID NO: 42).

P2F: CCCAAGCTTTGGTGATTATTCAGAG-TAGTTTTAGATGAGTGCAT (SEQ ID NO: 43) was prepared by adding a Hind III recognition sequence at 5' end site, and P2R:ACGCGTCGACTTTGTCTTTGAACTTTG-GTCCCTAGCTAATTACTA (SEQ ID NO: 44) was prepared by adding a Sal I recognition sequence at 5' end site. PCR was carried out using 25 ng of mouse genomic DNA as a template (genomic DNA from TT2F ES cells). The PCR product was digested with restriction enzymes Hind III and Sal I and ligated into pBluescript II KS-vector (Stratagene) which had been digested in advance with the restriction enzymes Hind III and Sal I. After sequence verification, the resulting plasmid was digested with the restriction enzymes Hind III and Sal and a Hind III-Sal I fragment containing the mouse P2 promoter fragment was isolated.

FIG. 5J. Preparation of Partial Cκ polyA Fragment by PCR

The following primers for PCR were synthesized based on sequence of the mouse Immunoglobulin kappa polyA region obtained from GenBank (gi:v00777) PPF:ACGCGTC-GACGCGGCCGGCCGCGCTAGCAGA-CAAAGGTCCTGAGACGCCAC CACCAGCTCCCC (SEQ ID NO: 45) was prepared by adding Sal I, Fse I, and Nhe I recognition sequence at 5' end site, and PPR: GAAGATCT-CAAGTGCAAAGACTCACTTTATTGAATATTTTCTG (SEQ ID NO: 46) was prepared by adding a Bgl II recognition sequence at 5' end site. PCR was carried out using 25 ng of mouse genomic DNA as a template (genomic DNA from TT2F ES cells). The PCR product was digested with restriction enzymes Sal I and Bgl II and ligated into the psp72 vector (Promega KK) which had been digested in advance with the restriction enzymes Sal I and Bgl II. After sequence verification, the purified plasmid was digested with the restriction enzymes Sal I and Bgl II, to generate the "partial Ck polyA fragment".

FIG. 5K. Preparation of Total Cκ PolyA Fragment by PCR.

The following primers for PCR were synthesized based on sequence of the mouse Immunoglobulin kappa polyA region obtained from GenBank (gi:v00777): TPF: GGAATTCA-GACAAAGGTCCTGAGACGCCACCACCAGCTCCCC (SEQ ID NO: 47) was prepared by adding an EcoR I recognition sequence at 5' end site, and TPR: CCCAAGCTTGC-CTCCTCAAACCTACCATGGCCCAGAGAAATAAG (SEQ ID NO: 48) was prepared by adding a Hind III recognition sequence at 5' end site. PCR was carried out using 25 ng of mouse genomic DNA as a template (genomic DNA from TT2F ES cells). The PCR product was digested with restriction enzymes EcoR I and Hind III and ligated into pBluescript II KS-vector (Stratagene) which had been digested in advance with the restriction enzymes EcoR I and Hind III. After sequence verification the plasmid was digested with the restriction enzymes EcoR I and Hind III, to generate the "total Cĸ polyA fragment".

FIG. 5L. Construction of DNA Fragment A that Consists of Total Cĸ polyA Fragment, P2 Promoter Fragment, and Partial Cĸ polyA Fragment.

The "total Cĸ poly A fragment", "P2 promoter fragment", and "partial Cĸ poly A fragment" generated as described above were ligated in the described order into pBluescript II KS-vector (Stratagene) which had been digested in advance with the restriction enzymes EcoR I and Bgl II. After sequence verification, the purified plasmid was digested with the restriction enzymes EcoR I and Bgl II, to generate "DNA fragment A".

FIG. 5M. Construction of PlgCĸΔ IRES ProA Plasmid

"DNA fragment A" was ligated into the "pIgCĸ A IRES fragment" isolated as described above. After sequence verification the plasmid pIgCĸ A IRES ProA was obtained.

FIG. 5N. Construction of Cĸ P2H Plasmid pIgCĸΔ IRES ProA plasmid was digested with Xho I and the main fragment that contained the upstream genomic region of mouse IgCĸ, mouse IgCĸ, DNA fragment A and Lox-P Puro thus isolated, was ligated with pΔCĸ Sal which had been digested in advance with the restriction enzyme Sal I. After sequence verification the plasmid Cĸ P2H was obtained.

FIG. 5O. Construction of Cĸ 5' Genomic Plasmid

The following primers for PCR were synthesized based on sequence of a DNA segment containing the mouse immunoglobulin kappa J and C region genes obtained from GenBank (gi: v00777). 5GF: ATAAGAATGCGGCCGCCTCAGAG-CAAATGGGTTCTACAGGCCTAACAACCT (SEQ ID NO: 49) was prepared by adding a Not I recognition sequence at 5'end site, and 5GR: CCGGAATTCCTAACACTCATTC-CTGTTGAAGCTCTTGACAATGG, (SEQ ID NO: 50) was prepared by adding an EcoR I recognition sequence at 5'end site. PCR was carried out using 25 ng of mouse genomic DNA (genomic DNA from TT2F ES cells as a template). The PCR product was digested with restriction enzymes Not I and EcoR I and ligated with pBluescript II KS-vector (Stratagene) which had been digested in advance with the restriction enzymes Not I and EcoR I. After sequence verification, the Cĸ 5' genomic plasmid was obtained.

FIG. 5P. Construction of Cĸ P2 KIΔ DT Plasmid

The Cĸ P2H plasmid was digested with EcoR I and Xho I and a 11 Kb was obtained and was ligated into the Cĸ 5' genomic plasmid which had been digested in advance with the restriction enzymes EcoR I and Xho I. After sequence verification the Cĸ P2 KIΔ DT plasmid was obtained.

FIG. 5Q. Construction of Cĸ P2 KI Vector

The DT-A fragment was isolated from the pKIĸ plasmid using restriction enzymes Xho I and Kpn I, and was ligated into the Cĸ P2 KIΔ DT plasmid which has been digested in advance with the restriction enzymes Xho I and Kpn I. After sequence verification the CĸP2 KI vector was obtained.

FIG. 5R. Assembly of the GIPF-KI Vector.

A GIPF cDNA fragment was amplified using the following primers for PCR, which were synthesized based on the sequence of human GIPF cDNA (SEQ ID NO: 2). SA3F: ACGCGTCGACCCACATGCGGCTTGGGCTGTGTGT (SEQ ID NO: 51) was prepared by adding a Sal I recognition sequence and Kozak sequence at 5' end site, and SA3R: ACGCGTCGACGTCGACCTAGGCAGGCCCTG (SEQ ID NO: 52) was prepared by adding a Sal I recognition sequence at 5' end site.

PCR was carried out using a pool of Marathon-Ready cDNA (fetal skin and fetal lung, BD Biosciences CLONTECH) as a template. The PCR product was digested with restriction enzyme Sal and ligated with pBluescript II KS-vector (Stratagene) which has been digested in advance with the restriction enzyme Sal I. After sequence verification a clone was obtained and verified to contain the correct GIPF cDNA sequence with no substitution in nucleotide sequence. The clone was digested with restriction enzyme Sal I, and the GIPF cDNA fragment was purified and ligated into CK P2 KI vector, which had been digested in advance with the restriction enzyme Sal I. After sequence verification, the GIPF-KI vector, was obtained (FIG. 5A).

B. Generation of GIPF-KI Transgenic Mice

General procedures for obtaining mouse embryos, cultivation, injection of the ES cells into the embryos, transplantation to the uteri of foster mothers were carried out in accordance with the method described in Aizawa Shinichi, "Biomanual Series 8, Gene Targeting", published by Yodosha, 1995.

The GIPF-KI vector was linearized with Not I and transferred into C57BL/6×CBA F1 derived mouse TT2F ES cells ((Uchida, 1995), Lifetech oriental) by electroporation according to the method described by Shinichi Aizawa, "Biomanual Series 8, Gene Targeting", published by Yodosha, 1995. The electroporated ES cells were suspended in 20 ml of ES medium [DMEM (GIBCO), 18% FCS (GIBCO), 0.1 mM 2-mercaptoethanol (GIBCO), 1000 U/ml LIF (leukemia inhibitory factor, CHEMICON International, Inc.)] and inoculated into two 100 mm tissue culture plastic plates (Corning) into which feeder cells (Invitrogen) were seeded in advance. After one day, the medium was replaced with a medium containing 0.75 g/ml of puromycin (Sigma). Seven to nine days thereafter, a total of 119 colonies formed were picked up. Each colony was grown up to confluence in a 12-well plate, and then four fifths of the culture was suspended in 0.2 ml of cryopreservation medium [ES medium+ 10% DMSO (Sigma)] and stored frozen at −80° C. The remaining one fifth was inoculated into a 12-well gelatin coated plate and cultured for 2 days. Then, genomic DNA was isolated using the Puregene DNA Isolation Kit (Gentra System). Genomic DNA isolated from puromycin resistant TT2F cells was digested with restriction enzyme EcoR I (Takara Shuzo) and then subjected to 0.8% agarose gel electrophoresis. Separated DNA fragments were transferred to a membrane (GeneScreen, NEN™ Life Science Products) and then hybridization was carried out using the DNA fragment as probe prepared from 3' region of IgJκ-Cĸgenomic DNA (Xho I-EcoR I, 1.3 Kb (SEQ ID NO: 67): WO 00/10383, Example No. 48). The band pattern of untargeted ES clone shows one band of MW of about 15 Kb and targeted ES clone shows two bands of MW of about 15 Kb and 13.4 Kb (FIG. 6). Two out of 48 targeted ES clones #10, 12 were selected after Southern analysis (rate of homologues recombination was about 4.2%). The selected ES clones were also tested by karyotype analysis according to the method described by Shinichi Aizawa, "Biomanual Series 8, Gene Targeting", published by Yodosha, 1995. Two ES clones #10, 12 that showed normal karyotype were used for implantation into embryos.

The cells in a frozen stock of the targeted ES cell clones #10, 12 were thawed, started to culture and injected into 8-cell stage embryos obtained by mating a male and a female mouse of Immunoglobulin heavy chain knock out mouse strain (Tomizuka et. al. *Proc. Natl. Acad. Sci. USA,* 97: 722-727, 2000); the injection rate was 10-12 cells per embryo. After the embryos were cultured overnight in the medium for ES cells to develop into blastocysts, about ten of the TT2F cell-injected embryos were transplanted to each side of the uterus of a foster mother ICR mouse (CREA JAPAN, INC.), which had been subjected to a pseudopregnant treatment for 2.5 days. As a result of transplantation of a total of 120 injected embryos, 24 offspring mice were born. Chimerism in the offspring was determined by the extent of TT2F cell-derived agouti coat color (dark brown) in the host embryo (ICR)-derived albino coat color. Out of the 24 offspring, 11 mice (knock-in mice) were recognized to have partial agouti coat color, indicating the contribution of the ES cells. Genomic DNA isolated from the tails of Knock-in mice was used for PCR analysis. The following two primers for PCR were synthesized based on sequence of GIPF-KI vector: SACF: CTGACTAGACTC-TATCTTGC (SEQ ID NO: 53), and SACR: CCACG-GAGACCACTCGCTCATT (SEQ ID NO: 54).

PCR was carried out using 25 ng of mouse tail genomic DNA as a template. The resulting reaction solution was subjected to 0.8% agarose gel electrophoresis, and 606 bp band was detected. Normal TT2F cell clones were used for control chimeric mice production.

Mice were kept under a 12/12-hour dark/light cycle (lights on at 8:00 am) and received 5 μm filtered water and CE-2 food (CLEA JAPAN, INC.) ad libitum. Male mice were housed individually after weaning period.

Example 5

Evaluation of the Biological Activity of GIPF Using Transgenic GIPF-KI Mice

The gross pathological changes and the histological changes of the small intestine and colon from the transgenic mice described above was evaluated as follows.

GIPF transgenic KI mice demonstrated auxetic growth of small intestine starting at the age of 4 weeks and significant abdominal distension during development. FIG. 7 shows that 15 week old GIPF transgenic KI mice had marked intestinal distension and increased small intestinal mass when compared to the corresponding control KI mouse. Histo-pathological evaluation, using hematoxylin and eosin (H&E) staining (Issacson, P. G., and Wright, D. H., 1983) was done on paraffin embedded sections (5 μm thick) of various tissues including liver, spleen, lung, kidney, heart, small intestine and large intestine. H&E sections of small intestine were shown in FIG. 8 (low magnification) and FIG. 9 (high magnification). A histopathology report was provided by IDEXX Laboratories, Inc. and is described below.

The only significant difference between the histologic appearance of the tissues from the control and the knock-in mouse was found in the small intestine. This change consisted of a marked, diffuse thickening of the mucosa by crypt epithelial hyperplasia with a marked increased in crypt length and complexity of branching. The crypts were lined by plump columnar epithelial cells with basophilic cytoplasm and basally-located large ovoid heterochromatic nuclei with frequent mitoses. Numerous apoptotic bodies were scattered throughout the crypt epithelium, suggesting an increased rate of cell turnover. The crypt epithelial cells also commonly differentiated into both Paneth cells and mucus-secreting goblet cells throughout the length of the crypts. The villous epithelium was not significantly altered. Similar changes were seen in the small intestinal mucosa associated with the Peyer's patch. The intestinal mucosa normally externally lines and may form small invaginations into the lymphoid tissue of the Peyer's patch. In the GIPF-KI mice, the hyperplastic changes were also seen on the surface and in invaginations, where they were associated with mild acute inflammation and accumulations of necrotic cells within crypts, i.e. crypt microabscesses. This Peyer's patch was sectioned tangentially therefore the amount and character of lymphoid tissue was difficult to evaluate. However, there were small numbers of plasma cells indicating transformation of B-lymphocytes into antibody-producing cells. There were no other visible alterations in lymphoid or inflammatory cell populations in the intestine or other tissues.

To measure intestinal epithelial cell proliferation in KI mice, immunohistochemistry using monoclonal rat anti-mouse Ki67 antigen (Dako Ltd., High Wycombe, UK) was performed on paraffin embedded sections of small intestine of control and GIPF KI mice according to manufacturer's instruction and the method previously described (Scholzen, T. et al. 2000). As shown in FIG. 10, GIPF KI mice demonstrated increased Ki67 positive epithelial cells in the small intestine suggesting increased proliferation by GIPF protein expression.

Three of the GIPF-KI mice were harvested at 12 months. These 12 month-old mice displayed the typical abdominal distention and increased intestinal mass seen in younger animals. H&E sections were prepared in various tissues including spleen, liver, adrenal, kidney, thymus, heart, lung, small intestine, large intestine, stomach and brain.

Histology of sections from the small intestine of the 12 month old GIPF-KI mice showed that GIPF had induced a marked increase in crypt length and to the same extent as that seen in 15 weeks old GIPF-KI animals. In addition, histological analysis of sections from other organs revealed that over the extended period of 12 months GIPF did not display any apparent tumorigenic activity. Spontaneous tumorigenesis was sometimes observed in some mice irregardless of whether the mice were normal or KI transgenic animals. A low incidence of hepatic adenomas was observed in 12 month-old control mice.

Example 6

The GIPF Adenoviral Vector

The GIPF cDNA (SEQ ID NO: 2) was cloned into pAdenoVator CMV5-Intron using NheI and XbaI sites in multicloning sites (MCS) to generate V5His6 tagged GIPF recombinant adenovirus. pAdenoVator-CMV5-Intron was obtained by modification of pAdenoVator CMV5-IRES-GFP (Qbiogene, Carlsbad, Calif., U.S.A). pAdenoVator-CMV5-IRES-GFP was digested with SpeI to remove its MCS, IRES and GFP and ligated with PCR amplified Intron-MCS-V5His-BGH polyA from pcDNA/Intron vector using primers: 5'-CACCCCTAGGTCAATATTGGCCATTAGC-3' (SEQ ID NO: 55) and 5'-CACCCCT-AGGTAGGCATCCCCAG-CATGC-3' (SEQ ID NO: 56).

Transformation of linearized transfer vector into bacterial cells, BJ5183, (Qbiogene, Carlsbad, Calif., U.S.A) which carry AdEasy-1 plasmid that encode Adenovirus-5 genome (E1/E3 deleted) was performed by electroporation according to the manufacturer's instructions. Recombinant adenovirus was generated and amplified in QBI-293A cells (Qbiogene, Carlsbad, Calif., U.S.A) and purified by CsCl banding as previously described (Garnier, A., J. Cote et al. 1994). Recombinant protein expression by 293A cells that had been infected with the recombinant adenovirus was measured by Western analysis using anti-V5 antibody (Invitrogene Inc., Carlsbad, Calif.). The titer of CsCl purified recombinant viruses was measured using the Adeno-X rapid titer kit (BD biosciences, Palo Alto, U.S.A.) according to the manufacturer's protocols. Briefly, a viral stock was tested by infecting 293A cells with serial dilutions of the recombinant adenovirus stock followed by fixation and staining of the transduced cells with mouse anti-hexon antibody 48 hours after infection. The signal was detected with a goat anti-mouse antibody conjugated to horseradish peroxidase and developed with metal-enhanced 3,3'-diaminobenzidine tetrahydro-chloride (DAB).

Example 7

Administration of GIPF Adenovirus as a Model to Evaluate the Biological Activity of GIPF The GIPF recombinant adenovirus was administered to normal mice to determine the effect of GIPF on the intestinal and colonic epithelium, and to confirm that the phenotype observed in the GIPF transgenic mice could be established in a non-transgenic animal. Prior to injection of adenovirus, BALB/C mice, 6-8 weeks of age, were anesthetized using isoflurane. $1 \times 10^{10}$ viral particles per mouse were injected through retro-orbital vein. The same titer of control virus (empty virus) or PBS alone were used as controls. Mice were sacrificed on day 3 or day 5 after virus injection (n=3 for all group). 4 hours before sacrifice, 1 mg of bromodeoxyuridine (BrdU) was injected intraperitoneally (IP) to determine in vivo proliferation of epithelial cells. Various tissues including small intestine, colon, spleen, liver and bone marrow were collected and fixed in formaline. Paraffin embedded sections were stained with hematoxylin and eosin (H&E) for histological evaluation. Sections were also processed for BrdU immunohistochemistry according to the manufacturer's instruction (Oncogene Research product, Boston, U.S.A.) as previously described (McKinley, J. N. et al. 2000). Immunohistochemistry using monoclonal rat anti-mouse Ki67 antigen (Dako Ltd., High Wycombe, UK) was also performed to assess the proliferation of intestinal epithelial cells according to manufacturer's instruction and the method previously described (Scholzen, T. et al. 2000).

H&E staining of sections from the small intestine that had been sacrificed 3 days following the adenovirus injection (FIG. 11) show that the small intestine of mice that had received the GIPF adenovirus was significantly altered, and displayed the same histological characteristics seen in the GIPF transgenic mice (FIGS. 8 and 9). The histological changes caused by GIPF included a marked, diffuse thickening of the mucosa by crypt epithelial hyperplasia with a marked increased in crypt length and complexity of branching. The crypts were lined by plump columnar epithelial cells with basophilic cytoplasm and basally-located large ovoid heterochromatic nuclei with frequent mitoses. The crypt epithelial cells also commonly differentiated into both Paneth cells and mucus-secreting goblet cells throughout the length of the crypts. The effect of GIPF on crypt epithelial proliferation was further enhanced in 5 days after virus injection which was shown in FIG. 12. To evaluate the effect of GIPF on the proliferation of intestinal epithelial cells, BrdU incorporation and Ki67 immuno-staining were performed on small intestinal sections of control and mice that had received GIPF adenovirus. As shown in FIGS. 13 and 14, the mice that had received the GIPF adenovirus had small intestinal crypts that had significantly more BrdU and Ki67 positive cells, respectively. The biological effect of GIPF on the proliferation of crypt epithelial cells was also observed at a lower viral dose of $1 \times 10^9$ viral particles per mouse (FIG. 15). In addition to the effect seen in the small intestine, GIPF also induced crypt epithelial hyperplasia with a marked increased in crypt length and an increased number and size of Goblet cells in the colon (FIG. 16).

Example 8

Expression Vectors Encoding GIPF and GIPF Analogs

The cDNA encoding GIPF (SEQ ID NO: 3) was cloned into pcDNA/Intron vector using KpnI and XbaI sites to generate wild type and carboxy-terminal V5His6-tagged GIPF (SEQ ID NO: 5). The mammalian expression vector pcDNA/Intron was obtained by genetically modifying the pcDNA3.1TOPO vector (Invitrogene Inc., Carlsbad, Calif.) by introducing an engineered chimeric intron derived from the pCI mammalian expression vector (Promega, Madison, Wis.). pCI was digested with BGIII and KpnI, and the intron sequence was cloned into pcDNA3.1, which had been digested with BgIII and KpnI. The GIPF ORF of SEQ ID NO: 2 (SEQ ID NO: 3) was first cloned into pcDNA3.1N5His-TOPO (Invitrogen) by PCR using the following forward 5' CACCATGCGGCTTGGGCTGTCTC 3' (SEQ ID NO: 57) reverse 5' GGCAGGCCCTGCAGATGTGAGTG 3' (SEQ ID NO: 58), and the KpnI-XbaI insert from pcDNA 3.1N5His-TOPO that contains the entire GIPF ORF was ligated into the modified pcDNA/Intron vector to generate pcDNA/Intron construct.

Analogs of the full-length GIPF protein were generated as follows. Mutation of the predicted consensus furin cleavage sites (amino acid 28 R/Q) of GIPF in pcDNA/Intron was performed by site directed mutagenesis using primers 5'-GATCAAGGGGAAACAGCAGAGGCGGATCAG-3' (SEQ ID NO: 59) and 5'-CTGATCCGCCTCTGC TGTTTCCCCTTGATC-3' (SEQ ID NO: 60). The GIPF deletion mutant (deleted amino acid residues 21-31) (SEQ ID NO: 16) was generated using the stitching method. The deletion was introduced by PCR amplification of two fragments using primers set1: 5'-CACCGCTAGCCTCGAGAAT-TCACGCGTG-3' (SEQ ID NO: 61) and phospho 5'-GCT-GATGGTGAGGTGCGTC-3' (SEQ ID NO: 62), set2: phospho 5'-ATCAGTGCCGAGGGGAGCCAG-3' (SEQ ID NO: 63) and 5'-GCCCTCTAGAGCGGCAGGCCCTGCA-GATG-3' (SEQ ID NO: 64) followed by ligation of the two fragments. The GIPF cDNA carrying deletion of amino acids 21-31 was amplified by PCR using the forward and reverse primers of SEQ ID NO: 61 and 64, respectively, digested with NheI and XbaI, and subcloned into pcDNA/Intron vector using NheI and XbaI sites in its multicloning sites. Sequences were confirmed for both mutants.

The thrombospondin (TSP) domain (nt 451 to nt 618 of the ORF of GIPF (SEQ ID NO: 13) was also cloned into pcDNA/Intron vector for mammalian expression. The cDNA encoding the TSP domain was amplified by PCR using NheI forward primer: CCGGCTAGCCACCATGGCGCAATGTGAAATGA (SEQ ID NO: 65) and NotI reverse primer: CCATGCGGCCGC-CCTCCTCACTGTGCACCT (SEQ ID NO: 66). NheI and NotI restriction enzymes digested PCR product was ligated into NheI and NotI digested pcDNA/Intron vector. To generate recombinant adenovirus, the TSP domain from PCR amplification described above was cloned into pAdenoVator-CMV5-Intron using NheI and NotI restriction enzymes. The sequence of the PCR-amplified TSP domain was confirmed.

Other analogs that lack various portions of the furin-like cysteine-rich region of GIPF are described in Example 19.

The biological activity of the GIPF analogs described above was assessed in vivo and in vitro using methods described in the examples below. The biological activity of the GIPF analogs is assessed using the GIPF transgenic model.

Example 9

Purification of Recombinant GIPF

A. Expression and Purification GIPFt in Eukaryotic Cells:

V5-His-tagged GIPF (GIPFt) (SEQ ID NO: 5) was expressed in HEK293 and CHO cells and purified as follows:

A stable cell culture of HEK293 cells that had been transfected with the GIPF pcDNA/Intron construct comprising the DNA encoding the V5-His-tagged GIPF polypeptide (SEQ ID NO: 5) was grown in serum free 293 free-style media (GIBCO). A suspension culture was seeded at cell density of 1 million cells/ml, and harvested after 4-6 days. The level of the V5-His-tagged GIPF that had been secreted into the culture medium was assayed by ELISA.

A stable cell culture of CHO cells that had been transformed with a pDEF 2S vector comprising nucleotide sequence that encodes a V5-His tagged GIPF (SEQ ID NO: 5) was grown in serum free EX-CELL302 media (JRH). The expression vector contains DNA sequence that encodes DHFR, which allows for positive selection and amplification in the presence of methotrexate (MTX). The level of the V5-His-tagged GIPF that had been secreted into the culture medium was assayed by ELISA.

The media containing the secreted GIPF protein was harvested and frozen at −80° C. The media was thawed at 4° C., and protease inhibitors, EDTA and Pefabloc (Roche, Basel, Switzerland) were added at a final concentration of 1 mM each to prevent degradation of GIPF. The media were filtered through a 0.22 µm PES filter (Corning), and concentrated 10-fold using TFF system (Pall Filtron) with a 10 kDa molecular weight cut-off membrane. The buffers of the concentrated media were exchanged with 20 mM sodium phosphate, 0.5M NaCl, pH 7. The addition of 0.5 M NaCl in the phosphate buffer is crucial to keep full solubility of V5-His tagged GIPF at pH 7 during purification. Following ultrafiltration and diafiltration, a mammalian protease inhibitor cocktail (Sigma) was added to a final dilution of 1:500 (v/v).

A HiTrap $Ni^{2+}$-chelating affinity column (Pharmacia) was equilibrated with 20 mM sodium phosphate, pH 7, 0.5 M NaCl. The buffer-exchanged media was filtered with 0.22 µm PES filter and loaded onto $Ni^{2+}$-chelating affinity column. The $Ni^{2+}$ Column was washed with 10 column volumes (CV) of 20 mM imidazole for 10 Column Volume and protein was eluted with a gradient of 20 mM to 300 mM imidazole over 35 CV. The fractions were analyzed by SDS-PAGE and Western blot. Fractions containing V5-His tagged GIPF were analyzed and pooled to yield a GIPF protein solution that was between 75-80% pure.

The buffer containing the GIPF protein isolated using the $Ni^{2+}$ column was exchanged with 20 mM sodium phosphate, 0.3 M Arginine, pH 7 to remove the NaCl. NaCl was replaced with 0.3 M Arg in the phosphate buffer to maintain full solubility of V5-His tagged GIPF protein during the subsequent purification steps. The GIPF protein isolated using the $Ni^{2+}$ column was loaded onto a SP Sepharose high performance cation exchange column (Pharmacia, Piscataway, N.J.) that had been equilibrated with 20 mM sodium phosphate, 0.3 M Arginine, pH 7. The column was washed with 0.1 M NaCl for 8 CV, and eluted with a gradient of 0.1 M to 1 M NaCl over 30 CV. Fractions containing V5-His tagged GIPF were pooled to yield a protein solution that was between 90-95% pure.

The buffer of the pooled fractions was exchanged with 20 mM sodium phosphate, pH 7, 0.15 M NaCl, the protein was concentrated to 1 or 2 mg/mL, and passed through a sterile 0.22 µm filter. The pure GIPF preparation was stored at −80° C.

The protein yield obtained at the end of each purification step was analyzed and quantified by ELISA, protein Bradford assay and HPLC. The percent recovery of GIPFt protein was determined at every step of the purification process, and is shown in Table 2 below.

TABLE 2

| Steps | Step Recovery | Overall Recovery |
|---|---|---|
| Media Concentration/Diafiltration | 100% | 100% |
| Ni-chelating Affinity | 65% | 65% |
| SP Cation Exchange | 80% | 52% |
| Final Formulation and filter | 95% | 49% |

SDS-PAGE analysis of the purified GIPF protein was performed under reducing and non-reducing conditions, and showed that the V5-His tagged GIPF protein derived from both CHO and 293 cells exists as a monomer. GIPF protein is glycosylated and migrates on SDS-PAGE under non-reducing conditions with molecular weight (MW) of approximately 42 kDa. There is slight difference in the MW of the GIPF protein purified from CHO cells and that purified from HEK293 cells. This difference may be explained by the extent to which GIPF is glycosylated in different cell types. N-terminal sequence analysis showed that HEK293 cells produced two forms of the polypeptide: the dominant mature form (SEQ ID NO: 10) which corresponds to the GIPF protein of SEQ ID NO: 4 that lacks the signal sequence, and the mature form (SEQ ID NO: 12), which corresponds to the GIPF protein of SEQ ID NO: 4 that lacks both the signal peptide and the furin cleavage sequence. The two forms separated well on the SP column, and were expressed at a ratio of mature to dominant mature forms of approximately 1:2.

The effect of NaCl and Arginine (Arg) on the solubility of the GIPF protein at pH 7 was determined, and is shown in FIG. 17 A. It was determined that in the absence of 0.3M Arg a 50% loss of protein was incurred during the purification. FIG. 17 B shows the solubility of purified protein in PBS (20 mM sodium phosphate, 0.15 M NaCl, pH 7). GIPF protein remains in solution at concentrations of up to 8 mg/mL at 4° C., pH7, for 7 days.

In summary, the purification of V5-His-tagged GIPF from cultures of HEK293 or CHO cells was performed by 1) concentrating and diafiltering the GIPF protein present in the culture media, 2) performing $Ni^{2+}$-chelating affinity chromatography, and 3) SP cation exchange chromatography. The purification process yields a GIPF protein that is >90% pure. The overall recovery of the current purification process is approximately 50%. Addition of 0.5 M NaCl to the buffer during the purification process of media diafiltration and Ni column is crucial to keep GIPF fully soluble at pH 7. For binding GIPF onto the SP column, NaCl was removed, and 0.3 M Arg was added to maintain high solubility and increase protein recovery. The addition of 0.5 M NaCl and 0.3 Arg during the first and second purification steps showed to increase the overall recovery by at least from 25% to 50%.

The dominant mature and mature forms of the V5His-tagged GIPF were used to test the biological activity of GIPF the in vivo setting described in Example 10. The protein purified by the method of this example consistently induced significant proliferation of intestinal crypt epithelial cells, which underlies the distension of the small intestine of the mice that were administered the purified GIPF protein.

B. Expression and Purification of GIPFwt in Eukaryotic Cells:

The untagged, wild type GIPF protein (GIPFwt; SEQ ID NO: 4) was expressed and purified in a manner similar to that described for the tagged GIPF protein. A stable cell culture of HEK293 cells that had been transfected with the pcDNA/Intron vector comprising the DNA (SEQ ID NO: 3) encoding the full-length GIPF polypeptide (GIPFwt) (SEQ ID NO: 4) was adapted to grow in suspension and grown in serum-free 293 free-style medium (GIBCO) in the presence of 25 µg/ml geneticin.

Cell culture growth in spinner: For small-scale production in spinners, an aliquot of a frozen stock of cells was grown and expanded in 293 free-style media with addition of 0.5% Fetal Bovine Serum (FBS). Cells were seeded and expanded in spinners at cell density of 0.3-0.5 million/mL for each passage. When enough cells are accumulated and cell density reaches 1 million cells/mL for production, the media was exchanged with serum-free 293 free-style media to remove 0.5% FBS, and harvested after 6 days. The initial cell viability was between 80-90% and it decreased to 30% at the time of harvest. The level of GIFPwt that had been secreted into the culture medium was assayed by ELISA and western. Growth of GIPFwt in the spinners yielded 1.2-1.5 mg/l.

Cell Culture Growth in Bioreactors—Fed-batch mode was used for large-scale production in bioreactors. A serum-free adapted suspension culture of HEK293 cells was seeded at cell density of 0.2-0.4 million/ml when passage of cells. Cells were grown in serum free 293 free-style medium and expanded from 50-500 ml shake flasks to 20-50 stir tanks for inoculation of a 200l and 500l bioreactor. When enough cells were accumulated, the cells were inoculated into a bioreactor at a density of 0.2-0.4 million cells/ml. When the cell density reached 1 million cells/ml, vitamins and MEM amino acids (GIBCO) were added to boost and support the growth. Cells were harvested from the bioreactor after 6-7 days when the cell viability had decreased to 25-30%. The level of GIPFwt that had been secreted into the culture medium was assayed by ELISA and western. Western analysis of the secreted GIPF showed that no degradation of the protein had occurred. Western analysis was performed using a purified anti-GIPF polyclonal antibody, and the detection of the protein by ELISA was performed using a purified chicken anti-GIPF polyclonal antibody as the capture antibody, and the rabbit anti-GIPF polyclonal antibody as the detection antibody. The rabbit and chicken polyclonal antibodies were raised against the whole protein. Growth of GIPFwt in the bioreactors yielded 2.6-3 mg/l.

Ultrafiltration-Diafiltration—the medium containing the secreted GIPFwt protein was harvested by centrifugation. Protease inhibitors 1 mM EDTA and 0.2 mM Pefabloc (Roche, Basel, Switzerland) were added to prevent degradation of GIPF. The medium was filtered through a 0.22 µm PES filter (Corning), and concentrated 10-fold using TFF system (Pall Filtron) or hollow-fiber system (Spectrum) with 10 kDa cut-off membrane. The buffer of the concentrated medium was exchanged with 20 mM sodium phosphate, 0.3 M Arg, pH 7. The addition of 0.3 M Arg in the phosphate buffer is crucial to keep GIPFwt fully soluble at pH 7 during purification. After ultrafiltration and diafiltration, a mammalian protease inhibitor cocktail (Sigma) was added at 1:500 (v/v) dilution.

Q anion exchange chromatography—an anion exchange Q sepharose HP column (Amersham) was equilibrated with 20 mM sodium phosphate (NaP) buffer at pH7.0 and containing 0.3 M Arg. The 10-fold concentrated and buffer-exchanged medium was filtered with 0.22 µm PES filter and loaded onto the Q sepharose column to bind impurities and nucleic acids.

SP cation exchange chromatography: the Q-sepharose flow through containing GIPFwt was collected and loaded onto a cation exchange SP sepharose HP (Amersham), which bound the GIPF protein. The SP sepharose column was washed with 15 column volumes (CV) of 20 mM NaP, 0.3 M Arg, 0.1 M NaCl, pH 7, and GIPF was eluted with a gradient of 0.1 M to 0.7 M NaCl over 40 column volumes. The fractions were analyzed by SDS-PAGE and Western blot. Fractions containing GIPFwt were analyzed and pooled. The buffer of the pooled fractions was exchanged with 20 mM sodium phosphate, pH 7, 0.15 M NaCl. The purity of the purified protein was determined to be 92-95% when analyzed by Coomassie staining of an SDS-gel. The protein was concentrated to 1 mg/ml, and passed through a sterile 0.22 µm filter and stored at −80° C.

The yield obtained at the end of each step in the purification process was quantified by ELISA and by the Bradford assay, and the percent recovery of GIPF protein was calculated as shown in Table 3.

TABLE 3

| Steps | Step Recovery | Overall Recovery |
|---|---|---|
| Media Concentration/Diafiltration | 100% | 100% |
| Q Anion Exchange | 95% | 95% |
| SP Cation Exchange | 75% | 71% |
| Final Formulation and filter | 98% | 70% |
|  |  | 48% (dominant mature form only) |

The endotoxin level of the final formulated GIPF protein solution was analyzed using chromogenic LAL (Limulus Amebocyte Lysate) assay kit (Charles River), and determined to be 0.24 EU per mg of GIPF.

C. Expression and Purification GIPFt in Yeast:

GIPFt was expressed and purified from a yeast culture, and the biological activity compared to that of GIPFt that had been purified from the HEK 293 cell culture described above.

The nucleotide sequence encoding GIPFt (SEQ ID NO: 5) was cloned into a *Pichia* expression vector pPICZαA which contains a yeast α-factor secretion signal sequence. The *Pichia Pastoris* wild type X-33 strain was used to express GIPFt. The protocols for the use of the *Pichia* vectors, expression and purification of recombinant proteins are available from Invitrogen Life Technologies (Carlsbad, Calif., USA), and are also described in "*Pichia* Protocols: Methods in Molecular Biology" (D. R. Higgins and J. Cregg eds., The Humana Press, Totowa, N.J. 1998)).

Briefly, GIPFt was purified using the SP cation exchange chromatography followed by affinity chromatography on an IMAC $Ni^{2+}$ column. The $Ni^{2+}$ column was washed with 20 mM imidazole, and GIPF was eluted in a 20-300 mM imidazole gradient over 30 column volumes. SDS-PAGE of the purified product displayed a broad and smeared protein band of about 50 kDa, indicating that GIPFt is glycosylated to varying degrees. The biological activity analyzed in vitro and in vivo as described in Examples 17 and 20, respectively.

GIPFt protein that was expressed in *Pichia pastoris* induced the proliferation of the mouse intestinal epithelium, and stabilized β-catenin, albeit to a lesser extent than that obtained with the GIPF protein that was purified from HEK293 cells (data not shown).

D. Purification of the Murine Ortholog of GIPF-mGIPFt:

SEQ ID NO: 68, which encodes the mouse ortholog of the human GIPF, was cloned into the pcDNA/Intron vector to express a V5-His tagged protein mGIPFt. The tagged mouse protein was expressed in HEK 293 cells, and purified according to the method described above for the purification of the human GIPFt protein. The protein was purified to 80% purity, and was formulated in PBS. The biological activity of mGIPFt was analyzed in vivo and in vitro, and shown to possess the same proliferative properties as human GIPF (Example 20).

E. Characteristics of Purified Recombinant GIPF

SDS-PAGE analysis of the purified GIPF proteins (GIFPt and GIPFwt) was performed under reducing and non-reducing conditions, and showed that the V5-His tagged GIPF proteins derived from 293 cells exists as a monomer. GIPFt and GIPFwt proteins are glycosylated and migrate on SDS-PAGE under non-reducing conditions with a molecular weight (MW) of approximately 42 kDa and 38 kDa, respectively. Matrix-assisted laser desorption/ionization mass spectroscopy (MALDI) showed that the respective molecular weights for GIPFt and GIPFwt are 37.8 kDa and 32.9 kDa., while the theoretical molecular weight for GIPFt and GIPF wt that lack the signal peptide is 30.2 kDa and 26.8 kDa, respectively. The discrepancy in the molecular weights suggested that it might have been accounted for by the glycosylation of the protein. Subsequently, complete deglycosylation of N-linked and O-linked oligosaccharides was performed using N- and O-glycanase (Prozyme, San Leandro, Calif., USA) according to the manufacturer's instructions. SDS-PAGE analysis of the deglycosylated protein resulted in a decrease in apparent molecular weight of 4-5 kDa. Deglycosylation did not affect the biological activity of GIPF when assayed in vitro and in vivo as described in Examples 17 and 20, respectively (data not shown).

Protein stability—To test the activity of GIPF following denaturation, GIPF was boiled for 5 minutes, and rapidly cooled on ice. GIPF retained full activity was determined in vitro (see Example 17) and in vivo (see Example 21). These findings indicate that GIPF is a stable protein.

Capping of Cysteine residues—Reduction and alkylation of cysteine residues was performed to abolish the activity of GIPF. Reduction of the disulfide bonds of GIPF (1 mg/ml) was obtained by incubating GIPF in 30 mM DTT, pH 8, at 37° C. for 1 hr. Subsequently, the free sulfhydryls were by S-carboxymethylation with 20 mM Iodoacetamide at 37° C. in dark for 30 minutes (Crestfield A M; Moore S; Stein W H. J. Biol. Chem. 1963; 238, 622). The reaction was stopped by freezing, and excess DTT and Iodoacetamide were removed by dialysis against PBS. The biological activity of capped GIPF was analyzed using both in vitro and in vivo assays. The biological activity of GIPF was obliterated by capping (see Examples 17 and 20).

N-terminal sequence analysis showed that HEK293 cells produced two forms of either the GIPFt or GIPFwt polypeptide: the dominant mature form (SEQ ID NO: 10) which corresponds to the GIPF protein of SEQ ID NO: 4 that lacks the signal sequence, and the mature form (SEQ ID NO: 12), which corresponds to the GIPF protein of SEQ ID NO: 4 that lacks both the signal peptide and the furin cleavage sequence. The two forms separated well on the SP column, and were expressed at a ratio of mature to dominant mature forms of approximately 1:2. While both the dominant mature and mature forms of GIPFt induce proliferation of intestinal crypt cells in vivo, the dominant mature form was used to test the therapeutic effect of GIPF in the animal models of disease described in Examples 11, 12, 13, and 14. CHO cells express only the dominant mature form of GIPF.

Mutagenesis of Furin cleavage site ($Arg^{28} \rightarrow Gln$)—To show that the mature form of GIPF produced from HEK 293 cells occurs from the natural processing by furin protease, the conserved sequence of the furin cleavage site was mutated to replace $Arg^{28}$QRR by $Gln^{28}$-QRR. The mutant protein (SEQ ID NO: 18) was expressed in HEK293 cells and purified according to the method used for the purification of GIFPt (Example 9A). N-terminal sequencing of the purified protein confirmed that only the dominant mature form was expressed in the culture. This finding confirms that the mature form is generated as a result of proteolytic cleavage by cellular furin protease activity. In addition, the overall recovery of the purified dominant mature form increased from 50% to 68%.

In summary, the purification processes yield a GIPFt protein that is >90% pure, and a GIPFwt that is 92-95% pure. The overall recovery of the dominant mature form of GIPF using either purification processes is approximately 50%. However, the yield can be increased by expressing a protein that has a mutated furin cleavage site. Addition of 0.5 M NaCl to the buffer during the purification process of media diafiltration and Ni column is crucial to keep GIPF fully soluble at pH 7. For binding GIPF onto the SP column, NaCl was removed, and 0.3 M Arg was added to maintain high solubility and increase protein recovery.

The dominant mature and mature forms of GIPFt and GIFP wt were used to test the biological activity of GIPF in vivo. The proteins purified by the methods of this example consistently induced significant proliferation of intestinal crypt epithelial cells, which underlies the distension of the small intestine of the mice that were administered the purified GIPF protein.

The biological activity of GIPF was unaffected by deglycosylation or boiling, but was obliterated by capping cysteine residues with iodoacetamide.

Example 10

In Vivo Biological Testing of Recombinant GIPF Protein Expressed in HEK293 and CHO Cells The in vivo biological effects of GIPFt protein that was derived from HEK293 and CHO cells were evaluated in normal mice as follows.

The pharmacokinetics (PK) of recombinant GIPF V5His6-tagged protein (GIPFt) were determined in mice. 6-8 weeks old BALB/c mice were injected i.v. via the tail vein with single dose of either 40 mg/KG GIPFt protein or formulation buffer as control. Blood was withdrawn at 0, 30 min, 1 hr, 3 hr, 6 hr and 24 hr after injection and serum protein level at each time point was analyzed by Western analysis using anti V5 antibody (Invitrogene Inc., Carlsbad, Calif.) (FIG. 18A). FIG. 18A shows that no significant degradation of serum GIPF protein was detected. The half-life of GIPF protein in serum was calculated by semi logarithmic plot of the protein concentration after injection using Positope (Invitrogene Inc., Carlsbad, Calif.) as a standard V5 tagged protein, and was estimated to be 5.3 hours (FIG. 18B).

To investigate whether purified recombinant GIPFt protein could generate a phenotype similar to that observed in the GIPF knock-in mice and in the mice that had been injected with recombinant adenovirus, 6-8 weeks old BALB/c mice were injected daily through tail vein with either 4 mg/KG GIPFt protein or formulation buffer as control for 7 days. Mice were sacrificed on day 8 at 24 hours after last injection. Four hours prior to being sacrificed, 1 mg of bromodeoxyuridine (BrdU) was injected ip to determine the in vivo proliferative activity of GIPF. Various tissues including small intestine, colon, spleen, liver and bone marrow were collected and fixed in formaline. Paraffin embedded sections were stained with hematoxylin and eosin for histological evaluation. Sections were also processed for BrdU immunohistochemistry according to the manufacturer's instruction (Oncogene Research product, Boston, U.S.A.) and previously described (McKinley, J. N. et al. 2000). In all experiments, at least 3 animals were analyzed per group and experiments were repeated at least twice.

Figure 19:
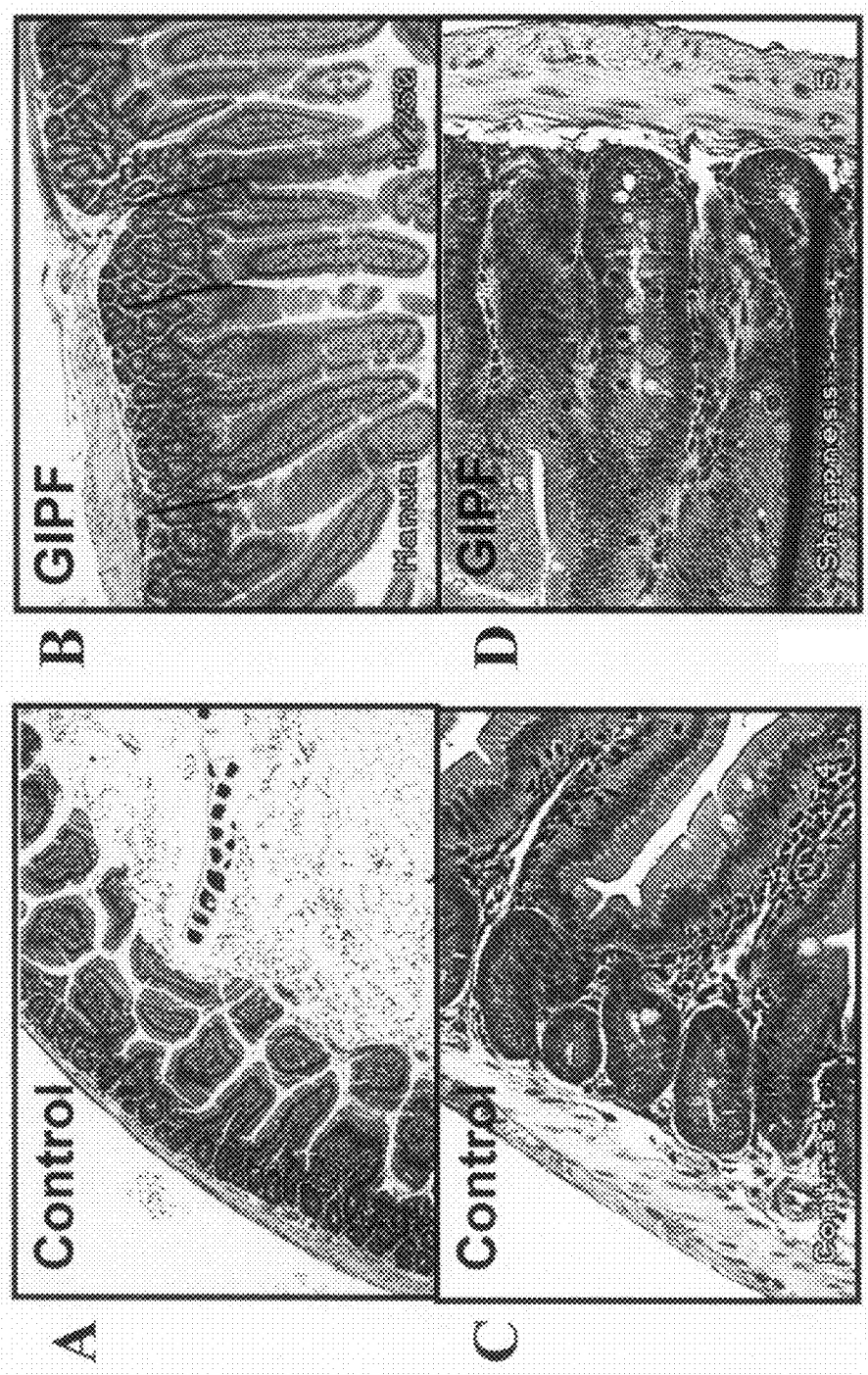

H&E staining of gastrointestinal sections showed that significant proliferation of intestinal crypt epithelial cells in the small intestine and colon was seen in the mice that had received GIPF (FIGS. 19 and 21, respectively). This result is consistent with the results obtained in the transgenic GIPF knock-in mice, and in the mice that received GIPF adenovirus (see Examples above) The proliferative effect of GIPF protein was confirmed by assaying BrdU incorporation in both small intestine (FIG. 20) and colon (FIG. 22).

Example 11

Prophylactic Effect of GIPF on Radiation-Induced Mucositis

The efficacy of GIPF as a prophylactic and therapeutic agent was tested in an animal model of radiation-induced mucositis.

Forty eight adult male BDF1 mice, aged 10-12 weeks, were used. On delivery from the supplier and prior to the experiment, the animals were housed for two weeks in individually ventilated cages on a 12 hour light:dark cycle to stabilize the circadian rhythm. Animals were allowed food and water ad libitum.

The animals were divided into 8 groups of 6 animals, and were treated as follows:
1. Injected with 2 mg/kg GIPF iv at 72, 48, and 24 hours prior to being exposed to 13 Gy X-ray (whole body);
2. Injected with 5 mg/kg GIPF iv at 72, 48, and 24 hours prior to being exposed to 13 Gy X-ray (whole body);
3. Injected with 125 µg KGF iv at 72, 48, and 24 hours prior to being exposed to 13 Gy X-ray (whole body);
4. Injected with saline vehicle iv at 72, 48, and 24 hours prior to being exposed to 13 Gy X-ray (whole body);
5. Untreated, non-irradiated controls;
6. Injected with 2 mg/kg GIPF iv 24, 48, and 72 hours post irradiation with 13 Gy X-rays (whole body);
7. Injected with 5 mg/kg GIPF iv 24, 48, and 72 hours post irradiation with 13 Gy X-rays (whole body);
8. Injected with saline iv at 24, 48, and 72 hours post irradiation with 13 Gy X-rays (whole body).

All injections were given at 15:00 hours. Intestinal damage was induced using a single dose of 13 Gy X-irradiation (delivered at 0.7 Gy/min) at 15:00.

Four days after irradiation the animals were culled. The small intestine was removed and fixed in Carnoy's fixative prior to processing for histological analysis. Transverse sections 3 µm thick were cut and stained with haematoxylin and eosin. Immediately after sacrifice the duodenum, mid colon, liver, lung, tongue, spleen, stomach and pancreas were also removed and fixed in formal saline overnight prior to storage in 70% ethanol.

For each animal ten intestinal circumferences were analyzed (60 per group)—a circumference is equivalent to a given length of intestine and therefore a convenient baseline unit of length. The number of surviving crypts per circumference were scored and the average per group determined (Table 4). Only crypts containing 10 or more strongly H&E stained cells (excluding Paneth cells) and only intact circumferences not containing Peyers patches were scored.

The average crypt width (measured at its widest point) was also measured in order to correct for scoring errors due to crypt size difference. The correction is applied thus:

$$\text{Corrected number of crypts/circumference} = \frac{\text{Mean crypt width in untreated control}}{\text{Mean crypt width in treated animal}} \times \text{Mean number of surviving crypts in treatment group}$$

All the animals survived the treatment and exhibited no obvious adverse effects. FIG. 23 A-D shows sections from the small intestine from the animals the untreated group 5 (A), the saline pre-treated group 4 (B), the KGF-treated group 3 (C) and the GIPF-treated group 2 (D). Foci of regeneration (surviving crypts with one or more clonogenic cells) are clearly visible in the tissue section from the saline-treated animals (group 4) (FIG. 23B) Other than these foci the mesenchyme is entirely denuded, and these animals would have developed diarrhea and died due to the mucositis if they had been allowed to live beyond four days post irradiation. GIPF afforded protection of the intestinal architecture (FIG. 23 D) in a manner comparable to the to that provided by KGF (FIG. 23 C).

TABLE 4

| Experimental Group | No. of crypts/ Circumference (Mean ± SD) | Crypt Width (µm) (Mean ± SD) | Corrected crypts/ Circumference (Mean ± SD) |
|---|---|---|---|
| 1. | 12.96 ± 4.9 | 51.98 ± 5.4 | 7.4 ± 3.3 |
| 2. | 15.4 ± 4.9 | 45.03 ± 2.8 | 10.1 ± 3.3 |
| 3. | 22.1 ± 3.8 | 54.46 ± 2.1 | 12.0 ± 1.2 |
| 4. | 7.2 ± 2.6 | 55.27 ± 6.4 | 3.8 ± 1.2 |
| 5. | 109.1 ± 5.3 | 29.56 ± 3.0 | |
| 6. | 10.7 ± 4.5 | 57.16 ± 3.9 | 5.5 ± 2.3 |
| 7. | 10.6 ± 4.1 | 55.50 ± 4.7 | 5.6 ± 2.1 |
| 8. | 9.4 ± 1.9 | 56.85 ± 6.9 | 5.0 ± 1.4 |

It is immediately obvious that pre-treatment with GIPF increased considerably the number of crypts that survived the 13 Gy irradiation. Pre-treatment with GIPF at a dose of 2 mg/kg (group 1) increased survival by 1.95 fold that of the crypts from the untreated group 4 (also known as the protection factor), and the GIPF dose of 5 mg/kg (group 2) further increased crypt survival by 2.66 fold. This is extremely impressive and almost comparable with the effect seen with treatment with the known optimal dosing of KGF (group 3), which increased crypt survival by 3.16 fold.

Therefore, GIPF was shown to protect the epithelium of the small intestine from the injurious effects of irradiation, and could be used as a potent prophylactic in patients for whom radiation therapy has been indicated.

Example 12

Chemotherapy-Induced Mucositis Model

The efficacy of the recombinant human GIPF (GIPFwt) in treating chemotherapy-induced mucositis was evaluated in healthy and in tumor-bearing mice. The experimental protocol was based on that previously described by Boushey et al. (Cancer Res 61:687-693 (2001)).

One million CT26 murine colon carcinoma cells (ATCC, Manassas, Va., USA) were injected sc into syngeneic female BALB/c mice, and the tumors were allowed to develop for 5 days. Healthy and tumor-bearing animals were divided into experimental groups of 6 mice each and treated as follows:
1. tumor bearing mice, vehicle (50% DMSO) injected ip from day 1 to day 5, saline injected iv from day 0 to day 7 (TVS)
2. tumor bearing mice, vehicle (50% DMSO) injected ip from day 1 to day 5, 50 µg GIPF in 100 µl saline injected iv daily from day 0 to day 7 (TVG);
3. tumor bearing mice, 50 mg/kg 5-FU injected ip from day 1 to day 5, saline injected iv from day 0 to day 7 (TDS);
4. tumor bearing mice, 50 mg/kg 5-FU injected ip from day 1 to day 5, 50 µg GIPF in 100 µl saline injected iv from day 0 to day 7 (TDG);
5. healthy mice, 50 mg/kg 5-FU injected ip from day 1 to day 5, saline injected iv from day 0 to day 7 (NDS);
6. healthy mice, 50 mg/kg 5-FU injected ip from day 1 to day 5, 50 µg GIPF in 100 µl saline injected iv from day 0 to day 7 (NDG).

On days 0, 2, 4, 6, and 8 measurements of animal body weight, severity of diarrhea, and size of the tumors were recorded. A diarrhea score of 0-3 reflected a corresponding worsening of the symptom from 0 being normal to 3 being severe. The change in body weight was calculated as the percent body weight of that of the untreated group. The length, width and height of the tumor were measured with calipers, and the volume of the tumor was calculated as (length×width×height)/2.

All animals were euthanized on day 8. The large and small intestine were removed and weighed, their length was measured, and the diameter of the mid-jejenum was recorded. A segment (1 cm) of the mid-jejenum was excised about 14-15 cm from the pylorus, and a segment (1 cm) of the transverse colon was excised at about 4 cm from the ileocaecal junction. The bowel segments were flushed and fixed using 10% neutral buffered formalin for histological analysis. Histological examination and morphometry of the mucosa were performed on tissue sections using the ImagePro Software (Imagepro, Ltd., Ashford, Middlesex, UK).

The effect of GIPFwt on the severity of diarrhea, body weight and tumor size are summarized as follows:

| | Diarrhea score (mean ± SD): | Body weight (% of untreated) |
|---|---|---|
| Group 3 TDS | 2.83 ± 0.41 | 74.7 ± 5.2 |
| Group 4 TDG | 0.33 ± 0.52 | 85.1 ± 5.7 |
| Group 5 NDS | 3 ± 0 | 73.2 ± 4.3 |
| Group 6 NDG | 0.5 ± 0.55 | 87.0 ± 6.0 |

| Tumor volume (mean ± SD; mm$^3$): | |
|---|---|
| Group 1 TVS | 95.8 ± 8.1 |
| Group 2 TVG | 95.1 ± 4.2 |
| Group 3 TDS | 21.8 ± 3.0; p < 0.05 |
| Group 4 TDG | 16.7 ± 8.6; p < 0.05 |

GIPF reduced significantly the severity of the diarrhea caused by 5-FU in the healthy and the tumor-bearing mice of groups 6 and 4, respectively, when compared to the scores for the normal and tumor-bearing mice of groups 5 and 3, which did not receive GIPF. Similarly, GIPF reduced the loss of body weight that the 5-FU-treated animals experienced.

The tumors from the untreated tumor-bearing mice (group 1) were similar in size to those from the GIPF-treated tumor-bearing mice (group 2). Thus, GIPF did not affect the growth of the tumor. As expected, 5-FU reduced the size of the tumors in the mice of group 3, and it also reduced the size of the tumors of the mice of group 4 Thus, GIPF did not impede the activity of 5-FU in reducing the size of the tumors (FIG. 24).

The effect of GIPF on the gross appearance of the intestines is shown in FIG. 25, and the corresponding measurement of intestinal diameter, weight and length are given in Table 5. The intestines of the normal and tumor-bearing mice that had received 5-FU was atrophied (FIG. 25E), and numerous lesions associated with bleeding were observed, while the appearance of the intestines from the mice that had received GIPF was overtly normal and accompanied by the typical distension due to the proliferative effect of GIPF on the in intestinal epithelium (FIGS. 25 B, C, D, and F).

TABLE 5

| CT26 tumor-bearing mice | Group 1 | Group 2 | Group 3 | Group 4 |
|---|---|---|---|---|
| Diameter Midjejenum (mm) | 2.66 ± 0.15 | 3.65 ± 0.21* | 2.53 ± 0.15 | 3.58 ± 0.14$^\#$ |
| Weight | | | | |
| Small bowel (g) | 1.16 ± 0.09 | 1.47 ± 0.14* | 0.90 ± 0.01 | 1.51 ± 0.13$^\#$ |
| Large bowel (g) | 0.32 ± 0.02 | 0.38 ± 0.02* | 0.25 ± 0.03 | 0.39 ± 0.02$^\#$ |
| Length | | | | |
| Small bowel (cm) | 35.2 ± 2.0 | 40.5 ± 1.0* | 30.2 ± 1.3 | 39.7 ± 2.1$^\#$ |
| Large bowel (cm) | 8.7 ± 0.3 | 9.7 ± 0.3* | 6.3 ± 0.3 | 9.5 ± 0.5$^\#$ |

| Normal mice | Group 5 | Group 6 |
|---|---|---|
| Diameter Midjejenum (mm) | 2.38 ± 0.13 | 3.44 ± 0.13** |
| Weight | | |
| Small bowel (g) | 0.88 ± 0.08 | 1.43 ± 0.13** |
| Large bowel (g) | 0.25 ± 0.02 | 0.38 ± 0.04** |
| Length | | |
| Small bowel (cm) | 30.3 ± 1.9 | 39.3 ± 1.0** |
| Large bowel (cm) | 6.9 ± 0.9 | 9.7 ± 1.0** |

*P < 0.05 (ANOVA, group 2 vs group 1)
$^\#$P < 0.05 (ANOVA, group4 vs group 3)
**P < 0.05 (ANOVA, group 6 vs group 4)

Histological analysis of intestinal sections of the small intestine and colon of all experimental groups showed that GIPF preserved the intestinal architecture of the mice that had received 5-FU by preventing the massive damage to the villi and crypt compartments of the intestinal mucosa caused by 5-FU (FIG. 26), FIG. 26 A shows the effects of 5-FU on the small intestine, and FIG. 26B shows the effects of 5-FU on the colon. Micromorphometry measurements of villus height and crypt depth in the midjejenum confirm that the effect of GIPF is significant (FIG. 27), GIPF protects that small intestine and colon from the deleterious effects of 5-FU, and it does not hinder the therapeutic effects of 5-FU. Therefore, GIPF may be used in conjunction with chemotherapeutic agents to reduce the deleterious side-effects of antineoplastic therapies.

Example 13

Prophylactic Effect of GIPF on Chemotherapy and Radiation-Induced Oral Mucositis The effect of GIPF on the proliferation of the dorsal (buccal) and ventral epithelium of the tongue was studied in mice that had been subjected to X-ray irradiation or dosed with 5-FU, as described in Examples 11 and 12, respectively.

Immunohistochemistry using monoclonal rat anti-mouse Ki67 antigen (Dako Ltd., High Wycombe, UK) was performed, according to manufacturer's instruction and the method previously described (Scholzen, T. et al. 2000), on paraffin embedded sections of tongue from non-irradiated and irradiated mice (groups 1, 2, and 3 in Example 11).

GIPF visibly increased the number of nuclei that stained for Ki67 in the ventral and dorsal tongue epithelium of irradiated animals when compared to that from animals that were not given GIPF (FIGS. 28 and 29). The epithelial proliferative index, which is calculated as the percent ventral epithelial cells that stained positive for Ki67, confirmed that GIPF reduced significantly the loss of cellularity caused by the radiation to the ventral tongue epithelium (FIG. 30).

Histological analysis of sections from the tongue of animals that had been treated with 5-FU (groups 2-6 in Example 12) shows that GIPF maintains the morphology of the dorsal and ventral epithelial layers in normal and tumor-bearing animals that had been treated with 5-FU (FIG. 31).

The epithelial layer of the tongue from all animals that had been treated with GIPF was remarkably less damaged by 5-FU than that of the experimental animals that had not received GIPF.

Therefore, GIPF may be used as a therapeutic agent for the treatment and/or prevention of chemotherapy and radiation therapy-induced oral mucositis. Quantitative animal models of oral mucositis (e.g. Wardly et al., Arch Oral Biol 43:567-577 (1998); Potten et al., Cell Prolif 35:32-47 (2002)) can be used to study further the therapeutic properties of GIPF, when administered in combination with other cytotoxic agent to further assess the potential role of GIPF in reducing the severity of the cellular depletion and to increase the rate of regeneration of the epithelial layers of the oral and intestinal epithelium.

Example 14

Therapeutic Effect of GIPF on Dextran Sulfate Sodium-Induced Colitis

The efficacy of recombinant human GIPF (GIPFwt) in treating colitis was tested in a mouse model of dextran sulfate sodium (DSS)-induced colitis, and compared to that the efficacy of GLP-2 (L'Heureux and Brubaker J Pharmacol Exp Ther 306:347-354 (2003); Kriegelstein et al., J Clin Invest 110:1773-1782 (2002); Siegmund et al., J Pharmacol Exp Ther 296:99-105 (2001)).

Six to eight-week old female BALB/c mice (Charles River Laboratories, Wilmington, Mass., USA) were housed in ventilated cages and acclimated for one week to a 12 hour light:dark cycle. Twenty four mice having similar body weight (approximately 20 g; <5% variance) were housed in 4 cages and fed ad libitum a 4% DSS (v/w) drinking solution for 7 days.

On day 7, the body weight of each animal was recorded, and the scores for loss in body weight, the consistency of stools, and anal bleeding were determined as shown in Table 6 below.

TABLE 6

| SCORE | Weight Loss (%) | Stool Consistency | Occult/Gross Rectal bleeding |
|---|---|---|---|
| 0 | None | Normal | Normal |
| 1 | 0-5% | | |
| 2 | 5-10% | Loose | Hemoccult |
| 3 | 10-20% | | |
| 4 | >20% | Diarrhea | Gross |

The scores were used to calculate the IBD activity index (IBDAI), which was used as an indicator of the severity of the colitis, and is calculated as the average of the scores given for the tabulated parameters. The scores for weight loss, stool consistency, and rectal bleeding were determined daily, and the IBDAI was recorded daily for the duration of the experiment.

On day 7, the 4% (v/w) DSS drinking solution was substituted with a 1% (v/w) DSS solution to maintain the disease activity without exacerbating the effect of the DSS. Sixteen of the DSS-fed animals were selected for consistent and comparable disease activity, and were dived into groups of 4 animals and were treated as follows:

1. Water, saline injected iv daily (10 am) for 7 days
2. DSS (1%) for 7 days, saline injected iv daily (10 am) for 7 days
3. DSS (1%) for 7 days, 100 μg GIPF injected daily iv (10 am) for 7 days
4. DSS (1%) for 7 days, 50 μg GIPF injected daily iv (10 am) for 7 days
5. DSS (1%) for 7 days, 10 μg GLP-2 injected sc twice daily (10 am and 6 pm) for 7 days.

The GIPF protein used in these experiments was the human recombinant GIPF protein (SEQ ID NO: 4; GIPFwt), which was expressed and purified according to the method described in Example 9. The analog of GLP-2, h[Gly$^2$]GLP-2 was synthesized and purchased from Biosource International (Camarillo, Calif., USA).

On day 14, food was removed from the cages to allow for purging of the intestine, and the animals were culled by cervical dislocation. All animals were injected with 4 mg/0.1 ml BrdU two hours prior to sacrifice. The large and small intestine were removed and weighed, their length was measured, and the diameter of the mid-jejenum was recorded. A segment (1 cm) of the mid-jejenum was excised about 14-15 cm from the pylorus, and a segment (1 cm) of the transverse colon was excised at about 4 cm from the ileocaecal junction. The bowel segments were flushed and fixed using 10% neutral buffered formalin for histological analysis. Histological examination and morphometry of the mucosa were performed on tissue sections using the Imagepro Software (Imagepro, Ltd., Ashford, Middlesex, UK). The IBDIAs for the mice of experimental groups 2-5 are shown in FIG. 32, and the corresponding scores for weight loss, stool consistency and rectal bleeding are shown in FIGS. 33, 34, and 35, respectively. These data show that GIPF afforded a therapeutic effect by reducing the severity of the colitis as early as day 11. By day 14, the GIPF-treated mice of groups 3 and 4 had significantly lower IBDIA (1.75 and 1.83, respectively) than the untreated mice of group 2 (3.75). GLP-2 had a moderate effect on the severity of the colitis, and by day 14 it reduced the IBDAI of the DSS-treated mice to 3.25.

An example of the gross pathology of the intestine and colon of the mice from groups 1, 2, 3, and 5 is shown in FIG. 36. Animals receiving DSS with saline developed severe colitis that was typically associated with atrophy, hyperemia, and diarrhea when compared to the control group. The small and large intestine of the animals that were treated with GIPF showed some distension, and were remarkably similar to those of the control group. These findings indicate that GIPF may be used as an effective therapeutic agent for the treatment of inflammatory bowel disease. While GLP-2 afforded some therapeutic effect, the small and large intestine from this group seemed marginally less injured than that from the animals in the control group. The significance of the changes is reflected by the measurements of the small and large intestines shown below in Table 7.

TABLE 7

|  | Group 1 | Group 2 | Group 3 | Group 4 | Group 5 |
|---|---|---|---|---|---|
| Diameter Midjejenum (mm) | 2.25 ± 0.09 | 1.72 ± 0.05* | 2.50 ± 0.18# | 2.23 ± 0.10# | 1.97 ± 0.04** |
| Weight | | | | | |
| Small bowel (g) | 0.94 ± 0.06 | 0.78 ± 0.05* | 0.91 ± 0.09# | 0.89 ± 0.05# | 0.88 ± 0.07 |
| Large bowel (g) | 0.26 ± 0.02 | 0.18 ± 0.01* | 0.23 ± 0.01# | 0.22 ± 0.01# | 0.18 ± 0.01 |
| Length | | | | | |
| Small bowel (cm) | 32.0 ± 1.4 | 26.6 ± 0.9* | 31.1 ± 0.9# | 30.3 ± 0.6# | 28.9 ± 0.8** |
| Large bowel (cm) | 7.3 ± 0.3 | 4.9 ± 0.5* | 6.6 ± 0.5# | 6.4 ± 0.3# | 5.4 ± 0.6 |

*P < 0.05 (ANOVA, group 2 vs group 1)
P < 0.05 (ANOVA, groups 3 or 4 vs group 2)
**P < 0.05 (ANOVA, group 5 vs group 2)

H & E staining of paraffin embedded sections showed that DSS caused massive infiltration by inflammatory cells and disintegration of the villus and crypt compartments of the mucosa of the small intestine and colon (FIG. 37). Consistent with the observations of the gross pathology described above, GIPF reversed the effects caused by DSS, and restored the intestinal architecture of the crypts and villi. The crypts of the GIPF-treated animals were distended when compared to those from the control group. GLP-2 afforded some therapeutic effect, albeit to a far lesser level than GIPF (data not shown). Micromorphometry of the villi and crypts (FIG. 38) confirmed that the curative effect of GIPF was reflected by a significant restoration of the villus height and the crypt depth, which had been severely destroyed by the colitis. The repair of the mucosal architecture by GIPF was underscored by a significant proliferation of crypt cells (FIGS. 39 and 40). The crypt proliferative index, which is calculated as the percent crypt cells that stained positive for BrdU, was significantly greater in the DSS-treated mice that received GIPFwt than in the DSS-treated mice that were injected with saline (P<0.05) (FIG. 40).

Example 15

Therapeutic Effect of GIPF Following Massive Intestinal Resection

The effect of GIPF in augmenting the adaptive response to massive intestinal resection is tested in a rat animal model of short bowel syndrome (SBS). The animal model used in the study of the effects of enterorophic agents has been described (Scott et al. Am J Physiol G911-G921 (1998); Helmrath et al., J Am Coll Surg 183:441-449 (1996)), and the experimental protocol is herein incorporated by reference).

The animals are divided into a resected group that will have a 75% surgical resection of the midjejenunoileum, a sham-resected operated control group in which the intestine is sectioned and reanastomosed, and an unoperated control group. The animals are administered saline or GIPF at a dose of 2 mg/Kg. The 75% intestinal resection is chosen to maximize any adaptive response, and retention of equal portions of the proximal jejunumnum and distal ileum is based on the nutritional implications of removing the specialized absorptive capacity of the terminal ileum for vitamin B12 and bile acids and the ileal brake. In the rat, the retention of 25% of the small intestine inclusive of a portion of distal ileum, is sufficient to allow resected animals to achieve the same growth rate as control animals.

The metabolic, morphological, histological, and functional response of the gut to resection and treatment with GIPF is assessed during the course of the experiment and also as end-point analysis on Day 10. Food intake and growth, gross and microscopic small intestinal morphology, and functional evaluation of mucosal absorptive characteristics are evaluated as described (Scott et al., supra).

GIPF significantly increases the food consumption and reduces the loss in body weight that typically accompanies resection of the small bowel. GIPF also increased the length of the remnant intestine, its diameter, wet weight, and mucosal wet weight, and increases the absorptive capacity of the remnant small intestine. H&E staining of cross-sections of the small intestine shows that GIPF elongates both the villus height and crypt depth, and increases crypt cell proliferation in the gut of the animals with resected small intestines. Thus, GIPF reduces the effects of bowel resection by augmenting intestinal adaptation.

Example 16

Effect of GIPF on the Proliferation of Tumor Cells

GIPF induces a strong proliferative effect on intestinal crypt epithelial cells in vivo. To investigate the proliferative effect on in vitro, the effect of recombinant GIPFwt was tested on the proliferation of various tumor and normal cell lines in vitro.

The rate of cell proliferation of the following cell lines (ATCC) was measured by assaying the incorporation of $^3$H-thymidine:

| | |
|---|---|
| Caco-2 | human colorectal adenocarcinoma; epithelial |
| COLO205 | human ascites from metastatic colorectal adenocarcinoma; epithelial |
| HCC70 | human mammary gland ductal carcinoma; epithelial |
| HCT116 | Human colorectal carcinoma; epithelial |
| HT-29 | Human colorectal adenocarcinoma; epithelial |
| IEC-18 | Rat ileum; epithelial |
| IEC-6 | rat small intestine; epithelial |
| LS513 | human caecum; colorectal carcinoma; epithelial |

| | |
|---|---|
| MCF7 | human pleural effusion from metastatic breast adenocarcinoma; epithelial |
| NCI-H1373 | human lung adenocarcinoma |
| PC-3 | human bone metastasis from prostate adenocarcinoma; epithelial |
| SCC-25 | Human tongue squamous cell carcinoma |
| SCC-4 | Human tongue squamous cell carcinoma |
| SK-BR-3 | Human pleural effusion from metastatic colon adenocarcinoma; epithelial |
| SK-MES-1 | Human pleural effusion from metastatic squamous cell lung carcinoma; epithelial |
| SW620 | Human lymph node metastasis from colorectal adenocarcinoma; epithelial |
| T84 | Human lung metastasis from colorectal carcinoma; epithelial |
| 293 | Human fetal kidney; epithelial |

Cells were seeded at 10,000-50,000 cells per well, and depending on cell lines and treated with scaled doses of GIPFwt (1.37-1000 ng/ml). The rate of proliferation of the GIPF-treated cells was compared to that of untreated cells, or cells that were grown in 10% complete media (growth media, 2.5% dialyzed FBS, and pen/strep). The cells were incubated for 48 hours at 37° C., and pulsed with 0.5 µCi $^3$H-thymidine for the last 20-24 hours of incubation. Cells were harvested, the amount of $^3$H-thymidine that had been incorporated was determined, and the results determined from duplicate samples of replicate experiments.

GIPFwt did not affect the rate of proliferation of most of the tumor cells that were tested. An increase in the rate of proliferation was induced only at the higher doses of GIPF in IEC28, T84, HCT116, and HT29 cells. The extent of the proliferation was less than 40% of rate of the untreated cells.

Therefore, these findings indicate that GIPF may not exacerbate the rate of proliferation of tumors existing in vivo, and GIPF may be used for treating cancer patients who are suffering from mucositis caused by antineoplastic therapies.

Example 17

Effect of GIPF on Intracellular Signaling

The wnt/β-catenin signaling pathway plays a pivotal role in development and homeostasis. In the small intestine, wnt signaling is known to play a critical role as a regulator of intestinal crypt proliferation by stabilizing β-catenin, which subsequently induces the transactivation of T-cell factor (TCF) target genes (Wetering et al., Cell 111:241-250 (2002); Batle et al., Cell, 111:251-263, (2002); Perreault et al., J Biol Chem 276:43328-43333 (2001); Booth et al., Nat Med 8:1360-1361 (2002)).

To evaluate the effect of GIPF on the wnt/β-catenin signaling pathway, the stabilization of β-catenin was measured in various cultured cell lines. Cells were seeded at 1 million cells/well for a 6-well plate in Dulbecco's modified Eagle's medium supplemented with 10% FBS. The following day, cells were grown in serum-free medium, and treated either with GIPF at 50 ng/ml or LiCl$_2$ (positive control) at 10 mM in low serum conditions (0.1% FBS). Cytoplasmic fractions were prepared as described by Haertel-Weismann et al., (J Biol Chem 175:32046-32051 (2000)). The proteins were resolved by gradient (4-20%) SDS-PAGE, and the level of β-catenin was assessed using a β-catenin rabbit antibody (Abcam) that was visualized using a peroxidase conjugated secondary antibody (Cell Signaling).

Among tested cell lines, GIPF induced the stabilization of β-catenin in a human endocrinic L cell line (NCI-H716, data not shown), and in HEK 293 cells in a dose-dependent and time-related manner (FIGS. 41A and B, respectively). Consistent with the findings described in Example 18, boiling GIPF did not affect its ability to stabilize β-catenin, but, the effect was abolished by treatment with proteinase K, and by reduction with DTT (FIG. 41 C).

To further investigate the signaling pathway through which GIPF leads to the accumulation of β-catenin, the activity of GSK3β was analyzed in HEK293 cells. In the canonical wnt signaling pathway, Wnt activates β-catenin by inhibiting GSK3β, which would otherwise phosphorylate β-catenin and mark it for destruction by the proteosome.

GIPF increased the phosphorylation of GSK3β in HEK 293 cells in a time-dependent manner (FIG. 42). These data indicated that GIPF may activate β-catenin by canonical wnt signaling pathway by inhibiting β-catenin phosphorylation by GSK3. However, GIPF did not induce the stabilization of β-catenin in other cell lines including the mouse epithelial cell line C57MG in which Wnt3A has been shown to have a potent effect on induces β-catenin activation. Furthermore, Dickkopf-1 (Dkk1), which is a potent inhibitor of the Wnt signaling pathway (Kuhnert, PNAS 101:266-271, 2004), did not completely inhibit β-catenin stabilization by GIPF in 293 cells (data not shown). These data suggest that GIPF may stabilize β-catenin via a pathway that is distinct from the known canonical Wnt/β-catenin pathway.

Example 18

Effect of GIPF on the Expression of β-Catenin Target Genes

Accumulation β-catenin results in its translocation to the nucleus where it associates with transcription factors of the TCF/LEF family. Due to its transactivating ability the β-catenin-transcription-factor-complex binds to DNA and activates wnt target genes. To further investigate GIPF-induced β-catenin signaling, we determined the activation of down stream target genes in HEK293 and NCI-H716 cells by quantitative PCR.

$1\times10^6$ HEK-293 cells and $2\times10^6$ NCI-H716 cells (ATCC) were seeded in 6-well plates and allowed to attach 6 hrs in complete media. Cells were then changed to 0.1% FBS Assay media and incubated overnight. The day of the assay, treatments were added to the cells in an additional 1 ml of Assay media. Cells were incubated for 8 hours at 37° C./5% CO2 with either 20 mMLiCl (Sigma), 10 ng/ml Wnt-3A (R&D Systems), 250 ng/ml GIPFt, or 250 ng/ml capped GIPF protein. A well of untreated cells, maintained in Assay media, was included as a background for gene expression. Total RNA was isolated from both cell types using RNeasy Mini kit and DNaseI kit (Qiagen), quality and concentration of the total RNA was quantified. For each sample, 4 ug of total RNA was primed at 70° C. for 3 mins with 3 ug Random Hexamers and 2 mM each dNTP. Reactions were cooled on ice for 1 min. Reaction volume was brought to 22 ul with 5×M-MLV Buffer (Promega), 25 mM MgCl$_2$, 0.1 M DTT and RNaseOut (Invitrogen). Upon addition of 400 units M-MLV Reverse Transcriptase (Promega) the reactions were incubated 10 mins at 23° C., 50 mins at 42° C., and 5 mins at 70° C. to terminate the reaction. cDNA was then diluted and treated with 1 unit of RNaseH (Invitrogen) to digest remaining RNA. OD260 nm quantified cDNA concentration. For each 10 ul quantitative SYBR Green PCR reaction, 2 ul cDNA (440 ng) was used, in conjunction with 1.25 µM of each forward and reverse primer, and 2×SYBR Green mastermix (Eurogentec). Reactions were performed in triplicate. Primers for Quantitative PCR were designed for the following human β-catenin target genes: Axin-2 (SEQ ID NOs: 70 and 71), CD44 (SEQ ID NOs 72 and 73), EphrinB2 (SEQ ID NOs: 74 and 75), c-myc (SEQ ID NOs: 76 and 77), Proglucagon (SEQ ID NOs: 78 and 79), and Cox-2 (SEQ ID NOs: 80 and 81). Human EF1 (SEQ ID NOs: 82 and 83) was used as housekeeping gene to standardize expression levels.

GIPF increased the expression of Axin-2 in HEK-293 and NCI-H716 cells, and caused the upregulation of CD44 and EphrinB2 to levels that were greater than resulting from stimulation with Wnt3A or Lithium. The expression levels of Cox-2, c-myc and proglucagon genes were not affected by GIPF (data not shown).

These data provided insight into the mechanisms involved in GIPF-induced target gene activation. Further studies are performed to elucidate the events downstream of GIPF signaling.

Example 19

In Vitro Assay for the Activity of GIFP

Eleven deletion mutants of GIPF (SEQ ID NOs: 84, 86, 88, 90, 92, 94, 96, 98, 100, 102, and 104) were subcloned into the pIntron/IgK vector, and transiently expressed in HEK293 cells. The position of each of the encoded polypeptide fragments (SEQ ID NOs: 85, 87, 89, 91, 93, 95, 97, 99, 101, 103, 105 and 178) within the full-length GIPF polypeptide is shown in FIG. 43. The mammalian expression vector pIntron/IgK was obtained by genetically modifying the pSectag vector (Invitrogen Inc., Carlsbad, Calif.) by introducing an engineered chimeric intron derived from the pCI mammalian expression vector (Promega, Madison, Wis.). pcDNA/Intron vector was digested with BGIII and NheI, and the intron sequence was cloned into pSectag, which had been digested with BgIII and NheI. The forward and reverse primers used to amplify and subclone the polynucleotide fragments correspond to SEQ ID NOs: 106-119, as indicated in the sequence listing. The forward primer of SEQ ID NO: 106 was used with the reverse primers for fragments 1-7 (primer SEQ ID NOs: 107-113; the forward primer of SEQ ID NO: 114 was used with the reverse primers for fragments 8-10 (SEQ ID NOs: 115-117).

The polypeptide fragments were transiently expressed in HEK 293 cells and the activity of the fragments in stabilizing β-catenin was assayed as described in Example 17. The polypeptide fragment of SEQ ID NO: 91 induced the greatest stabilization of β-catenin when compared to the activity displayed by the other fragments tested. This finding suggests that the furin-like cysteine-rich domain of GIPF may be essential for mediating the proliferative activity of GIPF. However, the activity of the polypeptide of SEQ ID NO: 91 was lower than that of the full-length GIPF (FIG. 44). Therefore, other portions of the GIPF protein are necessary to enable the maximum stabilization of β-catenin.

Example 20

Rapid In Vivo Assay for the Activity of Recombinant GIFP

A rapid in vivo assay was developed to test the test the bioactivity of purified GIPF.

The activity of human and mouse GIPF (GIPFwt and mGIPFt) was tested in mice that had been grouped and treated as follows:
1. Saline, injected i.v.
2. GIPFwt, injected 100 μg i.v.
3. GIPFwt, injected 50 μg i.v.
4. mGIPFt, injected 100 μg i.v.
5. mGIPFt, injected 50 μg i.v.
6. GIPFwt, boiled, injected 100 μg i.v.
7. GIPFwt, capped, injected 100 μg i.v.
8. GIPFwt, injected 100 μg s.c.

Twenty four female BALB/c mice were used in the experiments. GIPF was injected daily for three days. Animals were sacrificed on day 4. Prior to being sacrificed, 0.5 ml of blood was collected for hematological analysis, and two hours prior to being sacrificed, all animals were injected i.p with 0.4 ml of a 1 mg/ml solution of BrdU. The small intestine and colon were dissected, measured as described above, and segments of midjejenum and colon processed for histological analysis as described in previous Examples.

The results are shown in FIG. 45. The distension of the intestines from the mice that had received mouse GIPF protein, mGIPFt, was comparable to that induced by the human GIPFwt. In addition, the phenotype of the intestines of the mice that received GIPFwt via subcutaneous administration was comparable to that of the mice that had received GIPFwt via the i.v. route. As previously noted, boiling of GIPFwt does not affect its ability to cause the distension of the intestine. These findings were consistent with the measurements of length, weight, and diameter of the intestines from all animal groups (Table 8).

TABLE 8

| Animal Group | Diameter (mm) midjejenum Mean ± SD | Weight (g) Small bowel Mean ± SD | Weight (g) Large bowel Mean ± SD | Length (cm) Small bowel Mean ± SD | Length (cm) Large bowel Mean ± SD |
|---|---|---|---|---|---|
| 1 | 2.31 ± 0.15 | 0.90 ± 0.04 | 0.24 ± 0.03 | 29.5 ± 1.5 | 6.7 ± 0.3 |
| 2 | 3.64 ± 0.14* | 1.34 ± 0.10* | 0.33 ± 0.02* | 36.0 ± 1.3* | 8.5 ± 0.5* |
| 3 | 3.55 ± 0.12* | 1.32 ± 0.07* | 0.32 ± 0.03* | 36.5 ± 0.5* | 8.7 ± 0.3* |
| 4 | 3.68 ± 0.06* | 1.39 ± 0.05* | 0.35 ± 0.02* | 37.8 ± 0.8* | 8.8 ± 0.3* |
| 5 | 3.45 ± 0.09* | 1.23 ± 0.04* | 0.33 ± 0.01* | 36.5 ± 0.5* | 8.5 ± 0.5* |
| 6 | 3.07 ± 0.12* | 1.25 ± 0.06* | 0.34 ± 0.01* | 35.5 ± 0.5* | 8.3 ± 0.3* |
| 7 | 2.28 ± 0.11 | 0.88 ± 0.07 | 0.21 ± 0.03 | 31.0 ± 1.3 | 6.3 ± 0.3 |
| 8 | 3.03 ± 0.10* | 1.12 ± 0.04* | 0.28 ± 0.02* | 34.2 ± 0.8* | 7.8 ± 0.3* |

*P < 0.05 (ANOVA, groups 1-8 vs group 1)

All hematological results were within the normal range for the animals, thus indicating that GIFP did not produce any immediate adverse effects. The effect of GIPFwt and mGIPFt on villus height and crypt depth showed that GIPF significantly increased crypt depth in healthy mice after the 3-day regimen. In contrast to the effect of GIPF on increasing the villus height in the intestine of diseased animals, GIPF did not affect the height of the villi from normal, healthy animals. (FIG. 46).

These data show that the proliferative effect of the human recombinant GIPF is not the result of an ectopic effect. In addition, GIPF exhibits its biological activity whether it is administered intravenously of subcutaneously.

Example 21

In Vitro Assays for the Activity of GIPF in Isolated Crypt Cells

The effect of GIPF on signaling and proliferation of crypt epithelial cells, was assayed in isolated mouse colonic crypt cells according to the method of Fujimoteo, et al., (Fujimoto et al., Gastroenterology 117:858-865 (2002)).

Colons were dissected from mice and sterilized in a 0.04% sodium hypochlorite solution for 15 minutes. After rinsing in PBS, colons were incubated in the DTT/EDTA solution (0.5 mM DTT, 3 mM EDTA in PBS) for 90 min at room temperature. After the incubation, the tissue was washed once in PBS and 10 ml of PBS was added. The tube was shaken vigorously to liberate the crypts from the submucosa. The PBS containing the crypts was transferred to a centrifuge tube and the shaking step was repeated until the crypt yield diminished. The crypts were centrifuged gently (400 rpm for 5 min) and washed with fresh PBS. The crypts were resuspended in 20 ml of 0.3% pancreatin (Sigma) in PBS and incubated for 90 min at room temperature shaking every 10 minutes for first 30 minutes and every 30 minutes there after. At the end of the incubation, an equal volume of PBS was added and the crypts were centrifuged at 1000 rpm for 5 min and washed with EDTA/DTT solution 1-2 more times until all mucous was removed. Crypt cells were resuspended in 1× media (RPMI 1640 supplemented with 5% FCS, glutamine, $NaHCO_3$, insulin, transferrine, selenium, penicillin/streptomycin). Cell clumps were broken up using 21G then 23G needles with syringe. Cells were counted and used to assay for the stabilization of β-catenin; for determining the proliferative activity by incorporation of $^3$H-thymidine; and for testing the ability of GIPF to affect the clonogenicity of crypt cells.

A. The effect of GIPF on the activation of β-catenin in vivo was studied in crypt cells that had been isolated from Balb/c mice 6 hours after they had been injected i.v. with 100 μg of GIPFwt, as described above.

As shown in FIG. 47, GIPFwt induced significant stabilization of β-catenin in the cytosol from isolated crypt cells when compared to that seen in the crypt cells from the control mice. FIG. 47A shows the level of non-phosphorylated active β-catenin, and FIG. 47B shows the level of total β-catenin present in the cytosol. The non-phosphorylated β-catenin was recognized by a β-catenin antibody that was purchased from Upstate (Waltham, Mass., USA), while the total β-catenin level was assayed using an antibody from Abcam (Cambridge, Mass., USA), which recognizes both the phosphorylated and non-phosphorylated protein. This result indicates that GIPF-induced crypt epithelial cell proliferation in mice may be mediated β-catenin signaling.

B. The effect of GIPFwt on the proliferation of isolated crypt cells was assayed in vitro for the incorporation of $^3$H-thymidine. The results showed that GIPFwt protein increased the proliferation of isolated crypt cells in a dose-dependent manner.

Therefore, the GIPF induces proliferation of isolated crypt cells by stabilizing β-catenin, and the isolated intestinal cells may be used to elucidate the signaling pathways that underlie the proliferative effect of GIPF.

C. The clonogenic assay described by Whitehead et al. (Whitehead et al. Gastroenterology, 117:858-865 (1999)) is performed to study the ability of GIPF in controlling the proliferation and/or differentiation of the intestinal mucosa. In brief, an underlay containing an equal mixture of 1% agar and 2×RPMI medium plus 10% FBS is added to 35 mm dishes. Isolated colonic crypt cells are added to top layer media (equal parts of 0.8% agarose and 2×RPMI medium plus 10% FBS) at 50,000 cells per ml and 2 ml of cell suspension is aliquoted into each well. The plates are incubated in the presence of GIPF at 50, 100, and 200 ng/ml for 3-4 weeks at 37° C. After the incubation, the plates are examined and the number of colonies are counted. Colonies are defined as aggregates of more than 40 cells.

GIPF stimulates colony formation. The clonogenic assay is used to test the proliferative activity of GIPF and GIPF analogs in vitro.

Example 22

Effect of GIPF on TNBS-Induced Colitis

The hapten agent 2,4,6-trinitrobenzenesulfonic acid (TNBS) induces a chronic colitis that is characterized by severe, transmural inflammation associated with diarrhea, rectal prolapse, and weight loss. These clinical and histopathological features indicate that TNBS-induced colitis mimics important characteristics of human Crohn's disease (Neurath et al., J Exp Med 182:1281-1290 (1995)).

The therapeutic effect of GIPF was tested in mice with TNBS-induced colitis. Intestinal inflammation was induced in 6-8 week-old female BALBc mice (group 2) by a single rectal administration of 1 mg TNBS, as described by Neurath et al, supra). A control animal group (Group 1) received rectal administration of vehicle alone (45% ethanol). The therapeutic effect of hGIPF was tested by administering subcutaneous daily doses of 100 μg (group 3) or 50 μg (group 4) hGIPF (4 mg/kg or 2 mg/kg) to animals that had received TNBS for 3 days. The mice were sacrificed after 7 days, and the induction of colitis by TNBS was assessed. hGIPF significantly reduced the loss of body weight induced by TNBS in the animals of group 2 (FIG. 48). hGIPF also reduced the severe diarrhea, ulceration, bleeding and atrophy of the colon that the TNBS-treated animals of groups 2 suffered (data not shown).

Histologic changes were evaluated in H&E stained paraffin-embedded sections of the colon from the control and TNBS groups. hGIPF reduced the TNBS-induced transmural infiltration and mucosal crypt structural disintegration in the mouse colon (FIG. 49). The graph in FIG. 49 represents the effect of hGIPF determined by the histological grading of colonic colitis as follows:

| Histological (microscopic) grading of colonic colitis | |
|---|---|
| SCORE | CRITERIA |
| 0 | Normal |
| 1 | Low level of (occasional) leukocyte infiltration, no structural changes |
| 2 | Moderate leukocyte infiltration in lamina pripria, surface epithelial lesion, no ulceration |
| 3 | High leukocyte infiltration with inflammatory cells extending into the submucosa, mucosal erosion, focal ulceration, moderate thickening of the colon wall |
| 4 | Very high leukocyte infiltration with transmural inflammation, extensive mucosal damage, loss of goblet cells, high vascular density, thickening of the colon wall, ulceration |

In addition, hGIPF diminished the increase in TNBS-induced myeloperoxidase, which is a hallmark of neutrophil infiltration in the mouse colon. GIPF treatment significantly reduces the TNBS-induced diarrhea, inflammation and thickening of the colon wall, and loss of goblet cells, relative to the animals that are not treated with GIPF. Therefore, GIPF may potentially be used as a therapeutic to treat patients with Crohns disease.

Example 23

Therapeutic Effect of GIPF on Chronic Dextran Sulfate Sodium-Induced Colitis in Mice The efficacy of recombinant human GIPF (GIPFwt) in treating colitis was tested in a mouse model of chronic dextran sulfate sodium (DSS)-induced colitis (L'Heureux and Brubaker J Pharmacol Exp Ther 306:347-354 (2003); Kriegelstein et al., Clin Invest 110:1773-1782 (2002); Siegmund et al., J Pharmacol Exp Ther 296:99-105 (2001)).

Six to eight-week old female BALB/c mice (Charles River Laboratories, Wilmington, Mass., USA) were housed in ventilated cages and acclimated for one week to a 12 hour light: dark cycle. Mice were fed 4% DSS (v/w) in drinking water from Day 0 to 7 to induce colitis. From Day 7 to Day 21, mice were given water without DSS to induce the $1^{st}$ remission phase. From Day 21 to Day 28, mice were again given 4% DSS to induce the $1^{st}$ relapse phase. From Day 28 to Day 35, mice were again given water without DSS to induce the $2^{nd}$ remission phase. On Day 35, mice were randomized into various experimental groups and GIPF therapy was started on Day 35 and continued to Day 42. Mice were monitored daily from Day 35 to Day 42 for signs of disease activity. On Day 42, the experiment was terminated, the mice were sacrificed and intestinal tissue was harvested for analysis.

GIPF significantly reduced DSS-induced colitis in mice in a dose-dependent fashion as reflected by a significant decrease in the inflammatory bowel disease activity index (IBDAI) (FIG. 50; *$P<0.05$ (ANOVA, DSS/Saline vs. DSS/hGIPF groups); #$P<0.05$ (ANOVA, DSS/Saline vs. DSS/KGF); **$P<0.05$ (ANOVA, DSS/Saline vs. DSS/GLP-2)). The definition of IBDAI is given in Example 14. H&E stained sections of the small intestine and colon showed that hGIPF prevented the DSS-induced damage to the intestinal mucosa of the mice, and reversed the DSS-induced shortening of the villus height and crypt depth (FIG. 51). GIPF also superseded the suppressive effect of DSS on the proliferation of crypt cells in the small intestine (FIG. 52; *$P<0.05$ (ANOVA, DSS/Saline vs. Water/Saline); #$P<0.05$ (ANOVA, DSS/hGIPF vs. DSS/Saline) **$P<0.05$ (ANOVA, DSS/KGF vs. DSS/Saline); ##$P<0.05$ (ANOVA, DSS/GLP-2 vs. DSS/Saline)). The crypt proliferative index is defined in Example 14.

In summary, therapeutic treatment of GIPF significantly reduces chronic DSS-induced colitis in mice, indicating that GIPF may be a potentially useful therapy to treat human inflammatory bowel disease.

Example 24

Reduction of 5-FU-Induced Toxicity by hGIPF

The efficacy of hGIPF in reducing the gastrointestinal toxicity of 5-FU was evaluated in normal BDF-1 mice.

Mice were divided into the following groups:
1) Vehicle injected with saline treatment
2) 5-FU injected with saline treatment
3) 5-FU injected with GIPF treatment Female BDF-1 mice, at age of 11-13-week, were given daily subcutaneous injections of either saline or 100 μg per dose hGIPF beginning at Day −3. From Day 0 to Day 4, each mouse was injected intraperitoneally with a dose of 50 mg/kg of 5FU for 4 consecutive days. Mice were monitored for body weight, occurrence of diarrhea, and mortality on a daily basis.

GIPF treatment significantly reduced 5-FU-induced gastrointestinal toxicity, including reducing maximum body weight loss, diarrhea score, and mortality (Table 9), thus indicating that GIPF is effective in reducing chemotherapy-induced gastrointestinal toxicity in mice.

TABLE 9

| | | Toxicity | | | |
| --- | --- | --- | --- | --- | --- |
| 5-FU | TREATMENT | Maximum weight loss (%) | Diarrhea score | Mortality (%) | Survival Time (day) |
| YES | NO | 33.1 ± 3.6 | 2.8 ± 0.5 | 92 | 8.5 ± 1.2 |
| YES | hGIPF | 12.5 ± 6.9* | 0.9 ± 0.6* | 8.3 | 10.0 ± 0.0* |
| YES | KGF | 16.8 ± 7.9* | 1.7 ± 0.8* | 25 | 9.0 ± 1.0 |
| YES | GLP-2 | 17.4 ± 8.3* | 1.9 ± 0.8 | 42 | 8.4 ± 1.1 |

*$P < 0.05$ (ANOVA, 5-FU/hGIPF, 5-FU/KGF or 5-FU/GLP-2 vs. 5_FU/saline

Example 25

In Vivo GIPF Activity in a Non-Human Primate

A repeat-dose study of the activity of GIPF was performed in Cynomolgus monkeys to determine the activity of GIPF in a non-human primate.

Nine female non-naïve, monkeys were screened for health by SNBL USA (Everett, Wash., USA) staff veterinarian or a veterinary technician and underwent hematology and serum chemistry screening. Of the nine female animals confirmed healthy, 8 were selected and assigned to the study groups. The animals, which were previously quarantined, were acclimated to the study room at the SNBL USA facility for a minimum of 14 days prior to initiation of the study.

Protocol: Eight females were assigned to four treatment groups as outlined in the table below and dosed via intravenous bolus injection of GIPF protein once daily for three days. On the fourth day, all animals were administered one intravenous bolus injection of bromodeoxy uridine (BrdU) (50 mg/kg) approximately 4 hours prior to necropsy. Select tissues were collected at necropsy.

Study Design

| Group | Dose Levels (mg/kg) | Concentration (mg/mL) | Dose volume (mL/kg) | Animal number |
|---|---|---|---|---|
| 1 | 0 mg/kg (control) | 0 | 3.3 mL/kg | 2 |
| 2 | 0.1 mg/kg | 1.5 mg/mL | 0.067 mL/kg | 2 |
| 3 | 1.0 mg/kg | 1.5 mg/mL | 0.67 mL/kg | 2 |
| 4 | 5.0 mg/kg | 1.5 mg/mL | 3.3 mL/kg | 2 |

Observations and Examination: Clinical observations were made during acclimation and throughout the study as follows. Mortality and stool checks were performed once daily in the morning and clinical observations for general health and appearance were performed once daily in the afternoon beginning at the start of acclimation to the end of in-life. Additional clinical observations were performed, if necessary and recorded. A staff veterinarian or veterinary technician evaluated each animal if clinical observations indicate a declining condition and the Study Director were notified.

Blood sample collection: Blood was collected once during acclimation and once on the day of necropsy before administration of BrdU for hematology and serum chemistry.

Gross pathology examination: At necropsy, the external surfaces of the body, all orifices, and the cranial, thoracic, and abdominal cavities and their contents were examined. Organ Weight and histopathology examination were performed macroscopically, collected and preserved in 10% neutral buffered formalin for histopathologic examination. Examined tissues are listed below.

| Brain | Large Intestine[a] | Small Intestine[a] |
|---|---|---|
| brain stem | cecum | jejunum |
| cerebellum | colon | duodenum |
| cerebrum | rectum | ileum |
| Spleen | Liver | Tongue |

Tissue proliferation assay by using BrdU IHC: paraffin-embedded sections were prepared for BrdU assay.

Result: Gross pathological examination at necropsy found no obvious changes in examined organs suggesting no acute toxicity of hGIPF in this treatment regimen. In addition, hematology and serum chemistry on blood samples collected before and after hGIPF treatment demonstrated no changes in blood cell components as well as tested serum biochemistry parameters.

There appears to be a dose-related increase in the length of the small intestine. Average intestinal length (in cm) for groups 1, 2, 3, and 4 was 120.65, 122.555, 133.350, and 142.875 respectively. In addition, as summarized in the table below (Table 10), microscopic evaluation of histology of individual tissues demonstrated crypt hyperplasia of duodenum, jejunum and ileum in all GIPF treated groups. Hyperplasia of crypts was also observed in cecum, colon and rectum in a dose related manner. This result suggests that hGIPF has a proliferative effect on crypt epithelial cells of monkey intestine that is consistent with that observed in mouse and rat.

To confirm the proliferative effect of hGIPF, immunohistochemistry was performed to analyze the incorporation of BrdU in the small and large intestine. hGIPF increases BrdU positive proliferation index in both small intestine and colon.

These finding show that hGIPF increases the proliferation of the crypt epithelium in a non-human primate.

Individual Histopathology Findings

Grade

_: No abnormal changes

±: Very slight

+: slight

2+: Moderate

3+: Marked

TABLE 10

Individual Histopathology Findings in Female Cynomolgus Monkeys

| Tissue | Findings | Group 1 #1 | Group 1 #2 | Group 2 #1 | Group 2 #2 | Group 3 #1 | Group 3 #2 | Group 4 #1 | Group 4 #2 |
|---|---|---|---|---|---|---|---|---|---|
| Duodenum | Crypt hyperplasia | − | − | − | ± | ± | ± | + | 2+ |
| Jejunum | Crypt hyperplasia | − | − | ± | ± | ± | ± | ± | + |
| Ileum | Crypt hyperplasia | − | − | − | ± | + | ± | + | + |
| Cecum | Crypt hyperplasia, | − | − | − | − | ± | ± | + | + |
|  | increased gland length | − | − | − | − | − | − | ± | + |
| Colon | Crypt hyperplasia, | − | − | − | − | ± | ± | ± | + |
|  | increased gland length | − | − | − | − | − | − | − | ± |
| Rectum | Crypt hyperplasia | − | − | − | − | ± | + | ± | + |
| Liver | — | − | − | − | − | − | − | − | − |
| Spleen | — | − | − | − | − | − | − | − | − |
| Cerebrum | — | − | − | − | − | − | − | − | − |
| Cerebellum | — | − | − | − | − | − | − | − | − |
| Brain stem | — | − | − | − | − | − | − | − | − |

Example 26

Adsorption Distribution Metabolism Excretion (ADME) Study Using Radioactively Labeled $^{125}$I-hGIPF Protein Study aim: To determine the plasma pharmacokinetics and tissue distribution of [$^{125}$I]-hGIPF in mice.

Protein labeling: hGIPF protein was labeled with [$^{125}$I] by IODO-GEN labeling method (Amersham). The initial specific activity upon labeling was 35 uCi/ug (1020 Ci/mmol). Labeled protein was further purified prior to injection into mice.

Animals: male CD-1® [Crl:CD-1® (ICR) BR mice were acclimated for 7 days prior to the injection and housed individually in clean suspended wire-mesh cages. The cages were elevated above cage-board or other suitable material, changed at least three times each week. Each mouse was given a 1.67 mg/kg dose of hGIPF that contained 3 µCi of $^{125}$I-hGIPF protein. After receiving the radiolabeled dose, animals that were scheduled for collection of urine and feces were housed individually in metabolism units.

Study Design:

| Group | Samples Collected | Dosage Level | Dosage Volume | Times of Euthanasia | Number of Animals per Time Point | Total Number of Animals |
|---|---|---|---|---|---|---|
| 1 | Blood and Tissues | 1.67 mg/kg | 10 mL/kg | 5, and 30 min and 1, 3, 6, and 24 hr post-dosing | 3 | 18 |
| 2 | Urine, Feces, Tissues and Carcass | 1.67 mg/kg | 10 mL/kg | 24 hr post-dosing | 3 | 3 |

All animals received for this study were treated with sodium iodide to block uptake by the thyroid of free iodide derived from the labeled test article. An oral (gavage) administration of 0.1 mL of 1% NaI solution was given at approximately 48, 24 and 1 hours before dosing with the radiolabeled protein. Each animal received a single dose of [$^{125}$I]-hGIPF that was administered via an intravenous injection. The animals were divided into two groups and analyzed as outlined in the Study Design above. At the indicated times for euthanasia, blood samples were collected, and the cellular fraction and plasma were separated for analysis. Tissue samples of liver, kidney, lung, tongue, spleen, brain, esophagus, stomach, small intestine, large intestine, and large intestine including its contents were collected, and the incorporation of [$^{125}$I]-hGIPF in the tissues was determined.

Analyses for the incorporation of $^{125}$I-hGIPF was performed by gamma counting in a DPC GAMMA-C12 multi-crystal gamma counter according to WIL Standard Operating Procedures. The results of gamma counting were corrected for isotopic half-life. Calculations of the amounts of radioactivity in various materials generated in the study were performed using programs of the WIL Toxicology Data Management System or spreadsheets according to WIL Standard Operating Procedures. Generally, only descriptive statistics (e.g., totals, arithmetic means, standard deviations, standard errors, coefficients of variation, percentages) were used. Where possible, standard pharmacokinetic parameters (e.g., $C_{max}$, $t_{max}$, AUC (Area Under the Curve), $T_{1/2}$ (half-life)) were calculated using standard pharmacokinetic equations.

Results: The data showing the concentration and the kinetics of [$^{125}$I]-hGIPF in mouse plasma, red blood cells, liver, kidney, lung, heart, brain, spleen, esophagus, stomach, small intestine, and large intestine are shown in Tables 11-14.

TABLE 11

CONCENTRATION AND KINETICS OF [$^{125}$I]-hGIPF EQUIVALENTS IN MOUSE PLASMA AND RED BLOOD CELLS FOLLOWING INTRAVENOUS ADMINISTRATION AT 1.67 MG/KG

| Time (hr) | Plasma (ng/g) (Mean ± SD) | Red Blood Cells (ng/g) (Mean ± SD) |
|---|---|---|
| 0.083 | 11145 (113) | 2745 |
| 0.5 | 3894 (485) | 2121 |
| 1 | 2506 (490) | 1658 |
| 3 | 1347 (68) | 971 |
| 6 | 476 (204) | 295 |
| 24 | 60 (7) | 23 |
| $C_{max}$ (ng/g) | 11145 | 2745 |
| $t_{max}$ (h) | 0.083 | 0.083 |
| $AUC_{0-24}$ (ng·h/g) | 16607 | 9458 |
| Terminal Phase Kinetics (Linear Regression of Log Concentration vs. Time from 3-24 hr) | | |
| Slope (b) | −0.05939 | −0.07225 |
| Y-Intercept (ng) | 1517.75 | 1161.79 |
| Coefficient of Determination ($r^2$) | 0.960 | 0.967 |
| Elimination Rate Constant ($h^{-1}$) | 0.1367 | 0.1664 |
| Half-life (h) | 5 | 4 |

N = 3 except 24 h, N = 6.

TABLE 12

CONCENTRATION AND KINETICS OF [$^{125}$I]-hGIPF EQUIVALENTS IN MOUSE LIVER, KIDNEY, LUNG, HEART, BRAIN, AND SPLEEN FOLLOWING INTRAVENOUS ADMINISTRATION AT 1.67 MG/KG

| | Liver (ng/g) (Mean ± SD) | Kidney (ng/g) (Mean ± SD) | Lungs (ng/g) (Mean ± SD) | Tongue (ng/g) (Mean ± SD) | Brain (ng/g) (Mean ± SD) | Spleen (ng/g) (Mean ± SD) |
|---|---|---|---|---|---|---|
| 0.083 hr | 9104 (959) | 24581 (5032) | 3332 (462) | 1157 (88) | 141 (25) | 1956 (354) |
| 0.5 hr | 4982 (1319) | 21283 (4731) | 1997 (375) | 1124 (202) | 105 (28) | 1905 (663) |
| 1 hr | 3635 (413) | 17039 (1543) | 1575 (375) | 1044 (292) | 95 (18) | 1380 (106) |
| 3 hr | 2706 (185) | 13445 (1084) | 633 (450) | 588 (32) | 51 (7) | 840 (74) |
| 6 hr | 1757 (213) | 8933 (800) | 337 (106) | 227 (91) | 17 (9) | 457 (193) |
| 24 hr | 875 (75) | 4707 (485) | 63 (13) | 35 (7) | 5 (3) | 157 (49) |
| $C_{max}$ (ng/g) | 9104 | 24581 | 3332 | 1157 | 141 | 1955.54 |
| $t_{max}$ (h) | 0.083 | 0.083 | 0.083 | 0.083 | 0.083 | 0.083 |
| $AUC_{0-24}$ (ng·h/g) | 42191 | 206968 | 9404 | 6282 | 554 | 11400 |

TABLE 12-continued

CONCENTRATION AND KINETICS OF [$^{125}$I]-hGIPF EQUIVALENTS IN MOUSE LIVER, KIDNEY, LUNG, HEART, BRAIN, AND SPLEEN FOLLOWING INTRAVENOUS ADMINISTRATION AT 1.67 MG/KG

|  | Liver (ng/g) (Mean ± SD) | Kidney (ng/g) (Mean ± SD) | Lungs (ng/g) (Mean ± SD) | Tongue (ng/g) (Mean ± SD) | Brain (ng/g) (Mean ± SD) | Spleen (ng/g) (Mean ± SD) |
|---|---|---|---|---|---|---|
| Terminal Phase Kinetics (Linear Regression of log Concentration vs. Time from 3-24 hr) | | | | | | |
| Slope (b) | −0.02106 | −0.01953 | −0.04512 | −0.05344 | −0.04209 | −0.03164 |
| Y-Intercept (ng) | 2742.03 | 13559.24 | 746.08 | 649.87 | 47.18 | 873.39 |
| Coefficient of Determination ($r^2$) | 0.936 | 0.932 | 0.982 | 0.958 | 0.883 | 0.947 |
| Elimination Rate Constant ($h^{-1}$) | 0.0485 | 0.0450 | 0.1039 | 0.1230 | 0.0969 | 0.0728 |
| Half-life (h) | 14 | 15 | 7 | 6 | 7 | 10 |

N = 3 except 24 h, N = 6.

TABLES 13 A and B

CONCENTRATION AND KINETICS OF [$^{125}$I]-hGIPF EQUIVALENTS IN MOUSE ESOPHAGUS, STOMACH, SMALL INTESTINE, AND LARGE INTESTINE FOLLOWING INTRAVENOUS ADMINISTRATION AT 1.67 MG/KG

|  | Esophagus (ng/g) (Mean ± SD) | Stomach (ng/g) (Mean ± SD) | Small Intestine (ng/g) (Mean ± SD) | Large Intestine (ng/g) (Mean ± SD) |
|---|---|---|---|---|
| A | | | | |
| 0.083 hr | 1560 (321) | 1960 (166) | 1117 (135) | 1016 (150) |
| 0.5 hr | 1743 (178) | 2855 (1140) | 1191 (423) | 910 (135) |
| 1 hr | 1666 (743) | 5545 (3546) | 1053 (369) | 1006 (189) |
| 3 hr | 1199 (330) | 3678 (2047) | 664 (28) | 694 (141) |
| 6 hr | 350 (63) | 1021 (475) | 222 (110) | 383 (175) |
| 24 hr | 48 (43) | 106 (40) | 32 (6) | 74 (13) |
| $C_{max}$ (ng/g) | 1743 | 5545 | 1191 | 1016 |
| $t_{max}$ (h) | 0.5 | 1 | 0.5 | 0.083 |
| $AUC_{0-24}$ (ng-h/g) | 10372 | 29604 | 6421 | 8344 |
| B Terminal Phase Kinetics (Linear Regression of log Concentration vs. Time from 3-24 hr) | | | | |
| Slope (b) | −0.06022 | −0.06683 | −0.05745 | −0.04408 |
| Y-Intercept (ng) | 1247.25 | 3997.67 | 715.76 | 822.73 |
| Coefficient of Determination ($r^2$) | 0.936 | 0.947 | 0.948 | 0.984 |
| Elimination Rate Constant ($h^{-1}$) | 0.1387 | 0.1539 | 0.1323 | 0.1015 |
| Half-life (h) | 5 | 5 | 5 | 7 |

**N = 3 except 24 h, N = 6.

TABLES 14A AND B

RECOVERY OF hGIPF EQUIVALENTS FROM MICE 24 HOURS AFTER IV ADMINISTRATION AT 1.67 MG/KG

A

| Anim. No. | % GIPF/Tissues | % GIPF/Intestinal Contents | % GIPF/Urine | % GIPF/Feces | % GIPF/Carcass | Total Recovery† |
|---|---|---|---|---|---|---|
| 1 | 7.43 | 0.13 | 85.70 | 3.48 | 1.87 | 98.6 |
| 2 | 7.61 | 0.13 | 76.70 | 3.12 | 1.82 | 89.4 |
| 3 | 7.03 | 0.32 | 87.47 | 3.53 | 1.76 | 100.1 |
| Mean: | 7.35 | 0.19 | 83.29 | 3.38 | 1.82 | 96.0 |
| SD: | 0.30 | 0.11 | 5.77 | 0.23 | 0.06 | 5.81 |

TABLES 14A AND B-continued

RECOVERY OF hGIPF EQUIVALENTS FROM MICE 24 HOURS AFTER IV ADMINISTRATION AT 1.67 MG/KG

B
As expected, the earliest $T_{max}$ and the greatest $C_{max}$ were observed in highly perfused tissues i.e. liver, kidney, spleen and lung, and the longest half life was seen in kidney and liver (Table 11).

| Tissues | | | | | | | | | | |
|---|---|---|---|---|---|---|---|---|---|---|
| Liver | Small Int. | Colon | Brain | Spleen | Lung | Kidney | Stomach | Esoph. | Tongue | Sum |
| 2.39 | 0.07 | 0.06 | 0.01 | 0.02 | 0.02 | 4.83 | 0.03 | 0.01 | 0.01 | 7.43 |
| 2.13 | 0.10 | 0.06 | 0.00 | 0.02 | 0.02 | 5.17 | 0.10 | 0.00 | 0.01 | 7.61 |
| 2.64 | 0.07 | 0.04 | 0.01 | 0.02 | 0.02 | 4.21 | 0.03 | 0.00 | 0.01 | 7.03 |

†Sum of tissues, GI contents, urine including cage rinse, feces, and carcass

The tissues of the gastrointestinal tract including esophagus, stomach and small intestine each displayed a protracted Tmax (Table 12). Table 13 A shows the percent recovery of radiolabeled GIPF in tissues from various organs and in the intestinal contents, urine, feces and carcass of animals 24 hours after administration of radiolabeled hGIPF. The recovery of hGIPF from individual organ tissues is given in Table 13B. The data show that the distribution of radiolabeled hGIPF is unusually high for organs of the gastrointestinal tract following administration via the intravenous route, thus suggesting that hGIPF may have a high affinity for gastrointestinal tissues.

Example 27

Irradiation-Induced Mucositis

Evaluation of Optimal Treatment Regimen

The objective of this study was to define a therapeutic protocol that would provide the maximum prophylactic effect of GIPF against irradiation-induced mucositis.

Adult male BDF-1 mice 10~12 weeks of age at the time of use. The animals were housed for 1 week on a 12 hr light/dark cycle and were allowed food and water ad libitum throughout. Animals were randomly divided into 6 groups of 5 animals each (total 30 mice) and were treated as follows:
1. Untreated, unirradiated control.
2. 4 mg/kg hGIPF iv at 3, 2, 1 day prior to 13 Gy X-ray exposure (whole body irradiation).
3. 4 mg/kg hGIPF iv at 4, 3, 2 days prior to 13 Gy X-ray exposure (whole body irradiation).
4. 4 mg/kg hGIPF iv 5, 4, 3 days prior to 13 Gy X-ray exposure (whole body irradiation).
5. 4 mg/kg hGIPF iv 6, 5, 4 days prior to 13 Gy X-ray exposure (whole body irradiation).
6. saline iv 72, 48, 24 hours prior to 13 Gy X-ray exposure (whole body irradiation).

Animals were exposed to whole body irradiation with single dose of 13 Gy X-ray delivered at 2.7 Gy/min. Animals were inspected daily after irradiation.

4 days after irradiation the animals were sacrificed. Two hours prior to sacrifice, animals were injected with 4 mg BrdU in a volume of 0.4 ml. Upon dissection, the length and weight of small and large intestine were measured and ~1 cm of tissue segments of the small intestine (mid-jejunum), colon (transverse colon), tongue, esophagus and stomach were fixed in 10% formaline.

Cross sections of the small intestine were analyzed for BrdU uptake. The number of surviving crypts per section were scored and the average per group determined. Only crypts containing 10 or more strongly H&E stained cells (excluding Paneth cells) and only intact sections devoid of Peyers patches were scored.

The average crypt width (measured at its widest point) was also measured in order to correct for scoring errors due to crypt size difference. The correction is applied thus:

$$\text{Corrected number of crypts/cross section} = \frac{\text{Mean crypt width in untreated control}}{\text{Mean crypt width in treated animal}} \times \text{Mean number of surviving crypts in treatment group}$$

Results: The effect of hGIPF on the survival of crypts following exposure to radiation is shown in FIG. 53. The data show that hGIPF significantly reduced radiation-induced intestinal mucositis when hGIPF was administered to the animals at 24 hr or 48 hr prior to the total body irradiation (Table 15).

These findings confirm that hGIPF may be used as a prophylactic to offset the deleterious effects of radiation-induced intestinal mucositis, and that dosing at 24 hours prior to total body irradiation provides the greatest protection to the intestinal crypts.

TABLE 15

| | hGIPF therapy | | |
|---|---|---|---|
| Irradiation dose (Gy) | GIPF (mg/kg/day) | Treatment schedule | hGIPF protection factor (mean ± SD) |
| 13 | None | None | 1.0 ± 0.5 |
| 13 | 4 | Day −3 to −1 | 15.8 ± 6.2* |
| 13 | 4 | Day −4 to −2 | 9.4 ± 6.8* |
| 13 | 4 | Day −5 to −3 | 4.8 ± 3.3 |
| 13 | 4 | Day −6 to −4 | 5.3 ± 4.4 |

*$P < 0.05$ (ANOVA, 13 Gy/hGIPF vs. 13 Gy/Saline)

Example 28

Cell Lineage-Dependent Proliferation Assay in Mouse Small Intestine

The effect of hGIPF on intestinal crypts was studied to determine whether the effect of hGIPF prior to the onset of morphological changes occurs by affecting either of both the stem cells and the transitional proliferating cells of the crypt.

Animals were randomly divided into the following groups:

1. PBS (1 mouse per group): 1, 3, 6, 12, 24 or 48 hr after injection
2. hGIPF (2 mice per group, 100 ug single injection): 1, 3, 6, 12, 24 or 48 hr after injection Each animal was injected with BrdU (4 mg/kg) 2 hour prior to sacrifice.

Crypt depth, crypt proliferation index, and cell positional proliferation analysis were performed in mid jejunal sections of small intestine. The crypt proliferative index was measured by BrdU immunohistochemistry at the indicated times (3, 6, 12, 24 and 48 hours) after single injection of hGIPF (100 ug). 40 crypts from 2 mice were analyzed for BrdU incorporation and the results are given as the mean±SD (*P<0.01, ANOVA).

Results: As shown in Table 16, hGIPF increased proliferation of small intestinal crypt cells as early as 3 hours and the proliferation reached a peak at 24 hours following hGIPF treatment. hGIPF-induced crypt proliferation was reversed within 48 hours. In addition, positional analysis of the BrdU positive cells (Potten et al., Int J Exp Path 78:219-243 (1997)) demonstrated a significant increase in the proliferation of crypt cells at position 3~5 (from the bottom of crypts where stem cells are located) as well as upper part of the crypts.

These data suggest that hGIPF may affect both stem cells and the dividing transit cell population.

TABLE 16

| TIME (hr) | % BrdU positive cells PBS control group | % BrdU positive cells hGIPF group |
|---|---|---|
| 3 | 38.0 ± 12.47 | 47.7 ± 8.38 |
| 6 | 36.45 ± 8.33 | 49.75 ± 11.3 |
| 12 | 39.16 ± 8.57 | 51.24 ± 9.86 |
| 24 | 36.55 ± 9.62 | 74.97 ± 9.0 |
| 48 | 33.0 ± 5.32 | 19.5 ± 6.5 |

Example 29

Effect of hGIPF on the Differentiation and Migration Crypt Cells

The number of Goblet and Paneth cells was scored following treatment of mice with hGIPF to determine whether hGIPF affects the population and distribution of these cell types in the small intestine.

Alcian blue staining was performed to visualize Goblet cells in mid jejunal sections from PBS and hGIPF-treated mice (n=3). Animals were given daily injections of hGIPF (100 ug) or PBS for 3 or 7 days. To visualize Paneth cells, immunohistochemistry (IHC) was performed on the mid jejunal sections of the same animals using anti-lysozyme antibody.

Results: Immunohistochemical analysis and Alcian blue staining of small intestine demonstrated no significant changes in Paneth cells and Goblet cells numbers in the small intestine of hGIPF treated mice. hGIPF did not affect the maturation and migration of differentiated cells along the crypt/villus axis.

Example 30

Transgenic Chimaeric Mice that Express hGIPF in Intestinal Epithelial Cells

1. Preparation of Long Fragment of Mouse Villin Gene Promoter (FIG. 54A)

Villin, an actin bundling protein found in the apical brush border of absorptive tissues, is one of the first structural genes to be transcriptionally activated in the embryonic intestinal endoderm. In the adult, villin is broadly expressed in every cell of the intestinal epithelium on both the vertical axis (crypt to villus tip) and the horizontal axis (duodenum through colon) of the intestine. Madison et al. documented that a 12.4 kb region of the mouse villin gene drives high level expression of two different reporter genes (LacZ and Cre recombinase) within the entire intestinal epithelium of transgenic mice (*J. Biol. Chem.* 277, p 33275-33283, 2002). To generate transgenic chimaeric mice expressing human GIPF in intestinal epithelial cells we constructed a expression vector in which the GIPF cDNA is linked to this transcriptional regulatory sequences directing its expression in intestinal epithelial cells.

Nucleotide sequence information of upstream region of mouse villin gene was obtained from public database (ensembl). Mouse BAC (RP23-278N11; GenBank Accession Number: AC098570) DNA was digested with EcoRI and BamHI (Roche) and subjected to 0.8% agarose gel electrophoresis to isolate an approximately 11 kb fragment. Following the digestion of pBluescriptIISK(-) (STRATAGENE) with EcoRI and BamHI (Roche), the vector fragment was isolated by 0.8% agarose gel electrophoresis and treated with calf intestine alkaline phosphatase to dephosphorylate its both ends. The above approximately 11 kb DNA fragment was ligated to the dephosphorylated vector fragment and the ligation mixture was transfected to XL10-Gold Ultracompetenet Cells (STRATAGENE). DNA samples prepared from the resultant transformants was subjected to PCR amplification using the primer set described below (SEQ ID NO: 120 and 121). Sequence analysis of the amplified fragment showed the inclusion of an approximately 11.2 kb of mouse villin gene promoter fragment (pPvil 11.2). The pPvil 11.2 was digested with the restriction enzymes, ClaI and BamHI, and the reaction mixture was subjected to 0.8% agarose gel electrophoresis to isolate approximately 11.2 kb fragment.

```
PviIEIBI-FW1
GATCAGCAGCTGGAACAAACACAG      (SEQ ID NO: 120)

PviIEIBI-RV1
TGCACAATCAGTCAATGAACAGAGC     (SEQ ID NO: 121)
```

(2) Preparation of Short Fragment of Mouse Villin Gene Promoter (FIG. 54B)

Based on the nucleotide sequence of mouse villin gene upstream region obtained from the public database (ensembl), two synthetic DNAs were synthesized (SEQ ID NO: 122 and 123).

```
                              (SEQ ID NO: 122)
PviIBI-FW
GGCGGATCCCTGAGTTGGAGGCCAGTTTGG (SEQ ID NO: 123)
PviIBI-NcoIXbaIRV
GCTCTAGACCATGGTGGACGAGCCTAGAGGAGAAGGCAT
```

KOD-puls (TOYOBO) was used for the PCR reaction. The PCR reaction mixture contained 10 pmole of each primer and mouse BAC (RP23-278N11; GenBank Accession Number: AC098570) DNA as a template. This PCR amplification was performed using an initial denaturing incubation at 94° C. for two minutes. Then 30 cycles of denaturation, annealing and amplification were performed by incubation at 94° C. for 15 sec and 68° C. for two minutes. A PCR product (approximately 1.9 kb) was purified by 0.8% agarose gel electrophoresis and QIAquick Gel Extraction Kit (QIAGEN). Following the digestion of an isolated PCR product with BamHI and XbaI, the digested fragment was purified by 0.8% agarose gel electrophoresis and QIA quick Gel Extraction Kit (QIAGEN). The purified fragment was ligated to pBluescriptIISK(−) (STRATAGENE) that was digested with XhoI and XbaI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was digested with NcoI. Following the treatment of digested fragment with Klenow fragment (TAKARA BIO) for blunting its both ends, it was further digested with XbaI and purified by 0.8% agarose gel electrophoresis. The resultant fragment was treated with *E. Coli* C75 alkaline phosphatase to dephosphorylate its both ends.

(3) Preparation of GIPF Fragment (FIG. 54C)

```
                                              (SEQ ID NO: 124)
Hy01XhISphIFW
CCGCTCGAGGCATGCGGCTTGGGCTGTGTGTGGTGGCCCTG (SEQ ID NO: 125)
Hy01BgXb-RV
GCTCTAGAAGATCTCTAGGCAGGCCCTGCAGATGTGAGTGGCCC
```

KOD-puls-(TOYOBO) was used for the PCR reaction. The PCR reaction mixture contained 10 pmole of each primer (SEQ ID NO: 124 and 125) and the GIPF cDNA as a template. This PCR amplification was performed using an initial denaturing incubation at 94° C. for three minutes. Then 30 cycles of denaturation, annealing and amplification were performed by incubation at 94° C. for 15 sec and 68° C. for two minutes. A PCR product (approximately 800 bp) was purified by electrophoresis using 0.8% agar and QIAquick Gel Extraction Kit (QIAGEN). Following the digestion of isolated PCR product with XhoI and XbaI, it was ligated to pBluescriptIISK(−) that was digested with XhoI and XbaI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was digested with SphI. Following the treatment of digested fragment with Blunting high (TOYOBO) for blunting its both ends, it was further digested with XbaI and purified by 0.8% agarose gel electrophoresis.

(4) Construction of pPvil 2-01 (FIG. 54D)

The GIPF fragment prepared in (3) was ligated to pPvil2 prepared in (2), and the ligation mixture was transfected to DH5α. The DNA samples prepared from the resultant transformants were analyzed by nucleotide sequencing to confirm the structure of inserted fragment. The clone including a fragment with a correct nucleotide sequence was selected (pPvil 2-01).

(5) Preparation of pIRES-GFP (FIG. 54E)

Following the digestion of pIRES2-EGFP (BD Bioscience Clontech) with EcoRI and NotI, the fragment including the IRES-GFP region was purified by 0.8% agarose gel electrophoresis and QIA quick Gel Extraction Kit (QIAGEN). The purified fragment (IRES-GFP) was ligated to pcDNA3 (Invitrogen) that was digested with XhoI and XbaI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was selected (pIRES-GFP).

(6) Construction of pUC119 IRES-GFP (FIG. 54F)

Following the digestion of pIRES-GFP with BamHI and XbaI, the fragment including the IRES-GFP region was purified by 0.8% agarose gel electrophoresis and QIA quick Gel Extraction Kit (QIAGEN). The purified fragment (IRES-GFP) was ligated to pUC119 that was digested with BamHI and XbaI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was selected (pUC119 IRES-GFP).

(7) Construction of pUC119 IRES-GFP+As (FIG. 54G)

The DNA fragment prepared by annealing of synthesized oligonucleotides described below (SEQ ID NO: 126 and 127) was ligated to pUC119 IRES-GFP that was digested with EcoRI and BamHI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was selected (pUC119 IRES-GFP+As).

```
                                              (SEQ ID NO: 126)
EI-BIAscI-(BI) S       AATTCGGATCCGGCGCGCC (SEQ ID NO: 127)
EI-BIAscI-(BI) AS      GATCGGCGCGCCGGATCCG
```

Figure 54H:
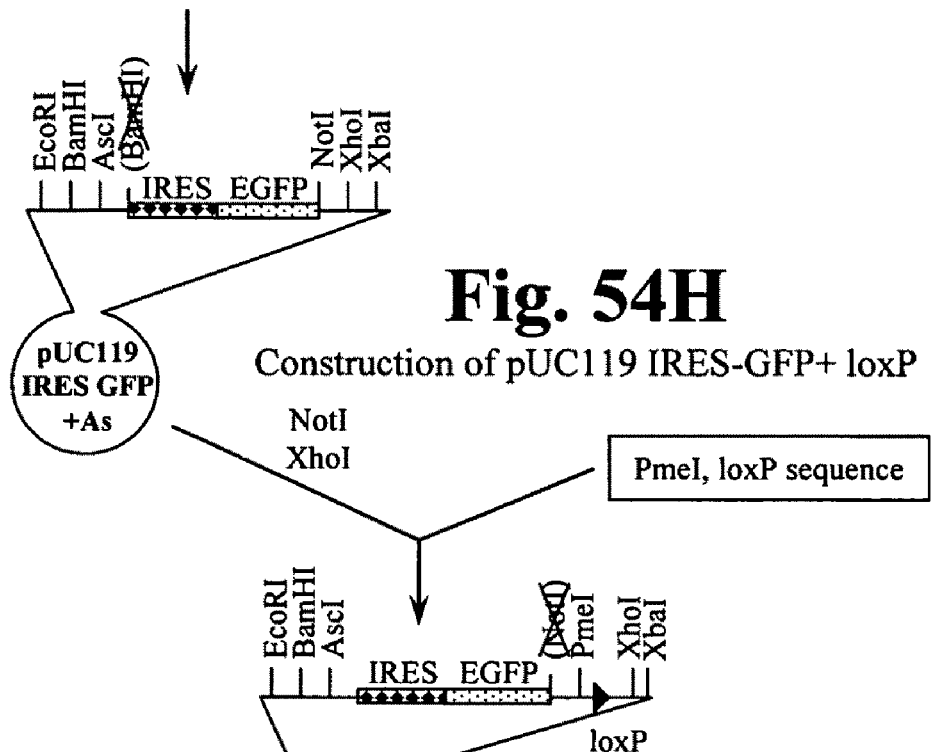

(8) Construction of pUC119 IRES-GFP+loxP (FIG. 54H)

The DNA fragment prepared by annealing of synthesized oligonucleotides described below (SEQ ID NO: 128 and 129) was ligated to pUC119 IRES-GFP+As that was digested with NotI and XhoI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was selected (pUC119 IRES-GFP+loxP).

```
Nt-PmIoxP-Xh S
                                              (SEQ ID NO: 128)
GGCCGTTTAAACATAACTTCGTATAATGTATGCTATACGAAGTTATC

Nt-PmIoxP-Xh AS
                                              (SEQ ID NO: 129)
TCGAGATAACTTCGTATAGCATACATTATACGAAGTTATGTTTAAAC
```

Figure 54I:

(9) Preparation of Bovine Growth Hormone (BGH) PolyA Fragment (FIG. 54I)

```
BGHpAFW
                                          (SEQ ID NO: 130)
CGGGATCCGTTTAAACCTGTGCCTTCTAGTTGCCAGCCATC

BGHpARV
                                          (SEQ ID NO: 131)
CGGATATCCCATAGAGCCCACCGCATGCCCAGC
```

KOD-puls-(TOYOBO) was used for the PCR reaction. The PCR reaction mixture contained. 10 pmole of each primer (SEQ ID NO: 130 and 131) and the IRES-GFP fragment prepared in (6) as a template. This PCR amplification was performed using an initial denaturing incubation at 94° C. for three minutes. Then 30 cycles of denaturation, annealing and amplification were performed by incubation at 94° C. for 15 sec and 68° C. for two minutes. A PCR product (approximately 0.2 kb) was purified by 0.8% agarose gel electrophoresis and QIAquick Gel Extraction Kit (QIAGEN). Following the digestion of isolated PCR product with BamHI and EcoRV, it was ligated to pBluescriptIISK(−) that was digested with BamHI and EcoRV, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was digested with PmeI and EcoRV, and the fragment including the bovine growth hormone (BGH) polyA region was purified by electrophoresis using 0.8% agar and QIAquick Gel Extraction Kit (QIAGEN).

Figure 54J:
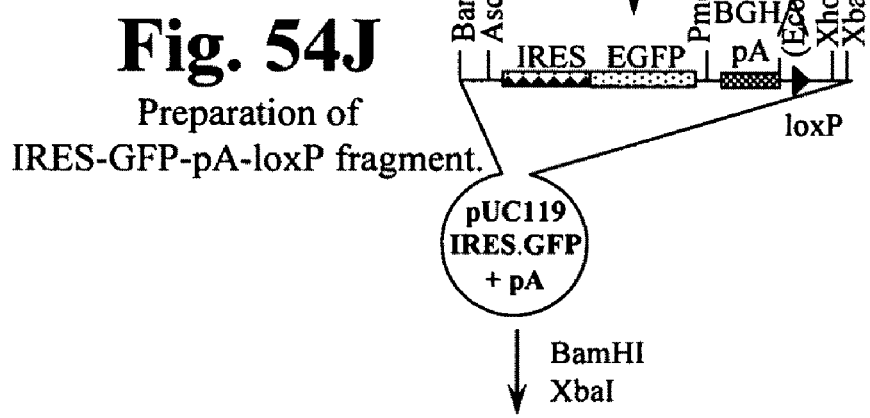

(10) Preparation of DNA Fragment Including IRES-GFP, Bovine Growth Hormone PolyA and loxP Sequences (FIG. 54J)

The pUC119 IRES-GFP+loxP was digested with PmeI and purified by 0.8% agarose gel electrophoresis. The BGH polyA fragment prepared in (9) was ligated to the purified pUC119 IRES-GFP+loxP vector that was treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a BGH polyA fragment in a same direction to coding sequence of GFP was selected (pIRES-GFP+pA). The pIRES-GFP+pA was digested with BamHI and XbaI, and the fragment including the IRES-GFP, bovine growth hormone polyA and loxP sequences was purified by electrophoresis using 0.8% agar and QIAquick Gel Extraction Kit (QIAGEN).

Figure 54K:
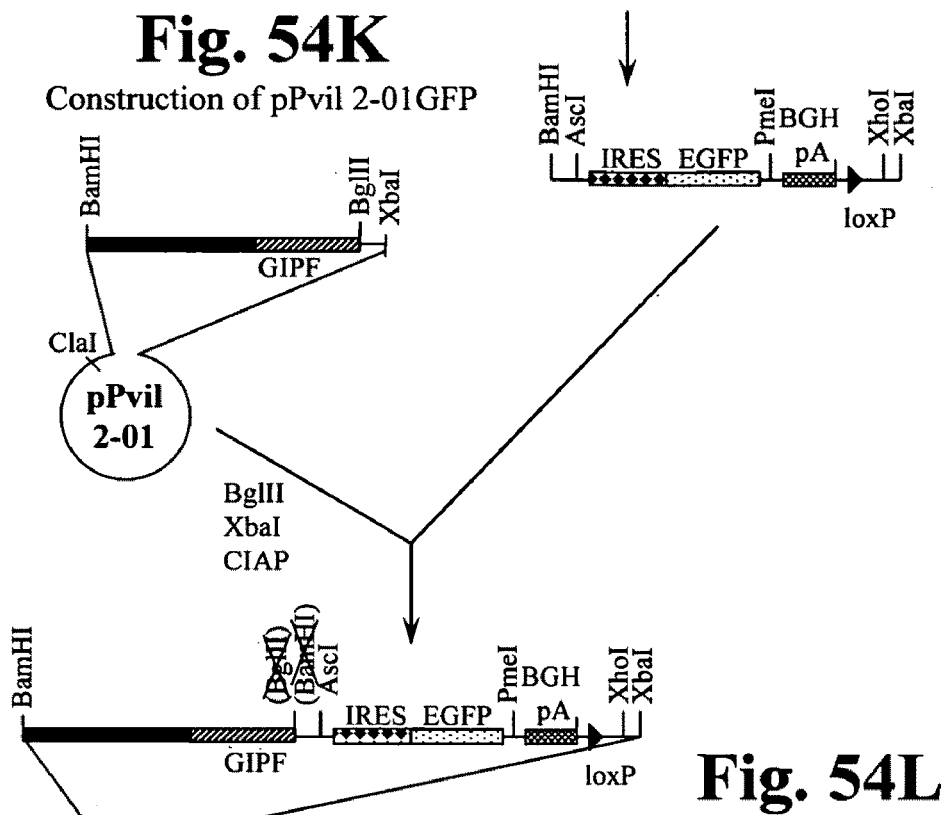

(11) Construction of pPvil 2-01GFP (FIG. 54K)

The DNA fragment including the IRES-GFP, bovine growth hormone polyA and loxP sequences [see (10)] was ligated to pPvil2GIPF that was digested with BglII and XbaI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was selected (pPvil 2-01 GFP).

Figure 54L:
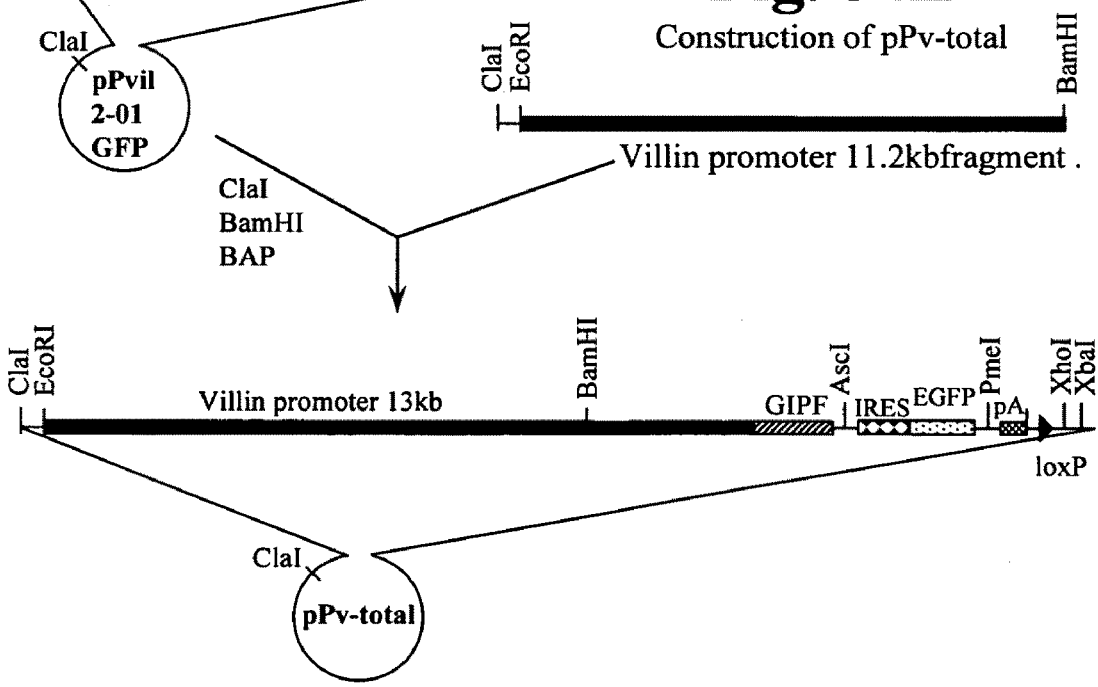

(12) Construction of pPv-Total (FIG. 54L)

The approximately 11.2 kb of long fragment of mouse Villin gene promoter [see (1)] was ligated to pPvil2-01 GFP that was digested with BglII and ClaI, and treated with E. coli C75 alkaline phosphatase to dephosphorylate its both ends. The ligation mixture was transfected to XL10-Gold Ultracompetent Cells (STRATAGENE) and the DNA samples prepared from the resultant transformants were analyzed by nucleotide sequencing to confirm the structure of inserted fragment. The clone including the fragment with a correct nucleotide sequence was selected (pPv-total).

(13) Construction of pLoxP-STneoR (FIG. 54M)

The pLoxP-STneo described in WO 00/10383 was digested with XhoI and treated with Blunting high (TOYOBO) for blunting its both ends. The resultant DNA fragment including loxP-Neo$^r$-loxP unit was purified by 0.8% agarose gel electrophoresis. The DNA fragment prepared by annealing of synthesized oligonucleotides described below (SEQ ID NO: 132 and 133) was ligated to pBlueLAB (WO 00/10383) that was digested with PacI and FseI, and purified by 0.8% agarose gel electrophoresis. The ligation mixture was transfected to DH5α and the DNA samples prepared from the resultant transformants were analyzed by nucleotide sequencing to confirm the structure of inserted fragment. The clone including a fragment with a correct nucleotide sequence was selected (pBlueLAB2). The above DNA fragment including loxP-Neo$^r$-loxP unit was ligated to the pBlueLAB2 vector that was digested with EcoRV, and was treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including the fragment in an opposite direction to pLoxP-STneo (WO 00/10383) was selected (pLoxP-STneoR).

```
AsiSI-S    □TAACCGCGATCGCGGCCGG    (SEQ ID NO: 132)

AsiSI-AS   □CCGCGATGGCCCTTAAT      (SEQ ID NO: 133)
```

(14) Construction of pPv01GFP (FIG. 54N)

The pPv-total plasmid DNA was digested with restriction enzymes, ClaI and XhoI, and the DNA fragment including Pv-GIPF unit was purified by 0.8% agarose gel electrophoresis. The purified DNA fragment was ligated to pLoxP-StneoR that was digested with ClaI and XhoI, and treated with calf intestine alkaline phosphatase to dephosphorylate its both ends. The ligation mixture was transfected to XL10-Gold Ultracompetent Cells (STRATAGENE) and the DNA samples prepared from the resultant transformants were analyzed by nucleotide sequencing to confirm the structure of inserted fragment. The clone including a fragment with a correct nucleotide sequence was selected (pPv01 GFP).

(15) Preparation of pPv01GFP Plasmid DNA for Electroporation to Mouse ES Cells

The plasmid DNA of pPv01GFP (60 μg) was digested with ClaI in the reaction mixture containing 1 mM spermidine (pH7.0, Sigma) for 5 hours at 37° C. The reaction mixture was then subjected to phenol/chloroform extraction and ethanol precipitation (0.3M NaHCO$_3$) for 16 hours at −20° C. The linearized vector fragment was dissolved in HBS buffer (0.5 μg/μl) and used for the following electroporation experiments.

(16) Production of Transgenic Chimaeric Mice Expressing Human GIPF and GFP in Intestinal Epithelial Cells General procedures for obtaining mouse embryos, cultivation, injection of the ES cells into the embryos, transplantation to the uteri of foster mothers were carried out in accordance with the method described in Shinichi Aizawa, "Biomanual Series 8, Gene Targeting", published by Yodosha, 1995.

The linearized pPv01GFP vector was transfect into C57BL/6×CBA F1 strain derived mouse TT2F ES cells ((Uchida, 1995), Lifetech oriental) by electroporation according to the method described by Shinichi Aizawa, "Biomanual Series 8, Gene Targeting", published by Yodosha, 1995. The electroporated ES cells were suspended in 20 ml of ES medium and inoculated into two 100 mm tissue culture plastic plates (Corning) into which feeder cells were seeded in advance. After one day, the medium was replaced with a medium containing a 200 µg/ml of G418 (Invitrogen). Seven to nine days thereafter, a total of 24 colonies for each vector were picked up. Each colonies was grown up to confluence in a 12-well plate, and then four fifth of the culture was suspended in 0.2 ml of cryopreservation medium (ES medium+10% DMSO (Sigma)) and stored frozen at −80° C. The remaining one fifth was inoculated into a 12-well gelatin coated plate and cultured for 2 days. Then, genomic DNA was isolated using the Puregene DNA Isolation Kit (Gentra System). Genomic DNA isolated from G418 resistant TT2F cells was digested with restriction enzymes EcoRI and XhoI and then subjected to 0.8% agarose gel electrophoresis. Using EcoRI-XhoI digestion, retention of an intact expression unit including Villin promoter, human GIPF cDNA, GFP cDNA and BGH polyA sequences of pPv01GFP in the G418-resistant clones can be determined by the detection of an approximately 16 kb band. Separated DNA fragments were transferred to a membrane (Gene Screen, NEN Life science Products) and then hybridization was carried out using the DNA fragment as probe prepared from IRES region of pPV01GFP [see (13)] by PCR using a primer set as described below (SEQ ID NO: 134 and 135) (IRESprobeF1, R1). We selected the ES clones that showed a single 16 kb band in the Southern blotting. The selected ES clones were also tested by karyotype analysis according to the method described in Shinichi Aizawa, "Biomanual Series 8, Gene Targeting", published by Yodosha, 1995. One ES clone, #2, that showed normal karyotype were used for injection into embryos.

```
IRESprobeF1 (SEQ ID NO: 134):
CTAACGTTACTGGCCGAAGC

IRESprobeR1 (SEQ ID NO: 135):
ATTATCATGGTGTTTTTCAAAGGAA
```

The cells in a frozen stock of the transfected ES cell clones #2 were thawed, started to culture and injected into 8 cell stage embryos obtained by mating a male and a female mouse of MCH(ICR) mouse strain (CREA JAPAN, INC.); the injection rate was 10-12 cells per embryo. After the embryos were cultured overnight in the medium for ES cells to develop into blastocysts, about ten of the ES cell-injected embryos were transplanted to each side of the uterus of a foster mother ICR mouse (CREA JAPAN, INC.), which had been subjected to a pseudopregnant treatment for 2.5 days. Contribution of the TT2F (agouti) ES clone-derived tissues in host embryo (albino) derived tissues can be determined eye pigmentation in embryos and coat color in viable offspring.

(17) Expression of Human GIPF-GFP mRNA in Transgenic Chimaeric Mice

Total RNA samples were prepared from intestinal tract of pPv01 GFP/TT2F-#2 derived chimaeras at various developmental stages (E13.5, E16.5, E19.5, day 3, day 7) and were subjected to semi-quantitative RT-PCR analysis to examine GIPF-GFP mRNA expression. First-strand cDNA was synthesized with Superscript III (Invitrogen) using random hexamers and 500 ng of total RNA extracted from the intestinal tract of pPv01GFP/TT2F-#2 derived chimaeras and control TT2F-derived chimaeras by using Isogen (Nippon Gene) and RNasy Mini (QIAGEN). Semi-quantitative RT-PCR analysis was carried out using the cDNA at specific annealing temperatures for each primer pair. PCR products were electrophoresed on 2% agar gels and stained with ethidium bromide. The integrity of RNA was controlled by the amplification of cDNA generated by the murine GAPDH. The nucleotide sequences and annealing temperature of primer sets for GIPF (Pv01RT F1, R1; SEQ ID NO: 136 and 137), Axin 2 (Axin2 F, R; SEQ ID NO: 138 and 139)) and mGAPDH (mGAPDH5, 3; SEQ ID NO: 140 and 141) are listed below.

```
Pv01RT F1
GCTCTGACACCAAGGAGACC         (SEQ ID NO: 136)

Pv01RT R1 (60° C.)
CCCTAGGAATGCTCGTCAAG         (SEQ ID NO: 137)

Axin2 F(MUS)
CAGGAGCCTCACCCTTCG           (SEQ ID NO: 138)

Axin2 R(MUS) (60° C.)
ACGCCGAGGTGCTTGCCC           (SEQ ID NO: 139)

mGAPDH5
CAGCATGGAGAAGGCCGGGGCCCAC    (SEQ ID NO: 140)

mGAPDH3 (65° C.)
ATCATACTTGGCAGGTTTCTCCAGG    (SEQ ID NO: 141)
```

As shown in FIG. 55, the GIPF-GFP transcripts were detectable at E13.5 in intestinal tract of pPv01GFP/TT2F-#2 derived chimaeras and not detected in in all the liver samples examined, which is well consistent with the previous study (Madison et al., *J. Biol. Chem.* 277, p 33275-33283, 2002) describing that expression of transgene driven by 13 kb villin promoter is first detectable in the embryonic hindgut and midgut at 12.5 dpc., and the expression is largely specific for intestinal epithelium. It is also evident that the expression level of GIPF-GFP transcripts is gradually elevated with age during the course of development. Eek-hoon et al. reported that endogenous Axin2 mRNA expression could be induced by activation of the Wnt signaling pathway (*Mol. Cell. Biol.* 22, 1172-1183, 2002). It is also known that the Wnt signaling play a critical role in the development of intestinal tract. We therefore examined Axin2 expression in intestinal tract of pPv01GFP/TT2F-#2 derived chimaeras. The result (FIG. 55) shows that the elevated expression of Axin2 mRNA is apparent at day 3 and 7 when compared to the control chimaeras, suggesting that the expression of human GIPF results in activation Wnt signaling pathway in intestinal tract of newborn.

(18) Stabilization of β-Catenin in Intestinal Tract of Transgenic Chimaeric Mice To evaluate the effect of GIPF on the Wnt/β-catenin signaling pathway, the stabilization of β-catenin was measured in small intestine and colon sampled from pPv01GFP/TT2F-#2 derived chimaeras at day 10. The procedure for β-catenin stabilization assay is described in Example 17. As shown in FIG. 56, the expression of GIPF strongly induced the stabilization of β-catenin in both small intestine and colon sampled from pPv01GFP/TT2F-#2 (Pv01#2) derived chimaeras when compared to the control chimaeras (wild-type).

(19) Evaluation of Phenotypic Changes in Intestinal Tract of Transgenic Chimaeric Mice Newborn pPv01GFP/TT2F-#2 derived chimaeric pups showed a significant abdominal distention at day 3 and the extent of this phenotype gradually intensified with age. Visual inspection of day 3 chimaeras at necropsy showed a remarkable enlargement in diameter throughout the small intestine, associated with augmented surface vascularisation. Whole embryos, pups or gastrointestinal tracts were fixed in Bouin solution. Paraffin embedded sections were stained with hematoxiyline and eosin (H&E) for histological evaluation. As shown FIG. 57, histopathological analysis of H&E sections from pPv01GFP/TT2F-#2 (Pv01#2) revealed increase in number of crypts and branching from embryonic day 19.5 (E 19.5) to day 14 (d14) compared to control.

Example 31

Figure 58A:
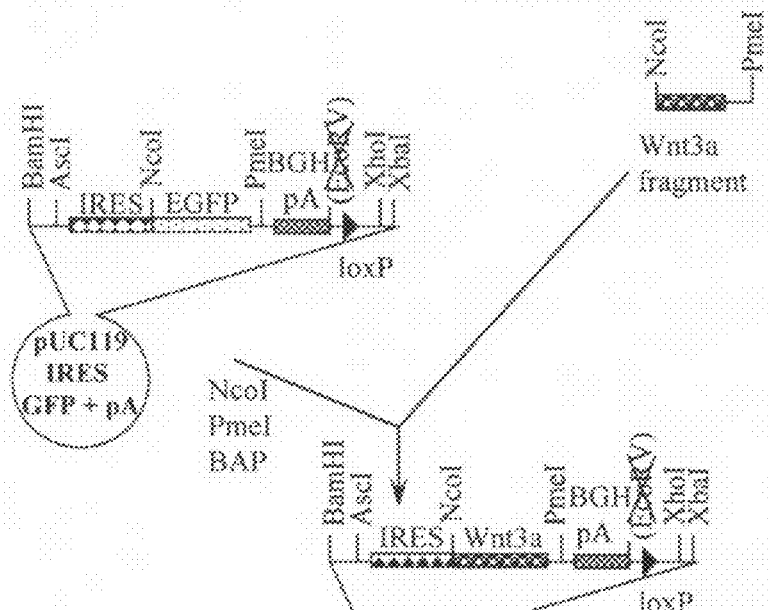

Transgenic Chimaeric Mice that Express GIPF and Wnt3a in Intestinal Epithelial Cells (1) Preparation of Wnt3a Fragment (FIG. 58A)

```
                                        (SEQ ID NO: 142)
Wnt3aFW  □CGGGATCCCCATGGCTCCTCTCGGATACCTCTTAGTGCT (SEQ ID NO: 143)
Wnt3aRV  □GCTCTAGAGTTTAAACCTACTTGCAGGTGTGCACGTCATAG
```

KOD-puls-(TOYOBO) was used for the PCR reaction. The PCR reaction mixture contained 10 pmole of each primer (SEQ ID NO: 142 and 143) and the human Wnt3a cDNA as a template. This PCR amplification was performed using an initial denaturing incubation at 94° C. for three minutes. Then 30 cycles of denaturation, annealing and amplification were performed by incubation at 94° C. for 15 sec and 68° C. for two minutes. A PCR product (approximately 1.06 kb) was purified by 0.8% agarose gel electrophoresis and QIAquick Gel Extraction Kit (QIAGEN). Following the digestion of isolated PCR product with BamHI and EcoRV, it was ligated to pBluescriptIISK(–) that was digested with BamHI and XbaI, and treated with calf intestine alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence was digested with NcoI and PmeI, and the fragment including the Wnt3a cDNA was purified by electrophoresis using 0.8% agar and QIAquick Gel Extraction Kit (QIAGEN).

Figure 58B:

(2) Preparation of IRES/Wnt3a+pA Fragment (FIG. 58B)

The pIRES/GFP+pA plasmid DNA [see Example 30-(13)] was digested with NcoI and PmeI, and the vector fragment including without the GFP coding sequence was purified by 0.8% agarose gel electrophoresis. The fragment including the Wnt3a cDNA [see (1)] was ligated to purified vector fragment that was treated with E. coli C75 alkaline phosphatase to dephosphorylate its both ends. The ligation mixture was transfected to DH5α and the DNA samples prepared from the resultant transformants were analyzed by nucleotide sequencing to confirm the structure of inserted fragment. The clone including a fragment with a correct nucleotide sequence (pIRES/Wnt3a+pA) was digested with AscI and XhoI, and the DNA fragment including the IRES/Wnt3a+pA unit was purified by 0.8% agarose gel electrophoresis and QIAquick Gel Extraction Kit (QIAGEN).

Figure 58C:
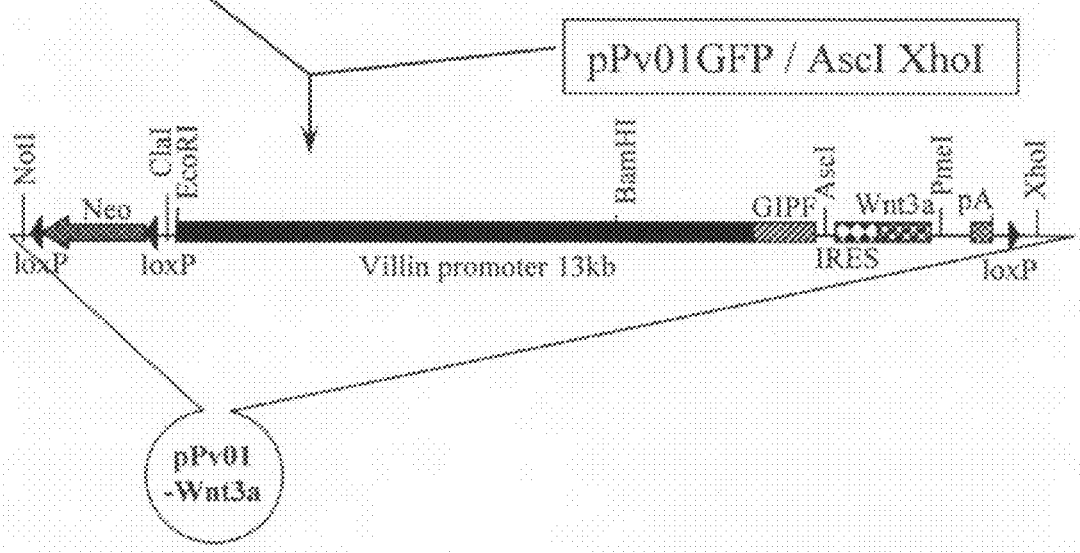

(3) Construction of pPv01Wnt3a (FIG. 58C)

The pPv01GFP plasmid DNA [see Example 30-(13)] was digested with restriction enzymes, AscI and XhoI, and the digested reaction mixture was subjected to 0.8% agarose gel electrophoresis. The vector fragment without the IRES/GFP+pA region was isolated and treated with calf intestine alkaline phosphatase to dephosphorylate its both ends. The ligation mixture of IRES/Wnt3a+pA fragment [see (2)] and the above vector fragment was transfected to XL10-Gold Ultracompetent cells (STRATAGENE). The DNA samples prepared from the resultant transformants were analyzed by nucleotide sequencing to confirm the structure of inserted fragment. The clone including a fragment with a correct nucleotide sequence was selected (pPv01Wnt3a).

(4) Preparation of pPv01Wnt3a Plasmid DNA for Electroporation to Mouse ES Cells

The plasmid DNA of pPv01Wnt3a (60 µg) was digested with ClaI in the reaction mixture containing 1 mM spermidine (pH7.0, Sigma) for 5 hours at 37° C. The reaction mixture was then subjected to phenol/chloroform extraction and ethanol precipitation (0.3M NaHCO$_3$) for 16 hours at –20° C. The linearized vector fragment was dissolved in HBS buffer (0.5 µg/ul) and used for the following electroporation experiments.

(5) Production of Transgenic Chimaeric Mice Expressing Human GIPF and Wnt3a in Intestinal Epithelial Cells General procedures for obtaining mouse embryos, cultivation, injection of the ES cells into the embryos, transplantation to the uteri of foster mothers were carried out in accordance with the method described in Shinichi Aizawa, "Biomanual Series 8, Gene Targeting", published by Yodosha, 1995.

The linearized pPv01Wnt3a vector was transfect into C57BL/6×CBA F1 strain derived mouse TT2F ES cells ((Uchida, 1995), Lifetech oriental) by electroporation according to the method described by Shinichi Aizawa, "Biomanual Series 8, Gene Targeting", published by Yodosha, 1995. The electroporated ES cells were suspended in 20 ml of ES medium and inoculated into two 100 mm tissue culture plastic plates (Corning) into which feeder cells were seeded in advance. After one day, the medium was replaced with a medium containing a 200 µg/ml of G418 (Invitrogen). Seven to nine days thereafter, a total of 24 colonies for each vector were picked up. Each colonies was grown up to confluence in a 12-well plate, and then four fifth of the culture was suspended in 0.2 ml of cryopreservation medium (ES medium+10% DMSO (Sigma)) and stored frozen at –80° C. The remaining one fifth was inoculated into a 12-well gelatin coated plate and cultured for 2 days. Then, genomic DNA was isolated using the Puregene DNA Isolation Kit (Gentra System). Genomic DNA isolated from G418 resistant TT2F cells was digested with restriction enzymes EcoRI and XhoI and then subjected to 0.8% agarose gel electrophoresis. Using EcoRI-XhoI digestion, retention of an intact expression unit including Villin promoter, human GIPF cDNA, Wnt3a cDNA and BGH polyA sequences of pPv01Wnt3a in the G418-resistant clones can be determined by the detection of an approximately 16 kb band. Separated DNA fragments were transferred to a membrane (Gene Screen, NEN Life science Products) and then hybridization was carried out using the DNA fragment as probe prepared from IRES region of pPV01GFP [see Example 30-(13)] by PCR using a primer set described in Example 30-(16) (IRESprobeF1, R1). We selected the clones that showed a single 16 kb band in the Southern blotting. The selected ES clones were also tested by karyotype analysis according to the method described in Shinichi Aizawa, "Biomanual Series 8, Gene Targeting", published by Yodosha, 1995. Two ES clone, #7 and #13 that showed normal karyotype were used for injection into embryos.

The cells in a frozen stock of the transfected ES cell clones #7 and #13 were thawed, started to culture and injected into 8 cell stage embryos obtained by mating a male and a female mouse of MCH(ICR) mouse strain (CREA JAPAN, INC.);

the injection rate was 10-12 cells per embryo. After the embryos were cultured overnight in the medium for ES cells to develop into blastocysts, about ten of the ES cell-injected embryos were transplanted to each side of the uterus of a foster mother ICR mouse (CREA JAPAN, INC.), which had been subjected to a pseudopregnant treatment for 2.5 days. Contribution of the TT2F (agouti) ES clone-derived tissues in host embryo (albino) derived tissues can be determined eye pigmentation in embryos and coat color in viable offspring.

(6) Expression of Human GIPF/Wnt3a mRNA in Transgenic Chimaeric Mice

Total RNA samples were prepared from intestinal tract of pPv01Wnt3a/TT2F-#7, and #13 derived newborn chimaeras and were subjected to semi-quantitative RT-PCR analysis to examine GIPF-GFP mRNA expression. First-strand cDNA was synthesized with Superscript III (Invitrogen) using random hexamers and 500 ng of total RNA extracted from the intestinal tract of pPv01Wnt3a/TT2F-#7, and #13 derived chimaeras and control TT2F-derived chimaeras by using Isogen (Nippon Gene) and RNasy Mini (QIAGEN). Semi-quantitative RT-PCR analysis was carried out using the cDNA at specific annealing temperatures for each primer pair. PCR products were electrophoresed on 2% agar gels and stained with ethidium bromide. The integrity of RNA was controlled by the amplification of cDNA generated by the murine GAPDH. The nucleotide sequences and annealing temperature of primer sets for GIPF (Pv01RT F1, R1), Axin 2 (Axin2 F, R) and mGAPDH (mGAPDH5, 3) are listed below.

```
Pv01RT F1
GCTCTGACACCAAGGAGACC              (SEQ ID NO: 136)

Pv01RT R1 (60° C.)
CCCTAGGAATGCTCGTCAAG              (SEQ ID NO: 137)

Axin2 F(MUS)
CAGGAGCCTCACCCTTCG                (SEQ ID NO: 138)

Axin2 R(MUS) (60° C.)
ACGCCGAGGTGCTTGCCC                (SEQ ID NO: 139)

mGAPDH5
CACCATGGAGAAGGCCGGGGCCCAC         (SEQ ID NO: 140)

mGAPDH3 (65° C.)
ATCATACTTGGCAGGTTTCTCCAGG         (SEQ ID NO: 141)
```

As shown in FIG. 59, the GIPF-Wnt3a transcripts were detectable in intestinal tissues of pPv01Wnt3a/TT2F-#7 and -#13 derived from newborn chimaeras (Pv01Wnt3a: 1 to 4). The result (FIG. 59) also shows that the elevated expression of Axin2 mRNA is apparent when compared to the control chimaeras (TT2F: 5 and 6).

(7) Stabilization of β-Catenin in Intestinal Tract of Transgenic Chimaeric Mice

To evaluate the effect of GIPF on the Wnt/β-catenin signaling pathway, the stabilization of β-catenin was measured in small intestine and colon sampled from pPv01Wnt3a/TT2F-#7 and -#13 derived chimaeras. The procedure for β-catenin stabilization assay is described in Example 17. As shown in FIG. 60, the co-expression of GIPF and Wnt3a induced the stabilization of β-catenin in duodenum and colon sampled from pPv01Wnt3a/TT2F-#7 embryo (E20.5: 1 and 2) when compared to the control chimaeras (wild-type: 3 and 4).

(8) Evaluation of Phenotypic Changes in Intestinal Tract of Transgenic Chimaeric Mice Newborn pPv01Wnt3a/TT2F-#7 and -#13 derived chimaeric pups showed a significant abdominal distention. Visual inspection of newborn chimaeras at necropsy showed a remarkable enlargement in diameter throughout the small intestine, associated with augmented surface vascularisation. Whole embryos, pups or gastrointestinal tracts were fixed in Bouin solution. Paraffin embedded sections were stained with hematoxiyline and eosin (H&E) for histological evaluation. As shown FIG. 61, histopathological analysis of H&E sections from pPv01Wnt3a/TT2F-#13 embryonic day 20.5 embryo (E 20.5) revealed increase in number of villous cells, irregular branching and hyperplasia of villi. The extent of these phenotypes were stronger than those of pPv01GFP/TT2F-#2 derived chimaeras [Example 30-(19)], suggesting the enhancement of GIPF action by Wnt3a expression.

Example 32

RS-KO Mouse ES Cells

A. Construction of the RS-KO Vector

Figure 62A:
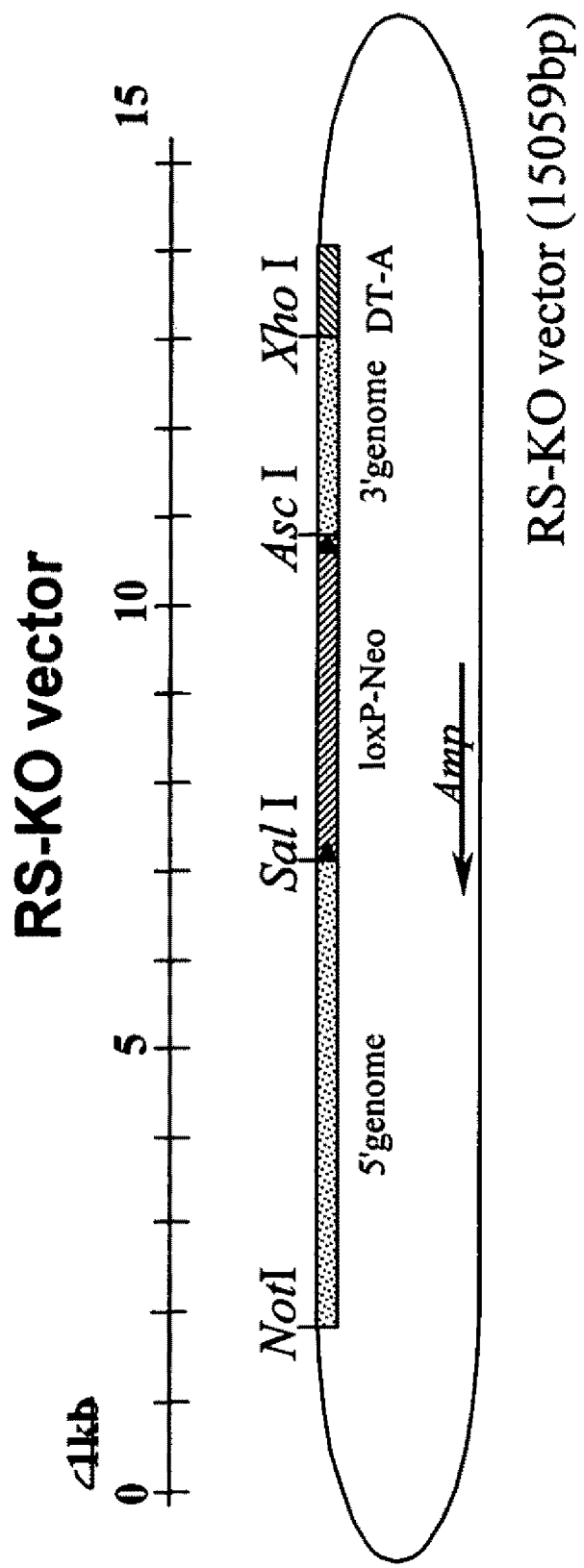

The construction of the RS-KO vector (FIG. 62A) was performed according to the method described below, and depicted in FIGS. 62B-1K.

FIG. 62B Addition of the new restriction sites (NruI, SgrAI, and AscI) to pBluescript II SK(−) (Stratagene).

The oligo DNA fragments (SEQ ID NO: 144 and 145) for the addition of the new restriction sites in pBluescript II SK(−) were synthesized.

```
LinkA1:
TCGAGTCGCGACACCGGCGGGCGCGCCC      (SEQ ID NO: 144)

LinkA2:
TCGAGGGCGCGCCCGCCGGTGTCGCGAC      (SEQ ID NO: 145)
```

The prepared LinkA1 and LinkA2 were ligated into pBluescript II SK(−) that was pre-digested with the restriction enzymes SalI and XhoI. The resulting plasmid pBlueLA contained the newly added restriction sites (NruI, SgrAI, and AscI).

FIG. 62C Addition of the New Restriction Sites (PacI, FseI, and SalI) to pBlueLA.

The oligo DNA fragments (SEQ ID NO: 146 and 147) for the addition of the new restriction sites in pBlueLA were synthesized.

```
LinkB1:
GGCCGCTTAATTAAGGCCGGCCGTCGACG     SEQ ID NO: 146)

LinkB2:
AATTCGTCGACGGCCGGCCTTAATTAAGC     SEQ ID NO: 147)
```

The prepared LinkB1 and LinkB2 were ligated into pBlueLA that was pre-digested with the restriction enzymes NotI and EcoRI. The resulting plasmid pBlueLAB contained the newly added restriction sites (PacI, FseI, and SalI).

FIG. 62D Preparation of LoxP-Neo-B Fragment
LoxP-Neo-B fragment was prepared by T4 DNA polymerase treatment of LoxP-Neo that was obtained from Xho/digestion of pLoxP-STneo (WO 00/10383).

FIG. 62E Preparation of pBlueLAB-LoxP-Neo Plasmid
LoxP-Neo-B fragment was ligated into pBlueLAB that was pre-digested with the restriction enzyme EcoRV. The resulting plasmid pBlueLAB-LoxP-Neo contained LoxP-Neo-B fragment.

FIG. 62F Preparation of DT-A Fragment
pMC1 DT-A□GIBCO BRL□ was digested with XhoI and SalI, and the resulting DT-A fragment was separated and recovered from agarose gel electrophoresis.

FIG. 62G Preparation of pBlueLAB-LoxP-Neo-DT-A Plasmid

DT-A fragment was ligated into pBlueLAB-LoxP-Neo that was pre-digested with the restriction enzyme XhoI. The resulting plasmid pBlueLAB-LoxP-Neo-DT-A contained DT-A fragment.

FIG. 62H Preparation of 3'Genomic Region of RS Element

The forward (RS3'FW2; SEQ ID NO: 148) and reverse (RS3'RV3; SEQ ID NO: 149) primers for PCR were synthesized based on the sequence of the mouse obtained from GenBank (Accession Number☐AC090291), and used to amplify the DNA of 3' genomic region of RS element.
RS3'FW2: TTGGCGCGCCCTCCCTAGGACTGCAGT-TGAGCTCAGATTTGA (SEQ ID NO: 148) was prepared by adding a AscI recognition sequence at 5' end site, and RS3'RV3: CCGCTCGAGTCTTACTGTCTCAGCAA-CAATAATATAAACAGGGG (SEQ ID NO: 149) was prepared by adding a XhoI recognition sequence at 5' end site. PCR was carried out using BAC clone RP23-43514 (GenBank Accession Number AC090291) as template. The PCR product was digested with restriction enzymes AscI and XhoI, and ligated into pBlueLAB that was pre-digested with the restriction enzymes AscI and XhoI. The resulting plasmid contained the designated DNA sequence of 3'genomic region of RS element with no substitution in nucleotide sequence within the region between AscI and XhoI was treated with AscI and XhoI and then the 3'genomic region of RS element (about 2 Kb) was obtained.

FIG. 62I Insertion of 3'Genomic Region of RS Element into pBlueLAB-LoxP-Neo-DT-A The 3'genomic region of RS element was ligated into pBlueLAB-LoxP-Neo-DT-A that was pre-digested with AscI and XhoI. After verifying the connecting regions between pBlueLAB-LoxP-Neo-DT-A and the 3'genomic region of RS element, the plasmid pBlueLAB-LoxP-Neo-DT-A-3'RS was obtained.

FIG. 62J Preparation of 5'Genomic Region of Mouse RS Element

The forward (RS5'FW3; SEQ ID NO: 150) and the reverse (RS5'RV3; SEQ ID NO: 151) primers for PCR were synthesized based on the sequence of the mouse obtained from GenBank (Accession Number AC090291), and used to amplify the DNA of 5'genomic region of RS element.
RS5'FW3: ATAAGTGCGGCCGCAAAGCTGGTGGGT-TAAGACTATCTCGTGAAGTG (SEQ ID NO: 150) was prepared by adding a NotI recognition sequence at 5' end site, and RS5'RV3: ACGCGTCGACTCACAGGTTGGTC-CCTCTCTGTGTGTGGTTGCTGT (SEQ ID NO: 151) was prepared by adding a SalI recognition sequence at 5' end site. PCR was carried out using BAC clone RP23-43514 (GenBank Accession Number AC090291) as template. The PCR product was digested with restriction enzymes NotI and SalI, and ligated into pBlueLAB that was pre-digested with the restriction enzymes NotI and SalI. The resulting plasmid contained the designated DNA sequence of 5'genomic region of RS element with no substitution in nucleotide sequence within the region between NotI and SalI was treated with NotI and SalI and then the 5'genomic region of RS element (about 5 Kb) was obtained.

FIG. 62K Insertion of 5'Genomic Region of RS Element into pBlueLAB-LoxP-Neo-DT-A-3'RS The 5'genomic region of RS element was ligated into pBlueLAB-LoxP-Neo-DT-A-3'RS that was pre-digested with NotI and SalI. After verifying the connecting regions between pBlueLAB-LoxP-Neo-DT-A-3'RS and the 5'genomic region of RS element, the RS-KO vector was constructed.

B. Preparation of RS-KO Mouse ES Cells

General procedures for obtaining mouse embryos and cultivation were carried out in accordance with the method described in Aizawa Shinichi, "Biomanual Series 8, Gene Targeting", published by Yodosha, 1995. The RS-KO vector was linearized with NotI and transferred into C57BL/6×CBA F1 derived mouse TT2F ES cells ((Uchida, 1995), Lifetech oriental) by electroporation according to the method described by Shinichi Aizawa, "Biomanual Series 8, Gene Targeting", published by Yodosha, 1995. The electroporated ES cells were suspended in 20 ml of ES medium [DMEM (GIBCO), 18% FBS (GIBCO), 0.1 mM 2-mercaptoethanol (GIBCO), 1000 U/ml LIF (leukemia inhibitory factor, CHEMICON International, Inc.)] and inoculated into two 100 mm tissue culture plastic plates (Corning) into which feeder cells (Invitrogen) were seeded in advance. After one day, the medium was replaced with a medium containing 0.75 g/ml of puromycin (Sigma). Seven days thereafter, puromycin resistant colonies formed were picked up. Each colony was grown up to confluence in a 24-well plate, and then two third of the culture was suspended in 0.2 ml of cryopreservation medium [FBS+10% DMSO (Sigma)] and stored frozen at −80° C. The remaining one third was inoculated into a 12-well gelatin coated plate and cultured for 2 days. Then, genomic DNA was isolated using the Puregene DNA Isolation Kit (Gentra System).

3'KO-probe for Southern analysis was prepared as follows. RS3' Southern FW1 (SEQ ID NO: 152) and RS3' Southern RV2 (SEQ ID NO: 153) primers were synthesized based on the sequence of the mouse obtained from GenBank (Accession Number AC090291), and used to amplify about 600 mer long DNA fragment of 3' genomic region of RS element.

```
RS3'Southern FW1:
TCTTACTAGAGTTCTCACTAGCTCT☐  SEQ ID NO: 152)

RS3'Southern RV2:
GGAACCAAAGAATGAGGAAGCTGTT☐  SEQ ID NO: 153)
```

Genomic DNA isolated from puromycin resistant TT2F cells was digested with restriction enzyme EcoR I (Takara Shuzo) and then subjected to 0.8% agarose gel electrophoresis.

Separated DNA fragments were transferred to a membrane (GeneScreen, NEN™ Life Science Products) and then hybridization was carried out using the DNA fragment as probe prepared from 3' genomic region of RS element DNA (3'KO-probe). The band pattern of untargeted ES clone shows one band of MW of about 5.7 Kb and targeted ES clone shows two bands of MW of about 5.7 Kb and 7.4 Kb (FIG. 63). The selected RS-KO mouse ES clones were also tested by karyotype analysis according to the method described by Shinichi Aizawa, "Biomanual Series 8, Gene Targeting", published by Yodosha, 1995. The RS-KO mouse ES clones that showed normal karyotype were used for further experiments.

Example 33

Transgenic GIPF Deletion Mutant Animals

A. Construction of the pCk m4 KI Vector.

The construction of the GIPF deletion mutant 4 Ck knock-in (pCk m4 KI) vector (FIG. 64A) was performed according to the method described below, and depicted in FIGS. 64B-64K.

FIG. 64B Preparation of Ck P2 KI+AS KI

The oligo DNA fragments (SEQ ID NO: 154 and 155) for the addition of the new restriction sites in Ck P2 KI were synthesized.

```
Ascl top linker:
GGCCAGGCGCGCCTTGC          (SEQ ID NO: 154)

Ascl bottom linker:
GGCCGCAAGGCGCGCCT          (SEQ ID NO: 155)
```

The prepared AscI top linker and AscI bottom linker were ligated into Ck P2 KI that was pre-digested with the restriction enzyme NotI. The resulting plasmid Ck P2 KI+AS KI contained the newly added restriction site (AscI).

FIG. 64C Preparation of pBlueLAB+Nh

The oligo DNA fragments (SEQ ID NO: 156 and 157) for the addition of the new restriction sites in pBlueLAB were synthesized.

```
Pac-Nhe-Fse S:
TAAGGGCTAGCTAGGGCGGG       (SEQ ID NO: 156)

Pac-Nhe-Fse AS:
CCCTAGCTAGCCCTTAAT         (SEQ ID NO: 157)
```

The prepared Pac-Nhe-Fse S and Pac-Nhe-Fse AS were ligated into pBlueLAB that was pre-digested with the restriction enzymes PacI and FseI. The resulting plasmid pBlueLAB+Nh contained the newly added restriction site (NheI).

FIG. 64D Preparation of pBlueLAB+NhHp

The oligo DNA fragments (SEQ ID NO: 158 and 159) for the addition of the new restriction sites in pBlueLAB+Nh were synthesized.

```
S/HpaI/Hd-S:   TCGAGTTAAC   (SEQ ID NO: 158)

S/HpaI/Hd-AS:  AGCTGTTAAC   (SEQ ID NO: 159)
```

The prepared S/HpaI/Hd-S and S/HpaI/Hd-AS were ligated into pBlueLAB+Nh that was pre-digested with the restriction enzymes SalI and HindIII. The resulting plasmid pBlueLAB+NhHp contained the newly added restriction site (HpaI).

Figure 64E:
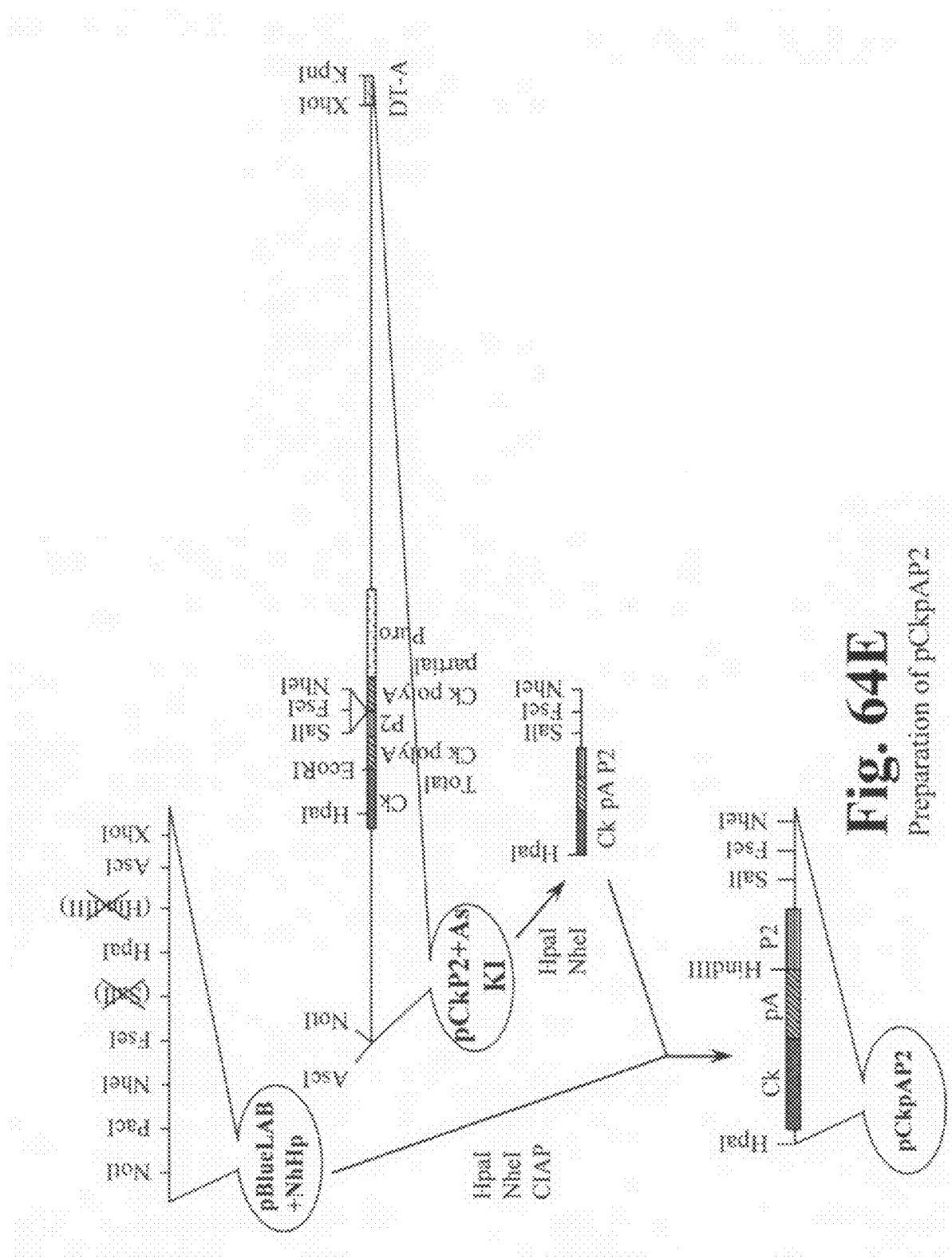

FIG. 64E Preparation of pCkpAP2 pCkP2+As KI was digested with HpaI and NheI, and the resulting 952 bp fragment was separated and recovered from agarose gel electrophoresis. The 952 bp fragment was ligated into pBlueLAB+NhHp that was pre-digested with the restriction enzymes HpaI and NheI. The resulting plasmid pCkpAP2 contained the 952 bp fragment.

FIG. 64F Preparation of pCkpAMCS

The oligo DNA fragments (SEQ ID NO: 160 and 161) for the addition of the new restriction sites in pCkpAP2 were synthesized.

```
SPFNlinker-S:
AGCTGTCGACTTAATTAAGGCCGGCCG   (SEQ ID NO: 160)

SPFNlinker-AS:
CTAGCGGCCGGCCTTAATTAAGTCGAC   (SEQ ID NO: 161)
```

The prepared SPFNlinker-S and SPFNlinker-AS were ligated into CkpAMCS that was pre-digested with the restriction enzymes HindIII and NheI. The resulting plasmid CkpAMCS contained the newly added restriction site (PacI).

FIG. 64G Preparation of pCkP2ΔP pCkpAMCS was digested with HpaI and NheI, and the resulting about 700 bp long fragment was separated and recovered from agarose gel electrophoresis. The 700 bp fragment was ligated into pCkP2+As KI that was pre-digested with the restriction enzymes HpaI and NheI. The resulting plasmid pCkP2ΔP contained the 700 bp fragment.

FIG. 64H Preparation of pBS+PFN

The oligo DNA fragments (SEQ ID NO: 162 and 163) for the addition of the new restriction sites in pBluescript II SK (−) were synthesized.

```
S/PFN/Hd-S:
TCGACTTAATTAAGGCGGGGCCTAGCTAGCA    (SEQ ID NO:. 162)

S/PFN/Hd-AS:
AGCTTGCTAGCTAGGGCCGGCCTTAATTAAG    (SEQ ID NO: 163)
```

The prepared S/PFN/Hd-S and S/PFN/Hd-AS were ligated into pBluescript II SK(−) that was pre-digested with the restriction enzymes SalI and HindIII. The resulting plasmid pBS☐PFN contained the newly added restriction sites (PacI, FseI, and NheI).

FIG. 64I Preparation of pPSs3.8

The forward (PsecSP FW1; SEQ ID NO: 164) and reverse (PsecSP RV; SEQ ID NO: 165) primers for PCR were synthesized based on the sequence of the mouse obtained from GenBank (Accession Number K02159), and used to amplify the DNA of promoter and leader sequence coding region of IgK. The leader sequence coding region contained intrinsic intron sequence.

PsecSP FW1: CCTTAATTAAAGTTATGTGTCCTAGAGGGCTGCAAACTCAAGATC (SEQ ID NO: 164) was prepared by adding a PacI recognition sequence at 5' end site, and PsecSP RV: TTGGCCGGCCTTGGCGCCAGTGGAACCTGGAATGATAAACACAAAGATTATTG (SEQ ID NO: 165) was prepared by adding a FseI recognition sequence at Send site. PCR was carried out using the mouse genome from TT2F ES cells ((Uchida, 1995), Lifetech oriental) as template. The PCR product was digested with restriction enzymes PacI and FseI, and ligated into pBS☐PFN that was pre-digested with the restriction enzymes PacI and FseI. The resulting plasmid pPSs3.8 contained the DNA fragment of promoter and leader sequence coding region of IgK.

FIG. 64J Preparation of m4(+SP) and m4(−SP)

The forward (Sal kozak GIPF F; SEQ ID NO: 166) and reverse (GIPF m4 RV Fse; SEQ ID NO: 167) primers for PCR were synthesized based on the sequence of the deletion mutant #4 (FIG. 43; SEQ ID NO: 91) and used to amplify the DNA of leader sequence of GIPF and deletion mutant #4 sequence of GIPF.

Sal kozak GIPF F: MG CGT CGA CCA CCA TGC GGC TTG GGC TGT GTG (SEQ ID NO: 166) was prepared by adding a SalI recognition sequence at 5' end site, and GIPF m4 RV Fse: ATG GCC GGC CCT ACA TGG TGC CAT TGG CAG (SEQ ID NO: 167) was prepared by adding a FseI recognition sequence at 5' end site. PCR was carried out using the GIPF KI vector as template. The PCR product was digested with restriction enzymes SalI and FseI, and then the m4(+SP) fragment was obtained.

The forward (Hy01(−SP) FW; SEQ ID NO: 168) and reverse (GIPF m4 RV Fse; SEQ ID NO:169) primers for PCR were synthesized based on the sequence of the deletion mutant #4 (FIG. 43; SEQ ID NO: 91) and used to amplify the DNA of deletion mutant#4 sequence of GIPF.

Hy01(−SP) FW: AGCCGGGGGATCAAGGGGAAAAG-GCAGAGG (SEQ ID NO: 168) was prepared by adding a phosphoric acid at 5' end site, and GIPF m4 RV Fse: ATG GCC GGC CCT ACA TGG TGC CAT TGG CAG (SEQ ID NO: 169) was prepared by adding a FseI recognition sequence at 5' end site. PCR was carried out using the GIPF KI vector as template. The PCR product was digested with restriction enzyme FseI, and then the m4(−SP) fragment was obtained.

FIG. 64K Construction of pCk m4 KI Vector

The m4(+SP) fragment was ligated into pCkP2+As KI that was pre-digested with the restriction enzymes SalI and FseI. The resulting pCk m4 KI vector contained the m4(+SP) fragment, that was used for the generation of the GIPF deletion mutant mice.

B. Construction of the pPSm4 KI Vector.

The construction of the GIPF deletion mutant 4 PS knock-in (pPS m4 KI) vector (FIG. 65A) was performed according to the method described below, and depicted in FIGS. 65B-65C.

Figure 65B:
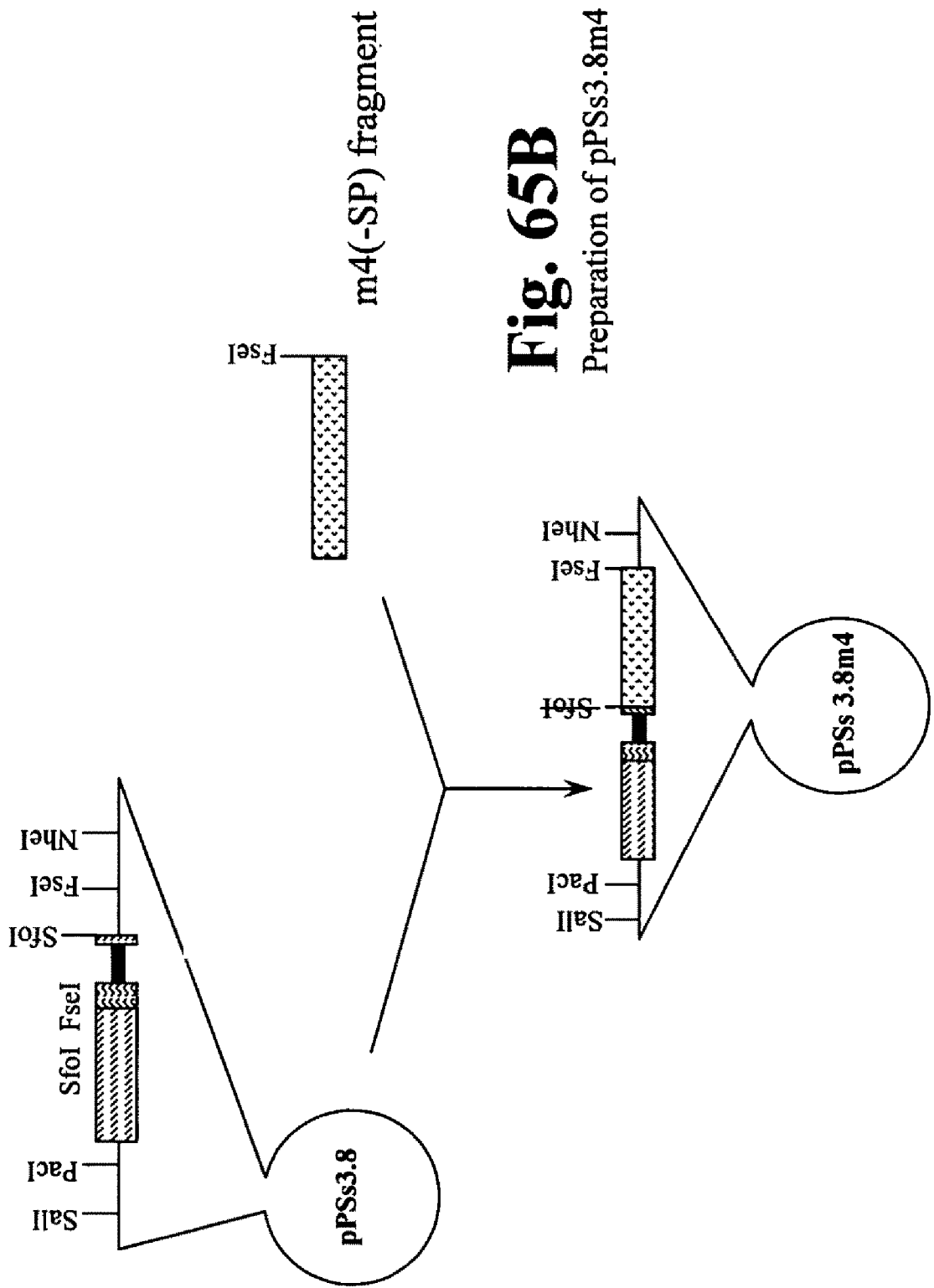

FIG. 65B Preparation of pPSs3.8 m4

The m4(−SP) fragment was ligated into pPSs3.8 that was pre-digested with the restriction enzymes SfoI and FseI. The resulting pPSs3.8 m4 contained the m4(−SP) fragment.

Figure 65C:
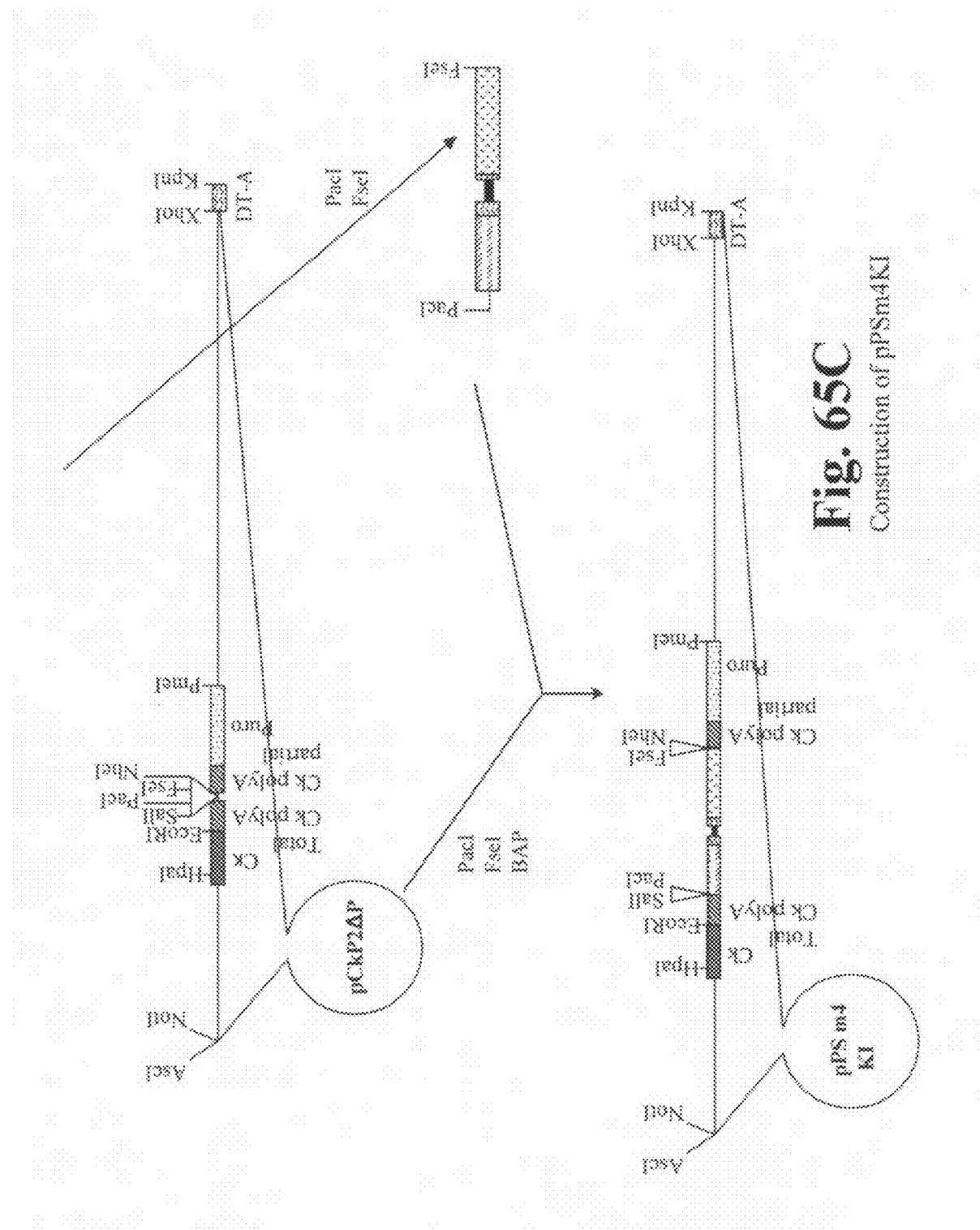

FIG. 65C Construction of pPSm4 KI Vector pPSs3.8 m4 was digested with PacI and FseI, and the resulting about 1.2 Kb long fragment was separated and recovered from agarose gel electrophoresis. The 1.2 Kb fragment was ligated into CkP2ΔP that was pre-digested with the restriction enzymes PacI and FseI. The resulting pPSm4 KI vector contained the 1.2 Kb fragment, that was used for the generation of the GIPF deletion mutant mice.

C. Generation of GIPF Deletion Mutant Mice

General procedures for obtaining mouse embryos, cultivation, injection of the ES cells into the embryos, transplantation to the uteri of foster mothers were carried out in accordance with the method described in Aizawa Shinichi, "Biomanual Series 8, Gene Targeting", published by Yodosha, 1995.

The pCkm4 KI vector and pPSm4 KI vector were linearized with NotI and transferred into RS-KO mouse ES cells by electroporation according to the method described by Shinichi Aizawa, "Biomanual Series 8, Gene Targeting", published by Yodosha, 1995. The electroporated RS-KO mouse ES cells were suspended in 20 ml of ES medium [DMEM (GIBCO), 18% FBS (GIBCO), 0.1 mM 2-mercaptoethanol (GIBCO), 1000 U/ml LIF (leukemia inhibitory factor, CHEMICON International, Inc.)] and inoculated into two 100 mm tissue culture plastic plates (Corning) into which feeder cells (Invitrogen) were seeded in advance. After one day, the medium was replaced with a medium containing 0.75 g/ml of puromycin (Sigma). Seven to nine days thereafter, 24 colonies formed from pCkm4 KI vector electroporated RS-KO mouse ES cells and 24 colonies formed from pPSm4 KI vector electroporated RS-KO mouse ES cells were picked up, respectively. Each colony was grown up to confluence in a 12-well plate, and then two third of the culture was suspended in 0.2 ml of cryopreservation medium [FBS+10% DMSO (Sigma)] and stored frozen at −80° C. The remaining one third was inoculated into a 12-well gelatin coated plate and cultured for 2 days. Then, genomic DNA was isolated using the Puregene DNA Isolation Kit (Gentra System). Genomic DNA isolated from puromycin resistant RS-KO mouse ES cells was digested with restriction enzyme EcoR I (Takara Shuzo) and then subjected to 0.8% agarose gel electrophoresis. Separated DNA fragments were transferred to a membrane (GeneScreen, NEN™ Life Science Products) and then hybridization was carried out using the DNA fragment as probe prepared from 3' region of IgJκ-Cκgenomic DNA (Xho 1-EcoR I, 1.3 Kb (SEQ ID NO: 67): WO 00/10383, Example No. 48). The band pattern of untargeted ES clone shows one band of MW of 15.6 Kb. pCkm4 KI targeted RS-KO mouse ES clone shows two bands of MW of 15.6 Kb and 12.9 Kb and pPSm4 KI targeted RS-KO mouse ES clone shows two bands of MW of 15.6 Kb and 12.5 Kb, respectively (FIGS. 66 and 67). One out of 10 pCkm4 KI targeted RS-KO mouse ES clones #3 was selected after Southern analysis (rate of homologues recombination was about 41.7%) and one out of 7 pPSm4 KI targeted RS-KO mouse ES clone #7 was selected after Southern analysis (rate of homologues recombination was about 29.2%). The selected ES clones were also tested by karyotype analysis according to the method described by Shinichi Aizawa, "Biomanual Series 8, Gene Targeting", published by Yodosha, 1995. One clone #3 of pCkm4 KI targeted RS-KO mouse ES clones and one clone #7 of pPSm4 KI targeted RS-KO mouse ES clones that showed normal karyotype were used for implantation into embryos, respectively.

The cells in a frozen stock of the pCkm4 KI targeted RS-KO mouse ES cell clone #3 and the pPSm4 KI targeted RS-KO mouse ES cell clone #7 were thawed, started to culture and injected into 8-cell stage embryos obtained by mating a male and a female mouse of Immunoglobulin heavy chain knock out mouse strain (Tomizuka et. Al. Proc. Natl. Acad. Sci. USA, 97: 722-727, 2000); the injection rate was 10-12 cells per embryo. After the embryos were cultured overnight in the medium for ES cells to develop into blastocysts, about ten of the ES cell-injected embryos were transplanted to each side of the uterus of a foster mother ICR mouse (CREA JAPAN, INC.), which had been subjected to a pseudopregnant treatment for 2.5 days. As a result of transplantation of each of 80 injected embryos, 15 and 20 offspring mice were born, respectively. Chimerism in the offspring was determined by the extent of TT2F cell-derived agouti coat color (dark brown) in the host embryo (ICR)-derived albino coat color. Out of the 15 offspring, 9 mice (pCkm4 knock-in mice) were recognized to have partial agouti coat color, indicating the contribution of the RS-KO mouse ES cells and out of the 20 offspring, 16 mice (pPSm4 knock-in mice) were recognized to have partial agouti coat color, indicating the contribution of the RS-KO mouse ES cells. GIPF deletion mutant mice were obtained same as described above from the other clones of the pCkm4 KI targeted RS-KO mouse ES cells and the pPSm4 KI targeted RS-KO mouse ES cells.

Mice were kept under a 12/12-hour dark/light cycle (lights on at 8:00 am) and received 5 μm filtered water and CE-2 food (CLEA JAPAN, INC.) ad libitum. Male mice were housed individually after weaning period.

Example 34

Transgenic GIPF Variant Animals

A. Construction of the pCk VR KI Vector.

The construction of the GIPF variant Ck knock-in (pCk VR KI) vector (FIG. 68A) was performed according to the method described below, and depicted in FIGS. 68B-68C.

FIG. 6B Preparation of GIPF variant with kozak (VR+kz) and GIPF variant (VR).

The forward (VR Ck Fw; SEQ ID NO: 171) and reverse (VR KI Rv; SEQ ID NO: 171) primers for PCR were synthesized based on the sequence of GenBank (Accession Number AK098225), and used to amplify the DNA of GIPF variant with kozak at 5' end site.
VR Ck Fw: ACG CGT CGA CCA CCA TGA TAT TCC GAG TCA GTG C (SEQ ID NO: 170) was prepared by adding a SalI recognition sequence at 5' end site, and VR KI Rv: GGC CGG CCC TAG GCA GGC CCT GCA GAT GTG AGT GG (SEQ ID NO: 171) was prepared by adding a FseI recognition sequence at 5' end site. PCR was carried out using the GIPF KI vector as template. The PCR product was digested with restriction enzymes SalI and FseI, and then VR+kz was obtained.

The forward (VR Fw; SEQ ID NO: 172) and reverse (VR KI Rv; SEQ ID NO: 173) primers for PCR were synthesized based on the sequence of GenBank (Accession Number AK098225), and used to amplify the DNA of GIPF variant. VR Fw: ATG ATA TTC CGA GTC AGT GCC GAG GGG AGC CAG (SEQ ID NO: 172) was prepared by adding a phosphoric acid at 5' end site, and VR KI Rv: GGC CGG CCC TAG GCA GGC CCT GCA GAT GTG AGT GG (SEQ ID NO: 173) was prepared by adding a FseI recognition sequence at 5' end site. PCR was carried out using the GIPF KI vector as template. The PCR product was digested with restriction enzyme FseI, and then the VR was obtained.

Figures 68B, 68C:
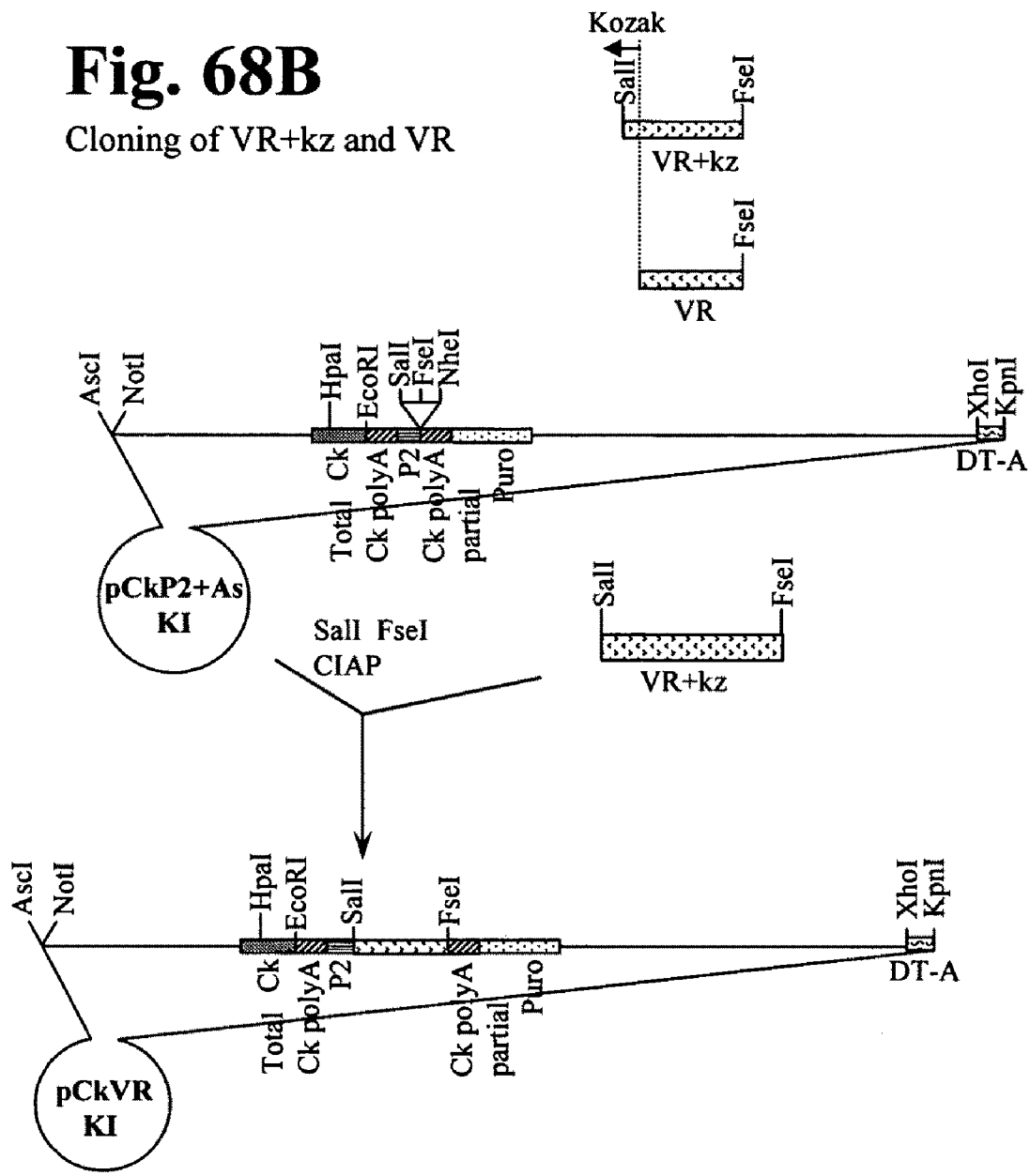

FIG. 68C Construction of pCk VR KI Vector

The VR+kz was ligated into pCkP2+As KI that was pre-digested with the restriction enzymes SalI and FseI. The resulting pCk VR KI vector contained the VR+kz, that was used for the generation of the GIPF variant mice.

B. Construction of the pPS VR KI Vector.

Figure 69A:
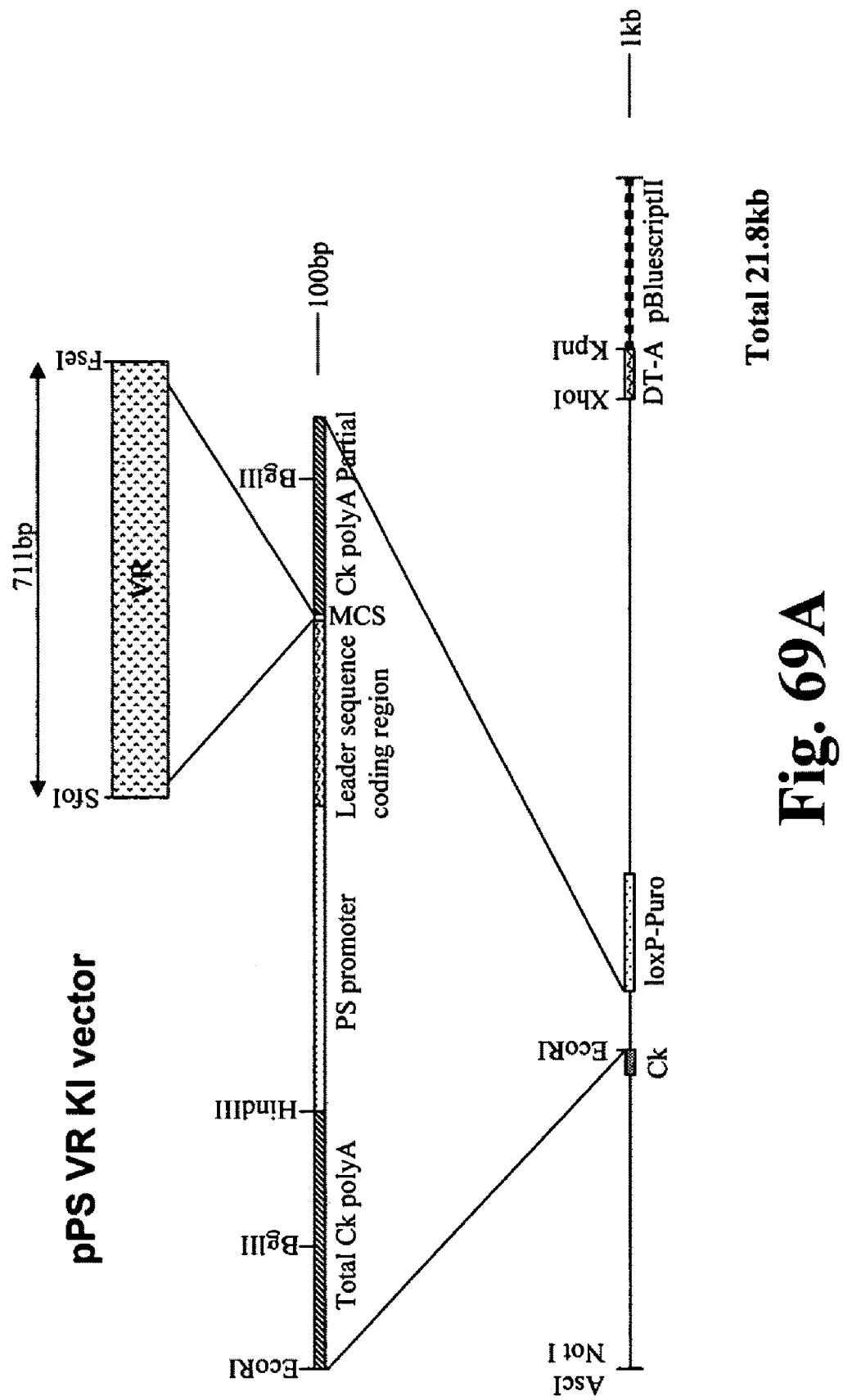

The construction of the GIPF variant PS knock-in (pPS VR KI) vector (FIG. 69A) was performed according to the method described below, and depicted in FIGS. 69B-69C.

FIG. 69B Preparation of pPSs3.8VR

The VR was ligated into pPSs3.8 that was pre-digested with the restriction enzymes SfoI and FseI. The resulting pPSs3.8VR contained the VR.

FIG. 69C Construction of pPS VR KI Vector pPSs3.8VR was digested with SalI and FseI, and the resulting about 1.5 Kb long fragment was separated and recovered from agarose gel electrophoresis. The 1.5 Kb fragment was ligated into □CkP2ΔP that was pre-digested with the restriction enzymes SalI and FseI. The resulting pPS VR KI vector contained the 1.5 Kb fragment, that was used for the generation of the GIPF variant mice.

C. Generation of GIPF Variant Mice

General procedures for obtaining mouse embryos, cultivation, injection of the ES cells into the embryos, transplantation to the uteri of foster mothers were carried out in accordance with the method described in Aizawa Shinichi, "Biomanual Series 8, Gene Targeting", published by Yodosha, 1995.

The pCkVR KI vector and pPSVR KI vector were linearized with Not I and transferred into RS-KO mouse ES cells by electroporation according to the method described by Shinichi Aizawa, "Biomanual Series 8, Gene Targeting", published by Yodosha, 1995. The electroporated RS-KO mouse ES cells were suspended in 20 ml of ES medium [DMEM (GIBCO), 18% FBS (GIBCO), 0.1 mM 2-mercaptoethanol (GIBCO), 1000 U/ml LIF (leukemia inhibitory factor, CHEMICON International, Inc.)] and inoculated into two 100 mm tissue culture plastic plates (Corning) into which feeder cells (Invitrogen) were seeded in advance. After one day, the medium was replaced with a medium containing 0.75 g/ml of puromycin (Sigma). Seven to nine days thereafter, 24 colonies formed from pCkVR KI vector electroporated RS-KO mouse ES cells and 24 colonies formed from pPSVR KI vector electroporated RS-KO mouse ES cells were picked up, respectively. Each colony was grown up to confluence in a 12-well plate, and then two third of the culture was suspended in 0.2 ml of cryopreservation medium [FBS+10% DMSO (Sigma)] and stored frozen at −80° C. The remaining one third was inoculated into a 12-well gelatin coated plate and cultured for 2 days. Then, genomic DNA was isolated using the Puregene DNA Isolation Kit (Gentra System). Genomic DNA isolated from puromycin resistant RS-KO mouse ES cells was digested with restriction enzyme EcoR I (Takara Shuzo) and then subjected to 0.8% agarose gel electrophoresis. Separated DNA fragments were transferred to a membrane (GeneScreen, NEN™ Life Science Products) and then hybridization was carried out using the DNA fragment as probe prepared from 3' region of IgJκ-Cκgenomic DNA (Xho I-EcoR I, 1.3 Kb (SEQ ID NO: 67): WO 00/10383, Example No. 48). The band pattern of untargeted ES clone shows one band of MW of 15.6 Kb. pCkVR KI targeted RS-KO mouse ES clone shows two bands of MW of 15.6 Kb and 13.1 Kb and pPSVR KI targeted RS-KO mouse ES clone shows two bands of MW of 15.6 Kb and 12.9 Kb, respectively (FIGS. 70 and 71). One out of 12 pCkVR KI targeted RS-KO mouse ES clones #3 was selected after Southern analysis (rate of homologues recombination was about 37.5%) and one out of 8 PPSVR KI targeted RS-KO mouse ES clone #14 was selected after Southern analysis (rate of homologues recombination was about 25%). The selected ES clones were also tested by karyotype analysis according to the method described by Shinichi Aizawa, "Biomanual Series 8, Gene Targeting", published by Yodosha, 1995. One clone #3 of pCkVR KI targeted RS-KO mouse ES clones and one clone #14 of PPSVR KI targeted RS-KO mouse ES clones that showed normal karyotype were used for implantation into embryos, respectively.

The cells in a frozen stock of the pCkVR KI targeted RS-KO mouse ES cell clone #3 and the pPSVR KI targeted RS-KO mouse ES cell clone #14 were thawed, started to culture and injected into 8-cell stage embryos obtained by mating a male and a female mouse of Immunoglobulin heavy chain knock out mouse strain (Tomizuka et. Al. Proc. Natl. Acad. Sci. USA, 97: 722-727, 2000); the injection rate was 10-12 cells per embryo. After the embryos were cultured overnight in the medium for ES cells to develop into blastocysts, about ten of the ES cell-injected embryos were transplanted to each side of the uterus of a foster mother ICR mouse (CREA JAPAN, INC.), which had been subjected to a pseudopregnant treatment for 2.5 days. As a result of transplantation of each of 220 injected embryos, 68 and 60 offspring mice were born, respectively. Chimerism in the offspring was determined by the extent of TT2F cell-derived agouti coat color (dark brown) in the host embryo (ICR)-derived albino coat color. Out of the 68 offspring, 47 mice (pCkVR knock-in mice) were recognized to have partial agouti coat color, indicating the contribution of the RS-KO mouse ES cells and out of the 60 offspring, 38 mice (PPSVR knock-in mice) were recognized to have partial agouti coat color, indicating the contribution of the RS-KO mouse ES cells. GIPF variant mice were obtained same as described above from the other clones of the pCkVR KI targeted RS-KO mouse ES cells and the pPSVR KI targeted RS-KO mouse ES cells.

Mice were kept under a 12/12-hour dark/light cycle (lights on at 8:00 am) and received 5 μm filtered water and CE-2 food (CLEA JAPAN, INC.) ad libitum. Male mice were housed individually after weaning period.

Example 35

Evaluation of the Biological Activity of GIPF Deletion Mutant Using Transgenic GIPF Deletion Mutant-KI Mice The gross pathological changes and the histological changes of the small intestine and colon from the transgenic mice described above were evaluated as follows. GIPF deletion mutant-KI (Ckm4-KI and PSm4-KI) mice were harvested at 4 weeks of age. Gross appearance of GIPF deletion mutant-KI gastrointestinal tract showed little difference compared to control (FIG. 72). For histopathological evaluation, gastrointestinal tract were removed and fixed in formalin. Paraffin embedded sections were stained with hematoxiyline and eosin (H&E) for histological evaluation. H&E sections of small intestine were shown FIG. 73 (low magnification) and FIG. 74 (high magnification).

H&E sections from GIPF deletion mutant-KI mouse small intestine revealed mild increase of crypt length and number compared to control. The increase of crypt length and number in PSm4-KI was tended to be greater than Ckm4-KI.

Expression of GIPF deletion mutant #4 gene expression and the induction of β-catenin targeted Axin-2 gene expression were analyzed using small intestine and colon samples derived from GIPF deletion mutant-KI mice. 50 mg of ileum, colon and liver samples were removed and rapidly froze by use of liquid nitrogen. Frozen sections were homogenized with 1 ml of ISOGEN (NIPPON GENE) and total RNA was extracted under the recommended conditions. To remove genomic DNA, the RNA solution was treated with DNase (WAKO; Deoxyribonuclease RT grade) at 37° C. for 15 mins. Then total RNA was purified with RNasy Mini (QIAGEN) under the recommended conditions. For each sample, cDNA was synthesized from 500 ng of total RNA using Super Script III (Invitrogen) under the recommended conditions. Then cDNA was treated with 1 unit of RNaseH (Invitrogen) at 37° C. for 20 mins to digest remaining RNA. PCR was carried out using synthesized cDNA as a template. The following two primers were used detection of GIPF deletion mutant: PSm4RT F1: ATCAAGGGGAAAAGGCAGAG (SEQ ID NO: 174), and CkpolyA R2: CGCTTGTGGGGAAGCCTCCAAGACC (SEQ ID NO: 175). For detection of Axin-2, following two primers were used: Axin2 F (MUS): CAGGAGCCTCACCCTTCG (SEQ ID NO: 138), and Axin2 R (MUS): ACGCCGAGGTGCTTGCCC (SEQ ID NO: 139). Mouse GAPDH primers: mGAPDH5: CACCATGGAGAAGGCCGGGGCCCAC (SEQ ID NO: 140), and mGAPDH3: ATCATACTTGGCAGGTTTCTCCAGG (SEQ ID NO: 141) were used for the detection of housekeeping gene expression. The reaction mixture of PCR was prepared by adding sterilized distilled water to 2.5 ul of 10×LA PCR Buffer II (Takara Shuzo), 4 ul of 2.5 mM each dNTP Mixture (Takara Shuzo), 0.5 ul of 10 mM each primer, 2 ul of 10× cDNA diluted with sterilized distilled water and 0.5 ul of LA Taq (Takara Shuzo) to make 25 ul. For detection of GIPF deletion mutant and Axin-2, reaction mixture of PCR was incubated at 94° C. for 2 mins, reaction of 33 cycles was carried out, with 94° C. for 30 seconds, 60° C. for 30 seconds and 72° C. for 30 seconds. For detection of GAPDH, reaction mixture of PCR was incubated at 94° C. for 2 mins, reaction of 22 cycles was carried out, with 94° C. for 30 seconds, 65° C. for 30 seconds and 72° C. for 30 seconds.

GIPF deletion mutant gene expression was detected in ileum and colon from PSm4-KI mice. The expression level of Axin-2 was increased in PSm4-KI mice compared to control (FIG. 75). This data suggested that deletion mutant form of GIPF had activity to induce β-catenin targeted gene expression and responsible for activation of down stream of β-catenin signaling pathway.

Thus it suggested that GIPF deletion mutant #4 had activity to stimulate β-catenin signaling pathway.

Example 36

Evaluation of the Biological Activity of GIPF Variant Using Transgenic GIPF Variant-KI Mice The gross pathological changes and the histological changes of the small intestine and colon from the transgenic mice described above were evaluated as follows. GIPF variant-KI (CkVR-KI and PSVR-KI) mice were harvested at 4 weeks of age. Gross appearance of harvested PSVR-KI showed that they had remarkable intestinal distension and increased small intestinal mass when compared to control mouse (FIG. 76). For histopathological evaluation, gastrointestinal tract were removed and fixed in formalin. Paraffin embedded sections were stained with hematoxiyline and eosin (H&E) for histological evaluation. H&E sections of small intestine were shown FIG. 77 (low magnification) and FIG. 78 (high magnification).

H&E sections from small intestine revealed remarkable difference between PSVR-KI and control. As shown FIG. 76, crypt cell hyperplasia of PSVR-KI demonstrated increased in crypt length and number of Paneth cells compared to control mouse. On the other hand, CkVR-KI did not show obvious intestinal distension or increase of crypt length (data not shown). The difference of observed phenotypes between CkVR-KI and PSVR-KI was estimated because of the difference of their KI-vector structure.

Expression of GIPF variant gene expression and the induction of β-catenin targeted Axin-2 gene expression were analyzed using small intestine and colon samples derived from GIPF variant-KI mice. 50 mg of ileum, colon and liver samples were removed and rapidly froze by use of liquid nitrogen. Frozen sections were homogenized with 1 ml of ISOGEN (NIPPON GENE) and total RNA was extracted under the recommended conditions. To remove genomic DNA, the RNA solution was treated with DNase (WAKO; Deoxyribonuclease RT grade) at 37° C. for 15 mins. Then total RNA was purified with RNasy Mini (QIAGEN) under the recommended conditions. For each sample, cDNA was synthesized from 500 ng of total RNA using Super Script III (Invitrogen) under the recommended conditions. Then cDNA was treated with 1 unit of RNaseH (Invitrogen) at 37° C. for 20 mins to digest remaining RNA. PCR was carried out using synthesized cDNA as a template. The following two primers were used detection of GIPF variant: PSFLJRT F1: ATAACTTCTGCACCAAGTGTAAGGA (SEQ ID NO: 176), and CkpolyA R2: CGCTTGTGGGGAAGCCTCCAAGACC (SEQ ID NO: 175). For detection of Axin-2, following two primers were used: Axin2 F (MUS): CAGGAGCCTCACCCTTCG (SEQ ID NO: 138), and Axin2 R (MUS): ACGCCGAGGTGCTTGCCC (SEQ ID NO: 139). Mouse GAPDH primers: mGAPDH5: CACCATGGAGAAGGCCGGGGCCCAC (SEQ ID NO: 140), and mGAPDH3: ATCATACTTGGCAGGTTTCTCCAGG (SEQ ID NO: 141) were used for the detection of housekeeping gene expression. The reaction mixture of PCR was prepared by adding sterilized distilled water to 2.5 ul of 10×LA PCR Buffer II (Takara Shuzo), 4 ul of 2.5 mM each dNTP Mixture (Takara Shuzo), 0.5 ul of 10 mM each primer, 2 ul of 10× cDNA diluted with sterilized distilled water and 0.5 ul of LA Taq (Takara Shuzo) to make 25 ul. For detection of GIPF variant and Axin-2, reaction mixture of PCR was incubated at 94° C. for 2 mins, reaction of 33 cycles was carried out, with 94° C. for 30 seconds, 60° C. for 30 seconds and 72° C. for 30 seconds. For detection of GAPDH, reaction mixture of PCR was incubated at 94° C. for 2 mins, reaction of 23 cycles was carried out, with 94° C. for 30 seconds, 65° C. for 30 seconds and 72° C. for 30 seconds.

GIPF variant gene expression was detected in ileum and colon from PSVR-KI mice. The expression level of Axin-2 was increased in PSVR-KI mouse compared to control (FIG. 79). This data suggested that GIPF variant had activity to induce β-catenin targeted gene expression and responsible for activation of down stream of β-catenin signaling pathway.

Thus it indicated that GIPF variant had activity to stimulate β-catenin signaling pathway.

Example 37

CD4+CD45RB$^{high}$ T-Cell Transfer Model

Induction of chronic intestinal inflammation similar to inflammatory bowel disease by transferring CD4+ CD45RB$^{high}$ T lymphocyte subsets to immunodeficient SCID mice was reported by Aranda et al., (J Immunol 158: 3464-3473). Accordingly, the therapeutic efficacy of GIPF to immunologically induced colitis was tested in a CD4+ CD45RB$^{high}$ T-cell transferred model as follows.

Adult female C.B-17/Icr Crj-scid/scid mice (CHARLES RIVER JAPAN, INC.), aged 7 weeks were used. On delivery from the supplier and prior to experiment, the animals were housed for two weeks in individually ventilated cages on a 12 hour light:dark cycle to atbilize the circadian rhythm. Animals were allowed to food and water ad libitum.

At the day cell transfer (day 0), CD4+CD45RB$^{high}$ T-cells were collected form spleens of 20 BALB/c female mice. Splenocytes were suspended in 2% FBS, 2 mM EDTA, PBS sorting buffer and CD4 positive cells were sorted by FACS (Becton Dickinson FACS Aria). Then sorted CD4 positive cells were resuspended in sorting buffer to 2×10$^7$ cells/ml and CD4 positive and CD45RB$^{high}$ cell fraction was gated. Collected CD4+CD45RB$^{high}$ T-cells were centrifuged and suspended in 6 ml of PBS to 1.1×10$^6$ cells/ml. 4.5×10$^5$ cells/ mouse of CD4+CD45RB$^{high}$ T-cells were transferred to 13 female C.B-17/Icr Crj-scid/scid mice by ip injection.

After T-cell transfer, serum amyloid A(SAA) concentration was monitored for inflammation progress. Also, progression of colitis was monitored by reduction of body weight, stool consistency and occult blood test. SAA concentration was increased from 7 days after transfer and inflammatory was elucidated in T-cell transferred mice. 12 days after T-cell transfer, loose stool and occult blood positive individuals were appeared. 30 days after T-cell transfer, diarrhea and gross bleeding were observed in T-cell transferred mice. Further 40 days, body weight loss was observed in T-cell transferred mice. From day 61 after T-cell transfer, 100 ug/dose GIPF was injected iv for 3 days to 4 of T-cell transferred mice. Also PBS was injected iv for 3 days to 3 of T-cell transferred mice as negative control. At 70 days after T-cell transfer, these animals were sacrificed. The intestine was removed and fixed in formalin. Paraffin embedded sections were stained with hematoxylin and eosin (H&E) for histological evaluation.

As shown FIG. 80, H&E staining of sections from the large intestine that injected 100 ug/dose of GIPF showed clear gland structures, increased in the number of mitotic cell and less necrotic cell debris compared to PBS injected mice. The histopathological changes in large intestinal mucosa caused by T-cell transfer were actually reduced by GIPF injection. Therefore, GIPF may be used for treating patients suffering from mucositis caused by inflammatory bowel disease including Crohn's disease.

The invention claimed is:

1. A method of stimulating epithelial cell proliferation in the gastrointestinal tract or oral cavity of a subject in need thereof, comprising administering to the subject a therapeutically effective amount of a composition comprising a polypeptide, wherein said polypeptide comprises (i) the amino acid sequence of SEQ ID NO: 4, 10, 12 or 91 or (ii) an amino acid sequence with at least 90% sequence identity to the amino acid sequence of SEQ ID NO: 4, 10, 12 or 91.

2. The method of claim 1, wherein the method comprises stimulating epithelial cell proliferation in the esophagus.

3. The method of claim 1, wherein the method comprises stimulating epithelial cell proliferation in the small intestine.

4. The method of claim 1, wherein the method comprises stimulating epithelial cell proliferation in the large intestine.

5. The method of claim 1, wherein the method comprises stimulating epithelial cell proliferation in the stomach.

6. The method of claim 1, wherein the subject has undergone or will undergo radiation therapy or chemotherapy.

7. The method of claim 1, wherein the subject is a human.

* * * * *

SEQUENCE LISTING

```
<160> NUMBER OF SEQ ID NOS: 178

<210> SEQ ID NO 1
<211> LENGTH: 380
<212> TYPE: DNA
<213> ORGANISM: Homo sapiens

<400> SEQUENCE: 1
ttcccgggtc gacttcacgc gtcggaggaa gggaggccag ggccggcggg agaatgccaa      60
caggaacctg gccaggaagg agagcaagga ggcgggtgct ggctctcgaa gacgcaaggg     120
gcagcaacag cagcagcagc aagggacagt gggccactc acatctgcag ggcctgccta     180
gggacactgt ccagcctcca ggcccatgca gaaagagttc agtgctactc tgcgtgattc     240
aagctttcct gaactggaac gtcgggggca aagcatacac acacactcca atccatccat     300
gcatacacag acacaagaca cacacgctca aacccctgtc cacatataca accatacata     360
cttgcacatg tgtgttcatg                                                 380

<210> SEQ ID NO 2
<211> LENGTH: 2339
<212> TYPE: DNA
<213> ORGANISM: Homo sapiens

<400> SEQUENCE: 2
```

```
cgggtcgacg atttcgtcgc gccctcgccc ctcccgggcc tgcccccgtc gcgactggca      60
gcacgaagct gagattgtgg tttcctggtg attcaggtgg gagtgggcca gaagatcacc     120
gctggcaagg actggtgttt gtcaactgta aggactcatg aacagatct accagggatt     180 ctcagacctt agtttgagaa atgctgcaat taaaggcaaa tcctatcact ctgagtgatc     240
gctttggtgt cgaggcaatc aaccataaag ataaatgcaa atatggaaat tgcataacag     300
tactcagtat taaggttggt ttttggagta gtccctgctg acgtgacaaa aagatctctc     360
atatgatatt ccgaggtatc tttgaggaag tctctctttg aggacctccc tttgagctga     420
tggagaactg ggctccccac accctctctg tccccagctg agattatggt ggatttgggc     480
tacggcccag gcctgggcct cctgctgctg acccagcccc agaggtgtta gcaagagccg     540
tgtgctatcc accctccccg agaccacccc tccgaccagg gcctggagc tggcgcgtga     600 ctatgcggct tgggctgtgt gtggtggccc tggttctgag ctggacgcac ctcaccatca     660
gcagccgggg gatcaagggg aaaaggcaga ggcggatcag tgccgagggg agccaggcct     720
gtgccaaagg ctgtgagctc tgctctgaag tcaacggctg cctcaagtgc tcacccaagc     780
tgttcatcct gctggagagg aacgacatcc gccaggtggg cgtctgcttg ccgtcctgcc     840
cacctggata cttcgacgcc cgcaaccccg acatgaacaa gtgcatcaaa tgcaagatcg     900
agcactgtga ggcctgcttc agccataact tctgcaccaa gtgtaaggag gcttgtacc     960 tgcacaaggg ccgctgctat ccagcttgtc ccgagggctc ctcagctgcc aatggcacca    1020
tggagtgcag tagtcctgcg caatgtgaaa tgagcgagtg gtctccgtgg gggccctgct    1080
ccaagaagca gcagctctgt ggtttccgga ggggctccga ggagcggaca cgcagggtgc    1140
tacatgcccc tgtgggggac catgctgcct gctctgacac caaggagacc cggaggtgca    1200
cagtgaggag agtgccgtgt cctgaggggc agaagaggag gaagggaggc cagggccggc    1260
gggagaatgc caacaggaac ctggccagga aggagagcaa ggaggcgggt gctggctctc    1320
gaagacgcaa ggggcagcaa cagcagcagc agcaagggac agtggggcca ctcacatctg    1380
cagggcctgc ctaggacac tgtccagcct ccaggcccat gcagaaagag ttcagtgcta    1440
ctctgcgtga ttcaagcttt cctgaactgg aacgtcgggg gcaaagcata cacacacact    1500
ccaatccatc catgcataca cagacacaag acacacacgc tcaaacccct gtccacatat    1560
acaaccatac atacttgcac atgtgtgttc atgtacacac gcagacacag acaccacaca    1620
cacacataca cacacacaca cacacgcaca cctgaggcca ccagaagaca cttccatccc    1680
tcgggcccag cagtacacac ttggtttcca gagctcccag tggacatgtc agagacaaca    1740
cttcccagca tctgagacca aactgcagag gggagccttc tggagaagct gctgggatcg    1800
gaccagccac tgtggcagat gggagccaag cttgaggact gctggtggcc tgggaagaaa    1860
ccttcttccc atcctgttca gcactcccag ctgtgtgact ttatcgttgg agagtattgt    1920
taccttccag gatacatatc agggttaacc tgactttgaa aactgcttaa aggtttattt    1980
caaattaaaa caaaaaaatc aacgacagca gtagacacag gcaccacatt cctttgcagg    2040
gtgtgagggt ttggcgaggt atgcgtagga gcaagaaggg acaggaatt tcaagagacc    2100 ccaaatagcc tgctcagtag agggtcatgc agacaaggaa gaaaacttag gggctgctct    2160
gacggtggta aacaggctgt ctatatcctt gttactcaga gcatggcccg gcagcagtgt    2220
tgtcacaggg cagcttgtta ggaatgataa tctcaggtct cattccagac ctggagagcc    2280
atgagtctaa attttaagat tcctgatgat tggcatgtta cccaaatttg agaagtgct    2339
```

<210> SEQ ID NO 3

<211> LENGTH: 789
<212> TYPE: DNA
<213> ORGANISM: Homo sapiens

<400> SEQUENCE: 3

```
atgcggcttg ggctgtgtgt ggtggccctg gttctgagct ggacgcacct caccatcagc      60
agccggggga tcaaggggaa aaggcagagg cggatcagtg ccgagggag ccaggcctgt      120
gccaaaggct gtgagctctg ctctgaagtc aacggctgcc tcaagtgctc acccaagctg     180
ttcatcctgc tggagaggaa cgacatccgc caggtgggcg tctgcttgcc gtcctgccca     240
cctggatact cgacgcccg caaccccgac atgaacaagt gcatcaaatg caagatcgag     300
cactgtgagg cctgcttcag ccataacttc tgcaccaagt gtaaggaggg cttgtacctg    360
cacaagggcc gctgctatcc agcttgtccc gagggctcct cagctgccaa tggcaccatg    420
gagtgcagta gtcctgcgca atgtgaaatg agcgagtggt ctccgtgggg gccctgctcc    480
aagaagcagc agctctgtgg tttccggagg ggctccgagg agcggacacg cagggtgcta    540
catgcccctg tggggaccca tgctgcctgc tctgacacca aggagacccg gaggtgcaca    600
gtgaggagag tgccgtgtcc tgaggggcag aagaggagga agggaggcca gggcggcgg    660
gagaatgcca acaggaacct ggccaggaag gagagcaagg aggcgggtgc tggctctcga    720
agacgcaagg ggcagcaaca gcagcagcag caagggacag tggggccact cacatctgca    780
gggcctgcc                                                            789
```

<210> SEQ ID NO 4
<211> LENGTH: 263
<212> TYPE: PRT
<213> ORGANISM: Homo sapiens

<400> SEQUENCE: 4

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205
```

Gly Gln Lys Arg Arg Lys Gly Gly Gln Gly Arg Glu Asn Ala Asn
            210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 5
<211> LENGTH: 927
<212> TYPE: DNA
<213> ORGANISM: Artificial sequence
<220> FEATURE:
<223> OTHER INFORMATION: GIPF V5His tag

<400> SEQUENCE: 5

| | | |
|---|---|---|
| atgcggcttg ggctgtgtgt ggtggccctg gttctgagct ggacgcacct caccatcagc | 60 |
| agccggggga tcaaggggaa aaggcagagg cggatcagtg ccgaggggag ccaggcctgt | 120 |
| gccaaaggct gtgagctctg ctctgaagtc aacggctgcc tcaagtgctc acccaagctg | 180 |
| ttcatcctgc tggagaggaa cgacatccgc caggtgggcg tctgcttgcc gtcctgccca | 240 |
| cctggatact cgacgcccg caaccccgac atgaacaagt gcatcaaatg caagatcgag | 300 |
| cactgtgagg cctgcttcag ccataacttc tgcaccaagt gtaaggaggg cttgtacctg | 360 |
| cacaagggcc gctgctatcc agcttgtccc gagggctcct cagctgccaa tggcaccatg | 420 |
| gagtgcagta gtcctgcgca atgtgaaatg agcgagtggt ctccgtgggg gccctgctcc | 480 |
| aagaagcagc agctctgtgg tttccggagg ggctccgagg agcggacacg cagggtgcta | 540 |
| catgcccctg tggggaccca tgctgcctgc tctgacacca aggagacccg gaggtgcaca | 600 |
| gtgaggagag tgccgtgtcc tgaggggcag aagaggagga agggaggcca gggccggcgg | 660 |
| gagaatgcca acaggaacct ggccaggaag gagagcaagg aggcgggtgc tggctctcga | 720 |
| agacgcaagg ggcagcaaca gcagcagcag caagggacag tggggccact cacatctgca | 780 |
| gggcctgcca agggcaattc tgcagatatc cagcacagtg gcggccgctc gagtctagag | 840 |
| ggcccgcggt tcgaaggtaa gcctatccct aaccctctcc tcggtctcga ttctacgcgt | 900 |
| accggtcatc atcaccatca ccattga | 927 |

<210> SEQ ID NO 6
<211> LENGTH: 308
<212> TYPE: PRT
<213> ORGANISM: Artificial sequence
<220> FEATURE:
<223> OTHER INFORMATION: GIPF V5His tag

<400> SEQUENCE: 6

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

```
Pro Gly Tyr Phe Asp Ala Arg Asn Pro Asp Met Asn Lys Cys Ile Lys
                 85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala Lys Gly Asn Ser Ala Asp Ile Gln His
            260                 265                 270

Ser Gly Gly Arg Ser Ser Leu Glu Gly Pro Arg Phe Glu Gly Lys Pro
        275                 280                 285

Ile Pro Asn Pro Leu Leu Gly Leu Asp Ser Thr Arg Thr Gly His His
    290                 295                 300

His His His His
305

<210> SEQ ID NO 7
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 7 atg cgg ctt ggg ctg tgt gtg gtg gcc ctg gtt ctg agc tgg acg cac      48
Met Arg Leu Gly Leu Cys Val Val Ala Leu Val Leu Ser Trp Thr His
1               5                   10                  15 ctc acc atc agc                                                      60
Leu Thr Ile Ser
            20

<210> SEQ ID NO 8
<211> LENGTH: 20
<212> TYPE: PRT
<213> ORGANISM: Homo sapiens

<400> SEQUENCE: 8

Met Arg Leu Gly Leu Cys Val Val Ala Leu Val Leu Ser Trp Thr His
1               5                   10                  15

Leu Thr Ile Ser
            20

<210> SEQ ID NO 9
```

<211> LENGTH: 732
<212> TYPE: DNA
<213> ORGANISM: Homo sapiens
<220> FEATURE:
<221> NAME/KEY: CDS
<222> LOCATION: (1)..(729)

<400> SEQUENCE: 9

| | | | | | | | | | | | | | | | | |
|---|---|---|---|---|---|---|---|---|---|---|---|---|---|---|---|---|
| agc | cgg | ggg | atc | aag | ggg | aaa | agg | cag | agg | cgg | atc | agt | gcc | gag | ggg | 48 |
| Ser | Arg | Gly | Ile | Lys | Gly | Lys | Arg | Gln | Arg | Arg | Ile | Ser | Ala | Glu | Gly | |
| 1 | | | | 5 | | | | | 10 | | | | | 15 | | |
| agc | cag | gcc | tgt | gcc | aaa | ggc | tgt | gag | ctc | tgc | tct | gaa | gtc | aac | ggc | 96 |
| Ser | Gln | Ala | Cys | Ala | Lys | Gly | Cys | Glu | Leu | Cys | Ser | Glu | Val | Asn | Gly | |
| | | | 20 | | | | | 25 | | | | | 30 | | | |
| tgc | ctc | aag | tgc | tca | ccc | aag | ctg | ttc | atc | ctg | ctg | gag | agg | aac | gac | 144 |
| Cys | Leu | Lys | Cys | Ser | Pro | Lys | Leu | Phe | Ile | Leu | Leu | Glu | Arg | Asn | Asp | |
| | 35 | | | | | 40 | | | | | 45 | | | | | |
| atc | cgc | cag | gtg | ggc | gtc | tgc | ttg | ccg | tcc | tgc | cca | cct | gga | tac | ttc | 192 |
| Ile | Arg | Gln | Val | Gly | Val | Cys | Leu | Pro | Ser | Cys | Pro | Pro | Gly | Tyr | Phe | |
| 50 | | | | | 55 | | | | | 60 | | | | | | |
| gac | gcc | cgc | aac | ccc | gac | atg | aac | aag | tgc | atc | aaa | tgc | aag | atc | gag | 240 |
| Asp | Ala | Arg | Asn | Pro | Asp | Met | Asn | Lys | Cys | Ile | Lys | Cys | Lys | Ile | Glu | |
| 65 | | | | | 70 | | | | | 75 | | | | | 80 | |
| cac | tgt | gag | gcc | tgc | ttc | agc | cat | aac | ttc | tgc | acc | aag | tgt | aag | gag | 288 |
| His | Cys | Glu | Ala | Cys | Phe | Ser | His | Asn | Phe | Cys | Thr | Lys | Cys | Lys | Glu | |
| | | | | 85 | | | | | 90 | | | | | 95 | | |
| ggc | ttg | tac | ctg | cac | aag | ggc | cgc | tgc | tat | cca | gct | tgt | ccc | gag | ggc | 336 |
| Gly | Leu | Tyr | Leu | His | Lys | Gly | Arg | Cys | Tyr | Pro | Ala | Cys | Pro | Glu | Gly | |
| | | | 100 | | | | | 105 | | | | | 110 | | | |
| tcc | tca | gct | gcc | aat | ggc | acc | atg | gag | tgc | agt | agt | cct | gcg | caa | tgt | 384 |
| Ser | Ser | Ala | Ala | Asn | Gly | Thr | Met | Glu | Cys | Ser | Ser | Pro | Ala | Gln | Cys | |
| | | 115 | | | | | 120 | | | | | 125 | | | | |
| gaa | atg | agc | gag | tgg | tct | ccg | tgg | ggg | ccc | tgc | tcc | aag | aag | cag | cag | 432 |
| Glu | Met | Ser | Glu | Trp | Ser | Pro | Trp | Gly | Pro | Cys | Ser | Lys | Lys | Gln | Gln | |
| | 130 | | | | | 135 | | | | | 140 | | | | | |
| ctc | tgt | ggt | ttc | cgg | agg | ggc | tcc | gag | gag | cgg | aca | cgc | agg | gtg | cta | 480 |
| Leu | Cys | Gly | Phe | Arg | Arg | Gly | Ser | Glu | Glu | Arg | Thr | Arg | Arg | Val | Leu | |
| 145 | | | | | 150 | | | | | 155 | | | | | 160 | |
| cat | gcc | cct | gtg | ggg | gac | cat | gct | gcc | tgc | tct | gac | acc | aag | gag | acc | 528 |
| His | Ala | Pro | Val | Gly | Asp | His | Ala | Ala | Cys | Ser | Asp | Thr | Lys | Glu | Thr | |
| | | | | 165 | | | | | 170 | | | | | 175 | | |
| cgg | agg | tgc | aca | gtg | agg | aga | gtg | ccg | tgt | cct | gag | ggg | cag | aag | agg | 576 |
| Arg | Arg | Cys | Thr | Val | Arg | Arg | Val | Pro | Cys | Pro | Glu | Gly | Gln | Lys | Arg | |
| | | | 180 | | | | | 185 | | | | | 190 | | | |
| agg | aag | gga | ggc | cag | ggc | cgg | cgg | gag | aat | gcc | aac | agg | aac | ctg | gcc | 624 |
| Arg | Lys | Gly | Gly | Gln | Gly | Arg | Arg | Glu | Asn | Ala | Asn | Arg | Asn | Leu | Ala | |
| | | 195 | | | | | 200 | | | | | 205 | | | | |
| agg | aag | gag | agc | aag | gag | gcg | ggt | gct | ggc | tct | cga | aga | cgc | aag | ggg | 672 |
| Arg | Lys | Glu | Ser | Lys | Glu | Ala | Gly | Ala | Gly | Ser | Arg | Arg | Arg | Lys | Gly | |
| | 210 | | | | | 215 | | | | | 220 | | | | | |
| cag | caa | cag | cag | cag | cag | caa | ggg | aca | gtg | ggg | cca | ctc | aca | tct | gca | 720 |
| Gln | Gln | Gln | Gln | Gln | Gln | Gly | Thr | Val | Gly | Pro | Leu | Thr | Ser | Ala | | |
| 225 | | | | | 230 | | | | | 235 | | | | | 240 | |
| ggg | cct | gcc | tag | | | | | | | | | | | | | 732 |
| Gly | Pro | Ala | | | | | | | | | | | | | | |

<210> SEQ ID NO 10
<211> LENGTH: 243
<212> TYPE: PRT
<213> ORGANISM: Homo sapiens

<400> SEQUENCE: 10

```
Ser Arg Gly Ile Lys Gly Lys Arg Gln Arg Ile Ser Ala Glu Gly
  1               5                  10                  15

Ser Gln Ala Cys Ala Lys Gly Cys Glu Leu Cys Ser Glu Val Asn Gly
             20                  25                  30

Cys Leu Lys Cys Ser Pro Lys Leu Phe Ile Leu Leu Glu Arg Asn Asp
         35                  40                  45

Ile Arg Gln Val Gly Val Cys Leu Pro Ser Cys Pro Pro Gly Tyr Phe
 50                  55                  60

Asp Ala Arg Asn Pro Asp Met Asn Lys Cys Ile Lys Cys Lys Ile Glu
 65              70                  75                  80

His Cys Glu Ala Cys Phe Ser His Asn Phe Cys Thr Lys Cys Lys Glu
             85                  90                  95

Gly Leu Tyr Leu His Lys Gly Arg Cys Tyr Pro Ala Cys Pro Glu Gly
                100                 105                 110

Ser Ser Ala Ala Asn Gly Thr Met Glu Cys Ser Ser Pro Ala Gln Cys
             115                 120                 125

Glu Met Ser Glu Trp Ser Pro Trp Gly Pro Cys Ser Lys Lys Gln Gln
    130                 135                 140

Leu Cys Gly Phe Arg Arg Gly Ser Glu Glu Arg Thr Arg Arg Val Leu
145                 150                 155                 160

His Ala Pro Val Gly Asp His Ala Ala Cys Ser Asp Thr Lys Glu Thr
                165                 170                 175

Arg Arg Cys Thr Val Arg Arg Val Pro Cys Pro Glu Gly Gln Lys Arg
            180                 185                 190

Arg Lys Gly Gly Gln Gly Arg Arg Glu Asn Ala Asn Arg Asn Leu Ala
            195                 200                 205

Arg Lys Glu Ser Lys Glu Ala Gly Ala Gly Ser Arg Arg Arg Lys Gly
            210                 215                 220

Gln Gln Gln Gln Gln Gln Gly Thr Val Gly Pro Leu Thr Ser Ala
225                 230                 235                 240

Gly Pro Ala

<210> SEQ ID NO 11
<211> LENGTH: 696
<212> TYPE: DNA
<213> ORGANISM: Homo sapiens
<220> FEATURE:
<221> NAME/KEY: CDS
<222> LOCATION: (1)..(696)

<400> SEQUENCE: 11 atc agt gcc gag ggg agc cag gcc tgt gcc aaa ggc tgt gag ctc tgc      48
Ile Ser Ala Glu Gly Ser Gln Ala Cys Ala Lys Gly Cys Glu Leu Cys
  1               5                  10                  15 tct gaa gtc aac ggc tgc ctc aag tgc tca ccc aag ctg ttc atc ctg      96
Ser Glu Val Asn Gly Cys Leu Lys Cys Ser Pro Lys Leu Phe Ile Leu
             20                  25                  30 ctg gag agg aac gac atc cgc cag gtg ggc gtc tgc ttg ccg tcc tgc     144
Leu Glu Arg Asn Asp Ile Arg Gln Val Gly Val Cys Leu Pro Ser Cys
         35                  40                  45 cca cct gga tac ttc gac gcc cgc aac ccc gac atg aac aag tgc atc     192
Pro Pro Gly Tyr Phe Asp Ala Arg Asn Pro Asp Met Asn Lys Cys Ile
 50                  55                  60 aaa tgc aag atc gag cac tgt gag gcc tgc ttc agc cat aac ttc tgc     240
Lys Cys Lys Ile Glu His Cys Glu Ala Cys Phe Ser His Asn Phe Cys
 65                  70                  75                  80 acc aag tgt aag gag ggc ttg tac ctg cac aag ggc cgc tgc tat cca     288
Thr Lys Cys Lys Glu Gly Leu Tyr Leu His Lys Gly Arg Cys Tyr Pro
```

```
                 85                  90                  95
gct tgt ccc gag ggc tca tca gct gcc aat ggc acc atg gag tgc agt       336
Ala Cys Pro Glu Gly Ser Ser Ala Ala Asn Gly Thr Met Glu Cys Ser
            100                 105                 110 agt cct gcg caa tgt gaa atg agc gag tgg tct ccg tgg ggg ccc tgc       384
Ser Pro Ala Gln Cys Glu Met Ser Glu Trp Ser Pro Trp Gly Pro Cys
            115                 120                 125 tcc aag aag cag cag ctc tgt ggt ttc cgg agg ggc tcc gag gag cgg       432
Ser Lys Lys Gln Gln Leu Cys Gly Phe Arg Arg Gly Ser Glu Glu Arg
            130                 135                 140 aca cgc agg gtg cta cat gcc cct gtg ggg gac cat gct gcc tgc tct       480
Thr Arg Arg Val Leu His Ala Pro Val Gly Asp His Ala Ala Cys Ser
145                 150                 155                 160 gac acc aag gag acc cgg agg tgc aca gtg agg aga gtg ccg tgt cct       528
Asp Thr Lys Glu Thr Arg Arg Cys Thr Val Arg Arg Val Pro Cys Pro
                165                 170                 175 gag ggg cag aag agg aag gga ggc cag ggc cgg cgg gag aat gcc           576
Glu Gly Gln Lys Arg Arg Lys Gly Gly Gln Gly Arg Arg Glu Asn Ala
            180                 185                 190 aac agg aac ctg gcc agg aag gag agc aag gag gcg ggt gct ggc tct       624
Asn Arg Asn Leu Ala Arg Lys Glu Ser Lys Glu Ala Gly Ala Gly Ser
            195                 200                 205 cga aga cgc aag ggg cag caa cag cag cag cag caa ggg aca gtg ggg       672
Arg Arg Arg Lys Gly Gln Gln Gln Gln Gln Gln Gln Gly Thr Val Gly
210                 215                 220 cca ctc aca tct gca ggg cct gcc                                       696
Pro Leu Thr Ser Ala Gly Pro Ala
225                 230

<210> SEQ ID NO 12
<211> LENGTH: 232
<212> TYPE: PRT
<213> ORGANISM: Homo sapiens

<400> SEQUENCE: 12

Ile Ser Ala Glu Gly Ser Gln Ala Cys Ala Lys Gly Cys Glu Leu Cys
1               5                   10                  15

Ser Glu Val Asn Gly Cys Leu Lys Cys Ser Pro Lys Leu Phe Ile Leu
            20                  25                  30

Leu Glu Arg Asn Asp Ile Arg Gln Val Gly Val Cys Leu Pro Ser Cys
        35                  40                  45

Pro Pro Gly Tyr Phe Asp Ala Arg Asn Pro Asp Met Asn Lys Cys Ile
    50                  55                  60

Lys Cys Lys Ile Glu His Cys Glu Ala Cys Phe Ser His Asn Phe Cys
65                  70                  75                  80

Thr Lys Cys Lys Glu Gly Leu Tyr Leu His Lys Gly Arg Cys Tyr Pro
                85                  90                  95

Ala Cys Pro Glu Gly Ser Ser Ala Ala Asn Gly Thr Met Glu Cys Ser
            100                 105                 110

Ser Pro Ala Gln Cys Glu Met Ser Glu Trp Ser Pro Trp Gly Pro Cys
            115                 120                 125

Ser Lys Lys Gln Gln Leu Cys Gly Phe Arg Arg Gly Ser Glu Glu Arg
            130                 135                 140

Thr Arg Arg Val Leu His Ala Pro Val Gly Asp His Ala Ala Cys Ser
145                 150                 155                 160

Asp Thr Lys Glu Thr Arg Arg Cys Thr Val Arg Arg Val Pro Cys Pro
                165                 170                 175

Glu Gly Gln Lys Arg Arg Lys Gly Gly Gln Gly Arg Arg Glu Asn Ala
```

```
                    180                 185                 190
Asn Arg Asn Leu Ala Arg Lys Glu Ser Lys Glu Ala Gly Ala Gly Ser
            195                 200                 205

Arg Arg Arg Lys Gly Gln Gln Gln Gln Gln Gln Gly Thr Val Gly
        210                 215                 220

Pro Leu Thr Ser Ala Gly Pro Ala
225                 230

<210> SEQ ID NO 13
<211> LENGTH: 168
<212> TYPE: DNA
<213> ORGANISM: Homo sapiens
<220> FEATURE:
<221> NAME/KEY: CDS
<222> LOCATION: (1)..(168)

<400> SEQUENCE: 13 agc gag tgg tct ccg tgg ggg ccc tgc tcc aag aag cag cag ctc tgt      48
Ser Glu Trp Ser Pro Trp Gly Pro Cys Ser Lys Lys Gln Gln Leu Cys
1               5                   10                  15 ggt ttc cgg agg ggc tcc gag gag cgg aca cgc agg gtg cta cat gcc      96
Gly Phe Arg Arg Gly Ser Glu Glu Arg Thr Arg Arg Val Leu His Ala
            20                  25                  30 cct gtg ggg gac cat gct gcc tgc tct gac acc aag gag acc cgg agg     144
Pro Val Gly Asp His Ala Ala Cys Ser Asp Thr Lys Glu Thr Arg Arg
        35                  40                  45 tgc aca gtg agg aga gtg ccg tgt                                     168
Cys Thr Val Arg Arg Val Pro Cys
    50                  55

<210> SEQ ID NO 14
<211> LENGTH: 56
<212> TYPE: PRT
<213> ORGANISM: Homo sapiens

<400> SEQUENCE: 14

Ser Glu Trp Ser Pro Trp Gly Pro Cys Ser Lys Lys Gln Gln Leu Cys
1               5                   10                  15

Gly Phe Arg Arg Gly Ser Glu Glu Arg Thr Arg Arg Val Leu His Ala
            20                  25                  30

Pro Val Gly Asp His Ala Ala Cys Ser Asp Thr Lys Glu Thr Arg Arg
        35                  40                  45

Cys Thr Val Arg Arg Val Pro Cys
    50                  55

<210> SEQ ID NO 15
<211> LENGTH: 756
<212> TYPE: DNA
<213> ORGANISM: Artificial sequence
<220> FEATURE:
<223> OTHER INFORMATION: GIPF +sigP-furin
<220> FEATURE:
<221> NAME/KEY: CDS
<222> LOCATION: (1)..(756)

<400> SEQUENCE: 15 atg cgg ctt ggg ctg tgt gtg gtg gcc ctg gtt ctg agc tgg acg cac      48
Met Arg Leu Gly Leu Cys Val Val Ala Leu Val Leu Ser Trp Thr His
1               5                   10                  15 ctc acc atc agc atc agt gcc gag ggg agc cag gcc tgt gcc aaa ggc      96
Leu Thr Ile Ser Ile Ser Ala Glu Gly Ser Gln Ala Cys Ala Lys Gly
            20                  25                  30 tgt gag ctc tgc tct gaa gtc aac ggc tgc ctc aag tgc tca ccc aag     144
```

```
Cys Glu Leu Cys Ser Glu Val Asn Gly Cys Leu Lys Cys Ser Pro Lys
             35                  40                  45 ctg ttc atc ctg ctg gag agg aac gac atc cgc cag gtg ggc gtc tgc    192
Leu Phe Ile Leu Leu Glu Arg Asn Asp Ile Arg Gln Val Gly Val Cys
 50                  55                  60 ttg ccg tcc tgc cca cct gga tac ttc gac gcc cgc aac ccc gac atg    240
Leu Pro Ser Cys Pro Pro Gly Tyr Phe Asp Ala Arg Asn Pro Asp Met
 65                  70                  75                  80 aac aag tgc atc aaa tgc aag atc gag cac tgt gag gcc tgc ttc agc    288
Asn Lys Cys Ile Lys Cys Lys Ile Glu His Cys Glu Ala Cys Phe Ser
                 85                  90                  95 cat aac ttc tgc acc aag tgt aag gag ggc ttg tac ctg cac aag ggc    336
His Asn Phe Cys Thr Lys Cys Lys Glu Gly Leu Tyr Leu His Lys Gly
                100                 105                 110 cgc tgc tat cca gct tgt ccc gag ggc tcc tca gct gcc aat ggc acc    384
Arg Cys Tyr Pro Ala Cys Pro Glu Gly Ser Ser Ala Ala Asn Gly Thr
                115                 120                 125 atg gag tgc agt agt cct gcg caa tgt gaa atg agc gag tgg tct ccg    432
Met Glu Cys Ser Ser Pro Ala Gln Cys Glu Met Ser Glu Trp Ser Pro
130                 135                 140 tgg ggg ccc tgc tcc aag aag cag cag ctc tgt ggt ttc cgg agg ggc    480
Trp Gly Pro Cys Ser Lys Lys Gln Gln Leu Cys Gly Phe Arg Arg Gly
145                 150                 155                 160 tcc gag gag cgg aca cgc agg gtg cta cat gcc cct gtg ggg gac cat    528
Ser Glu Glu Arg Thr Arg Arg Val Leu His Ala Pro Val Gly Asp His
                165                 170                 175 gct gcc tgc tct gac acc aag gag acc cgg agg tgc aca gtg agg aga    576
Ala Ala Cys Ser Asp Thr Lys Glu Thr Arg Arg Cys Thr Val Arg Arg
                180                 185                 190 gtg ccg tgt cct gag ggg cag aag agg agg aag gga ggc cag ggc cgg    624
Val Pro Cys Pro Glu Gly Gln Lys Arg Arg Lys Gly Gly Gln Gly Arg
                195                 200                 205 cgg gag aat gcc aac agg aac ctg gcc agg aag gag agc aag gag gcg    672
Arg Glu Asn Ala Asn Arg Asn Leu Ala Arg Lys Glu Ser Lys Glu Ala
210                 215                 220 ggt gct ggc tct cga aga cgc aag ggg cag caa cag cag cag cag caa    720
Gly Ala Gly Ser Arg Arg Arg Lys Gly Gln Gln Gln Gln Gln Gln Gln
225                 230                 235                 240 ggg aca gtg ggg cca ctc aca tct gca ggg cct gcc                    756
Gly Thr Val Gly Pro Leu Thr Ser Ala Gly Pro Ala
                245                 250

<210> SEQ ID NO 16
<211> LENGTH: 252
<212> TYPE: PRT
<213> ORGANISM: Artificial sequence
<220> FEATURE:
<223> OTHER INFORMATION: Synthetic Construct

<400> SEQUENCE: 16

Met Arg Leu Gly Leu Cys Val Val Ala Leu Val Leu Ser Trp Thr His
  1               5                  10                  15

Leu Thr Ile Ser Ile Ser Ala Glu Gly Ser Gln Ala Cys Ala Lys Gly
                 20                  25                  30

Cys Glu Leu Cys Ser Glu Val Asn Gly Cys Leu Lys Cys Ser Pro Lys
             35                  40                  45

Leu Phe Ile Leu Leu Glu Arg Asn Asp Ile Arg Gln Val Gly Val Cys
 50                  55                  60

Leu Pro Ser Cys Pro Pro Gly Tyr Phe Asp Ala Arg Asn Pro Asp Met
 65                  70                  75                  80
```

```
Asn Lys Cys Ile Lys Cys Lys Ile Glu His Cys Glu Ala Cys Phe Ser
                85                  90                  95
His Asn Phe Cys Thr Lys Cys Lys Glu Gly Leu Tyr Leu His Lys Gly
            100                 105                 110
Arg Cys Tyr Pro Ala Cys Pro Glu Gly Ser Ser Ala Ala Asn Gly Thr
        115                 120                 125
Met Glu Cys Ser Ser Pro Ala Gln Cys Glu Met Ser Glu Trp Ser Pro
    130                 135                 140
Trp Gly Pro Cys Ser Lys Lys Gln Leu Cys Gly Phe Arg Arg Gly
145                 150                 155                 160
Ser Glu Glu Arg Thr Arg Arg Val Leu His Ala Pro Val Gly Asp His
                165                 170                 175
Ala Ala Cys Ser Asp Thr Lys Glu Thr Arg Arg Cys Thr Val Arg Arg
            180                 185                 190
Val Pro Cys Pro Glu Gly Gln Lys Arg Arg Lys Gly Gly Gln Gly Arg
        195                 200                 205
Arg Glu Asn Ala Asn Arg Asn Leu Ala Arg Lys Glu Ser Lys Glu Ala
    210                 215                 220
Gly Ala Gly Ser Arg Arg Arg Lys Gly Gln Gln Gln Gln Gln Gln
225                 230                 235                 240
Gly Thr Val Gly Pro Leu Thr Ser Ala Gly Pro Ala
                245                 250

<210> SEQ ID NO 17
<211> LENGTH: 789
<212> TYPE: DNA
<213> ORGANISM: Artificial sequence
<220> FEATURE:
<223> OTHER INFORMATION: GIPF - mutated furin cleavage site
<220> FEATURE:

```
                           130                 135                 140
cct gcg caa tgt gaa atg agc gag tgg tct ccg tgg ggg ccc tgc tcc        480
Pro Ala Gln Cys Glu Met Ser Glu Trp Ser Pro Trp Gly Pro Cys Ser
145                 150                 155                 160 aag aag cag cag ctc tgt ggt ttc cgg agg ggc tcc gag gag cgg aca        528
Lys Lys Gln Gln Leu Cys Gly Phe Arg Arg Gly Ser Glu Glu Arg Thr
                165                 170                 175 cgc agg gtg cta cat gcc cct gtg ggg gac cat gct gcc tgc tct gac        576
Arg Arg Val Leu His Ala Pro Val Gly Asp His Ala Ala Cys Ser Asp
                180                 185                 190 acc aag gag acc cgg agg tgc aca gtg agg aga gtg ccg tgt cct gag        624
Thr Lys Glu Thr Arg Arg Cys Thr Val Arg Arg Val Pro Cys Pro Glu
                195                 200                 205 ggg cag aag agg agg aag gga ggc cag ggc cgg cgg gag aat gcc aac        672
Gly Gln Lys Arg Arg Lys Gly Gly Gln Gly Arg Arg Glu Asn Ala Asn
210                 215                 220 agg aac ctg gcc agg aag gag agc aag gag gcg ggt gct ggc tct cga        720
Arg Asn Leu Ala Arg Lys Glu Ser Lys Glu Ala Gly Ala Gly Ser Arg
225                 230                 235                 240 aga cgc aag ggg cag caa cag cag cag caa ggg aca gtg ggg cca            768
Arg Arg Lys Gly Gln Gln Gln Gln Gln Gln Gly Thr Val Gly Pro
                245                 250                 255 ctc aca tct gca ggg cct gcc                                            789
Leu Thr Ser Ala Gly Pro Ala
                260

<210> SEQ ID NO 18
<211> LENGTH: 263
<212> TYPE: PRT
<213> ORGANISM: Artificial sequence
<220> FEATURE:
<223> OTHER INFORMATION: Synthetic Construct

<400> SEQUENCE: 18

Met Arg Leu Gly Leu Cys Val Val Ala Leu Val Leu Ser Trp Thr His
1               5                   10                  15

Leu Thr Ile Ser Ser Arg Gly Ile Lys Gly Lys Gln Gln Arg Arg Ile
                20                  25                  30

Ser Ala Glu Gly Ser Gln Ala Cys Ala Lys Gly Cys Glu Leu Cys Ser
                35                  40                  45

Glu Val Asn Gly Cys Leu Lys Cys Ser Pro Lys Leu Phe Ile Leu Leu
            50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
                100                 105                 110

Lys Cys Lys Glu Gly Leu Tyr Leu His Lys Gly Arg Cys Tyr Pro Ala
                115                 120                 125

Cys Pro Glu Gly Ser Ser Ala Ala Asn Gly Thr Met Glu Cys Ser Ser
            130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
                180                 185                 190
```

```
Thr Lys Glu Thr Arg Arg Cys Thr Val Arg Arg Val Pro Cys Pro Glu
        195                 200                 205

Gly Gln Lys Arg Arg Lys Gly Gln Gly Arg Arg Glu Asn Ala Asn
        210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 19
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 19 agg cag agg cgg                                                     12
Arg Gln Arg Arg
1

<210> SEQ ID NO 20
<211> LENGTH: 4
<212> TYPE: PRT
<213> ORGANISM: Homo sapiens

<400> SEQUENCE: 20

Arg Gln Arg Arg
1

<210> SEQ ID NO 21
<211> LENGTH: 12
<212> TYPE: DNA
<213> ORGANISM: Artificial sequence
<220> FEATURE:
<223> OTHER INFORMATION: mutated furin protease cleavage site
<220> FEATURE:
<221> NAME/KEY: CDS
<222> LOCATION: (1)..(12)

<400> SEQUENCE: 21 cag cag agg cgg                                                     12
Gln Gln Arg Arg
1

<210> SEQ ID NO 22
<211> LENGTH: 4
<212> TYPE: PRT
<213> ORGANISM: Artificial sequence
<220> FEATURE:
<223> OTHER INFORMATION: Synthetic Construct

<400> SEQUENCE: 22

Gln Gln Arg Arg
1

<210> SEQ ID NO 23
<211> LENGTH: 272
<212> TYPE: PRT
<213> ORGANISM: Homo sapiens

<400> SEQUENCE: 23

Met His Leu Arg Leu Ile Ser Trp Leu Phe Ile Ile Leu Asn Phe Met
```

```
                1               5              10              15
Glu  Tyr  Ile  Gly  Ser  Gln  Asn  Ala  Ser  Arg  Gly  Arg  Arg  Gln  Arg  Arg
                    20                        25                        30

Met  His  Pro  Asn  Val  Ser  Gln  Gly  Cys  Gln  Gly  Gly  Cys  Ala  Thr  Cys
                    35                        40                        45

Ser  Asp  Tyr  Asn  Gly  Cys  Leu  Ser  Cys  Lys  Pro  Arg  Leu  Phe  Phe  Ala
                    50                        55                        60

Leu  Glu  Arg  Ile  Gly  Met  Lys  Gln  Ile  Gly  Val  Cys  Leu  Ser  Ser  Cys
 65                           70                        75                        80

Pro  Ser  Gly  Tyr  Tyr  Gly  Thr  Arg  Tyr  Pro  Asp  Ile  Asn  Lys  Cys  Thr
                    85                        90                        95

Lys  Cys  Lys  Ala  Asp  Cys  Asp  Thr  Cys  Phe  Asn  Lys  Asn  Phe  Cys  Thr
                    100                       105                       110

Lys  Cys  Lys  Ser  Gly  Phe  Tyr  Leu  His  Leu  Gly  Lys  Cys  Leu  Asp  Asn
                    115                       120                       125

Cys  Pro  Glu  Gly  Leu  Glu  Ala  Asn  Asn  His  Thr  Met  Glu  Cys  Val  Ser
                    130                       135                       140

Ile  Val  His  Cys  Glu  Val  Ser  Glu  Trp  Asn  Pro  Trp  Ser  Pro  Cys  Thr
145                           150                       155                       160

Lys  Lys  Gly  Lys  Thr  Cys  Gly  Phe  Lys  Arg  Gly  Thr  Glu  Thr  Arg  Val
                    165                       170                       175

Arg  Glu  Ile  Ile  Gln  His  Pro  Ser  Ala  Lys  Gly  Asn  Leu  Cys  Pro  Pro
                    180                       185                       190

Thr  Asn  Glu  Thr  Arg  Lys  Cys  Thr  Val  Gln  Arg  Lys  Lys  Cys  Gln  Lys
                    195                       200                       205

Gly  Glu  Arg  Gly  Lys  Lys  Gly  Arg  Glu  Arg  Lys  Arg  Lys  Lys  Pro  Asn
                    210                       215                       220

Lys  Gly  Glu  Ser  Lys  Glu  Ala  Ile  Pro  Asp  Ser  Lys  Ser  Leu  Glu  Ser
225                           230                       235                       240

Ser  Lys  Glu  Ile  Pro  Glu  Gln  Arg  Glu  Asn  Lys  Gln  Gln  Gln  Lys  Lys
                    245                       250                       255

Arg  Lys  Val  Gln  Asp  Lys  Gln  Lys  Ser  Val  Ser  Val  Ser  Thr  Val  His
                    260                       265                       270
```

<210> SEQ ID NO 24
<211> LENGTH: 16
<212> TYPE: PRT
<213> ORGANISM: Homo sapiens

<400> SEQUENCE: 24

```
Pro  Ala  Gln  Cys  Glu  Met  Ser  Glu  Trp  Ser  Pro  Trp  Gly  Pro  Cys  Ser
 1                 5                       10                      15
```

<210> SEQ ID NO 25
<211> LENGTH: 32
<212> TYPE: PRT
<213> ORGANISM: Homo sapiens

<400> SEQUENCE: 25

```
Gly  Lys  Arg  Gln  Arg  Arg  Ile  Ser  Ala  Glu  Gly  Ser  Gln  Ala  Cys  Ala
 1                 5                       10                      15

Lys  Gly  Cys  Glu  Leu  Cys  Ser  Gly  Val  Asn  Gly  Cys  Leu  Lys  Cys  Ser
                    20                      25                      30
```

<210> SEQ ID NO 26
<211> LENGTH: 17
<212> TYPE: PRT
<213> ORGANISM: Homo sapiens

```
<400> SEQUENCE: 26

Ile Glu His Cys Glu Ala Cys Phe Ser His Asn Phe Cys Thr Lys Cys
1               5                   10                  15
Lys

<210> SEQ ID NO 27
<211> LENGTH: 4
<212> TYPE: PRT
<213> ORGANISM: Homo sapiens

<400> SEQUENCE: 27

Asn Gly Thr Met
1

<210> SEQ ID NO 28
<211> LENGTH: 1170
<212> TYPE: PRT
<213> ORGANISM: Homo sapiens

<400> SEQUENCE: 28

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
                20                  25                  30

Ile Phe Glu Leu Thr Gly Ala Ala Arg Lys Gly Ser Gly Arg Arg Leu
            35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Thr Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
                100                 105                 110

Ser Gly Gln Val Phe Ser Val Val Ser Asn Gly Lys Ala Gly Thr Leu
            115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
    195                 200                 205

Gln Gly Val Leu Gln Asn Val Arg Phe Val Phe Gly Thr Thr Pro Glu
210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
    275                 280                 285
```

```
Thr Ile Val Thr Thr Leu Gln Asp Ser Ile Arg Lys Val Thr Glu Glu
    290                 295                 300
Asn Lys Glu Leu Ala Asn Glu Leu Arg Arg Pro Pro Leu Cys Tyr His
305                 310                 315                 320
Asn Gly Val Gln Tyr Arg Asn Asn Glu Glu Trp Thr Val Asp Ser Cys
                325                 330                 335
Thr Glu Cys His Cys Gln Asn Ser Val Thr Ile Cys Lys Lys Val Ser
            340                 345                 350
Cys Pro Ile Met Pro Cys Ser Asn Ala Thr Val Pro Asp Gly Glu Cys
        355                 360                 365
Cys Pro Arg Cys Trp Pro Ser Asp Ser Ala Asp Asp Gly Trp Ser Pro
    370                 375                 380
Trp Ser Glu Trp Thr Ser Cys Ser Thr Ser Cys Gly Asn Gly Ile Gln
385                 390                 395                 400
Gln Arg Gly Arg Ser Cys Asp Ser Leu Asn Asn Arg Cys Glu Gly Ser
                405                 410                 415
Ser Val Gln Thr Arg Thr Cys His Ile Gln Glu Cys Asp Lys Arg Phe
            420                 425                 430
Lys Gln Asp Gly Gly Trp Ser His Trp Ser Pro Trp Ser Ser Cys Ser
        435                 440                 445
Val Thr Cys Gly Asp Gly Val Ile Thr Arg Ile Arg Leu Cys Asn Ser
    450                 455                 460
Pro Ser Pro Gln Met Asn Gly Lys Pro Cys Glu Gly Glu Ala Arg Glu
465                 470                 475                 480
Thr Lys Ala Cys Lys Lys Asp Ala Cys Pro Ile Asn Gly Gly Trp Gly
                485                 490                 495
Pro Trp Ser Pro Trp Asp Ile Cys Ser Val Thr Cys Gly Gly Gly Val
            500                 505                 510
Gln Lys Arg Ser Arg Leu Cys Asn Asn Pro Thr Pro Gln Phe Gly Gly
        515                 520                 525
Lys Asp Cys Val Gly Asp Val Thr Glu Asn Gln Ile Cys Asn Lys Gln
    530                 535                 540
Asp Cys Pro Ile Asp Gly Cys Leu Ser Asn Pro Cys Phe Ala Gly Val
545                 550                 555                 560
Lys Cys Thr Ser Tyr Pro Asp Gly Ser Trp Lys Cys Gly Ala Cys Pro
                565                 570                 575
Pro Gly Tyr Ser Gly Asn Gly Ile Gln Cys Thr Asp Val Asp Glu Cys
            580                 585                 590
Lys Glu Val Pro Asp Ala Cys Phe Asn His Asn Gly Glu His Arg Cys
        595                 600                 605
Glu Asn Thr Asp Pro Gly Tyr Asn Cys Leu Pro Cys Pro Pro Arg Phe
    610                 615                 620
Thr Gly Ser Gln Pro Phe Gly Gln Gly Val Glu His Ala Thr Ala Asn
625                 630                 635                 640
Lys Gln Val Cys Lys Pro Arg Asn Pro Cys Thr Asp Gly Thr His Asp
                645                 650                 655
Cys Asn Lys Asn Ala Lys Cys Asn Tyr Leu Gly His Tyr Ser Asp Pro
            660                 665                 670
Met Tyr Arg Cys Glu Cys Lys Pro Gly Tyr Ala Gly Asn Gly Ile Ile
        675                 680                 685
Cys Gly Glu Asp Thr Asp Leu Asp Gly Trp Pro Asn Glu Asn Leu Val
    690                 695                 700
Cys Val Ala Asn Ala Thr Tyr His Cys Lys Lys Asp Asn Cys Pro Asn
```

-continued

```
            705                 710                 715                 720
Leu Pro Asn Ser Gly Gln Glu Asp Tyr Asp Lys Asp Gly Ile Gly Asp
                    725                 730                 735
Ala Cys Asp Asp Asp Asp Asn Asp Lys Ile Pro Asp Asp Arg Asp
            740                 745                 750
Asn Cys Pro Phe His Tyr Asn Pro Ala Gln Tyr Asp Tyr Asp Arg Asp
            755                 760                 765
Asp Val Gly Asp Arg Cys Asp Asn Cys Pro Tyr Asn His Asn Pro Asp
        770                 775                 780
Gln Ala Asp Thr Asp Asn Asn Gly Glu Gly Asp Ala Cys Ala Ala Asp
785                 790                 795                 800
Ile Asp Gly Asp Gly Ile Leu Asn Glu Arg Asp Asn Cys Gln Tyr Val
                805                 810                 815
Tyr Asn Val Asp Gln Arg Asp Thr Asp Met Asp Gly Val Gly Asp Gln
                820                 825                 830
Cys Asp Asn Cys Pro Leu Glu His Asn Pro Asp Gln Leu Asp Ser Asp
            835                 840                 845
Ser Asp Arg Ile Gly Asp Thr Cys Asp Asn Asn Gln Asp Ile Asp Glu
        850                 855                 860
Asp Gly His Gln Asn Asn Leu Asp Asn Cys Pro Tyr Val Pro Asn Ala
865                 870                 875                 880
Asn Gln Ala Asp His Asp Lys Asp Gly Lys Gly Asp Ala Cys Asp His
                885                 890                 895
Asp Asp Asp Asn Asp Gly Ile Pro Asp Asp Lys Asp Asn Cys Arg Leu
                900                 905                 910
Val Pro Asn Pro Asp Gln Lys Asp Ser Asp Gly Asp Gly Arg Gly Asp
                915                 920                 925
Ala Cys Lys Asp Asp Phe Asp His Asp Ser Val Pro Asp Ile Asp Asp
        930                 935                 940
Ile Cys Pro Glu Asn Val Asp Ile Ser Glu Thr Asp Phe Arg Arg Phe
945                 950                 955                 960
Gln Met Ile Pro Leu Asp Pro Lys Gly Thr Ser Gln Asn Asp Pro Asn
            965                 970                 975
Trp Val Val Arg His Gln Gly Lys Glu Leu Val Gln Thr Val Asn Cys
            980                 985                 990
Asp Pro Gly Leu Ala Val Gly Tyr Asp Glu Phe Asn Ala Val Asp Phe
            995                 1000                1005
Ser Gly Thr Phe Phe Ile Asn Thr Glu Arg Asp Asp Asp Tyr Ala
        1010                1015                1020
Gly Phe Val Phe Gly Tyr Gln Ser Ser Ser Arg Phe Tyr Val Val
        1025                1030                1035
Met Trp Lys Gln Val Thr Gln Ser Tyr Trp Asp Thr Asn Pro Thr
        1040                1045                1050
Arg Ala Gln Gly Tyr Ser Gly Leu Ser Val Lys Val Asn Ser
        1055                1060                1065
Thr Thr Gly Pro Gly Glu His Leu Arg Asn Ala Leu Trp His Thr
        1070                1075                1080
Gly Asn Thr Pro Gly Gln Val Arg Thr Leu Trp His Asp Pro Arg
        1085                1090                1095
His Ile Gly Trp Lys Asp Phe Thr Ala Tyr Arg Trp Arg Leu Ser
        1100                1105                1110
His Arg Pro Lys Thr Gly Phe Ile Arg Val Val Met Tyr Glu Gly
        1115                1120                1125
```

```
Lys Lys Ile Met Ala Asp Ser Gly Pro Ile Tyr Asp Lys Thr Tyr
1130                1135                1140

Ala Gly Gly Arg Leu Gly Leu Phe Val Phe Ser Gln Glu Met Val
1145                1150                1155

Phe Phe Ser Asp Leu Lys Tyr Glu Cys Arg Asp Pro
1160                1165                1170

<210> SEQ ID NO 29
<211> LENGTH: 23
<212> TYPE: DNA
<213> ORGANISM: Artificial sequence
<220> FEATURE:
<223> OTHER INFORMATION: forward primer

<400> SEQUENCE: 29
gaccatgctg cctgctctga cac                                          23

<210> SEQ ID NO 30
<211> LENGTH: 20
<212> TYPE: DNA
<213> ORGANISM: Artificial sequence
<220> FEATURE:
<223> OTHER INFORMATION: reverse primer

<400> SEQUENCE: 30
cacccgcctc cttgctctcc                                              20

<210> SEQ ID NO 31
<211> LENGTH: 22
<212> TYPE: DNA
<213> ORGANISM: Artificial sequence
<220> FEATURE:
<223> OTHER INFORMATION: forward primer

<400> SEQUENCE: 31
gggggagacc acaccacctg ct                                           22

<210> SEQ ID NO 32
<211> LENGTH: 24
<212> TYPE: DNA
<213> ORGANISM: Artificial sequence
<220> FEATURE:
<223> OTHER INFORMATION: reverse primer

<400> SEQUENCE: 32
ttggacctcg gctccttgct gttc                                         24

<210> SEQ ID NO 33
<211> LENGTH: 5495
<212> TYPE: DNA
<213> ORGANISM: Mus musculus
<220> FEATURE:
<221> NAME/KEY: misc_feature
<222> LOCATION: (1)..(5495)
<223> OTHER INFORMATION: n= G, A, T, or C

<400> SEQUENCE: 33
cttatctttc tcctttatta acggttgctg ttgtatccat aactcaattc caaaggatat    60
aaaccttaac atatagatat aattttgtgt accttctatg aaacagcatt aaagcaaaga   120
agttcaaata gaaagactgg cttagttatt attaactaag agatgctagt gagttctaaa   180
ttaataccat ttaaaattta taatttgcag aattaccacc accaccacca ctcagcccag   240
gaaaagttac aaagaactgg ctgtaccatt tgtttgtttt cctccttttt agagttcttt   300
tatttatgtg tgagtgaatg ccatgtactt gtggatgcag aggctgtcag attccttgca   360
```

```
gctggagtaa cagacagttg tgagctactt atagtactag aactaagatc ctatggaaga    420
gcagcgagtg ccactaactg ctgagccacc tctccagccc atttctttat ttttcaatga    480
acaaataata agcagtccta tgtgacatgc ttctaaagca aaagatataa tatttagtat    540
tatatacatt aataataaaa tacattatct tctaagaatt gaagtctcaa ctatgaaaat    600
cagcagttct ctgtcagaga agcccaagcg cttccacgca tgcttggaga gggggttaag    660
ctttcgccta cccactgctc tgttcctctt cagtgaggag ggttttttgta cagccagaca    720 gtggagtact accactgtgg tggacgttcg gtggaggcac caagctggaa atcaaacgta    780
agtagaatcc aaagtctctt tcttccgttg tctatgtctg tggcttctat gtctaaaaat    840
gatgtataaa atcttactct gaaaccagat tctggcactc tccaaggcaa agatacagag    900
taactccgta agcaaagctg gaataggct agacatgttc tctggagaat gaatgccagt    960
gtaataatta acacaagtga tagttttcaga aatgctcaaa gaagcagggt agcctgccct   1020
agacaaacct ttactcggtg ctcagaccat gctcagtttt tgtatggggg ttgagtgaag   1080
ggacaccagt gtgtgtacac gttcggaggg gggaccaagc tggaaataaa acgtaagtag   1140
tcttctcaac tcttgttcac taagtctaac cttgttaagt tgttctttgt tgtgtgtttt   1200
tcttaaggag atttcaggga tttagcaaat tccattctca gatcaggtgt taaggaggga   1260
aaactgtccc acaagaggtt ggaatgattt tcaggctaaa ttttaggctt tctaaaccaa   1320
agtaactaaa ctaggggaag agggataatt gtctacctag ggagggtttt gtggaggtaa   1380
agttaaaata aatcactgta aatcacattc agtgatggga ccagactgga aataaaacct   1440
aagtacattt ttgctcaact gcttgtgaag tttttggtccc attgtgtcct tgtatgagt    1500 ttgtggtgta cattagataa atgaactatt ccttgtaacc caaaacttaa atagaagaga   1560
accaaaaatc tagctactgt acaagctgag caaacagact gacctcatgt cagatttgtg   1620
ggagaaatga gaaaggaaca gttttttctct gaacttagcc tatctaactg gatcgcctca   1680
ggcaggtttt tgtaaagggg ggcgcagtga tatgaatcac tgtgattcac gttcggctcg   1740
gggacaaagt tggaaataaa acgtaagtag acttttgctc atttacttgt gacgttttgg   1800
ttctgtttgg gtaacttgtg tgaatttgtg acattttggc taaatgagcc attcctggca   1860
acctgtgcat caatagaaga tccccagaa aagagtcagt gtgaaagctg agcgaaaaac   1920
tcgtcttagg cttctgagac cagttttgta agggaatgt agaagaaaga gctgggcttt    1980
tcctctgaat ttggcccatc tagttggact ggcttcacag gcaggttttt gtagagaggg   2040
gcatgtcata gtcctcactg tggctcacgt tcggtgctgg gaccaagctg gagctgaaac   2100
gtaagtacac ttttctcatc tttttttatg tgtaagacac aggttttcat gttaggagtt   2160
aaagtcagtt cagaaaatct tgagaaaatg gagagggctc attatcagtt gacgtggcat   2220
acagtgtcag attttctgtt tatcaagcta gtgagattag gggcaaaaag aggctttagt   2280
tgagaggaaa gtaattaata ctatggtcac catccaagag attggatcgg agaataagca   2340
tgagtagtta ttgagatctg ggtctgactg caggtagcgt ggtcttctag acgtttaagt   2400
gggagatttg gagggatga ggaatgaagg aacttcagga tagaaagggg ctgaagtcaa    2460
gttcagctcc taaatggat gtgggagcaa actttgaaga taaactgaat gacccagagg    2520
atgaaacagc gcagatcaaa gaggggccta gagctctgag aagagaagga gactcatccg   2580
tgttgagttt ccacaagtac tgtcttgagt tttgcaataa aagtgggata gcagagttga   2640
gtgtnagccg tanagtatac tctctttttgt ctccctaagat ttttatgact acaaaaatca   2700
gtagtatgtc ctgaaataat cattaagctg tttgaaagta tgactgcttg ccatgtagat   2760
```

```
accatggctt gctgaatgat cagaagaggt gtgactctta ttctaaaatt tgtcacaaaa    2820
tgtcaaaatg agagactctg taggaacgag tcccttgaca gacagctgca aggggttttt    2880
ttcctttgtc tcatttctac atgaaagtaa atttgaaatg atcnttttt attataagag     2940 tagaaataca gttgggtttg aactatatgt tttaatnggc cncacggttt tgtaagacat    3000
ttggtccttt gttttcccag ttattactcg attgtaattt tatatcgcca gcantggtct    3060
gaaacggtnn nnnncgcaac ctcttcgttt actaactggg tgaccttcgg ctgtgccagc    3120
catttggcgt tcaccctgcc gcnggccnat gagaacccccc gcggtagnnc ccttgctccg   3180
cgggaaccac tttcctgagg acacagtgat aggaacagag ccactaatct gaagagaaca    3240
gagatgtgac agactacact aatgtgagaa aaacaaggaa agggtgactt attggagatt    3300
tcagaaataa aatgcattta ttattatatt cccttattta atttctattg ggaattagaa    3360
agggcataaa ctgctttatc cagtgttata ttaaaagctt aatgtatata atcttttaga    3420
ggtaaaatct acagccagca aaagtcatgg taaatattct ttgactgaac tctcactaaa    3480
ctcctctaaa ttatatgtca tattaactgg ttaaattaat ataaatttgt gacatgacct    3540
taactggtta ggtaggatat ttttcttcat gcaaaaatat gactaataat aatttagcac    3600
aaaaatattt cccaatactt taattctgtg atagaaaaat gtttaactca gctactataa    3660
tcccataatt ttgaaaacta tttattagct tttgtgtttg acccttccct gccaaaggca    3720
actatttaag gaccctttaa aactcttgaa actactttag agtcattaag ttatttaacc    3780
acttttaatt actttaaaat gatgtcaatt ccctttaac tattaattta ttttaagggg     3840
ggaaaggctg ctcataattc tattgttttt cttggtaaag aactctcagt ttctgttta     3900 ctacctctgt cacccaagag ttggcatctc aacagagggg actttccgag agccatctgg    3960
cagttgctta agatcagaag tgaagtctgc cagttcctcc taggcaggtg gcccagatta    4020
cagttgacct gttctggtgt ggctaaaaat tgtcccatgt ggttacaaac cattagacca    4080
gggtctgatg aattgctcag aatatttctg gacacccaaa tacagaccct ggcttaaggc    4140
ctgtccatac agtaggttta gcttggctac accaaaggaa gccatacaga ggctaatatc    4200
agagtattct tggaagagac aggagaaaat gaaagccagt ttctgctctt accttatgtg    4260
cttgtgttca gactcccaaa catcaggagt gtcagtaaac tggtctgaat ctctgtctga    4320
agcatggaac tgaaaagaat gtagtttcag ggaagaaagg caatagaagg aagcctgaga    4380
atatcttcaa agggtcagac tcnnnaattt actttctaaa gaagtagcta ggaactaggg    4440
aataacttag aaacaacaag attgtatata tgtgcatcct ggcccattgt tccttatctg    4500
tagggataag cgtgcttttt tgtgtgttgt atataacata actgtttaca cataatacac    4560
tgaaatggag cccttccttg ttacttcata ccatcctctg tgcttccttc ctcagggct    4620 gatgctgcac caactgtatc catcttccca ccatccagtg agcagttaac atctggaggt    4680
gcctcagtcg tgtgcttctt gaacaacttc taccccaaag acatcaatgt caagtggaag    4740
attgatggca gtgaacgaca aaatggcgtc ctgaacagtt ggactgatca ggacagcaaa    4800
gacagcacct acagcatgag cagcaccctc acgttgacca aggacgagta tgaacgacat    4860
aacagctata cctgtgaggc cactcacaag acatcaactt cacccattgt caagagcttc    4920
aacaggaatg agtgttagag acaaaggtcc tgagacgcca ccaccagctc cccagctcca    4980
tcctatcttc ccttctaagg tcttggaggc ttccccacaa gcgacctacc actgttgcgg    5040
tgctccaaac ctcctcccca cctccttctc ctcctcctcc ctttccttgc cttttatcat    5100
gctaatattt gcagaaaata ttcaataaag tgagtctttg cacttgagat ctctgtcttt    5160
```

```
cttactaaat ggtagtaatc agttgttttt ccagttacct gggtttctct tctaaagaag    5220
ttnaatgttt agttgccctg aaatccacca cacttaaagg ataaataaaa ccctccactt    5280
gccctggttg gctgtccact acatggcagt cctttctaag gttcacgagt actattcatg    5340
gcttatttct ctggccatgg taggtttgag gaggcatacc tcctagtttt cttcccctaa    5400
gtcgtcaaag tcctgaaggg ggacagtctt tacaagcaca tgttctgnnc tgattcaacc    5460
tacccagtaa acttggcgaa gcagtagcat catta                               5495
```

<210> SEQ ID NO 34
<211> LENGTH: 38
<212> TYPE: DNA
<213> ORGANISM: Artificial sequence
<220> FEATURE:
<223> OTHER INFORMATION: forward primer

<400> SEQUENCE: 34

```
atctcgagga accactttcc tgaggacaca gtgatagg                               38
```

<210> SEQ ID NO 35
<211> LENGTH: 38
<212> TYPE: DNA
<213> ORGANISM: Artificial sequence
<220> FEATURE:
<223> OTHER INFORMATION: reverse primer

<400> SEQUENCE: 35

```
atgaattcct aacactcatt cctgttgaag ctcttgac                               38
```

<210> SEQ ID NO 36
<211> LENGTH: 32
<212> TYPE: DNA
<213> ORGANISM: Artificial sequence
<220> FEATURE:
<223> OTHER INFORMATION: forward primer

<400> SEQUENCE: 36

```
atgaattcag acaaaggtcc tgagacgcca cc                                     32
```

<210> SEQ ID NO 37
<211> LENGTH: 42
<212> TYPE: DNA
<213> ORGANISM: Artificial sequence
<220> FEATURE:
<223> OTHER INFORMATION: reverse primer

<400> SEQUENCE: 37

```
atggatcctc gagtcgactg gatttcaggg caactaaaca tt                          42
```

<210> SEQ ID NO 38
<211> LENGTH: 32
<212> TYPE: DNA
<213> ORGANISM: Artificial sequence
<220> FEATURE:
<223> OTHER INFORMATION: forward primer

<400> SEQUENCE: 38

```
atgaattcgc ccctctccct cccccccccc ta                                     32
```

<210> SEQ ID NO 39
<211> LENGTH: 38
<212> TYPE: DNA
<213> ORGANISM: Artificial sequence
<220> FEATURE:
<223> OTHER INFORMATION: reverse primer

<400> SEQUENCE: 39
atgaattcgt cgacttgtgg caagcttatc atcgtgtt                    38

<210> SEQ ID NO 40
<211> LENGTH: 8
<212> TYPE: DNA
<213> ORGANISM: Artificial sequence
<220> FEATURE:
<223> OTHER INFORMATION: oligonucleotide

<400> SEQUENCE: 40 agtcgaca                                                      8

<210> SEQ ID NO 41
<211> LENGTH: 14
<212> TYPE: DNA
<213> ORGANISM: Artificial sequence
<220> FEATURE:
<223> OTHER INFORMATION: oligonucleotide

<400> SEQUENCE: 41
aatttgtcga ctgc                                              14

<210> SEQ ID NO 42
<211> LENGTH: 798
<212> TYPE: DNA
<213> ORGANISM: Mus musculus

<400> SEQUENCE: 42
tggtgattat tcagagtagt tttagatgag tgcatcttca tgaatctcca gcccatattc    60
tcccatgtgt ttatcagtta agaactgact agactctatc ttgctatttg catattacat   120
tttcagtaac cacaaatatc tcacagttgg tttatagcaa agtacttatg agaatagtag   180
taattagcta gggaccaaag ttcaaagaca aaatggattt tcaagtgcag attttcagct   240
tcctgctaat cagtgcctca ggtaacagag ggcagggaat ttgagatcag aatccaacca   300
aaattatttt ccctggggaa tttgagtcta aaatacagtt ttttcatttt ctttcatctg   360
aatgttgggt ggtataaaat tatttttgta tctctatttc tactaatccc tctctctcta   420
ttttgctttt ttctagtcat actgtccaga ggacaaattg ttctcaccca gtctccagca   480
atcatgtctg catctccagg ggagaaggtc accatgacct gcagtgccag ctcaagtgta   540
agttacatgt actggtacca gcagaagcca ggatcctccc ccagactcct gatttatgac   600
acatccaacc tggcttctgg agtccctgtt cgcttcagtg gcagtgggtc tgggacctct   660
tactctctca caatcagccg aatggaggct gaagatgctg ccacttatta ctgccagcag   720
tggagtagtt acccacccac acagtgatac agactggaac aaaaaccctc taagtcctta   780
gggtctagct acttcctc                                                 798

<210> SEQ ID NO 43
<211> LENGTH: 44
<212> TYPE: DNA
<213> ORGANISM: Artificial sequence
<220> FEATURE:
<223> OTHER INFORMATION: forward primer

<400> SEQUENCE: 43
cccaagcttt ggtgattatt cagagtagtt ttagatgagt gcat              44

<210> SEQ ID NO 44
<211> LENGTH: 45

```
<212> TYPE: DNA
<213> ORGANISM: Artificial sequence
<220> FEATURE:
<223> OTHER INFORMATION: reverse primer

<400> SEQUENCE: 44
acgcgtcgac tttgtctttg aactttggtc cctagctaat tacta              45

<210> SEQ ID NO 45
<211> LENGTH: 63
<212> TYPE: DNA
<213> ORGANISM: Artificial sequence
<220> FEATURE:
<223> OTHER INFORMATION: forward primer

<400> SEQUENCE: 45
acgcgtcgac gcggccggcc gcgctagcag acaaaggtcc tgagacgcca ccaccagctc   60
ccc                                                                63

<210> SEQ ID NO 46
<211> LENGTH: 43
<212> TYPE: DNA
<213> ORGANISM: Artificial sequence
<220> FEATURE:
<223> OTHER INFORMATION: reverse primer

<400> SEQUENCE: 46
gaagatctca agtgcaaaga ctcactttat tgaatatttt ctg                 43

<210> SEQ ID NO 47
<211> LENGTH: 42
<212> TYPE: DNA
<213> ORGANISM: Artificial sequence
<220> FEATURE:
<223> OTHER INFORMATION: forward primer

<400> SEQUENCE: 47
ggaattcaga caaaggtcct gagacgccac caccagctcc cc                  42

<210> SEQ ID NO 48
<211> LENGTH: 43
<212> TYPE: DNA
<213> ORGANISM: Artificial sequence
<220> FEATURE:
<223> OTHER INFORMATION: reverse primer

<400> SEQUENCE: 48
ccaagcttgc ctcctcaaac ctaccatggc ccagagaaat aag                 43

<210> SEQ ID NO 49
<211> LENGTH: 51
<212> TYPE: DNA
<213> ORGANISM: Artificial sequence
<220> FEATURE:
<223> OTHER INFORMATION: forward primer

<400> SEQUENCE: 49
ataagaatgc ggccgcctca gagcaaatgg gttctacagg cctaacaacc t         51

<210> SEQ ID NO 50
<211> LENGTH: 44
<212> TYPE: DNA
<213> ORGANISM: Artificial sequence
<220> FEATURE:
<223> OTHER INFORMATION: reverse primer

<400> SEQUENCE: 50
```
ccggaattcc taacactcat tcctgttgaa gctcttgaca atgg    44

<210> SEQ ID NO 51
<211> LENGTH: 34
<212> TYPE: DNA
<213> ORGANISM: Artificial sequence
<220> FEATURE:
<223> OTHER INFORMATION: forward primer

<400> SEQUENCE: 51
acgcgtcgac ccacatgcgg cttgggctgt gtgt    34

<210> SEQ ID NO 52
<211> LENGTH: 30
<212> TYPE: DNA
<213> ORGANISM: Artificial sequence
<220> FEATURE:
<223> OTHER INFORMATION: reverse primer

<400> SEQUENCE: 52
acgcgtcgac gtcgacctag gcaggccctg    30

<210> SEQ ID NO 53
<211> LENGTH: 20
<212> TYPE: DNA
<213> ORGANISM: Artificial sequence
<220> FEATURE:
<223> OTHER INFORMATION: forward primer

<400> SEQUENCE: 53
ctgactagac tctatcttgc    20

<210> SEQ ID NO 54
<211> LENGTH: 22
<212> TYPE: DNA
<213> ORGANISM: Artificial sequence
<220> FEATURE:
<223> OTHER INFORMATION: reverse primer

<400> SEQUENCE: 54
ccacggagac cactcgctca tt    22

<210> SEQ ID NO 55
<211> LENGTH: 28
<212> TYPE: DNA
<213> ORGANISM: Artificial sequence
<220> FEATURE:
<223> OTHER INFORMATION: forward primer

<400> SEQUENCE: 55 caccccctagg tcaatattgg ccattagc    28

<210> SEQ ID NO 56
<211> LENGTH: 28
<212> TYPE: DNA
<213> ORGANISM: Artificial sequence
<220> FEATURE:
<223> OTHER INFORMATION: reverse primer

<400> SEQUENCE: 56 caccccctagg taggcatccc cagcatgc    28

<210> SEQ ID NO 57
<211> LENGTH: 23
<212> TYPE: DNA
<213> ORGANISM: Artificial sequence -continued

```
<220> FEATURE:
<223> OTHER INFORMATION: forward primer

<400> SEQUENCE: 57
caccatgcgg cttgggctgt ctc                                             23

<210> SEQ ID NO 58
<211> LENGTH: 23
<212> TYPE: DNA
<213> ORGANISM: Artificial sequence
<220> FEATURE:
<223> OTHER INFORMATION: reverse primer

<400> SEQUENCE: 58
ggcaggccct gcagatgtga gtg                                             23

<210> SEQ ID NO 59
<211> LENGTH: 30
<212> TYPE: DNA
<213> ORGANISM: Artificial sequence
<220> FEATURE:
<223> OTHER INFORMATION: forward primer

<400> SEQUENCE: 59
gatcaagggg aaacagcaga ggcggatcag                                      30

<210> SEQ ID NO 60
<211> LENGTH: 30
<212> TYPE: DNA
<213> ORGANISM: Artificial sequence
<220> FEATURE:
<223> OTHER INFORMATION: reverse primer

<400> SEQUENCE: 60
ctgatccgcc tctgctgttt cccttgatc                                       30

<210> SEQ ID NO 61
<211> LENGTH: 28
<212> TYPE: DNA
<213> ORGANISM: Artificial sequence
<220> FEATURE:
<223> OTHER INFORMATION: forward primer

<400> SEQUENCE: 61
caccgctagc ctcgagaatt cacgcgtg                                        28

<210> SEQ ID NO 62
<211> LENGTH: 19
<212> TYPE: DNA
<213> ORGANISM: Artificial sequence
<220> FEATURE:
<223> OTHER INFORMATION: reverse primer

<400> SEQUENCE: 62
gctgatggtg aggtgcgtc                                                  19

<210> SEQ ID NO 63
<211> LENGTH: 21
<212> TYPE: DNA
<213> ORGANISM: Artificial sequence
<220> FEATURE:
<223> OTHER INFORMATION: forward primer

<400> SEQUENCE: 63
atcagtgccg aggggagcca g                                               21
```

```
<210> SEQ ID NO 64
<211> LENGTH: 29
<212> TYPE: DNA
<213> ORGANISM: Artificial sequence
<220> FEATURE:
<223> OTHER INFORMATION: reverse primer

<400> SEQUENCE: 64
gccctctaga gcggcaggcc ctgcagatg                                    29

<210> SEQ ID NO 65
<211> LENGTH: 31
<212> TYPE: DNA
<213> ORGANISM: Artificial sequence
<220> FEATURE:
<223> OTHER INFORMATION: forward primer

<400> SEQUENCE: 65
ccggctagcc accatggcgc aatgtgaaat g                                 31

<210> SEQ ID NO 66
<211> LENGTH: 30
<212> TYPE: DNA
<213> ORGANISM: Artificial sequence
<220> FEATURE:
<223> OTHER INFORMATION: reverse primer

<400> SEQUENCE: 66
ccatgcggcc gccctcctca ctgtgcacct                                   30

<210> SEQ ID NO 67
<211> LENGTH: 15
<212> TYPE: PRT
<213> ORGANISM: Artificial sequence
<220> FEATURE:
<223> OTHER INFORMATION: GIPF immunopeptide

<400> SEQUENCE: 67

Glu Ser Lys Glu Ala Gly Ala Gly Ser Arg Arg Arg Lys Gly Gln
1               5                   10                  15

<210> SEQ ID NO 68
<211> LENGTH: 798
<212> TYPE: DNA
<213> ORGANISM: Mus musculus
<220> FEATURE:
<221> NAME/KEY: CDS
<222> LOCATION: (61)..(795)

<400> SEQUENCE: 68
atgcggcttg ggctgtgcgt ggtggccctg gttctgagct ggacacacat cgccgtgggc    60 agc cgg ggg atc aag ggc aag aga cag agg cgg atc agt gct gag ggg    108
Ser Arg Gly Ile Lys Gly Lys Arg Gln Arg Arg Ile Ser Ala Glu Gly
1               5                   10                  15 agc caa gcc tgc gcc aag ggc tgt gag ctc tgt tca gaa gtc aac ggt    156
Ser Gln Ala Cys Ala Lys Gly Cys Glu Leu Cys Ser Glu Val Asn Gly
                20                  25                  30 tgc ctc aag tgc tcg ccc aag ctc ttc att ctg ctg gag agg aac gac    204
Cys Leu Lys Cys Ser Pro Lys Leu Phe Ile Leu Leu Glu Arg Asn Asp
            35                  40                  45 atc cgc cag gtg ggc gtc tgc ctg ccg tcc tgc cca cct gga tac ttt    252
Ile Arg Gln Val Gly Val Cys Leu Pro Ser Cys Pro Pro Gly Tyr Phe
        50                  55                  60 gat gcc cgc aac ccc gac atg aac aaa tgc atc aaa tgc aag atc gag    300
Asp Ala Arg Asn Pro Asp Met Asn Lys Cys Ile Lys Cys Lys Ile Glu
65                  70                  75                  80
```

| | | | | | | | | | | | | | | | | |
|---|---|---|---|---|---|---|---|---|---|---|---|---|---|---|---|---|
| cac | tgt | gag | gcc | tgc | ttc | agc | cac | aac | ttc | tgc | acc | aag | tgt | cag | gag | 348 |
| His | Cys | Glu | Ala | Cys | Phe | Ser | His | Asn | Phe | Cys | Thr | Lys | Cys | Gln | Glu | |
| | | | | 85 | | | | | 90 | | | | | 95 | | |
| gcc | ttg | tac | tta | cac | aag | ggc | cgc | tgc | tat | cca | gcc | tgc | cct | gag | ggc | 396 |
| Ala | Leu | Tyr | Leu | His | Lys | Gly | Arg | Cys | Tyr | Pro | Ala | Cys | Pro | Glu | Gly | |
| | | | 100 | | | | | 105 | | | | | 110 | | | |
| tct | aca | gcc | gct | aac | agc | acc | atg | gag | tgc | ggc | agt | cct | gca | caa | tgt | 444 |
| Ser | Thr | Ala | Ala | Asn | Ser | Thr | Met | Glu | Cys | Gly | Ser | Pro | Ala | Gln | Cys | |
| | | | 115 | | | | | 120 | | | | | 125 | | | |
| gaa | atg | agc | gag | tgg | tcc | ccg | tgg | gga | ccc | tgc | tcc | aag | aag | agg | aag | 492 |
| Glu | Met | Ser | Glu | Trp | Ser | Pro | Trp | Gly | Pro | Cys | Ser | Lys | Lys | Arg | Lys | |
| | | 130 | | | | | 135 | | | | | 140 | | | | |
| ctg | tgc | ggt | ttc | cgg | aag | gga | tcg | gag | gag | cgg | aca | cgc | aga | gtg | ctc | 540 |
| Leu | Cys | Gly | Phe | Arg | Lys | Gly | Ser | Glu | Glu | Arg | Thr | Arg | Arg | Val | Leu | |
| 145 | | | | | 150 | | | | | 155 | | | | | 160 | |
| cat | gct | ccc | ggg | gga | gac | cac | acc | acc | tgc | tcc | gac | acc | aaa | gag | acc | 588 |
| His | Ala | Pro | Gly | Gly | Asp | His | Thr | Thr | Cys | Ser | Asp | Thr | Lys | Glu | Thr | |
| | | | 165 | | | | | 170 | | | | | 175 | | | |
| cgc | aag | tgt | acc | gtg | cgc | agg | acg | ccc | tgc | cca | gag | ggg | cag | aag | agg | 636 |
| Arg | Lys | Cys | Thr | Val | Arg | Arg | Thr | Pro | Cys | Pro | Glu | Gly | Gln | Lys | Arg | |
| | | | 180 | | | | | 185 | | | | | 190 | | | |
| agg | aag | ggg | ggc | cag | ggc | cgg | agg | gag | aat | gcc | aac | agg | cat | ccg | gcc | 684 |
| Arg | Lys | Gly | Gly | Gln | Gly | Arg | Arg | Glu | Asn | Ala | Asn | Arg | His | Pro | Ala | |
| | | | 195 | | | | | 200 | | | | | 205 | | | |
| agg | aag | aac | agc | aag | gag | ccg | agg | tcc | aac | tct | cgg | aga | cac | aaa | ggg | 732 |
| Arg | Lys | Asn | Ser | Lys | Glu | Pro | Arg | Ser | Asn | Ser | Arg | Arg | His | Lys | Gly | |
| | | 210 | | | | | 215 | | | | | 220 | | | | |
| caa | cag | cag | cca | cag | cca | ggg | aca | aca | ggg | cca | ctc | aca | tca | gta | gga | 780 |
| Gln | Gln | Gln | Pro | Gln | Pro | Gly | Thr | Thr | Gly | Pro | Leu | Thr | Ser | Val | Gly | |
| 225 | | | | | 230 | | | | | 235 | | | | | 240 | |
| cct | acc | tgg | gca | cag | tga | | | | | | | | | | | 798 |
| Pro | Thr | Trp | Ala | Gln | | | | | | | | | | | | |
| | | | | 245 | | | | | | | | | | | | |

<210> SEQ ID NO 69
<211> LENGTH: 245
<212> TYPE: PRT
<213> ORGANISM: Mus musculus

<400> SEQUENCE: 69

Ser Arg Gly Ile Lys Gly Lys Arg Gln Arg Ile Ser Ala Glu Gly
1               5                   10                  15

Ser Gln Ala Cys Ala Lys Gly Cys Glu Leu Cys Ser Glu Val Asn Gly
            20                  25                  30

Cys Leu Lys Cys Ser Pro Lys Leu Phe Ile Leu Leu Glu Arg Asn Asp
        35                  40                  45

Ile Arg Gln Val Gly Val Cys Leu Pro Ser Cys Pro Pro Gly Tyr Phe
    50                  55                  60

Asp Ala Arg Asn Pro Asp Met Asn Lys Cys Ile Lys Cys Lys Ile Glu
65                  70                  75                  80

His Cys Glu Ala Cys Phe Ser His Asn Phe Cys Thr Lys Cys Gln Glu
                85                  90                  95

Ala Leu Tyr Leu His Lys Gly Arg Cys Tyr Pro Ala Cys Pro Glu Gly
            100                 105                 110

Ser Thr Ala Ala Asn Ser Thr Met Glu Cys Gly Ser Pro Ala Gln Cys
        115                 120                 125

Glu Met Ser Glu Trp Ser Pro Trp Gly Pro Cys Ser Lys Lys Arg Lys
    130                 135                 140

-continued

```
Leu Cys Gly Phe Arg Lys Gly Ser Glu Glu Arg Thr Arg Arg Val Leu
145                 150                 155                 160

His Ala Pro Gly Gly Asp His Thr Thr Cys Ser Asp Thr Lys Glu Thr
                165                 170                 175

Arg Lys Cys Thr Val Arg Arg Thr Pro Cys Pro Glu Gly Gln Lys Arg
            180                 185                 190

Arg Lys Gly Gly Gln Gly Arg Arg Glu Asn Ala Asn Arg His Pro Ala
        195                 200                 205

Arg Lys Asn Ser Lys Glu Pro Arg Ser Asn Ser Arg Arg His Lys Gly
    210                 215                 220

Gln Gln Gln Pro Gln Pro Gly Thr Thr Gly Pro Leu Thr Ser Val Gly
225                 230                 235                 240

Pro Thr Trp Ala Gln
            245
```

<210> SEQ ID NO 70
<211> LENGTH: 19
<212> TYPE: DNA
<213> ORGANISM: Artificial sequence
<220> FEATURE:
<223> OTHER INFORMATION: forward primer

<400> SEQUENCE: 70
gtgtgaggtc cacggaaac                                                19

<210> SEQ ID NO 71
<211> LENGTH: 20
<212> TYPE: DNA
<213> ORGANISM: Artificial sequence
<220> FEATURE:
<223> OTHER INFORMATION: reverse primer

<400> SEQUENCE: 71
ggtgcaaaga catagccaga                                               20

<210> SEQ ID NO 72
<211> LENGTH: 20
<212> TYPE: DNA
<213> ORGANISM: Artificial sequence
<220> FEATURE:
<223> OTHER INFORMATION: forward primer

<400> SEQUENCE: 72
gcaaacaaca cagggtgta                                                20

<210> SEQ ID NO 73
<211> LENGTH: 20
<212> TYPE: DNA
<213> ORGANISM: Artificial sequence
<220> FEATURE:
<223> OTHER INFORMATION: reverse primer

<400> SEQUENCE: 73
ggcaggtctg tgactgatgt                                               20

<210> SEQ ID NO 74
<211> LENGTH: 20
<212> TYPE: DNA
<213> ORGANISM: Artificial sequence
<220> FEATURE:
<223> OTHER INFORMATION: forward primer

<400> SEQUENCE: 74
tatgcagaac tgcgatttcc                                               20

<210> SEQ ID NO 75
<211> LENGTH: 22
<212> TYPE: DNA
<213> ORGANISM: Artificial sequence
<220> FEATURE:
<223> OTHER INFORMATION: reverse primer

<400> SEQUENCE: 75
ccaatttgtc tcctatctgt gg                                          22

<210> SEQ ID NO 76
<211> LENGTH: 19
<212> TYPE: DNA
<213> ORGANISM: Artificial sequence
<220> FEATURE:
<223> OTHER INFORMATION: forward primer

<400> SEQUENCE: 76
tgctccatga ggagacacc                                              19

<210> SEQ ID NO 77
<211> LENGTH: 19
<212> TYPE: DNA
<213> ORGANISM: Artificial sequence
<220> FEATURE:
<223> OTHER INFORMATION: reverse primer

<400> SEQUENCE: 77
cctgcctctt ttccacaga                                              19

<210> SEQ ID NO 78
<211> LENGTH: 20
<212> TYPE: DNA
<213> ORGANISM: Artificial sequence
<220> FEATURE:
<223> OTHER INFORMATION: forward primer

<400> SEQUENCE: 78
caacgttccc ttcaagacac                                             20

<210> SEQ ID NO 79
<211> LENGTH: 19
<212> TYPE: DNA
<213> ORGANISM: Artificial sequence
<220> FEATURE:
<223> OTHER INFORMATION: reverse primer

<400> SEQUENCE: 79
cgcttgtcct cgttcatct                                              19

<210> SEQ ID NO 80
<211> LENGTH: 20
<212> TYPE: DNA
<213> ORGANISM: Artificial sequence
<220> FEATURE:
<223> OTHER INFORMATION: forward primer

<400> SEQUENCE: 80
ctcaacaccg gaattttga                                              20

<210> SEQ ID NO 81
<211> LENGTH: 20
<212> TYPE: DNA
<213> ORGANISM: Artificial sequence
<220> FEATURE:
<223> OTHER INFORMATION: reverse primer

<400> SEQUENCE: 81
aattgcattt cgaaggaagg                                        20

<210> SEQ ID NO 82
<211> LENGTH: 23
<212> TYPE: DNA
<213> ORGANISM: Artificial sequence
<220> FEATURE:
<223> OTHER INFORMATION: forward primer

<400> SEQUENCE: 82
gtagattcgg gcaagtccac cac                                    23

<210> SEQ ID NO 83
<211> LENGTH: 22
<212> TYPE: DNA
<213> ORGANISM: Artificial sequence
<220> FEATURE:
<223> OTHER INFORMATION: reverse primer

<400> SEQUENCE: 83
ttcccatctc agcagcctcc tt                                     22

<210> SEQ ID NO 84
<211> LENGTH: 105
<212> TYPE: DNA
<213> ORGANISM: Homo sapiens
<220> FEATURE:
<221> NAME/KEY: CDS
<222> LOCATION: (1)..(105)

<400> SEQUENCE: 84 agc cgg ggg atc aag ggg aaa agg cag agg cgg atc agt gcc gag ggg     48
Ser Arg Gly Ile Lys Gly Lys Arg Gln Arg Arg Ile Ser Ala Glu Gly
1               5                   10                  15 agc cag gcc tgt gcc aaa ggc tgt gag ctc tgc tct gaa gtc aac ggc     96
Ser Gln Ala Cys Ala Lys Gly Cys Glu Leu Cys Ser Glu Val Asn Gly
            20                  25                  30 tgc ctc aag                                                        105
Cys Leu Lys
        35

<210> SEQ ID NO 85
<211> LENGTH: 35
<212> TYPE: PRT
<213> ORGANISM: Homo sapiens

<400> SEQUENCE: 85

Ser Arg Gly Ile Lys Gly Lys Arg Gln Arg Arg Ile Ser Ala Glu Gly
1               5                   10                  15

Ser Gln Ala Cys Ala Lys Gly Cys Glu Leu Cys Ser Glu Val Asn Gly
            20                  25                  30

Cys Leu Lys
        35

<210> SEQ ID NO 86
<211> LENGTH: 180
<212> TYPE: DNA
<213> ORGANISM: Homo sapiens
<220> FEATURE:
<221> NAME/KEY: CDS
<222> LOCATION: (1)..(180)

<400> SEQUENCE: 86

```
agc cgg ggg atc aag ggg aaa agg cag agg cgg atc agt gcc gag ggg        48
Ser Arg Gly Ile Lys Gly Lys Arg Gln Arg Arg Ile Ser Ala Glu Gly
1               5                   10                  15 agc cag gcc tgt gcc aaa ggc tgt gag ctc tgc tct gaa gtc aac ggc        96
Ser Gln Ala Cys Ala Lys Gly Cys Glu Leu Cys Ser Glu Val Asn Gly
            20                  25                  30 tgc ctc aag tgc tca ccc aag ctg ttc atc ctg ctg gag agg aac gac       144
Cys Leu Lys Cys Ser Pro Lys Leu Phe Ile Leu Leu Glu Arg Asn Asp
        35                  40                  45 atc cgc cag gtg ggc gtc tgc ttg ccg tcc tgc cca                       180
Ile Arg Gln Val Gly Val Cys Leu Pro Ser Cys Pro
    50                  55                  60

<210> SEQ ID NO 87
<211> LENGTH: 60
<212> TYPE: PRT
<213> ORGANISM: Homo sapiens

<400> SEQUENCE: 87

Ser Arg Gly Ile Lys Gly Lys Arg Gln Arg Arg Ile Ser Ala Glu Gly
1               5                   10                  15

Ser Gln Ala Cys Ala Lys Gly Cys Glu Leu Cys Ser Glu Val Asn Gly
            20                  25                  30

Cys Leu Lys Cys Ser Pro Lys Leu Phe Ile Leu Leu Glu Arg Asn Asp
        35                  40                  45

Ile Arg Gln Val Gly Val Cys Leu Pro Ser Cys Pro
    50                  55                  60

<210> SEQ ID NO 88
<211> LENGTH: 270
<212> TYPE: DNA
<213> ORGANISM: Homo sapiens
<220> FEATURE:
<221> NAME/KEY: CDS
<222> LOCATION: (1)..(270)

<400> SEQUENCE: 88 agc cgg ggg atc aag ggg aaa agg cag agg cgg atc agt gcc gag ggg        48
Ser Arg Gly Ile Lys Gly Lys Arg Gln Arg Arg Ile Ser Ala Glu Gly
1               5                   10                  15 agc cag gcc tgt gcc aaa ggc tgt gag ctc tgc tct gaa gtc aac ggc        96
Ser Gln Ala Cys Ala Lys Gly Cys Glu Leu Cys Ser Glu Val Asn Gly
            20                  25                  30 tgc ctc aag tgc tca ccc aag ctg ttc atc ctg ctg gag agg aac gac       144
Cys Leu Lys Cys Ser Pro Lys Leu Phe Ile Leu Leu Glu Arg Asn Asp
        35                  40                  45 atc cgc cag gtg ggc gtc tgc ttg ccg tcc tgc cca cct gga tac ttc       192
Ile Arg Gln Val Gly Val Cys Leu Pro Ser Cys Pro Pro Gly Tyr Phe
    50                  55                  60 gac gcc cgc aac ccc gac atg aac aag tgc atc aaa tgc aag atc gag       240
Asp Ala Arg Asn Pro Asp Met Asn Lys Cys Ile Lys Cys Lys Ile Glu
65                  70                  75                  80 cac tgt gag gcc tgc ttc agc cat aac ttc                               270
His Cys Glu Ala Cys Phe Ser His Asn Phe
                85                  90

<210> SEQ ID NO 89
<211> LENGTH: 90
<212> TYPE: PRT
<213> ORGANISM: Homo sapiens

<400> SEQUENCE: 89

Ser Arg Gly Ile Lys Gly Lys Arg Gln Arg Arg Ile Ser Ala Glu Gly
```

```
                1               5                  10                  15
            Ser Gln Ala Cys Ala Lys Gly Cys Glu Leu Cys Ser Glu Val Asn Gly
                            20                  25                  30

Cys Leu Lys Cys Ser Pro Lys Leu Phe Ile Leu Leu Glu Arg Asn Asp
                        35                  40                  45

Ile Arg Gln Val Gly Val Cys Leu Pro Ser Cys Pro Pro Gly Tyr Phe
                50                  55                  60

Asp Ala Arg Asn Pro Asp Met Asn Lys Cys Ile Lys Cys Lys Ile Glu
            65                  70                  75                  80

His Cys Glu Ala Cys Phe Ser His Asn Phe
                            85                  90

<210> SEQ ID NO 90
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 90 agc cgg ggg atc aag ggg aaa agg cag agg cgg atc agt gcc gag ggg        48
Ser Arg Gly Ile Lys Gly Lys Arg Gln Arg Arg Ile Ser Ala Glu Gly
1               5                   10                  15 agc cag gcc tgt gcc aaa ggc tgt gag ctc tgc tct gaa gtc aac ggc        96
Ser Gln Ala Cys Ala Lys Gly Cys Glu Leu Cys Ser Glu Val Asn Gly
                20                  25                  30 tgc ctc aag tgc tca ccc aag ctg ttc atc ctg ctg gag agg aac gac       144
Cys Leu Lys Cys Ser Pro Lys Leu Phe Ile Leu Leu Glu Arg Asn Asp
            35                  40                  45 atc cgc cag gtg ggc gtc tgc ttg ccg tcc tgc cca cct gga tac ttc       192
Ile Arg Gln Val Gly Val Cys Leu Pro Ser Cys Pro Pro Gly Tyr Phe
        50                  55                  60 gac gcc cgc aac ccc gac atg aac aag tgc atc aaa tgc aag atc gag       240
Asp Ala Arg Asn Pro Asp Met Asn Lys Cys Ile Lys Cys Lys Ile Glu
65                  70                  75                  80 cac tgt gag gcc tgc ttc agc cat aac ttc tgc acc aag tgt aag gag       288
His Cys Glu Ala Cys Phe Ser His Asn Phe Cys Thr Lys Cys Lys Glu
                85                  90                  95 ggc ttg tac ctg cac aag ggc cgc tgc tat cca gct tgt ccc gag ggc       336
Gly Leu Tyr Leu His Lys Gly Arg Cys Tyr Pro Ala Cys Pro Glu Gly
            100                 105                 110 tcc tca gct gcc aat ggc acc atg                                       360
Ser Ser Ala Ala Asn Gly Thr Met
        115                 120

<210> SEQ ID NO 91
<211> LENGTH: 120
<212> TYPE: PRT
<213> ORGANISM: Homo sapiens

<400> SEQUENCE: 91

Ser Arg Gly Ile Lys Gly Lys Arg Gln Arg Arg Ile Ser Ala Glu Gly
1               5                   10                  15

Ser Gln Ala Cys Ala Lys Gly Cys Glu Leu Cys Ser Glu Val Asn Gly
                20                  25                  30

Cys Leu Lys Cys Ser Pro Lys Leu Phe Ile Leu Leu Glu Arg Asn Asp
            35                  40                  45

Ile Arg Gln Val Gly Val Cys Leu Pro Ser Cys Pro Pro Gly Tyr Phe
        50                  55                  60
```

```
Asp Ala Arg Asn Pro Asp Met Asn Lys Cys Ile Lys Cys Lys Ile Glu
65                  70                  75                  80

His Cys Glu Ala Cys Phe Ser His Asn Phe Cys Thr Lys Cys Lys Glu
                85                  90                  95

Gly Leu Tyr Leu His Lys Gly Arg Cys Tyr Pro Ala Cys Pro Glu Gly
            100                 105                 110

Ser Ser Ala Ala Asn Gly Thr Met
        115                 120
```

<210> SEQ ID NO 92
<211> LENGTH: 450
<212> TYPE: DNA
<213> ORGANISM: Homo sapiens
<220> FEATURE:
<221> NAME/KEY: CDS
<222> LOCATION: (1)..(450)

<400> SEQUENCE: 92

```
agc cgg ggg atc aag ggg aaa agg cag agg cgg atc agt gcc gag ggg      48
Ser Arg Gly Ile Lys Gly Lys Arg Gln Arg Arg Ile Ser Ala Glu Gly
1               5                   10                  15 agc cag gcc tgt gcc aaa ggc tgt gag ctc tgc tct gaa gtc aac ggc      96
Ser Gln Ala Cys Ala Lys Gly Cys Glu Leu Cys Ser Glu Val Asn Gly
                20                  25                  30 tgc ctc aag tgc tca ccc aag ctg ttc atc ctg ctg gag agg aac gac     144
Cys Leu Lys Cys Ser Pro Lys Leu Phe Ile Leu Leu Glu Arg Asn Asp
            35                  40                  45 atc cgc cag gtg ggc gtc tgc ttg ccg tcc tgc cca cct gga tac ttc     192
Ile Arg Gln Val Gly Val Cys Leu Pro Ser Cys Pro Pro Gly Tyr Phe
50                  55                  60 gac gcc cgc aac ccc gac atg aac aag tgc atc aaa tgc aag atc gag     240
Asp Ala Arg Asn Pro Asp Met Asn Lys Cys Ile Lys Cys Lys Ile Glu
65                  70                  75                  80 cac tgt gag gcc tgc ttc agc cat aac ttc tgc acc aag tgt aag gag     288
His Cys Glu Ala Cys Phe Ser His Asn Phe Cys Thr Lys Cys Lys Glu
                85                  90                  95 ggc ttg tac ctg cac aag ggc cgc tgc tat cca gct tgt ccc gag ggc     336
Gly Leu Tyr Leu His Lys Gly Arg Cys Tyr Pro Ala Cys Pro Glu Gly
            100                 105                 110 tcc tca gct gcc aat ggc acc atg gag tgc agt agt cct gcg caa tgt     384
Ser Ser Ala Ala Asn Gly Thr Met Glu Cys Ser Ser Pro Ala Gln Cys
        115                 120                 125 gaa atg agc gag tgg tct ccg tgg ggg ccc tgc tcc aag aag cag cag     432
Glu Met Ser Glu Trp Ser Pro Trp Gly Pro Cys Ser Lys Lys Gln Gln
130                 135                 140 ctc tgt ggt ttc cgg agg                                             450
Leu Cys Gly Phe Arg Arg
145                 150
```

<210> SEQ ID NO 93
<211> LENGTH: 150
<212> TYPE: PRT
<213> ORGANISM: Homo sapiens

<400> SEQUENCE: 93

```
Ser Arg Gly Ile Lys Gly Lys Arg Gln Arg Arg Ile Ser Ala Glu Gly
1               5                   10                  15

Ser Gln Ala Cys Ala Lys Gly Cys Glu Leu Cys Ser Glu Val Asn Gly
                20                  25                  30

Cys Leu Lys Cys Ser Pro Lys Leu Phe Ile Leu Leu Glu Arg Asn Asp
            35                  40                  45
```

```
Ile Arg Gln Val Gly Val Cys Leu Pro Ser Cys Pro Pro Gly Tyr Phe
 50                  55                  60
Asp Ala Arg Asn Pro Asp Met Asn Lys Cys Ile Lys Cys Lys Ile Glu
 65                  70                  75                  80
His Cys Glu Ala Cys Phe Ser His Asn Phe Cys Thr Lys Cys Lys Glu
                 85                  90                  95
Gly Leu Tyr Leu His Lys Gly Arg Cys Tyr Pro Ala Cys Pro Glu Gly
             100                 105                 110
Ser Ser Ala Ala Asn Gly Thr Met Glu Cys Ser Ser Pro Ala Gln Cys
         115                 120                 125
Glu Met Ser Glu Trp Ser Pro Trp Gly Pro Cys Ser Lys Lys Gln Gln
     130                 135                 140
Leu Cys Gly Phe Arg Arg
145                 150

<210> SEQ ID NO 94
<211> LENGTH: 540
<212> TYPE: DNA
<213> ORGANISM: Homo sapiens
<220> FEATURE:
<221> NAME/KEY: CDS
<222> LOCATION: (1)..(540)

<400> SEQUENCE: 94 agc cgg ggg atc aag ggg aaa agg cag agg cgg atc agt gcc gag ggg       48
Ser Arg Gly Ile Lys Gly Lys Arg Gln Arg Arg Ile Ser Ala Glu Gly
  1               5                  10                  15 agc cag gcc tgt gcc aaa ggc tgt gag ctc tgc tct gaa gtc aac ggc       96
Ser Gln Ala Cys Ala Lys Gly Cys Glu Leu Cys Ser Glu Val Asn Gly
             20                  25                  30 tgc ctc aag tgc tca ccc aag ctg ttc atc ctg ctg gag agg aac gac      144
Cys Leu Lys Cys Ser Pro Lys Leu Phe Ile Leu Leu Glu Arg Asn Asp
         35                  40                  45 atc cgc cag gtg ggc gtc tgc ttg ccg tcc tgc cca cct gga tac ttc      192
Ile Arg Gln Val Gly Val Cys Leu Pro Ser Cys Pro Pro Gly Tyr Phe
 50                  55                  60 gac gcc cgc aac ccc gac atg aac aag tgc atc aaa tgc aag atc gag      240
Asp Ala Arg Asn Pro Asp Met Asn Lys Cys Ile Lys Cys Lys Ile Glu
 65                  70                  75                  80 cac tgt gag gcc tgc ttc agc cat aac ttc tgc acc aag tgt aag gag      288
His Cys Glu Ala Cys Phe Ser His Asn Phe Cys Thr Lys Cys Lys Glu
                 85                  90                  95 ggc ttg tac ctg cac aag ggc cgc tgc tat cca gct tgt ccc gag ggc      336
Gly Leu Tyr Leu His Lys Gly Arg Cys Tyr Pro Ala Cys Pro Glu Gly
             100                 105                 110 tcc tca gct gcc aat ggc acc atg gag tgc agt agt cct gcg caa tgt      384
Ser Ser Ala Ala Asn Gly Thr Met Glu Cys Ser Ser Pro Ala Gln Cys
         115                 120                 125 gaa atg agc gag tgg tct ccg tgg ggg ccc tgc tcc aag aag cag cag      432
Glu Met Ser Glu Trp Ser Pro Trp Gly Pro Cys Ser Lys Lys Gln Gln
     130                 135                 140 ctc tgt ggt ttc cgg agg ggc tcc gag gag cgg aca cgc agg gtg cta      480
Leu Cys Gly Phe Arg Arg Gly Ser Glu Glu Arg Thr Arg Arg Val Leu
145                 150                 155                 160 cat gcc cct gtg ggg gac cat gct gcc tgc tct gac acc aag gag acc      528
His Ala Pro Val Gly Asp His Ala Ala Cys Ser Asp Thr Lys Glu Thr
                 165                 170                 175 cgg agg tgc aca                                                      540
Arg Arg Cys Thr
            180
```

```
<210> SEQ ID NO 95
<211> LENGTH: 180
<212> TYPE: PRT
<213> ORGANISM: Homo sapiens

<400> SEQUENCE: 95

Ser Arg Gly Ile Lys Gly Lys Arg Gln Arg Ile Ser Ala Glu Gly
1               5                   10                  15

Ser Gln Ala Cys Ala Lys Gly Cys Glu Leu Cys Ser Glu Val Asn Gly
                20                  25                  30

Cys Leu Lys Cys Ser Pro Lys Leu Phe Ile Leu Leu Glu Arg Asn Asp
            35                  40                  45

Ile Arg Gln Val Gly Val Cys Leu Pro Ser Cys Pro Pro Gly Tyr Phe
        50                  55                  60

Asp Ala Arg Asn Pro Asp Met Asn Lys Cys Ile Lys Cys Lys Ile Glu
65                  70                  75                  80

His Cys Glu Ala Cys Phe Ser His Asn Phe Cys Thr Lys Cys Lys Glu
                85                  90                  95

Gly Leu Tyr Leu His Lys Gly Arg Cys Tyr Pro Ala Cys Pro Glu Gly
            100                 105                 110

Ser Ser Ala Ala Asn Gly Thr Met Glu Cys Ser Ser Pro Ala Gln Cys
        115                 120                 125

Glu Met Ser Glu Trp Ser Pro Trp Gly Pro Cys Ser Lys Lys Gln Gln
130                 135                 140

Leu Cys Gly Phe Arg Arg Gly Ser Glu Glu Arg Thr Arg Arg Val Leu
145                 150                 155                 160

His Ala Pro Val Gly Asp His Ala Ala Cys Ser Asp Thr Lys Glu Thr
                165                 170                 175

Arg Arg Cys Thr
            180

<210> SEQ ID NO 96
<211> LENGTH: 630
<212> TYPE: DNA
<213> ORGANISM: Homo sapiens
<220> FEATURE:
<221> NAME/KEY: CDS
<222> LOCATION: (1)..(630)

<400> SEQUENCE: 96 agc cgg ggg atc aag ggg aaa agg cag agg cgg atc agt gcc gag ggg      48
Ser Arg Gly Ile Lys Gly Lys Arg Gln Arg Arg Ile Ser Ala Glu Gly
1               5                   10                  15 agc cag gcc tgt gcc aaa ggc tgt gag ctc tgc tct gaa gtc aac ggc      96
Ser Gln Ala Cys Ala Lys Gly Cys Glu Leu Cys Ser Glu Val Asn Gly
                20                  25                  30 tgc ctc aag tgc tca ccc aag ctg ttc atc ctg ctg gag agg aac gac     144
Cys Leu Lys Cys Ser Pro Lys Leu Phe Ile Leu Leu Glu Arg Asn Asp
            35                  40                  45 atc cgc cag gtg ggc gtc tgc ttg ccg tcc tgc cca cct gga tac ttc     192
Ile Arg Gln Val Gly Val Cys Leu Pro Ser Cys Pro Pro Gly Tyr Phe
        50                  55                  60 gac gcc cgc aac ccc gac atg aac aag tgc atc aaa tgc aag atc gag     240
Asp Ala Arg Asn Pro Asp Met Asn Lys Cys Ile Lys Cys Lys Ile Glu
65                  70                  75                  80 cac tgt gag gcc tgc ttc agc cat aac ttc tgc acc aag tgt aag gag     288
His Cys Glu Ala Cys Phe Ser His Asn Phe Cys Thr Lys Cys Lys Glu
                85                  90                  95 ggc ttg tac ctg cac aag ggc cgc tgc tat cca gct tgt ccc gag ggc     336
```

```
Gly Leu Tyr Leu His Lys Gly Arg Cys Tyr Pro Ala Cys Pro Glu Gly
            100                 105                 110 tcc tca gct gcc aat ggc acc atg gag tgc agt agt cct gcg caa tgt       384
Ser Ser Ala Ala Asn Gly Thr Met Glu Cys Ser Ser Pro Ala Gln Cys
        115                 120                 125 gaa atg agc gag tgg tct ccg tgg ggg ccc tgc tcc aag aag cag cag       432
Glu Met Ser Glu Trp Ser Pro Trp Gly Pro Cys Ser Lys Lys Gln Gln
    130                 135                 140 ctc tgt ggt ttc cgg agg ggc tcc gag gag cgg aca cgc agg gtg cta       480
Leu Cys Gly Phe Arg Arg Gly Ser Glu Glu Arg Thr Arg Arg Val Leu
145                 150                 155                 160 cat gcc cct gtg ggg gac cat gct gcc tgc tct gac acc aag gag acc       528
His Ala Pro Val Gly Asp His Ala Ala Cys Ser Asp Thr Lys Glu Thr
                165                 170                 175 cgg agg tgc aca gtg agg aga gtg ccg tgt cct gag ggg cag aag agg       576
Arg Arg Cys Thr Val Arg Arg Val Pro Cys Pro Glu Gly Gln Lys Arg
            180                 185                 190 agg aag gga ggc cag ggc cgg cgg gag aat gcc aac agg aac ctg gcc       624
Arg Lys Gly Gly Gln Gly Arg Arg Glu Asn Ala Asn Arg Asn Leu Ala
        195                 200                 205 agg aag                                                               630
Arg Lys
    210

<210> SEQ ID NO 97
<211> LENGTH: 210
<212> TYPE: PRT
<213> ORGANISM: Homo sapiens

<400> SEQUENCE: 97

Ser Arg Gly Ile Lys Gly Lys Arg Gln Arg Ile Ser Ala Glu Gly
1               5                   10                  15

Ser Gln Ala Cys Ala Lys Gly Cys Glu Leu Cys Ser Glu Val Asn Gly
            20                  25                  30

Cys Leu Lys Cys Ser Pro Lys Leu Phe Ile Leu Leu Glu Arg Asn Asp
        35                  40                  45

Ile Arg Gln Val Gly Val Cys Leu Pro Ser Cys Pro Pro Gly Tyr Phe
50                  55                  60

Asp Ala Arg Asn Pro Asp Met Asn Lys Cys Ile Lys Cys Lys Ile Glu
65                  70                  75                  80

His Cys Glu Ala Cys Phe Ser His Asn Phe Cys Thr Lys Cys Lys Glu
                85                  90                  95

Gly Leu Tyr Leu His Lys Gly Arg Cys Tyr Pro Ala Cys Pro Glu Gly
            100                 105                 110

Ser Ser Ala Ala Asn Gly Thr Met Glu Cys Ser Ser Pro Ala Gln Cys
        115                 120                 125

Glu Met Ser Glu Trp Ser Pro Trp Gly Pro Cys Ser Lys Lys Gln Gln
    130                 135                 140

Leu Cys Gly Phe Arg Arg Gly Ser Glu Glu Arg Thr Arg Arg Val Leu
145                 150                 155                 160

His Ala Pro Val Gly Asp His Ala Ala Cys Ser Asp Thr Lys Glu Thr
                165                 170                 175

Arg Arg Cys Thr Val Arg Arg Val Pro Cys Pro Glu Gly Gln Lys Arg
            180                 185                 190

Arg Lys Gly Gly Gln Gly Arg Arg Glu Asn Ala Asn Arg Asn Leu Ala
        195                 200                 205

Arg Lys
    210
```

<210> SEQ ID NO 98
<211> LENGTH: 615
<212> TYPE: DNA
<213> ORGANISM: Homo sapiens
<220> FEATURE:
<221> NAME/KEY: CDS
<222> LOCATION: (1)..(615)

<400> SEQUENCE: 98

| aag | ctg | ttc | atc | ctg | ctg | gag | agg | aac | gac | atc | cgc | cag | gtg | ggc | gtc | 48 |
|---|---|---|---|---|---|---|---|---|---|---|---|---|---|---|---|---|
| Lys | Leu | Phe | Ile | Leu | Leu | Glu | Arg | Asn | Asp | Ile | Arg | Gln | Val | Gly | Val | |
| 1 | | | | 5 | | | | | 10 | | | | | 15 | | |

| tgc | ttg | ccg | tcc | tgc | cca | cct | gga | tac | ttc | gac | gcc | cgc | aac | ccc | gac | 96 |
|---|---|---|---|---|---|---|---|---|---|---|---|---|---|---|---|---|
| Cys | Leu | Pro | Ser | Cys | Pro | Pro | Gly | Tyr | Phe | Asp | Ala | Arg | Asn | Pro | Asp | |
| | | | 20 | | | | | 25 | | | | | 30 | | | |

| atg | aac | aag | tgc | atc | aaa | tgc | aag | atc | gag | cac | tgt | gag | gcc | tgc | ttc | 144 |
|---|---|---|---|---|---|---|---|---|---|---|---|---|---|---|---|---|
| Met | Asn | Lys | Cys | Ile | Lys | Cys | Lys | Ile | Glu | His | Cys | Glu | Ala | Cys | Phe | |
| | | 35 | | | | | 40 | | | | | 45 | | | | |

| agc | cat | aac | ttc | tgc | acc | aag | tgt | aag | gag | ggc | ttg | tac | ctg | cac | aag | 192 |
|---|---|---|---|---|---|---|---|---|---|---|---|---|---|---|---|---|
| Ser | His | Asn | Phe | Cys | Thr | Lys | Cys | Lys | Glu | Gly | Leu | Tyr | Leu | His | Lys | |
| 50 | | | | | 55 | | | | | 60 | | | | | | |

| ggc | cgc | tgc | tat | cca | gct | tgt | ccc | gag | ggc | tcc | tca | gct | gcc | aat | ggc | 240 |
|---|---|---|---|---|---|---|---|---|---|---|---|---|---|---|---|---|
| Gly | Arg | Cys | Tyr | Pro | Ala | Cys | Pro | Glu | Gly | Ser | Ser | Ala | Ala | Asn | Gly | |
| 65 | | | | 70 | | | | | 75 | | | | | 80 | | |

| acc | atg | gag | tgc | agt | agt | cct | gcg | caa | tgt | gaa | atg | agc | gag | tgg | tct | 288 |
|---|---|---|---|---|---|---|---|---|---|---|---|---|---|---|---|---|
| Thr | Met | Glu | Cys | Ser | Ser | Pro | Ala | Gln | Cys | Glu | Met | Ser | Glu | Trp | Ser | |
| | | | 85 | | | | | 90 | | | | | 95 | | | |

| ccg | tgg | ggg | ccc | tgc | tcc | aag | aag | cag | cag | ctc | tgt | ggt | ttc | cgg | agg | 336 |
|---|---|---|---|---|---|---|---|---|---|---|---|---|---|---|---|---|
| Pro | Trp | Gly | Pro | Cys | Ser | Lys | Lys | Gln | Gln | Leu | Cys | Gly | Phe | Arg | Arg | |
| | | | 100 | | | | | 105 | | | | | 110 | | | |

| ggc | tcc | gag | gag | cgg | aca | cgc | agg | gtg | cta | cat | gcc | cct | gtg | ggg | gac | 384 |
|---|---|---|---|---|---|---|---|---|---|---|---|---|---|---|---|---|
| Gly | Ser | Glu | Glu | Arg | Thr | Arg | Arg | Val | Leu | His | Ala | Pro | Val | Gly | Asp | |
| | | | 115 | | | | | 120 | | | | | 125 | | | |

| cat | gct | gcc | tgc | tct | gac | acc | aag | gag | acc | cgg | agg | tgc | aca | gtg | agg | 432 |
|---|---|---|---|---|---|---|---|---|---|---|---|---|---|---|---|---|
| His | Ala | Ala | Cys | Ser | Asp | Thr | Lys | Glu | Thr | Arg | Arg | Cys | Thr | Val | Arg | |
| | 130 | | | | | 135 | | | | | 140 | | | | | |

| aga | gtg | ccg | tgt | cct | gag | ggg | cag | aag | agg | aag | gga | ggc | cag | ggc | | 480 |
|---|---|---|---|---|---|---|---|---|---|---|---|---|---|---|---|---|
| Arg | Val | Pro | Cys | Pro | Glu | Gly | Gln | Lys | Arg | Lys | Gly | Gly | Gln | Gly | | |
| 145 | | | | | 150 | | | | | 155 | | | | | 160 | |

| cgg | cgg | gag | aat | gcc | aac | agg | aac | ctg | gcc | agg | aag | gag | agc | aag | gag | 528 |
|---|---|---|---|---|---|---|---|---|---|---|---|---|---|---|---|---|
| Arg | Arg | Glu | Asn | Ala | Asn | Arg | Asn | Leu | Ala | Arg | Lys | Glu | Ser | Lys | Glu | |
| | | | | 165 | | | | | 170 | | | | | 175 | | |

| gcg | ggt | gct | ggc | tct | cga | aga | cgc | aag | ggg | cag | caa | cag | cag | cag | cag | 576 |
|---|---|---|---|---|---|---|---|---|---|---|---|---|---|---|---|---|
| Ala | Gly | Ala | Gly | Ser | Arg | Arg | Arg | Lys | Gly | Gln | Gln | Gln | Gln | Gln | Gln | |
| | | | 180 | | | | | 185 | | | | | 190 | | | |

| caa | ggg | aca | gtg | ggg | cca | ctc | aca | tct | gca | ggg | cct | gcc | | | | 615 |
|---|---|---|---|---|---|---|---|---|---|---|---|---|---|---|---|---|
| Gln | Gly | Thr | Val | Gly | Pro | Leu | Thr | Ser | Ala | Gly | Pro | Ala | | | | |
| | 195 | | | | | 200 | | | | | 205 | | | | | |

<210> SEQ ID NO 99
<211> LENGTH: 205
<212> TYPE: PRT
<213> ORGANISM: Homo sapiens

<400> SEQUENCE: 99

| Lys | Leu | Phe | Ile | Leu | Leu | Glu | Arg | Asn | Asp | Ile | Arg | Gln | Val | Gly | Val |
|---|---|---|---|---|---|---|---|---|---|---|---|---|---|---|---|
| 1 | | | | 5 | | | | | 10 | | | | | 15 | |

| Cys | Leu | Pro | Ser | Cys | Pro | Pro | Gly | Tyr | Phe | Asp | Ala | Arg | Asn | Pro | Asp |
|---|---|---|---|---|---|---|---|---|---|---|---|---|---|---|---|
| | | | 20 | | | | | 25 | | | | | 30 | | |

| Met | Asn | Lys | Cys | Ile | Lys | Cys | Lys | Ile | Glu | His | Cys | Glu | Ala | Cys | Phe |
|---|---|---|---|---|---|---|---|---|---|---|---|---|---|---|---|
| | | 35 | | | | | 40 | | | | | 45 | | | |

```
Ser His Asn Phe Cys Thr Lys Cys Lys Glu Gly Leu Tyr Leu His Lys
 50                  55                  60

Gly Arg Cys Tyr Pro Ala Cys Pro Glu Gly Ser Ser Ala Ala Asn Gly
 65                  70                  75                  80

Thr Met Glu Cys Ser Ser Pro Ala Gln Cys Glu Met Ser Glu Trp Ser
                 85                  90                  95

Pro Trp Gly Pro Cys Ser Lys Lys Gln Gln Leu Cys Gly Phe Arg Arg
                100                 105                 110

Gly Ser Glu Glu Arg Thr Arg Arg Val Leu His Ala Pro Val Gly Asp
            115                 120                 125

His Ala Ala Cys Ser Asp Thr Lys Glu Thr Arg Arg Cys Thr Val Arg
130                 135                 140

Arg Val Pro Cys Pro Glu Gly Gln Lys Arg Arg Lys Gly Gly Gln Gly
145                 150                 155                 160

Arg Arg Glu Asn Ala Asn Arg Asn Leu Ala Arg Lys Glu Ser Lys Glu
                165                 170                 175

Ala Gly Ala Gly Ser Arg Arg Lys Gly Gln Gln Gln Gln Gln Gln Gln
            180                 185                 190

Gln Gly Thr Val Gly Pro Leu Thr Ser Ala Gly Pro Ala
        195                 200                 205

<210> SEQ ID NO 100
<211> LENGTH: 432
<212> TYPE: DNA
<213> ORGANISM: Homo sapiens
<220> FEATURE:
<221> NAME/KEY: CDS
<222> LOCATION: (1)..(432)

<400> SEQUENCE: 100 ctg cac aag ggc cgc tgc tat cca gct tgt ccc gag ggc tcc tca gct     48
Leu His Lys Gly Arg Cys Tyr Pro Ala Cys Pro Glu Gly Ser Ser Ala
 1               5                  10                  15 gcc aat ggc acc atg gag tgc agt agt cct gcg caa tgt gaa atg agc     96
Ala Asn Gly Thr Met Glu Cys Ser Ser Pro Ala Gln Cys Glu Met Ser
            20                  25                  30 gag tgg tct ccg tgg ggg ccc tgc tcc aag aag cag cag ctc tgt ggt    144
Glu Trp Ser Pro Trp Gly Pro Cys Ser Lys Lys Gln Gln Leu Cys Gly
        35                  40                  45 ttc cgg agg ggc tcc gag gag cgg aca cgc agg gtg cta cat gcc cct    192
Phe Arg Arg Gly Ser Glu Glu Arg Thr Arg Arg Val Leu His Ala Pro
 50                  55                  60 gtg ggg gac cat gct gcc tgc tct gac acc aag gag acc cgg agg tgc    240
Val Gly Asp His Ala Ala Cys Ser Asp Thr Lys Glu Thr Arg Arg Cys
 65                  70                  75                  80 aca gtg agg aga gtg ccg tgt cct gag ggg cag aag agg agg aag gga    288
Thr Val Arg Arg Val Pro Cys Pro Glu Gly Gln Lys Arg Arg Lys Gly
                 85                  90                  95 ggc cag ggc cgg cgg gag aat gcc aac agg aac ctg gcc agg aag gag    336
Gly Gln Gly Arg Arg Glu Asn Ala Asn Arg Asn Leu Ala Arg Lys Glu
            100                 105                 110 agc aag gag gcg ggt gct ggc tct cga aga cgc aag ggg cag caa cag    384
Ser Lys Glu Ala Gly Ala Gly Ser Arg Arg Arg Lys Gly Gln Gln Gln
        115                 120                 125 cag cag cag caa ggg aca gtg ggg cca ctc aca tct gca ggg cct gcc    432
Gln Gln Gln Gln Gly Thr Val Gly Pro Leu Thr Ser Ala Gly Pro Ala
130                 135                 140

<210> SEQ ID NO 101
```

<211> LENGTH: 144
<212> TYPE: PRT
<213> ORGANISM: Homo sapiens

<400> SEQUENCE: 101

Leu His Lys Gly Arg Cys Tyr Pro Ala Cys Pro Glu Gly Ser Ser Ala
1               5                   10                  15

Ala Asn Gly Thr Met Glu Cys Ser Ser Pro Ala Gln Cys Glu Met Ser
            20                  25                  30

Glu Trp Ser Pro Trp Gly Pro Cys Ser Lys Lys Gln Gln Leu Cys Gly
        35                  40                  45

Phe Arg Arg Gly Ser Glu Glu Arg Thr Arg Arg Val Leu His Ala Pro
50                  55                  60

Val Gly Asp His Ala Ala Cys Ser Asp Thr Lys Glu Thr Arg Arg Cys
65                  70                  75                  80

Thr Val Arg Arg Val Pro Cys Pro Glu Gly Gln Lys Arg Arg Lys Gly
                85                  90                  95

Gly Gln Gly Arg Arg Glu Asn Ala Asn Arg Asn Leu Ala Arg Lys Glu
            100                 105                 110

Ser Lys Glu Ala Gly Ala Gly Ser Arg Arg Arg Lys Gly Gln Gln Gln
        115                 120                 125

Gln Gln Gln Gln Gly Thr Val Gly Pro Leu Thr Ser Ala Gly Pro Ala
130                 135                 140

<210> SEQ ID NO 102
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 102 tgc agt agt cct gcg caa tgt gaa atg agc gag tgg tct ccg tgg ggg     48
Cys Ser Ser Pro Ala Gln Cys Glu Met Ser Glu Trp Ser Pro Trp Gly
1               5                   10                  15 ccc tgc tcc aag aag cag cag ctc tgt ggt ttc cgg agg ggc tcc gag     96
Pro Cys Ser Lys Lys Gln Gln Leu Cys Gly Phe Arg Arg Gly Ser Glu
            20                  25                  30 gag cgg aca cgc agg gtg cta cat gcc cct gtg ggg gac cat gct gcc    144
Glu Arg Thr Arg Arg Val Leu His Ala Pro Val Gly Asp His Ala Ala
        35                  40                  45 tgc tct gac acc aag gag acc cgg agg tgc aca gtg agg aga gtg ccg    192
Cys Ser Asp Thr Lys Glu Thr Arg Arg Cys Thr Val Arg Arg Val Pro
50                  55                  60 tgt cct gag ggg cag aag agg agg aag gga ggc cag ggc cgg cgg gag    240
Cys Pro Glu Gly Gln Lys Arg Arg Lys Gly Gly Gln Gly Arg Arg Glu
65                  70                  75                  80 aat gcc aac agg aac ctg gcc agg aag gag agc aag gag gcg ggt gct    288
Asn Ala Asn Arg Asn Leu Ala Arg Lys Glu Ser Lys Glu Ala Gly Ala
                85                  90                  95 ggc tct cga aga cgc aag ggg cag caa cag cag cag caa ggg aca        336
Gly Ser Arg Arg Arg Lys Gly Gln Gln Gln Gln Gln Gln Gly Thr
            100                 105                 110 gtg ggg cca ctc aca tct gca ggg cct gcc                            366
Val Gly Pro Leu Thr Ser Ala Gly Pro Ala
        115                 120

<210> SEQ ID NO 103
<211> LENGTH: 122
<212> TYPE: PRT

<213> ORGANISM: Homo sapiens

<400> SEQUENCE: 103

```
Cys Ser Ser Pro Ala Gln Cys Glu Met Ser Glu Trp Ser Pro Trp Gly
1               5                   10                  15
Pro Cys Ser Lys Lys Gln Gln Leu Cys Gly Phe Arg Arg Gly Ser Glu
            20                  25                  30
Glu Arg Thr Arg Arg Val Leu His Ala Pro Val Gly Asp His Ala Ala
        35                  40                  45
Cys Ser Asp Thr Lys Glu Thr Arg Arg Cys Thr Val Arg Arg Val Pro
    50                  55                  60
Cys Pro Glu Gly Gln Lys Arg Arg Lys Gly Gly Gln Gly Arg Arg Glu
65                  70                  75                  80
Asn Ala Asn Arg Asn Leu Ala Arg Lys Glu Ser Lys Glu Ala Gly Ala
                85                  90                  95
Gly Ser Arg Arg Arg Lys Gly Gln Gln Gln Gln Gln Gln Gly Thr
            100                 105                 110
Val Gly Pro Leu Thr Ser Ala Gly Pro Ala
            115                 120
```

<210> SEQ ID NO 104
<211> LENGTH: 228
<212> TYPE: DNA
<213> ORGANISM: Homo sapiens
<220> FEATURE:
<221> NAME/KEY: CDS
<222> LOCATION: (1)..(228)

<400> SEQUENCE: 104

```
cgc cag gtg ggc gtc tgc ttg ccg tcc tgc cca cct gga tac ttc gac     48
Arg Gln Val Gly Val Cys Leu Pro Ser Cys Pro Pro Gly Tyr Phe Asp
1               5                   10                  15 gcc cgc aac ccc gac atg aac aag tgc atc aaa tgc aag atc gag cac     96
Ala Arg Asn Pro Asp Met Asn Lys Cys Ile Lys Cys Lys Ile Glu His
            20                  25                  30 tgt gag gcc tgc ttc agc cat aac ttc tgc acc aag tgt aag gag ggc    144
Cys Glu Ala Cys Phe Ser His Asn Phe Cys Thr Lys Cys Lys Glu Gly
        35                  40                  45 ttg tac ctg cac aag ggc cgc tgc tat cca gct tgt ccc gag ggc tcc    192
Leu Tyr Leu His Lys Gly Arg Cys Tyr Pro Ala Cys Pro Glu Gly Ser
    50                  55                  60 tca gct gcc aat ggc acc atg gag tgc agt agt cct                    228
Ser Ala Ala Asn Gly Thr Met Glu Cys Ser Ser Pro
65                  70                  75
```

<210> SEQ ID NO 105
<211> LENGTH: 76
<212> TYPE: PRT
<213> ORGANISM: Homo sapiens

<400> SEQUENCE: 105

```
Arg Gln Val Gly Val Cys Leu Pro Ser Cys Pro Pro Gly Tyr Phe Asp
1               5                   10                  15
Ala Arg Asn Pro Asp Met Asn Lys Cys Ile Lys Cys Lys Ile Glu His
            20                  25                  30
Cys Glu Ala Cys Phe Ser His Asn Phe Cys Thr Lys Cys Lys Glu Gly
        35                  40                  45
Leu Tyr Leu His Lys Gly Arg Cys Tyr Pro Ala Cys Pro Glu Gly Ser
    50                  55                  60
Ser Ala Ala Asn Gly Thr Met Glu Cys Ser Ser Pro
```

<210> SEQ ID NO 106
<211> LENGTH: 26
<212> TYPE: DNA
<213> ORGANISM: Artificial sequence
<220> FEATURE:
<223> OTHER INFORMATION: forward primer

<400> SEQUENCE: 106
caccgctagc agccggggga tcaagg                                          26

<210> SEQ ID NO 107
<211> LENGTH: 28
<212> TYPE: DNA
<213> ORGANISM: Artificial sequence
<220> FEATURE:
<223> OTHER INFORMATION: reverse primer

<400> SEQUENCE: 107
cacgcggccg ctcttgaggc agccgttg                                        28

<210> SEQ ID NO 108
<211> LENGTH: 29
<212> TYPE: DNA
<213> ORGANISM: Artificial sequence
<220> FEATURE:
<223> OTHER INFORMATION: reverse primer

<400> SEQUENCE: 108
cacgcggccg cttgggcagg acggcaagc                                       29

<210> SEQ ID NO 109
<211> LENGTH: 31
<212> TYPE: DNA
<213> ORGANISM: Artificial sequence
<220> FEATURE:
<223> OTHER INFORMATION: reverse primer

<400> SEQUENCE: 109
cacgcggccg ctgaagttat ggctgaagca g                                    31

<210> SEQ ID NO 110
<211> LENGTH: 30
<212> TYPE: DNA
<213> ORGANISM: Artificial sequence
<220> FEATURE:
<223> OTHER INFORMATION: reverse primer

<400> SEQUENCE: 110
cacgcggccg ctcatggtgc cattggcagc                                      30

<210> SEQ ID NO 111
<211> LENGTH: 30
<212> TYPE: DNA
<213> ORGANISM: Artificial sequence
<220> FEATURE:
<223> OTHER INFORMATION: reverse primer

<400> SEQUENCE: 111
cacgcggccg ctcctccgga aaccacagag                                      30

<210> SEQ ID NO 112
<211> LENGTH: 30
<212> TYPE: DNA
<213> ORGANISM: Artificial sequence
<220> FEATURE:

```
<223> OTHER INFORMATION: reverse primer

<400> SEQUENCE: 112
cacgcggccg cttgtgcacc tccgggtctc                                       30

<210> SEQ ID NO 113
<211> LENGTH: 29
<212> TYPE: DNA
<213> ORGANISM: Artificial sequence
<220> FEATURE:
<223> OTHER INFORMATION: reverse primer

<400> SEQUENCE: 113
cacgcggccg ctcttcctgg ccaggttcc                                        29

<210> SEQ ID NO 114
<211> LENGTH: 29
<212> TYPE: DNA
<213> ORGANISM: Artificial sequence
<220> FEATURE:
<223> OTHER INFORMATION: forward primer

<400> SEQUENCE: 114
caccgctagc aagctgttca tcctgctgg                                        29

<210> SEQ ID NO 115
<211> LENGTH: 29
<212> TYPE: DNA
<213> ORGANISM: Artificial sequence
<220> FEATURE:
<223> OTHER INFORMATION: reverse primer

<400> SEQUENCE: 115
cacgcggccg ctggcaggcc ctgcagatg                                        29

<210> SEQ ID NO 116
<211> LENGTH: 27
<212> TYPE: DNA
<213> ORGANISM: Artificial sequence
<220> FEATURE:
<223> OTHER INFORMATION: forward primer

<400> SEQUENCE: 116
caccgctagc ctgcacaagg gccgctg                                          27

<210> SEQ ID NO 117
<211> LENGTH: 27
<212> TYPE: DNA
<213> ORGANISM: Artificial sequence
<220> FEATURE:
<223> OTHER INFORMATION: forward primer

<400> SEQUENCE: 117
caccgctagc tgcagtagtc ctgcgca                                          27

<210> SEQ ID NO 118
<211> LENGTH: 27
<212> TYPE: DNA
<213> ORGANISM: Artificial sequence
<220> FEATURE:
<223> OTHER INFORMATION: forward primer

<400> SEQUENCE: 118
caccgctagc cgccaggtgg gcgtctg                                          27

<210> SEQ ID NO 119
```

```
<211> LENGTH: 29
<212> TYPE: DNA
<213> ORGANISM: Artificial sequence
<220> FEATURE:
<223> OTHER INFORMATION: reverse primer

<400> SEQUENCE: 119
cacgcggccg ctaggactac tgcactcca                                29

<210> SEQ ID NO 120
<211> LENGTH: 24
<212> TYPE: DNA
<213> ORGANISM: Artificial sequence
<220> FEATURE:
<223> OTHER INFORMATION: Forward primer

<400> SEQUENCE: 120
gatcagcagc tggaacaaac acag                                     24

<210> SEQ ID NO 121
<211> LENGTH: 25
<212> TYPE: DNA
<213> ORGANISM: Artificial sequence
<220> FEATURE:
<223> OTHER INFORMATION: Reverse primer

<400> SEQUENCE: 121
tgcacaatca gtcaatcaac agagc                                    25

<210> SEQ ID NO 122
<211> LENGTH: 30
<212> TYPE: DNA
<213> ORGANISM: Artificial sequence
<220> FEATURE:
<223> OTHER INFORMATION: oligonucleotide

<400> SEQUENCE: 122
ggcggatccc tgagttggag gccagtttgg                               30

<210> SEQ ID NO 123
<211> LENGTH: 39
<212> TYPE: DNA
<213> ORGANISM: Artificial sequence
<220> FEATURE:
<223> OTHER INFORMATION: oligonucleotide 123

<400> SEQUENCE: 123
gctctagacc atggtggacg agcctagagg agaaggcat                     39

<210> SEQ ID NO 124
<211> LENGTH: 41
<212> TYPE: DNA
<213> ORGANISM: Artificial sequence
<220> FEATURE:
<223> OTHER INFORMATION: Forward primer

<400> SEQUENCE: 124
ccgctcgagg catgcggctt gggctgtgtg tggtggccct g                  41

<210> SEQ ID NO 125
<211> LENGTH: 44
<212> TYPE: DNA
<213> ORGANISM: Artificial sequence
<220> FEATURE:
<223> OTHER INFORMATION: Reverse primer

<400> SEQUENCE: 125
```
gctctagaag atctctaggc aggccctgca gatgtgagtg gccc                                44

<210> SEQ ID NO 126
<211> LENGTH: 19
<212> TYPE: DNA
<213> ORGANISM: Artificial sequence
<220> FEATURE:
<223> OTHER INFORMATION: Oligonucleotide

<400> SEQUENCE: 126
aattcggatc cggcgcgcc                                                            19

<210> SEQ ID NO 127
<211> LENGTH: 19
<212> TYPE: DNA
<213> ORGANISM: Artificial sequence
<220> FEATURE:
<223> OTHER INFORMATION: oligonucleotide

<400> SEQUENCE: 127
gatcggcgcg ccggatccg                                                            19

<210> SEQ ID NO 128
<211> LENGTH: 47
<212> TYPE: DNA
<213> ORGANISM: Artificial sequence
<220> FEATURE:
<223> OTHER INFORMATION: oligonucleotide

<400> SEQUENCE: 128
ggccgtttaa acataacttc gtataatgta tgctatacga agttatc                             47

<210> SEQ ID NO 129
<211> LENGTH: 47
<212> TYPE: DNA
<213> ORGANISM: Artificial sequence
<220> FEATURE:
<223> OTHER INFORMATION: oligonucleotide

<400> SEQUENCE: 129
tcgagataac ttcgtatagc atacattata cgaagttatg tttaaac                             47

<210> SEQ ID NO 130
<211> LENGTH: 41
<212> TYPE: DNA
<213> ORGANISM: forward primer
<220> FEATURE:
<223> OTHER INFORMATION: oligonucleotide

<400> SEQUENCE: 130
cgggatccgt ttaaacctgt gccttctagt tgccagccat c                                   41

<210> SEQ ID NO 131
<211> LENGTH: 33
<212> TYPE: DNA
<213> ORGANISM: Artificial sequence
<220> FEATURE:
<223> OTHER INFORMATION: reverse primer

<400> SEQUENCE: 131
cggatatccc atagagccca ccgcatcccc agc                                            33

<210> SEQ ID NO 132
<211> LENGTH: 19
<212> TYPE: DNA
<213> ORGANISM: Artificial sequence
<220> FEATURE:

```
<223> OTHER INFORMATION: oligonucleotide

<400> SEQUENCE: 132
taaccgcgat cgcggccgg                                                        19

<210> SEQ ID NO 133
<211> LENGTH: 17
<212> TYPE: DNA
<213> ORGANISM: Artificial sequence
<220> FEATURE:
<223> OTHER INFORMATION: oligonucleotide

<400> SEQUENCE: 133
ccgcgatcgc ccttaat                                                          17

<210> SEQ ID NO 134
<211> LENGTH: 20
<212> TYPE: DNA
<213> ORGANISM: Artificial sequence
<220> FEATURE:
<223> OTHER INFORMATION: forward primer

<400> SEQUENCE: 134
ctaacgttac tggccgaagc                                                       20

<210> SEQ ID NO 135
<211> LENGTH: 25
<212> TYPE: DNA
<213> ORGANISM: Artificial sequence
<220> FEATURE:
<223> OTHER INFORMATION: reverse primer

<400> SEQUENCE: 135
attatcatcg tgttttcaa aggaa                                                  25

<210> SEQ ID NO 136
<211> LENGTH: 20
<212> TYPE: DNA
<213> ORGANISM: Artificial sequence
<220> FEATURE:
<223> OTHER INFORMATION: forward primer

<400> SEQUENCE: 136
gctctgacac caaggagacc                                                       20

<210> SEQ ID NO 137
<211> LENGTH: 20
<212> TYPE: DNA
<213> ORGANISM: Artificial sequence
<220> FEATURE:
<223> OTHER INFORMATION: reverse primer

<400> SEQUENCE: 137
ccctaggaat gctcgtcaag                                                       20

<210> SEQ ID NO 138
<211> LENGTH: 18
<212> TYPE: DNA
<213> ORGANISM: Artificial sequence
<220> FEATURE:
<223> OTHER INFORMATION: forward primer

<400> SEQUENCE: 138
caggagcctc acccttcg                                                         18

<210> SEQ ID NO 139
```

```
<211> LENGTH: 18
<212> TYPE: DNA
<213> ORGANISM: Artificial sequence
<220> FEATURE:
<223> OTHER INFORMATION: reverse primer

<400> SEQUENCE: 139
acgccgaggt gcttgccc                                                  18

<210> SEQ ID NO 140
<211> LENGTH: 25
<212> TYPE: DNA
<213> ORGANISM: Artificial sequence
<220> FEATURE:
<223> OTHER INFORMATION: forward primer

<400> SEQUENCE: 140
caccatggag aaggccgggg cccac                                          25

<210> SEQ ID NO 141
<211> LENGTH: 25
<212> TYPE: DNA
<213> ORGANISM: Artificial sequence
<220> FEATURE:
<223> OTHER INFORMATION: reverse primer

<400> SEQUENCE: 141
atcatacttg gcaggtttct ccagg                                          25

<210> SEQ ID NO 142
<211> LENGTH: 39
<212> TYPE: DNA
<213> ORGANISM: Artificial sequence
<220> FEATURE:
<223> OTHER INFORMATION: forward primer

<400> SEQUENCE: 142
cgggatcccc atggctcctc tcggatacct cttagtgct                           39

<210> SEQ ID NO 143
<211> LENGTH: 41
<212> TYPE: DNA
<213> ORGANISM: Artificial sequence
<220> FEATURE:
<223> OTHER INFORMATION: reverse primer

<400> SEQUENCE: 143
gctctagagt ttaaacctac ttgcaggtgt gcacgtcata g                        41

<210> SEQ ID NO 144
<211> LENGTH: 28
<212> TYPE: DNA
<213> ORGANISM: Artificial sequence
<220> FEATURE:
<223> OTHER INFORMATION: oligonucleotide

<400> SEQUENCE: 144
tcgagtcgcg acaccggcgg gcgcgccc                                       28

<210> SEQ ID NO 145
<211> LENGTH: 28
<212> TYPE: DNA
<213> ORGANISM: Artificial sequence
<220> FEATURE:
<223> OTHER INFORMATION: oligonucleotide

<400> SEQUENCE: 145
```

```
tcgagggcgc gcccgccggt gtcgcgac                                          28

<210> SEQ ID NO 146
<211> LENGTH: 29
<212> TYPE: DNA
<213> ORGANISM: Artificial sequence
<220> FEATURE:
<223> OTHER INFORMATION: oligonucleotide

<400> SEQUENCE: 146
ggccgcttaa ttaaggccgg ccgtcgacg                                         29

<210> SEQ ID NO 147
<211> LENGTH: 29
<212> TYPE: DNA
<213> ORGANISM: Artificial sequence
<220> FEATURE:
<223> OTHER INFORMATION: oligonucleotide

<400> SEQUENCE: 147
aattcgtcga cggccggcct taattaagc                                         29

<210> SEQ ID NO 148
<211> LENGTH: 42
<212> TYPE: DNA
<213> ORGANISM: Artificial sequence
<220> FEATURE:
<223> OTHER INFORMATION: forward primer

<400> SEQUENCE: 148
ttggcgcgcc ctccctagga ctgcagttga gctcagattt ga                          42

<210> SEQ ID NO 149
<211> LENGTH: 44
<212> TYPE: DNA
<213> ORGANISM: Artificial sequence
<220> FEATURE:
<223> OTHER INFORMATION: reverse primer

<400> SEQUENCE: 149
ccgctcgagt cttactgtct cagcaacaat aatataaaca gggg                        44

<210> SEQ ID NO 150
<211> LENGTH: 49
<212> TYPE: DNA
<213> ORGANISM: Artificial sequence
<220> FEATURE:
<223> OTHER INFORMATION: forward primer

<400> SEQUENCE: 150
ataagaatgc ggccgcaaag ctggtgggtt aagactatct cgtgaagtg                   49

<210> SEQ ID NO 151
<211> LENGTH: 45
<212> TYPE: DNA
<213> ORGANISM: Artificial sequence
<220> FEATURE:
<223> OTHER INFORMATION: reverse primer

<400> SEQUENCE: 151
acgcgtcgac tcacaggttg gtccctctct gtgtgtggtt gctgt                       45

<210> SEQ ID NO 152
<211> LENGTH: 25
<212> TYPE: DNA
<213> ORGANISM: Artificial sequence
<220> FEATURE:
```

```
<223> OTHER INFORMATION: forward primer

<400> SEQUENCE: 152
tcttactaga gttctcacta gctct                                  25

<210> SEQ ID NO 153
<211> LENGTH: 25
<212> TYPE: DNA
<213> ORGANISM: Artificial sequence
<220> FEATURE:
<223> OTHER INFORMATION: reverse primer

<400> SEQUENCE: 153
ggaaccaaag aatgaggaag ctgtt                                  25

<210> SEQ ID NO 154
<211> LENGTH: 17
<212> TYPE: DNA
<213> ORGANISM: Artificial sequence
<220> FEATURE:
<223> OTHER INFORMATION: oligonucleotide

<400> SEQUENCE: 154
ggccaggcgc gccttgc                                           17

<210> SEQ ID NO 155
<211> LENGTH: 17
<212> TYPE: DNA
<213> ORGANISM: Artificial sequence
<220> FEATURE:
<223> OTHER INFORMATION: olignucleotide

<400> SEQUENCE: 155
ggccgcaagg cgcgcct                                           17

<210> SEQ ID NO 156
<211> LENGTH: 20
<212> TYPE: DNA
<213> ORGANISM: Artificial sequence
<220> FEATURE:
<223> OTHER INFORMATION: oligonucleotide

<400> SEQUENCE: 156
taagggctag ctagggccgg                                        20

<210> SEQ ID NO 157
<211> LENGTH: 18
<212> TYPE: DNA
<213> ORGANISM: Artificial sequence
<220> FEATURE:
<223> OTHER INFORMATION: oligonucleotide

<400> SEQUENCE: 157
ccctagctag cccttaat                                          18

<210> SEQ ID NO 158
<211> LENGTH: 10
<212> TYPE: DNA
<213> ORGANISM: Artificial sequence
<220> FEATURE:
<223> OTHER INFORMATION: oligonucleotide

<400> SEQUENCE: 158
tcgagttaac                                                   10

<210> SEQ ID NO 159
```

```
<211> LENGTH: 10
<212> TYPE: DNA
<213> ORGANISM: Artificial sequence
<220> FEATURE:
<223> OTHER INFORMATION: oligonucleotide

<400> SEQUENCE: 159
agctgttaac                                                              10

<210> SEQ ID NO 160
<211> LENGTH: 27
<212> TYPE: DNA
<213> ORGANISM: Artificial sequence
<220> FEATURE:
<223> OTHER INFORMATION: oligonucleotide

<400> SEQUENCE: 160
agctgtcgac ttaattaagg ccggccg                                           27

<210> SEQ ID NO 161
<211> LENGTH: 27
<212> TYPE: DNA
<213> ORGANISM: Artificial sequence
<220> FEATURE:
<223> OTHER INFORMATION: oligonucleotide

<400> SEQUENCE: 161
ctagcggccg gccttaatta agtcgac                                           27

<210> SEQ ID NO 162
<211> LENGTH: 31
<212> TYPE: DNA
<213> ORGANISM: Artificial sequence
<220> FEATURE:
<223> OTHER INFORMATION: oligonucleotide

<400> SEQUENCE: 162
tcgacttaat taaggccggc cctagctagc a                                      31

<210> SEQ ID NO 163
<211> LENGTH: 31
<212> TYPE: DNA
<213> ORGANISM: Artificial sequence
<220> FEATURE:
<223> OTHER INFORMATION: oligonucleotide

<400> SEQUENCE: 163
agcttgctag ctagggccgg ccttaattaa g                                      31

<210> SEQ ID NO 164
<211> LENGTH: 45
<212> TYPE: DNA
<213> ORGANISM: Artificial sequence
<220> FEATURE:
<223> OTHER INFORMATION: forward primer

<400> SEQUENCE: 164
ccttaattaa agttatgtgt cctagagggc tgcaaactca agatc                       45

<210> SEQ ID NO 165
<211> LENGTH: 53
<212> TYPE: DNA
<213> ORGANISM: Artificial sequence
<220> FEATURE:
<223> OTHER INFORMATION: reverse primer

<400> SEQUENCE: 165
```
ttggccggcc ttggcgccag tggaacctgg aatgataaac acaaagatta ttg    53

<210> SEQ ID NO 166
<211> LENGTH: 33
<212> TYPE: DNA
<213> ORGANISM: Artificial sequence
<220> FEATURE:
<223> OTHER INFORMATION: forward primer

<400> SEQUENCE: 166
aagcgtcgac caccatgcgg cttgggctgt gtg    33

<210> SEQ ID NO 167
<211> LENGTH: 30
<212> TYPE: DNA
<213> ORGANISM: Artificial sequence
<220> FEATURE:
<223> OTHER INFORMATION: reverse primer

<400> SEQUENCE: 167
atggccggcc ctacatggtg ccattggcag    30

<210> SEQ ID NO 168
<211> LENGTH: 30
<212> TYPE: DNA
<213> ORGANISM: Artificial sequence
<220> FEATURE:
<223> OTHER INFORMATION: forward primer

<400> SEQUENCE: 168
agccggggga tcaaggggaa aaggcagagg    30

<210> SEQ ID NO 169
<211> LENGTH: 30
<212> TYPE: DNA
<213> ORGANISM: Artificial sequence
<220> FEATURE:
<223> OTHER INFORMATION: reverse primer

<400> SEQUENCE: 169
atggccggcc ctacatggtg ccattggcag    30

<210> SEQ ID NO 170
<211> LENGTH: 34
<212> TYPE: DNA
<213> ORGANISM: Artificial sequence
<220> FEATURE:
<223> OTHER INFORMATION: forward primer

<400> SEQUENCE: 170
acgcgtcgac caccatgata ttccgagtca gtgc    34

<210> SEQ ID NO 171
<211> LENGTH: 35
<212> TYPE: DNA
<213> ORGANISM: Artificial sequence
<220> FEATURE:
<223> OTHER INFORMATION: reverse primer

<400> SEQUENCE: 171
ggccggccct aggcaggccc tgcagatgtg agtgg    35

<210> SEQ ID NO 172
<211> LENGTH: 33
<212> TYPE: DNA
<213> ORGANISM: Artificial sequence
<220> FEATURE:

<223> OTHER INFORMATION: forward primer

<400> SEQUENCE: 172
atgatattcc gagtcagtgc cgagggagc cag                33

<210> SEQ ID NO 173
<211> LENGTH: 35
<212> TYPE: DNA
<213> ORGANISM: Artificial sequence
<220> FEATURE:
<223> OTHER INFORMATION: reverse primer

<400> SEQUENCE: 173
ggccggccct aggcaggccc tgcagatgtg agtgg             35

<210> SEQ ID NO 174
<211> LENGTH: 20
<212> TYPE: DNA
<213> ORGANISM: Artificial sequence
<220> FEATURE:
<223> OTHER INFORMATION: forward primer

<400> SEQUENCE: 174
atcaagggga aaaggcagag                              20

<210> SEQ ID NO 175
<211> LENGTH: 25
<212> TYPE: DNA
<213> ORGANISM: Artificial sequence
<220> FEATURE:
<223> OTHER INFORMATION: reverse primer

<400> SEQUENCE: 175
cgcttgtggg gaagcctcca agacc                        25

<210> SEQ ID NO 176
<211> LENGTH: 25
<212> TYPE: DNA
<213> ORGANISM: Artificial sequence
<220> FEATURE:
<223> OTHER INFORMATION: forward primer

<400> SEQUENCE: 176
ataacttctg caccaagtgt aagga                        25

<210> SEQ ID NO 177
<211> LENGTH: 2333
<212> TYPE: DNA
<213> ORGANISM: Homo sapiens
<220> FEATURE:
<221> NAME/KEY: CDS
<222> LOCATION: (219)..(926)

<400> SEQUENCE: 177
aggcgagccg ggcgcccagg acagtcccgc agcgggcggg tgagcgggcc gcgccctcgc      60
ccctcccggg cctgccccg tcgcgactgg cagcacgaag ctgagattgt ggtttcctgg     120
tgattcaggt gggagtgggc cagaagatca ccgctggcaa ggactgggtt ggttttgga     180 gtagtccctg ctgacgtgac aaaaagatct ctcatatg ata ttc cga gtc agt gcc    236
                                          Ile Phe Arg Val Ser Ala
                                          1               5 gag ggg agc cag gcc tgt gcc aaa ggc tgt gag ctc tgc tct gaa gtc      284
Glu Gly Ser Gln Ala Cys Ala Lys Gly Cys Glu Leu Cys Ser Glu Val
         10                  15                  20 aac ggc tgc ctc aag tgc tca ccc aag ctg ttc atc ctg ctg gag agg      332
Asn Gly Cys Leu Lys Cys Ser Pro Lys Leu Phe Ile Leu Leu Glu Arg

```
                  Asn Gly Cys Leu Lys Cys Ser Pro Lys Leu Phe Ile Leu Leu Glu Arg
                           25                  30                  35 aac gac atc cgc cag gtg ggc gtc tgc ttg ccg tcc tgc cca cct gga         380
Asn Asp Ile Arg Gln Val Gly Val Cys Leu Pro Ser Cys Pro Pro Gly
 40                  45                  50 tac ttc gac gcc cgc aac ccc gac atg aac aag tgc atc aaa tgc aag         428
Tyr Phe Asp Ala Arg Asn Pro Asp Met Asn Lys Cys Ile Lys Cys Lys
 55                  60                  65                  70 atc gag cac tgt gag gcc tgc ttc agc cat aac ttc tgc acc aag tgt         476
Ile Glu His Cys Glu Ala Cys Phe Ser His Asn Phe Cys Thr Lys Cys
                 75                  80                  85 aag gag ggc ttg tac ctg cac aag ggc cgc tgc tat cca gct tgt ccc         524
Lys Glu Gly Leu Tyr Leu His Lys Gly Arg Cys Tyr Pro Ala Cys Pro
             90                  95                 100 gag ggc tcc tca gct gcc aat ggc acc atg gag tgc agt agt cct gcg         572
Glu Gly Ser Ser Ala Ala Asn Gly Thr Met Glu Cys Ser Ser Pro Ala
            105                 110                 115 caa tgt gaa gtg agc gag tgg tct ccg tgg ggg ccc tgc tcc aag aag         620
Gln Cys Glu Val Ser Glu Trp Ser Pro Trp Gly Pro Cys Ser Lys Lys
120                 125                 130 cag cag ctc tgt ggt ttc cgg agg ggc tcc gag gag cgg aca cgc agg         668
Gln Gln Leu Cys Gly Phe Arg Arg Gly Ser Glu Glu Arg Thr Arg Arg
135                 140                 145                 150 gtg cta cat gcc cct gtg ggg gac cat gct gcc tgc tct gac acc aag         716
Val Leu His Ala Pro Val Gly Asp His Ala Ala Cys Ser Asp Thr Lys
                155                 160                 165 gag acc cgg agg tgc aca gtg agg aga gtg ccg tgt cct gag ggg cag         764
Glu Thr Arg Arg Cys Thr Val Arg Arg Val Pro Cys Pro Glu Gly Gln
            170                 175                 180 aag agg agg aag gga ggc cag ggc cgg cgg gag aat gcc aac agg aac         812
Lys Arg Arg Lys Gly Gly Gln Gly Arg Arg Glu Asn Ala Asn Arg Asn
            185                 190                 195 ctg gcc agg aag gag agc aag gag gcg ggt gct ggc tct cga aga cgc         860
Leu Ala Arg Lys Glu Ser Lys Glu Ala Gly Ala Gly Ser Arg Arg Arg
        200                 205                 210 aag ggg cag caa cag cag cag cag caa ggg aca gtg ggg cca ctc aca         908
Lys Gly Gln Gln Gln Gln Gln Gln Gly Thr Val Gly Pro Leu Thr
215                 220                 225                 230 tct gca ggg cct gcc tag ggacactgtc cagcctccag gcccatgcag               956
Ser Ala Gly Pro Ala
                235 aaagagttca gtgctactct gcgtgattca agctttcctg aactggaacg tcggggggcaa     1016 agcatacaca cacactccaa tccatccatg catacacaga cacaagacac acacgctcaa     1076 accccctgtcc acatatacaa ccatacatac ttgcacatgt gtgttcatgt acacacgcag     1136 acacagacac cacacacaca catacacaca cacacacaca cacacacctg aggccaccag     1196 aagacacttc catccctcgg gcccagcagt acacacttgg tttccagagc tcccagtgga     1256 catgtcagag acaacacttc ccagcatctg agaccaaact gcagaggga gccttctgga     1316 gaagctgctg ggatcggacc agccactgtg cagatggga gccaagcttg aggactgctg     1376 gtgacctggg aagaaacctt cttcccatcc tgttcagcac tccagctgt gtgactttat     1436 cgttggagag tattgttacc cttccaggat acatatcagg gttaacctga ctttgaaaac     1496 tgcttaaagg tttatttcaa attaaaacaa aaaaatcaac gacagcagta gacacaggca     1556 ccacattcct ttgcagggtg tgagggtttg gcgaggtatg cgtaggagca agaagggaca     1616 gggaatttca agagaccca aatagcctgc tcagtagagg gtcatgcaga caaggaagaa     1676 aacttagggg ctgctctgac ggtggtaaac aggctgtcta tatccttgtt actcagagca     1736
```

-continued

```
tggcccggca gcagtgttgt cacagggcag cttgttagga atgagaatct caggtctcat  1796
tccagacctg gtgagccaga gtctaaattt taagattcct gatgattggc atgttaccca  1856
aatttgagaa gtgctgctgt aattcccctt aaaggacggg agaaagggcc ccggccatct  1916
tgcagcagga gggattctgg tcagctataa aggaggactt tccatctggg agaggcagaa  1976
tctatatact gaagggctag tggcactgcc aggggaaggg agtgcgtagg cttccagtga  2036
tggttgggga caatcctgcc caaaggcagg gcagtggatg gaataactcc ttgtggcatt  2096
ctgaagtgtg tgccaggctc tggactaggt gctaggtttc cagggaggag ccaaacacgg  2156
gccttgctct tgtggagctt agaggttggt ggggaagaaa ataggcatgc accaaggaat  2216
cgtacaaaca catatataac tacaaaagga tggtgccaag ggcaggtgac cactggcatc  2276
tatgcttagc tatgaaagtg aataaagcag aataaaaata aatactttc tctcagg      2333
```

<210> SEQ ID NO 178
<211> LENGTH: 235
<212> TYPE: PRT
<213> ORGANISM: Homo sapiens

<400> SEQUENCE: 178

```
Ile Phe Arg Val Ser Ala Glu Gly Ser Gln Ala Cys Ala Lys Gly Cys
1               5                   10                  15

Glu Leu Cys Ser Glu Val Asn Gly Cys Leu Lys Cys Ser Pro Lys Leu
            20                  25                  30

Phe Ile Leu Leu Glu Arg Asn Asp Ile Arg Gln Val Gly Val Cys Leu
        35                  40                  45

Pro Ser Cys Pro Pro Gly Tyr Phe Asp Ala Arg Asn Pro Asp Met Asn
    50                  55                  60

Lys Cys Ile Lys Cys Lys Ile Glu His Cys Glu Ala Cys Phe Ser His
65                  70                  75                  80

Asn Phe Cys Thr Lys Cys Lys Glu Gly Leu Tyr Leu His Lys Gly Arg
                85                  90                  95

Cys Tyr Pro Ala Cys Pro Glu Gly Ser Ser Ala Ala Asn Gly Thr Met
            100                 105                 110

Glu Cys Ser Ser Pro Ala Gln Cys Glu Val Ser Glu Trp Ser Pro Trp
        115                 120                 125

Gly Pro Cys Ser Lys Lys Gln Gln Leu Cys Gly Phe Arg Arg Gly Ser
    130                 135                 140

Glu Glu Arg Thr Arg Arg Val Leu His Ala Pro Val Gly Asp His Ala
145                 150                 155                 160

Ala Cys Ser Asp Thr Lys Glu Thr Arg Arg Cys Thr Val Arg Arg Val
                165                 170                 175

Pro Cys Pro Glu Gly Gln Lys Arg Arg Lys Gly Gly Gln Gly Arg Arg
            180                 185                 190

Glu Asn Ala Asn Arg Asn Leu Ala Arg Lys Glu Ser Lys Glu Ala Gly
        195                 200                 205

Ala Gly Ser Arg Arg Arg Lys Gly Gln Gln Gln Gln Gln Gln Gln Gly
    210                 215                 220

Thr Val Gly Pro Leu Thr Ser Ala Gly Pro Ala
225                 230                 235
```